US009745271B2

(12) United States Patent
Hood et al.

(10) Patent No.: US 9,745,271 B2
(45) Date of Patent: Aug. 29, 2017

(54) 5-SUBSTITUTED INDAZOLE-3-CARBOXAMIDES AND PREPARATION AND USE THEREOF

(71) Applicant: Samumed, LLC, San Diego, CA (US)

(72) Inventors: John Hood, San Diego, CA (US); Sunil Kumar KC, San Diego, CA (US); David Mark Wallace, San Diego, CA (US); Gopi Kumar Mittapalli, San Diego, CA (US); Brian Joseph Hofilena, San Diego, CA (US); Chi Ching Mak, San Diego, CA (US); Venkataiah Bollu, San Diego, CA (US); Brian Eastman, San Diego, CA (US)

(73) Assignee: Samumed, LLC, San Diego, CA (US)

( * ) Notice: Subject to any disclaimer, the term of this patent is extended or adjusted under 35 U.S.C. 154(b) by 0 days.

(21) Appl. No.: 14/664,517

(22) Filed: Mar. 20, 2015

(65) Prior Publication Data
US 2015/0266825 A1  Sep. 24, 2015

Related U.S. Application Data

(60) Provisional application No. 61/968,350, filed on Mar. 20, 2014.

(51) Int. Cl.
| *C07D 401/12* | (2006.01) |
| *C07D 231/56* | (2006.01) |
| *C07D 401/14* | (2006.01) |
| *C07D 405/14* | (2006.01) |
| *C07D 401/04* | (2006.01) |
| *C07D 405/12* | (2006.01) |
| *C07D 498/08* | (2006.01) |
| *C07B 59/00* | (2006.01) |
| *A61K 31/416* | (2006.01) |

(52) U.S. Cl.
CPC .......... *C07D 231/56* (2013.01); *C07B 59/002* (2013.01); *C07D 401/04* (2013.01); *C07D 401/12* (2013.01); *C07D 401/14* (2013.01); *C07D 405/12* (2013.01); *C07D 405/14* (2013.01); *C07D 498/08* (2013.01)

(58) Field of Classification Search
CPC .. C07D 231/56; C07D 405/14; C07D 401/12; C07D 401/14; C07D 498/08; C07D 405/12; C07D 401/04
See application file for complete search history.

(56) References Cited

U.S. PATENT DOCUMENTS

| 4,164,559 A | 8/1979 | Miyata |
| 4,474,752 A | 10/1984 | Haslam |
| 5,922,733 A | 7/1999 | Forbes |
| 6,120,484 A | 9/2000 | Silverstein |
| 6,377,849 B1 | 4/2002 | Lenarz |
| 6,440,102 B1 | 8/2002 | Arenberg |
| 6,648,873 B2 | 11/2003 | Arenberg |
| 6,831,175 B2 | 12/2004 | Li |
| 6,911,211 B2 | 6/2005 | Eini |
| 7,429,609 B2 | 9/2008 | Ohi |
| 7,482,342 B2 | 1/2009 | D'Orchymont |
| 2006/0264897 A1 | 11/2006 | Lobl |
| 2009/0203690 A1 | 8/2009 | Akritopoulou-Zanze |
| 2011/0021467 A1 | 1/2011 | D'Orchymont |
| 2011/0082144 A1 | 4/2011 | Lau |
| 2013/0079329 A1* | 3/2013 | Hood ..................... A61K 45/06 514/210.21 |
| 2014/0045815 A1* | 2/2014 | Hood ..................... A61K 45/06 514/210.21 |

FOREIGN PATENT DOCUMENTS

| WO | WO8705297 | 9/1987 |
| WO | WO9602537 | 2/1996 |
| WO | WO2004014864 A1 | 2/2004 |
| WO | WO2004029050 A1 | 4/2004 |
| WO | WO2005014554 A1 | 2/2005 |
| WO | WO2005035005 A1 | 4/2005 |
| WO | WO2005049019 A1 | 6/2005 |
| WO | WO2005092890 A2 | 10/2005 |
| WO | WO2006058007 A2 | 6/2006 |
| WO | WO2007038367 A1 | 4/2007 |
| WO | WO2007061360 A2 | 5/2007 |

(Continued)

OTHER PUBLICATIONS

Kerekes et al. "Aurora Kinase Inhibitors Based on the Imidazo[1,2-a]pyrazine Core: Fluorine and Deuterium Incorporation Improve Oral Absorption and Exposure" J. Med. Chem. 2011, 54, 201-210.*
Chou and Talalay, "Quantitative analysis of dose-effect relationships: the combined effects of multiple drugs or enzyme inhibitors," Adv Enzyme Regul., 22:27-55, 1984.
Johnson et.al., "A stem cell-based approach to cartilage repair," Science, 336(6082):717-721, Epub Apr. 5, 2012.
Leyns et al., "Frzb-1 is a secreted antagonist of Wnt signaling expressed in the Spemann organizer," Cell., 88 (6):747-756, Mar. 21, 1997.
Liu et.al., "Fibrotic lung fibroblasts show blunted inhibition by cAMP due to deficient cAMP response element-binding protein phosphorylation," J Pharmacol Exp Ther., 315(2):678-687, Epub Aug. 3, 2005.

(Continued)

*Primary Examiner* — Michael Barker
*Assistant Examiner* — Amanda L Aguirre
(74) *Attorney, Agent, or Firm* — Fish & Richardson P.C.

(57) ABSTRACT

Indazole compounds for treating various diseases and pathologies are disclosed. More particularly, the present disclosure concerns the use of an indazole compound or analogs thereof, in the treatment of disorders characterized by the activation of Wnt pathway signaling (e.g., cancer, abnormal cellular proliferation, angiogenesis, Alzheimer's disease, lung disease, fibrotic disorders, cartilage (chondral) defects, and osteoarthritis), the modulation of cellular events mediated by Wnt pathway signaling, and neurological conditions/disorders/diseases linked to overexpression of DYRK1A.

16 Claims, 1 Drawing Sheet

(56) References Cited

FOREIGN PATENT DOCUMENTS

WO WO2008154241 A1 12/2008
WO WO2013124158 A1 8/2013

OTHER PUBLICATIONS

Watt et.al., "RhoA signaling modulates cyclin D1 expression in human lung fibroblasts; implications for idiopathic pulmonary fibrosis," Respiratory Research, 7(1):88, Jun. 15, 2006.

* cited by examiner

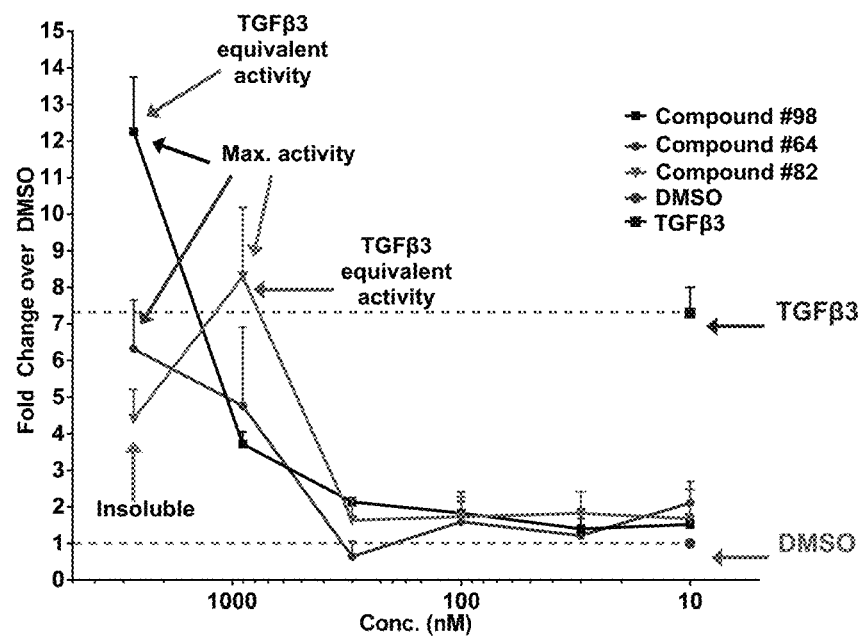

5-SUBSTITUTED INDAZOLE-3-CARBOXAMIDES AND PREPARATION AND USE THEREOF

RELATED APPLICATIONS

This application claims the benefit of U.S. Provisional Application No. 61/968,350, filed Mar. 20, 2014, which is incorporated herein by reference in its entirety.

BACKGROUND

Technical Field

This disclosure relates to inhibitors of one or more proteins in the Wnt pathway, including inhibitors of one or more Wnt proteins, and compositions comprising the same. More particularly, it concerns the use of an indazole compound or salts or analogs thereof, in the treatment of disorders characterized by the activation of Wnt pathway signaling (e.g., cancer, abnormal cellular proliferation, angiogenesis, Alzheimer's disease, lung disease, fibrotic disorders, cartilage (chondral) defects, and osteoarthritis), the modulation of cellular events mediated by Wnt pathway signaling, as well as genetic diseases and neurological conditions/disorders/diseases due to mutations or dysregulation of the Wnt pathway and/or of one or more Wnt signaling components. Also provided are methods for treating Wnt-related disease states.

Background

The Wnt growth factor family includes more than 10 genes identified in the mouse and at least 19 genes identified in the human. Members of the Wnt family of signaling molecules mediate many short- and long-range patterning processes during invertebrate and vertebrate development. The Wnt signaling pathway is known for its role in the inductive interactions that regulate growth and differentiation, and it also plays roles in the homeostatic maintenance of post-embryonic tissue integrity. Wnt stabilizes cytoplasmic β-catenin, which stimulates the expression of genes including c-myc, c-jun, fra-1, and cyclin D1. In addition, misregulation of Wnt signaling can cause developmental defects and is implicated in the genesis of several human cancers. The Wnt pathway has also been implicated in the maintenance of stem or progenitor cells in a growing list of adult tissues including skin, blood, gut, prostate, muscle, and the nervous system.

Dual specificity tyrosine-phosphorylation-regulated kinase 1A is an enzyme that in humans is encoded by the DYRK1A gene. DYRK1A is a member of the dual-specificity tyrosine phosphorylation-regulated kinase (DYRK) family. DYRK1A contains a nuclear targeting signal sequence, a protein kinase domain, a leucine zipper motif, and a highly conservative 13-consecutive-histidine repeat. It catalyzes its autophosphorylation on serine/threonine and tyrosine residues. It may play a significant role in a signaling pathway regulating cell proliferation and may be involved in brain development. DYRK1A is localized in the Down syndrome critical region of chromosome 21, and is considered to be a candidate gene for learning defects associated with Down syndrome. DYRK1A is also expressed in adult brain neurons, indicating that DYRK1A may play a role in the mature central nervous system. Thus, several lines of evidence point to some synaptic functions of DYRK1A. For instance, it has been found that DYRK1A phosphorylates and modulates the interaction of several components of the endocytic protein complex machinery (Dynamin 1, Amphiphysin, and Synaptojanin), suggesting a role in synaptic vesicle recycling. In addition, a polymorphism (SNP) in DYRK1A was found to be associated with HIV-1 replication in monocyte-derived macrophages, as well as with progression to AIDS in two independent cohorts of HIV-1-infected individuals.

SUMMARY

The present disclosure provides methods and reagents, involving contacting a cell with an agent, such as an indazole compound, in a sufficient amount to antagonize a Wnt activity, e.g., to reverse or control an aberrant growth state or correct a genetic disorder due to mutations in Wnt signaling components.

The present disclosure also provides methods and reagents, involving contacting a cell with an agent, such as an indazole compound, in a sufficient amount to antagonize DYRK1A activity, e.g., i) to normalize prenatal and early postnatal brain development; ii) to improve cognitive function in youth and adulthood; and iii) to attenuate Alzheimer's-type neurodegeneration.

Some embodiments disclosed herein include Wnt and/or DYRK1A inhibitors containing an indazole core. Other embodiments disclosed herein include pharmaceutical compositions and methods of treatment using these compounds.

One embodiment disclosed herein includes a compound having the structure of Formula I:

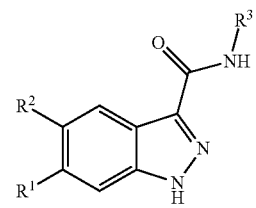

In some embodiments of Formula I:

$R^1$ is selected from the group consisting of H, halide, and —$C_{1-3}$ alkyl;

$R^2$ is selected from the group consisting of 6-10-membered heteroaryl($R^4$) and phenyl($R^5$)$_m$($R^6$);

with the proviso that $R^2$ is not

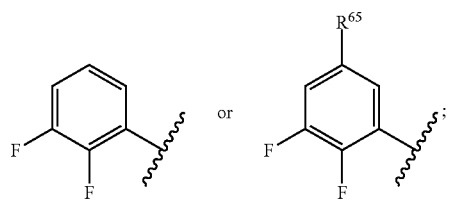

$R^3$ is selected from the group consisting of H, unsubstituted —$C_{1-9}$ alkyl, unsubstituted —$C_{1-9}$ haloalkyl, —($C_{1-6}$ alkyl)N($R^{68}$)$_2$, —($C_{2-6}$ alkyl)O($C_{1-6}$ alkyl), -carbocyclyl($R^7$)$_p$, -monocyclic heterocyclyl($R^8$)$_p$, -spirocyclic heterocyclyl($R^8$)$_p$, —($C_{1-3}$ alkyl)heterocyclyl($R^7$)$_p$, -bicyclic aryl($R^{10}$)$_q$, —($C_{1-3}$ alkyl)aryl($R^{10}$)$_q$,

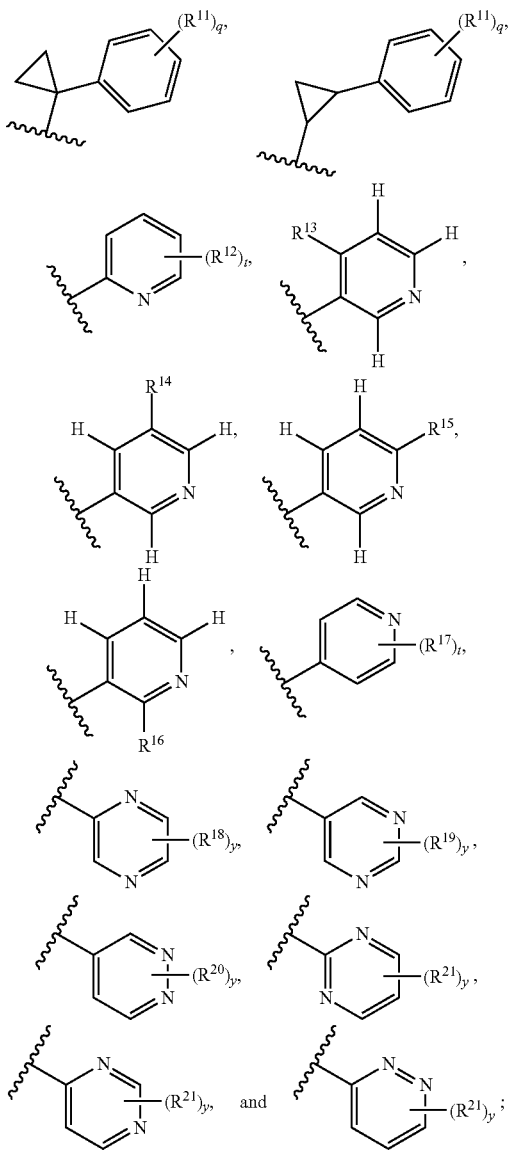

$R^4$ is 1 substituent to the 6-10-membered heteroaryl and is selected from the group consisting of H, Cl, Br, I, —CN, unsubstituted —$C_{1-6}$ haloalkyl, —($C_{1-3}$ alkyl)$_n$heterocyclyl $(R^{22})_p$, —Oaryl$(R^{23})_q$, —NHC(=O)$R^{24}$, and —($C_{1-6}$ alkyl)$_n$ N$(R^{25})_2$;

each $R^5$ is a substituent attached to the phenyl ring and independently selected at each occurrence from the group consisting of H and halide;

$R^6$ is 1 substituent attached to the phenyl ring and selected from the group consisting of H, —($C_{1-3}$ alkyl)$_n$heterocyclyl $(R^{26})_p$, —O-aryl$(R^{27})_q$, —NHC(=O)$R^{28}$, and —$(CH_2)_z$N$(R^{29})_2$;

each $R^7$ is a substituent attached to the carbocyclyl ring and is independently selected at each occurrence from the group consisting of H, halide, —$CF_3$, —CN, —N$(R^{25})_2$, and —$C_{1-6}$ alkyl;

each $R^8$ is a substituent attached to the heterocyclyl ring and is independently selected at each occurrence from the group consisting of H, halide, —($C_{1-3}$ alkyl)$_n$O$R^{30}$, —($C_{1-3}$ alkyl)carbocyclyl$(R^7)_p$, —CN, —N$(R^{25})_2$, —($C_{1-3}$ alkyl)$_n$ aryl$(R^{11})_q$, -heterocyclyl$(R^{31})_p$, —C(=O)$R^{32}$, unsubstituted —$C_{1-6}$ haloalkyl, and unsubstituted —$C_{1-6}$ alkyl;

each $R^9$ is a substituent attached to the heterocyclyl ring and is independently selected at each occurrence from the group consisting of H, halide, —($C_{1-3}$ alkyl)$_n$O$R^{33}$, —CN, -heterocyclyl$(R^{31})_p$, —C(=O)$R^{32}$, unsubstituted —$C_{1-6}$ haloalkyl, and unsubstituted —$C_{1-6}$ alkyl;

each $R^{10}$ is a substituent attached to the aryl ring and is independently selected at each occurrence from the group consisting of H, Cl, Br, I, unsubstituted —$C_{1-6}$ haloalkyl, —CN, —($C_{1-3}$ alkyl)$_n$heterocyclyl$(R^{31})_p$, —($C_{1-6}$ alkyl)$_n$N$(R^{40})(R^{41})$, and unsubstituted —$C_{1-6}$ alkyl;

each $R^{11}$ is a substituent attached to the aryl ring and is independently selected at each occurrence from the group consisting of H, halide, —$C_{1-6}$ haloalkyl, —CN, and —$C_{1-6}$ alkyl;

each $R^{12}$ is a substituent attached to the pyridinyl ring and is independently selected at each occurrence from the group consisting of H, halide, —$C_{1-6}$ haloalkyl, —CN, —$C_{1-6}$ alkyl, —O$R^{34}$, —$SO_2R^{35}$, —($C_{1-3}$ alkyl)$_n$heterocyclyl $(R^{36})_p$, —($C_{1-3}$ alkyl)$_n$aryl$(R^{37})_q$, —C(=O)N$(R^{38})_2$, —NHC(=O)$R^{39}$, and —($C_{1-6}$ alkyl)$_n$N$(R^{40})(R^{41})$;

each $R^{13}$ is selected from the group consisting of Cl, Br, I, unsubstituted —$C_{1-6}$ alkyl, unsubstituted —$C_{2-6}$ haloalkyl, —CN, —O$R^{34}$, —$SO_2R^{35}$, —($C_{1-3}$ alkyl)$_n$heterocyclyl $(R^{36})_p$, —($C_{1-3}$ alkyl)$_n$aryl$(R^{37})_q$, —C(=O)N$(R^{38})_2$, —NHC(=O)$R^{42}$, and —($C_{1-6}$ alkyl)$_n$N$(R^{40})(R^{41})$;

each $R^{14}$ is selected from the group consisting of Cl, Br, I, unsubstituted —$C_{1-6}$ haloalkyl, CN, unsubstituted —$C_{1-6}$ alkyl, —O$R^{48}$, —$SO_2R^{35}$, —($C_{2-3}$ alkyl)$_n$heterocyclyl $(R^{44})_p$, —($C_{1-3}$ alkyl)$_n$aryl$(R^{45})_q$, —C(=O)N$(R^{38})_2$, —NHC(=O)$R^{39}$, and —($C_{1-6}$ alkyl)$_n$N$(R^{46})(R^{47})$;

each $R^{15}$ is selected from the group consisting of halide, unsubstituted —$C_{1-6}$ alkyl, unsubstituted —$C_{2-6}$ haloalkyl, —O$R^{43}$, —$SO_2R^{49}$, —($C_{2-3}$ alkyl)heterocyclyl$(R^{50})_p$, -aryl$(R^{51})_q$, —($C_{1-3}$ alkyl)aryl$(R^{52})_q$, —C(=O)N$(R^{53})_2$, —NHC(=O)$R^{54}$, and —($C_{1-6}$ alkyl)$_n$N$(R^{55})(R^{56})$;

each $R^{16}$ is selected from the group consisting of halide, —CN, unsubstituted —$C_{1-6}$ alkyl, unsubstituted —$C_{2-6}$ haloalkyl, —O$R^{34}$, —$SO_2R^{35}$, —($C_{1-3}$ alkyl)$_n$heterocyclyl $(R^{57})_p$, —($C_{1-3}$ alkyl)$_n$aryl$(R^{37})_q$, —C(=O)N$(R^{38})_2$, —NHC(=O)$R^{39}$, and —($C_{1-6}$ alkyl)$_n$N$(R^{40})(R^{41})$;

each $R^{17}$ is a substituent attached to the pyridinyl ring and is independently selected at each occurrence from the group consisting of halide, —$C_{1-6}$haloalkyl, —CN, —$C_{1-6}$ alkyl, —O$R^{34}$, —$SO_2R^{35}$, —($C_{1-3}$ alkyl)$_n$heterocyclyl$(R^{36})_p$, —($C_{1-3}$ alkyl)$_n$aryl$(R^{37})_q$, —C(=O)N$(R^{38})_2$, —NHC(=O)$R^{39}$, and —($C_{1-6}$ alkyl)$_n$N$(R^{40})(R^{41})$;

each $R^{18}$ is a substituent attached to the heteroaryl ring and is independently selected at each occurrence from the group consisting of halide, —$C_{1-6}$ haloalkyl, —CN, —$C_{1-6}$ alkyl, —O$R^{34}$, —$SO_2R^{35}$, —($C_{1-3}$ alkyl)$_n$heterocyclyl $(R^{36})_p$, —($C_{1-3}$ alkyl)$_n$aryl$(R^{37})_q$, —C(=O)N$(R^{38})_2$, —NHC(=O)$R^{39}$, and —($C_{1-6}$ alkyl)$_n$N$(R^{40})(R^{41})$;

each $R^{19}$ is a substituent attached to the heteroaryl ring and is independently selected at each occurrence from the group consisting of halide, —$C_{1-6}$ haloalkyl, —CN, —$C_{1-6}$ alkyl, —O$R^{34}$, —$SO_2R^{35}$, —($C_{1-3}$ alkyl)$_n$heterocyclyl $(R^{36})_p$, —($C_{1-3}$ alkyl)$_n$aryl$(R^{37})_q$, —C(=O)N$(R^{38})_2$, —NHC(=O)$R^{39}$, and —($C_{1-6}$ alkyl)$_n$N$(R^{58})(R^{59})$;

each $R^{20}$ is a substituent attached to the heteroaryl ring and is independently selected at each occurrence from the group consisting of halide, —CN, unsubstituted —$C_{1-6}$ alkyl, unsubstituted —$C_{2-6}$ haloalkyl, —O$R^{34}$, —$SO_2R^{35}$, —($C_{1-3}$ alkyl)$_n$heterocyclyl$(R^{36})_p$, —($C_{1-3}$ alkyl)$_n$aryl $(R^{37})_q$, —C(=O)N$(R^{38})_2$, —NHC(=O)$R^{39}$, and —($C_{1-6}$ alkyl)$_n$N$(R^{40})(R^{41})$;

each $R^{21}$ is a substituent attached to the heteroaryl ring and is independently selected at each occurrence from the group consisting of H, halide, —$C_{1-6}$ haloalkyl, —CN, —$C_{1-6}$ alkyl, —$OR^{34}$, —$SO_2R^{35}$, —$(C_{1-3}$ alkyl$)_n$heterocyclyl$(R^{36})_p$, —$(C_{1-3}$ alkyl$)_n$aryl$(R^{37})_q$, —C(=O)N$(R^{38})_2$, —NHC(=O)$R^{39}$, and —$(C_{1-6}$ alkyl$)_n$N$(R^{40})(R^{41})$;

each $R^{22}$ is a substituent attached to the heterocyclyl ring and is independently selected at each occurrence from the group consisting of H, halide, —$CF_3$, —OH, —$CH_2OH$, —CN, —N$(R^{25})_2$, and —$C_{1-6}$ alkyl;

each $R^{23}$ is a substituent attached to the aryl ring and is independently selected at each occurrence from the group consisting of H, halide, —$CF_3$, —CN, and —$C_{1-6}$ alkyl;

each $R^{24}$ is independently selected at each occurrence from the group consisting of —$C_{1-6}$ alkyl, —N$(R^{60})_2$, and —$(C_{1-3}$ alkyl$)_n$carbocyclyl;

each $R^{25}$ is independently selected at each occurrence from the group consisting of H and —$C_{1-6}$ alkyl, alternatively, two adjacent $R^{25}$ are taken together with the nitrogen atom to which they are attached to form a 3 to 7 membered heterocyclic ring;

each $R^{26}$ is a substituent attached to the heterocyclyl ring and is independently selected at each occurrence from the group consisting of H, halide, —$CF_3$, —OH, —CN, and —$C_{1-6}$ alkyl;

each $R^{27}$ is a substituent attached to the aryl ring and is independently selected at each occurrence from the group consisting of H, halide, —$CF_3$, —CN, and —$C_{1-6}$ alkyl;

each $R^{28}$ is independently selected at each occurrence from the group consisting of —$C_{1-6}$ alkyl, —N$(R^{60})_2$, and —$(C_{1-3}$ alkyl$)_n$carbocyclyl;

each $R^{29}$ is independently selected at each occurrence from the group consisting of H and —$C_{1-6}$ alkyl;

each $R^{30}$ is independently selected at each occurrence from the group consisting of H and —$C_{1-6}$ alkyl;

each $R^{31}$ is a substituent attached to the heterocyclyl ring and is independently selected at each occurrence from the group consisting of H and halide;

each $R^{32}$ is independently selected at each occurrence from the group consisting of —$C_{1-6}$ alkyl and -carbocyclyl;

each $R^{33}$ is independently selected at each occurrence from the group consisting of H and —$C_{2-6}$ alkyl;

each $R^{34}$ is independently selected at each occurrence from the group consisting of H, —$CF_3$, —$C_{1-6}$ alkyl, -heterocyclyl$(R^{61})_p$, and -aryl$(R^{62})_q$;

each $R^{35}$ is independently selected at each occurrence from the group consisting of —$CF_3$ and —$C_{1-6}$ alkyl;

each $R^{36}$ is a substituent attached to the heterocyclyl ring and is independently selected at each occurrence from the group consisting of H, halide, —OH, —$CF_3$, —CN, and —$C_{1-6}$ alkyl;

each $R^{37}$ is a substituent attached to the aryl ring and is independently selected at each occurrence from the group consisting of H, halide, —$CF_3$, —CN, and Me;

each $R^{38}$ is independently selected at each occurrence from the group consisting of H, —$C_{1-6}$ alkyl, and -carbocyclyl, alternatively, two adjacent $R^{38}$ are taken together with the nitrogen atom to which they are attached to form a 3 to 7 membered heterocyclic ring;

each $R^{39}$ is independently selected at each occurrence from the group consisting of —$C_{1-6}$ alkyl and —$(C_{1-3}$ alkyl$)_n$carbocyclyl;

each $R^{40}$ is a substituent attached to the nitrogen and is independently selected at each occurrence from the group consisting of H, unsubstituted —$C_{1-6}$ haloalkyl, and unsubstituted —$C_{1-6}$ alkyl;

each $R^{41}$ is a substituent attached to the nitrogen and is independently selected at each occurrence from the group consisting of H, unsubstituted —$C_{1-6}$ haloalkyl, unsubstituted —$C_{1-6}$ alkyl, and —$(C_{1-6}$ alkyl$)_n$N$(R^{38})_2$;

each $R^{42}$ is independently selected at each occurrence from the group consisting of —$C_{1-6}$ alkyl, —$(C_{1-3}$ alkyl)carbocyclyl, and —$(C_{4-6}$ carbocyclyl);

each $R^{43}$ is independently selected at each occurrence from the group consisting of —$CF_3$, —$C_{3-6}$ alkyl, -heterocyclyl$(R^{61})_p$, and -aryl$(R^{63})_q$;

each $R^{44}$ is a substituent attached to the heterocyclyl ring and is independently selected at each occurrence from the group consisting of H, halide, —OH, —$CF_3$, —CN, and —$C_{1-6}$ alkyl;

each $R^{45}$ is a substituent attached to the aryl ring and is independently selected at each occurrence from the group consisting of Cl, Br, I, —$CF_3$, —CN, and Me;

each $R^{46}$ is a substituent attached to the nitrogen and is independently selected at each occurrence from the group consisting of H and —$C_{2-6}$ alkyl;

each $R^{47}$ is a substituent attached to the nitrogen and is independently selected at each occurrence from the group consisting of H, —$C_{2-6}$ alkyl, and —$(C_{1-6}$ alkyl$)_n$N$(R^{38})_2$;

each $R^{48}$ is independently selected at each occurrence from the group consisting of —$CF_3$, —$C_{2-6}$ alkyl, -heterocyclyl$(R^{61})_p$, and -aryl$(R^{62})_q$;

each $R^{49}$ is independently selected at each occurrence from the group consisting of —$CF_3$, ethyl, and —$C_{4-6}$ alkyl;

each $R^{50}$ is a substituent attached to the heterocyclyl ring and is independently selected at each occurrence from the group consisting of H, halide, —OH, —$CF_3$, —CN, and —$C_{1-6}$ alkyl;

each $R^{51}$ is independently selected at each occurrence from the group consisting of Cl, Br, I, —$CF_3$, —CN, and Me;

each $R^{52}$ is independently selected at each occurrence from the group consisting of Cl, Br, I, —$CF_3$, —CN, and Me;

each $R^{53}$ is independently selected at each occurrence from the group consisting of —$C_{1-4}$ alkyl, cyclopropyl, cyclobutyl, and cyclohexyl, alternatively, two adjacent $R^{53}$ are taken together with the nitrogen atom to which they are attached to form a 3- to 4-membered heterocyclic ring or 6- to 7-membered heterocyclic ring;

each $R^{54}$ is independently selected at each occurrence from the group consisting of —$C_{1-6}$ alkyl, —$(C_{1-3}$ alkyl)carbocyclyl, and —$(C_{4-6}$ carbocyclyl);

each $R^{55}$ is a substituent attached to the nitrogen and is an unsubstituted —$C_{2-6}$ alkyl;

each $R^{56}$ is a substituent attached to the nitrogen and is independently selected at each occurrence from the group consisting of H, unsubstituted —$C_{2-6}$ alkyl, and —$(C_{1-6}$ alkyl$)_n$N$(R^{64})_2$;

each $R^{57}$ is independently selected at each occurrence from the group consisting of H, halide, —OH, —$CF_3$, —CN, and —$C_{2-6}$ alkyl;

each $R^{58}$ is a substituent attached to the nitrogen and is independently selected at each occurrence from the group consisting of H and —$C_{1-6}$ alkyl;

each $R^{59}$ is a substituent attached to the nitrogen and is independently selected at each occurrence from the group consisting of —$C_{1-6}$ alkyl, and —$(C_{1-6}$ alkyl$)_n$N$(R^{38})_2$;

each $R^{60}$ is independently selected at each occurrence from the group consisting of H and —$C_{1-6}$ alkyl, alternatively, two adjacent $R^{60}$ are taken together with the nitrogen atom to which they are attached to form a 3- to 7-membered heterocyclic ring;

each $R^{61}$ is a substituent attached to the heterocyclyl ring and is independently selected at each occurrence from the group consisting of H, halide, —OH, —$CF_3$, —CN, and —$C_{1-6}$ alkyl;

each $R^{62}$ is a substituent attached to the aryl ring and is independently selected at each occurrence from the group consisting of H, halide, —$CF_3$, —CN, and —$C_{1-6}$ alkyl;

each $R^{63}$ is a substituent attached to the aryl ring and is independently selected at each occurrence from the group consisting of H, Cl, Br, I, —$CF_3$, —CN, and —$C_{1-6}$ alkyl;

each $R^{64}$ is independently selected at each occurrence from the group consisting of H and —$C_{2-6}$ alkyl, alternatively, two adjacent $R^{64}$ are taken together with the nitrogen atom to which they are attached to form a 3- to 7-membered heterocyclic ring;

$R^{65}$ is —($C_{1-3}$ alkyl)$_n$heterocyclyl($R^8$)$_p$;

each $R^{68}$ is independently selected at each occurrence from the group consisting of H and unsubstituted —$C_{1-6}$ alkyl;

m is an integer of 1 to 4;

each n is independently an integer of 0 to 1;

each p is independently an integer of 1 to 10;

each q is independently an integer of 1 to 5;

t is an integer of 1 to 4;

y is an integer of 1 to 3; and z is an integer of 1 to 5.

One embodiment disclosed herein includes a compound having the structure of Formula II:

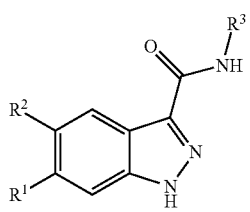

II

In some embodiments of Formula II:

$R^1$ is selected from the group consisting of H, halide, and —$C_{1-3}$ alkyl;

$R^2$ is selected from the group consisting of and;

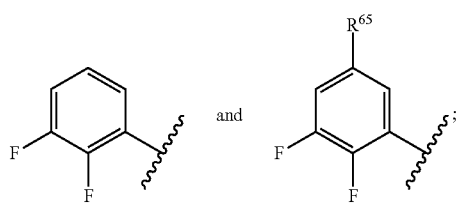

$R^3$ is selected from the group consisting of H, unsubstituted —$C_{1-9}$ alkyl, unsubstituted —$C_{1-9}$ haloalkyl, —($C_{1-6}$ alkyl)N($R^{68}$)$_2$, —($C_{2-6}$ alkyl)O($C_{1-6}$ alkyl), —($C_{1-3}$ alkyl)$_n$carbocyclyl($R^7$)$_p$, -heterocyclyl($R^8$)$_p$, —($C_{1-3}$ alkyl)heterocyclyl($R^9$)$_p$, —($C_{1-3}$ alkyl)$_n$aryl($R^{10}$)$_q$,

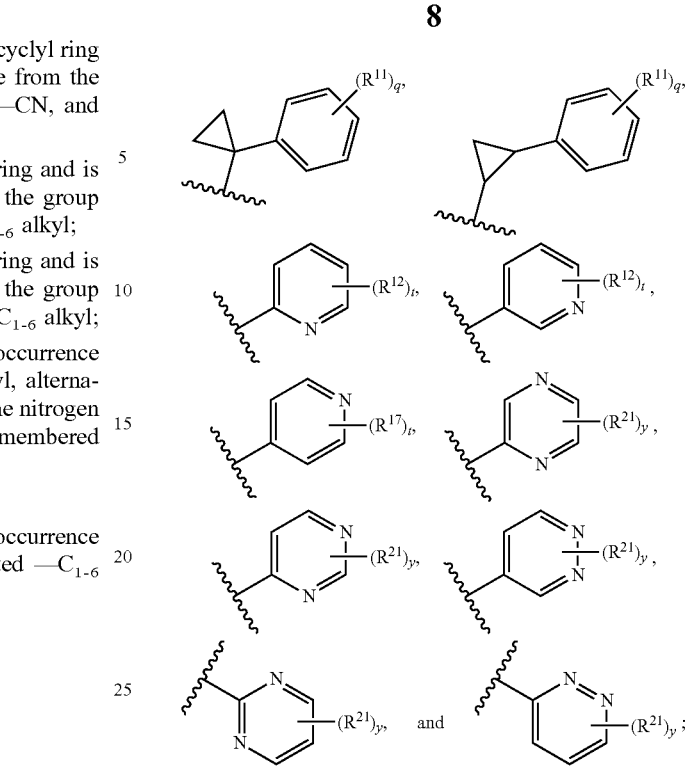

each $R^7$ is a substituent attached to the carbocyclyl ring and is independently selected at each occurrence from the group consisting of H, halide, —$CF_3$, —CN, —N($R^{25}$)$_2$, and —$C_{1-6}$ alkyl;

each $R^8$ is a substituent attached to the heterocyclyl ring and is independently selected at each occurrence from the group consisting of H, halide, —($C_{1-3}$ alkyl)$_n$OR$^{30}$, —($C_{1-3}$ alkyl)carbocyclyl($R^7$)$_p$, —CN, —N($R^{25}$)$_2$, —($C_{1-3}$ alkyl)$_n$aryl($R^{11}$)$_q$, -heterocyclyl($R^{31}$)$_p$, —C(=O)$R^{32}$, unsubstituted —$C_{1-6}$ haloalkyl, and unsubstituted —$C_{1-6}$ alkyl;

each $R^9$ is a substituent attached to the heterocyclyl ring and is independently selected at each occurrence from the group consisting of H, halide, —($C_{1-3}$ alkyl)$_n$OR$^{33}$, —($C_{1-3}$ alkyl)carbocyclyl($R^7$)$_p$, —CN, —($C_{1-3}$ alkyl)$_n$aryl($R^{11}$)$_q$, -heterocyclyl($R^{31}$)$_p$, —C(=O)$R^{32}$, unsubstituted —$C_{1-6}$ haloalkyl, and unsubstituted —$C_{1-6}$ alkyl;

each $R^{10}$ is a substituent attached to the aryl ring and is independently selected at each occurrence from the group consisting of H, halide, unsubstituted —$C_{1-6}$ haloalkyl, —CN, —($C_{1-3}$ alkyl)$_n$heterocyclyl($R^{31}$)$_p$, —($C_{1-6}$ alkyl)$_n$N($R^{40}$)($R^{41}$), and unsubstituted —$C_{1-6}$ alkyl;

each $R^{11}$ is a substituent attached to the aryl ring and is independently selected at each occurrence from the group consisting of H, halide, —$C_{1-6}$ haloalkyl, —CN, and —$C_{1-6}$ alkyl;

each $R^{12}$ is a substituent attached to the pyridinyl ring and is independently selected at each occurrence from the group consisting of H, halide, —$C_{1-6}$ haloalkyl, —CN, —$C_{1-6}$ alkyl, —OR$^{34}$, —SO$_2$R$^{35}$, —($C_{1-3}$ alkyl)$_n$heterocyclyl ($R^{36}$)$_p$, —($C_{1-3}$ alkyl)$_n$aryl($R^{37}$)$_q$, —C(=O)N($R^{38}$)$_2$, —NHC(=O)$R^{39}$, and —($C_{1-6}$ alkyl)$_n$N($R^{40}$)($R^{41}$);

each $R^{17}$ is a substituent attached to the pyridinyl ring and is independently selected at each occurrence from the group consisting of halide, —$C_{1-6}$ haloalkyl, —CN, —$C_{1-6}$ alkyl, —OR$^{34}$, —SO$_2$R$^{35}$, —($C_{1-3}$ alkyl)$_n$heterocyclyl($R^{36}$)$_p$, —($C_{1-3}$ alkyl)$_n$aryl($R^{37}$)$_q$, —C(=O)N($R^{38}$)$_2$, —NHC(=O)$R^{39}$, and —($C_{1-6}$ alkyl)$_n$N($R^{40}$)($R^{41}$);

each R²¹ is a substituent attached to the heteroaryl ring and is independently selected at each occurrence from the group consisting of H, halide, —C$_{1-6}$ haloalkyl, —CN, —C$_{1-6}$ alkyl, —OR³⁴, —SO$_2$R³⁵, —(C$_{1-3}$ alkyl)$_n$heterocyclyl(R³⁶)$_p$, —(C$_{1-3}$ alkyl)$_n$aryl(R³⁷)$_q$, —C(=O)N(R³⁸)$_2$, —NHC(=O)R³⁹, and —(C$_{1-6}$ alkyl)$_n$N(R⁴⁰)(R⁴¹);

each R²⁵ is independently selected at each occurrence from the group consisting of H and —C$_{1-6}$ alkyl, alternatively, two adjacent R²⁵ are taken together with the nitrogen atom to which they are attached to form a 3 to 7 membered heterocyclic ring;

each R³⁰ is independently selected at each occurrence from the group consisting of H and —C$_{1-6}$ alkyl;

each R³¹ is a substituent attached to the heterocyclyl ring and is independently selected at each occurrence from the group consisting of H, halide, —C$_{1-6}$ alkyl, and —C$_{1-6}$ haloalkyl;

each R³² is independently selected at each occurrence from the group consisting of —C$_{1-6}$ alkyl and -carbocyclyl;

each R³³ is independently selected at each occurrence from the group consisting of H and —C$_{2-6}$ alkyl;

each R³⁴ is independently selected at each occurrence from the group consisting of H, —CF$_3$, —C$_{1-6}$ alkyl, -heterocyclyl(R⁶¹)$_p$, and -aryl(R⁶²)$_q$;

each R³⁵ is independently selected at each occurrence from the group consisting of —CF$_3$ and —C$_{1-6}$ alkyl;

each R³⁶ is a substituent attached to the heterocyclyl ring and is independently selected at each occurrence from the group consisting of H, halide, —OH, —CF$_3$, —CN, and —C$_{1-6}$ alkyl;

each R³⁷ is a substituent attached to the aryl ring and is independently selected at each occurrence from the group consisting of H, halide, —CF$_3$, —CN, and Me;

each R³⁸ is independently selected at each occurrence from the group consisting of H, —C$_{1-6}$ alkyl, and -carbocyclyl, alternatively, two adjacent R³⁸ are taken together with the nitrogen atom to which they are attached to form a 3 to 7 membered heterocyclic ring;

each R³⁹ is independently selected at each occurrence from the group consisting of —C$_{1-6}$ alkyl and —(C$_{1-3}$ alkyl)$_n$carbocyclyl;

each R⁴⁰ is a substituent attached to the nitrogen and is independently selected at each occurrence from the group consisting of H, unsubstituted —C$_{1-6}$ haloalkyl, and unsubstituted —C$_{1-6}$ alkyl;

each R⁴¹ is a substituent attached to the nitrogen and is independently selected at each occurrence from the group consisting of H, unsubstituted —C$_{1-6}$ haloalkyl, unsubstituted —C$_{1-6}$ alkyl, and —(C$_{1-6}$ alkyl)$_n$N(R³⁸)$_2$;

each R⁶¹ is a substituent attached to the heterocyclyl ring and is independently selected at each occurrence from the group consisting of H, halide, —OH, —CF$_3$, —CN, and —C$_{1-6}$ alkyl;

each R⁶² is a substituent attached to the aryl ring and is independently selected at each occurrence from the group consisting of H, halide, —CF$_3$, —CN, and —C$_{1-6}$ alkyl;

R⁶⁵ is —(C$_{1-3}$ alkyl)$_n$heterocyclyl(R⁸)$_p$;

each R⁶⁸ is independently selected at each occurrence from the group consisting of H and unsubstituted —C$_{1-6}$ alkyl;

each n is independently an integer of 0 to 1;
each p is independently an integer of 1 to 10;
each q is independently an integer of 1 to 5;
t is an integer of 1 to 4; and
y is an integer of 1 to 3.

One embodiment disclosed herein includes a compound having the structure of Formula III:

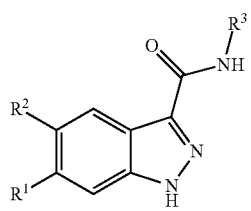

In some embodiments of Formula III:

R¹ is selected from the group consisting of H, halide, and —C$_{1-3}$ alkyl;

R² is a 6-10-membered heteroaryl(R⁴);

R³ is selected from the group consisting of H, unsubstituted —C$_{1-9}$ alkyl, unsubstituted —C$_{1-9}$ haloalkyl, —(C$_{1-6}$ alkyl)N(R⁶)$_2$, —(C$_{2-6}$ alkyl)O(C$_{1-6}$ alkyl), —(C$_{1-3}$ alkyl)$_n$carbocyclyl(R⁷)$_p$, —(C$_{1-3}$ alkyl)$_n$heterocyclyl(R⁸)$_p$, —(C$_{1-3}$ alkyl)$_n$aryl(R¹⁰)$_q$,

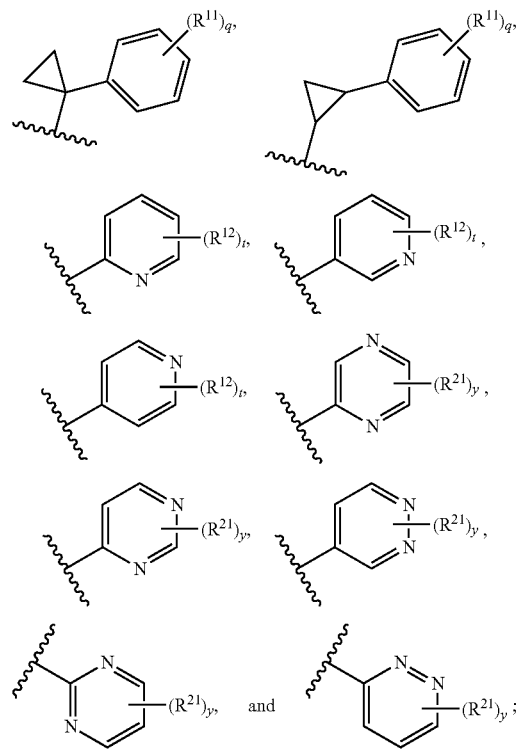

R⁴ is selected from the group consisting of

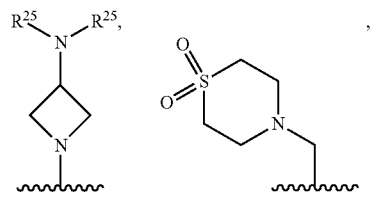

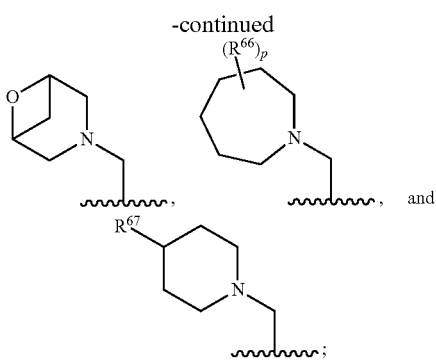

each $R^7$ is a substituent attached to the carbocyclyl ring and is independently selected at each occurrence from the group consisting of H, halide, —$CF_3$, —CN, —$N(R^{25})_2$, and —$C_{1-6}$ alkyl;

each $R^8$ is a substituent attached to the heterocyclyl ring and is independently selected at each occurrence from the group consisting of H, halide, —$(C_{1-3}$ alkyl$)_n OR^{30}$, —$(C_{1-3}$ alkyl)carbocyclyl$(R^7)_p$, —CN, —$N(R^{25})_2$, —$(C_{1-3}$ alkyl$)_n$aryl$(R^{11})_q$, -heterocyclyl$(R^{31})_p$, —C(=O)$R^{32}$, unsubstituted —$C_{1-6}$ haloalkyl, and unsubstituted —$C_{1-6}$ alkyl;

each $R^{10}$ is a substituent attached to the aryl ring and is independently selected at each occurrence from the group consisting of H, halide, unsubstituted —$C_{1-6}$ haloalkyl, —CN, —$(C_{1-3}$ alkyl$)_n$heterocyclyl$(R^{31})_p$, —$(C_{1-6}$ alkyl$)_n N(R^{40})(R^{41})$, and unsubstituted —$C_{1-6}$ alkyl;

each $R^{11}$ is a substituent attached to the aryl ring and is independently selected at each occurrence from the group consisting of H, halide, —$C_{1-6}$ haloalkyl, —CN, and —$C_{1-6}$ alkyl;

each $R^{12}$ is a substituent attached to the pyridinyl ring and is independently selected at each occurrence from the group consisting of H, halide, —$C_{1-6}$ haloalkyl, —CN, —$C_{1-6}$ alkyl, —$OR^{34}$, —$SO_2 R^{35}$, —$(C_{1-3}$ alkyl$)_n$heterocyclyl$(R^{36})_p$, —$(C_{1-3}$ alkyl$)_n$aryl$(R^{37})_q$, —C(=O)$N(R^{38})_2$, —NHC(=O)$R^{39}$, and —$(C_{1-6}$ alkyl$)_n N(R^{40})(R^{41})$;

each $R^{21}$ is a substituent attached to the heteroaryl ring and is independently selected at each occurrence from the group consisting of H, halide, —$C_{1-6}$ haloalkyl, —CN, —$C_{1-6}$ alkyl, —$OR^{34}$, —$SO_2 R^{35}$, —$(C_{1-3}$ alkyl$)_n$heterocyclyl$(R^{36})_p$, —$(C_{1-3}$ alkyl$)_n$aryl$(R^{37})_q$, —C(=O)$N(R^{38})_2$, —NHC(=O)$R^{39}$, and —$(C_{1-6}$ alkyl$)_n N(R^{40})(R^{41})$;

each $R^{25}$ is independently selected at each occurrence from the group consisting of H and —$C_{1-6}$ alkyl, alternatively, two adjacent $R^{25}$ are taken together with the nitrogen atom to which they are attached to form a 3 to 7 membered heterocyclic ring;

each $R^{30}$ is independently selected at each occurrence from the group consisting of H and —$C_{1-6}$ alkyl;

each $R^{31}$ is a substituent attached to the heterocyclyl ring and is independently selected at each occurrence from the group consisting of H, halide, —$C_{1-6}$ alkyl, and —$C_{1-6}$ haloalkyl;

each $R^{32}$ is independently selected at each occurrence from the group consisting of —$C_{1-6}$ alkyl and -carbocyclyl;

each $R^{34}$ is independently selected at each occurrence from the group consisting of H, —$CF_3$, —$C_{1-6}$ alkyl, -heterocyclyl$(R^{61})_p$, and -aryl$(R^{62})_q$;

each $R^{35}$ is independently selected at each occurrence from the group consisting of —$CF_3$ and —$C_{1-6}$ alkyl;

each $R^{36}$ is a substituent attached to the heterocyclyl ring and is independently selected at each occurrence from the group consisting of H, halide, —OH, —$CF_3$, —CN, and —$C_{1-6}$ alkyl;

each $R^{37}$ is a substituent attached to the aryl ring and is independently selected at each occurrence from the group consisting of H, halide, —$CF_3$, —CN, and Me;

each $R^{38}$ is independently selected at each occurrence from the group consisting of H, —$C_{1-6}$ alkyl, and -carbocyclyl, alternatively, two adjacent $R^{38}$ are taken together with the nitrogen atom to which they are attached to form a 3 to 7 membered heterocyclic ring;

each $R^{39}$ is independently selected at each occurrence from the group consisting of —$C_{1-6}$ alkyl and —$(C_{1-3}$ alkyl$)_n$carbocyclyl;

each $R^{40}$ is a substituent attached to the nitrogen and is independently selected at each occurrence from the group consisting of H, unsubstituted —$C_{1-6}$ haloalkyl, and unsubstituted —$C_{1-6}$ alkyl;

each $R^{41}$ is a substituent attached to the nitrogen and is independently selected at each occurrence from the group consisting of H, unsubstituted —$C_{1-6}$ haloalkyl, unsubstituted —$C_{1-6}$ alkyl, and —$(C_{1-6}$ alkyl$)_n N(R^{38})_2$;

each $R^{61}$ is a substituent attached to the heterocyclyl ring and is independently selected at each occurrence from the group consisting of H, halide, —OH, —$CF_3$, —CN, and —$C_{1-6}$ alkyl;

each $R^{62}$ is a substituent attached to the aryl ring and is independently selected at each occurrence from the group consisting of H, halide, —$CF_3$, —CN, and —$C_{1-6}$ alkyl;

each $R^{66}$ is a substituent attached to a carbon on the ring and is independently selected at each occurrence from the group consisting of H, halide, —$C_{1-6}$ haloalkyl, —CN, and —$C_{1-6}$ alkyl;

$R^{67}$ is selected from the group consisting of —$C_{1-6}$ haloalkyl and —$C_{1-6}$ alkyl;

each $R^{68}$ is independently selected at each occurrence from the group consisting of H and unsubstituted —$C_{1-6}$ alkyl;

each n is independently an integer of 0 to 1;
each p is independently an integer of 1 to 10;
each q is independently an integer of 1 to 5;
t is an integer of 1 to 4; and
y is an integer of 1 to 3.

One embodiment disclosed herein includes a compound having the structure of Formula IV:

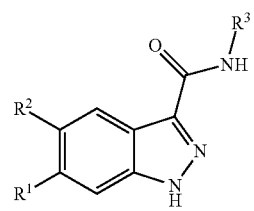

IV

In some embodiments of Formula IV:

$R^1$ is selected from the group consisting of H, halide, and —$C_{1-3}$ alkyl;

$R^2$ is selected from the group consisting of 6-10-membered heteroaryl$(R^4)$;

$R^3$ is selected from the group consisting of H, unsubstituted —$C_{1-9}$ alkyl, unsubstituted —$C_{1-9}$ haloalkyl, —$(C_{1-6}$ alkyl)$N(R^{68})_2$, —$(C_{2-6}$ alkyl)$O(C_{1-6}$ alkyl), -carbocyclyl$(R^7)_p$, —$(C_{1-3}$ alkyl$)_n$heterocyclyl$(R^9)_p$, —$(C_{1-3}$ alkyl)aryl$(R^{10})_q$,

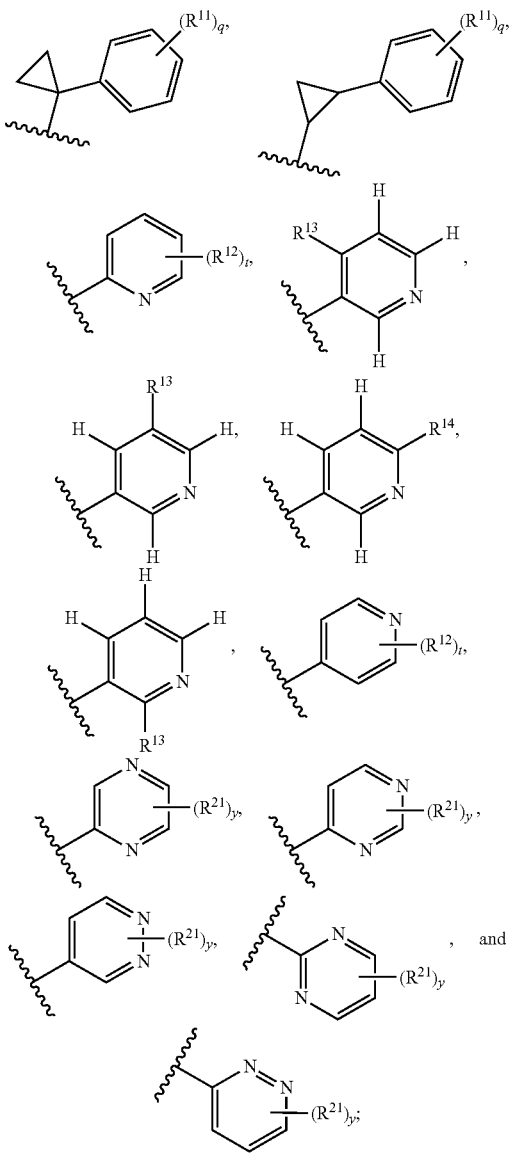

R[4] is selected from the group consisting of F and unsubstituted —C$_{1-6}$ alkyl;

each R[7] is a substituent attached to the carbocyclyl ring and is independently selected at each occurrence from the group consisting of H, halide, —CF$_3$, —CN, —N(R[25])$_2$, and —C$_{1-6}$ alkyl;

each R[9] is a substituent attached to the heterocyclyl ring and is independently selected at each occurrence from the group consisting of H, halide, —(C$_{1-3}$ alkyl)$_n$OR[33], —CN, -heterocyclyl(R[31])$_p$, —C(=O)R[32], unsubstituted —C$_{1-6}$ haloalkyl, and unsubstituted —C$_{1-6}$ alkyl;

each R[10] is a substituent attached to the aryl ring and is independently selected at each occurrence from the group consisting of H, Cl, Br, I, unsubstituted —C$_{1-6}$ haloalkyl, —CN, —(C$_{1-3}$ alkyl)$_n$heterocyclyl(R[31])$_p$, —(C$_{1-6}$ alkyl)$_n$N(R[40])(R[41]), and unsubstituted —C$_{1-6}$ alkyl;

each R[11] is a substituent attached to the aryl ring and is independently selected at each occurrence from the group consisting of H, halide, —C$_{1-6}$ haloalkyl, —CN, and —C$_{1-6}$ alkyl;

each R[12] is a substituent attached to the pyridinyl ring and is independently selected at each occurrence from the group consisting of H, halide, —C$_{1-6}$ haloalkyl, —CN, —C$_{1-6}$ alkyl, —OR[34], —SO$_2$R[35], —(C$_{1-3}$ alkyl)$_n$heterocyclyl(R[36])$_p$, —(C$_{1-3}$ alkyl)$_n$aryl(R[37])$_q$, —C(=O)N(R[38])$_2$, —NHC(=O)R[39], and —(C$_{1-6}$ alkyl)$_n$N(R[40])(R[41]);

R[13] is selected from the group consisting of halide, —C$_{1-6}$ haloalkyl, —CN, —C$_{1-6}$ alkyl, —OR[34], —SO$_2$R[35], —(C$_{1-3}$ alkyl)$_n$heterocyclyl(R[36])$_p$, —(C$_{1-3}$ alkyl)$_n$aryl(R[37])$_q$, —C(=O)N(R[38])$_2$, —NHC(=O)R[39], and —(C$_{1-6}$ alkyl)$_n$N(R[40])(R[41]);

R[14] is selected from the group consisting of halide, —C$_{2-6}$ haloalkyl, —CN, —C$_{1-6}$ alkyl, —OR[34], —SO$_2$R[35], —(C$_{1-3}$ alkyl)$_n$heterocyclyl(R[36])$_p$, —(C$_{1-3}$ alkyl)$_n$aryl(R[37])$_q$, —C(=O)N(R[38])$_2$, —NHC(=O)R[39], and —(C$_{1-6}$ alkyl)$_n$N(R[40])(R[41]);

each R[21] is a substituent attached to the heteroaryl ring and is independently selected at each occurrence from the group consisting of H, halide, —C$_{1-6}$ haloalkyl, —CN, —C$_{1-6}$ alkyl, —OR[34], —SO$_2$R[35], —(C$_{1-3}$ alkyl)$_n$heterocyclyl(R[36])$_p$, —(C$_{1-3}$ alkyl)$_n$aryl(R[37])$_q$, —C(=O)N(R[38])$_2$, —NHC(=O)R[39], and —(C$_{1-6}$ alkyl)$_n$N(R[40])(R[41]);

each R[25] is independently selected at each occurrence from the group consisting of H and —C$_{1-6}$ alkyl, alternatively, two adjacent R[25] are taken together with the nitrogen atom to which they are attached to form a 3 to 7 membered heterocyclic ring;

each R[31] is a substituent attached to the heterocyclyl ring and is independently selected at each occurrence from the group consisting of H and halide;

each R[32] is independently selected at each occurrence from the group consisting of —C$_{1-6}$ alkyl and -carbocyclyl;

each R[33] is independently selected at each occurrence from the group consisting of H and —C$_{2-6}$ alkyl;

each R[34] is independently selected at each occurrence from the group consisting of H, —CF$_3$, —C$_{1-6}$ alkyl, -heterocyclyl(R[61])$_p$, and -aryl(R[62])$_q$;

each R[35] is independently selected at each occurrence from the group consisting of —CF$_3$ and —C$_{1-6}$ alkyl;

each R[36] is a substituent attached to the heterocyclyl ring and is independently selected at each occurrence from the group consisting of H, halide, —OH, —CF$_3$, —CN, and —C$_{1-6}$ alkyl;

each R[37] is a substituent attached to the aryl ring and is independently selected at each occurrence from the group consisting of H, halide, —CF$_3$, —CN, and Me;

each R[38] is independently selected at each occurrence from the group consisting of H, —C$_{1-6}$ alkyl, and -carbocyclyl, alternatively, two adjacent R[38] are taken together with the nitrogen atom to which they are attached to form a 3 to 7 membered heterocyclic ring;

each R[39] is independently selected at each occurrence from the group consisting of —C$_{1-6}$ alkyl and —(C$_{1-3}$ alkyl)$_n$carbocyclyl;

each R[40] is a substituent attached to the nitrogen and is independently selected at each occurrence from the group consisting of H, unsubstituted —C$_{1-6}$ haloalkyl, and unsubstituted —C$_{1-6}$ alkyl;

each R[41] is a substituent attached to the nitrogen and is independently selected at each occurrence from the group consisting of H, unsubstituted —C$_{1-6}$ haloalkyl, unsubstituted —C$_{1-6}$ alkyl, and —(C$_{1-6}$ alkyl)$_n$N(R[38])$_2$;

each R[61] is a substituent attached to the heterocyclyl ring and is independently selected at each occurrence from the group consisting of H, halide, —OH, —CF$_3$, —CN, and —C$_{1-6}$ alkyl;

each R[62] is a substituent attached to the aryl ring and is independently selected at each occurrence from the group consisting of H, halide, —CF$_3$, —CN, and —C$_{1-6}$ alkyl;

each $R^{68}$ is independently selected at each occurrence from the group consisting of H and unsubstituted —$C_{1-6}$ alkyl;

each n is independently an integer of 0 to 1;
each p is independently an integer of 1 to 10;
each q is independently an integer of 1 to 5;
t is an integer of 1 to 4; and
y is an integer of 1 to 3.

One embodiment disclosed herein includes a compound having the structure of Formula V:

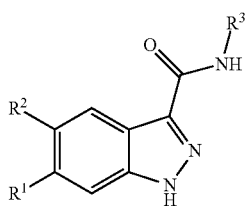

V

In some embodiments of Formula V:

$R^1$ is selected from the group consisting of H, halide, and $C_{1-3}$ alkyl;

$R^2$ is selected from the group consisting of 6-10-membered heteroaryl($R^4$) and phenyl($R^5$)$_m$($R^6$);

$R^3$ is selected from the group consisting of

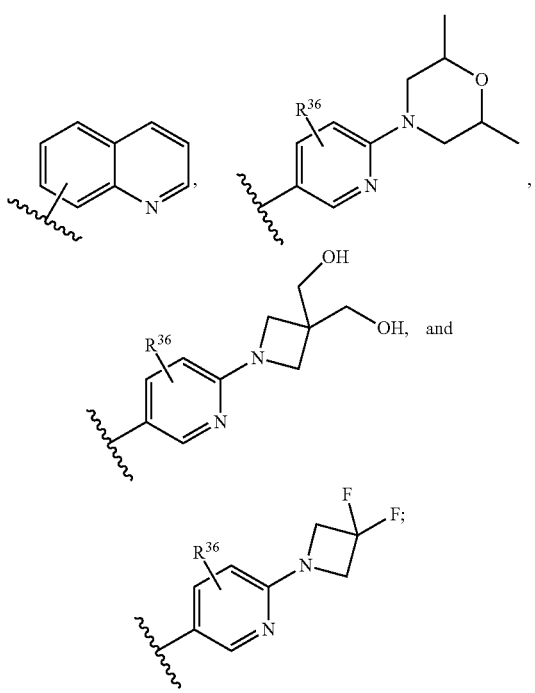

$R^4$ is 1 substituent attached to the 6-10-membered heteroaryl and is selected from the group consisting of H, halide —CN, unsubstituted —$C_{1-6}$ haloalkyl, unsubstituted —$C_{1-6}$ alkyl, —($C_{1-3}$ alkyl)$_n$heterocyclyl($R^{22}$)$_p$, —O-aryl($R^{23}$)$_q$, —NHC(=O)$R^{24}$, and —($C_{1-6}$ alkyl)$_n$N($R^{25}$)$_2$;

each $R^5$ is a substituent attached to the phenyl ring and independently selected at each occurrence from the group consisting of H and halide;

$R^6$ is 1 substituent attached to the phenyl ring and selected from the group consisting of H, —($C_{1-3}$ alkyl)$_n$heterocyclyl ($R^{26}$), —O-aryl($R^{27}$)$_q$, —NHC(=O)$R^{28}$, and —(CH$_2$)$_z$N ($R^{29}$)$_2$;

each $R^{22}$ is a substituent attached to the heterocyclyl ring and is independently selected at each occurrence from the group consisting of H, halide, —CF$_3$, —OH, —CH$_2$OH, —CN, —N($R^{25}$)$_2$, and —$C_{1-6}$ alkyl;

each $R^{23}$ is a substituent attached to the aryl ring and is independently selected at each occurrence from the group consisting of H, halide, —CF$_3$, —CN, and —$C_{1-6}$ alkyl;

each $R^{24}$ is independently selected at each occurrence from the group consisting of —$C_{1-6}$ alkyl, —N($R^{60}$)$_2$, and —($C_{1-3}$ alkyl)$_n$carbocyclyl;

each $R^{25}$ is independently selected at each occurrence from the group consisting of H and —$C_{1-6}$ alkyl, alternatively, two adjacent $R^{25}$ are taken together with the nitrogen atom to which they are attached to form a 3 to 7 membered heterocyclic ring;

each $R^{26}$ is a substituent attached to the heterocyclyl ring and is independently selected at each occurrence from the group consisting of H, halide, —CF$_3$, —OH, —CN, and —$C_{1-6}$ alkyl;

each $R^{27}$ is a substituent attached to the aryl ring and is independently selected at each occurrence from the group consisting of H, halide, —CF$_3$, —CN, and —$C_{1-6}$ alkyl;

each $R^{28}$ is independently selected at each occurrence from the group consisting of —$C_{1-6}$ alkyl, —N($R^{60}$)$_2$, and —($C_{1-3}$ alkyl)$_n$carbocyclyl;

each $R^{29}$ is independently selected at each occurrence from the group consisting of H and —$C_{1-6}$ alkyl;

each $R^{36}$ is a substituent attached to the heterocyclyl ring and is independently selected at each occurrence from the group consisting of H, halide, —OH, —CF$_3$, —CN, and —$C_{1-6}$ alkyl;

each $R^{60}$ is independently selected at each occurrence from the group consisting of H and —$C_{1-6}$ alkyl, alternatively, two adjacent $R^{60}$ are taken together with the nitrogen atom to which they are attached to form a 3- to 7-membered heterocyclic ring;

m is an integer of 1 to 4;
each n is independently an integer of 0 to 1;
each p is independently an integer of 1 to 10; and
each q is independently an integer of 1 to 5.

Some embodiments include stereoisomers and pharmaceutically acceptable salts of a compound of Formulas I, II, III, IV, and V.

Some embodiments include pro-drugs of a compound of Formulas I, II, III, IV, and V.

Some embodiments of the present disclosure include pharmaceutical compositions comprising a compound of Formulas I, II, III, IV, and V and a pharmaceutically acceptable carrier, diluent, or excipient.

Other embodiments disclosed herein include methods of inhibiting one or more members of the Wnt pathway, including one or more Wnt proteins by administering to a patient affected by a disorder or disease in which aberrant Wnt signaling is implicated, such as cancer and other diseases associated with abnormal angiogenesis, cellular proliferation, cell cycling and mutations in Wnt signaling components, a compound according to Formulas I, II, III, IV, and V. Accordingly, the compounds and compositions provided herein can be used to treat cancer, to reduce or inhibit angiogenesis, to reduce or inhibit cellular proliferation and correct a genetic disorder due to mutations in Wnt signaling components.

Other embodiments disclosed herein include methods of inhibiting DYRK1A by administering to a patient affected by a disorder or disease in which DYRK1A overexpression is implicated, such as Alzheimer's Disease, Amyotrophic Lateral Sclerosis, Down Syndrome, Frontotemporal Dementia with Parkinsonism-17 (FTDP-17), Lewy body dementia, Parkinson's Disease, Pick's Disease, and additional diseases with pronounced neurodegeneration such as Autism, Dementia, Epilepsy, Huntington's Disease, Multiple Sclerosis; diseases and disorders associated with acquired brain injury such as Chronic Traumatic Encephalopathy, Traumatic Brain Injury, Tumor and Stroke.

Additional non-limiting examples of diseases which can be treated with the compounds and compositions provided herein include a variety of cancers, chronic inflammation, diabetic retinopathy, pulmonary fibrosis, rheumatoid arthritis, sepsis, anklyosing spondylitism, psoriasis, scleroderma, mycotic and viral infections, osteochondrodysplasia, lung disease, osteoarthritis, articular cartilage (chondral) defects, degenerative disc disease (or intervertebral disc degeneration), polyposis coli, osteoporosis-pseudoglioma syndrome, familial exudative vitreoretinopathy, retinal angiogenesis, early coronary disease, tetra-amelia syndrome, Müllerian-duct regression and virilization, SERKAL syndrome, diabetes mellitus type 2, Fuhrmann syndrome, Al-Awadi/Raas-Rothschild/Schinzel phocomelia syndrome, odonto-onycho-dermal dysplasia, obesity, split-hand/foot malformation, caudal duplication syndrome, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman syndrome, Prader-Willi syndrome, Beckwith-Wiedemann Syndrome, Norrie disease, and Rett syndrome.

Some embodiments of the present disclosure include methods to prepare compounds of Formulas I, II, III, IV, and V.

It is to be understood that both the foregoing general description and the following detailed description are exemplary and explanatory only and are not restrictive of the invention, as claimed.

DETAILED DESCRIPTION OF THE DRAWINGS

The FIGURE is a line graph showing the assay plot of a chondrogenesis assay performed using various compounds provided herein as compared to a TGF-β3 positive control.

DETAILED DESCRIPTION

Compositions and methods for inhibiting one or more members of the Wnt pathway, including one or more Wnt proteins are useful.

Compositions and methods for inhibiting DYRK1A are useful.

Some embodiments provided herein relate to a method for treating a disease including, but not limited to, neurological diseases or disorders, cancers, chronic inflammation, diabetic retinopathy, pulmonary fibrosis, rheumatoid arthritis, sepsis, anklyosing spondylitism, psoriasis, scleroderma, mycotic and viral infections, bone and cartilage diseases, lung disease, osteoarthritis, articular cartilage (chondral) defects, degenerative disc disease (or intervertebral disc degeneration), polyposis coli, bone density and vascular defects in the eye (Osteoporosis-pseudoglioma Syndrome, OPPG), familial exudative vitreoretinopathy, retinal angiogenesis, early coronary disease, tetra-amelia, Müllerian-duct regression and virilization, SERKAL syndrome, type II diabetes, Fuhrmann syndrome, Al-Awadi/Raas-Rothschild/Schinzel phocomelia syndrome, odonto-onycho-dermal dysplasia, obesity, split-hand/foot malformation, caudal duplication, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman's syndrome, Prader-Willi syndrome, Beckwith-Wiedemann Syndrome, Norrie disease, and Rett syndrome.

In some embodiments, non-limiting examples of bone and cartilage diseases which can be treated with the compounds and compositions provided herein include bone spur (osteophytes), craniosynostosis, fibrodysplasia ossificans progressive, fibrous dysplasia, giant cell tumor of bone, hip labral tear, meniscal tears, osteoarthritis, articular cartilage (chondral) defects, degenerative disc disease (or intervertebral disc degeneration), osteochondritis dissecans, osteochondroma (bone tumor), osteopetrosis, relapsing polychondritis, and Salter-Harris fractures.

In some embodiments, non-limiting examples of a neurological disease or disorder associated with tau protein, amyloid or alpha-synuclein pathology which can be treated with the compounds and compositions provided herein include, but are not limited to, Alzheimer's Disease, Amyotrophic Lateral Sclerosis, Down Syndrome, Frontotemporal Dementia with Parkinsonism-17 (FTDP-17), Lewy body dementia, Parkinson's Disease, Pick's Disease, and additional diseases with pronounced neurodegeneration such as Autism, Dementia, Epilepsy, Huntington's Disease, Multiple Sclerosis; diseases and disorders associated with acquired brain injury such as Chronic Traumatic Encephalopathy, Traumatic Brain Injury, Tumor, and Stroke.

In some embodiments, non-limiting examples of diseases in which chronic inflammation is involved which can be treated with the compounds and compositions provided herein include eye disorders, joint pain, arthritis (rheumatoid, osteo, psoriatic gout), cancers (colon, breast, lung, pancreas, and others), gastrointestinal disorders (ulcerative colitis and inflammatory bowel diseases), pulmonary disorders (chronic obstructive pulmonary disorder and asthma), allergies, skin disorders (atopic dermatitis and psoriasis), diabetes, pancreatitis, tendonitis, hepatitis, heart disease, myocarditis, stroke, lupus, and neurological disorders such as multiple sclerosis, Parkinson's and dementia including Alzheimer's disease.

In some embodiments, non-limiting examples of cancers which can be treated with the compounds and compositions provided herein include colon, ovarian, pancreatic, breast, liver, prostate, and hematologic cancers.

In some embodiments, pharmaceutical compositions are provided that are effective for treatment of a disease of an animal, e.g., a mammal, caused by either the pathological activation or mutations of the Wnt pathway or DYRK1A overexpression. The composition includes a pharmaceutically acceptable carrier and a compound as described herein.

DEFINITIONS

Unless defined otherwise, all technical and scientific terms used herein have the same meaning as is commonly understood by one of ordinary skill in the art to which this disclosure belongs. All patents, applications, published applications, and other publications are incorporated by reference in their entirety. In the event that there is a plurality of definitions for a term herein, those in this section prevail unless stated otherwise.

As used herein, "alkyl" means a branched, or straight chain chemical group containing only carbon and hydrogen, such as methyl, ethyl, n-propyl, iso-propyl, n-butyl, iso-butyl, sec-butyl, tert-butyl, n-pentyl, iso-pentyl, sec-pentyl and neo-pentyl. Alkyl groups can either be unsubstituted or substituted with one or more substituents. Alkyl groups can be saturated or unsaturated (e.g., containing —C=C— or —C≡C— subunits), at one or several positions. Typically, alkyl groups will comprise 1 to 9 carbon atoms (for example, 1 to 6 carbon atoms, 1 to 4 carbon atoms, or 1 to 2 carbon atoms).

As used herein, "carbocyclyl" means a cyclic ring system containing only carbon atoms in the ring system backbone, such as cyclopropyl, cyclobutyl, cyclopentyl, cyclohexyl, and cyclohexenyl. Carbocyclyls may include multiple fused rings. Carbocyclyls may have any degree of saturation provided that at least one ring in the ring system is not aromatic. Carbocyclyl groups can either be unsubstituted or substituted with one or more substituents. Typically, carbocyclyl groups will comprise 3 to 10 carbon atoms, for example, 3 to 6 carbon atoms.

As used herein, "lower alkyl" means a subset of alkyl having 1 to 3 carbon atoms, which is linear or branched. Examples of lower alkyls include methyl, ethyl, n-propyl and isopropyl. Likewise, radicals using the terminology "lower" refer to radicals having 1 to about 3 carbons in the alkyl portion of the radical.

As used herein, "aryl" means an aromatic ring system containing a single-ring (e.g., phenyl) or multiple condensed rings (e.g., naphthyl or anthryl) with only carbon atoms present in the ring backbone. Aryl groups can either be unsubstituted or substituted with one or more substituents. In some embodiments, the aryl is phenyl.

As used herein, "arylalkyl" means an aryl-alkyl-group in which the aryl and alkyl moieties are as previously described. Preferred arylalkyl groups contain a $C_{1-4}$alkyl moiety. Exemplary arylalkyl groups include benzyl and 2-phenethyl.

As used herein, the term "heteroaryl" means a mono-, bi-, tri- or polycyclic group having 5 to 14 ring atoms, alternatively 5, 6, 9, or 10 ring atoms; having 6, 10, or 14 pi electrons shared in a cyclic array; wherein at least one ring in the system is aromatic, and at least one ring in the system contains one or more heteroatoms independently selected from the group consisting of N, O, and S. Heteroaryl groups can either be unsubstituted or substituted with one or more substituents. Examples of heteroaryls include thienyl, pyridinyl, furyl, oxazolyl, oxadiazolyl, pyrrolyl, imidazolyl, triazolyl, thiodiazolyl, pyrazolyl, isoxazolyl, thiadiazolyl, pyranyl, pyrazinyl, pyrimidinyl, pyridazinyl, triazinyl, thiazolyl benzothienyl, benzoxadiazolyl, benzofuranyl, benzimidazolyl, benzotriazolyl, cinnolinyl, indazolyl, indolyl, isoquinolinyl, isothiazolyl, naphthyridinyl, purinyl, thienopyridinyl, pyrido[2,3-d]pyrimidinyl, pyrrolo[2,3-b]pyridinyl, quinazolinyl, quinolinyl, thieno[2,3-c]pyridinyl, pyrazolo[3,4-b]pyridinyl, pyrazolo[3,4-c]pyridinyl, pyrazolo[4,3-c]pyridine, pyrazolo[4,3-b]pyridinyl, tetrazolyl, chromane, 2,3-dihydrobenzo[b][1,4]dioxine, benzo[d][1,3]dioxole, 2,3-dihydrobenzofuran, 2,3-dihydrobenzo[b][1,4]oxathiine, and others.

As used herein, "heteroarylalkyl" means a heteroaryl-alkyl-group in which the heteroaryl and alkyl moieties are as previously described. Preferred heteroarylalkyl groups contain a $C_{1-4}$ alkyl moiety. Exemplary heteroarylalkyl groups include pyridylmethyl.

As used herein, "acyl" means an H—CO— or alkyl-CO—, carbocyclyl-CO—, aryl-CO—, heteroaryl-CO—, or heterocyclyl-CO— group wherein the alkyl, carbocyclyl, aryl or heterocyclyl group is as herein described. In some embodiments, acyls contain a lower alkyl. Exemplary alkyl acyl groups include formyl, acetyl, propanoyl, 2-methylpropanoyl, t-butylacetyl, butanoyl, and palmitoyl.

As used herein, "alkoxycarbonyl" means an alkyl-O—CO— group in which the alkyl group is as described herein. Exemplary alkoxycarbonyl groups include methoxy- and ethoxycarbonyl.

As used herein, "alkoxy" means an alkyl-O— group in which the alkyl group is as described herein. Exemplary alkoxy groups include difluoromethoxy, methoxy, trifluoromethoxy, ethoxy, n-propoxy, i-propoxy, n-butoxy, s-butoxy, t-butoxy, pentoxy, hexoxy and heptoxy, and also the linear or branched positional isomers thereof.

As used herein, "halo", "halide" or "halogen" is a chloro, bromo, fluoro, or iodo atom radical. In some embodiments, a halo is a chloro, bromo or fluoro. For example, a halo can be fluoro.

As used herein, "haloalkyl" means a hydrocarbon substituent, which is a linear or branched, alkenyl or alkynyl substituted with one or more chloro, bromo, fluoro, or iodo atom(s). In some embodiments, a haloalkyl is a fluoroalkyl, wherein one or more of the hydrogen atoms have been substituted by fluoro. In some embodiments, haloalkyls are of 1 to about 3 carbons in length (e.g., 1 to about 2 carbons in length or 1 carbon in length). The term "haloalkylene" means a diradical variant of haloalkyl, and such diradicals may act as spacers between radicals, other atoms, or between a ring and another functional group.

As used herein, "heterocyclyl" means a nonaromatic cyclic ring system comprising at least one heteroatom in the ring system backbone. Heterocyclyls may compose a single monocyclic ring or include multiple fused rings, bridged bicyclic rings, and/or spirocyclic rings. Heterocyclyls may be substituted or unsubstituted with one or more substituents. In some embodiments, heterocycles have 5-7 members. In six-membered monocyclic heterocycles, the heteroatom(s) are selected from one up to three of O, N and/or S, and wherein when the heterocycle is five-membered, it can have one or two heteroatoms selected from O, N and/or S. Examples of heterocyclyl include azirinyl, aziridinyl, azetidinyl, oxetanyl, thietanyl, 1,4,2-dithiazolyl, dihydropyridinyl, 1,3-dioxanyl, 1,4-dioxanyl, 1,3-dioxolanyl, morpholinyl, thiomorpholinyl, piperazinyl, pyranyl, pyrrolidinyl, tetrahydrofuryl, tetrahydropyridinyl, oxazinyl, thiazinyl, thiinyl, thiazolidinyl, isothiazolidinyl, oxazolidinyl, isoxazolidinyl, piperidinyl, pyrazolidinyl imidazolidinyl, thiomorpholinyl, hexahydrotriazinyls, hexahydropyrimidinyl, hexahydropyridazinyl, oxathiazolidinyl, pyrazolonyl, triazolidinyl, and others.

As used herein, "monocyclic heterocyclyl" means a single nonaromatic ring comprising at least one heteroatom in the ring system backbone. Heterocyclyls may be substituted or unsubstituted with one or more substituents. In some embodiments, heterocycles have 5-7 members. In six membered monocyclic heterocycles, the heteroatom(s) are selected from one up to three of O, N and/or S, and wherein when the heterocycle is five membered, it can have one or two heteroatoms selected from O, N and/or S. Examples of heterocyclyl include azirinyl, aziridinyl, azetidinyl, oxetanyl, thietanyl, 1,4,2-dithiazolyl, dihydropyridinyl, 1,3-dioxanyl, 1,4-dioxanyl, 1,3-dioxolanyl, morpholinyl, thiomorpholinyl, piperazinyl, pyranyl, pyrrolidinyl, tetrahydrofuryl, tetrahydropyridinyl, oxazinyl, thiazinyl, thiinyl, thiazolidinyl, isothiazolidinyl, oxazolidinyl, isoxazolidinyl, piperidinyl, pyrazolidinyl imidazolidinyl, thiomorpholinyl, hexahydrotriazinyls, hexahydropyrimidinyl, hexahydropyridazinyl, oxathiazolidinyl, pyrazolonyl, triazolidinyl, and others.

As used herein, "spirocyclic heterocyclyl" means a non-aromatic bicyclic ring system with rings connected through just one atom and comprising at least one heteroatom in the ring system backbone. Spirocyclic heterocyclyls may include fused rings and/or a chain of spirocyclic rings connected through by two or more spiroatoms. Spirocyclic heterocyclyls may be substituted or unsubstituted with one or more substituents. In some embodiments, spirocyclic heterocyclyls have 5-11 members. In spirocyclic heterocyclyls, the heteroatom(s) are selected from one up to five of O, N and/or S. Examples of spirocyclic heterocyclyls include 7-azaspiro[3.5]nonane, 2-azaspiro[3.5]nonane, 6-azaspiro[3.5]nonane, 2-oxaspiro[3.5]nonane, 2-azaspiro[3.4]octane, 6-azaspiro[3.4]octane, 2-oxaspiro[3.4]octane, 2-azaspiro[3.3]heptane, 2-oxaspiro[3.3]heptane, and others.

The term "substituted" refers to moieties having substituents replacing a hydrogen on one or more non-hydrogen atoms of the molecule. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. Substituents can include, for example, an alkyl, a halide, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, or a sulfonyl moiety.

As used herein, when two groups are indicated to be "linked" or "bonded" to form a "ring", it is to be understood that a bond is formed between the two groups and may involve replacement of a hydrogen atom on one or both groups with the bond, thereby forming a carbocyclyl, heterocyclyl, aryl, or heteroaryl ring. The skilled artisan will recognize that such rings can and are readily formed by routine chemical reactions. In some embodiments, such rings have from 3-7 members, for example, 5 or 6 members.

The skilled artisan will recognize that some structures described herein may be resonance forms or tautomers of compounds that may be fairly represented by other chemical structures, even when kinetically, the artisan recognizes that such structures are only a very small portion of a sample of such compound(s). Such compounds are clearly contemplated within the scope of this disclosure, though such resonance forms or tautomers are not represented herein.

The compounds provided herein may encompass various stereochemical forms. The compounds also encompass diastereomers as well as optical isomers, e.g., mixtures of enantiomers including racemic mixtures, as well as individual enantiomers and diastereomers, which arise as a consequence of structural asymmetry in certain compounds. Separation of the individual isomers or selective synthesis of the individual isomers is accomplished by application of various methods which are well known to practitioners in the art. Unless otherwise indicated, when a disclosed compound is named or depicted by a structure without specifying the stereochemistry and has one or more chiral centers, it is understood to represent all possible stereoisomers of the compound.

The term "administration" or "administering" refers to a method of providing a dosage of a compound or pharmaceutical composition to a vertebrate or invertebrate, including a mammal, a bird, a fish, or an amphibian, where the method is, e.g., orally, subcutaneously, intravenously, intralymphatic, intranasally, topically, transdermally, intraperitoneally, intramuscularly, intrapulmonarily, vaginally, rectally, ontologically, neuro-otologically, intraocularly, subconjuctivally, via anterior eye chamber injection, intravitreally, intraperitoneally, intrathecally, intracystically, intrapleurally, via wound irrigation, intrabuccally, intra-abdominally, intra-articularly, intra-aurally, intrabronchially, intracapsularly, intrameningeally, via inhalation, via endotracheal or endobronchial instillation, via direct instillation into pulmonary cavities, intraspinally, intrasynovially, intrathoracically, via thoracostomy irrigation, epidurally, intratympanically, intracisternally, intravascularly, intraventricularly, intraosseously, via irrigation of infected bone, or via application as part of any admixture with a prosthetic device. The method of administration can vary depending on various factors, e.g., the components of the pharmaceutical composition, the site of the disease, the disease involved, and the severity of the disease.

A "diagnostic" as used herein is a compound, method, system, or device that assists in the identification or characterization of a health or disease state. The diagnostic can be used in standard assays as is known in the art.

The term "mammal" is used in its usual biological sense. Thus, it specifically includes humans, cattle, horses, monkeys, dogs, cats, mice, rats, cows, sheep, pigs, goats, and non-human primates but also includes many other species.

The term "pharmaceutically acceptable carrier", "pharmaceutically acceptable diluent" or "pharmaceutically acceptable excipient" includes any and all solvents, co-solvents, complexing agents, dispersion media, coatings, isotonic and absorption delaying agents and the like which are not biologically or otherwise undesirable. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions. In addition, various adjuvants such as are commonly used in the art may be included. These and other such compounds are described in the literature, e.g., in the Merck Index, Merck & Company, Rahway, N.J. Considerations for the inclusion of various components in pharmaceutical compositions are described, e.g., in Gilman et al. (Eds.) (2010); *Goodman and Gilman's: The Pharmacological Basis of Therapeutics,* 12th Ed., The McGraw-Hill Companies.

The term "pharmaceutically acceptable salt" refers to salts that retain the biological effectiveness and properties of the compounds provided herein and, which are not biologically or otherwise undesirable. In many cases, the compounds provided herein are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium, and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, for example, as described in WO 87/05297.

"Solvate" refers to the compound formed by the interaction of a solvent and a compound as provided herein or a salt thereof. Suitable solvates are pharmaceutically acceptable solvates including hydrates.

"Patient" as used herein, means a human or a non-human mammal, e.g., a dog, a cat, a mouse, a rat, a cow, a sheep, a pig, a goat, a non-human primate, or a bird, e.g., a chicken, as well as any other vertebrate or invertebrate. In some embodiments, the patient is a human.

A "therapeutically effective amount" or "pharmaceutically effective amount" of a compound as provided herein is one which is sufficient to achieve the desired physiological effect and may vary according to the nature and severity of the disease condition, and the potency of the compound. "Therapeutically effective amount" is also intended to include one or more of the compounds of Formula I in combination with one or more other agents that are effective to treat the diseases and/or conditions described herein. The combination of compounds can be a synergistic combination. Synergy, as described, for example, by Chou and Talalay, *Advances in Enzyme Regulation* (1984), 22, 27-55, occurs when the effect of the compounds when administered in combination is greater than the additive effect of the compounds when administered alone as a single agent. In general, a synergistic effect is most clearly demonstrated at sub-optimal concentrations of the compounds. It will be appreciated that different concentrations may be employed for prophylaxis than for treatment of an active disease. This amount can further depend upon the patient's height, weight, sex, age and medical history.

A therapeutic effect relieves, to some extent, one or more of the symptoms of the disease, and can include curing a disease. "Curing" means that the symptoms of a disease are eliminated. However, certain long-term or permanent effects of the disease may exist even after a cure is obtained (such as extensive tissue damage).

"Treat," "treatment," or "treating," as used herein refers to administering a compound or pharmaceutical composition as provided herein for therapeutic purposes. The term "therapeutic treatment" refers to administering treatment to a patient already suffering from a disease thus causing a therapeutically beneficial effect, such as ameliorating existing symptoms, ameliorating the underlying metabolic causes of symptoms, postponing or preventing the further development of a disorder, and/or reducing the severity of symptoms that will or are expected to develop.

Compounds

The compounds and compositions described herein can be used as anti-proliferative agents, e.g., anti-cancer and anti-angiogenesis agents, and/or as inhibitors of the Wnt signaling pathway, e.g., for treating diseases or disorders associated with aberrant Wnt signaling. In addition, the compounds can be used as inhibitors of one or more kinases, kinase receptors, or kinase complexes. Such compounds and compositions are also useful for controlling cellular proliferation, differentiation, and/or apoptosis.

The compounds and compositions described herein can be used to inhibit DYRK1A for treating a disorder or disease in which DYRK1A overexpression is implicated, such as Alzheimer's Disease, Amyotrophic Lateral Sclerosis, Down Syndrome, Frontotemporal Dementia with Parkinsonism-17 (FTDP-17), Lewy body dementia, Parkinson's Disease, Pick's Disease, and additional diseases with pronounced neurodegeneration such as Autism, Dementia, Epilepsy, Huntington's Disease, Multiple Sclerosis; diseases and disorders associated with acquired brain injury such as Chronic Traumatic Encephalopathy, Traumatic Brain Injury, Tumor, and Stroke.

Some embodiments of the present disclosure include compounds of Formula I:

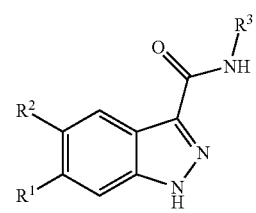

or salts, pharmaceutically acceptable salts, or prodrugs thereof, wherein:

$R^1$ is selected from the group consisting of H, halide, and —$C_{1-3}$ alkyl;

$R^2$ is selected from the group consisting of 6-10-membered heteroaryl($R^4$) and phenyl($R^5$)$_m$($R^6$);

with the proviso that $R^2$ is not or

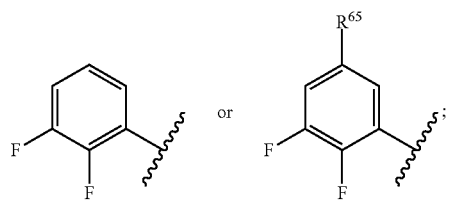

$R^3$ is selected from the group consisting of H, unsubstituted —$C_{1-9}$ alkyl, unsubstituted —$C_{1-9}$ haloalkyl, —($C_{1-6}$ alkyl)N($R^{68}$)$_2$, —($C_{2-6}$ alkyl)O($C_{1-6}$ alkyl), -carbocyclyl ($R^7$)$_p$, -monocyclic heterocyclyl($R^8$)$_p$, -spirocyclic heterocyclyl($R^8$)$_p$, —($C_{1-3}$ alkyl)heterocyclyl($R^7$)$_p$, -bicyclic aryl ($R^{10}$), —($C_{1-3}$ alkyl)aryl($R^{10}$)$_q$,

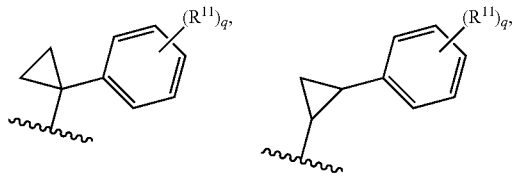

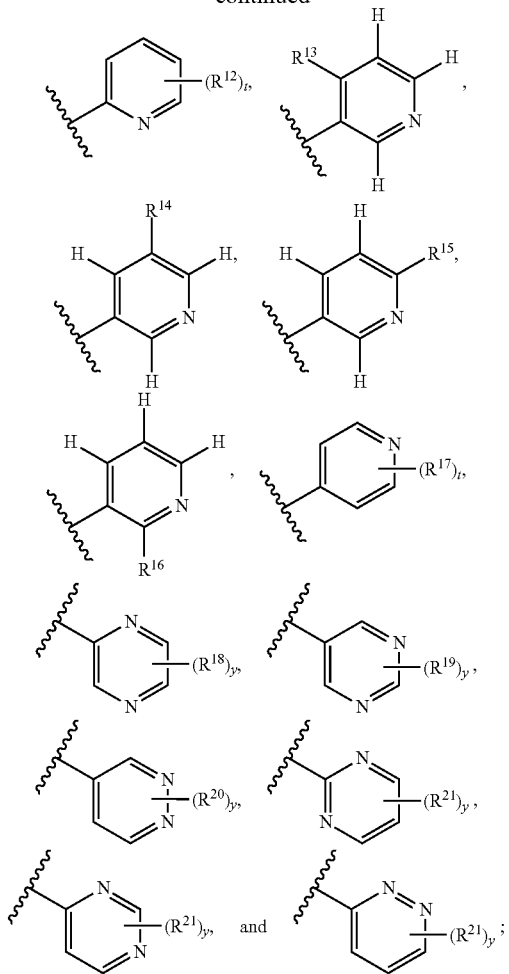

R⁴ is 1 substituent attached to the 6-10-membered heteroaryl and is selected from the group consisting of H, Cl, Br, I, —CN, unsubstituted —C$_{1-6}$ haloalkyl, —(C$_{1-3}$ alkyl)$_n$heterocyclyl(R²²)$_p$, —O-aryl(R²³)$_q$, —NHC(=O)R²⁴, and —(C$_{1-6}$ alkyl)$_n$N(R²⁵)$_2$;

each R⁵ is a substituent attached to the phenyl ring and independently selected at each occurrence from the group consisting of H and halide;

R⁶ is 1 substituent attached to the phenyl ring and selected from the group consisting of H, —(C$_{1-3}$ alkyl)$_n$heterocyclyl (R²⁶)$_p$, —O-aryl(R²⁷)$_q$, —NHC(=O)R²⁸, and —(CH$_2$)$_z$N (R²⁹)$_2$;

each R⁷ is a substituent attached to the carbocyclyl ring and is independently selected at each occurrence from the group consisting of H, halide, —CF$_3$, —CN, —N(R²⁵)$_2$, and —C$_{1-6}$ alkyl;

each R⁸ is a substituent attached to the heterocyclyl ring and is independently selected at each occurrence from the group consisting of H, halide, —(C$_{1-3}$ alkyl)$_n$OR³⁰, —(C$_{1-3}$ alkyl)carbocyclyl(R⁷)$_p$, —CN, —N(R²⁵)$_2$, —(C$_{1-3}$ alkyl)$_n$aryl(R¹¹)$_q$, -heterocyclyl(R³¹)$_p$, —C(=O)R³², unsubstituted —C$_{1-6}$ haloalkyl, and unsubstituted —C$_{1-6}$ alkyl;

each R⁹ is a substituent attached to the heterocyclyl ring and is independently selected at each occurrence from the group consisting of H, halide, —(C$_{1-3}$ alkyl)$_n$OR³³, —CN, -heterocyclyl(R³¹)$_p$, —C(=O)R³², unsubstituted —C$_{1-6}$ haloalkyl, and unsubstituted —C$_{1-6}$ alkyl;

each R¹⁰ is a substituent attached to the aryl ring and is independently selected at each occurrence from the group consisting of H, Cl, Br, I, unsubstituted —C$_{1-6}$ haloalkyl, —CN, —(C$_{1-3}$ alkyl)$_n$heterocyclyl(R³¹)$_p$, —(C$_{1-6}$ alkyl)$_n$N (R⁴⁰)(R⁴¹), and unsubstituted —C$_{1-6}$ alkyl;

each R¹¹ is a substituent attached to the aryl ring and is independently selected at each occurrence from the group consisting of H, halide, —C$_{1-6}$ haloalkyl, —CN, and —C$_{1-6}$ alkyl;

each R¹² is a substituent attached to the pyridinyl ring and is independently selected at each occurrence from the group consisting of H, halide, —C$_{1-6}$ haloalkyl, —CN, —C$_{1-6}$ alkyl, —OR³⁴, —SO$_2$R³⁵, —(C$_{1-3}$ alkyl)$_n$heterocyclyl (R³⁶)$_p$, —(C$_{1-3}$ alkyl)$_n$aryl(R³⁷)$_q$, —C(=O)N(R³⁸)$_2$, —NHC(=O)R³⁹, and —(C$_{1-6}$ alkyl)$_n$N(R⁴⁰)(R⁴¹);

each R¹³ is selected from the group consisting of Cl, Br, I, unsubstituted —C$_{1-6}$ alkyl, unsubstituted —C$_{2-6}$ haloalkyl, CN, —OR³⁴, —SO$_2$R³⁵, —(C$_{1-3}$ alkyl)$_n$heterocyclyl(R³⁶)$_p$, —(C$_{1-3}$ alkyl)$_n$aryl(R³⁷)$_q$, —C(=O)N(R³⁸)$_2$, —NHC(=O) R⁴², and —(C$_{1-6}$ alkyl)$_n$N(R⁴⁰)(R⁴¹);

each R¹⁴ is selected from the group consisting of Cl, Br, I, unsubstituted —C$_{1-6}$ haloalkyl, CN, unsubstituted —C$_{1-6}$ alkyl, —OR⁴⁸, —SO$_2$R³⁵, —(C$_{2-3}$ alkyl)$_n$heterocyclyl (R⁴⁴)$_p$, —(C$_{1-3}$ alkyl)$_n$aryl(R⁴⁵)$_q$, —C(=O)N(R³⁸)$_2$, —NHC(=O)R³⁹, and —(C$_{1-6}$ alkyl)$_n$N(R⁴⁶)(R⁴⁷);

each R¹⁵ is selected from the group consisting of halide, unsubstituted —C$_{1-6}$ alkyl, unsubstituted —C$_{2-6}$ haloalkyl, —OR⁴³, —SO$_2$R⁴⁹, —(C$_{2-3}$ alkyl)heterocyclyl(R⁵⁰)$_p$, -aryl (R⁵¹)$_q$, —(C$_{1-3}$ alkyl)aryl(R⁵²)$_q$, —C(=O)N(R⁵³)$_2$, —NHC (=O)R⁵⁴, and —(C$_{1-6}$ alkyl)$_n$N(R⁵⁵)(R⁵⁶);

each R¹⁶ is selected from the group consisting of halide, —CN, unsubstituted —C$_{1-6}$ alkyl, unsubstituted —C$_{2-6}$ haloalkyl, —OR³⁴, —SO$_2$R³⁵, —(C$_{1-3}$ alkyl)$_n$heterocyclyl (R⁵⁷)$_p$, —(C$_{1-3}$ alkyl)$_n$aryl(R³⁷)$_q$, —C(=O)N(R³⁸)$_2$, —NHC(=O)R³⁹, and —(C$_{1-6}$ alkyl)$_n$N(R⁴⁰)(R⁴¹);

each R¹⁷ is a substituent attached to the pyridinyl ring and is independently selected at each occurrence from the group consisting of halide, —C$_{1-6}$ haloalkyl, —CN, —C$_{1-6}$ alkyl, —OR³⁴, —SO$_2$R³⁵, —(C$_{1-3}$ alkyl)$_n$heterocyclyl(R³⁶)$_p$, —(C$_{1-3}$ alkyl)$_n$aryl(R³⁷)$_q$, —C(=O)N(R³⁸)$_2$, —NHC(=O) R³⁹, and —(C$_{1-6}$ alkyl)$_n$N(R⁴⁰)(R⁴¹);

each R¹⁸ is a substituent attached to the heteroaryl ring and is independently selected at each occurrence from the group consisting of halide, —C$_{1-6}$ haloalkyl, —CN, —C$_{1-6}$ alkyl, —OR³⁴, —SO$_2$R³⁵, —(C$_{1-3}$ alkyl)$_n$heterocyclyl (R³⁶)$_p$, —(C$_{1-3}$ alkyl)$_n$aryl(R³⁷)$_q$, —C(=O)N(R³⁸)$_2$, —NHC(=O)R³⁹, and —(C$_{1-6}$ alkyl)$_n$N(R⁴⁰)(R⁴¹);

each R¹⁹ is a substituent attached to the heteroaryl ring and is independently selected at each occurrence from the group consisting of halide, —C$_{1-6}$ haloalkyl, —CN, —C$_{1-6}$ alkyl, —OR³⁴, —SO$_2$R³⁵, —(C$_{1-3}$ alkyl)$_n$heterocyclyl (R³⁶)$_p$, —(C$_{1-3}$ alkyl)$_n$aryl(R³⁷)$_q$, —C(=O)N(R³⁸)$_2$, —NHC(=O)R³⁹, and —(C$_{1-6}$ alkyl)$_n$N(R⁵⁸)(R⁵⁹);

each R²⁰ is a substituent attached to the heteroaryl ring and is independently selected at each occurrence from the group consisting of halide, —CN, unsubstituted —C$_{1-6}$ alkyl, unsubstituted —C$_{2-6}$ haloalkyl, —OR³⁴, —SO$_2$R³⁵, —(C$_{1-3}$ alkyl)$_n$heterocyclyl(R³⁶)$_p$, —(C$_{1-3}$ alkyl)$_n$aryl (R³⁷)$_q$, —C(=O)N(R³⁸)$_2$, —NHC(=O)R³⁹, and —(C$_{1-6}$ alkyl)$_n$N(R⁴⁰)(R⁴¹);

each R²¹ is a substituent attached to the heteroaryl ring and is independently selected at each occurrence from the group consisting of H, halide, —C$_{1-6}$ haloalkyl, —CN, —C$_{1-6}$ alkyl, —OR³⁴, —SO$_2$R³⁵, —(C$_{1-3}$ alkyl)$_n$heterocyclyl(R³⁶)$_p$, —(C$_{1-3}$ alkyl)$_n$aryl(R³⁷)$_q$, —C(=O)N(R³⁸)$_2$, —NHC(=O)R³⁹, and —(C$_{1-6}$ alkyl)$_n$N(R⁴⁰)(R⁴¹);

each $R^{22}$ is a substituent attached to the heterocyclyl ring and is independently selected at each occurrence from the group consisting of H, halide, —$CF_3$, —OH, —$CH_2OH$, —CN, —$N(R^{25})_2$, and —$C_{1-6}$ alkyl;

each $R^{23}$ is a substituent attached to the aryl ring and is independently selected at each occurrence from the group consisting of H, halide, —$CF_3$, —CN, and —$C_{1-6}$ alkyl;

each $R^{24}$ is independently selected at each occurrence from the group consisting of —$C_{1-6}$ alkyl, —$N(R^{60})_2$, and —$(C_{1-3}$ alkyl$)_n$carbocyclyl;

each $R^{25}$ is independently selected at each occurrence from the group consisting of H and —$C_{1-6}$ alkyl, alternatively, two adjacent $R^{25}$ are taken together with the nitrogen atom to which they are attached to form a 3 to 7 membered heterocyclic ring;

each $R^{26}$ is a substituent attached to the heterocyclyl ring and is independently selected at each occurrence from the group consisting of H, halide, —$CF_3$, —OH, —CN, and —$C_{1-6}$ alkyl;

each $R^{27}$ is a substituent attached to the aryl ring and is independently selected at each occurrence from the group consisting of H, halide, —$CF_3$, —CN, and —$C_{1-6}$ alkyl;

each $R^{28}$ is independently selected at each occurrence from the group consisting of —$C_{1-6}$ alkyl, —$N(R^{60})_2$, and —$(C_{1-3}$ alkyl$)_n$carbocyclyl;

each $R^{29}$ is independently selected at each occurrence from the group consisting of H and —$C_{1-6}$ alkyl;

each $R^{30}$ is independently selected at each occurrence from the group consisting of H and —$C_{1-6}$ alkyl;

each $R^{31}$ is a substituent attached to the heterocyclyl ring and is independently selected at each occurrence from the group consisting of H and halide;

each $R^{32}$ is independently selected at each occurrence from the group consisting of —$C_{1-6}$ alkyl and -carbocyclyl;

each $R^{33}$ is independently selected at each occurrence from the group consisting of H and —$C_{2-6}$ alkyl;

each $R^{34}$ is independently selected at each occurrence from the group consisting of H, —$CF_3$, —$C_{1-6}$ alkyl, -heterocyclyl$(R^{61})_p$, and -aryl$(R^{62})_q$;

each $R^{35}$ is independently selected at each occurrence from the group consisting of —$CF_3$ and —$C_{1-6}$ alkyl;

each $R^{36}$ is a substituent attached to the heterocyclyl ring and is independently selected at each occurrence from the group consisting of H, halide, —OH, —$CF_3$, —CN, and —$C_{1-6}$ alkyl;

each $R^{37}$ is a substituent attached to the aryl ring and is independently selected at each occurrence from the group consisting of H, halide, —$CF_3$, —CN, and Me;

each $R^{38}$ is independently selected at each occurrence from the group consisting of H, —$C_{1-6}$ alkyl, and -carbocyclyl, alternatively, two adjacent $R^{38}$ are taken together with the nitrogen atom to which they are attached to form a 3 to 7 membered heterocyclic ring;

each $R^{39}$ is independently selected at each occurrence from the group consisting of —$C_{1-6}$ alkyl and —$(C_{1-3}$ alkyl$)_n$carbocyclyl;

each $R^{40}$ is a substituent attached to the nitrogen and is independently selected at each occurrence from the group consisting of H, unsubstituted —$C_{1-6}$ haloalkyl, and unsubstituted —$C_{1-6}$ alkyl;

each $R^{41}$ is a substituent attached to the nitrogen and is independently selected at each occurrence from the group consisting of H, unsubstituted —$C_{1-6}$ haloalkyl, unsubstituted —$C_{1-6}$ alkyl, and —$(C_{1-6}$ alkyl$)_n N(R^{38})_2$;

each $R^{42}$ is independently selected at each occurrence from the group consisting of —$C_{1-6}$ alkyl, —$(C_{1-3}$ alkyl)carbocyclyl, and —$(C_{4-6}$ carbocyclyl);

each $R^{43}$ is independently selected at each occurrence from the group consisting of —$CF_3$, —$C_{3-6}$ alkyl, -heterocyclyl$(R^{61})_p$, and -aryl$(R^{63})_q$;

each $R^{44}$ is a substituent attached to the heterocyclyl ring and is independently selected at each occurrence from the group consisting of H, halide, —OH, —$CF_3$, —CN, and —$C_{1-6}$ alkyl;

each $R^{45}$ is a substituent attached to the aryl ring and is independently selected at each occurrence from the group consisting of Cl, Br, I, —$CF_3$, —CN, and Me;

each $R^{46}$ is a substituent attached to the nitrogen and is independently selected at each occurrence from the group consisting of H and —$C_{2-6}$ alkyl;

each $R^{47}$ is a substituent attached to the nitrogen and is independently selected at each occurrence from the group consisting of H, —$C_{2-6}$ alkyl, and —$(C_{1-6}$ alkyl$)_n N(R^{38})_2$;

each $R^{48}$ is independently selected at each occurrence from the group consisting of —$CF_3$, —$C_{2-6}$ alkyl, -heterocyclyl$(R^{61})_p$, and -aryl$(R^{62})_q$;

each $R^{49}$ is independently selected at each occurrence from the group consisting of —$CF_3$, ethyl, and —$C_{4-6}$ alkyl;

each $R^{50}$ is a substituent attached to the heterocyclyl ring and is independently selected at each occurrence from the group consisting of H, halide, —OH, —$CF_3$, —CN, and —$C_{1-6}$ alkyl;

each $R^{51}$ is independently selected at each occurrence from the group consisting of Cl, Br, I, —$CF_3$, —CN, and Me;

each $R^{52}$ is independently selected at each occurrence from the group consisting of Cl, Br, I, —$CF_3$, —CN, and Me;

each $R^{53}$ is independently selected at each occurrence from the group consisting of —$C_{1-4}$ alkyl, cyclopropyl, cyclobutyl, and cyclohexyl, alternatively, two adjacent $R^{53}$ are taken together with the nitrogen atom to which they are attached to form a 3- to 4-membered heterocyclic ring or 6- to 7-membered heterocyclic ring;

each $R^{54}$ is independently selected at each occurrence from the group consisting of —$C_{1-6}$ alkyl, —$(C_{1-3}$ alkyl)carbocyclyl, and —$(C_{4-6}$ carbocyclyl);

each $R^{55}$ is a substituent attached to the nitrogen and is an unsubstituted —$C_{2-6}$ alkyl;

each $R^{56}$ is a substituent attached to the nitrogen and is independently selected at each occurrence from the group consisting of H, unsubstituted —$C_{2-6}$ alkyl, and —$(C_{1-6}$ alkyl$)_n N(R^{64})_2$;

each $R^{57}$ is independently selected at each occurrence from the group consisting of H, halide, —OH, —$CF_3$, —CN, and —$C_{2-6}$ alkyl;

each $R^{58}$ is a substituent attached to the nitrogen and is independently selected at each occurrence from the group consisting of H and —$C_{1-6}$ alkyl;

each $R^{59}$ is a substituent attached to the nitrogen and is independently selected at each occurrence from the group consisting of —$C_{1-6}$ alkyl, and —$(C_{1-6}$ alkyl$)_n N(R^{38})_2$;

each $R^{60}$ is independently selected at each occurrence from the group consisting of H and —$C_{1-6}$ alkyl, alternatively, two adjacent $R^{60}$ are taken together with the nitrogen atom to which they are attached to form a 3- to 7-membered heterocyclic ring;

each $R^{61}$ is a substituent attached to the heterocyclyl ring and is independently selected at each occurrence from the group consisting of H, halide, —OH, —$CF_3$, —CN, and —$C_{1-6}$ alkyl;

each $R^{62}$ is a substituent attached to the aryl ring and is independently selected at each occurrence from the group consisting of H, halide, —$CF_3$, —CN, and —$C_{1-6}$ alkyl;

each $R^{63}$ is a substituent attached to the aryl ring and is independently selected at each occurrence from the group consisting of H, Cl, Br, I, —$CF_3$, —CN, and —$C_{1-6}$ alkyl;

each $R^{64}$ is independently selected at each occurrence from the group consisting of H and —$C_{2-6}$ alkyl, alternatively, two adjacent $R^{64}$ are taken together with the nitrogen atom to which they are attached to form a 3- to 7-membered heterocyclic ring;

$R^{65}$ is —$(C_{1-3}$ alkyl$)_n$heterocyclyl$(R^8)_p$;

each $R^{68}$ is independently selected at each occurrence from the group consisting of H and unsubstituted —$C_{1-6}$ alkyl;

m is an integer of 1 to 4;

each n is independently an integer of 0 to 1;

each p is independently an integer of 1 to 10;

each q is independently an integer of 1 to 5;

t is an integer of 1 to 4;

y is an integer of 1 to 3;

z is an integer of 1 to 5; and with the proviso that a compound of Formula I is not a compound selected from the group consisting of:

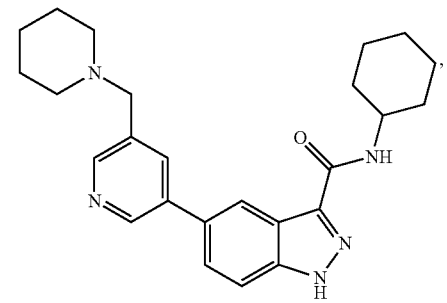

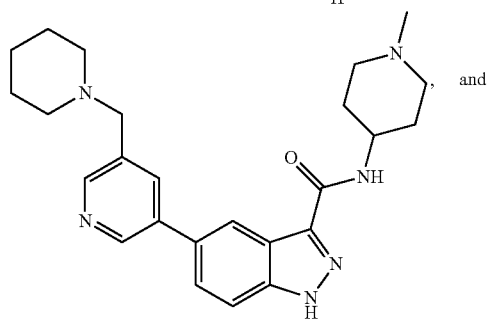

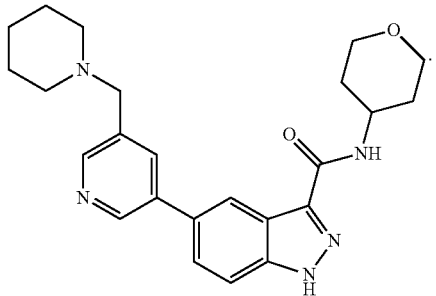

In some embodiments of Formula I, $R^1$ is selected from the group consisting of H, F, and Me.

In some embodiments of Formula I, $R^1$ is H.

In some embodiments of Formula I, $R^1$ is F.

In some embodiments of Formula I, $R^2$ is pyridinyl$(R^4)$.

In some embodiments of Formula I, $R^2$ is pyridin-3-yl $(R^4)$.

In some embodiments of Formula I, $R^4$ is —$(C_{1-3}$ alkyl$)_n$ heterocyclyl$(R^{22})_p$.

In some embodiments of Formula I, $R^4$ is -heterocyclyl $(R^{22})_p$.

In some embodiments of Formula I, $R^4$ is selected from the group consisting of

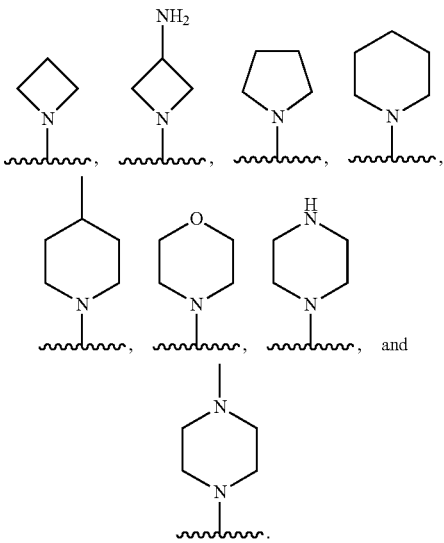

In some embodiments of Formula I, $R^4$ is —$(CH_2)$heterocyclyl$(R^{20})_p$.

In some embodiments of Formula I, $R^4$ is selected from the group consisting of

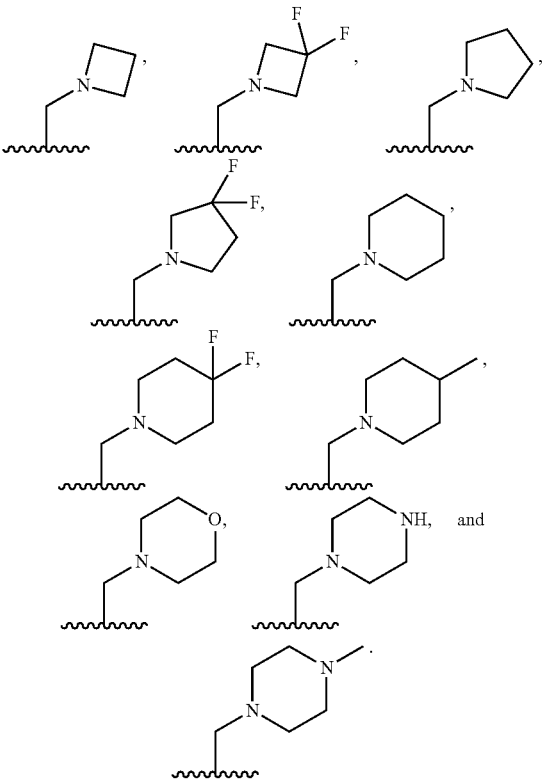

In some embodiments of Formula I, $R^2$ is phenyl$(R^5)_m$ $(R^6)$.

In some embodiments of Formula I, $R^5$ is H.

In some embodiments of Formula I, $R^6$ is $-(C_{1-3}\text{ alkyl})_n$ heterocyclyl$(R^{26})_p$.

In some embodiments of Formula I, $R^6$ is -heterocyclyl$(R^{26})_p$.

In some embodiments of Formula I, $R^6$ is selected from the group consisting of

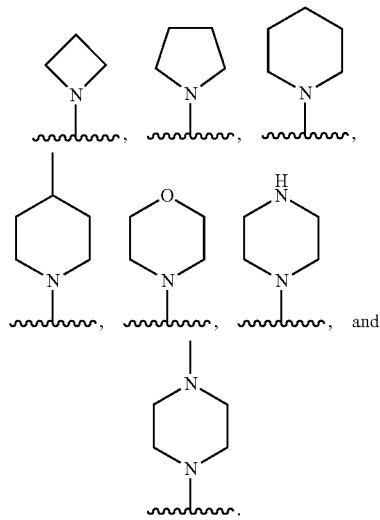

In some embodiments of Formula I, $R^6$ is $-(CH_2)$heterocyclyl$(R^{26})_p$.

In some embodiments of Formula I, $R^6$ is selected from the group consisting of

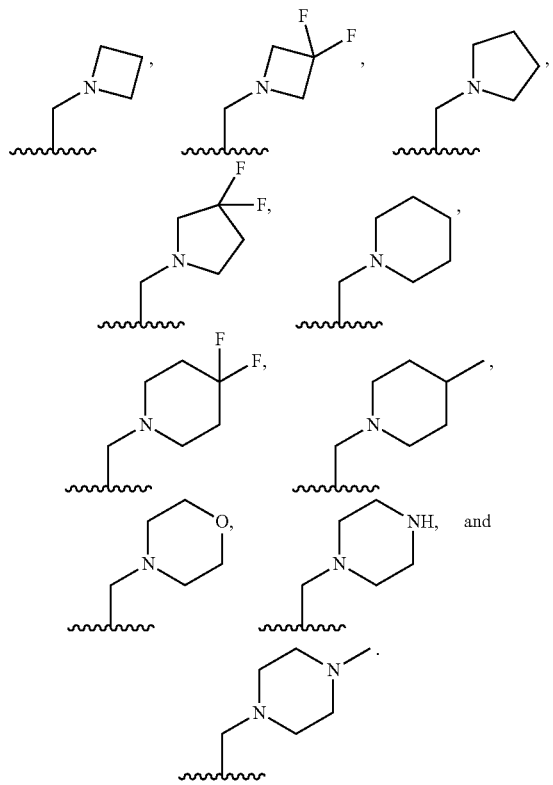

In some embodiments of Formula I, $R^3$ is H.

In some embodiments of Formula I, $R^3$ is $-C_{1-9}$ alkyl.

In some embodiments of Formula I, $R^3$ is selected from the group consisting of

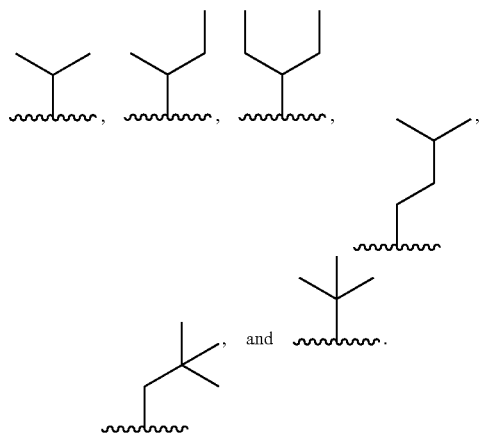

In some embodiments of Formula I, $R^3$ is -carbocyclyl$(R^7)_p$.

In some embodiments of Formula I, $R^3$ is selected from the group consisting of

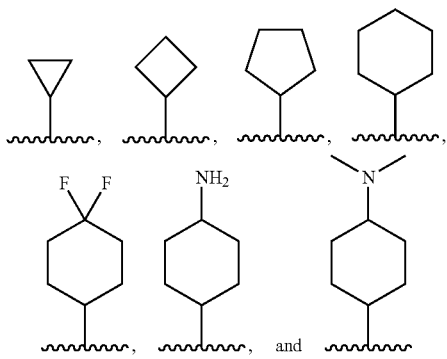

In some embodiments of Formula I, $R^3$ is -monocyclic heterocyclyl$(R^8)_p$.

In some embodiments of Formula I, of

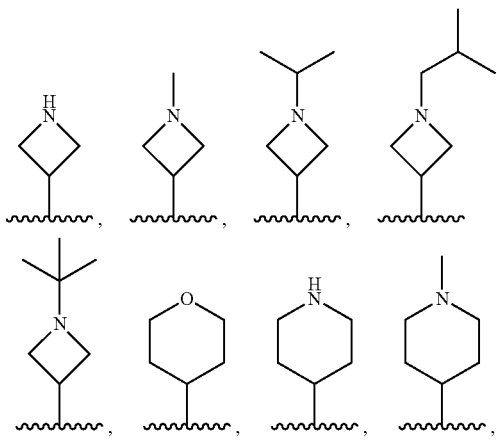

In some embodiments of Formula I each $R^{13}$ is selected from the group consisting of unsubstituted —$C_{1-6}$ alkyl, unsubstituted —$C_{2-6}$ haloalkyl, CN, —$OR^{34}$, —$SO_2R^{35}$, —($C_{1-3}$ alkyl)$_n$heterocyclyl($R^{36}$)$_p$, —($C_{1-3}$ alkyl)$_n$aryl ($R^{37}$)$_q$, —C(=O)N($R^{38}$)$_2$, —NHC(=O)$R^{42}$, and —($C_{1-6}$ alkyl)$_n$N($R^{40}$)($R^{41}$).

In some embodiments of Formula I, each $R^{14}$ is selected from the group consisting of unsubstituted —$C_{1-6}$ haloalkyl, CN, unsubstituted —$C_{1-6}$ alkyl, —$OR^{48}$, —$SO_2R^{35}$, —($C_{2-3}$ alkyl)$_n$heterocyclyl($R^{44}$)$_p$, —($C_{1-3}$ alkyl)$_n$aryl($R^{45}$)$_q$, —C(=O)N($R^{38}$)$_2$, —NHC(=O)$R^{39}$, and —($C_{1-6}$ alkyl)$_n$N ($R^{46}$)($R^{47}$).

In some embodiments of Formula I, each $R^{15}$ is selected from the group consisting of unsubstituted —$C_{1-6}$ alkyl, —$OR^{43}$, —($C_{2-3}$ alkyl)heterocyclyl($R^{50}$)$_p$, -aryl($R^{51}$)$_q$, —($C_{1-3}$ alkyl)aryl($R^{52}$)$_q$, —C(=O)N($R^{53}$)$_2$, —NHC(=O) $R^{54}$, and —($C_{1-6}$ alkyl)$_n$N($R^{55}$)($R^{56}$).

In some embodiments of Formula I, each $R^{16}$ is selected from the group consisting of —CN, unsubstituted —$C_{1-6}$ alkyl, unsubstituted —$C_{2-6}$ haloalkyl, —$OR^{34}$, —$SO_2R^{35}$, —($C_{1-3}$ alkyl)$_n$heterocyclyl($R^{57}$)$_p$, —($C_{1-3}$ alkyl)$_n$aryl ($R^{37}$)$_q$, —C(=O)N($R^{38}$)$_2$, —NHC(=O)$R^{39}$, and —($C_{1-6}$ alkyl)$_n$N($R^{40}$)($R^{41}$).

In some embodiments of Formula I, each $R^{17}$ is a substituent attached to the pyridinyl ring and is independently selected at each occurrence from the group consisting of —$C_{1-6}$ haloalkyl, —CN, —$C_{1-6}$ alkyl, —$OR^{34}$, —$SO_2R^{35}$, —($C_{1-3}$ alkyl)$_n$heterocyclyl($R^{36}$)$_p$, —($C_{1-3}$ alkyl)$_n$aryl ($R^{37}$)$_q$, —C(=O)N($R^{38}$)$_2$, —NHC(=O)$R^{39}$, and —($C_{1-6}$ alkyl)$_n$N($R^{40}$)($R^{41}$).

In some embodiments of Formula I, each $R^{33}$ is independently selected at each occurrence from the group consisting of H and —$C_{2-6}$ alkyl.

In some embodiments of Formula I, each $R^{37}$ is a substituent attached to the aryl ring and is independently selected at each occurrence from the group consisting of H, halide, —$CF_3$, —CN, and Me.

In some embodiments of Formula I, each $R^{53}$ is independently at each occurrence —$C_{1-4}$ alkyl.

In some embodiments of Formula I, each $R^{63}$ is a substituent attached to the aryl ring and is independently selected at each occurrence from the group consisting of —$CF_3$, —CN, and —$C_{1-6}$ alkyl.

In some embodiments of Formula I, $R^2$ is pyridinyl$R^4$.

In some embodiments of Formula I, $R^2$ is pyridin-3-yl$R^4$.

Some embodiments of the present disclosure include compounds of Formula II:

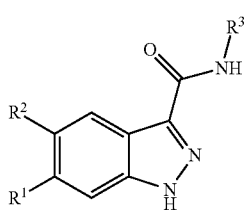

or salts, pharmaceutically acceptable salts, or prodrugs thereof, wherein:

$R^1$ is selected from the group consisting of H, halide, and —$C_{1-3}$ alkyl;

R² is selected from the group consisting of

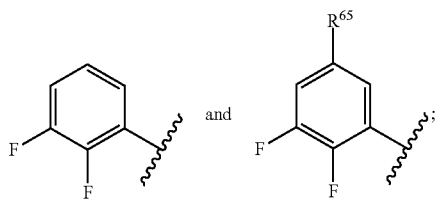

R³ is selected from the group consisting of H, unsubstituted —C₁₋₉ alkyl, unsubstituted —C₁₋₉ haloalkyl, —(C₁₋₆ alkyl)N(R⁶⁸)₂, —(C₂₋₆ alkyl)O(C₁₋₆ alkyl), —(C₁₋₃ alkyl)$_n$ carbocyclyl(R⁷)$_p$, -heterocyclyl(R⁸)$_p$, —(C₁₋₃ alkyl)heterocyclyl(R⁹)$_p$, —(C₁₋₃ alkyl)$_n$aryl(R¹⁰)$_q$,

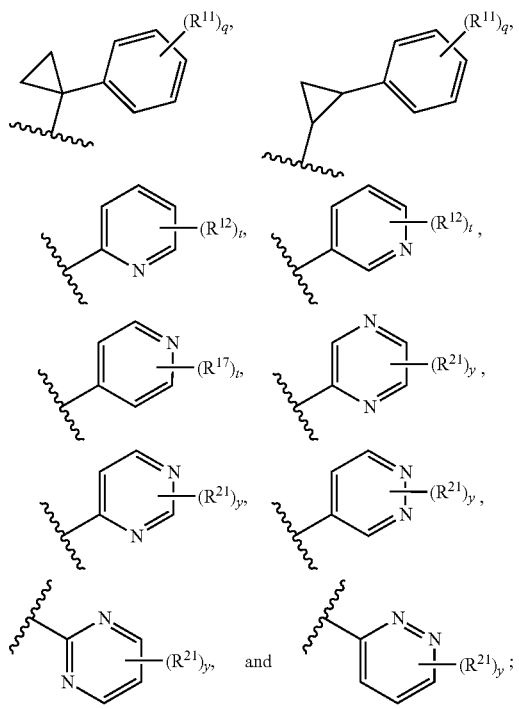

each R⁷ is a substituent attached to the carbocyclyl ring and is independently selected at each occurrence from the group consisting of H, halide, —CF₃, —CN, —N(R²⁵)₂, and —C₁₋₆ alkyl;

each R⁸ is a substituent attached to the heterocyclyl ring and is independently selected at each occurrence from the group consisting of H, halide, —(C₁₋₃ alkyl)$_n$OR³, —(C₁₋₃ alkyl)carbocyclyl(R⁷)$_p$, —CN, —N(R²⁵)₂, —(C₁₋₃ alkyl)$_n$aryl(R¹¹)$_q$, -heterocyclyl(R³¹)$_p$, —C(=O)R³², unsubstituted —C₁₋₆ haloalkyl, and unsubstituted —C₁₋₆ alkyl;

each R⁹ is a substituent attached to the heterocyclyl ring and is independently selected at each occurrence from the group consisting of H, halide, —(C₁₋₃ alkyl)$_n$OR³³, —(C₁₋₃ alkyl)carbocyclyl(R⁷)$_p$, —CN, —(C₁₋₃ alkyl)$_n$aryl(R¹¹)$_q$, -heterocyclyl(R³¹)$_p$, —C(=O)R³², unsubstituted —C₁₋₆ haloalkyl, and unsubstituted —C₁₋₆ alkyl;

each R¹⁰ is a substituent attached to the aryl ring and is independently selected at each occurrence from the group consisting of H, halide, unsubstituted —C₁₋₆ haloalkyl, —CN, —(C₁₋₃ alkyl)$_n$heterocyclyl(R³¹)$_p$, —(C₁₋₆ alkyl)$_n$N(R⁴⁰)(R⁴¹), and unsubstituted —C₁₋₆ alkyl;

each R¹¹ is a substituent attached to the aryl ring and is independently selected at each occurrence from the group consisting of H, halide, —C₁₋₆ haloalkyl, —CN, and —C₁₋₆ alkyl;

each R¹² is a substituent attached to the pyridinyl ring and is independently selected at each occurrence from the group consisting of H, halide, —C₁₋₆ haloalkyl, —CN, —C₁₋₆ alkyl, —OR³⁴, —SO₂R³⁵, —(C₁₋₃ alkyl)$_n$heterocyclyl(R³⁶)$_p$, —(C₁₋₃ alkyl)$_n$aryl(R³⁷)$_q$, —C(=O)N(R³⁸)₂, —NHC(=O)R³⁹, and —(C₁₋₆ alkyl)$_n$N(R⁴⁰)(R⁴¹);

each R¹⁷ is a substituent attached to the pyridinyl ring and is independently selected at each occurrence from the group consisting of halide, —C₁₋₆ haloalkyl, —CN, —C₁₋₆ alkyl, —OR³⁴, —SO₂R³⁵, —(C₁₋₃ alkyl)$_n$heterocyclyl(R³⁶)$_p$, —(C₁₋₃ alkyl)$_n$aryl(R³⁷)$_q$, —C(=O)N(R³⁸)₂, —NHC(=O)R³⁹, and —(C₁₋₆ alkyl)$_n$N(R⁴⁰)(R⁴¹);

each R²¹ is a substituent attached to the heteroaryl ring and is independently selected at each occurrence from the group consisting of H, halide, —C₁₋₆ haloalkyl, —CN, —C₁₋₆ alkyl, —OR³⁴, —SO₂R³⁵, —(C₁₋₃ alkyl)$_n$heterocyclyl(R³⁶)$_p$, —(C₁₋₃ alkyl)$_n$aryl(R³⁷)$_q$, —C(=O)N(R³⁸)₂, —NHC(=O)R³⁹, and —(C₁₋₆ alkyl)$_n$N(R⁴⁰)(R⁴¹);

each R²⁵ is independently selected at each occurrence from the group consisting of H and —C₁₋₆ alkyl, alternatively, two adjacent R²⁵ are taken together with the nitrogen atom to which they are attached to form a 3 to 7 membered heterocyclic ring;

each R³⁰ is independently selected at each occurrence from the group consisting of H and —C₁₋₆ alkyl;

each R³¹ is a substituent attached to the heterocyclyl ring and is independently selected at each occurrence from the group consisting of H, halide, —C₁₋₆ alkyl, and —C₁₋₆ haloalkyl;

each R³² is independently selected at each occurrence from the group consisting of —C₁₋₆ alkyl and -carbocyclyl;

each R³³ is independently selected at each occurrence from the group consisting of H and —C₂₋₆ alkyl;

each R³⁴ is independently selected at each occurrence from the group consisting of H, —CF₃, —C₁₋₆ alkyl, -heterocyclyl(R⁶¹)$_p$, and -aryl(R⁶²)$_q$;

each R³⁵ is independently selected at each occurrence from the group consisting of —CF₃ and —C₁₋₆ alkyl;

each R³⁶ is a substituent attached to the heterocyclyl ring and is independently selected at each occurrence from the group consisting of H, halide, —OH, —CF₃, —CN, and —C₁₋₆ alkyl;

each R³⁷ is a substituent attached to the aryl ring and is independently selected at each occurrence from the group consisting of H, halide, —CF₃, —CN, and Me;

each R³⁸ is independently selected at each occurrence from the group consisting of H, —C₁₋₆ alkyl, and -carbocyclyl, alternatively, two adjacent R³⁸ are taken together with the nitrogen atom to which they are attached to form a 3 to 7 membered heterocyclic ring;

each R³⁹ is independently selected at each occurrence from the group consisting of —C₁₋₆ alkyl and —(C₁₋₃ alkyl)$_n$carbocyclyl;

each R⁴⁰ is a substituent attached to the nitrogen and is independently selected at each occurrence from the group consisting of H, unsubstituted —C₁₋₆ haloalkyl, and unsubstituted —C₁₋₆ alkyl;

each R⁴¹ is a substituent attached to the nitrogen and is independently selected at each occurrence from the group consisting of H, unsubstituted —C₁₋₆ haloalkyl, unsubstituted —C₁₋₆ alkyl, and —(C₁₋₆ alkyl)$_n$N(R⁸)₂;

each $R^{61}$ is a substituent attached to the heterocyclyl ring and is independently selected at each occurrence from the group consisting of H, halide, —OH, —CF$_3$, —CN, and —C$_{1-6}$ alkyl;

each $R^{62}$ is a substituent attached to the aryl ring and is independently selected at each occurrence from the group consisting of H, halide, —CF$_3$, —CN, and —C$_{1-6}$ alkyl;

$R^{65}$ is —(C$_{1-3}$ alkyl)$_n$heterocyclyl(R$^8$)$_p$;

each $R^{68}$ is independently selected at each occurrence from the group consisting of H and unsubstituted —C$_{1-6}$ alkyl;

each n is independently an integer of 0 to 1;

each p is independently an integer of 1 to 10;

each q is independently an integer of 1 to 5;

t is an integer of 1 to 4; and y is an integer of 1 to 3.

In some embodiments of Formula II, $R^2$ is

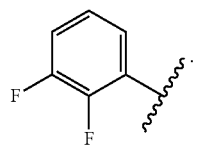

In some embodiments of Formula II, $R^2$ is

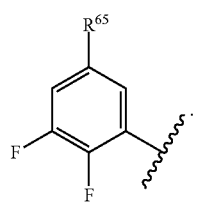

and $R^{65}$ is —(C$_{1-3}$ alkyl)$_n$heterocyclyl(R$^8$)$_p$;

In some embodiments of Formula II, $R^2$ is

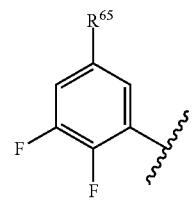

and $R^{65}$ is —(C$_{1-2}$ alkyl)$_n$heterocyclyl(R$^8$)$_p$;

In some embodiments of Formula II, $R^2$ is

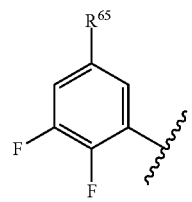

and $R^{65}$ is —(CH$_2$)heterocyclyl(R$^8$)$_p$.

In some embodiments of Formula II, $R^2$ is

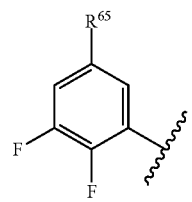

and $R^{65}$ is —(CH$_2$)heterocyclyl(R$^8$)$_p$, p is 1-2, and $R^8$ is halide.

In some embodiments of Formula II, $R^2$ is

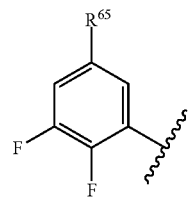

and $R^{65}$ is —(CH$_2$)heterocyclyl(R$^8$)$_p$, p is 1-2, and R is F.

In some embodiments of Formula II, $R^2$ is

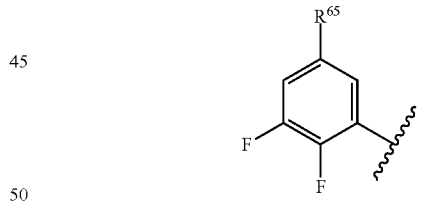

and $R^{65}$ is —(CH$_2$)heterocyclyl(R$^8$)$_p$, p is 1, and $R^8$ is an unsubstituted —C$_{1-4}$ alkyl.

In some embodiments of Formula II, $R^2$ is

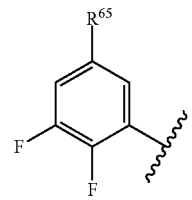

and $R^{65}$ is —(CH$_2$)heterocyclyl(R$^8$)$_p$, p is 1, and $R^8$ is an unsubstituted —C$_{1-4}$ alkyl.

In some embodiments of Formula II, R² is

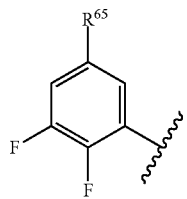

and R⁶⁵ is —(CH₂)heterocyclyl(R⁸)$_p$, p is 1, and R⁸ is an unsubstituted —C$_{1-3}$ alkyl.

In some embodiments of Formula II, R² is

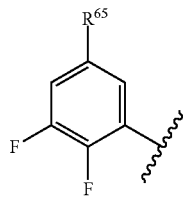

and R⁶⁵ is —(CH₂)heterocyclyl(R⁸)$_p$, p is 1, and R⁸ is an unsubstituted —C$_{1-2}$ alkyl.

In some embodiments of Formula II, R² is

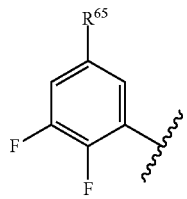

and R⁶⁵ is —(CH₂)heterocyclyl(R⁸)$_p$, p is 1, and R⁸ is methyl.

In some embodiments of Formula II, R² is

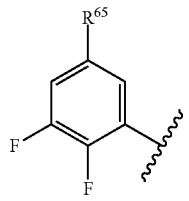

and R⁶⁵ is —(CH₂)heterocyclyl(R⁸)$_p$, p is 1, and R⁸ is an unsubstituted —C$_{1-6}$ haloalkyl.

In some embodiments of Formula II, R² is

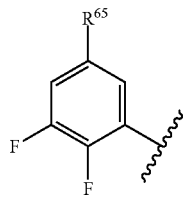

and R⁶⁵ is —(CH₂)heterocyclyl(R⁸)$_p$, p is 1, and R⁸ is an unsubstituted —C$_{1-4}$ haloalkyl.

In some embodiments of Formula II, R² is

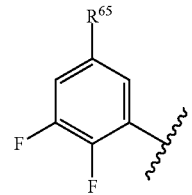

and R⁶⁵ is —(CH₂)heterocyclyl(R⁸)$_p$, p is 1, and R⁸ is an unsubstituted —C$_{1-3}$ haloalkyl.

In some embodiments of Formula II, R² is

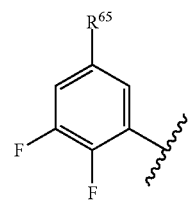

and R⁶⁵ is —(CH₂)heterocyclyl(R⁸)$_p$, p is 1, and R⁸ is an unsubstituted —C$_{1-2}$ haloalkyl.

In some embodiments of Formula II, R² is

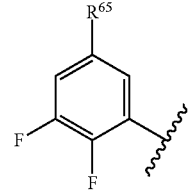

and R⁶⁵ is selected from the group consisting of

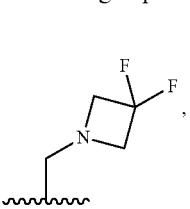

-continued

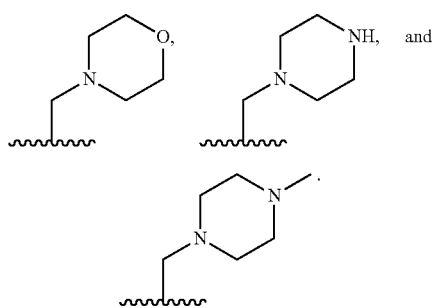

In some embodiments of Formula II, R² is

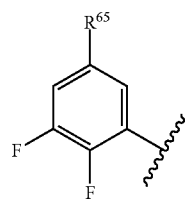

and R⁶⁵ is -heterocyclyl(R⁸)$_p$.

In some embodiments of Formula II, R² is

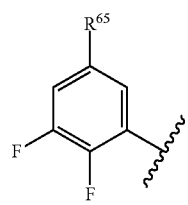

and R⁶⁵ is selected from the group consisting of

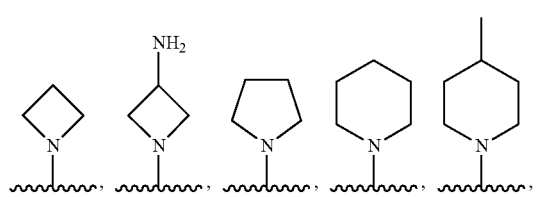

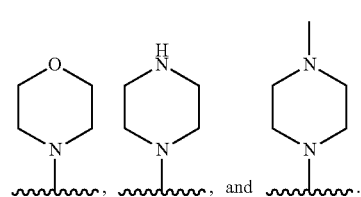

Some embodiments of the present disclosure include compounds of Formula III:

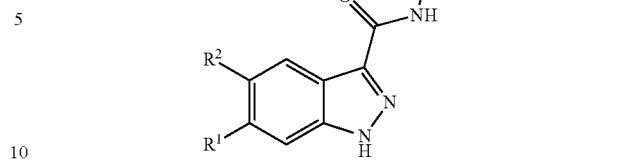

or salts, pharmaceutically acceptable salts, or prodrugs thereof, wherein:

R¹ is selected from the group consisting of H, halide, and —C$_{1-3}$ alkyl;

R² is a 6-10-membered heteroaryl(R⁴);

R³ is selected from the group consisting of H, unsubstituted —C$_{1-9}$ alkyl, unsubstituted —C$_{1-9}$ haloalkyl, —(C$_{1-6}$ alkyl)N(R⁶⁸)$_2$, —(C$_{2-6}$ alkyl)O(C$_{1-6}$ alkyl), —(C$_{1-3}$ alkyl)$_n$carbocyclyl(R⁷)$_p$, —(C$_{1-3}$ alkyl)$_n$heterocyclyl(R⁸)$_p$, —(C$_{1-3}$ alkyl)$_n$aryl(R¹⁰)$_q$,

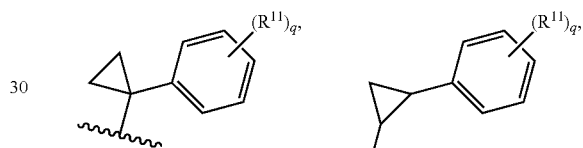

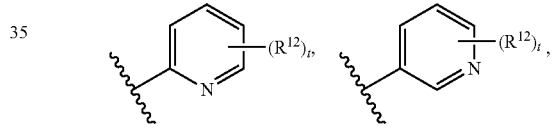

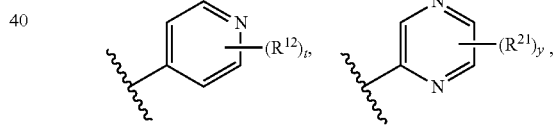


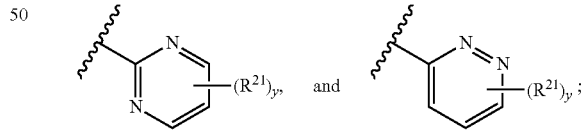

R⁴ is selected from the group consisting of

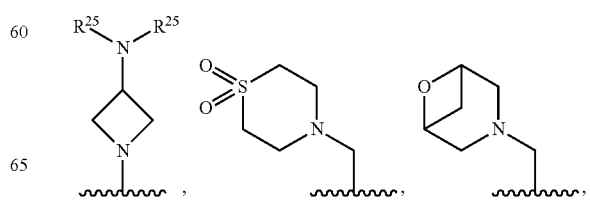

-continued

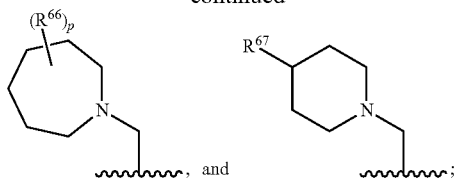

each R⁷ is a substituent attached to the carbocyclyl ring and is independently selected at each occurrence from the group consisting of H, halide, —CF₃, —CN, —N(R²⁵)₂, and —C₁₋₆ alkyl;

each R⁸ is a substituent attached to the heterocyclyl ring and is independently selected at each occurrence from the group consisting of H, halide, —(C₁₋₃ alkyl)$_n$OR³⁰, —(C₁₋₃ alkyl)carbocyclyl(R⁷)$_p$, —CN, —N(R²⁵)₂, —(C₁₋₃ alkyl)$_n$aryl(R¹¹)$_q$, -heterocyclyl(R³¹)$_p$, —C(=O)R³², unsubstituted —C₁₋₆ haloalkyl, and unsubstituted —C₁₋₆ alkyl;

each R¹⁰ is a substituent attached to the aryl ring and is independently selected at each occurrence from the group consisting of H, halide, unsubstituted —C₁₋₆ haloalkyl, —CN, —(C₁₋₃ alkyl)$_n$heterocyclyl(R³¹)$_p$, —(C₁₋₆ alkyl)$_n$N(R⁴⁰)(R⁴¹), and unsubstituted —C₁₋₆ alkyl;

each R¹¹ is a substituent attached to the aryl ring and is independently selected at each occurrence from the group consisting of H, halide, —C₁₋₆ haloalkyl, —CN, and —C₁₋₆ alkyl;

each R¹² is a substituent attached to the pyridinyl ring and is independently selected at each occurrence from the group consisting of H, halide, —C₁₋₆ haloalkyl, —CN, —C₁₋₆ alkyl, —OR³⁴, —SO₂R³⁵, —(C₁₋₃ alkyl)$_n$heterocyclyl(R³⁶)$_p$, —(C₁₋₃ alkyl)$_n$aryl(R³⁷)$_q$, —C(=O)N(R³⁸)₂, —NHC(=O)R³⁹, and —(C₁₋₆ alkyl)$_n$N(R⁴⁰)(R⁴¹);

each R²¹ is a substituent attached to the heteroaryl ring and is independently selected at each occurrence from the group consisting of H, halide, —C₁₋₆ haloalkyl, —CN, —C₁₋₆ alkyl, —OR³⁴, —SO₂R³⁵, —(C₁₋₃ alkyl)$_n$heterocyclyl(R³⁶)$_p$, —(C₁₋₃ alkyl)$_n$aryl(R³⁷)$_q$, —C(=O)N(R³⁸)₂, —NHC(=O)R³⁹, and —(C₁₋₆ alkyl)$_n$N(R⁴⁰)(R⁴¹);

each R²⁵ is independently selected at each occurrence from the group consisting of H and —C₁₋₆ alkyl, alternatively, two adjacent R²⁵ are taken together with the nitrogen atom to which they are attached to form a 3 to 7 membered heterocyclic ring;

each R³⁰ is independently selected at each occurrence from the group consisting of H and —C₁₋₆ alkyl;

each R³¹ is a substituent attached to the heterocyclyl ring and is independently selected at each occurrence from the group consisting of H, halide, —C₁₋₆ alkyl, and —C₁₋₆ haloalkyl;

each R³² is independently selected at each occurrence from the group consisting of —C₁₋₆ alkyl and -carbocyclyl;

each R³⁴ is independently selected at each occurrence from the group consisting of H, —CF₃, —C₁₋₆ alkyl, -heterocyclyl(R⁶¹)$_p$, and -aryl(R⁶²)$_q$;

each R³⁵ is independently selected at each occurrence from the group consisting of —CF₃ and —C₁₋₆ alkyl;

each R³⁶ is a substituent attached to the heterocyclyl ring and is independently selected at each occurrence from the group consisting of H, halide, —OH, —CF₃, —CN, and —C₁₋₆ alkyl;

each R³⁷ is a substituent attached to the aryl ring and is independently selected at each occurrence from the group consisting of H, halide, —CF₃, —CN, and Me;

each R³⁸ is independently selected at each occurrence from the group consisting of H, —C₁₋₆ alkyl, and -carbocyclyl, alternatively, two adjacent R³⁸ are taken together with the nitrogen atom to which they are attached to form a 3 to 7 membered heterocyclic ring;

each R³⁹ is independently selected at each occurrence from the group consisting of —C₁₋₆ alkyl and —(C₁₋₃ alkyl)$_n$carbocyclyl;

each R⁴⁰ is a substituent attached to the nitrogen and is independently selected at each occurrence from the group consisting of H, unsubstituted —C₁₋₆ haloalkyl, and unsubstituted —C₁₋₆ alkyl;

each R⁴⁰ is a substituent attached to the nitrogen and is independently selected at each occurrence from the group consisting of H, unsubstituted —C₁₋₆ haloalkyl, unsubstituted —C₁₋₆ alkyl, and —(C₁₋₆ alkyl)$_n$N(R³⁸)₂;

each R⁶¹ is a substituent attached to the heterocyclyl ring and is independently selected at each occurrence from the group consisting of H, halide, —OH, —CF₃, —CN, and —C₁₋₆ alkyl;

each R⁶² is a substituent attached to the aryl ring and is independently selected at each occurrence from the group consisting of H, halide, —CF₃, —CN, and —C₁₋₆ alkyl;

each R⁶⁶ is a substituent attached to a carbon on the ring and is independently selected at each occurrence from the group consisting of H, halide, —C₁₋₆ haloalkyl, —CN, and —C₁₋₆ alkyl;

R⁶⁷ is selected from the group consisting of —C₁₋₆ haloalkyl and —C₁₋₆ alkyl;

each R⁶⁸ is independently selected at each occurrence from the group consisting of H and unsubstituted —C₁₋₆ alkyl;

each n is independently an integer of 0 to 1;

each p is independently an integer of 1 to 10;

each q is independently an integer of 1 to 5;

t is an integer of 1 to 4; and y is an integer of 1 to 3.

Some embodiments of the present disclosure include compounds of Formula IV:

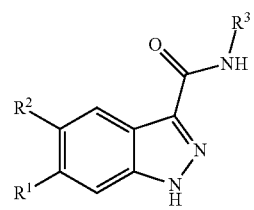

IV or salts, pharmaceutically acceptable salts, or prodrugs thereof, wherein:

R¹ is selected from the group consisting of H, halide, and —C₁₋₃ alkyl;

R² is selected from the group consisting of 6-10-membered heteroaryl(R⁴);

R³ is selected from the group consisting of H, unsubstituted —C₁₋₉ alkyl, unsubstituted —C₁₋₉ haloalkyl, —(C₁₋₆ alkyl)N(R⁶⁸)₂, —(C₂₋₆ alkyl)O(C₁₋₆ alkyl), -carbocyclyl (R⁷)$_p$, —(C₁₋₃ alkyl)$_n$heterocyclyl(R⁹)$_p$, —(C₁₋₃ alkyl)$_n$aryl(R¹⁰)$_q$,

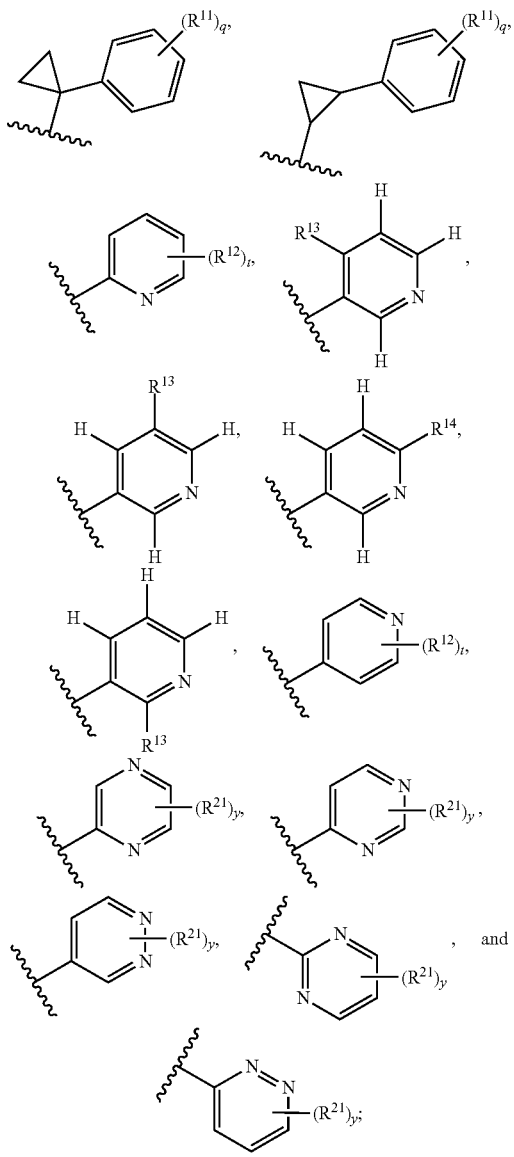

R⁴ is selected from the group consisting of F and unsubstituted —C$_{1-6}$ alkyl;

each R⁷ is a substituent attached to the carbocyclyl ring and is independently selected at each occurrence from the group consisting of H, halide, —CF$_3$, —CN, —N(R$^{25}$)$_2$, and —C$_{1-6}$ alkyl;

each R⁹ is a substituent attached to the heterocyclyl ring and is independently selected at each occurrence from the group consisting of H, halide, —(C$_{1-3}$ alkyl)$_n$OR$^{33}$, —CN, -heterocyclyl(R$^{31}$)$_p$, —C(=O)R$^{32}$, unsubstituted —C$_{1-6}$ haloalkyl, and unsubstituted —C$_{1-6}$ alkyl;

each R¹⁰ is a substituent attached to the aryl ring and is independently selected at each occurrence from the group consisting of H, Cl, Br, I, unsubstituted —C$_{1-6}$ haloalkyl, —CN, —(C$_{1-3}$ alkyl)$_n$heterocyclyl(R$^{31}$)$_p$, —(C$_{1-6}$ alkyl)$_n$N(R$^{40}$)(R$^{41}$), and unsubstituted —C$_{1-6}$ alkyl;

each R¹¹ is a substituent attached to the aryl ring and is independently selected at each occurrence from the group consisting of H, halide, —C$_{1-6}$ haloalkyl, —CN, and —C$_{1-6}$ alkyl;

each R¹² is a substituent attached to the pyridinyl ring and is independently selected at each occurrence from the group consisting of H, halide, —C$_{1-6}$ haloalkyl, —CN, —C$_{1-6}$ alkyl, —OR$^{34}$, —SO$_2$R$^{35}$, —(C$_{1-3}$ alkyl)$_n$heterocyclyl(R$^{36}$)$_p$, —(C$_{1-3}$ alkyl)$_n$aryl(R$^{37}$)$_q$, —C(=O)N(R$^{38}$)$_2$, —NHC(=O)R$^{39}$, and —(C$_{1-6}$ alkyl)$_n$N(R$^{40}$)(R$^{41}$);

R¹³ is selected from the group consisting of halide, —C$_{1-6}$ haloalkyl, —CN, —C$_{1-6}$ alkyl, —OR$^{34}$, —SO$_2$R$^{35}$, —(C$_{1-3}$ alkyl)$_n$heterocyclyl(R$^{36}$)$_p$, —(C$_{1-3}$ alkyl)$_n$aryl(R$^{37}$)$_q$, —C(=O)N(R$^{38}$)$_2$, —NHC(=O)R$^{39}$, and —(C$_{1-6}$ alkyl)$_n$N(R$^{40}$)(R$^{41}$);

R¹⁴ is selected from the group consisting of halide, —C$_{2-6}$ haloalkyl, —CN, —C$_{1-6}$ alkyl, —OR$^{34}$, —SO$_2$R$^{35}$, —(C$_{1-3}$ alkyl)$_n$heterocyclyl(R$^{36}$)$_p$, —(C$_{1-3}$ alkyl)$_n$aryl(R$^{37}$)$_q$, —C(=O)N(R$^{38}$)$_2$, —NHC(=O)R$^{39}$, and —(C$_{1-6}$ alkyl)$_n$N(R$^{40}$)(R$^{41}$);

each R²¹ is a substituent attached to the heteroaryl ring and is independently selected at each occurrence from the group consisting of H, halide, —C$_{1-6}$ haloalkyl, —CN, —C$_{1-6}$ alkyl, —OR$^{34}$, —SO$_2$R$^{35}$, —(C$_{1-3}$ alkyl)$_n$heterocyclyl(R$^{36}$)$_p$, —(C$_{1-3}$ alkyl)$_n$aryl(R$^{37}$)$_q$, —C(=O)N(R$^{38}$)$_2$, —NHC(=O)R$^{39}$, and —(C$_{1-6}$ alkyl)$_n$N(R$^{40}$)(R$^{41}$);

each R²⁵ is independently selected at each occurrence from the group consisting of H and —C$_{1-6}$ alkyl, alternatively, two adjacent R²⁵ are taken together with the nitrogen atom to which they are attached to form a 3 to 7 membered heterocyclic ring;

each R³¹ is a substituent attached to the heterocyclyl ring and is independently selected at each occurrence from the group consisting of H and halide;

each R³² is independently selected at each occurrence from the group consisting of —C$_{1-6}$ alkyl and -carbocyclyl;

each R³³ is independently selected at each occurrence from the group consisting of H and —C$_{2-6}$ alkyl;

each R³⁴ is independently selected at each occurrence from the group consisting of H, —CF$_3$, —C$_{1-6}$ alkyl, -heterocyclyl(R$^{61}$)$_p$, and -aryl(R$^{62}$)$_q$;

each R³⁵ is independently selected at each occurrence from the group consisting of —CF$_3$ and —C$_{1-6}$ alkyl;

each R³⁶ is a substituent attached to the heterocyclyl ring and is independently selected at each occurrence from the group consisting of H, halide, —OH, —CF$_3$, —CN, and —C$_{1-6}$ alkyl;

each R³⁷ is a substituent attached to the aryl ring and is independently selected at each occurrence from the group consisting of H, halide, —CF$_3$, —CN, and Me;

each R³⁸ is independently selected at each occurrence from the group consisting of H, —C$_{1-6}$ alkyl, and -carbocyclyl, alternatively, two adjacent R³⁸ are taken together with the nitrogen atom to which they are attached to form a 3 to 7 membered heterocyclic ring;

each R³⁹ is independently selected at each occurrence from the group consisting of —C$_{1-6}$ alkyl and —(C$_{1-3}$ alkyl)$_n$carbocyclyl;

each R⁴⁰ is a substituent attached to the nitrogen and is independently selected at each occurrence from the group consisting of H, unsubstituted —C$_{1-6}$ haloalkyl, and unsubstituted —C$_{1-6}$ alkyl;

each R⁴¹ is a substituent attached to the nitrogen and is independently selected at each occurrence from the group consisting of H, unsubstituted —C$_{1-6}$ haloalkyl, unsubstituted —C$_{1-6}$ alkyl, and —(C$_{1-6}$ alkyl)$_n$N(R$^{38}$)$_2$;

each R⁶¹ is a substituent attached to the heterocyclyl ring and is independently selected at each occurrence from the group consisting of H, halide, —OH, —CF$_3$, —CN, and —C$_{1-6}$ alkyl;

each R⁶² is a substituent attached to the aryl ring and is independently selected at each occurrence from the group consisting of H, halide, —CF$_3$, —CN, and —C$_{1-6}$ alkyl;

each $R^{68}$ is independently selected at each occurrence from the group consisting of H and unsubstituted —$C_{1-6}$ alkyl;
each n is independently an integer of 0 to 1;
each p is independently an integer of 1 to 10;
each q is independently an integer of 1 to 5;
t is an integer of 1 to 4; and
y is an integer of 1 to 3.

Some embodiments of the present disclosure include compounds of Formula V:

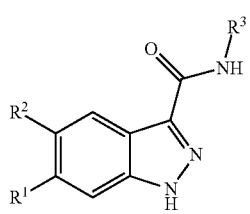

V or salts, pharmaceutically acceptable salts, or prodrugs thereof,
wherein:
$R^1$ is selected from the group consisting of H, halide, and $C_{1-3}$ alkyl;
$R^2$ is selected from the group consisting of 6-10-membered heteroaryl($R^4$) and phenyl($R^5$)$_m$($R^6$);
$R^3$ is selected from the group consisting of

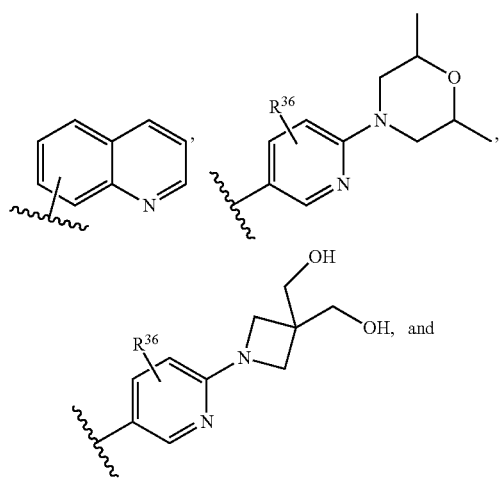

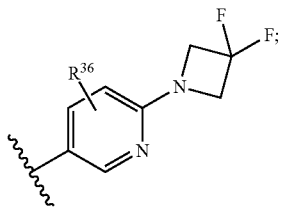

$R^4$ is 1 substituent attached to the 6-10-membered heteroaryl and is selected from the group consisting of H, halide —CN, unsubstituted —$C_{1-6}$ haloalkyl, unsubstituted —$C_{1-6}$ alkyl, —($C_{1-3}$ alkyl)$_n$heterocyclyl($R^{22}$)$_p$, —O-aryl($R^{23}$)$_q$, —NHC(=O)$R^{24}$, and —($C_{1-6}$ alkyl)$_n$N($R^{25}$)$_2$;
each $R^5$ is a substituent attached to the phenyl ring and independently selected at each occurrence from the group consisting of H and halide;

$R^6$ is 1 substituent attached to the phenyl ring and selected from the group consisting of H, —($C_{1-3}$ alkyl)$_n$heterocyclyl ($R^{26}$)$_p$, —O-aryl($R^{27}$)$_q$, —NHC(=O)$R^{28}$, and —(CH$_2$)$_z$N ($R^{29}$)$_2$;
each $R^{22}$ is a substituent attached to the heterocyclyl ring and is independently selected at each occurrence from the group consisting of H, halide, —CF$_3$, —OH, —CH$_2$OH, —CN, —N($R^{25}$)$_2$, and —$C_{1-6}$ alkyl;
each $R^{23}$ is a substituent attached to the aryl ring and is independently selected at each occurrence from the group consisting of H, halide, —CF$_3$, —CN, and —$C_{1-6}$ alkyl;
each $R^{24}$ is independently selected at each occurrence from the group consisting of —$C_{1-6}$ alkyl, —N($R^{60}$)$_2$, and —($C_{1-3}$ alkyl)$_n$carbocyclyl;
each $R^{25}$ is independently selected at each occurrence from the group consisting of H and —$C_{1-6}$ alkyl, alternatively, two adjacent $R^{25}$ are taken together with the nitrogen atom to which they are attached to form a 3 to 7 membered heterocyclic ring;
each $R^{26}$ is a substituent attached to the heterocyclyl ring and is independently selected at each occurrence from the group consisting of H, halide, —CF$_3$, —OH, —CN, and —$C_{1-6}$ alkyl;
each $R^{27}$ is a substituent attached to the aryl ring and is independently selected at each occurrence from the group consisting of H, halide, —CF$_3$, —CN, and —$C_{1-6}$ alkyl;
each $R^{28}$ is independently selected at each occurrence from the group consisting of —$C_{1-6}$ alkyl, —N($R^{60}$)$_2$, and —($C_{1-3}$ alkyl)$_n$carbocyclyl;
each $R^{29}$ is independently selected at each occurrence from the group consisting of H and —$C_{1-6}$ alkyl;
each $R^{36}$ is a substituent attached to the heterocyclyl ring and is independently selected at each occurrence from the group consisting of H, halide, —OH, —CF$_3$, —CN, and —$C_{1-6}$ alkyl;
each $R^{60}$ is independently selected at each occurrence from the group consisting of H and —$C_{1-6}$ alkyl, alternatively, two adjacent $R^{60}$ are taken together with the nitrogen atom to which they are attached to form a 3- to 7-membered heterocyclic ring;
m is an integer of 1 to 4;
each n is independently an integer of 0 to 1;
each p is independently an integer of 1 to 10; and
each q is independently an integer of 1 to 5.

Some embodiments of the present disclosure include compounds of Formula VI:

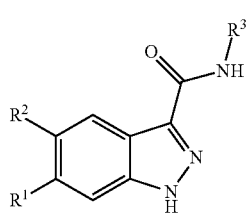

VI or salts, pharmaceutically acceptable salts, or prodrugs thereof,
wherein:
$R^1$ is selected from the group consisting of H, halide, and $C_{1-3}$ alkyl;
$R^2$ is selected from the group consisting of 6-10-membered heteroaryl($R^4$) and phenyl($R^5$)$_m$($R^6$);

R³ is

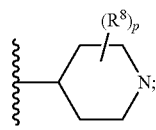

R⁴ is 1 substituent attached to the 6-10-membered heteroaryl and is selected from the group consisting of H, halide, —CN, unsubstituted —$C_{1-6}$ haloalkyl, —($C_{1-3}$ alkyl)$_n$ heterocyclyl($R^{22}$)$_p$, —O-aryl($R^{23}$)$_q$, —NHC(=O)$R^{24}$, and —($C_{1-6}$ alkyl)$_n$N($R^{25}$)$_2$;

each R⁵ is a substituent attached to the phenyl ring and independently selected at each occurrence from the group consisting of H and halide;

R⁶ is 1 substituent attached to the phenyl ring and selected from the group consisting of H, —($C_{1-3}$ alkyl)$_n$heterocyclyl ($R^{26}$)$_p$, —O-aryl($R^{27}$)$_q$, —NHC(=O)$R^{28}$, and —(CH$_2$)$_z$N ($R^{29}$)$_2$;

each R⁷ is a substituent attached to the carbocyclyl ring and is independently selected at each occurrence from the group consisting of H, halide, —CF$_3$, —CN, —N($R^{25}$)$_2$, and —$C_{1-6}$ alkyl;

each R⁸ is a substituent attached to either a carbon or a nitrogen on the heterocyclyl ring and is independently selected at each occurrence from the group consisting of H, halide, —($C_{1-3}$ alkyl)$_n$carbocyclyl($R^7$)$_p$, —CN, —N($R^{25}$)$_2$, —($C_{1-3}$ alkyl)$_n$aryl($R^{11}$)$_q$, -heterocyclyl($R^{31}$)$_p$, unsubstituted —$C_{1-6}$ haloalkyl, and unsubstituted —$C_{1-9}$ alkyl;

each R¹¹ is a substituent attached to the aryl ring and is independently selected at each occurrence from the group consisting of H, halide, —$C_{1-6}$ haloalkyl, —CN, and —$C_{1-6}$ alkyl;

each R²² is a substituent attached to the heterocyclyl ring and is independently selected at each occurrence from the group consisting of H, halide, —CF$_3$, —OH, —CH$_2$OH, —CN, —N($R^{25}$)$_2$, and —$C_{1-6}$ alkyl;

each R²³ is a substituent attached to the aryl ring and is independently selected at each occurrence from the group consisting of H, halide, —CF$_3$, —CN, and —$C_{1-6}$ alkyl;

each R²⁴ is independently selected at each occurrence from the group consisting of —$C_{1-6}$ alkyl, —N($R^{60}$)$_2$, and —($C_{1-3}$ alkyl)$_n$carbocyclyl;

each R²⁵ is independently selected at each occurrence from the group consisting of H and —$C_{1-6}$ alkyl, alternatively, two adjacent $R^{25}$ are taken together with the nitrogen atom to which they are attached to form a 3 to 7 membered heterocyclic ring;

each R²⁶ is a substituent attached to the heterocyclyl ring and is independently selected at each occurrence from the group consisting of H, halide, —CF$_3$, —OH, —CN, and —$C_{1-6}$ alkyl;

each R²⁷ is a substituent attached to the aryl ring and is independently selected at each occurrence from the group consisting of H, halide, —CF$_3$, —CN, and —$C_{1-6}$ alkyl;

each R²⁸ is independently selected at each occurrence from the group consisting of —$C_{1-6}$ alkyl, —N($R^{60}$)$_2$, and —($C_{1-3}$ alkyl)$_n$carbocyclyl;

each R²⁹ is independently selected at each occurrence from the group consisting of H and —$C_{1-6}$ alkyl;

each R³¹ is a substituent attached to the heterocyclyl ring and is independently selected at each occurrence from the group consisting of H and halide;

each R⁶⁰ is independently selected at each occurrence from the group consisting of H and —$C_{1-6}$ alkyl, alternatively, two adjacent R⁶ are taken together with the nitrogen atom to which they are attached to form a 3- to 7-membered heterocyclic ring;

m is an integer of 1 to 4;
each n is independently an integer of 0 to 1;
each p is independently an integer of 1 to 10;
each q is independently an integer of 1 to 5;
z is an integer of 1 to 5; and
with the proviso that a compound of Formula VI is not

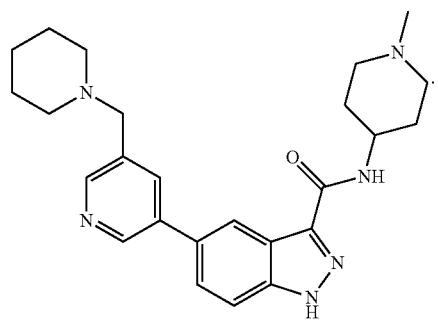 [SMILES: CN1CCC(NC(=O)c2n[nH]c3ccc(-c4cncc(CN5CCCCC5)c4)cc23)CC1]

Some embodiments of the present disclosure include compounds of Formula VII:

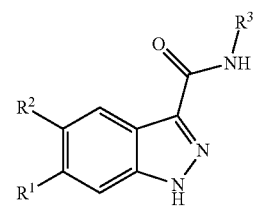

VII or salts, pharmaceutically acceptable salts, or prodrugs thereof,
wherein:
R¹ is selected from the group consisting of H, halide, and $C_{1-3}$ alkyl;
R² is selected from the group consisting of 6-10-membered heteroaryl(R⁴) and phenyl(R⁵)$_m$(R⁶);
R³ is

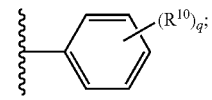

R⁴ is a one substituent to the 6-10-membered heteroaryl and selected from the group consisting of H, halide, —CN, unsubstituted —$C_{1-6}$ haloalkyl, —($C_{1-3}$ alkyl)$_n$heterocyclyl ($R^{22}$)$_p$, —O-aryl($R^{23}$)$_q$, —NHC(=O)$R^{24}$, and —($C_{1-6}$ alkyl)$_n$N($R^{25}$)$_2$;

each R⁵ is a substituent attached to the phenyl ring and independently selected at each occurrence from the group consisting of H and halide;

R⁶ is 1 substituent attached to the phenyl ring and selected from the group consisting of H, —($C_{1-3}$ alkyl)$_n$heterocyclyl ($R^{26}$)$_p$, —O-aryl($R^{27}$)$_q$, —NHC(=O)$R^{28}$, and —(CH$_2$)$_z$N ($R^{29}$)$_2$;

each R¹⁰ is a substituent attached to the aryl ring and is independently selected at each occurrence from the group consisting of Cl, Br, I, unsubstituted —$C_{1-6}$ haloalkyl, —$N(R^{40})(R^{41})$, unsubstituted —$C_{1-6}$ alkyl, and —$(C_{1-3}$ alkyl$)_n$heterocyclyl$(R^{31})_p$, wherein the heterocyclyl is selected from the group consisting of a 6-membered ring containing only N and C, a 5-membered ring containing C, N, O and S, a 4-membered ring containing C, N, O and S, and a 3-membered ring containing C, N, O and S;

each $R^{22}$ is a substituent attached to the heterocyclyl ring and is independently selected at each occurrence from the group consisting of H, halide, —$CF_3$, —OH, —$CH_2OH$, —CN, —$N(R^{25})_2$, and —$C_{1-6}$ alkyl;

each $R^{23}$ is a substituent attached to the aryl ring and is independently selected at each occurrence from the group consisting of H, halide, —$CF_3$, —CN, and —$C_{1-6}$ alkyl;

each $R^{24}$ is independently selected at each occurrence from the group consisting of —$C_{1-6}$ alkyl, —$N(R^{60})_2$, and —$(C_{1-3}$ alkyl$)_n$carbocyclyl;

each $R^{25}$ is independently selected at each occurrence from the group consisting of H and —$C_{1-6}$ alkyl, alternatively, two adjacent $R^{25}$ are taken together with the nitrogen atom to which they are attached to form a 3 to 7 membered heterocyclic ring;

each $R^{26}$ is a substituent attached to the heterocyclyl ring and is independently selected at each occurrence from the group consisting of H, halide, —$CF_3$, —OH, —CN, and —$C_{1-6}$ alkyl;

each $R^{27}$ is a substituent attached to the aryl ring and is independently selected at each occurrence from the group consisting of H, halide, —$CF_3$, —CN, and —$C_{1-6}$ alkyl;

each $R^{28}$ is independently selected at each occurrence from the group consisting of —$C_{1-6}$ alkyl, —$N(R^{60})_2$, and —$(C_{1-3}$ alkyl$)_n$carbocyclyl;

each $R^{29}$ is independently selected at each occurrence from the group consisting of H and —$C_{1-6}$ alkyl;

each $R^{31}$ is a substituent attached to the heterocyclyl ring and is independently selected at each occurrence from the group consisting of H, halide, —$C_{1-6}$ alkyl, and —$C_{1-6}$ haloalkyl;

each $R^{38}$ is independently selected at each occurrence from the group consisting of H, —$C_{1-6}$ alkyl, and -carbocyclyl;

each $R^{40}$ is a substituent attached to the nitrogen and is independently selected at each occurrence from the group consisting of H, unsubstituted —$C_{1-6}$ haloalkyl, and unsubstituted —$C_{1-6}$ alkyl;

each $R^{41}$ is a substituent attached to the nitrogen and is independently selected at each occurrence from the group consisting of H, unsubstituted —$C_{1-6}$ haloalkyl, unsubstituted —$C_{1-6}$ alkyl, and —$(C_{1-6}$ alkyl$)_n$N$(R^{38})_2$;

each $R^{60}$ is independently selected at each occurrence from the group consisting of H and —$C_{1-6}$ alkyl, alternatively, two adjacent $R^{60}$ are taken together with the nitrogen atom to which they are attached to form a 3- to 7-membered heterocyclic ring;

m is an integer of 1 to 4;

each n is independently an integer of 0 to 1;

each p is independently an integer of 1 to 10;

each q is independently an integer of 1 to 5; and z is an integer of 1 to 5.

Some embodiments of the present disclosure include compounds of Formula VIII:

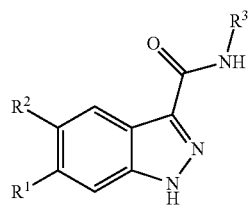

VIII or salts, pharmaceutically acceptable salts, or prodrugs thereof, wherein:

$R^1$ is selected from the group consisting of H, halide, and $C_{1-3}$ alkyl;

$R^2$ is selected from the group consisting of 6-10-membered heteroaryl$(R^4)$ and phenyl$(R^5)_m(R^6)$;

$R^3$ is an unsubstituted —$C_{1-9}$ alkyl;

$R^4$ is 1 substituent attached to the 6-10-membered heteroaryl and is selected from the group consisting of H, halide, unsubstituted —$C_{1-6}$ haloalkyl, —$(C_{1-3}$ alkyl$)_n$heterocyclyl$(R^{22})_p$, —O-aryl$(R^{23})_q$, —NHC(=O)$R^{24}$, and —$(C_{1-6}$ alkyl$)_n$N$(R^{25})_2$;

each $R^5$ is a substituent attached to the phenyl ring and independently selected at each occurrence from the group consisting of H and halide;

$R^6$ is 1 substituent attached to the phenyl ring and selected from the group consisting of H, —$(C_{1-3}$ alkyl$)_n$heterocyclyl$(R^{26})_p$, —O-aryl$(R^{27})_q$, —NHC(=O)$R^{28}$, and —$(CH_2)_z$N$(R^{29})_2$;

each $R^{22}$ is a substituent attached to the heterocyclyl ring and is independently selected at each occurrence from the group consisting of H, halide, —$CF_3$, —OH, —$CH_2OH$, —CN, —$N(R^{25})_2$, and —$C_{1-6}$ alkyl;

each $R^{23}$ is a substituent attached to the aryl ring and is independently selected at each occurrence from the group consisting of H, halide, —$CF_3$, —CN, and —$C_{1-6}$ alkyl;

each $R^{24}$ is independently selected at each occurrence from the group consisting of —$C_{1-6}$ alkyl, —$N(R^{60})_2$, and —$(C_{1-3}$ alkyl$)_n$carbocyclyl;

each $R^{25}$ is independently selected at each occurrence from the group consisting of H and —$C_{1-6}$ alkyl, alternatively, two adjacent $R^{25}$ are taken together with the nitrogen atom to which they are attached to form a 3 to 7 membered heterocyclic ring;

each $R^{26}$ is a substituent attached to the heterocyclyl ring and is independently selected at each occurrence from the group consisting of H, halide, —$CF_3$, —OH, —CN, and —$C_{1-6}$ alkyl;

each $R^{27}$ is a substituent attached to the aryl ring and is independently selected at each occurrence from the group consisting of H, halide, —$CF_3$, —CN, and —$C_{1-6}$ alkyl;

each $R^{28}$ is independently selected at each occurrence from the group consisting of —$C_{1-6}$ alkyl, —$N(R^{60})_2$, and —$(C_{1-3}$ alkyl$)_n$carbocyclyl;

each $R^{29}$ is independently selected at each occurrence from the group consisting of H and —$C_{1-6}$ alkyl;

each $R^{60}$ is independently selected at each occurrence from the group consisting of H and —$C_{1-6}$ alkyl, alternatively, two adjacent $R^{60}$ are taken together with the nitrogen atom to which they are attached to form a 3- to 7-membered heterocyclic ring;

m is an integer of 1 to 4;

each n is independently an integer of 0 to 1;

each p is independently an integer of 1 to 10;

each q is independently an integer of 1 to 5; and z is an integer of 1 to 5.

Some embodiments of the present disclosure include compounds of Formula IX:

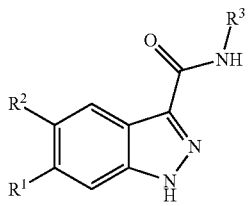

IX or salts, pharmaceutically acceptable salts, or prodrugs thereof, wherein:

$R^1$ is selected from the group consisting of H, halide, and —$C_{1-3}$ alkyl;

$R^2$ is selected from the group consisting of 6-10-membered heteroaryl($R^4$) and phenyl($R^5$)$_m$($R^6$);

with the proviso that $R^2$ is not

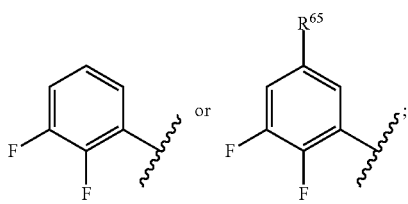

$R^3$ is selected from the group consisting of H, unsubstituted —$C_{1-9}$ alkyl, unsubstituted —$C_{1-9}$ haloalkyl, —($C_{1-6}$ alkyl)N($R^{68}$)$_2$, —($C_{2-6}$ alkyl)O($C_{1-6}$ alkyl), -carbocyclyl ($R^7$)$_p$, -monocyclic heterocyclyl($R^8$)$_p$, -spirocyclic heterocyclyl($R^8$)$_p$, —($C_{1-3}$ alkyl)heterocyclyl($R^9$)$_p$, -bicyclic aryl ($R^{10}$)$_q$, —($C_{1-3}$ alkyl)aryl($R^{10}$)$_q$,

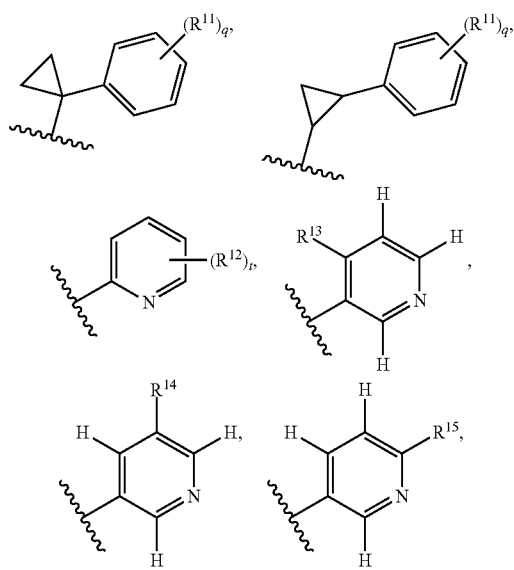

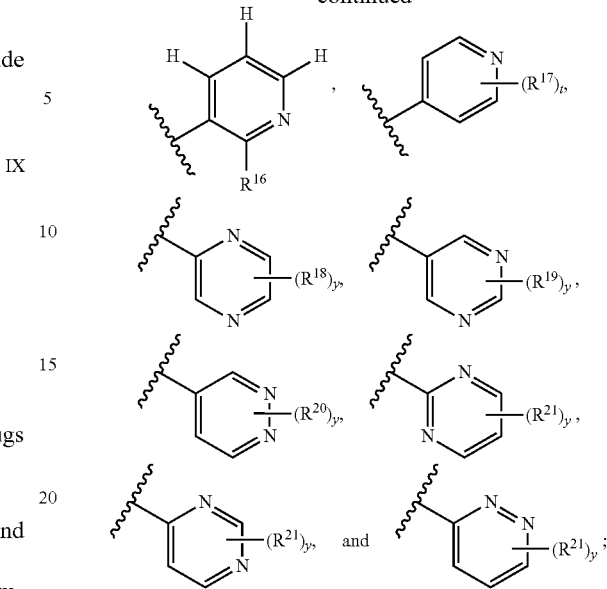

$R^4$ is 1 substituent attached to the 6-10-membered heteroaryl and is selected from the group consisting of H, Cl, Br, I, —CN, unsubstituted —$C_{1-6}$ haloalkyl, —($C_{1-3}$ alkyl)$_n$ heterocyclyl($R^{22}$)$_p$, —Oaryl($R^{23}$)$_q$, —NHC(=O)$R^{24}$, and —($C_{1-6}$ alkyl)$_n$N($R^{25}$)$_2$;

each $R^5$ is a substituent attached to the phenyl ring and independently selected at each occurrence from the group consisting of H and halide;

$R^6$ is 1 substituent attached to the phenyl ring and selected from the group consisting of H, —($C_{1-3}$ alkyl)$_n$heterocyclyl ($R^{26}$)$_p$, —O-aryl($R^{27}$)$_q$, —NHC(=O)$R^{28}$, and —(CH$_2$)$_z$N ($R^{29}$)$_2$;

each $R^7$ is a substituent attached to the carbocyclyl ring and is independently selected at each occurrence from the group consisting of H, halide, —CF$_3$, —CN, —N($R^{25}$)$_2$, and —$C_{1-6}$ alkyl;

each $R^8$ is a substituent attached to the heterocyclyl ring and is independently selected at each occurrence from the group consisting of H, halide, —($C_{1-3}$ alkyl)$_n$OR$^{30}$, —($C_{1-3}$ alkyl)carbocyclyl($R^7$)$_p$, —CN, —N($R^{25}$)$_2$, —($C_{1-3}$ alkyl)$_n$ aryl($R^{11}$)$_q$, -heterocyclyl($R^{31}$)$_p$, —C(=O)$R^{32}$, unsubstituted —$C_{1-6}$ haloalkyl, and unsubstituted —$C_{1-6}$ alkyl;

each $R^9$ is a substituent attached to the heterocyclyl ring and is independently selected at each occurrence from the group consisting of H, halide, —CN, -heterocyclyl($R^{31}$)$_p$, —C(=O)$R^{32}$, unsubstituted —$C_{1-6}$ haloalkyl, and unsubstituted —$C_{1-6}$ alkyl;

each $R^{10}$ is a substituent attached to the aryl ring and is independently selected at each occurrence from the group consisting of H, unsubstituted —$C_{1-6}$ haloalkyl, —CN, —($C_{1-3}$ alkyl)$_n$heterocyclyl($R^{31}$)$_p$, —($C_{1-6}$ alkyl)$_n$N($R^{40}$) ($R^{41}$), and unsubstituted —$C_{1-6}$ alkyl;

each $R^{11}$ is a substituent attached to the aryl ring and is independently selected at each occurrence from the group consisting of H, halide, —$C_{1-6}$ haloalkyl, —CN, and —$C_{1-6}$ alkyl;

each $R^{12}$ is a substituent attached to the pyridinyl ring and is independently selected at each occurrence from the group consisting of H, halide, —$C_{1-6}$ haloalkyl, —CN, —$C_{1-6}$ alkyl, —OR$^{34}$, —SO$_2$R$^{35}$, —($C_{1-3}$ alkyl)$_n$heterocyclyl ($R^{36}$)$_p$, —($C_{1-3}$ alkyl)$_n$aryl($R^{37}$)$_q$, —C(=O)N($R^{38}$)$_2$, —NHC(=O)$R^{39}$, and —($C_{1-6}$ alkyl)$_n$N($R^{40}$)($R^{41}$);

each $R^{13}$ is selected from the group consisting of unsubstituted —$C_{1-6}$ alkyl, unsubstituted —$C_{2-6}$ haloalkyl, CN, —$OR^{34}$, —$SO_2R^{35}$, —$(C_{1-3}$ alkyl$)_n$heterocyclyl$(R^{36})_p$, —$(C_{1-3}$ alkyl$)_n$aryl$(R^{37})_q$, —C(=O)N$(R^{38})_2$, —NHC(=O)$R^{42}$, and —$(C_{1-6}$ alkyl$)_n$N$(R^{40})(R^{41})$;

each $R^{14}$ is selected from the group consisting of unsubstituted —$C_{1-6}$ haloalkyl, CN, unsubstituted —$C_{1-6}$ alkyl, —$OR^{48}$, —$SO_2R^{35}$, —$(C_{2-3}$ alkyl$)_n$heterocyclyl$(R^{44})_p$, —$(C_{1-3}$ alkyl$)_n$aryl$(R^{45})_q$, —C(=O)N$(R^{38})_2$, —NHC(=O)$R^{39}$, and —$(C_{1-6}$ alkyl$)_n$N$(R^{46})(R^{47})$;

each $R^{15}$ is selected from the group consisting of unsubstituted —$C_{1-6}$ alkyl, —$OR^{43}$, —$(C_{2-3}$ alkyl)heterocyclyl$(R^{50})_p$, -aryl$(R^{51})_q$, —$(C_{1-3}$ alkyl)aryl$(R^{52})_q$, —C(=O)N$(R^{53})_2$, —NHC(=O)$R^{54}$, and —$(C_{1-6}$ alkyl$)_n$N$(R^{55})(R^{56})$;

each $R^{16}$ is selected from the group consisting of —CN, unsubstituted —$C_{1-6}$ alkyl, unsubstituted —$C_{2-6}$ haloalkyl, —$OR^{34}$, —$SO_2R^{35}$, —$(C_{1-3}$ alkyl$)_n$heterocyclyl$(R^{57})_p$, —$(C_{1-3}$ alkyl$)_n$aryl$(R^{37})_q$, —C(=O)N$(R^{38})_2$, —NHC(=O)$R^{39}$, and —$(C_{1-6}$ alkyl$)_n$N$(R^{40})(R^{41})$;

each $R^{17}$ is a substituent attached to the pyridinyl ring and is independently selected at each occurrence from the group consisting of —$C_{1-6}$ haloalkyl, —CN, —$C_{1-6}$ alkyl, —$OR^{34}$, —$SO_2R^{35}$, —$(C_{1-3}$ alkyl$)_n$heterocyclyl$(R^{36})_p$, —$(C_{1-3}$ alkyl$)_n$aryl$(R^{37})_q$, —C(=O)N$(R^{38})_2$, —NHC(=O)$R^{39}$, and —$(C_{1-6}$ alkyl$)_n$N$(R^{40})(R^{41})$;

each $R^{18}$ is a substituent attached to the heteroaryl ring and is independently selected at each occurrence from the group consisting of halide, —$C_{1-6}$ haloalkyl, —CN, —$C_{1-6}$ alkyl, —$OR^{34}$, —$SO_2R^{35}$, —$(C_{1-3}$ alkyl$)_n$heterocyclyl$(R^{36})_p$, —$(C_{1-3}$ alkyl$)_n$aryl$(R^{37})_q$, —C(=O)N$(R^{38})_2$, —NHC(=O)$R^{39}$, and —$(C_{1-6}$ alkyl$)_n$N$(R^{40})(R^{41})$;

each $R^{19}$ is a substituent attached to the heteroaryl ring and is independently selected at each occurrence from the group consisting of halide, —$C_{1-6}$ haloalkyl, —CN, —$C_{1-6}$ alkyl, —$OR^{34}$, —$SO_2R^{35}$, —$(C_{1-3}$ alkyl$)_n$heterocyclyl$(R^{36})_p$, —$(C_{1-3}$ alkyl$)_n$aryl$(R^{37})_q$, —C(=O)N$(R^{38})_2$, —NHC(=O)$R^{39}$, and —$(C_{1-6}$ alkyl$)_n$N$(R^{58})(R^{59})$;

each $R^{20}$ is a substituent attached to the heteroaryl ring and is independently selected at each occurrence from the group consisting of halide, —CN, unsubstituted —$C_{1-6}$ alkyl, unsubstituted —$C_{2-6}$ haloalkyl, —$OR^{34}$, —$SO_2R^{35}$, —$(C_{1-3}$ alkyl$)_n$heterocyclyl$(R^{36})_p$, —$(C_{1-3}$ alkyl$)_n$aryl$(R^{37})_q$, —C(=O)N$(R^{38})_2$, —NHC(=O)$R^{39}$, and —$(C_{1-6}$ alkyl$)_n$N$(R^{40})(R^{41})$;

each $R^{21}$ is a substituent attached to the heteroaryl ring and is independently selected at each occurrence from the group consisting of H, halide, —$C_{1-6}$ haloalkyl, —CN, —$C_{1-6}$ alkyl, —$OR^{34}$, —$SO_2R^{35}$, —$(C_{1-3}$ alkyl$)_n$heterocyclyl$(R^{36})_p$, —$(C_{1-3}$ alkyl$)_n$aryl$(R^{37})_q$, —C(=O)N$(R^{38})_2$, —NHC(=O)$R^{39}$, and —$(C_{1-6}$ alkyl$)_n$N$(R^{40})(R^{41})$;

each $R^{22}$ is a substituent attached to the heterocyclyl ring and is independently selected at each occurrence from the group consisting of H, halide, —$CF_3$, —OH, —$CH_2OH$, —CN, —N$(R^{25})_2$, and —$C_{1-6}$ alkyl;

each $R^{23}$ is a substituent attached to the aryl ring and is independently selected at each occurrence from the group consisting of H, halide, —$CF_3$, —CN, and —$C_{1-6}$ alkyl;

each $R^{24}$ is independently selected at each occurrence from the group consisting of —$C_{1-6}$ alkyl, —N$(R^{60})_2$, and —$(C_{1-3}$ alkyl$)_n$carbocyclyl;

each $R^{25}$ is independently selected at each occurrence from the group consisting of H and —$C_{1-6}$ alkyl, alternatively, two adjacent $R^{25}$ are taken together with the nitrogen atom to which they are attached to form a 3 to 7 membered heterocyclic ring;

each $R^{26}$ is a substituent attached to the heterocyclyl ring and is independently selected at each occurrence from the group consisting of H, halide, —$CF_3$, —OH, —CN, and —$C_{1-6}$ alkyl;

each $R^{27}$ is a substituent attached to the aryl ring and is independently selected at each occurrence from the group consisting of H, halide, —$CF_3$, —CN, and —$C_{1-6}$ alkyl;

each $R^{28}$ is independently selected at each occurrence from the group consisting of —$C_{1-6}$ alkyl, —N$(R^{60})_2$, and —$(C_{1-3}$ alkyl$)_n$carbocyclyl;

each $R^{29}$ is independently selected at each occurrence from the group consisting of H and —$C_{1-6}$ alkyl;

each $R^{30}$ is independently selected at each occurrence from the group consisting of H and —$C_{1-6}$ alkyl;

each $R^{31}$ is a substituent attached to the heterocyclyl ring and is independently selected at each occurrence from the group consisting of H and halide;

each $R^{32}$ is independently selected at each occurrence from the group consisting of —$C_{1-6}$ alkyl and -carbocyclyl;

each $R^{34}$ is independently selected at each occurrence from the group consisting of H, —$CF_3$, —$C_{1-6}$ alkyl, -heterocyclyl$(R^{61})_p$, and -aryl$(R^{62})_q$;

each $R^{35}$ is independently selected at each occurrence from the group consisting of —$CF_3$ and —$C_{1-6}$ alkyl;

each $R^{36}$ is a substituent attached to the heterocyclyl ring and is independently selected at each occurrence from the group consisting of H, halide, —OH, —$CF_3$, —CN, and —$C_{1-6}$ alkyl;

each $R^{37}$ is a substituent attached to the aryl ring and is independently selected at each occurrence from the group consisting of H, halide, —$CF_3$, —CN, and Me;

each $R^{38}$ is independently selected at each occurrence from the group consisting of H, —$C_{1-6}$ alkyl, and -carbocyclyl, alternatively, two adjacent $R^{38}$ are taken together with the nitrogen atom to which they are attached to form a 3 to 7 membered heterocyclic ring;

each $R^{39}$ is independently selected at each occurrence from the group consisting of —$C_{1-6}$ alkyl and —$(C_{1-3}$ alkyl$)_n$carbocyclyl;

each $R^{40}$ is a substituent attached to the nitrogen and is independently selected at each occurrence from the group consisting of H, unsubstituted —$C_{1-6}$ haloalkyl, and unsubstituted —$C_{1-6}$ alkyl;

each $R^{41}$ is a substituent attached to the nitrogen and is independently selected at each occurrence from the group consisting of H, unsubstituted —$C_{1-6}$ haloalkyl, unsubstituted —$C_{1-6}$ alkyl, and —$(C_{1-6}$ alkyl$)_n$N$(R^{38})_2$;

each $R^{42}$ is independently selected at each occurrence from the group consisting of —$C_{1-6}$ alkyl, —$(C_{1-3}$ alkyl)carbocyclyl, and —$(C_{4-6}$ carbocyclyl);

each $R^{43}$ is independently selected at each occurrence from the group consisting of —$C_{3-6}$ alkyl, -heterocyclyl$(R^{61})_p$, and -aryl$(R^{63})_q$;

each $R^{44}$ is a substituent attached to the heterocyclyl ring and is independently selected at each occurrence from the group consisting of H, halide, —OH, —$CF_3$, —CN, and —$C_{1-6}$ alkyl;

each $R^{45}$ is a substituent attached to the aryl ring and is independently selected at each occurrence from the group consisting of Cl, Br, I, —$CF_3$, —CN, and Me;

each $R^{46}$ is a substituent attached to the nitrogen and is independently selected at each occurrence from the group consisting of H and —$C_{2-6}$ alkyl;

each $R^{47}$ is a substituent attached to the nitrogen and is independently selected at each occurrence from the group consisting of H, —$C_{2-6}$ alkyl, and —$(C_{1-6}$ alkyl$)_n$N$(R^{38})_2$;

each $R^{48}$ is independently selected at each occurrence from the group consisting of —$C_{3-6}$ alkyl, -heterocyclyl $(R^{61})_p$, and -aryl$(R^{62})_q$;

each $R^{50}$ is a substituent attached to the heterocyclyl ring and is independently selected at each occurrence from the group consisting of H, halide, —OH, —$CF_3$, —CN, and —$C_{1-6}$ alkyl;

each $R^{51}$ is independently selected at each occurrence from the group consisting of Cl, Br, I, —$CF_3$, —CN, and Me;

each $R^{52}$ is independently selected at each occurrence from the group consisting of Cl, Br, I, —$CF_3$, —CN, and Me;

each $R^{53}$ is independently at each occurrence —$C_{1-4}$ alkyl;

each $R^{54}$ is independently selected at each occurrence from the group consisting of —$C_{1-6}$ alkyl, —($C_{1-3}$ alkyl) carbocyclyl, and —($C_{4-6}$ carbocyclyl);

each $R^{55}$ is a substituent attached to the nitrogen and is an unsubstituted —$C_{2-6}$ alkyl;

each $R^{56}$ is a substituent attached to the nitrogen and is independently selected at each occurrence from the group consisting of H, unsubstituted —$C_{2-6}$ alkyl, and —($C_{1-6}$ alkyl)$_n$N($R^{64}$)$_2$;

each $R^{57}$ is independently selected at each occurrence from the group consisting of H, halide, —OH, —$CF_3$, —CN, and —$C_{2-6}$ alkyl;

each $R^{58}$ is a substituent attached to the nitrogen and is independently selected at each occurrence from the group consisting of H and —$C_{1-6}$ alkyl;

each $R^{59}$ is a substituent attached to the nitrogen and is independently selected at each occurrence from the group consisting of —$C_{1-6}$ alkyl, and —($C_{1-6}$ alkyl)$_n$N($R^{38}$)$_2$;

each $R^{60}$ is independently selected at each occurrence from the group consisting of H and —$C_{1-6}$ alkyl, alternatively, two adjacent $R^{60}$ are taken together with the nitrogen atom to which they are attached to form a 3- to 7-membered heterocyclic ring;

each $R^{61}$ is a substituent attached to the heterocyclyl ring and is independently selected at each occurrence from the group consisting of H, halide, —OH, —$CF_3$, —CN, and —$C_{1-6}$ alkyl;

each $R^{62}$ is a substituent attached to the aryl ring and is independently selected at each occurrence from the group consisting of H, halide, —$CF_3$, —CN, and —$C_{1-6}$ alkyl;

each $R^{63}$ is a substituent attached to the aryl ring and is independently selected at each occurrence from the group consisting of —$CF_3$, —CN, and —$C_{1-6}$ alkyl;

each $R^{64}$ is independently selected at each occurrence from the group consisting of H and —$C_{2-6}$ alkyl, alternatively, two adjacent $R^{64}$ are taken together with the nitrogen atom to which they are attached to form a 3- to 7-membered heterocyclic ring;

$R^{65}$ is —($C_{1-3}$ alkyl)$_n$heterocyclyl($R^8$)$_p$;

each $R^{68}$ is independently selected at each occurrence from the group consisting of H and unsubstituted —$C_{1-6}$ alkyl;

m is an integer of 1 to 4;
each n is independently an integer of 0 to 1;
each p is independently an integer of 1 to 10;
each q is independently an integer of 1 to 5;
t is an integer of 1 to 4;
y is an integer of 1 to 3;
z is an integer of 1 to 5; and with the proviso that a compound of Formula IX is not a compound selected from the group consisting of:

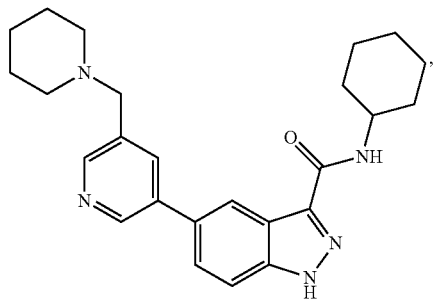

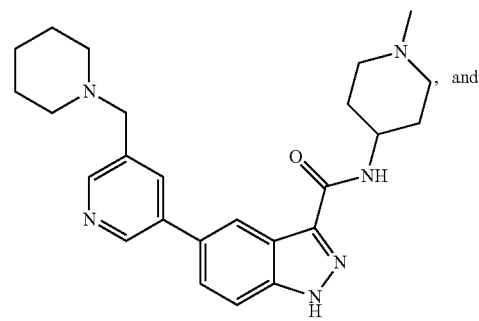, and

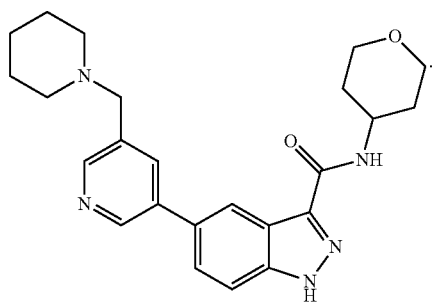.

Some embodiments of the present disclosure include compounds of Formula X:

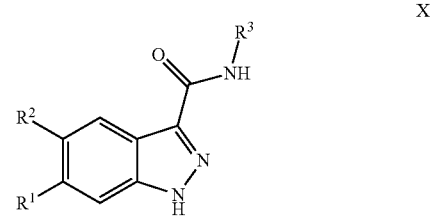

or salts, pharmaceutically acceptable salts, or prodrugs thereof,
wherein:

$R^1$ is selected from the group consisting of H, halide, and —$C_{1-3}$ alkyl;

$R^2$ is selected from the group consisting of 6-10-membered heteroaryl($R^4$) and phenyl($R^5$)$_m$($R^6$);

with the proviso that $R^2$ is not

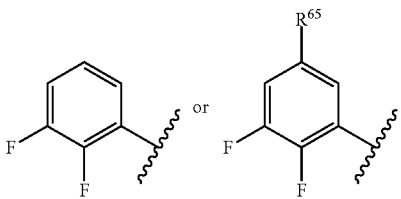

$R^3$ is selected from the group consisting of H, unsubstituted $C_{1-9}$ alkyl, -unsubstituted —$C_{1-9}$ haloalkyl, —$(C_{1-6}$ alkyl)$N(R^{68})_2$, —$(C_{2-6}$ alkyl)$O(C_{1-6}$ alkyl), -carbocyclyl$(R^7)_p$, -monocyclic heterocyclyl$(R^8)_p$, -spirocyclic heterocyclyl$(R^8)_p$, —$(C_{1-3}$ alkyl)heterocyclyl$(R^9)_p$, -bicyclic aryl$(R^{10})_q$, —$(C_{1-3}$ alkyl)aryl$(R^{10})_q$,

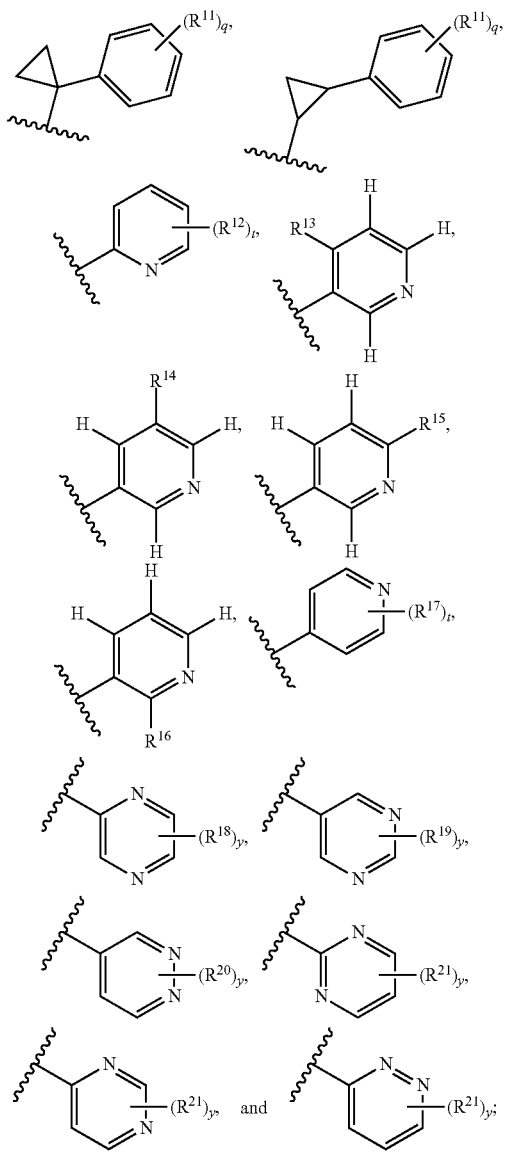

$R^4$ is 1 substituent attached to the 6-10-membered heteroaryl and is selected from the group consisting of unsubstituted —$C_{1-6}$ haloalkyl, —$(C_{1-3}$ alkyl)$_n$heterocyclyl$(R^{22})_p$, —O-aryl$(R^{23})_q$, —NHC(=O)$R^{24}$, and —$(C_{1-6}$ alkyl)$_n$N$(R^{25})_2$;

each $R^5$ is a substituent attached to the phenyl ring and independently selected at each occurrence from the group consisting of H and halide;

$R^6$ is 1 substituent attached to the phenyl ring and selected from the group consisting of H, —$(C_{1-3}$ alkyl)$_n$heterocyclyl$(R^{26})_p$, —O-aryl$(R^{27})_q$, —NHC(=O)$R^{28}$, and —$(CH_2)_z$N$(R^{29})_2$;

each $R^7$ is a substituent attached to the carbocyclyl ring and is independently selected at each occurrence from the group consisting of H, halide, —$CF_3$, —CN, —N$(R^{25})_2$, and —$C_{1-6}$ alkyl;

each $R^8$ is a substituent attached to the heterocyclyl ring and is independently selected at each occurrence from the group consisting of H, halide, —$(C_{1-3}$ alkyl)$_n$O$R^{30}$, —$(C_{1-3}$ alkyl)carbocyclyl$(R^7)_p$, —CN, —N$(R^{25})_2$, —$(C_{1-3}$ alkyl)$_n$aryl$(R^{11})_q$, -heterocyclyl$(R^{31})_p$, —C(=O)$R^{32}$, unsubstituted —$C_{1-6}$ haloalkyl, and unsubstituted —$C_{1-6}$ alkyl;

each $R^9$ is a substituent attached to the heterocyclyl ring and is independently selected at each occurrence from the group consisting of H, halide, —CN, -heterocyclyl$(R^{31})_p$, —C(=O)$R^{32}$, unsubstituted —$C_{1-6}$ haloalkyl, and unsubstituted —$C_{1-6}$ alkyl;

each $R^{10}$ is a substituent attached to the aryl ring and is independently selected at each occurrence from the group consisting of H, unsubstituted —$C_{1-6}$ haloalkyl, —CN, —$(C_{1-3}$ alkyl)$_n$heterocyclyl$(R^{31})_p$, —$(C_{1-6}$ alkyl)$_n$N$(R^{40})(R^{41})$, and unsubstituted —$C_{1-6}$ alkyl;

each $R^{11}$ is a substituent attached to the aryl ring and is independently selected at each occurrence from the group consisting of H, halide, —$C_{1-6}$ haloalkyl, —CN, and —$C_{1-6}$ alkyl;

each $R^{12}$ is a substituent attached to the pyridinyl ring and is independently selected at each occurrence from the group consisting of H, halide, —$C_{1-6}$ haloalkyl, —CN, —$C_{1-6}$ alkyl, —O$R^{34}$, —SO$_2R^{35}$, —$(C_{1-3}$ alkyl)$_n$heterocyclyl$(R^{36})_p$, —$(C_{1-3}$ alkyl)$_n$aryl$(R^{37})_q$, —C(=O)N$(R^{38})_2$, —NHC(=O)$R^{39}$, and —$(C_{1-6}$ alkyl)$_n$N$(R^{40})(R^{41})$;

each $R^{13}$ is selected from the group consisting of Cl, Br, I, unsubstituted —$C_{1-6}$ alkyl, unsubstituted —$C_{2-6}$ haloalkyl, CN, —O$R^{34}$, —SO$_2R^{35}$, —$(C_{1-3}$ alkyl)$_n$heterocyclyl$(R^{36})_p$, —$(C_{1-3}$ alkyl)$_n$aryl$(R^{37})_q$, —C(=O)N$(R^{38})_2$, —NHC(=O)$R^{42}$, and —$(C_{1-6}$ alkyl)$_n$N$(R^{40})(R^{41})$;

each $R^{14}$ is selected from the group consisting of Cl, Br, I, unsubstituted —$C_{1-6}$ haloalkyl, CN, unsubstituted —$C_{1-6}$ alkyl, —O$R^{48}$, —SO$_2R^{35}$, —$(C_{2-3}$ alkyl)$_n$heterocyclyl$(R^{44})_p$, —$(C_{1-3}$ alkyl)$_n$aryl$(R^{45})_q$, —C(=O)N$(R^{38})_2$, —NHC(=O)$R^{39}$, and —$(C_{1-6}$ alkyl)$_n$N$(R^{46})(R^{47})$;

each $R^{15}$ is selected from the group consisting of halide, unsubstituted —$C_{1-6}$ alkyl, unsubstituted —$C_{2-6}$ haloalkyl, —O$R^{43}$, —$(C_{2-3}$ alkyl)heterocyclyl$(R^{50})_p$, -aryl$(R^{51})_q$, —$(C_{1-3}$ alkyl)aryl$(R^{52})_q$, —C(=O)N$(R^{53})_2$, —NHC(=O)$R^{54}$, and —$(C_{1-6}$ alkyl)$_n$N$(R^{55})(R^{56})$;

each $R^{16}$ is selected from the group consisting of halide, —CN, unsubstituted —$C_{1-6}$ alkyl, unsubstituted —$C_{2-6}$ haloalkyl, —O$R^{34}$, —SO$_2R^{35}$, —$(C_{1-3}$ alkyl)$_n$heterocyclyl$(R^{57})_p$, —$(C_{1-3}$ alkyl)$_n$aryl$(R^{37})_q$, —C(=O)N$(R^{38})_2$, —NHC(=O)$R^{39}$, and —$(C_{1-6}$ alkyl)$_n$N$(R^{40})(R^{41})$;

each $R^{17}$ is a substituent attached to the pyridinyl ring and is independently selected at each occurrence from the group consisting of halide, —$C_{1-6}$ haloalkyl, —CN, —$C_{1-6}$ alkyl, —O$R^{34}$, —SO$_2R^{35}$, —$(C_{1-3}$ alkyl)$_n$heterocyclyl$(R^{36})_p$, —$(C_{1-3}$ alkyl)$_n$aryl$(R^{37})_q$, —C(=O)N$(R^{38})_2$, —NHC(=O)$R^{39}$, and —$(C_{1-6}$ alkyl)$_n$N$(R^{40})(R^{41})$;

each $R^{18}$ is a substituent attached to the heteroaryl ring and is independently selected at each occurrence from the group consisting of halide, —$C_{1-6}$ haloalkyl, —CN, —$C_{1-6}$ alkyl, —$OR^{34}$, —$SO_2R^{35}$, —$(C_{1-3}$ alkyl$)_n$heterocyclyl$(R^{36})_p$, —$(C_{1-3}$ alkyl$)_n$aryl$(R^{37})_q$, —$C(=O)N(R^{38})_2$, —$NHC(=O)R^{39}$, and —$(C_{1-6}$ alkyl$)_n N(R^{40})(R^{41})$;

each $R^{19}$ is a substituent attached to the heteroaryl ring and is independently selected at each occurrence from the group consisting of halide, —$C_{1-6}$ haloalkyl, —CN, —$C_{1-6}$ alkyl, —$OR^{34}$, —$SO_2R^{35}$, —$(C_{1-3}$ alkyl$)_n$heterocyclyl$(R^{36})_p$, —$(C_{1-3}$ alkyl$)_n$aryl$(R^{37})_q$, —$C(=O)N(R^{38})_2$, —$NHC(=O)R^{39}$, and —$(C_{1-6}$ alkyl$)_n N(R^{58})(R^{59})$;

each $R^{20}$ is a substituent attached to the heteroaryl ring and is independently selected at each occurrence from the group consisting of halide, —CN, unsubstituted —$C_{1-6}$ alkyl, unsubstituted —$C_{2-6}$ haloalkyl, —$OR^{34}$, —$SO_2R^{35}$, —$(C_{1-3}$ alkyl$)_n$heterocyclyl$(R^{36})_p$, —$(C_{1-3}$ alkyl$)_n$aryl$(R^{37})_q$, —$C(=O)N(R^{38})_2$, —$NHC(=O)R^{39}$, and —$(C_{1-6}$ alkyl$)_n N(R^{40})(R^{41})$;

each $R^{21}$ is a substituent attached to the heteroaryl ring and is independently selected at each occurrence from the group consisting of H, halide, —$C_{1-6}$ haloalkyl, —CN, —$C_{1-6}$ alkyl, —$OR^{34}$, —$SO_2R^{35}$, —$(C_{1-3}$ alkyl$)_n$heterocyclyl$(R^{36})_p$, —$(C_{1-3}$ alkyl$)_n$aryl$(R^{37})_q$, —$C(=O)N(R^{38})_2$, —$NHC(=O)R^{39}$, and —$(C_{1-6}$ alkyl$)_n N(R^{40})(R^{41})$;

each $R^{22}$ is a substituent attached to the heterocyclyl ring and is independently selected at each occurrence from the group consisting of H, halide, —$CF_3$, —OH, —$CH_2OH$, —CN, —$N(R^{25})_2$, and —$C_{1-6}$ alkyl;

each $R^{23}$ is a substituent attached to the aryl ring and is independently selected at each occurrence from the group consisting of H, halide, —$CF_3$, —CN, and —$C_{1-6}$ alkyl;

each $R^{24}$ is independently selected at each occurrence from the group consisting of —$C_{1-6}$ alkyl, —$N(R^{60})_2$, and —$(C_{1-3}$ alkyl$)_n$carbocyclyl;

each $R^{25}$ is independently selected at each occurrence from the group consisting of H and —$C_{1-6}$ alkyl, alternatively, two adjacent $R^{25}$ are taken together with the nitrogen atom to which they are attached to form a 3 to 7 membered heterocyclic ring;

each $R^{26}$ is a substituent attached to the heterocyclyl ring and is independently selected at each occurrence from the group consisting of H, halide, —$CF_3$, —OH, —CN, and —$C_{1-6}$ alkyl;

each $R^{27}$ is a substituent attached to the aryl ring and is independently selected at each occurrence from the group consisting of H, halide, —$CF_3$, —CN, and —$C_{1-6}$ alkyl;

each $R^{28}$ is independently selected at each occurrence from the group consisting of —$C_{1-6}$ alkyl, —$N(R^{60})_2$, and —$(C_{1-3}$ alkyl$)_n$carbocyclyl;

each $R^{29}$ is independently selected at each occurrence from the group consisting of H and —$C_{1-6}$ alkyl;

each $R^{30}$ is independently selected at each occurrence from the group consisting of H and —$C_{1-6}$ alkyl;

each $R^{31}$ is a substituent attached to the heterocyclyl ring and is independently selected at each occurrence from the group consisting of H and halide;

each $R^{32}$ is independently selected at each occurrence from the group consisting of —$C_{1-6}$ alkyl and -carbocyclyl;

each $R^{34}$ is independently selected at each occurrence from the group consisting of H, —$CF_3$, —$C_{1-6}$ alkyl, -heterocyclyl$(R^{61})_p$, and -aryl$(R^{62})_q$;

each $R^{35}$ is independently selected at each occurrence from the group consisting of —$CF_3$ and —$C_{1-6}$ alkyl;

each $R^{36}$ is a substituent attached to the heterocyclyl ring and is independently selected at each occurrence from the group consisting of H, halide, —OH, —$CF_3$, —CN, and —$C_{1-6}$ alkyl;

each $R^{37}$ is a substituent attached to the aryl ring and is independently selected at each occurrence from the group consisting of H, halide, —$CF_3$, —CN, and Me;

each $R^{38}$ is independently selected at each occurrence from the group consisting of H, —$C_{1-6}$ alkyl, and -carbocyclyl, alternatively, two adjacent $R^{38}$ are taken together with the nitrogen atom to which they are attached to form a 3 to 7 membered heterocyclic ring;

each $R^{39}$ is independently selected at each occurrence from the group consisting of —$C_{1-6}$ alkyl and —$(C_{1-3}$ alkyl$)_n$carbocyclyl;

each $R^{40}$ is a substituent attached to the nitrogen and is independently selected at each occurrence from the group consisting of H, unsubstituted —$C_{1-6}$ haloalkyl, and unsubstituted —$C_{1-6}$ alkyl;

each $R^{41}$ is a substituent attached to the nitrogen and is independently selected at each occurrence from the group consisting of H, unsubstituted —$C_{1-6}$ haloalkyl, unsubstituted —$C_{1-6}$ alkyl, and —$(C_{1-6}$ alkyl$)_n N(R^{38})_2$;

each $R^{42}$ is independently selected at each occurrence from the group consisting of —$C_{1-6}$ alkyl, —$(C_{1-3}$ alkyl) carbocyclyl, and —$(C_{4-6}$ carbocyclyl);

each $R^{43}$ is independently selected at each occurrence from the group consisting of —$C_{3-6}$ alkyl, -heterocyclyl $(R^{61})_p$, and -aryl$(R^{63})_q$;

each $R^{44}$ is a substituent attached to the heterocyclyl ring and is independently selected at each occurrence from the group consisting of H, halide, —OH, —$CF_3$, —CN, and —$C_{1-6}$ alkyl;

each $R^{45}$ is a substituent attached to the aryl ring and is independently selected at each occurrence from the group consisting of Cl, Br, I, —$CF_3$, —CN, and Me;

each $R^{46}$ is a substituent attached to the nitrogen and is independently selected at each occurrence from the group consisting of H and —$C_{2-6}$ alkyl;

each $R^{47}$ is a substituent attached to the nitrogen and is independently selected at each occurrence from the group consisting of H, —$C_{2-6}$ alkyl, and —$(C_{1-6}$ alkyl$)_n N(R^{38})_2$;

each $R^{48}$ is independently selected at each occurrence from the group consisting of —$C_{3-6}$ alkyl, -heterocyclyl $(R^{61})_p$, and -aryl$(R^{62})_q$;

each $R^{50}$ is a substituent attached to the heterocyclyl ring and is independently selected at each occurrence from the group consisting of H, halide, —OH, —$CF_3$, —CN, and —$C_{1-6}$ alkyl;

each $R^{51}$ is independently selected at each occurrence from the group consisting of Cl, Br, I, —$CF_3$, —CN, and Me;

each $R^{52}$ is independently selected at each occurrence from the group consisting of Cl, Br, I, —$CF_3$, —CN, and Me;

each $R^{53}$ is independently at each occurrence —$C_{1-4}$ alkyl;

each $R^{54}$ is independently selected at each occurrence from the group consisting of —$C_{1-6}$ alkyl, —$(C_{1-3}$ alkyl) carbocyclyl, and —$(C_{4-6}$ carbocyclyl);

each $R^{55}$ is a substituent attached to the nitrogen and is an unsubstituted —$C_{2-6}$ alkyl;

each $R^{56}$ is a substituent attached to the nitrogen and is independently selected at each occurrence from the group consisting of H, unsubstituted —$C_{2-6}$ alkyl, and —$(C_{1-6}$ alkyl$)_n N(R^{64})_2$;

each $R^{57}$ is independently selected at each occurrence from the group consisting of H, halide, —OH, —CF$_3$, —CN, and —C$_{2-6}$ alkyl;

each $R^{58}$ is a substituent attached to the nitrogen and is independently selected at each occurrence from the group consisting of H and —C$_{1-6}$ alkyl;

each $R^{59}$ is a substituent attached to the nitrogen and is independently selected at each occurrence from the group consisting of —C$_{1-6}$ alkyl, and —(C$_{1-6}$ alkyl)$_n$N(R$^{38}$)$_2$;

each $R^{60}$ is independently selected at each occurrence from the group consisting of H and —C$_{1-6}$ alkyl, alternatively, two adjacent $R^{60}$ are taken together with the nitrogen atom to which they are attached to form a 3- to 7-membered heterocyclic ring;

each $R^{61}$ is a substituent attached to the heterocyclyl ring and is independently selected at each occurrence from the group consisting of H, halide, —OH, —CF$_3$, —CN, and —C$_{1-6}$ alkyl;

each $R^{62}$ is a substituent attached to the aryl ring and is independently selected at each occurrence from the group consisting of H, halide, —CF$_3$, —CN, and —C$_{1-6}$ alkyl;

each $R^{63}$ is a substituent attached to the aryl ring and is independently selected at each occurrence from the group consisting of —CF$_3$, —CN, and —C$_{1-6}$ alkyl;

each $R^{64}$ is independently selected at each occurrence from the group consisting of H and —C$_{2-6}$ alkyl, alternatively, two adjacent $R^{64}$ are taken together with the nitrogen atom to which they are attached to form a 3- to 7-membered heterocyclic ring;

$R^{65}$ is —(C$_{1-3}$ alkyl)$_n$heterocyclyl(R$^8$)$_p$;

each $R^{68}$ is independently selected at each occurrence from the group consisting of H and unsubstituted —C$_{1-6}$ alkyl;

m is an integer of 1 to 4;
each n is independently an integer of 0 to 1;
each p is independently an integer of 1 to 10;
each q is independently an integer of 1 to 5;
t is an integer of 1 to 4;
y is an integer of 1 to 3;
z is an integer of 1 to 5; and
with the proviso that a compound of Formula X is not a compound selected from the group consisting of:

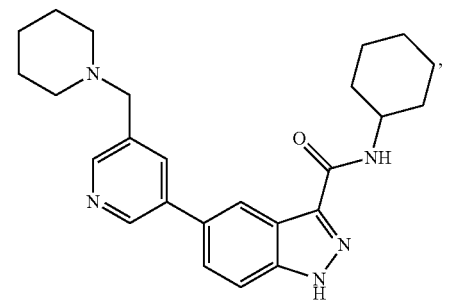

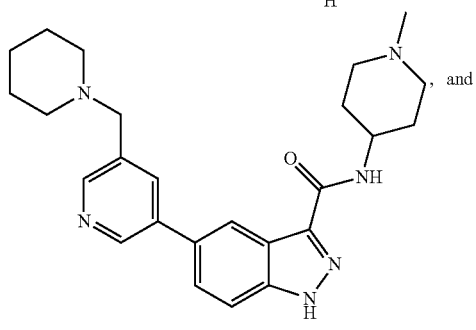

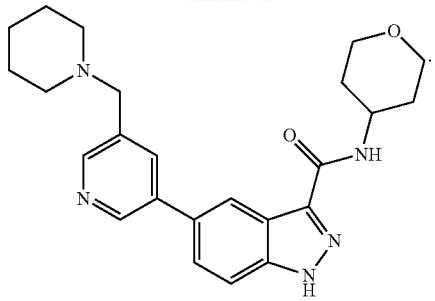

In some embodiments of Formulas I, V, VI, VII, VIII, IX, and X, m is an integer of 1 to 4.

In some embodiments of Formulas I, II, III, IV, V, VI, VII, VIII, IX, and X, each n is independently an integer of 0 to 1.

In some embodiments of Formulas I, II, III, IV, V, VI, VII, VIII, IX, and X, n is 1.

In some embodiments of Formulas I, II, III, IV, V, VI, VII, VIII, IX, and X, n is 0.

In some embodiments of Formulas I, II, III, IV, V, VI, VII, VIII, IX, and X, each p is independently an integer of 1 to 10.

In some embodiments of Formulas I, II, III, IV, V, VI, VII, VIII, IX, and X, each p is independently an integer of 1 to 4.

In some embodiments of Formulas I, II, III, IV, V, VI, VII, VIII, IX, and X, each p is independently an integer of 1 to 2.

In some embodiments of Formulas I, II, III, IV, V, VI, VII, VIII, IX, and X, p is 1.

In some embodiments of Formulas I, II, III, IV, V, VI, VII, VIII, IX, and X, each q is independently an integer of 1 to 5.

In some embodiments of Formulas I, II, III, IV, V, VI, VII, VIII, IX, and X, each q is independently an integer of 1 to 3.

In some embodiments of Formulas I, II, III, IV, V, VI, VII, VIII, IX, and X, each q is independently an integer of 1 to 2.

In some embodiments of Formulas I, II, III, IV, V, VI, VII, VIII, IX, and X, q is 1.

In some embodiments of Formulas I, II, III, IV, IX, and X, each t is independently an integer of 1 to 4.

In some embodiments of Formulas I, II, III, IV, IX, and X, each t is independently an integer of 1 to 3.

In some embodiments of Formulas I, II, III, IV, IX, and X, each t is independently an integer of 1 to 2.

In some embodiments of Formulas I, II, III, IV, IX, and X, t is 1.

In some embodiments of Formulas I, III, IV, IX, and X, each y is independently an integer of 1 to 3.

In some embodiments of Formulas I, III, IV, IX, and X, each y is independently an integer of 1 to 2.

In some embodiments of Formulas I, III, IV, IX, and X, y is 1.

In some embodiments of Formulas I, VI, VII, VIII, IX, and X, z is an integer of 1 to 5.

In some embodiments of Formulas I, VI, VII, VIII, IX, and X, z is an integer of 1 to 2.

In some embodiments of Formulas I, VI, VII, VIII, IX, and X, z is 1.

In some embodiments of Formulas I, II, III, IV, V, VI, VII, VIII, IX, and X, $R^1$ is selected from the group consisting of H, F, and Me.

In some embodiments of Formulas I, II, III, IV, V, VI, VII, VIII, IX, and X, $R^1$ is H.

In some embodiments of Formulas I, II, III, IV, V, VI, VII, VIII, IX, and X, $R^1$ is F.

In some embodiments of Formulas I, III, IV, V, VI, VII, VIII, IX, and X, $R^2$ is a 6-membered heteroaryl($R^4$).

In some embodiments of Formulas I, III, IV, V, VI, VII, VIII, IX, and X, $R^2$ is a 10-membered heteroaryl($R^4$).

In some embodiments of Formulas I, III, IV, V, VI, VII, VIII, IX, and X, $R^2$ is -pridinyl($R^4$).

In some embodiments of Formulas I, III, IV, V, VI, VII, VIII, IX, and X, $R^2$ is -pridin-2-yl($R^4$).

In some embodiments of Formulas I, III, IV, V, VI, VII, VIII, IX, and X, $R^2$ is -pridin-3-yl($R^4$).

In some embodiments of Formulas I, III, IV, V, VI, VII, VIII, IX, and X, $R^2$ is -pridin-4-yl($R^4$).

In some embodiments of Formulas I, III, IV, V, VI, VII, VIII, IX, and X, $R^2$ is -isoquinolinyl($R^4$).

In some embodiments of Formulas I, III, IV, V, VI, VII, VIII, IX, and X, $R^2$ is -isoquinolin-4-yl($R^4$).

In some embodiments of Formulas I, III, IV, V, VI, VII, VIII, IX, and X, $R^2$ is -pyrimidinyl($R^4$).

In some embodiments of Formulas I, III, IV, V, VI, VII, VIII, IX, and X, $R^2$ is -pyrimidin-5-yl($R^4$).

In some embodiments of Formulas I, III, IV, V, VI, VII, VIII, IX, and X, $R^2$ is -pyrazinyl($R^4$).

In some embodiments of Formulas I, III, IV, V, VI, VII, VIII, IX, and X, $R^2$ is -pyrazin-2-yl($R^4$).

In some embodiments of Formulas I, III, IV, V, VI, VII, VIII, IX, and X, $R^2$ is -isoquinolinyl($R^4$).

In some embodiments of Formulas I, III, IV, V, VI, VII, VIII, IX, and X, $R^4$ is H.

In some embodiments of Formulas I, III, IV, V, VI, VII, VIII, IX, and X, $R^4$ is Cl.

In some embodiments of Formulas I, III, IV, V, VI, VII, VIII, IX, and X, $R^4$ is —($C_{1-3}$ alkyl)$_n$heterocyclyl($R^{22}$)$_p$.

In some embodiments of Formulas I, III, IV, V, VI, VII, VIII, IX, and X, $R^4$ is —($CH_2$)heterocyclyl($R^{22}$)$_p$.

In some embodiments of Formulas I, III, IV, V, VI, VII, VIII, IX, and X, $R^4$ is selected from the group consisting of

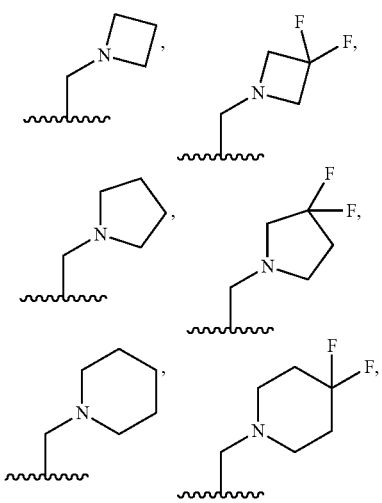

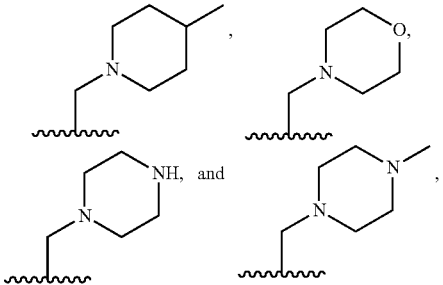

In some embodiments of Formulas I, III, IV, V, VI, VII, VIII, IX, and X, $R^4$ is -heterocyclyl($R^{22}$)$_p$.

In some embodiments of Formulas I, III, IV, V, VI, VII, VIII, IX, and X, $R^4$ is selected from the group consisting of

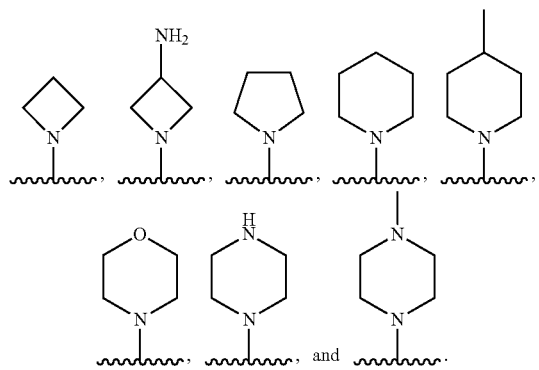

In some embodiments of Formulas I, III, IV, V, VI, VII, VIII, IX, and X, $R^4$ is —O-aryl($R^{23}$)$_q$.

In some embodiments of Formulas I, III, IV, V, VI, VII, VIII, IX, and X, $R^4$ is —O-phenyl($R^{23}$)$_q$.

In some embodiments of Formulas I, III, IV, V, VI, VII, VIII, IX, and X, $R^4$ is —NHC(=O)$R^{24}$.

In some embodiments of Formulas I, III, IV, V, VI, VII, VIII, IX, and X, $R^4$ is —($C_{1-6}$ alkyl)$_n$N($R^{25}$)$_2$.

In some embodiments of Formulas I, III, IV, V, VI, VII, VIII, IX, and X, $R^4$ is —($CH_2$)N($R^{25}$)$_2$.

In some embodiments of Formulas I, III, IV, V, VI, VII, VIII, IX, and X, $R^4$ is —($CH_2$)N($R^{25}$)$_2$ and $R^{25}$ is independently —$C_{1-2}$ alkyl.

In some embodiments of Formulas I, III, IV, V, VI, VII, VIII, IX, and X, $R^4$ is —($CH_2$)N(Me)$_2$.

In some embodiments of Formulas I, III, IV, V, VI, VII, VIII, IX, and X, $R^2$ is -pridinyl($R^4$) and $R^4$ is —($C_{1-3}$ alkyl)$_n$heterocyclyl($R^{22}$)$_p$.

In some embodiments of Formulas I, III, IV, V, VI, VII, VIII, IX, and X, $R^2$ is -pridin-3-yl($R^4$) and $R^4$ is —($CH_2$)heterocyclyl($R^{22}$)$_p$.

In some embodiments of Formulas I, III, IV, V, VI, VII, VIII, IX, and X, $R^2$ is -pridin-3-yl($R^4$) and $R^4$ is selected from the group consisting of

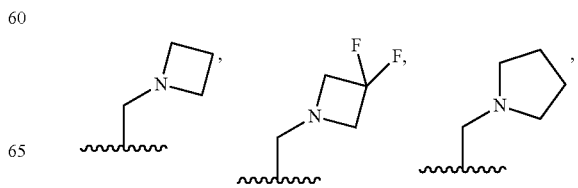

-continued

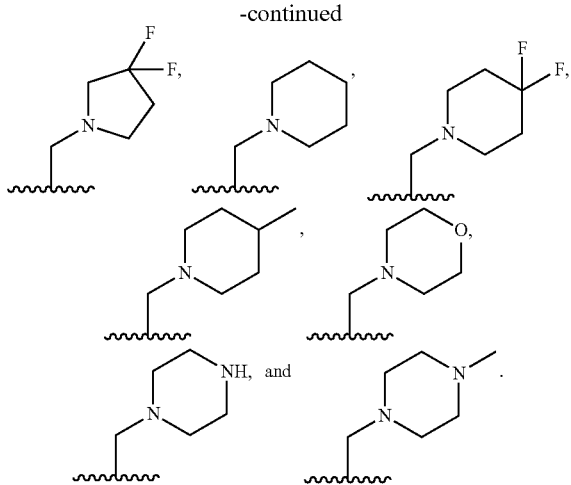

In some embodiments of Formulas I, III, IV, V, VI, VII, VIII, IX, and X, $R^2$ is -pridin-3-yl($R^4$) and $R^4$ is -heterocyclyl($R^{22}$)$_p$.

In some embodiments of Formulas I, III, IV, V, VI, VII, VIII, IX, and X, $R^2$ is -pridin-3-yl($R^4$) and $R^4$ is selected from the group consisting of

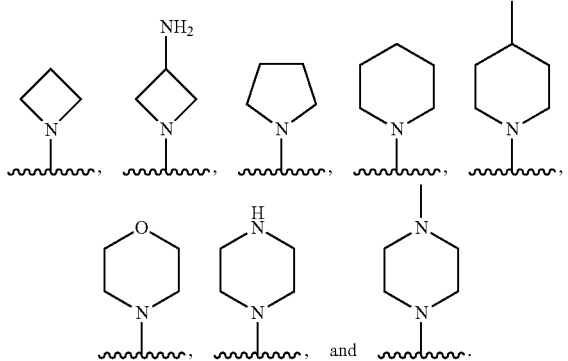

In some embodiments of Formulas I, III, IV, V, VI, VII, VIII, IX, and X, $R^2$ is -pridinyl($R^4$) and $R^4$ is —O-aryl($R^{23}$)$_q$.

In some embodiments of Formulas I, III, IV, V, VI, VII, VIII, IX, and X, $R^2$ is -pridinyl($R^4$) and $R^4$ is —O-phenyl($R^{23}$)$_q$.

In some embodiments of Formulas I, III, IV, V, VI, VII, VIII, IX, and X, $R^2$ is -pridinyl($R^4$) and $R^4$ is —NHC(=O)$R^{24}$.

In some embodiments of Formulas I, III, IV, V, VI, VII, VIII, IX, and X, $R^2$ is -pridinyl($R^4$) and $R^4$ is —($C_{1-6}$ alkyl)$_n$N($R^{25}$)$_2$.

In some embodiments of Formulas I, III, IV, V, VI, VII, VIII, IX, and X, $R^2$ is -pridinyl($R^4$) and $R^4$ is —($CH_2$)N($R^{25}$)$_2$.

In some embodiments of Formulas I, III, IV, V, VI, VII, VIII, IX, and X, $R^2$ is -pridin-3-yl($R^4$) and $R^4$ is —($CH_2$)N($R^{25}$)$_2$ and $R^{25}$ is independently —$C_{1-2}$ alkyl.

In some embodiments of Formulas I, III, IV, V, VI, VII, VIII, IX, and X, $R^2$ is -pridin-3-yl($R^4$) and $R^4$ is —($CH_2$)N(Me)$_2$.

In some embodiments of Formulas I, III, IV, V, VI, VII, VIII, IX, and X, $R^2$ is -pyrazinyl($R^4$) and $R^4$ is —($C_{1-3}$ alkyl)$_n$heterocyclyl($R^{22}$)$_p$.

In some embodiments of Formulas I, III, IV, V, VI, VII, VIII, IX, and X, $R^2$ is -pyrazin-2-yl($R^4$) and $R^4$ is —($CH_2$)heterocyclyl($R^{22}$)$_p$.

In some embodiments of Formulas I, III, IV, V, VI, VII, VIII, IX, and X, $R^2$ is -pyrazin-2-yl($R^4$) and $R^4$ is selected from the group consisting of

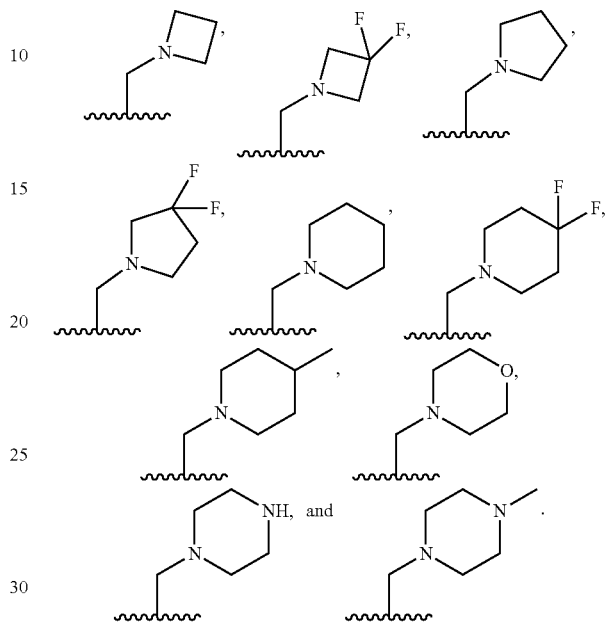

In some embodiments of Formulas I, III, IV, V, VI, VII, VIII, IX, and X, $R^2$ is -pyrazin-2-yl($R^4$) and $R^4$ is -heterocyclyl($R^{22}$)$_p$.

In some embodiments of Formulas I, III, IV, V, VI, VII, VIII, IX, and X, $R^2$ is -pyrazin-2-yl($R^4$) and $R^4$ is selected from the group consisting of

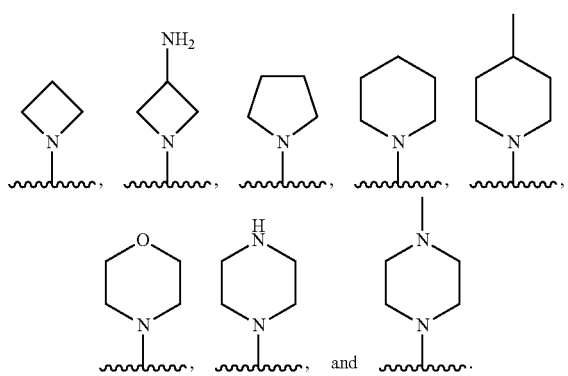

In some embodiments of Formulas I, III, IV, V, VI, VII, VIII, IX, and X, $R^2$ is -pyrazinyl($R^4$) and $R^4$ is —O-aryl($R^{23}$)$_q$.

In some embodiments of Formulas I, III, IV, V, VI, VII, VIII, IX, and X, $R^2$ is -pyrazinyl($R^4$) and $R^4$ is —O-phenyl($R^{23}$)$_q$.

In some embodiments of Formulas I, III, IV, V, VI, VII, VIII, IX, and X, $R^2$ is -pyrazinyl($R^4$) and $R^4$ is —NHC(=O)$R^{24}$.

In some embodiments of Formulas I, III, IV, V, VI, VII, VIII, IX, and X, $R^2$ is -pyrazinyl($R^4$) and $R^4$ is —($C_{1-6}$ alkyl)$_n$N($R^{25}$)$_2$.

In some embodiments of Formulas I, III, IV, V, VI, VII, VIII, IX, and X, $R^2$ is -pyrazinyl($R^4$) and $R^4$ is —($CH_2$)N($R^{25}$)$_2$.

In some embodiments of Formulas I, III, IV, V, VI, VII, VIII, IX, and X, $R^2$ is -pyrazin-2-yl($R^4$) and $R^4$ is —($CH_2$)N($R^{25}$)$_2$ and $R^{25}$ is independently —$C_{1-2}$ alkyl.

In some embodiments of Formulas I, III, IV, V, VI, VII, VIII, IX, and X, $R^2$ is -pyrazin-2-yl($R^4$) and $R^4$ is —($CH_2$)N(Me)$_2$.

In some embodiments of Formulas IV, V, VI, VII, and VIII, $R^4$ is F.

In some embodiments of Formulas IV, V, VI, VII, and VIII, $R^4$ is an unsubstituted —$C_{1-6}$ alkyl.

In some embodiments of Formulas IV, V, VI, VII, and VIII, $R^4$ is an unsubstituted —$C_{1-4}$ alkyl.

In some embodiments of Formulas IV, V, VI, VII, and VIII, $R^4$ is an unsubstituted —$C_{1-3}$ alkyl.

In some embodiments of Formulas IV, V, VI, VII, and VIII, $R^4$ is an unsubstituted —$C_{1-2}$ alkyl.

In some embodiments of Formulas IV, V, VI, VII, and VIII, $R^4$ is methyl.

In some embodiments of Formulas IV, V, VI, VII, and VIII, $R^2$ is a 6-membered heteroaryl($R^4$) and $R^4$ is F.

In some embodiments of Formulas IV, V, VI, VII, and VIII, $R^2$ is a 10-membered heteroaryl($R^4$) and $R^4$ is F.

In some embodiments of Formulas IV, V, VI, VII, and VIII, $R^2$ is -pridinyl($R^4$) and $R^4$ is F.

In some embodiments of Formulas IV, V, VI, VII, and VIII, $R^2$ is -pridin-3-yl($R^4$) and $R^4$ is F.

In some embodiments of Formulas IV, V, VI, VII, and VIII, $R^2$ is -pyrazin-2-yl($R^4$) and $R^4$ is F.

In some embodiments of Formulas I, V, VI, VII, VIII, IX, and X, $R^2$ is -phenyl($R^5$)$_m$($R^6$).

In some embodiments of Formulas I, V, VI, VII, VIII, IX, and X, $R^5$ is H.

In some embodiments of Formulas I, II, V, VI, VII, VIII, IX, and X, R is F.

In some embodiments of Formulas I, V, VI, VII, VIII, IX, and X, $R^5$ is Cl.

In some embodiments of Formulas I, II, V, VI, VII, VIII, IX, and X, $R^5$ is F and m is 2.

In some embodiments of Formulas II, V, VI, VII, and VIII, $R^2$ is

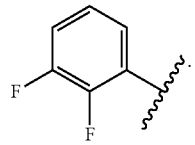

In some embodiments of Formulas I, V, VI, VII, VIII, IX, and X, $R^6$ is H.

In some embodiments of Formulas I, V, VI, VII, VIII, IX, and X, $R^6$ is —($C_{1-3}$ alkyl)$_n$heterocyclyl($R^{26}$)$_p$.

In some embodiments of Formulas I, V, VI, VII, VIII, IX, and X, $R^6$ is —($CH_2$)heterocyclyl($R^{26}$)$_p$.

In some embodiments of Formulas I, V, VI, VII, VIII, IX, and X, $R^6$ is —($CH_2$)heterocyclyl($R^{26}$)$_p$ and $R^{26}$ is H.

In some embodiments of Formulas I, V, VI, VII, VIII, IX, and X, $R^6$ is —($CH_2$)heterocyclyl($R^{26}$)$_p$, p is 1, and $R^{26}$ is —$C_{1-6}$ alkyl.

In some embodiments of Formulas I, V, VI, VII, VIII, IX, and X, $R^6$ is —($CH_2$)heterocyclyl($R^{26}$)$_p$, p is 1, and $R^{26}$ is —$C_{1-5}$ alkyl.

In some embodiments of Formulas I, V, VI, VII, VIII, IX, and X, $R^6$ is —($CH_2$)heterocyclyl($R^{26}$)$_p$, p is 1, and $R^{26}$ is —$C_{1-4}$ alkyl.

In some embodiments of Formulas I, V, VI, VII, VIII, IX, and X, $R^6$ is —($CH_2$)heterocyclyl($R^{26}$)$_p$, p is 1, and $R^{26}$ is —$C_{1-3}$ alkyl.

In some embodiments of Formulas I, V, VI, VII, VIII, IX, and X, $R^6$ is —($CH_2$)heterocyclyl($R^{26}$)$_p$, p is 1, and $R^{26}$ is —$C_{1-2}$ alkyl.

In some embodiments of Formulas I, V, VI, VII, VIII, IX, and X, $R^6$ is —($CH_2$)heterocyclyl($R^{26}$)$_p$, p is 1, and $R^{26}$ is methyl.

In some embodiments of Formulas I, V, VI, VII, VIII, IX, and X, $R^6$ is —($CH_2$)heterocyclyl($R^{26}$)$_p$, p is 1-2, and $R^{26}$ is halide.

In some embodiments of Formulas I, V, VI, VII, VIII, IX, and X, $R^6$ is —($CH_2$)heterocyclyl($R^2$)$_p$, p is 1-2, and $R^{26}$ is F.

In some embodiments of Formulas I, V, VI, VII, VIII, IX, and X, $R^6$ is —($CH_2$)heterocyclyl($R^{26}$)$_p$, p is 1-2, and $R^{26}$ is Cl.

In some embodiments of Formulas I, V, VI, VII, VIII, IX, and X, $R^6$ is selected from the group consisting of

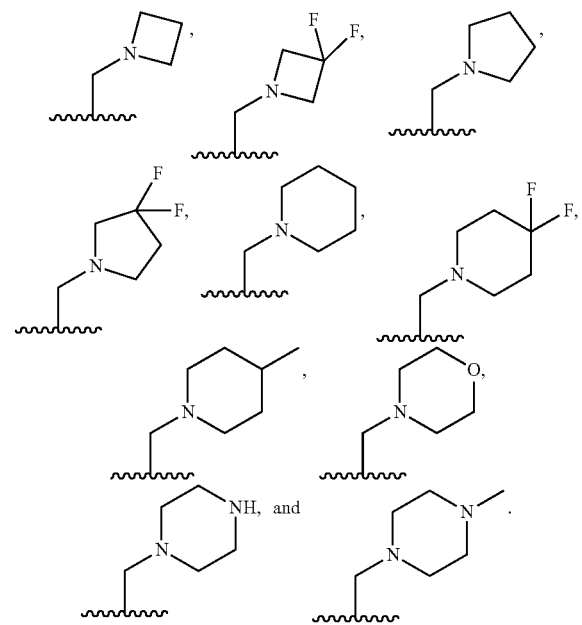

In some embodiments of Formulas I, V, VI, VII, VIII, IX, and X, $R^6$ is -heterocyclyl($R^{26}$)$_p$.

In some embodiments of Formulas I, V, VI, VII, VIII, IX, and X, $R^6$ is -heterocyclyl($R^{26}$)$_p$ and $R^{26}$ is H.

In some embodiments of Formulas I, V, VI, VII, VIII, IX, and X, $R^6$ is -heterocyclyl($R^{26}$)$_p$, p is 1, and $R^{26}$ is —$C_{1-6}$ alkyl.

In some embodiments of Formulas I, V, VI, VII, VIII, IX, and X, $R^6$ is -heterocyclyl($R^{26}$)$_p$, p is 1, and $R^{26}$ is —$C_{1-5}$ alkyl.

In some embodiments of Formulas I, V, VI, VII, VIII, IX, and X, $R^6$ is -heterocyclyl($R^{26}$)$_p$, p is 1, and $R^{26}$ is —$C_{1-4}$ alkyl.

In some embodiments of Formulas I, V, VI, VII, VIII, IX, and X, $R^6$ is -heterocyclyl($R^{26}$)$_p$, p is 1, and $R^{26}$ is —$C_{1-3}$ alkyl.

In some embodiments of Formulas I, V, VI, VII, VIII, IX, and X, $R^6$ is -heterocyclyl$(R^{26})_p$, p is 1, and $R^{26}$ is —$C_{1-2}$ alkyl.

In some embodiments of Formulas I, V, VI, VII, VIII, IX, and X, $R^6$ is -heterocyclyl$(R^{26})_p$, p is 1, and $R^{26}$ is methyl.

In some embodiments of Formulas I, V, VI, VII, VIII, IX, and X, $R^6$ is -heterocyclyl$(R^{26})_p$, p is 1-2, and $R^{26}$ is halide.

In some embodiments of Formulas I, V, VI, VII, VIII, IX, and X, $R^6$ is -heterocyclyl$(R^{26})_p$, p is 1-2, and $R^{26}$ is F.

In some embodiments of Formulas I, V, VI, VII, VIII, IX, and X, $R^6$ is -heterocyclyl$(R^{26})_p$, p is 1-2, and $R^{26}$ is Cl.

In some embodiments of Formulas I, V, VI, VII, VIII, IX, and X, $R^6$ is selected from the group consisting of

[chemical structures: azetidinyl, pyrrolidinyl, piperidinyl, 4-methylpiperidinyl, morpholinyl, piperazinyl, and N-methylpiperazinyl]

In some embodiments of Formulas I, II, III, IV, IX, and X, $R^3$ is H.

In some embodiments of Formulas I, II, III, IV, VIII, IX, and X, $R^3$ is —$C_{1-9}$ alkyl.

In some embodiments of Formulas I, II, III, IV, VIII, IX, and X, $R^3$ is —$C_{1-6}$ alkyl.

In some embodiments of Formulas I, II, III, IV, VIII, IX, and X, $R^3$ is —$C_{1-5}$ alkyl.

In some embodiments of Formulas I, II, III, IV, VIII, IX, and X, $R^3$ is —$C_{1-4}$ alkyl.

In some embodiments of Formulas I, II, III, IV, VIII, IX, and X, $R^3$ is —$C_{1-3}$ alkyl.

In some embodiments of Formulas I, II, III, IV, VIII, IX, and X, $R^3$ is —$C_{1-2}$ alkyl.

In some embodiments of Formulas I, II, III, IV, VIII, IX, and X, $R^3$ is methyl.

In some embodiments of Formulas I, II, III, IV, VIII, IX, and X, $R^3$ is —$C_{2-6}$ alkyl.

In some embodiments of Formulas I, II, III, IV, VIII, IX, and X, $R^3$ is —$C_{3-6}$ alkyl.

In some embodiments of Formulas I, II, III, IV, VIII, IX, and X, $R^3$ is —$C_{4-6}$ alkyl.

In some embodiments of Formulas I, II, III, IV, VIII, IX, and X, $R^3$ is —$C_{5-6}$ alkyl.

In some embodiments of Formulas I, II, III, IV, VIII, IX, and X, $R^3$ is —$C_{2-5}$ alkyl.

In some embodiments of Formulas I, II, III, IV, VIII, IX, and X, $R^3$ is —$C_{2-4}$ alkyl.

In some embodiments of Formulas I, II, III, IV, VIII, IX, and X, $R^3$ is —$C_{2-3}$ alkyl.

In some embodiments of Formulas I, II, III, IV, VIII, IX, and X, $R^3$ is —$C_{3-5}$ alkyl.

In some embodiments of Formulas I, II, III, IV, VIII, IX, and X, $R^3$ is —$C_{3-4}$ alkyl.

In some embodiments of Formulas I, II, III, IV, VIII, IX, and X, $R^3$ is selected from the group consisting of

[chemical structures: branched alkyl groups]

In some embodiments of Formulas I, II, III, IV, IX, and X, $R^3$ is —($C_{1-6}$ alkyl)N$(R^{68})_2$.

In some embodiments of Formulas I, II, III, IV, IX, and X, $R^3$ is —($C_{1-4}$ alkyl)N$(R^{68})_2$.

In some embodiments of Formulas I, II, III, IV, IX, and X, $R^3$ is —($C_{1-3}$ alkyl)N$(R^{68})_2$.

In some embodiments of Formulas I, II, III, IV, IX, and X, $R^3$ is —($C_{1-2}$ alkyl)N$(R^{68})_2$.

In some embodiments of Formulas I, II, III, IV, IX, and X, $R^3$ is —(CH$_2$CH$_2$)N$(R^{68})_2$.

In some embodiments of Formulas I, II, III, IV, IX, and X, $R^3$ is —(CH$_2$CH$_2$)N$(R^{68})_2$ and each $R^{68}$ is independently an unsubstituted —$C_{1-3}$ alkyl.

In some embodiments of Formulas I, II, III, IV, IX, and X, $R^3$ is —(CH$_2$CH$_2$)N$(R^{68})_2$ and each $R^{68}$ is independently an unsubstituted —$C_{1-2}$ alkyl.

In some embodiments of Formulas I, II, III, IV, IX, and X, $R^3$ is —(CH$_2$CH$_2$)N(Me)$_2$.

In some embodiments of Formulas I, II, III, IV, IX, and X, $R^3$ is —(CH$_2$CH$_2$CH$_2$)N$(R^{68})_2$.

In some embodiments of Formulas I, II, III, IV, IX, and X, $R^3$ is —(CH$_2$CH$_2$CH$_2$)N$(R^{68})_2$ and each $R^{68}$ is independently an unsubstituted —$C_{1-3}$ alkyl.

In some embodiments of Formulas I, II, III, IV, IX, and X, $R^3$ is —(CH$_2$CH$_2$CH$_2$)N$(R^{68})_2$ and each $R^{68}$ is independently an unsubstituted —$C_{1-2}$ alkyl.

In some embodiments of Formulas I, II, III, IV, IX, and X, $R^3$ is —(CH$_2$CH$_2$CH$_2$)N(Me)$_2$.

In some embodiments of Formulas I, II, III, IV, IX, and X, $R^3$ is —($C_{2-6}$ alkyl)O($C_{1-6}$ alkyl).

In some embodiments of Formulas I, II, III, IV, IX, and X, $R^3$ is —($C_{2-5}$ alkyl)O($C_{1-6}$ alkyl).

In some embodiments of Formulas I, II, III, IV, IX, and X, $R^3$ is —($C_{2-4}$ alkyl)O($C_{1-6}$ alkyl).

In some embodiments of Formulas I, II, III, IV, IX, and X, $R^3$ is —($C_{2-3}$ alkyl)O($C_{1-6}$ alkyl).

In some embodiments of Formulas I, II, III, IV, IX, and X, $R^3$ is —(CH$_2$CH$_2$)O($C_{1-6}$ alkyl).

In some embodiments of Formulas I, II, III, IV, IX, and X, $R^3$ is —(CH$_2$CH$_2$)O($C_{1-4}$ alkyl).

In some embodiments of Formulas I, II, III, IV, IX, and X, $R^3$ is —(CH$_2$CH$_2$)O($C_{1-3}$ alkyl).

In some embodiments of Formulas I, II, III, IV, IX, and X, $R^3$ is —(CH$_2$CH$_2$)O($C_{1-2}$ alkyl).

In some embodiments of Formulas I, II, III, IV, IX, and X, $R^3$ is —(CH$_2$CH$_2$)OMe.

In some embodiments of Formulas I, II, III, IV, IX, and X, $R^3$ is —(CH$_2$CH$_2$)OEt.

In some embodiments of Formulas I, II, III, IV, IX, and X, $R^3$ is —(CH$_2$CH$_2$)OnPr.

In some embodiments of Formulas I, II, III, IV, IX, and X, $R^3$ is —(CH$_2$CH$_2$)OiPr.

In some embodiments of Formulas I, II, III, IV, IX, and X, $R^3$ is —(CH$_2$CH$_2$CH$_2$)O($C_{1-6}$ alkyl).

In some embodiments of Formulas I, II, III, IV, IX, and X, $R^3$ is —(CH$_2$CH$_2$CH$_2$)O(C$_{1-4}$ alkyl).

In some embodiments of Formulas I, II, III, IV, IX, and X, $R^3$ is —(CH$_2$CH$_2$CH$_2$)O(C$_{1-3}$ alkyl).

In some embodiments of Formulas I, II, III, IV, IX, and X, $R^3$ is —(CH$_2$CH$_2$CH$_2$)O(C$_{1-2}$ alkyl).

In some embodiments of Formulas I, II, III, IV, IX, and X, $R^3$ is —(CH$_2$CH$_2$CH$_2$)OMe.

In some embodiments of Formulas I, II, III, IV, IX, and X, $R^3$ is —(CH$_2$CH$_2$CH$_2$)OEt.

In some embodiments of Formulas I, II, III, IV, IX, and X, $R^3$ is —(CH$_2$CH$_2$CH$_2$)OnPr.

In some embodiments of Formulas I, II, III, IV, IX, and X, $R^3$ is —(CH$_2$CH$_2$CH$_2$)OiPr.

In some embodiments of Formulas I, II, III, IV, IX, and X, $R^3$ is -carbocyclyl($R^7$)$_p$.

In some embodiments of Formulas I, II, III, IV, IX, and X, $R^3$ is -carbocyclyl($R^7$)$_p$, wherein the carbocyclyl is selected from the group consisting of cyclopropyl, cyclobutyl, cyclopentyl, and cyclohexyl.

In some embodiments of Formulas I, II, III, IV, IX, and X, $R^3$ is -carbocyclyl($R^7$)$_p$ and $R^7$ is H.

In some embodiments of Formulas I, II, III, IV, IX, and X, $R^3$ is -carbocyclyl($R^7$)$_p$ and $R^7$ is halide.

In some embodiments of Formulas I, II, III, IV, IX, and X, $R^3$ is -carbocyclyl($R^7$)$_p$, p is 1-2, and $R^7$ is halide.

In some embodiments of Formulas I, II, III, IV, IX, and X, $R^3$ is -carbocyclyl($R^7$)$_p$, p is 1-2, and $R^7$ is F.

In some embodiments of Formulas I, II, III, IV, IX, and X, $R^3$ is -carbocyclyl($R^7$)$_p$ and $R^7$ is —CF$_3$.

In some embodiments of Formulas I, II, III, IV, IX, and X, $R^3$ is -carbocyclyl($R^7$)$_p$ and $R^7$ is —CN.

In some embodiments of Formulas I, II, III, IV, IX, and X, $R^3$ is -carbocyclyl($R^7$)$_p$ and $R^7$ is —N($R^{25}$)$_2$.

In some embodiments of Formulas I, II, III, IV, IX, and X, $R^3$ is -carbocyclyl($R^7$)$_p$, p is 1, $R^7$ is —N($R^{25}$)$_2$, and $R^{25}$ is independently selected from H and —C$_{1-6}$ alkyl.

In some embodiments of Formulas I, II, III, IV, IX, and X, $R^3$ is -carbocyclyl($R^7$)$_p$, p is 1, $R^7$ is —N($R^{25}$)$_2$, and $R^{25}$ is independently selected from H and —C$_{1-2}$ alkyl.

In some embodiments of Formulas I, II, III, IV, IX, and X, $R^3$ is -carbocyclyl($R^7$)$_p$, p is 1, and $R^7$ is —NH$_2$.

In some embodiments of Formulas I, II, III, IV, IX, and X, $R^3$ is -carbocyclyl($R^7$)$_p$, p is 1, and $R^7$ is —NMe$_2$.

In some embodiments of Formulas I, II, III, IV, IX, and X, $R^3$ is selected from the group consisting of In some embodiments of Formulas I, II, III, IV, IX, and X, $R^3$ is -monocyclic heterocyclyl($R^8$)$_p$.

In some embodiments of Formulas I, II, III, IV, IX, and X, $R^3$ is -monocyclic heterocyclyl($R^8$)$_p$, p is 1, and $R^8$ is an unsubstituted —C$_{1-6}$ alkyl.

In some embodiments of Formulas I, II, III, IV, IX, and X, $R^3$ is -monocyclic heterocyclyl($R^8$)$_p$, p is 1, and $R^8$ is an unsubstituted —C$_{1-5}$ alkyl.

In some embodiments of Formulas I, II, III, IV, IX, and X, $R^3$ is -monocyclic heterocyclyl($R^8$)$_p$, p is 1, and $R^8$ is an unsubstituted —C$_{1-4}$ alkyl.

In some embodiments of Formulas I, II, III, IV, IX, and X, $R^3$ is -monocyclic heterocyclyl($R^8$)$_p$, p is 1, and $R^8$ is an unsubstituted —C$_{1-3}$ alkyl.

In some embodiments of Formulas I, II, III, IV, IX, and X, $R^3$ is -monocyclic heterocyclyl($R^8$)$_p$, p is 1, and $R^8$ is an unsubstituted —C$_{1-2}$ alkyl.

In some embodiments of Formulas I, II, III, IV, IX, and X, $R^3$ is -monocyclic heterocyclyl($R^8$)$_p$, p is 1, and $R^8$ is an unsubstituted —C$_{2-6}$ alkyl.

In some embodiments of Formulas I, II, III, IV, IX, and X, $R^3$ is -monocyclic heterocyclyl($R^8$)$_p$, p is 1, and $R^8$ is an unsubstituted —C$_{3-6}$ alkyl.

In some embodiments of Formulas I, II, III, IV, IX, and X, $R^3$ is -monocyclic heterocyclyl($R^8$)$_p$, p is 1, and $R^8$ is an unsubstituted —C$_{4-6}$ alkyl.

In some embodiments of Formulas I, II, III, IV, IX, and X, $R^3$ is -monocyclic heterocyclyl($R^8$)$_p$, p is 1, and $R^8$ is an unsubstituted —C$_{5-6}$ alkyl.

In some embodiments of Formulas I, II, III, IV, IX, and X, $R^3$ is -monocyclic heterocyclyl($R^8$)$_p$, p is 1, and $R^8$ is an unsubstituted —C$_{2-5}$ alkyl.

In some embodiments of Formulas I, II, III, IV, IX, and X, $R^3$ is -monocyclic heterocyclyl($R^8$)$_p$, p is 1, and $R^8$ is an unsubstituted —C$_{2-4}$ alkyl.

In some embodiments of Formulas I, II, III, IV, IX, and X, $R^3$ is -monocyclic heterocyclyl($R^8$)$_p$, p is 1, and $R^8$ is an unsubstituted —C$_{2-3}$ alkyl.

In some embodiments of Formulas I, II, III, IV, IX, and X, $R^3$ is -monocyclic heterocyclyl($R^8$)$_p$, p is 1, and $R^8$ is an unsubstituted —C$_{3-5}$ alkyl.

In some embodiments of Formulas I, II, III, IV, IX, and X, $R^3$ is -monocyclic heterocyclyl($R^8$)$_p$, p is 1, and $R^8$ is an unsubstituted —C$_{3-4}$ alkyl.

In some embodiments of Formulas I, II, III, IV, IX, and X, $R^3$ is -monocyclic heterocyclyl($R^8$)$_p$, p is 1, and $R^8$ is an unsubstituted —C$_{2-4}$ alkyl where the alkyl contains a —C≡C—.

In some embodiments of Formulas I, II, III, IV, IX, and X, $R^3$ is -monocyclic heterocyclyl($R^8$)$_p$, p is 1, and $R^8$ is an unsubstituted —C$_{1-6}$ haloalkyl.

In some embodiments of Formulas I, II, III, IV, IX, and X, $R^3$ is -monocyclic heterocyclyl($R^8$)$_p$, p is 1, and $R^8$ is an unsubstituted —C$_{1-6}$ haloalkyl wherein the halo is F.

In some embodiments of Formulas I, II, III, IV, IX, and X, $R^3$ is -monocyclic heterocyclyl($R^8$)$_p$, p is 1, and $R^8$ is an unsubstituted —C$_{1-5}$ haloalkyl wherein the halo is F.

In some embodiments of Formulas I, II, III, IV, IX, and X, $R^3$ is -monocyclic heterocyclyl($R^8$)$_p$, p is 1, and $R^8$ is an unsubstituted —C$_{1-4}$ haloalkyl wherein the halo is F.

In some embodiments of Formulas I, II, III, IV, IX, and X, $R^3$ is -monocyclic heterocyclyl($R^8$)$_p$, p is 1, and $R^8$ is an unsubstituted —C$_{1-3}$ haloalkyl wherein the halo is F.

In some embodiments of Formulas I, II, III, IV, IX, and X, $R^3$ is -monocyclic heterocyclyl($R^8$)$_p$, p is 1, and $R^8$ is an unsubstituted —C$_{1-2}$ haloalkyl wherein the halo is F.

In some embodiments of Formulas I, II, III, IV, IX, and X, $R^3$ is -monocyclic heterocyclyl($R^8$)$_p$, p is 1, and $R^8$ is an unsubstituted —C$_{2-4}$ haloalkyl wherein the halo is F.

In some embodiments of Formulas I, II, III, IV, IX, and X, $R^3$ is -monocyclic heterocyclyl$(R^8)_p$, p is 1, and $R^8$ is an unsubstituted —$C_{2-3}$ haloalkyl wherein the halo is F.

In some embodiments of Formulas I, II, III, IV, IX, and X, $R^3$ is selected from the group consisting of

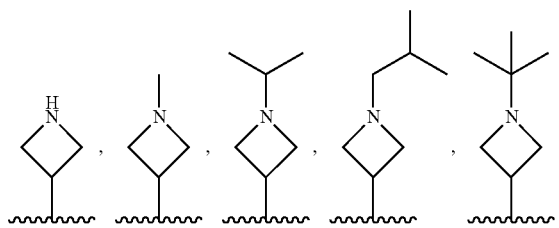

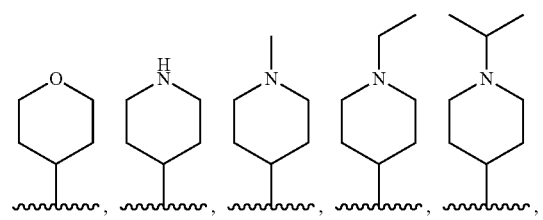

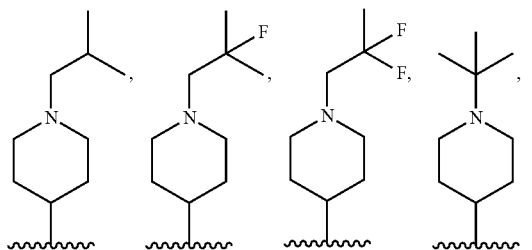

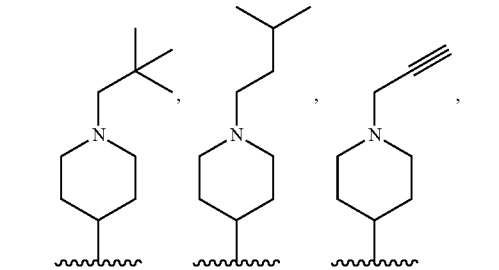

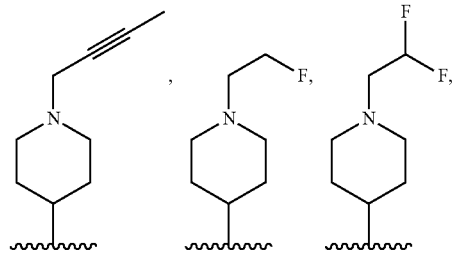

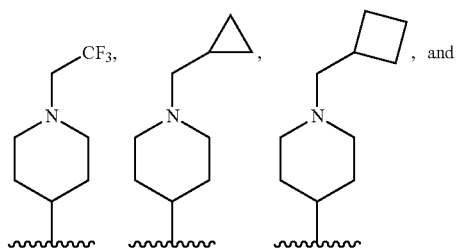

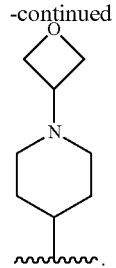

In some embodiments of Formulas I, II, III, IV, IX, and X, $R^3$ is selected from the group consisting of

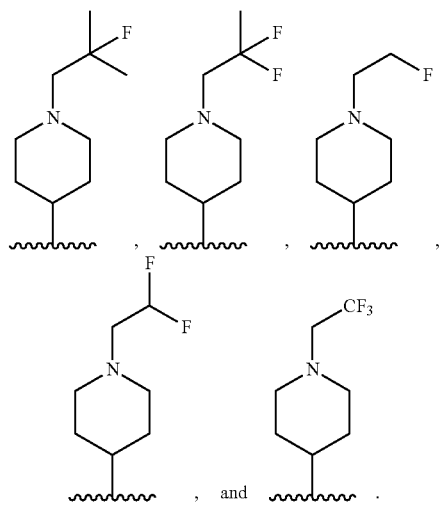

In some embodiments of Formulas I, II, IV, IX, and X, $R^3$ is —$(C_{1-3}$ alkyl)heterocyclyl$(R^9)_p$.

In some embodiments of Formulas I, II, IV, IX, and X, $R^3$ is —$(C_{1-2}$ alkyl)heterocyclyl$(R^9)_p$.

In some embodiments of Formulas I, II, IV, IX, and X, $R^3$ is —$(CH_2CH_2)$heterocyclyl$(R^9)_p$.

In some embodiments of Formulas I, II, IV, IX, and X, $R^3$ is

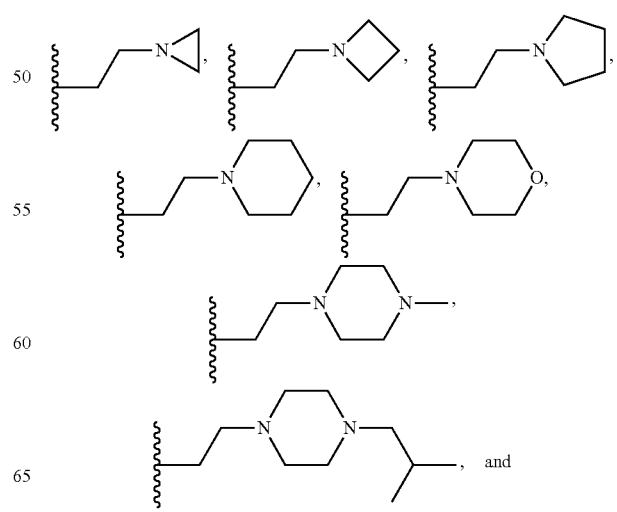

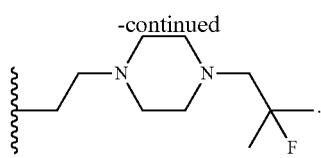

In some embodiments of Formulas I, II, IV, IX, and X, $R^3$ is —(CH$_2$)heterocyclyl(R$^9$)$_p$.

In some embodiments of Formulas II, III, and IV, $R^3$ is —(C$_{1-3}$ alkyl)$_n$aryl(R$^{10}$)$_q$.

In some embodiments of Formulas II, III, and IV, $R^3$ is -aryl(R$^{10}$)$_q$.

In some embodiments of Formulas II, III, and IV, $R^3$ is -phenyl(R$^{10}$)$_q$.

In some embodiments of Formulas II, III, and IV, $R^3$ is -phenyl(R$^{10}$)$_q$, q is 1, and R$^{10}$ is —(C$_{1-3}$ alkyl)$_n$heterocyclyl(R$^{31}$)$_p$.

In some embodiments of Formulas II, III, and IV, $R^3$ is -phenyl(R$^{10}$)$_q$, q is 1, and R$^{10}$ is —(CH$_2$)heterocyclyl(R$^{31}$)$_p$.

In some embodiments of Formulas II, III, and IV, $R^3$ is -phenyl(R$^{10}$)$_q$, q is 1, R$^{10}$ is —(CH$_2$)heterocyclyl(R$^{31}$)$_p$, and R$^{31}$ is H.

In some embodiments of Formulas II, III, and IV, $R^3$ is -phenyl(R$^{10}$)$_q$, q is 1, R$^{10}$ is —(CH$_2$)heterocyclyl(R$^{31}$)$_p$, p is 1-2, and R$^{31}$ is F.

In some embodiments of Formulas II and III, $R^3$ is -phenyl(R$^{10}$)$_q$, q is 1, and R$^{10}$ is —(CH$_2$)heterocyclyl(R$^{31}$)$_p$, p is 1, and R$^{31}$ is —C$_{1-6}$ alkyl.

In some embodiments of Formulas II and III, $R^3$ is -phenyl(R$^{10}$)$_q$, q is 1, and R$^{10}$ is —(CH$_2$)heterocyclyl(R$^{31}$)$_p$, p is 1, and R$^{31}$ is —C$_{1-5}$ alkyl.

In some embodiments of Formulas II and III, $R^3$ is -phenyl(R$^{10}$)$_q$, q is 1, and R$^{10}$ is —(CH$_2$)heterocyclyl(R$^{31}$)$_p$, p is 1, and R$^{31}$ is —C$_{1-4}$ alkyl.

In some embodiments of Formulas II and III, $R^3$ is -phenyl(R$^{10}$)$_q$, q is 1, and R$^{10}$ is —(CH$_2$)heterocyclyl(R$^{31}$)$_p$, p is 1, and R$^{31}$ is —C$_{1-3}$ alkyl.

In some embodiments of Formulas II and III, $R^3$ is -phenyl(R$^{10}$)$_q$, q is 1, and R$^{10}$ is —(CH$_2$)heterocyclyl(R$^{31}$)$_p$, p is 1, and R$^{31}$ is —C$_{1-2}$ alkyl.

In some embodiments of Formulas II and III, $R^3$ is -phenyl(R$^{10}$)$_q$, q is 1, and R$^{10}$ is —(CH$_2$)heterocyclyl(R$^{31}$)$_p$, p is 1, and R$^{31}$ is methyl.

In some embodiments of Formulas II and III, $R^3$ is -phenyl(R$^{10}$)$_q$, q is 1, and R$^{10}$ is —(CH$_2$)heterocyclyl(R$^{31}$)$_p$, p is 1, and R$^{31}$ is —C$_{1-6}$ haloalkyl.

In some embodiments of Formulas II and III, $R^3$ is -phenyl(R$^{10}$)$_q$, q is 1, and R$^{10}$ is —(CH$_2$)heterocyclyl(R$^{31}$)$_p$, p is 1, and R$^{31}$ is —C$_{2-4}$ haloalkyl.

In some embodiments of Formulas II, III, and IV, $R^3$ is -phenyl(R$^{10}$)$_q$, q is 1, R$^{10}$ is -heterocyclyl(R$^{31}$)$_p$.

In some embodiments of Formulas II, III, and IV, $R^3$ is -phenyl(R$^{10}$)$_q$, q is 1, R$^{10}$ is -heterocyclyl(R$^{31}$)$_p$, and R$^{31}$ is H.

In some embodiments of Formulas II, III, and IV, $R^3$ is -phenyl(R$^{10}$)$_q$, q is 1, R$^{10}$ is -heterocyclyl(R$^{31}$)$_p$, p is 1-2, and R$^{31}$ is F.

In some embodiments of Formulas II and III, $R^3$ is -phenyl(R$^{10}$)$_q$, q is 1, and R$^{10}$ is -heterocyclyl(R$^{31}$)$_p$, p is 1, and R$^{31}$ is —C$_{1-6}$ alkyl.

In some embodiments of Formulas II and III, $R^3$ is -phenyl(R$^{10}$)$_q$, q is 1, and R$^{10}$ is -heterocyclyl(R$^{31}$)$_p$, p is 1, and R$^{31}$ is —C$_{1-5}$ alkyl.

In some embodiments of Formulas II and III, $R^3$ is -phenyl(R$^{10}$)$_q$, q is 1, and R$^{10}$ is -heterocyclyl(R$^{31}$)$_p$, p is 1, and R$^{31}$ is —C$_{1-4}$ alkyl.

In some embodiments of Formulas II and III, $R^3$ is -phenyl(R$^{10}$)$_q$, q is 1, and R$^{10}$ is -heterocyclyl(R$^{31}$)$_p$, p is 1, and R$^{31}$ is —C$_{1-3}$ alkyl.

In some embodiments of Formulas II and III, $R^3$ is -phenyl(R$^{10}$)$_q$, q is 1, and R$^{10}$ is -heterocyclyl(R$^{31}$)$_p$, p is 1, and R$^{31}$ is —C$_{1-2}$ alkyl.

In some embodiments of Formulas II and III, $R^3$ is -phenyl(R$^{10}$)$_q$, q is 1, and R$^{10}$ is -heterocyclyl(R$^{31}$)$_p$, p is 1, and R$^{31}$ is methyl.

In some embodiments of Formulas II and III, $R^3$ is -phenyl(R$^{10}$)$_q$, q is 1, and R$^{10}$ is -heterocyclyl(R$^{31}$)$_p$, p is 1, and R$^{31}$ is —C$_{1-6}$ haloalkyl.

In some embodiments of Formulas II and III, $R^3$ is -phenyl(R$^{10}$)$_q$, q is 1, and R$^{10}$ is -heterocyclyl(R$^{31}$)$_p$, p is 1, and R$^{31}$ is —C$_{2-4}$ haloalkyl.

In some embodiments of Formulas I, II, III, IV, IX, and X, $R^3$ is —(C$_{1-3}$ alkyl)aryl(R$^{10}$)$_q$.

In some embodiments of Formulas I, II, III, IV, IX, and X, $R^3$ is —(C$_{1-3}$ alkyl)phenyl(R$^{10}$)$_q$.

In some embodiments of Formulas I, II, III, IV, IX, and X, $R^3$ is —(C$_{1-2}$ alkyl)phenyl(R$^{10}$)$_q$.

In some embodiments of Formulas I, II, III, IV, IX, and X, $R^3$ is —(CH$_2$)phenyl(R$^{10}$)$_q$.

Illustrative compounds of Formulas I, II, III, IV, V, VI, VII, VIII, IX and/or X are shown in Table 1.

TABLE 1

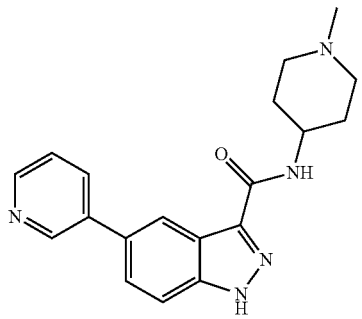 [SMILES: CN1CCC(NC(=O)c2n[nH]c3ccc(-c4cccnc4)cc23)CC1]

1

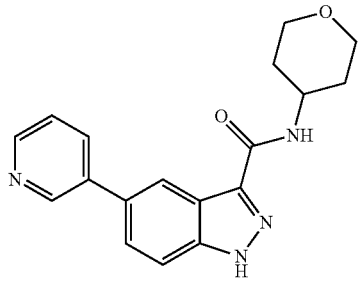 [SMILES: O=C(NC1CCOCC1)c1n[nH]c2ccc(-c3cccnc3)cc12]

2

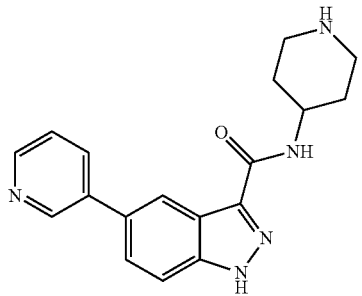 [SMILES: O=C(NC1CCNCC1)c1n[nH]c2ccc(-c3cccnc3)cc12]

3

TABLE 1-continued
| | |
|---|---|
| 4 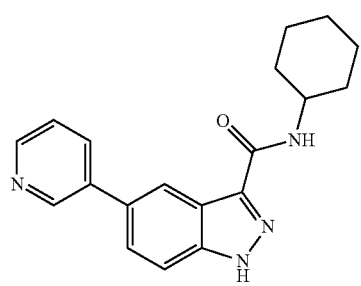 | 9 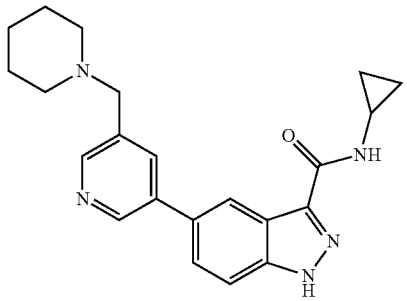 |
| 5 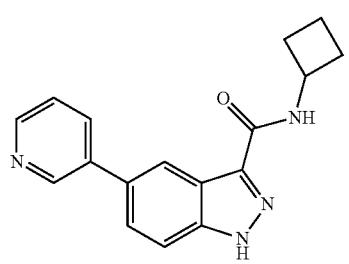 [SMILES: O=C(NC1CCC1)c1n[nH]c2ccc(-c3cccnc3)cc12] | 10 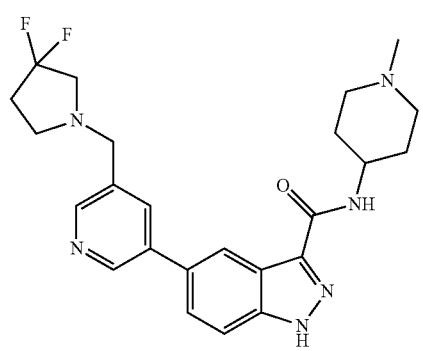 [SMILES: CN1CCC(NC(=O)c2n[nH]c3ccc(-c4cncc(CN5CCC(F)(F)C5)c4)cc23)CC1] |
| 6 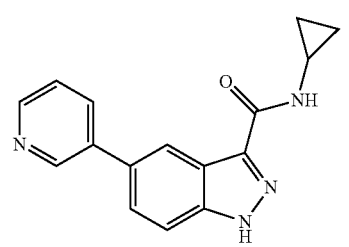 | 11 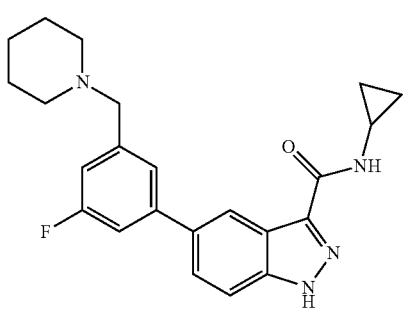 [SMILES: O=C(NC1CC1)c1n[nH]c2ccc(-c3cc(F)cc(CN4CCCCC4)c3)cc12] |
| 7 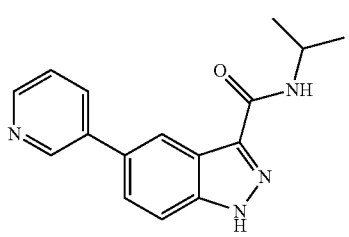 | 12 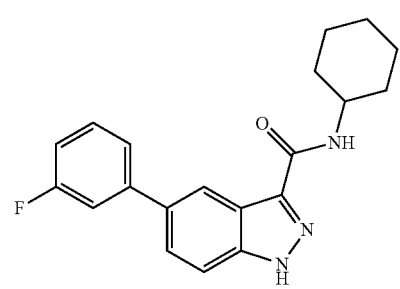 [SMILES: O=C(NC1CCCCC1)c1n[nH]c2ccc(-c3cccc(F)c3)cc12] |
| 8 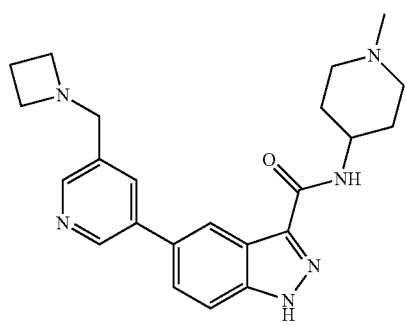 | 13 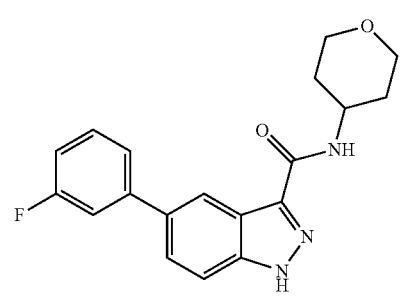 [SMILES: O=C(NC1CCOCC1)c1n[nH]c2ccc(-c3cccc(F)c3)cc12] |

TABLE 1-continued
| | |
|---|---|
| 14 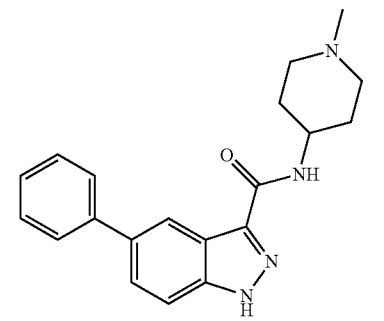 [SMILES: CN1CCC(NC(=O)c2n[nH]c3ccc(-c4ccccc4)cc23)CC1] | 19 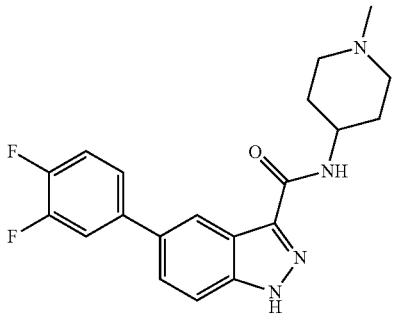 |
| 15 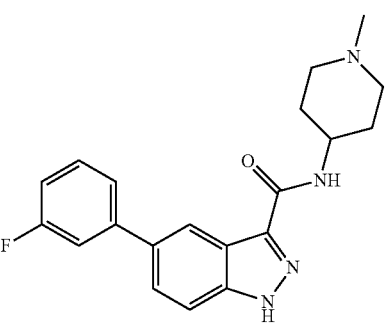 [SMILES: CN1CCC(NC(=O)c2n[nH]c3ccc(-c4cccc(F)c4)cc23)CC1] | 20 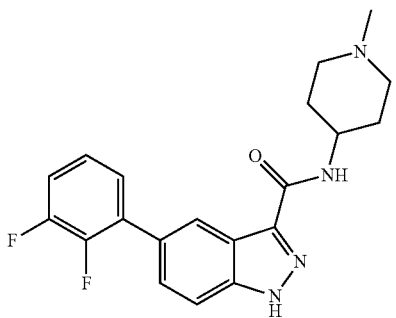 |
| 16 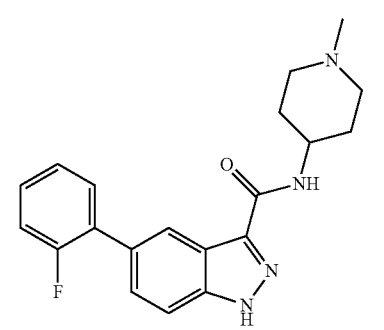 [SMILES: CN1CCC(NC(=O)c2n[nH]c3ccc(-c4ccccc4F)cc23)CC1] | 21  |
| 17 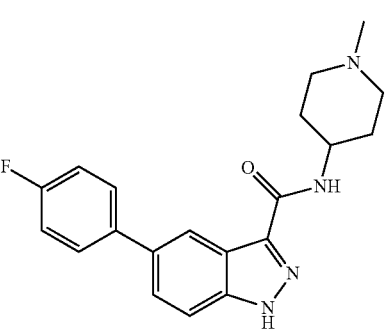 [SMILES: CN1CCC(NC(=O)c2n[nH]c3ccc(-c4ccc(F)cc4)cc23)CC1] | 22  |
| 18 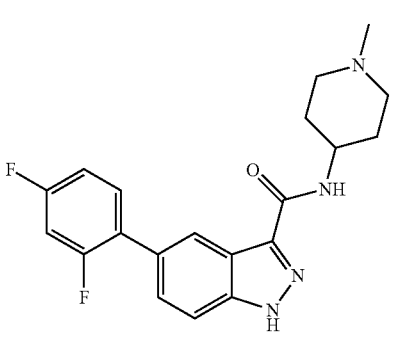 [SMILES: CN1CCC(NC(=O)c2n[nH]c3ccc(-c4ccc(F)cc4F)cc23)CC1] | 23 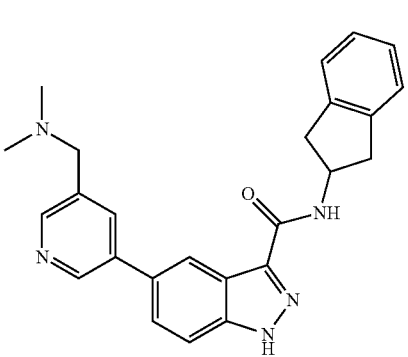 [SMILES: CN(C)Cc1cncc(-c2ccc3[nH]nc(C(=O)NC4Cc5ccccc5C4)c3c2)c1] |

TABLE 1-continued

TABLE 1-continued
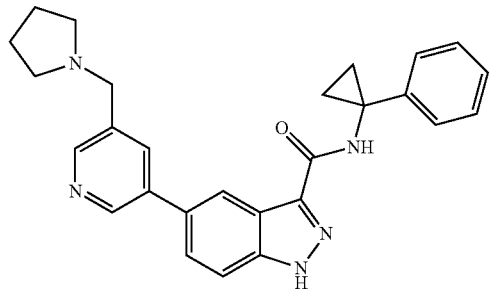 [SMILES: O=C(NC1(c2ccccc2)CC1)c1n[nH]c2ccc(-c3cncc(CN4CCCC4)c3)cc12] 34
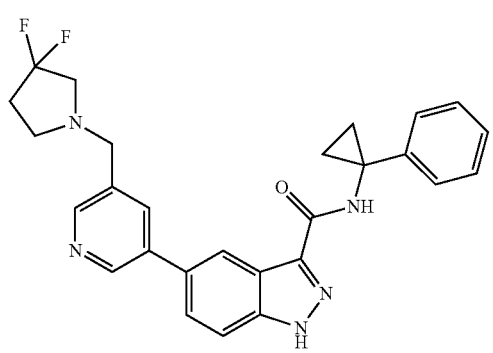 [SMILES: O=C(NC1(c2ccccc2)CC1)c1n[nH]c2ccc(-c3cncc(CN4CCC(F)(F)C4)c3)cc12] 35
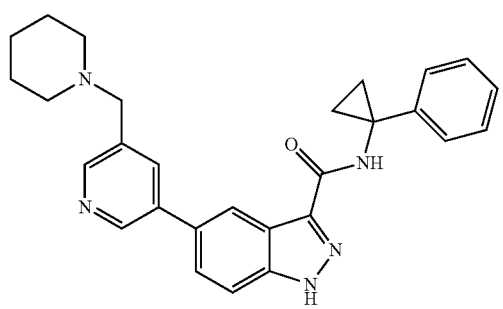 [SMILES: O=C(NC1(c2ccccc2)CC1)c1n[nH]c2ccc(-c3cncc(CN4CCCCC4)c3)cc12] 36
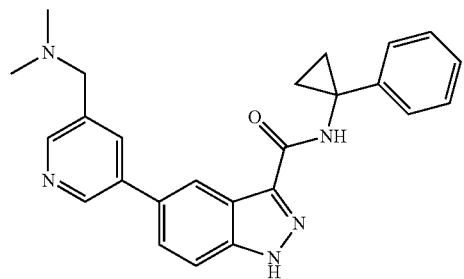 [SMILES: CN(C)Cc1cncc(-c2ccc3[nH]nc(C(=O)NC4(c5ccccc5)CC4)c3c2)c1] 37
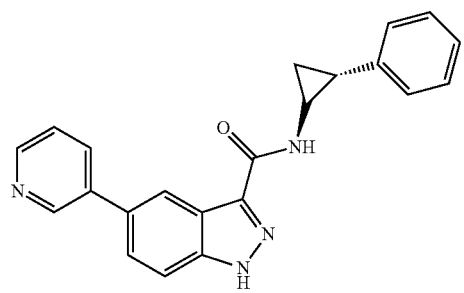 38
TABLE 1-continued
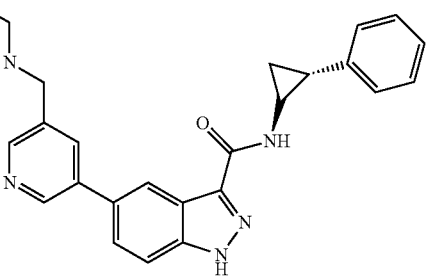 39
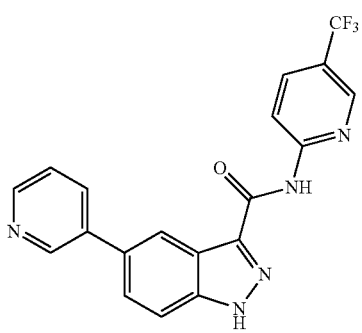 [SMILES: O=C(Nc1ccc(C(F)(F)F)cn1)c1n[nH]c2ccc(-c3cccnc3)cc12] 40
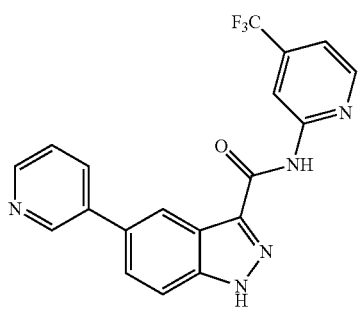 [SMILES: O=C(Nc1cc(C(F)(F)F)ccn1)c1n[nH]c2ccc(-c3cccnc3)cc12] 41
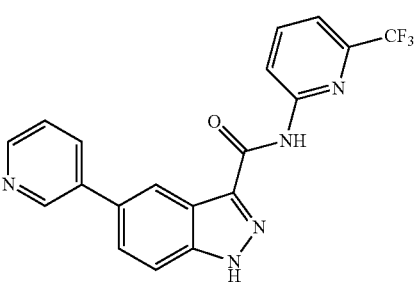 [SMILES: O=C(Nc1cccc(C(F)(F)F)n1)c1n[nH]c2ccc(-c3cccnc3)cc12] 42
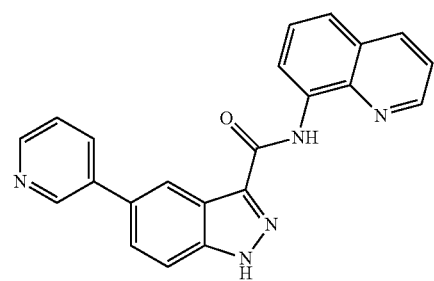 [SMILES: O=C(Nc1cccc2cccnc12)c1n[nH]c2ccc(-c3cccnc3)cc12] 43

TABLE 1-continued
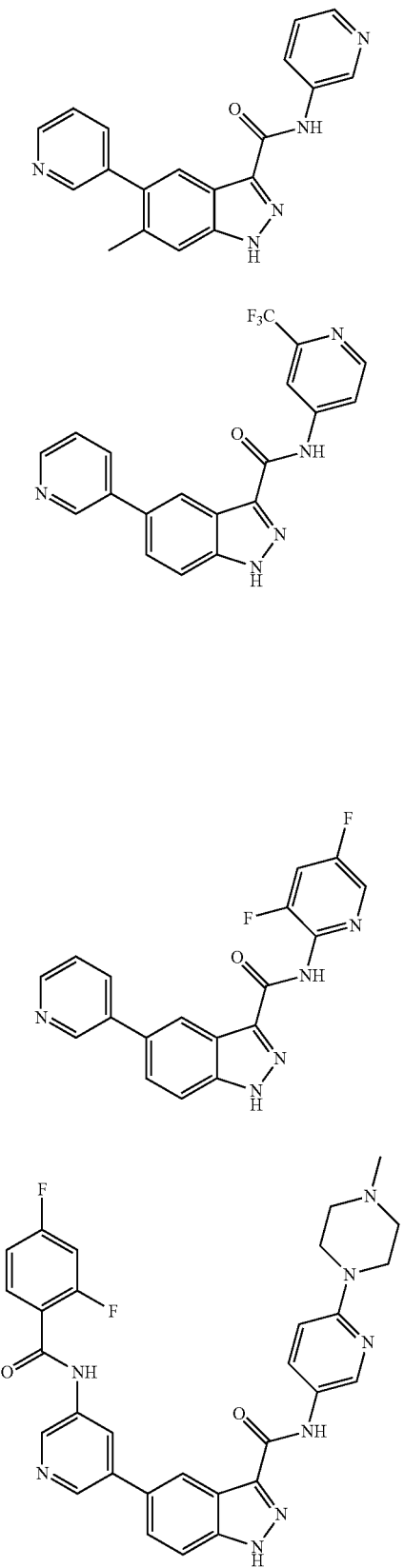
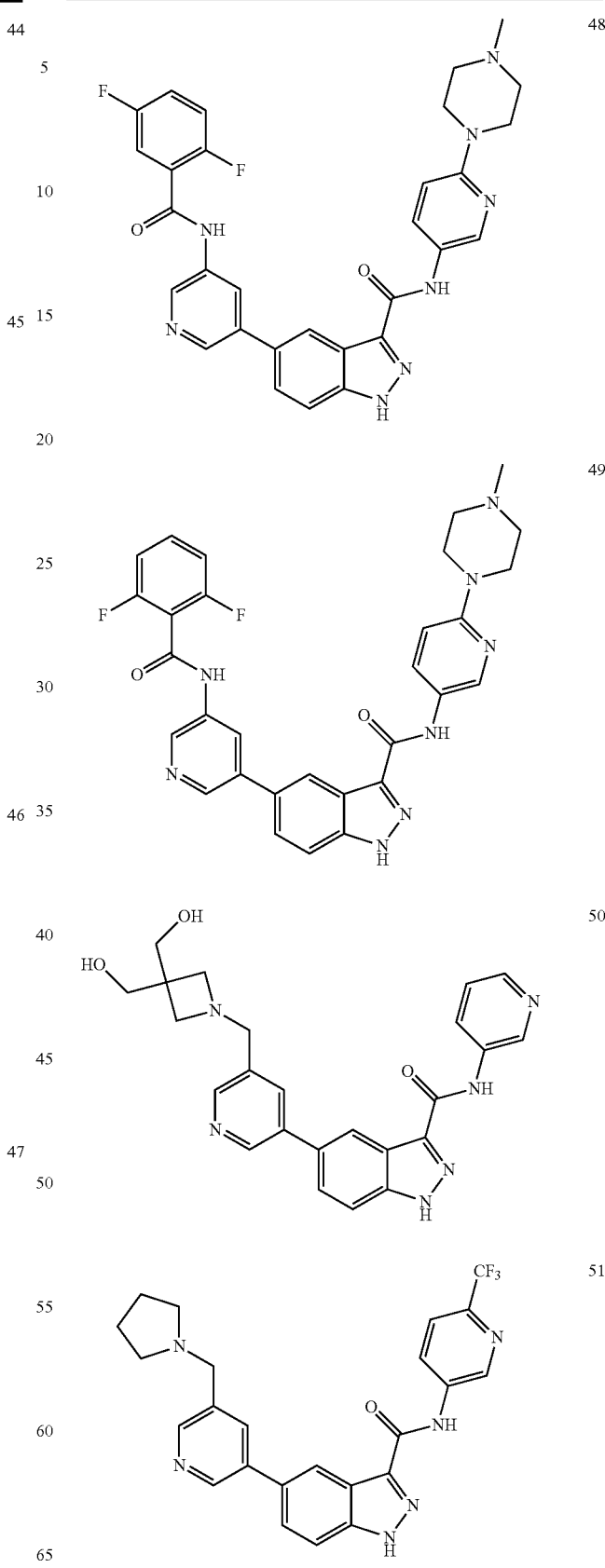

TABLE 1-continued
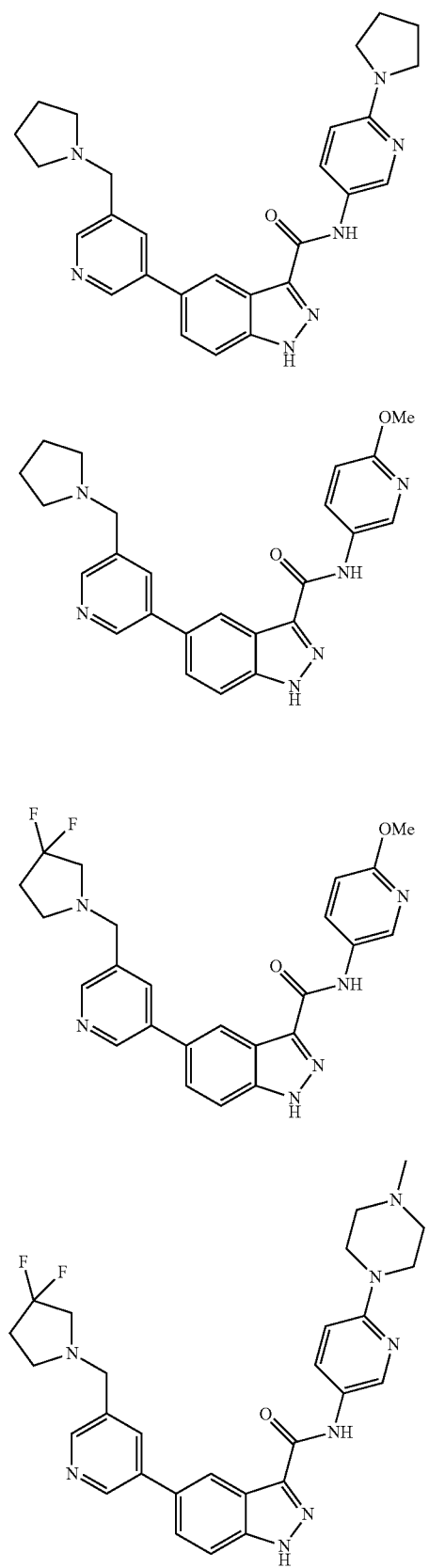
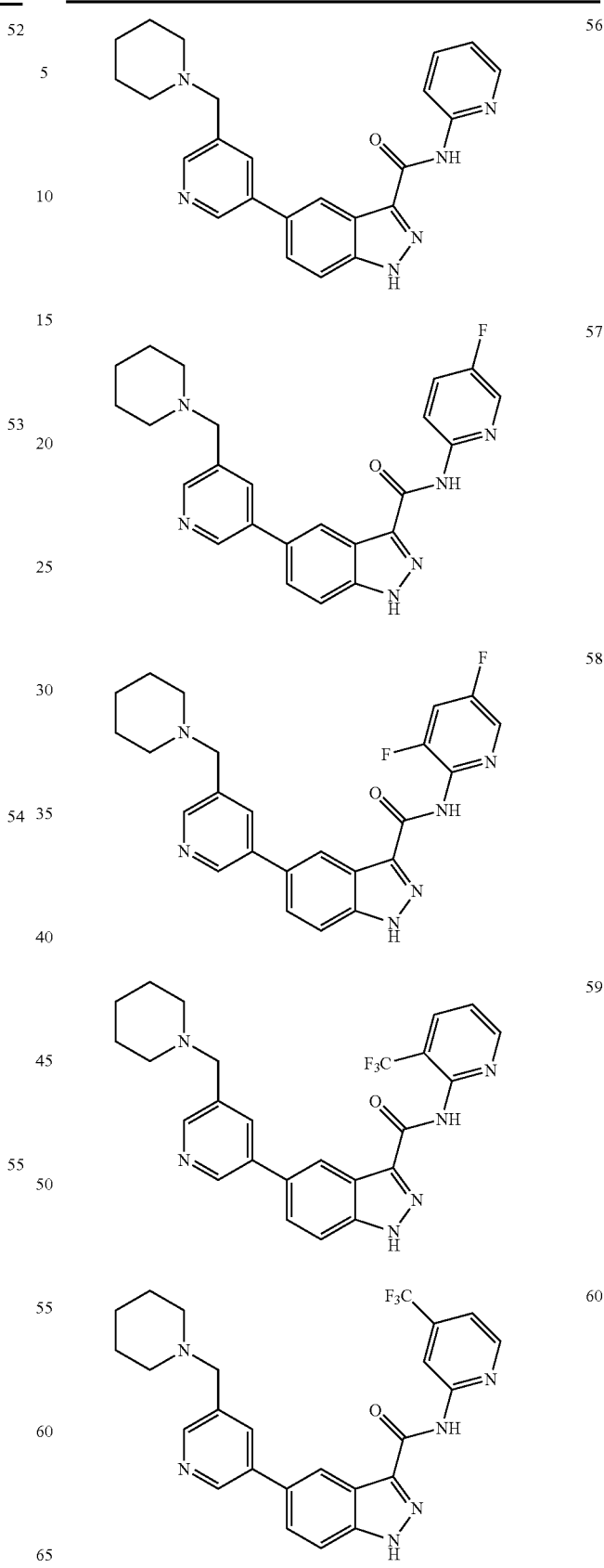

TABLE 1-continued
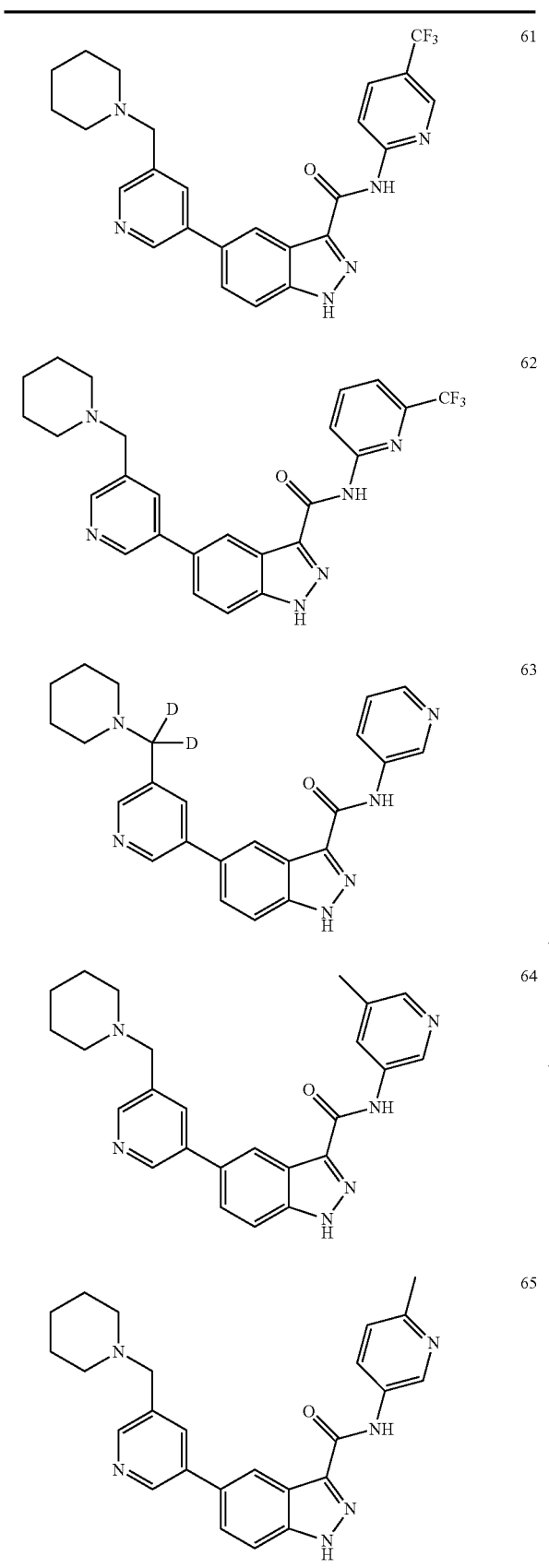
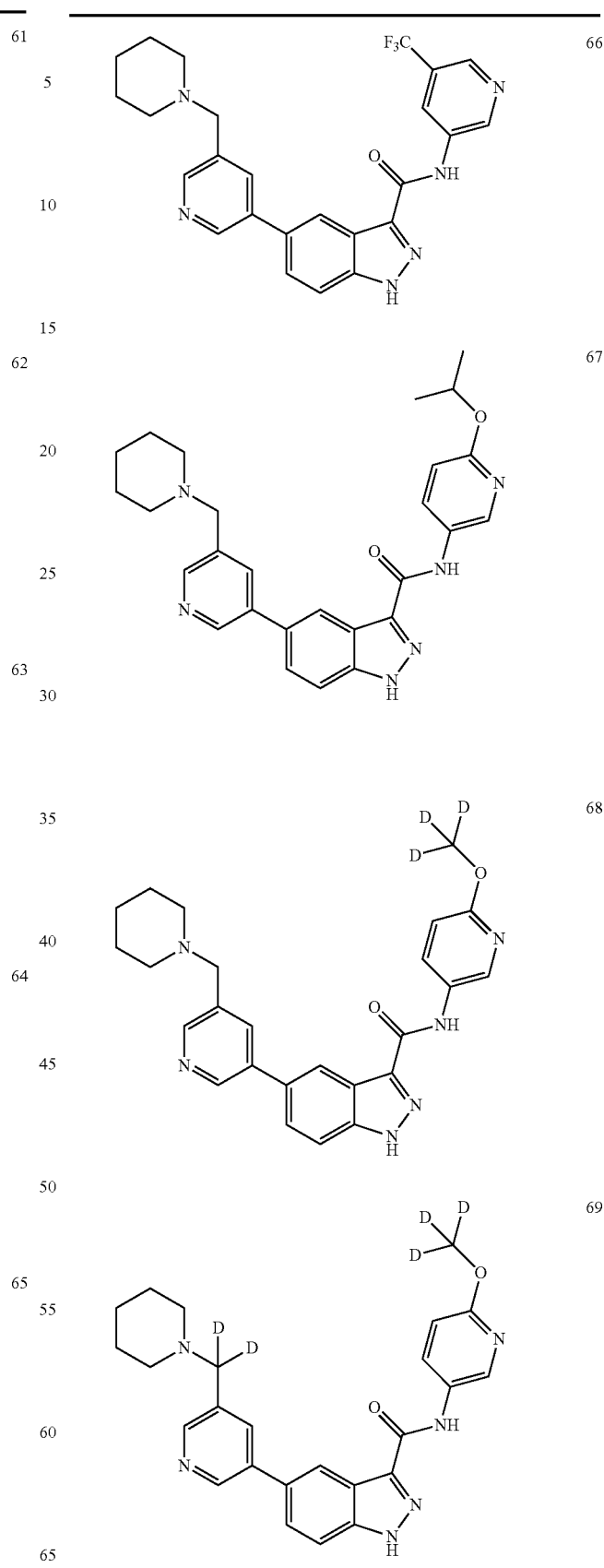

TABLE 1-continued
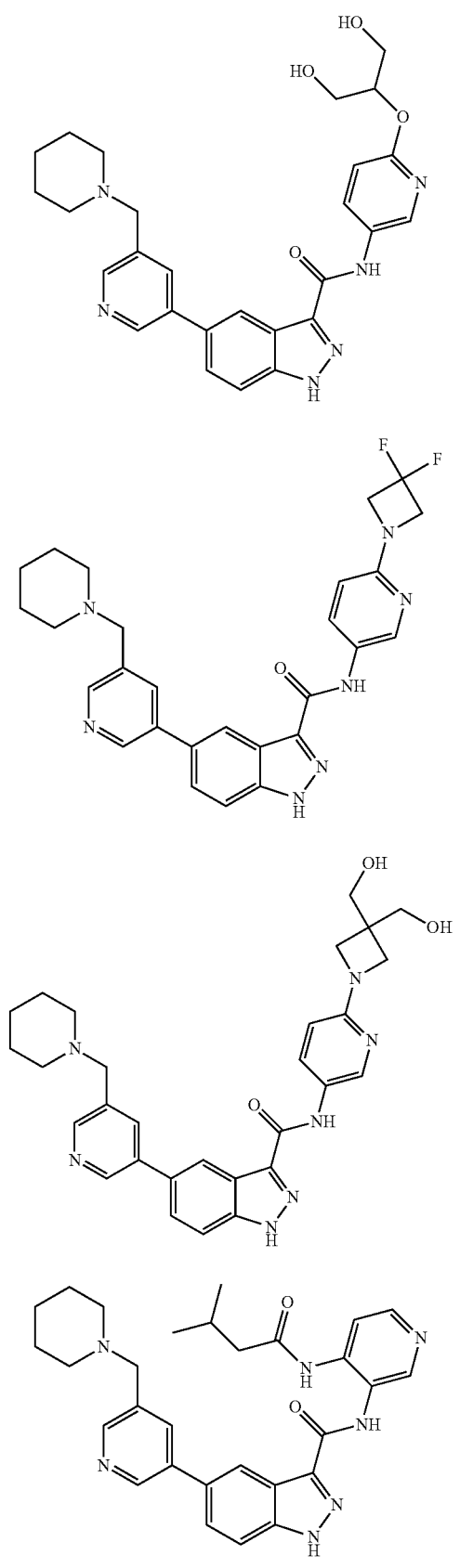
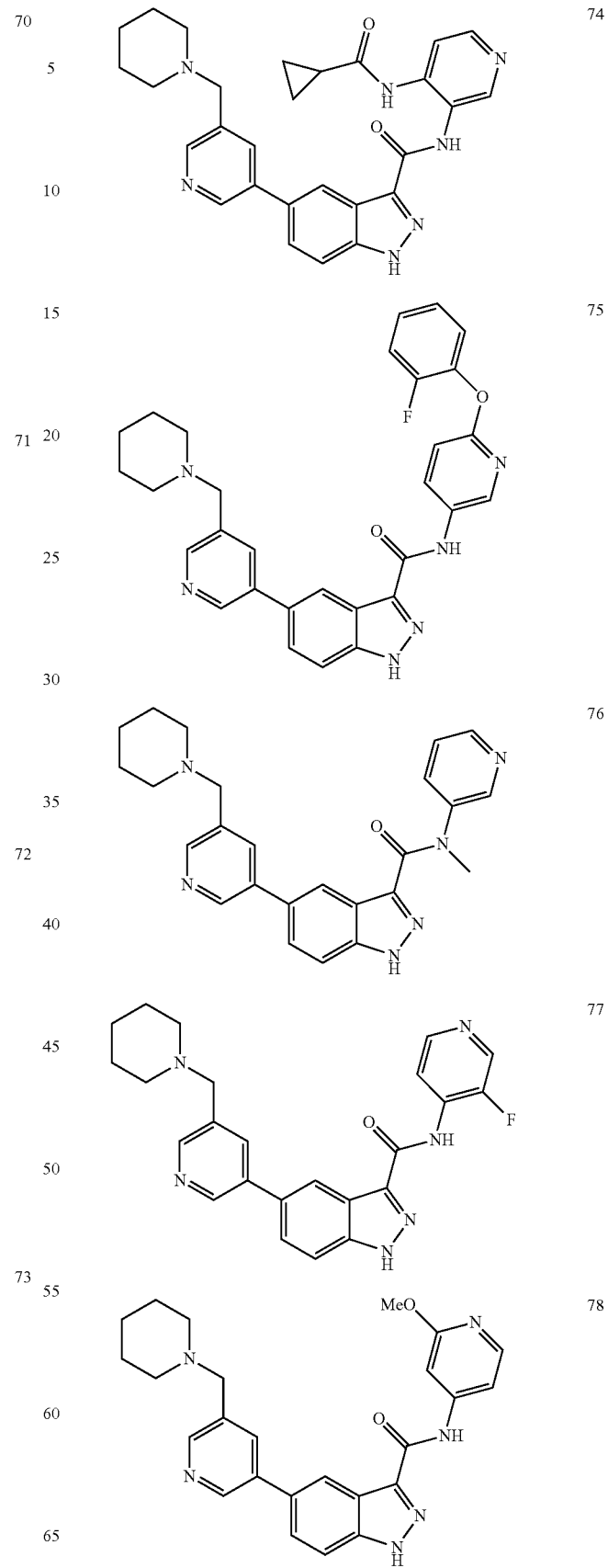

TABLE 1-continued
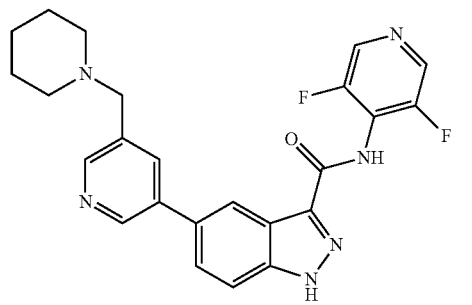 [SMILES: O=C(Nc1c(F)cncc1F)c1n[nH]c2ccc(-c3cncc(CN4CCCCC4)c3)cc12]
79
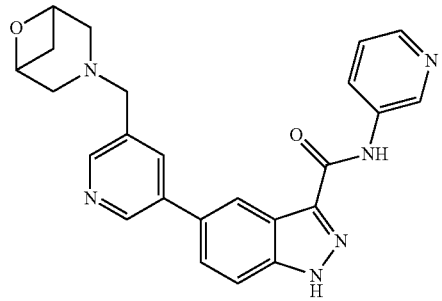
84
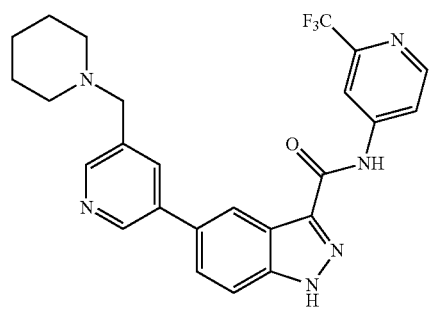 [SMILES: O=C(Nc1ccnc(C(F)(F)F)c1)c1n[nH]c2ccc(-c3cncc(CN4CCCCC4)c3)cc12]
80
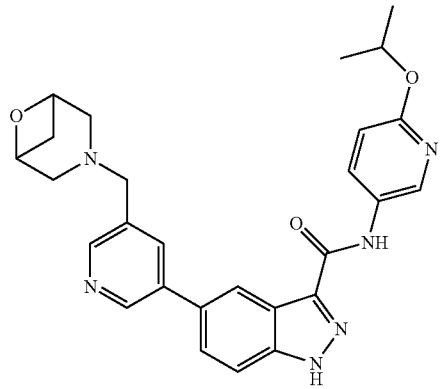
85
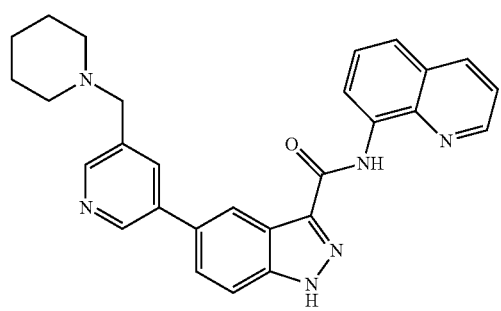 [SMILES: O=C(Nc1cccc2cccnc12)c1n[nH]c2ccc(-c3cncc(CN4CCCCC4)c3)cc12]
81
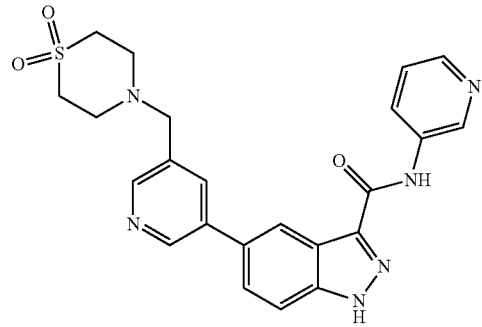
86
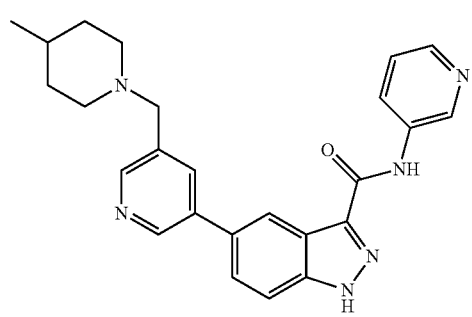 [SMILES: CC1CCN(Cc2cncc(-c3ccc4[nH]nc(C(=O)Nc5cccnc5)c4c3)c2)CC1]
82
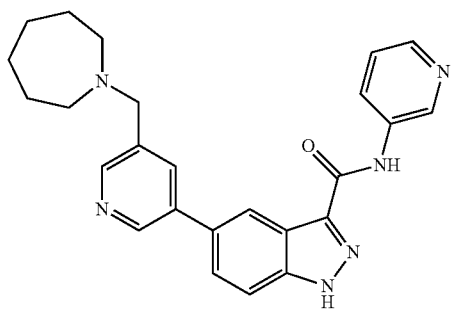
87
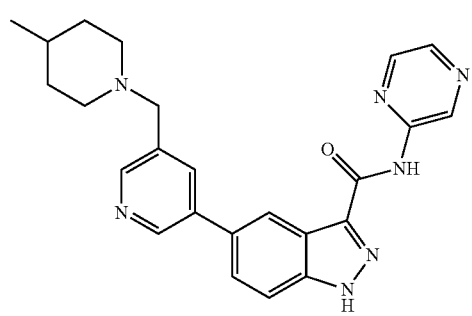 [SMILES: CC1CCN(Cc2cncc(-c3ccc4[nH]nc(C(=O)Nc5cnccn5)c4c3)c2)CC1]
83
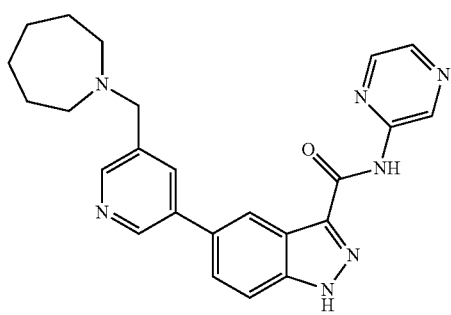 [SMILES: O=C(Nc1cnccn1)c1n[nH]c2ccc(-c3cncc(CN4CCCCCC4)c3)cc12]
88

TABLE 1-continued
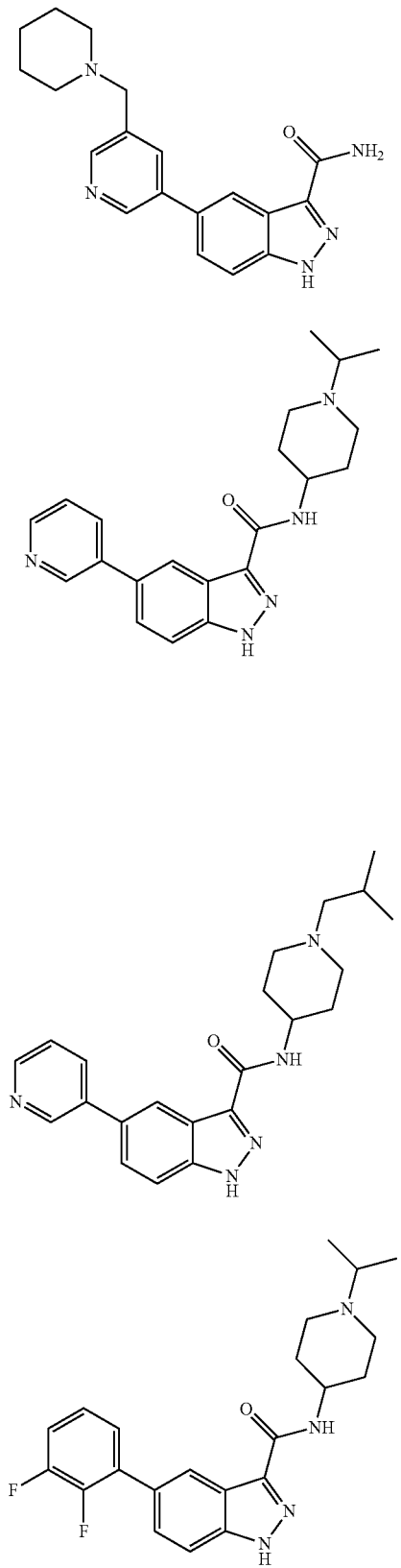
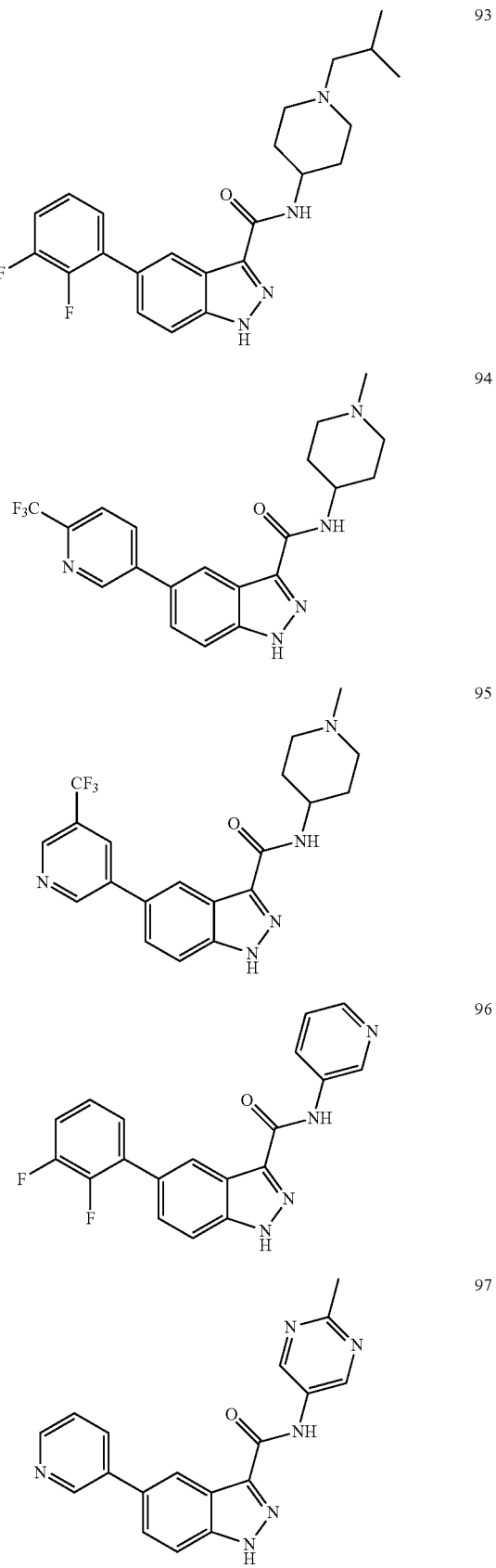

TABLE 1-continued
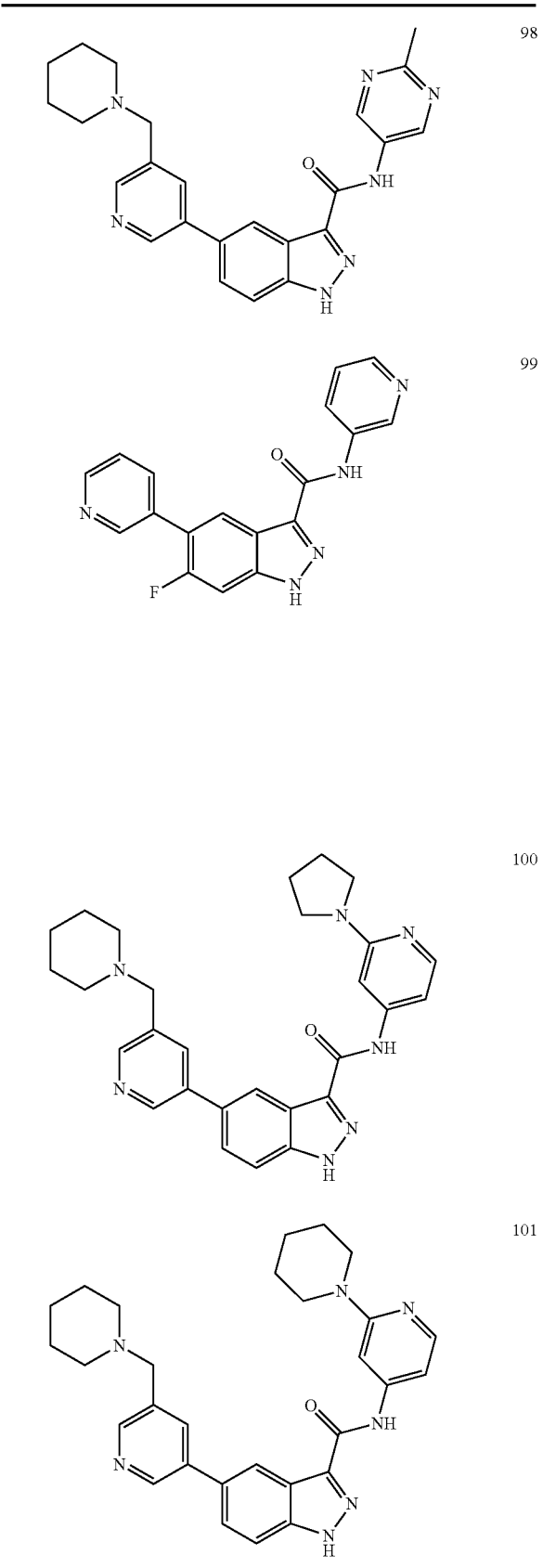

TABLE 1-continued
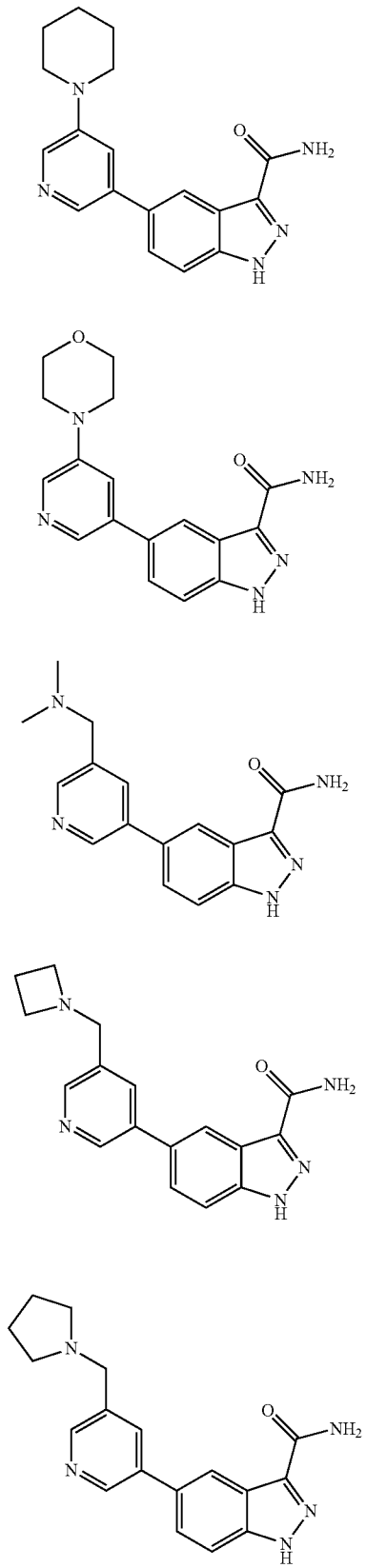
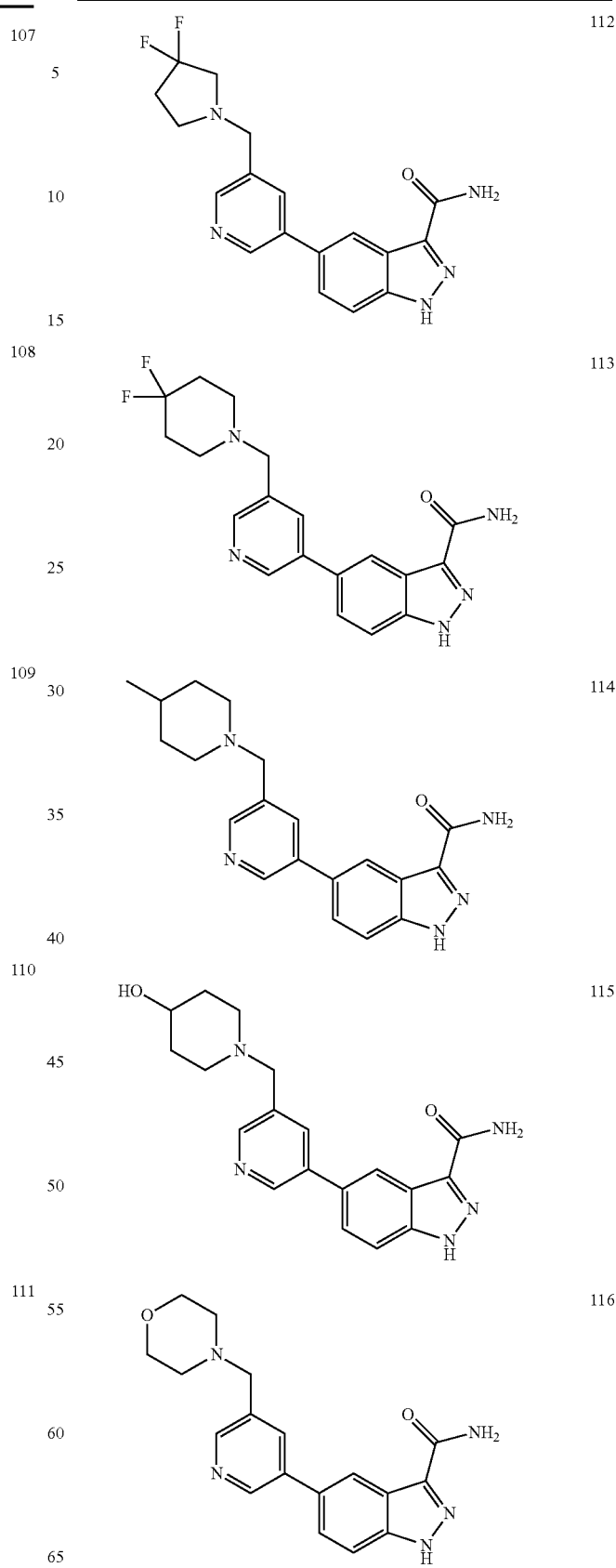

TABLE 1-continued
| | |
|---|---|
| 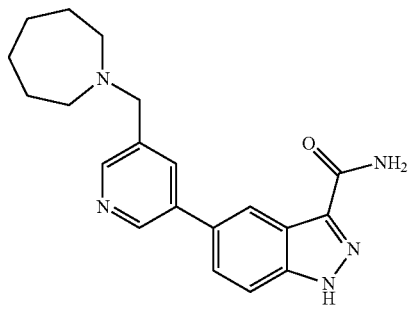 [SMILES: NC(=O)c1n[nH]c2ccc(-c3cncc(CN4CCCCCC4)c3)cc12] | 117 |
| 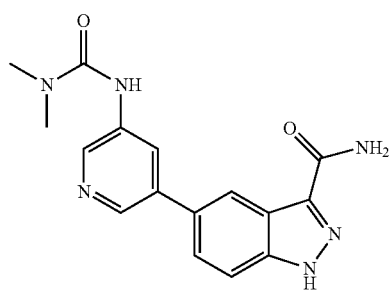 [SMILES: CN(C)C(=O)Nc1cncc(-c2ccc3[nH]nc(C(N)=O)c3c2)c1] | 118 |
| 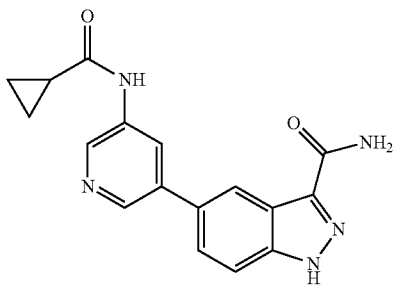 [SMILES: NC(=O)c1n[nH]c2ccc(-c3cncc(NC(=O)C4CC4)c3)cc12] | 119 |
| 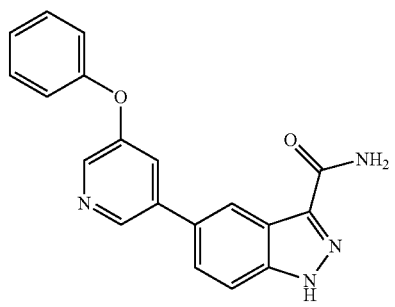 [SMILES: NC(=O)c1n[nH]c2ccc(-c3cncc(Oc4ccccc4)c3)cc12] | 120 |
| 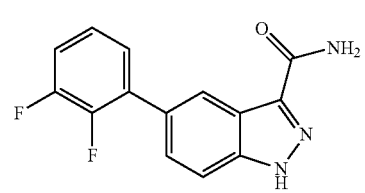 [SMILES: NC(=O)c1n[nH]c2ccc(-c3cccc(F)c3F)cc12] | 121 |
| 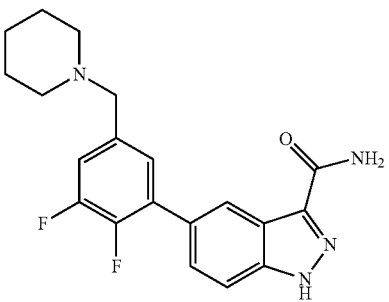 [SMILES: NC(=O)c1n[nH]c2ccc(-c3cc(CN4CCCCC4)cc(F)c3F)cc12] | 122 |
| 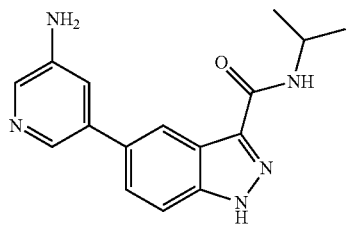 [SMILES: CC(C)NC(=O)c1n[nH]c2ccc(-c3cncc(N)c3)cc12] | 123 |
| 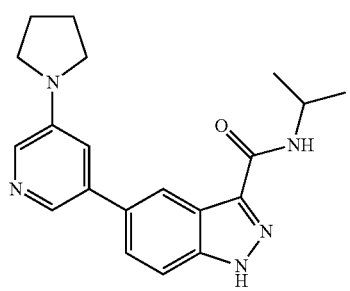 [SMILES: CC(C)NC(=O)c1n[nH]c2ccc(-c3cncc(N4CCCC4)c3)cc12] | 124 |
| 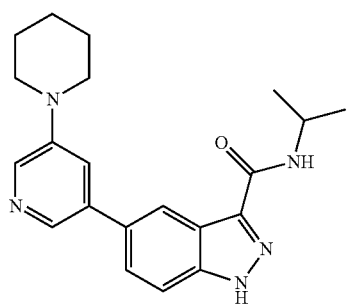 [SMILES: CC(C)NC(=O)c1n[nH]c2ccc(-c3cncc(N4CCCCC4)c3)cc12] | 125 |
| 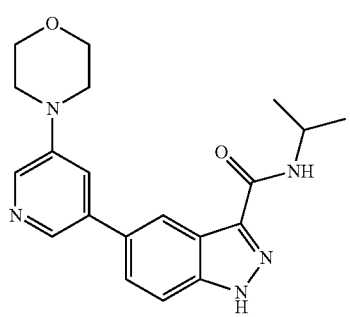 [SMILES: CC(C)NC(=O)c1n[nH]c2ccc(-c3cncc(N4CCOCC4)c3)cc12] | 126 |

TABLE 1-continued
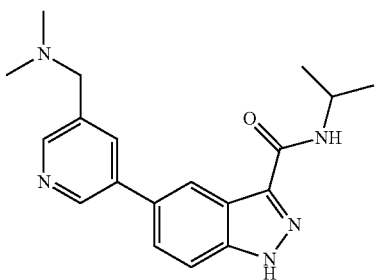 [SMILES: CC(C)NC(=O)c1n[nH]c2ccc(-c3cncc(CN(C)C)c3)cc12] 127
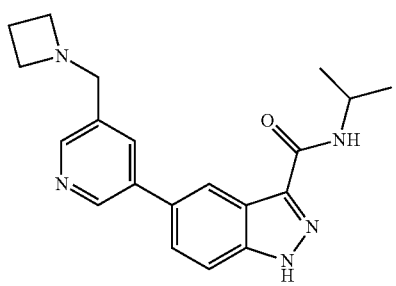 [SMILES: CC(C)NC(=O)c1n[nH]c2ccc(-c3cncc(CN4CCC4)c3)cc12] 128
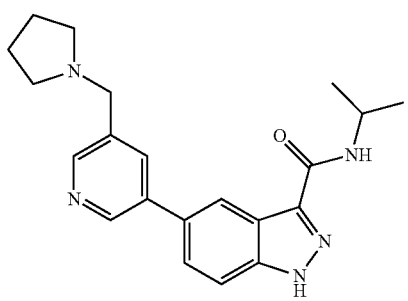 129
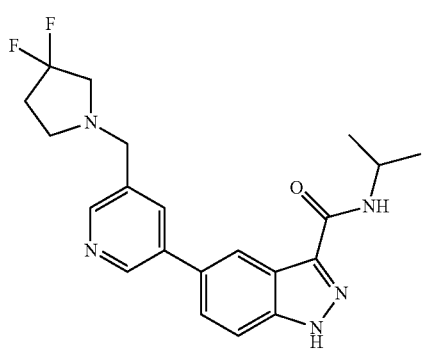 [SMILES: CC(C)NC(=O)c1n[nH]c2ccc(-c3cncc(CN4CCC(F)(F)C4)c3)cc12] 130
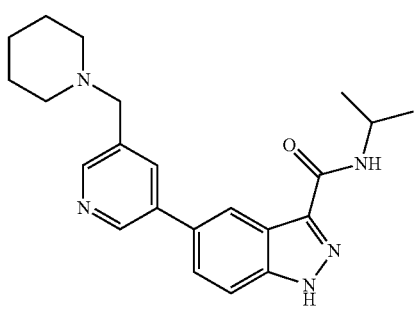 [SMILES: CC(C)NC(=O)c1n[nH]c2ccc(-c3cncc(CN4CCCCC4)c3)cc12] 131
TABLE 1-continued
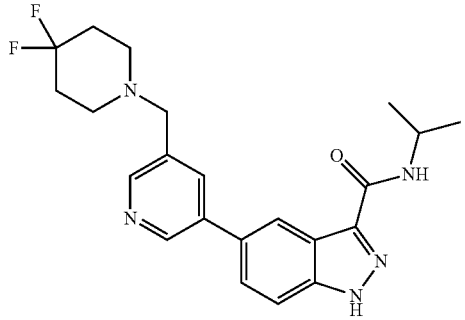 [SMILES: CC(C)NC(=O)c1n[nH]c2ccc(-c3cncc(CN4CCC(F)(F)CC4)c3)cc12] 132
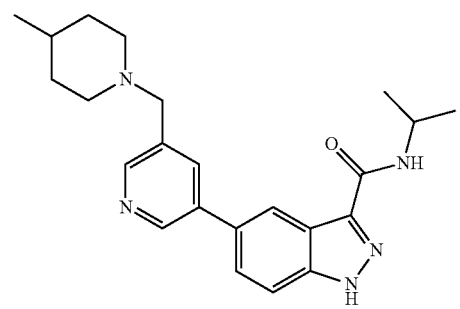 [SMILES: CC1CCN(Cc2cncc(-c3ccc4[nH]nc(C(=O)NC(C)C)c4c3)c2)CC1] 133
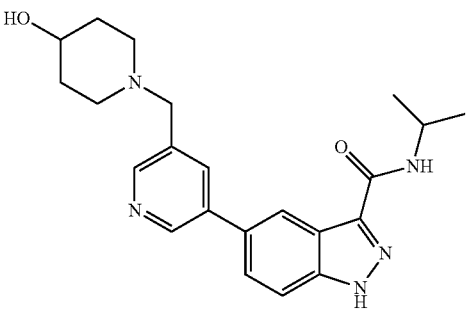 [SMILES: CC(C)NC(=O)c1n[nH]c2ccc(-c3cncc(CN4CCC(O)CC4)c3)cc12] 134
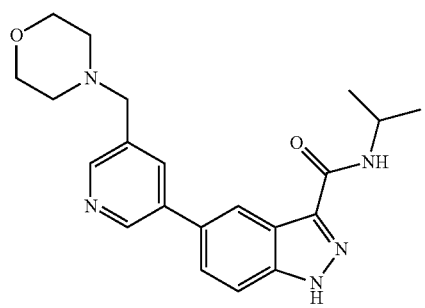 [SMILES: CC(C)NC(=O)c1n[nH]c2ccc(-c3cncc(CN4CCOCC4)c3)cc12] 135
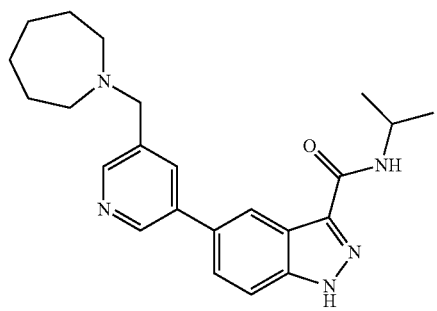 [SMILES: CC(C)NC(=O)c1n[nH]c2ccc(-c3cncc(CN4CCCCCC4)c3)cc12] 136

TABLE 1-continued

| | |
|---|---|
| 137 | 142 |
| 138 | 143 |
| 139 | 144 |
| 140 | 145 |
| 141 | 146 |

TABLE 1-continued
| 147 | 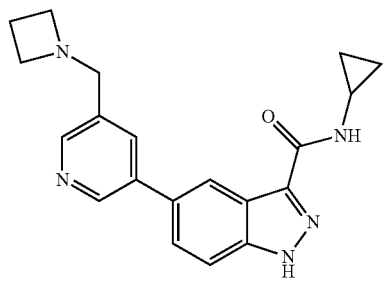 [SMILES: O=C(NC1CC1)c1n[nH]c2ccc(-c3cncc(CN4CCC4)c3)cc12] |
| 148 | 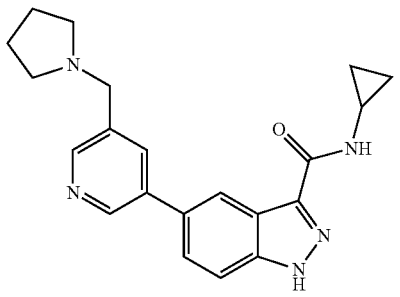 [SMILES: O=C(NC1CC1)c1n[nH]c2ccc(-c3cncc(CN4CCCC4)c3)cc12] |
| 149 | 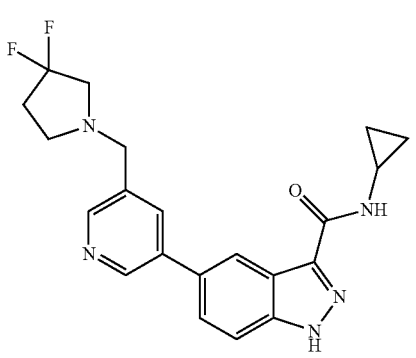 [SMILES: O=C(NC1CC1)c1n[nH]c2ccc(-c3cncc(CN4CCC(F)(F)C4)c3)cc12] |
| 150 | 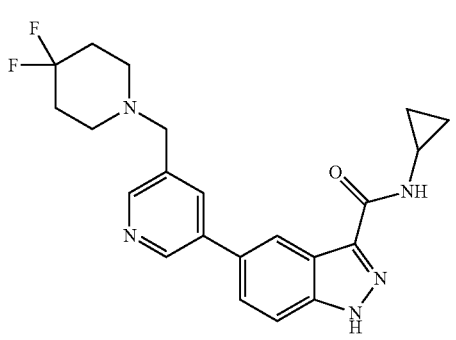 [SMILES: O=C(NC1CC1)c1n[nH]c2ccc(-c3cncc(CN4CCC(F)(F)CC4)c3)cc12] |
| 151 |  |
TABLE 1-continued
| 152 | 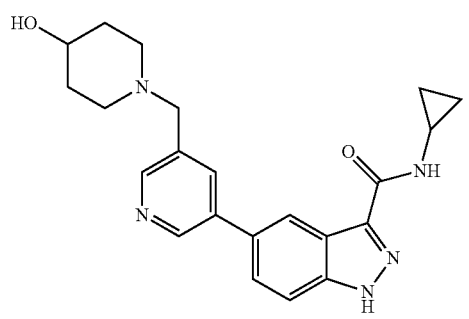 [SMILES: O=C(NC1CC1)c1n[nH]c2ccc(-c3cncc(CN4CCC(O)CC4)c3)cc12] |
| 153 | 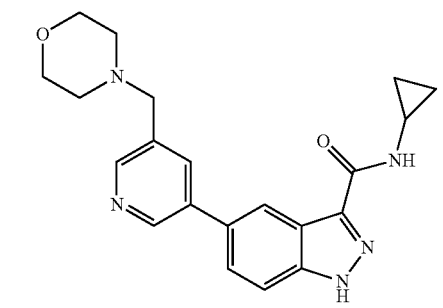 [SMILES: O=C(NC1CC1)c1n[nH]c2ccc(-c3cncc(CN4CCOCC4)c3)cc12] |
| 154 | 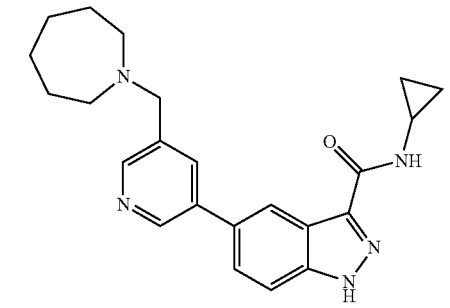 [SMILES: O=C(NC1CC1)c1n[nH]c2ccc(-c3cncc(CN4CCCCCC4)c3)cc12] |
| 155 | 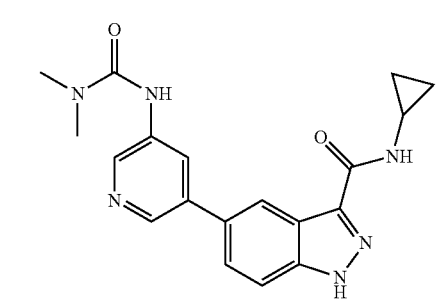 [SMILES: CN(C)C(=O)Nc1cncc(-c2ccc3[nH]nc(C(=O)NC4CC4)c3c2)c1] |
| 156 | 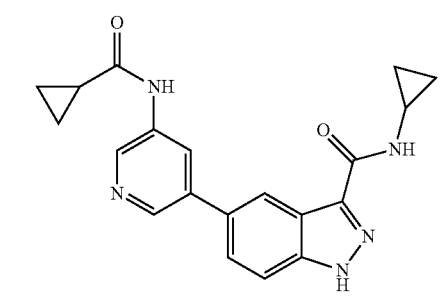 [SMILES: O=C(NC1CC1)c1n[nH]c2ccc(-c3cncc(NC(=O)C4CC4)c3)cc12] |

TABLE 1-continued
| 157 | 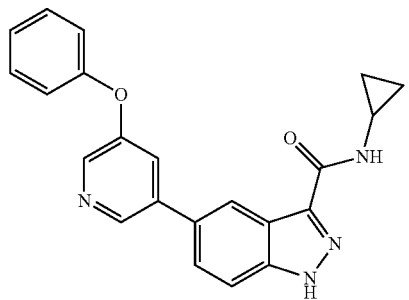 [SMILES: O=C(NC1CC1)c1n[nH]c2ccc(-c3cncc(Oc4ccccc4)c3)cc12] |
| 158 |  |
| 159 | 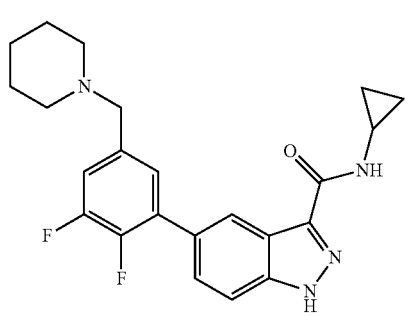 [SMILES: O=C(NC1CC1)c1n[nH]c2ccc(-c3cc(CN4CCCCC4)cc(F)c3F)cc12] |
| 160 |  |
| 161 |  |
TABLE 1-continued
| 162 | 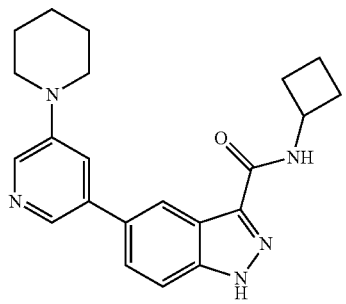 [SMILES: O=C(NC1CCC1)c1n[nH]c2ccc(-c3cncc(N4CCCCC4)c3)cc12] |
| 163 | 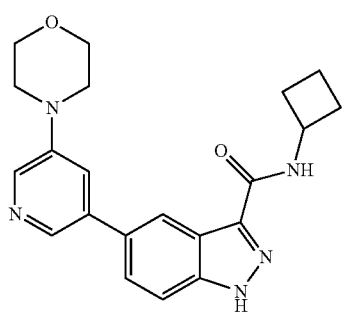 [SMILES: O=C(NC1CCC1)c1n[nH]c2ccc(-c3cncc(N4CCOCC4)c3)cc12] |
| 164 | 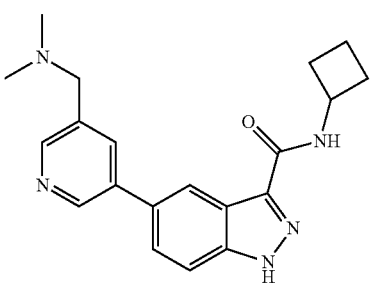 [SMILES: CN(C)Cc1cncc(-c2ccc3[nH]nc(C(=O)NC4CCC4)c3c2)c1] |
| 165 | 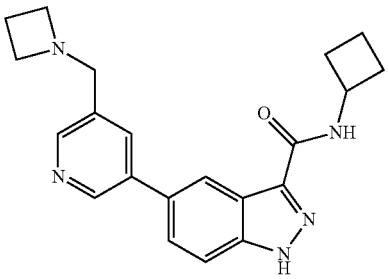 [SMILES: O=C(NC1CCC1)c1n[nH]c2ccc(-c3cncc(CN4CCC4)c3)cc12] |
| 166 | 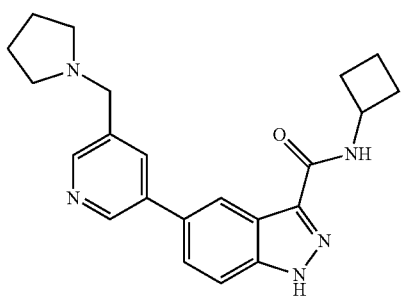 [SMILES: O=C(NC1CCC1)c1n[nH]c2ccc(-c3cncc(CN4CCCC4)c3)cc12] |

TABLE 1-continued
| 167 | 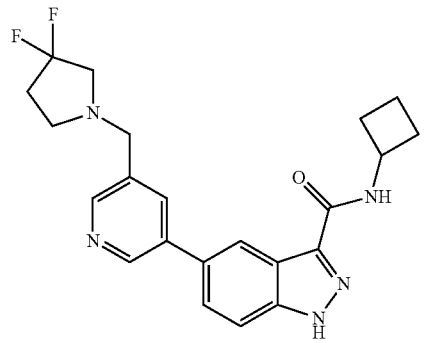 [SMILES: O=C(NC1CCC1)c1n[nH]c2ccc(-c3cncc(CN4CCC(F)(F)C4)c3)cc12] |
| 168 | 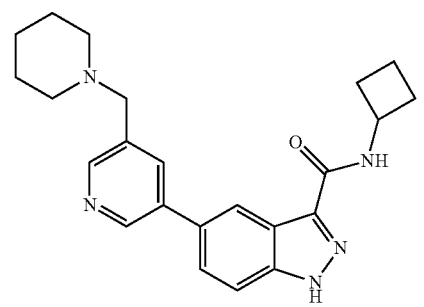 [SMILES: O=C(NC1CCC1)c1n[nH]c2ccc(-c3cncc(CN4CCCCC4)c3)cc12] |
| 169 | 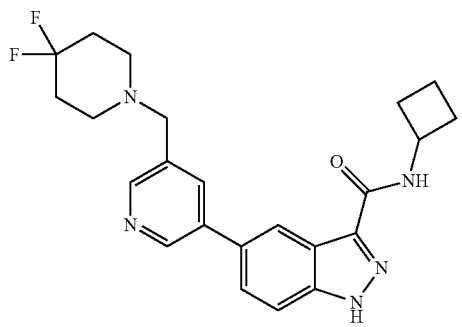 [SMILES: O=C(NC1CCC1)c1n[nH]c2ccc(-c3cncc(CN4CCC(F)(F)CC4)c3)cc12] |
| 170 | 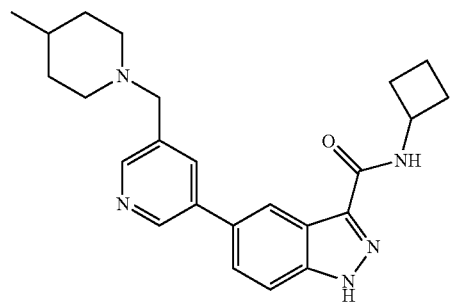 [SMILES: CC1CCN(Cc2cncc(-c3ccc4[nH]nc(C(=O)NC5CCC5)c4c3)c2)CC1] |
| 171 | 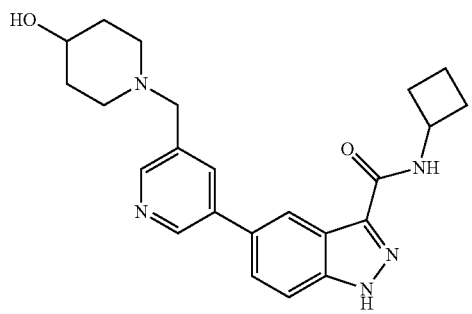 [SMILES: O=C(NC1CCC1)c1n[nH]c2ccc(-c3cncc(CN4CCC(O)CC4)c3)cc12] |
TABLE 1-continued
| 172 | 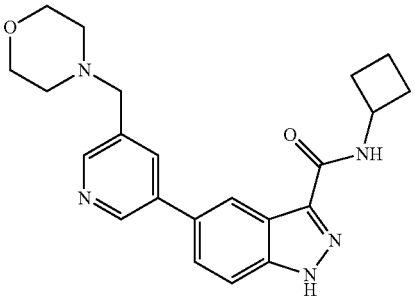 [SMILES: O=C(NC1CCC1)c1n[nH]c2ccc(-c3cncc(CN4CCOCC4)c3)cc12] |
| 173 |  |
| 174 |  |
| 175 | 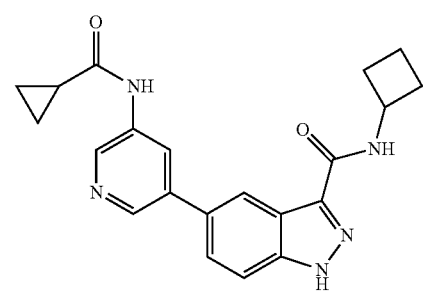 [SMILES: O=C(NC1CCC1)c1n[nH]c2ccc(-c3cncc(NC(=O)C4CC4)c3)cc12] |
| 176 | 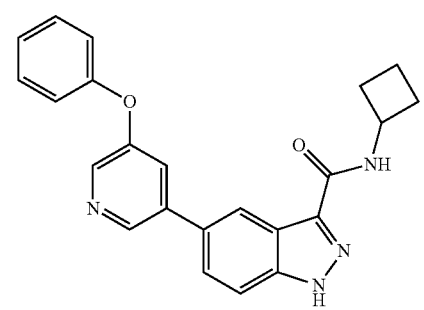 [SMILES: O=C(NC1CCC1)c1n[nH]c2ccc(-c3cncc(Oc4ccccc4)c3)cc12] |

TABLE 1-continued
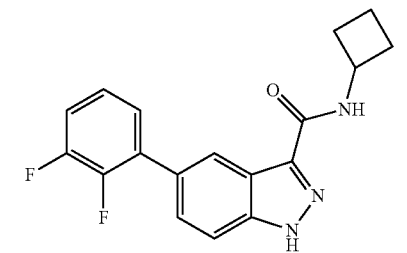 [SMILES: O=C(NC1CCC1)c1n[nH]c2ccc(-c3cccc(F)c3F)cc12] 177
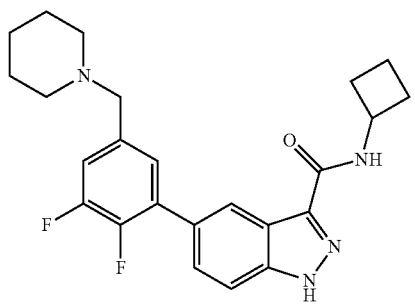 [SMILES: O=C(NC1CCC1)c1n[nH]c2ccc(-c3cc(CN4CCCCC4)cc(F)c3F)cc12] 178
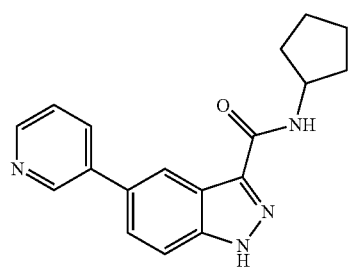 [SMILES: O=C(NC1CCCC1)c1n[nH]c2ccc(-c3cccnc3)cc12] 179
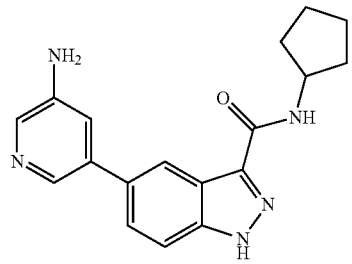 [SMILES: Nc1cncc(-c2ccc3[nH]nc(C(=O)NC4CCCC4)c3c2)c1] 180
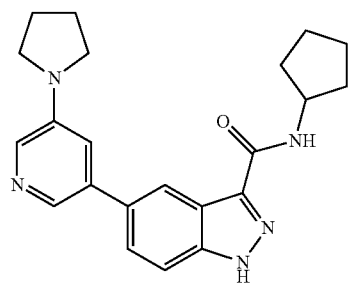 [SMILES: O=C(NC1CCCC1)c1n[nH]c2ccc(-c3cncc(N4CCCC4)c3)cc12] 181
TABLE 1-continued
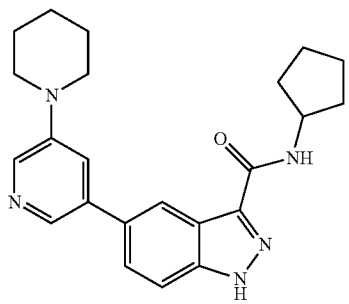 [SMILES: O=C(NC1CCCC1)c1n[nH]c2ccc(-c3cncc(N4CCCCC4)c3)cc12] 182
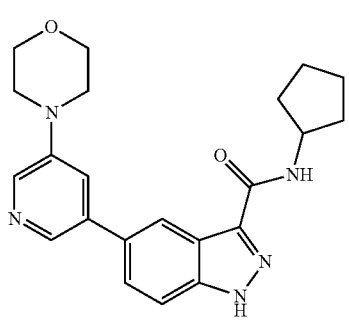 [SMILES: O=C(NC1CCCC1)c1n[nH]c2ccc(-c3cncc(N4CCOCC4)c3)cc12] 183
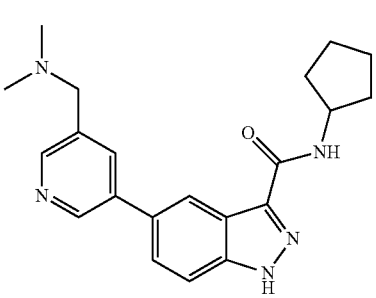 [SMILES: CN(C)Cc1cncc(-c2ccc3[nH]nc(C(=O)NC4CCCC4)c3c2)c1] 184
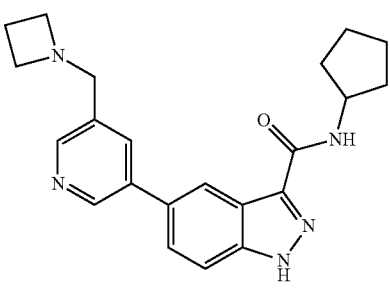 [SMILES: O=C(NC1CCCC1)c1n[nH]c2ccc(-c3cncc(CN4CCC4)c3)cc12] 185
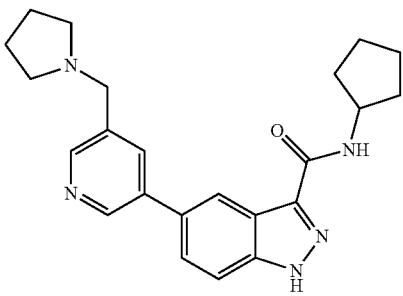 [SMILES: O=C(NC1CCCC1)c1n[nH]c2ccc(-c3cncc(CN4CCCC4)c3)cc12] 186

TABLE 1-continued
| 187 | 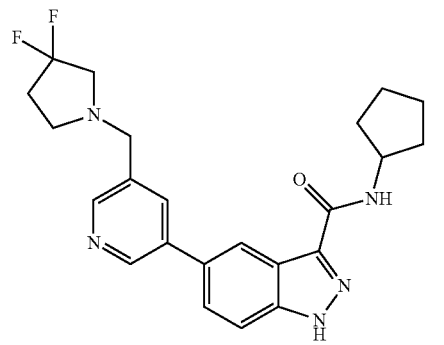 [SMILES: O=C(NC1CCCC1)c1n[nH]c2ccc(-c3cncc(CN4CCC(F)(F)C4)c3)cc12] |
| 188 | 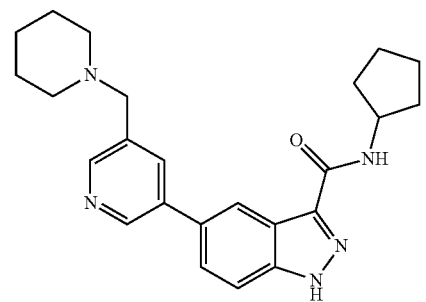 [SMILES: O=C(NC1CCCC1)c1n[nH]c2ccc(-c3cncc(CN4CCCCC4)c3)cc12] |
| 189 | 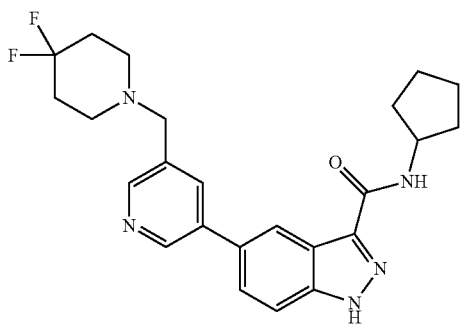 [SMILES: O=C(NC1CCCC1)c1n[nH]c2ccc(-c3cncc(CN4CCC(F)(F)CC4)c3)cc12] |
| 190 | 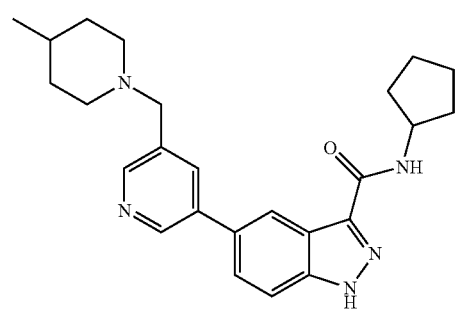 [SMILES: CC1CCN(Cc2cncc(-c3ccc4[nH]nc(C(=O)NC5CCCC5)c4c3)c2)CC1] |
| 191 | 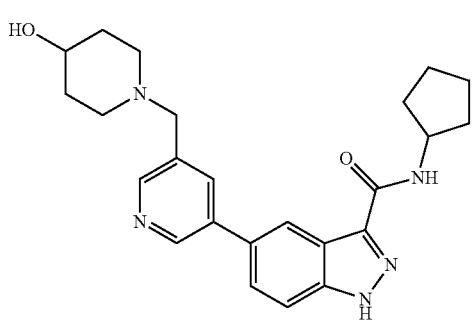 [SMILES: O=C(NC1CCCC1)c1n[nH]c2ccc(-c3cncc(CN4CCC(O)CC4)c3)cc12] |
TABLE 1-continued
| 192 | 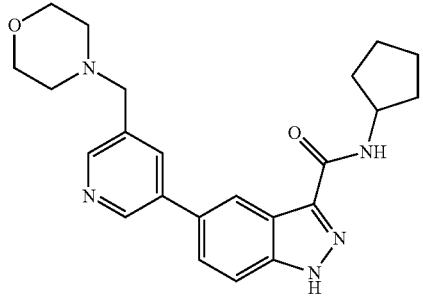 [SMILES: O=C(NC1CCCC1)c1n[nH]c2ccc(-c3cncc(CN4CCOCC4)c3)cc12] |
| 193 | 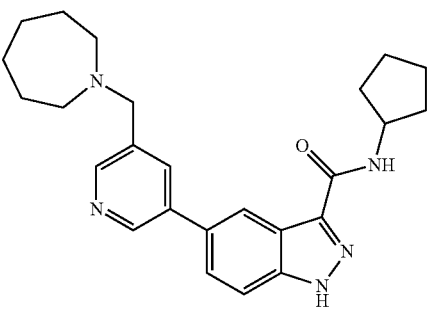 [SMILES: O=C(NC1CCCC1)c1n[nH]c2ccc(-c3cncc(CN4CCCCCC4)c3)cc12] |
| 194 |  |
| 195 | 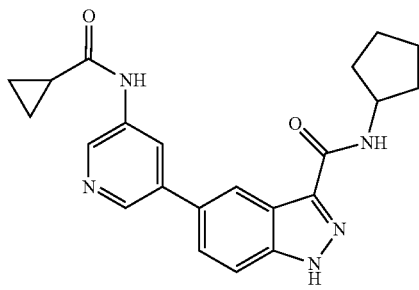 [SMILES: O=C(NC1CCCC1)c1n[nH]c2ccc(-c3cncc(NC(=O)C4CC4)c3)cc12] |
| 196 | 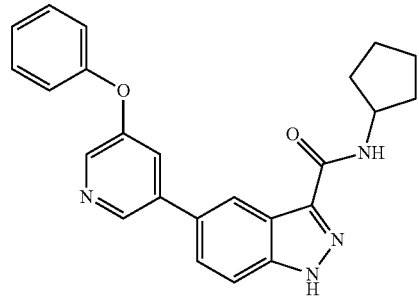 [SMILES: O=C(NC1CCCC1)c1n[nH]c2ccc(-c3cncc(Oc4ccccc4)c3)cc12] |

TABLE 1-continued
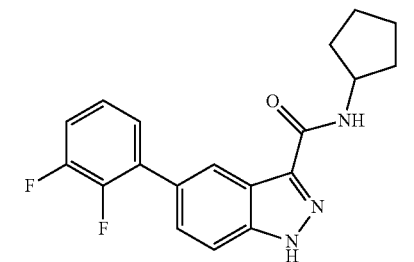 [SMILES: O=C(NC1CCCC1)c1n[nH]c2ccc(-c3cccc(F)c3F)cc12] 197
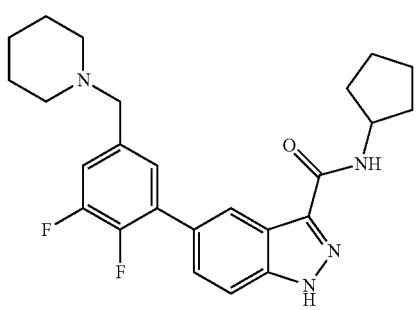 [SMILES: O=C(NC1CCCC1)c1n[nH]c2ccc(-c3cc(CN4CCCCC4)cc(F)c3F)cc12] 198
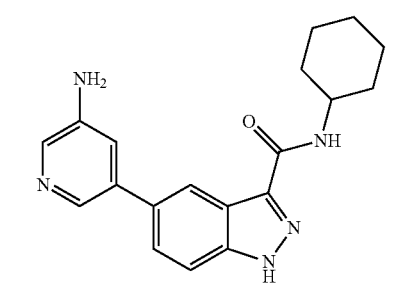 [SMILES: Nc1cncc(-c2ccc3[nH]nc(C(=O)NC4CCCCC4)c3c2)c1] 199
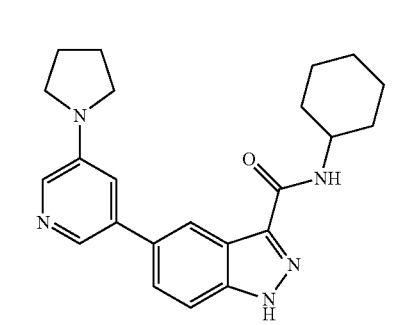 [SMILES: O=C(NC1CCCCC1)c1n[nH]c2ccc(-c3cncc(N4CCCC4)c3)cc12] 200
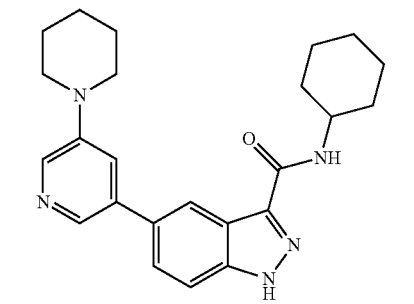 [SMILES: O=C(NC1CCCCC1)c1n[nH]c2ccc(-c3cncc(N4CCCCC4)c3)cc12] 201
TABLE 1-continued
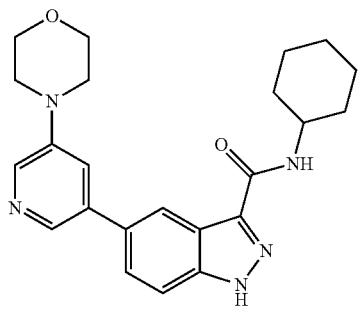 [SMILES: O=C(NC1CCCCC1)c1n[nH]c2ccc(-c3cncc(N4CCOCC4)c3)cc12] 202
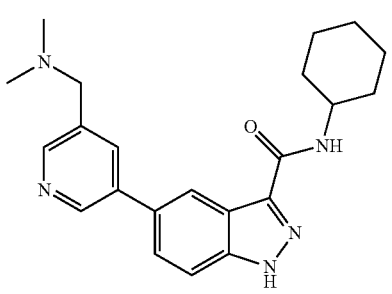 [SMILES: CN(C)Cc1cncc(-c2ccc3[nH]nc(C(=O)NC4CCCCC4)c3c2)c1] 203
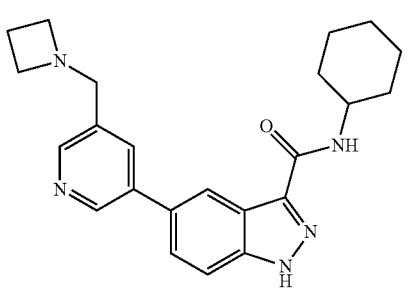 [SMILES: O=C(NC1CCCCC1)c1n[nH]c2ccc(-c3cncc(CN4CCC4)c3)cc12] 204
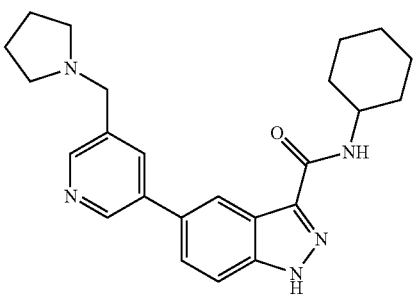 [SMILES: O=C(NC1CCCCC1)c1n[nH]c2ccc(-c3cncc(CN4CCCC4)c3)cc12] 205
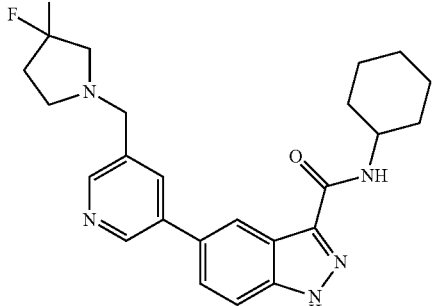 206

TABLE 1-continued
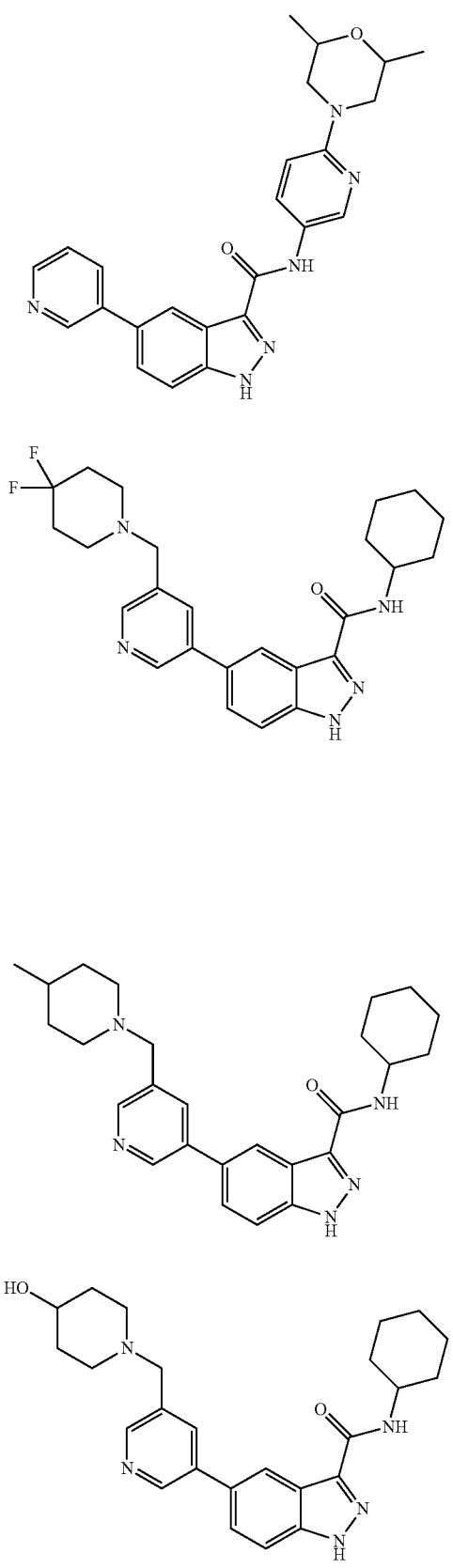
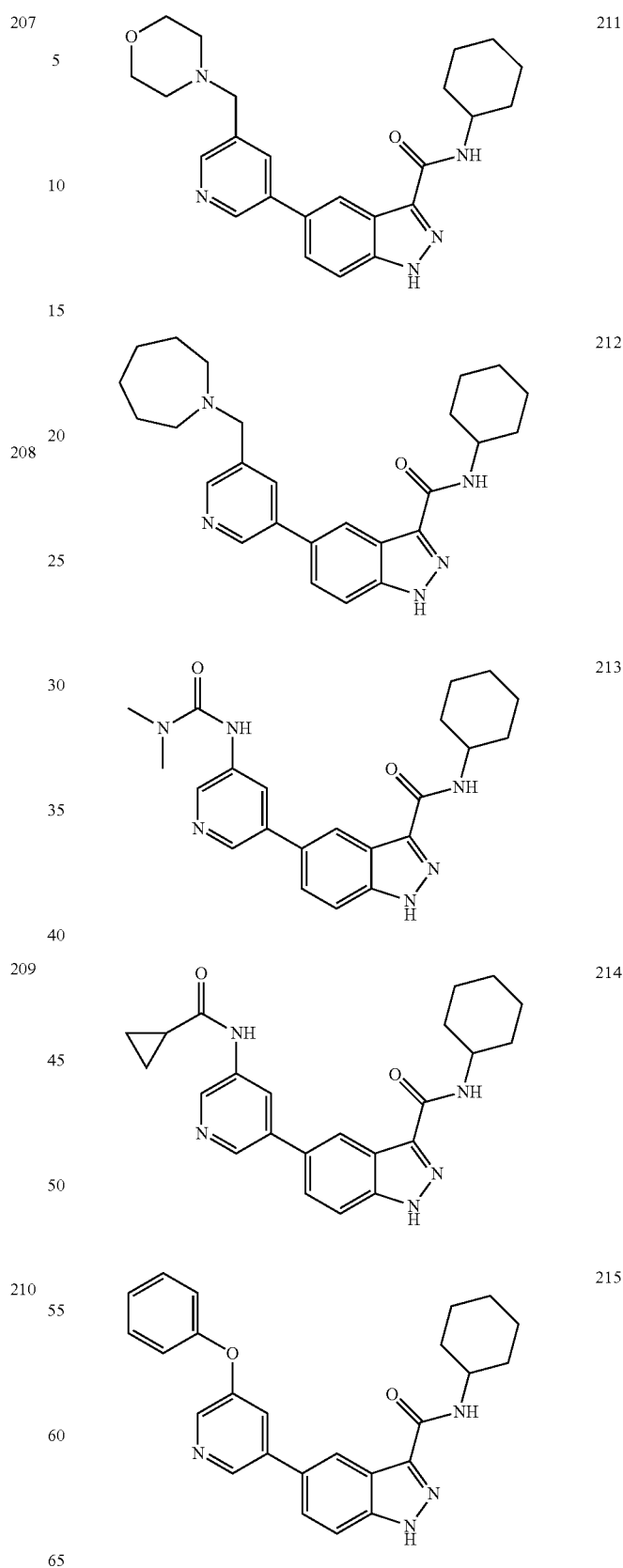

TABLE 1-continued

TABLE 1-continued
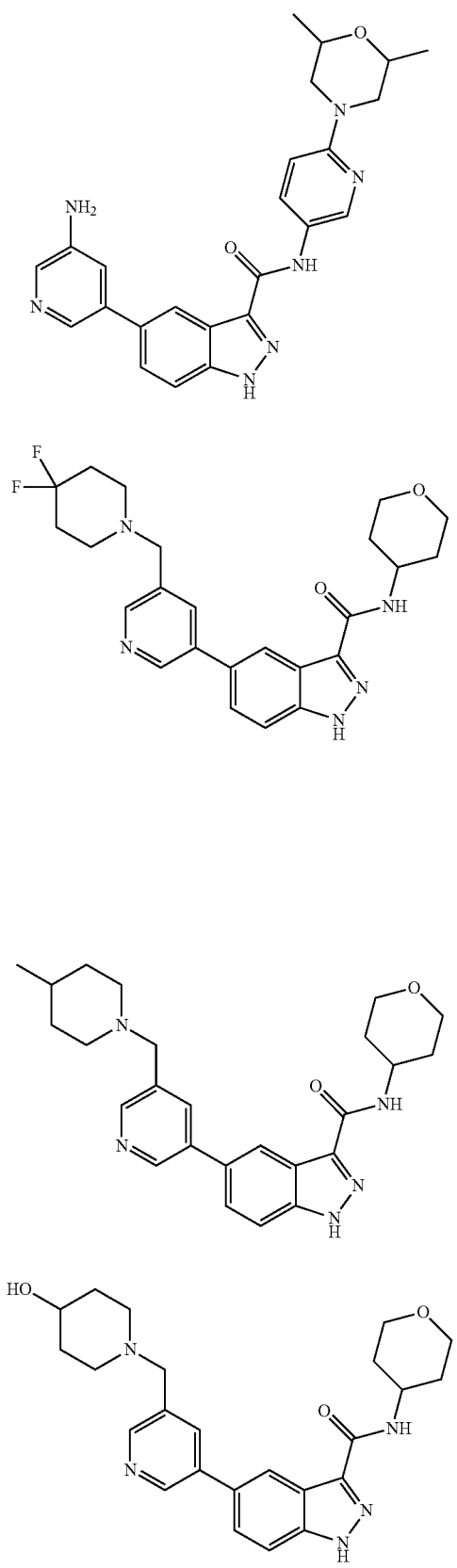
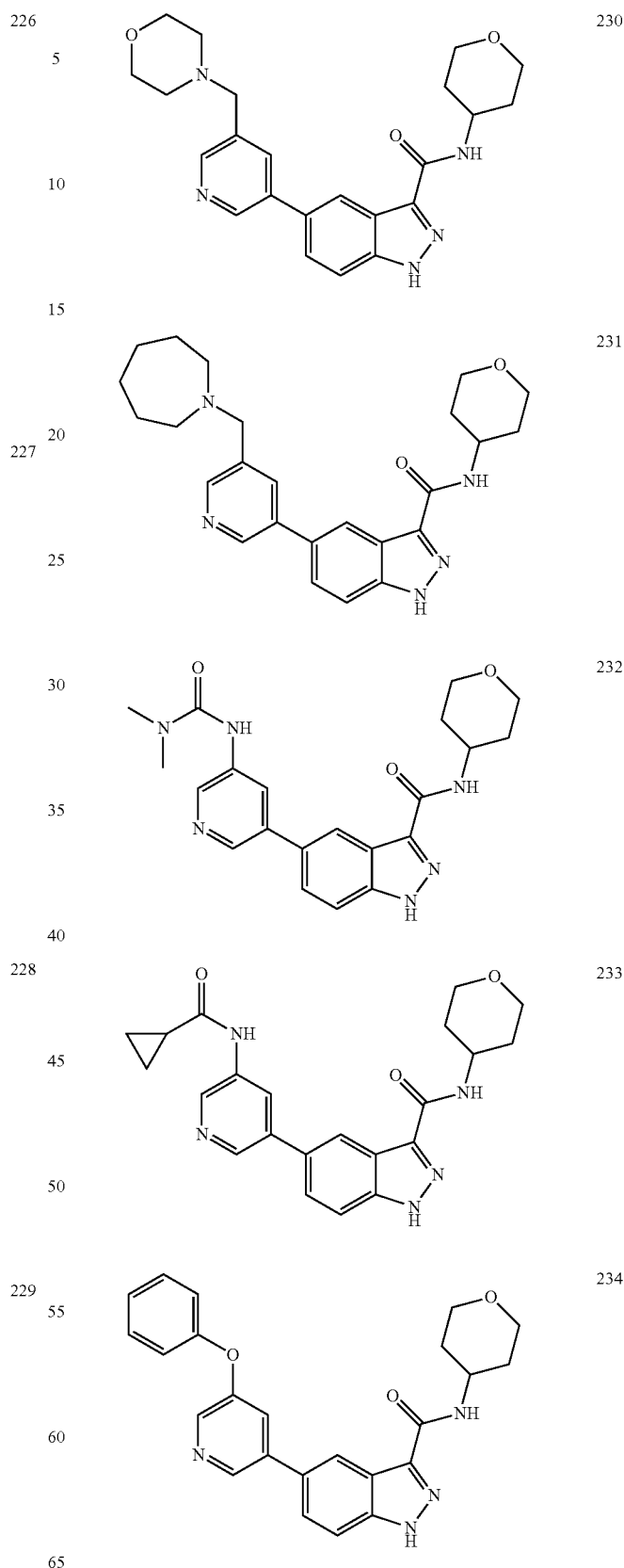

TABLE 1-continued
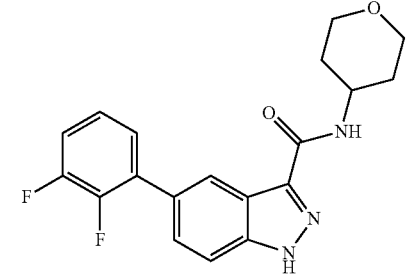 [SMILES: O=C(NC1CCOCC1)c1n[nH]c2ccc(-c3cccc(F)c3F)cc12] 235
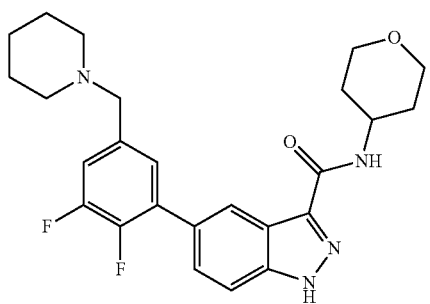 [SMILES: O=C(NC1CCOCC1)c1n[nH]c2ccc(-c3cc(CN4CCCCC4)cc(F)c3F)cc12] 236
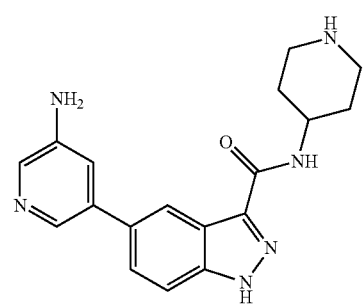 [SMILES: Nc1cncc(-c2ccc3[nH]nc(C(=O)NC4CCNCC4)c3c2)c1] 237
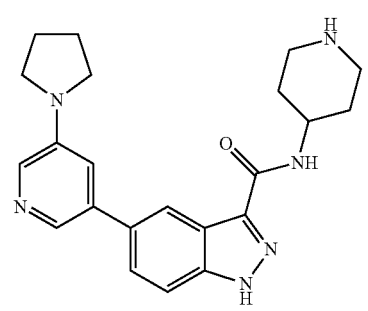 [SMILES: O=C(NC1CCNCC1)c1n[nH]c2ccc(-c3cncc(N4CCCC4)c3)cc12] 238
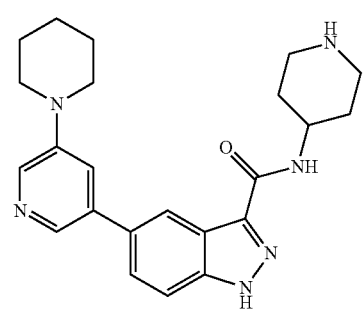 [SMILES: O=C(NC1CCNCC1)c1n[nH]c2ccc(-c3cncc(N4CCCCC4)c3)cc12] 239
TABLE 1-continued
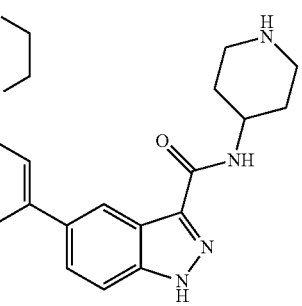 240
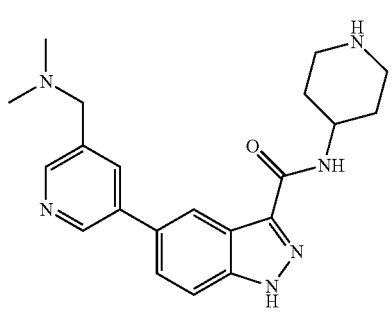 [SMILES: CN(C)Cc1cncc(-c2ccc3[nH]nc(C(=O)NC4CCNCC4)c3c2)c1] 241
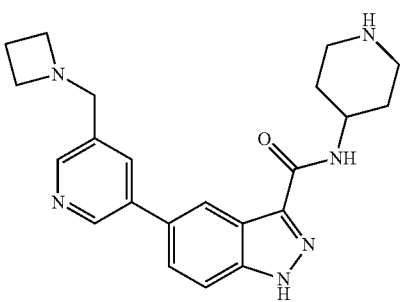 [SMILES: O=C(NC1CCNCC1)c1n[nH]c2ccc(-c3cncc(CN4CCC4)c3)cc12] 242
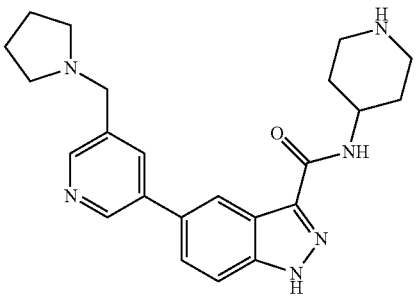 [SMILES: O=C(NC1CCNCC1)c1n[nH]c2ccc(-c3cncc(CN4CCCC4)c3)cc12] 243
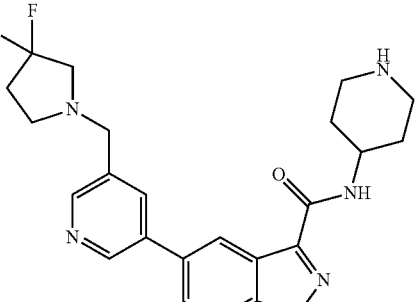 244

TABLE 1-continued
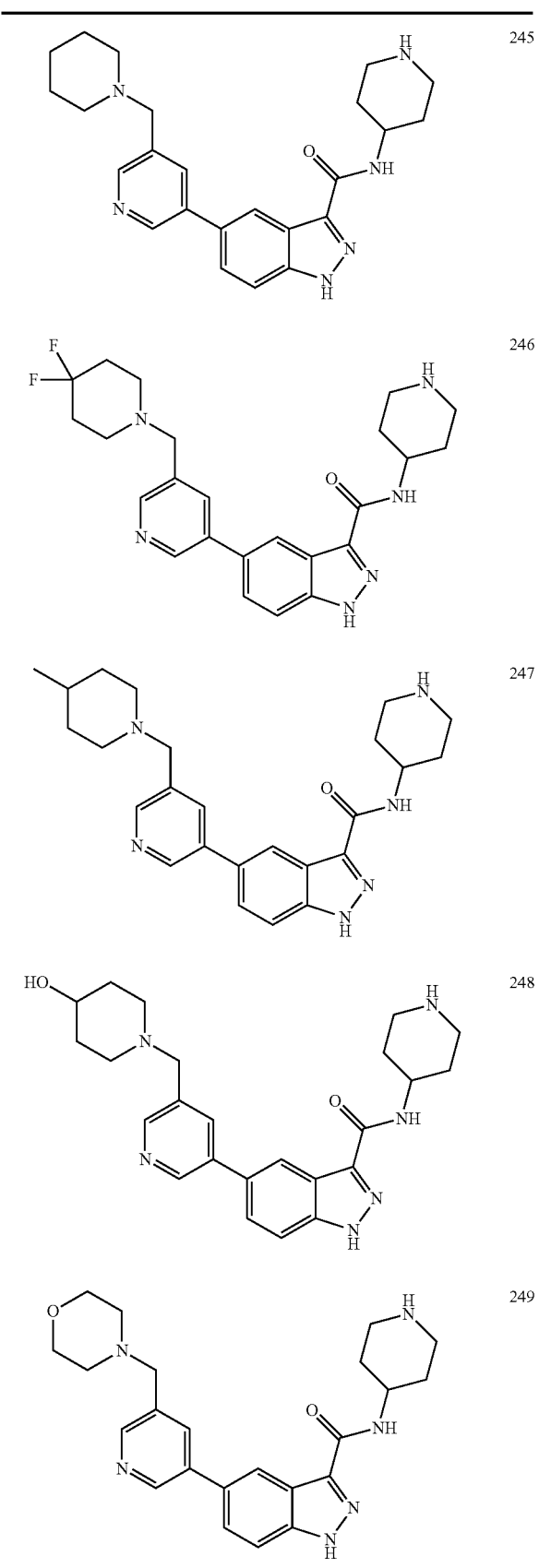
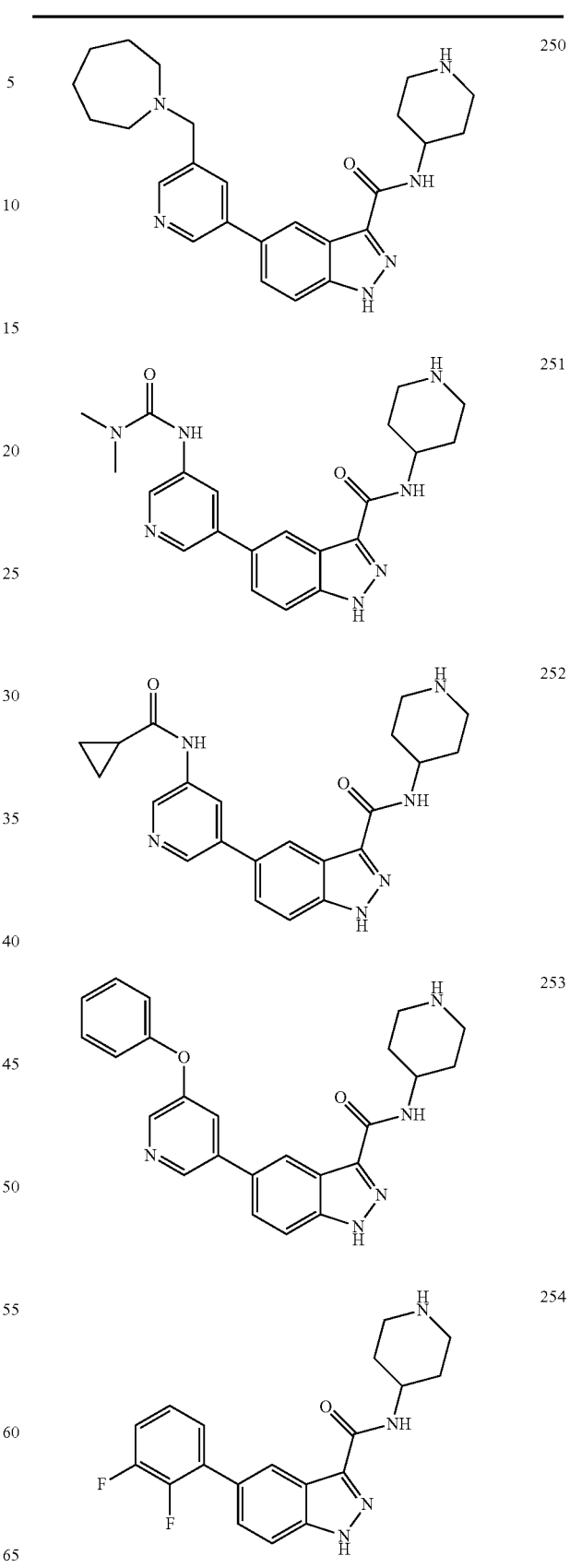

TABLE 1-continued
255
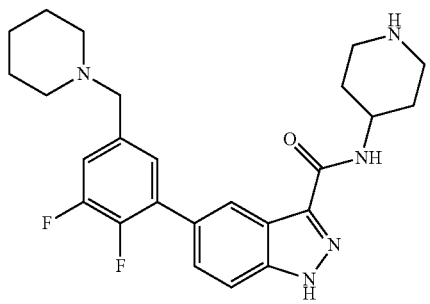 [SMILES: O=C(NC1CCNCC1)c1n[nH]c2ccc(-c3cc(CN4CCCCC4)cc(F)c3F)cc12]
256
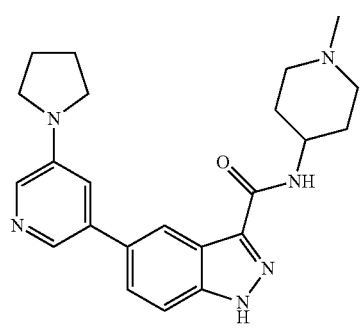 [SMILES: CN1CCC(NC(=O)c2n[nH]c3ccc(-c4cncc(N5CCCC5)c4)cc23)CC1]
257
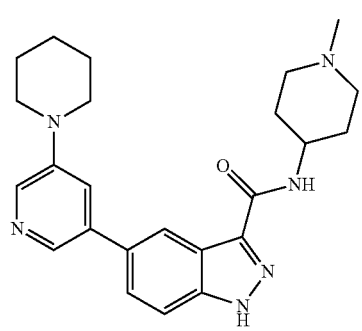 [SMILES: CN1CCC(NC(=O)c2n[nH]c3ccc(-c4cncc(N5CCCCC5)c4)cc23)CC1]
258
259
TABLE 1-continued
260
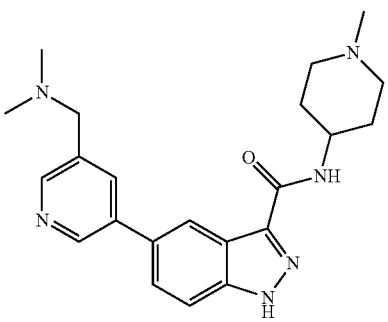 [SMILES: CN(C)Cc1cncc(-c2ccc3[nH]nc(C(=O)NC4CCN(C)CC4)c3c2)c1]
261
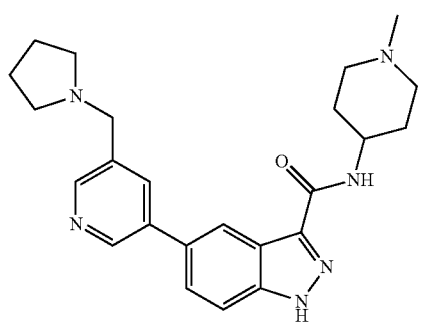 [SMILES: CN1CCC(NC(=O)c2n[nH]c3ccc(-c4cncc(CN5CCCC5)c4)cc23)CC1]
262
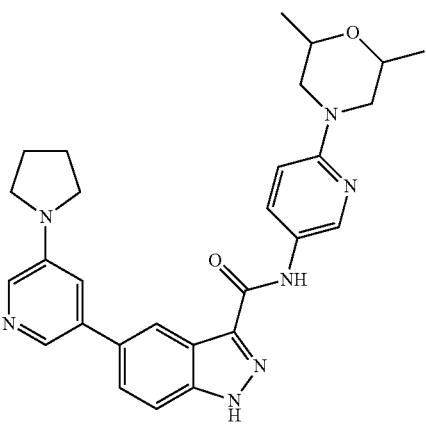 [SMILES: CC1CN(c2ccc(NC(=O)c3n[nH]c4ccc(-c5cncc(N6CCCC6)c5)cc34)cn2)CC(C)O1]
263
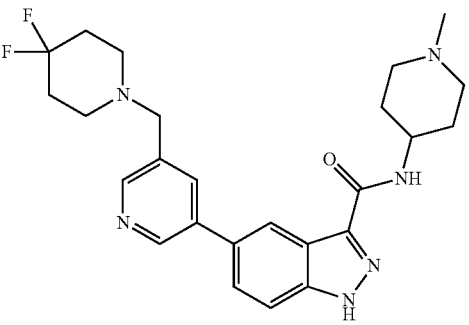 [SMILES: CN1CCC(NC(=O)c2n[nH]c3ccc(-c4cncc(CN5CCC(F)(F)CC5)c4)cc23)CC1]

TABLE 1-continued
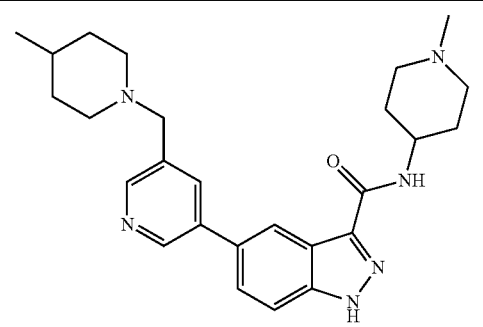 264
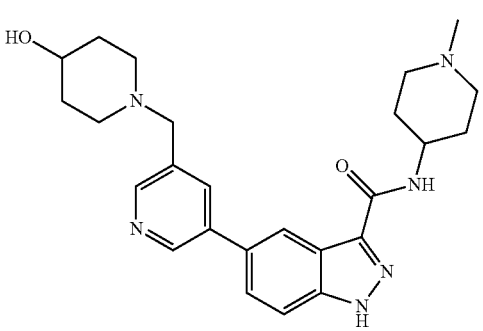 [SMILES: CN1CCC(NC(=O)c2n[nH]c3ccc(-c4cncc(CN5CCC(O)CC5)c4)cc23)CC1] 265
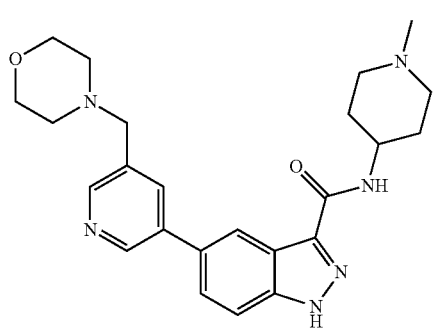 [SMILES: CN1CCC(NC(=O)c2n[nH]c3ccc(-c4cncc(CN5CCOCC5)c4)cc23)CC1] 266
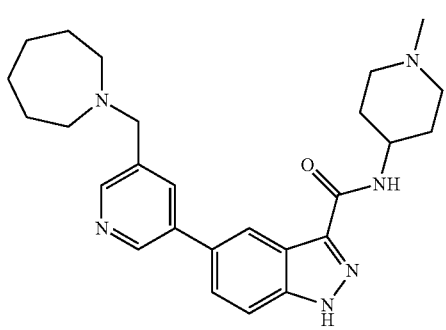 [SMILES: CN1CCC(NC(=O)c2n[nH]c3ccc(-c4cncc(CN5CCCCCC5)c4)cc23)CC1] 267
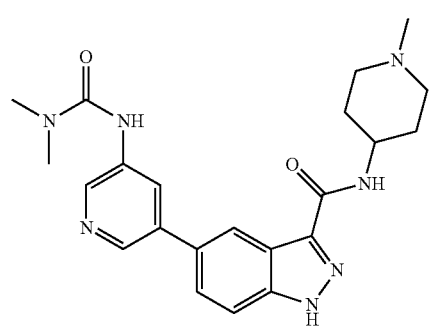 [SMILES: CN1CCC(NC(=O)c2n[nH]c3ccc(-c4cncc(NC(=O)N(C)C)c4)cc23)CC1] 268
TABLE 1-continued
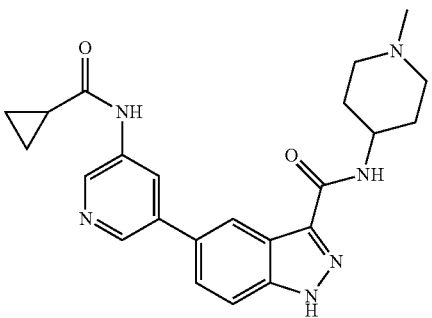 [SMILES: CN1CCC(NC(=O)c2n[nH]c3ccc(-c4cncc(NC(=O)C5CC5)c4)cc23)CC1] 269
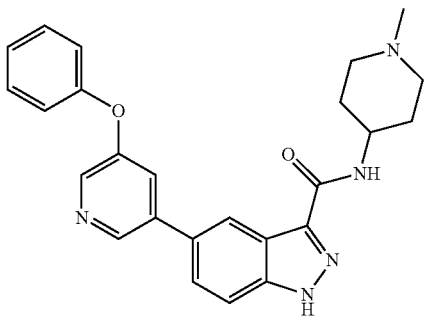 [SMILES: CN1CCC(NC(=O)c2n[nH]c3ccc(-c4cncc(Oc5ccccc5)c4)cc23)CC1] 270
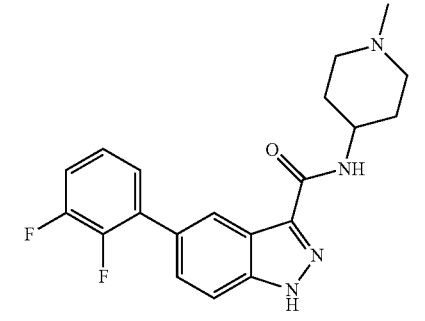 [SMILES: CN1CCC(NC(=O)c2n[nH]c3ccc(-c4cccc(F)c4F)cc23)CC1] 271
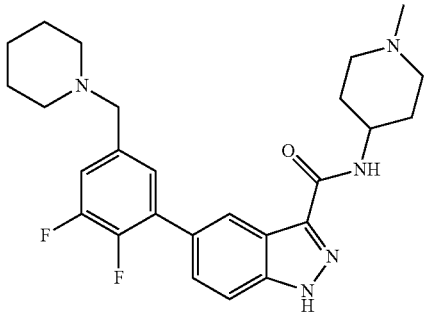 [SMILES: CN1CCC(NC(=O)c2n[nH]c3ccc(-c4cc(CN5CCCCC5)cc(F)c4F)cc23)CC1] 272
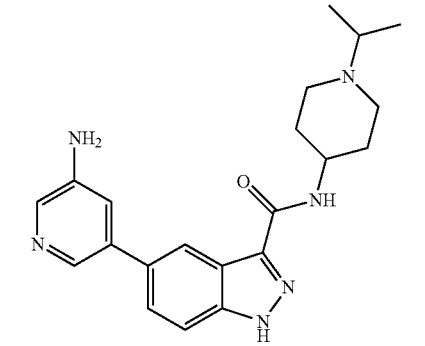 [SMILES: CC(C)N1CCC(NC(=O)c2n[nH]c3ccc(-c4cncc(N)c4)cc23)CC1] 273

TABLE 1-continued
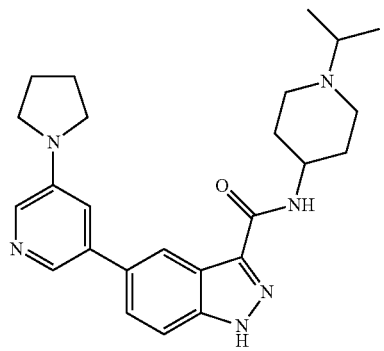 [SMILES: CC(C)N1CCC(NC(=O)c2n[nH]c3ccc(-c4cncc(N5CCCC5)c4)cc23)CC1]
274
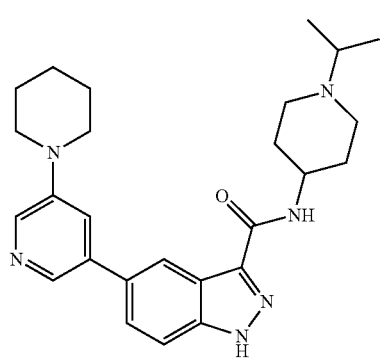 [SMILES: CC(C)N1CCC(NC(=O)c2n[nH]c3ccc(-c4cncc(N5CCCCC5)c4)cc23)CC1]
275
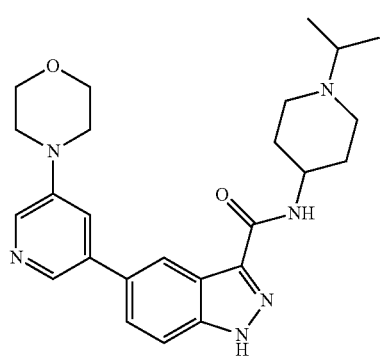 [SMILES: CC(C)N1CCC(NC(=O)c2n[nH]c3ccc(-c4cncc(N5CCOCC5)c4)cc23)CC1]
276
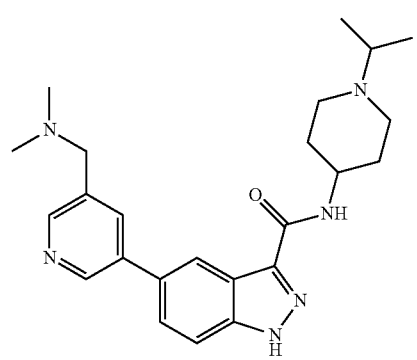 [SMILES: CC(C)N1CCC(NC(=O)c2n[nH]c3ccc(-c4cncc(CN(C)C)c4)cc23)CC1]
277
TABLE 1-continued
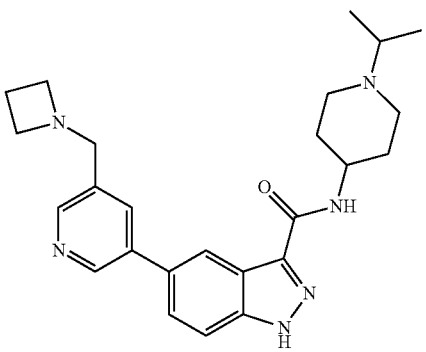 [SMILES: CC(C)N1CCC(NC(=O)c2n[nH]c3ccc(-c4cncc(CN5CCC5)c4)cc23)CC1]
278
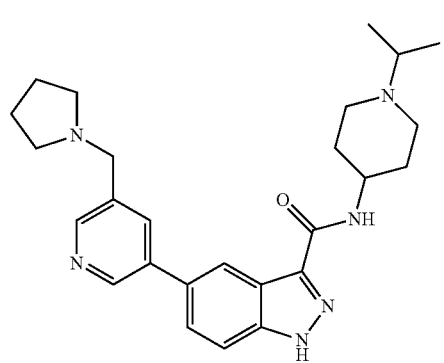 [SMILES: CC(C)N1CCC(NC(=O)c2n[nH]c3ccc(-c4cncc(CN5CCCC5)c4)cc23)CC1]
279
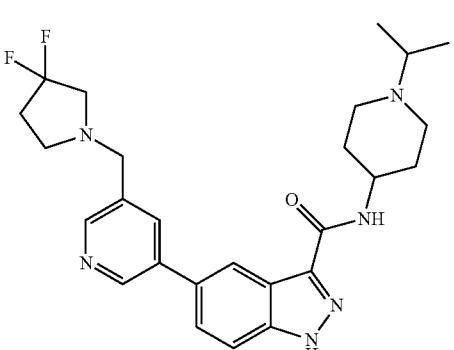
280
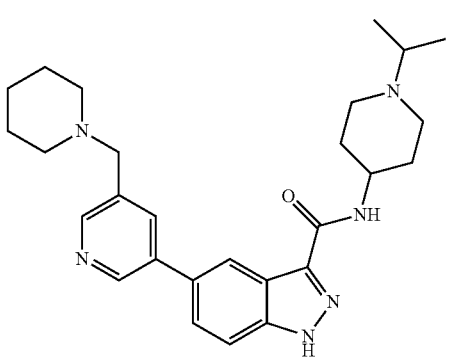 [SMILES: CC(C)N1CCC(NC(=O)c2n[nH]c3ccc(-c4cncc(CN5CCCCC5)c4)cc23)CC1]
281

TABLE 1-continued
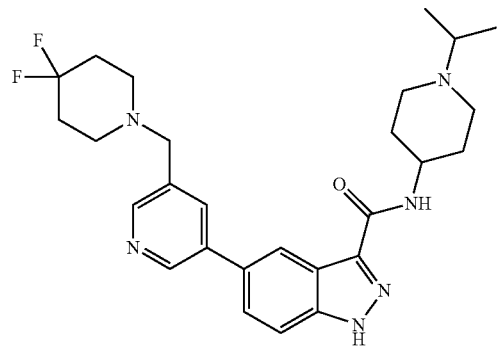 [SMILES: CC(C)N1CCC(NC(=O)c2n[nH]c3ccc(-c4cncc(CN5CCC(F)(F)CC5)c4)cc23)CC1] 282
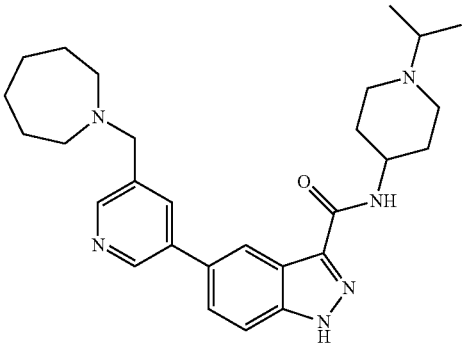 286
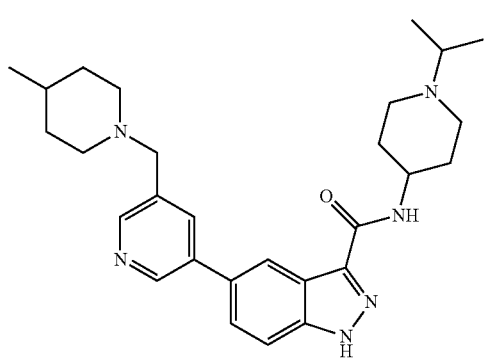 [SMILES: CC1CCN(Cc2cncc(-c3ccc4[nH]nc(C(=O)NC5CCN(C(C)C)CC5)c4c3)c2)CC1] 283
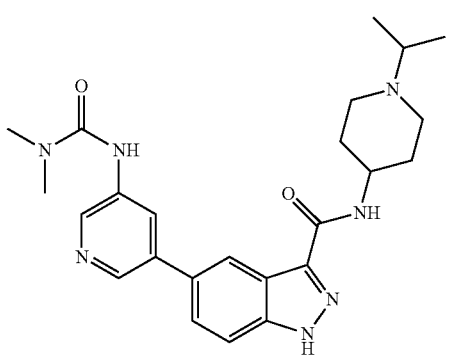 287
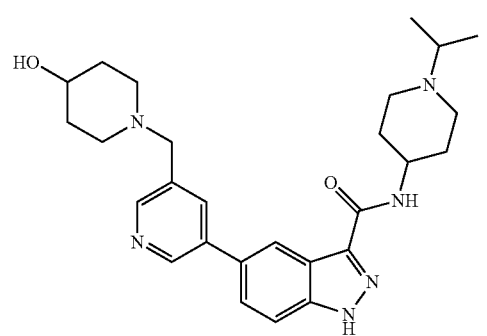 [SMILES: CC(C)N1CCC(NC(=O)c2n[nH]c3ccc(-c4cncc(CN5CCC(O)CC5)c4)cc23)CC1] 284
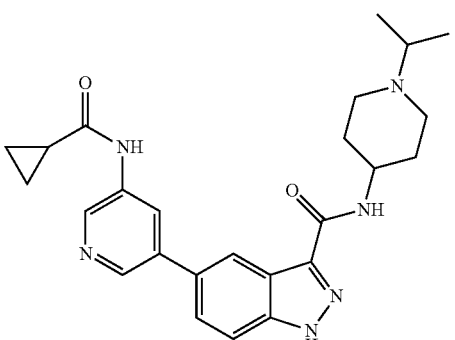 288
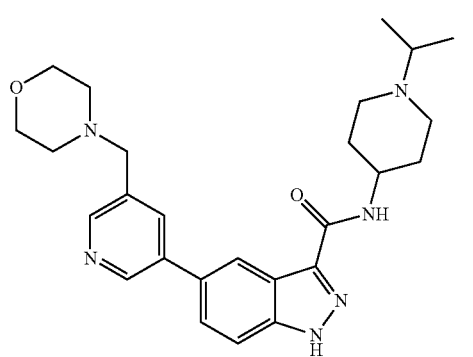 [SMILES: CC(C)N1CCC(NC(=O)c2n[nH]c3ccc(-c4cncc(CN5CCOCC5)c4)cc23)CC1] 285
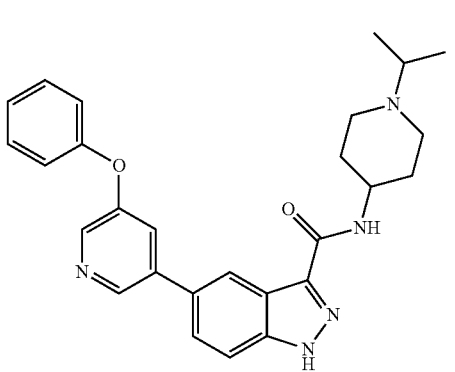 [SMILES: CC(C)N1CCC(NC(=O)c2n[nH]c3ccc(-c4cncc(Oc5ccccc5)c4)cc23)CC1] 289

TABLE 1-continued
290
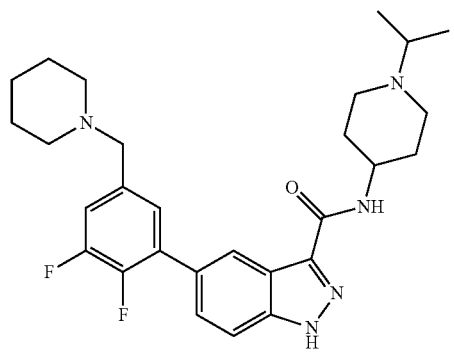 [SMILES: CC(C)N1CCC(NC(=O)c2n[nH]c3ccc(-c4cc(CN5CCCCC5)cc(F)c4F)cc23)CC1]
291
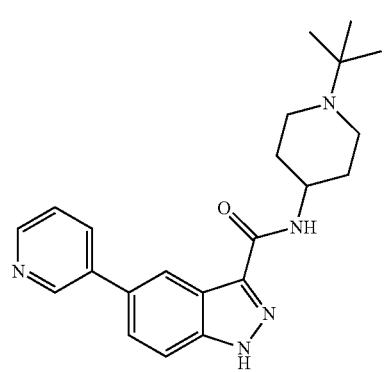 [SMILES: CC(C)(C)N1CCC(NC(=O)c2n[nH]c3ccc(-c4cccnc4)cc23)CC1]
292
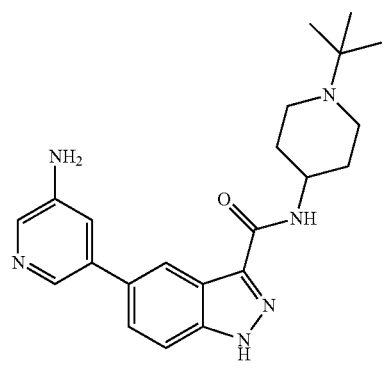 [SMILES: CC(C)(C)N1CCC(NC(=O)c2n[nH]c3ccc(-c4cncc(N)c4)cc23)CC1]
293
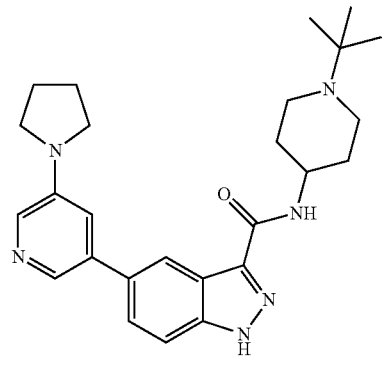 [SMILES: CC(C)(C)N1CCC(NC(=O)c2n[nH]c3ccc(-c4cncc(N5CCCC5)c4)cc23)CC1]
TABLE 1-continued
294
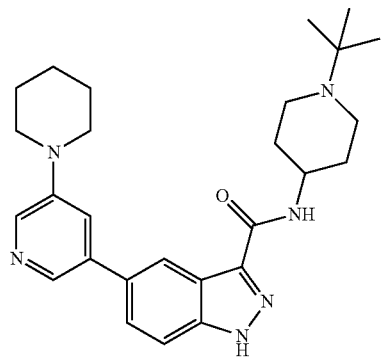 [SMILES: CC(C)(C)N1CCC(NC(=O)c2n[nH]c3ccc(-c4cncc(N5CCCCC5)c4)cc23)CC1]
295
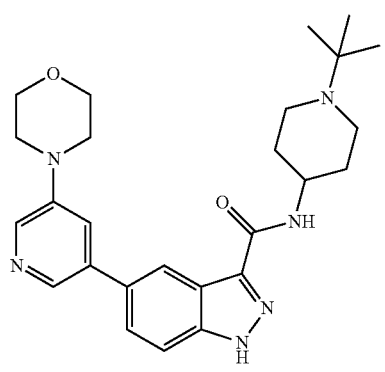 [SMILES: CC(C)(C)N1CCC(NC(=O)c2n[nH]c3ccc(-c4cncc(N5CCOCC5)c4)cc23)CC1]
296
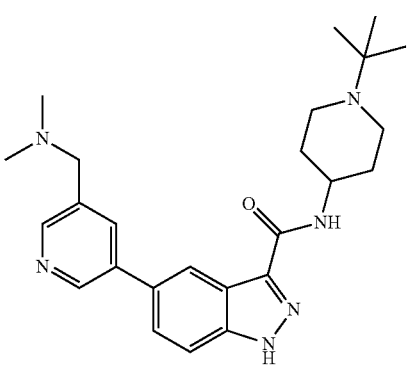 [SMILES: CN(C)Cc1cncc(-c2ccc3[nH]nc(C(=O)NC4CCN(C(C)(C)C)CC4)c3c2)c1]
297
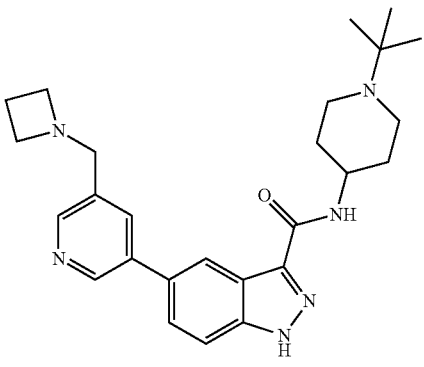 [SMILES: CC(C)(C)N1CCC(NC(=O)c2n[nH]c3ccc(-c4cncc(CN5CCC5)c4)cc23)CC1]

TABLE 1-continued
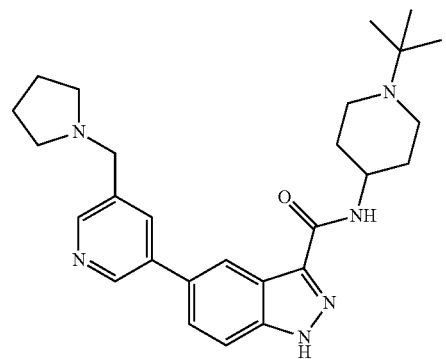 [SMILES: CC(C)(C)N1CCC(NC(=O)c2n[nH]c3ccc(-c4cncc(CN5CCCC5)c4)cc23)CC1]
298
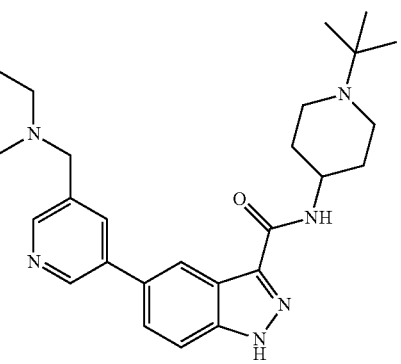
302
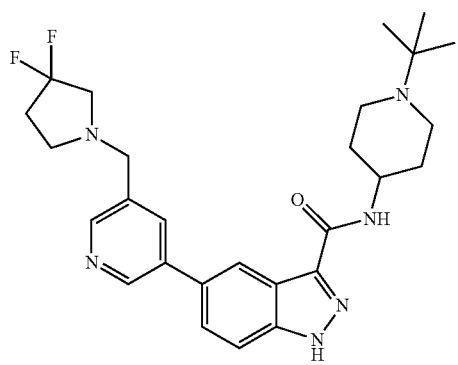 [SMILES: CC(C)(C)N1CCC(NC(=O)c2n[nH]c3ccc(-c4cncc(CN5CCC(F)(F)C5)c4)cc23)CC1]
299
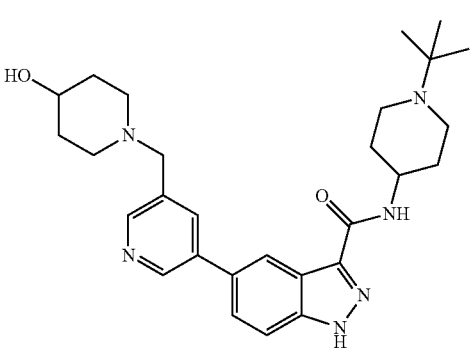
303
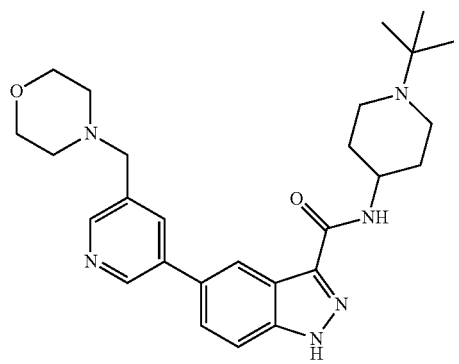
304
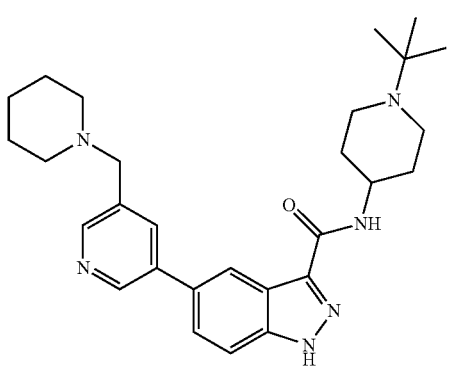 [SMILES: CC(C)(C)N1CCC(NC(=O)c2n[nH]c3ccc(-c4cncc(CN5CCCCC5)c4)cc23)CC1]
300
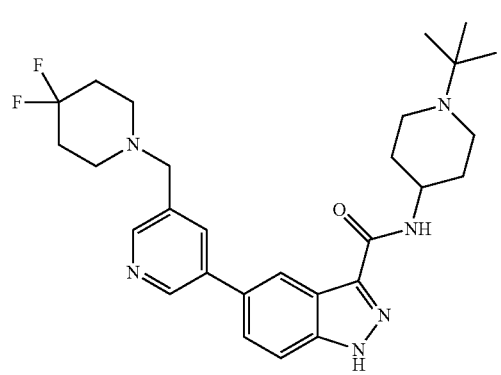 [SMILES: CC(C)(C)N1CCC(NC(=O)c2n[nH]c3ccc(-c4cncc(CN5CCC(F)(F)CC5)c4)cc23)CC1]
301
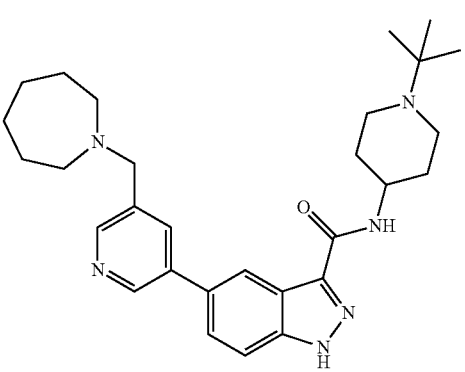 [SMILES: CC(C)(C)N1CCC(NC(=O)c2n[nH]c3ccc(-c4cncc(CN5CCCCCC5)c4)cc23)CC1]
305

| | |
|---|---|
| 306 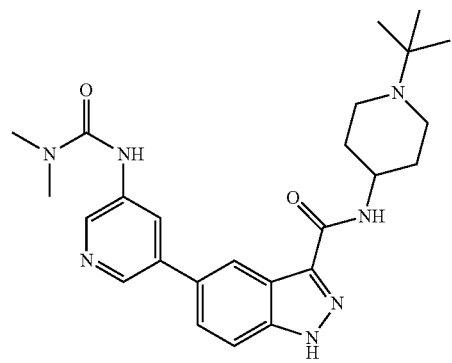 [SMILES: CN(C)C(=O)Nc1cncc(-c2ccc3[nH]nc(C(=O)NC4CCN(C(C)(C)C)CC4)c3c2)c1] | 310 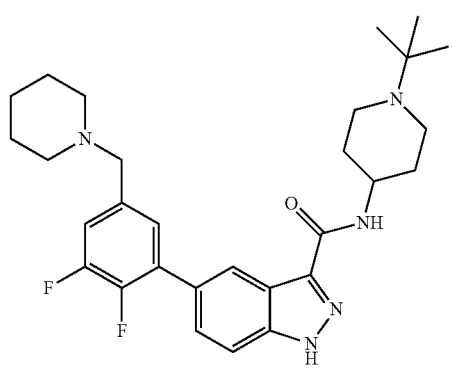 |
| 307 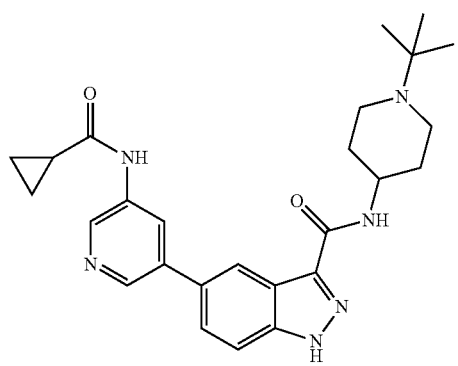 [SMILES: CC(C)(C)N1CCC(NC(=O)c2n[nH]c3ccc(-c4cncc(NC(=O)C5CC5)c4)cc23)CC1] | 311 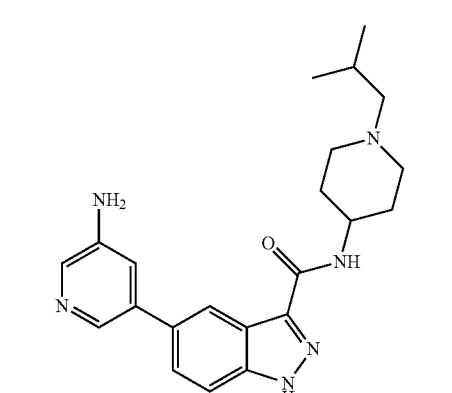 |
| 308 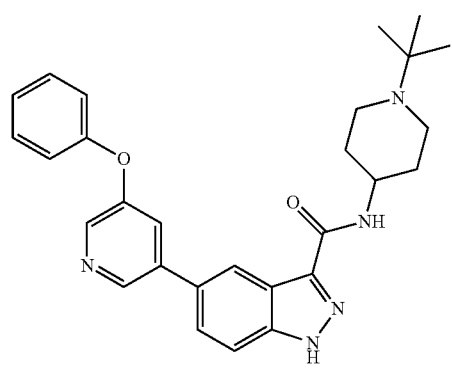 [SMILES: CC(C)(C)N1CCC(NC(=O)c2n[nH]c3ccc(-c4cncc(Oc5ccccc5)c4)cc23)CC1] | 312 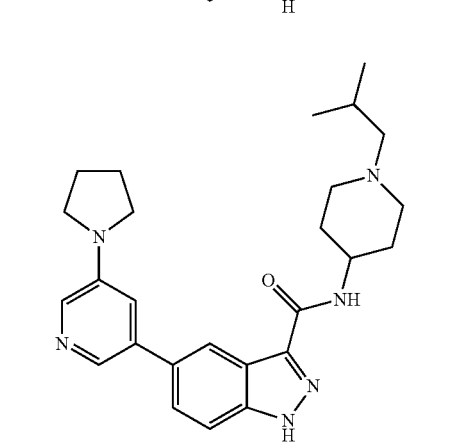 |
| 309 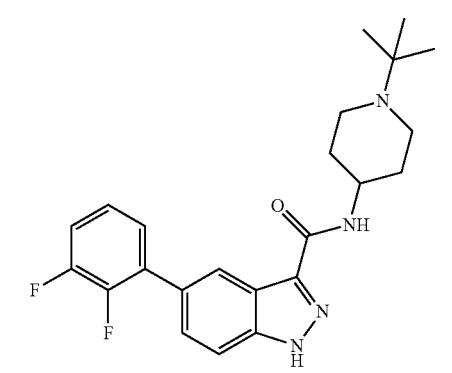 [SMILES: CC(C)(C)N1CCC(NC(=O)c2n[nH]c3ccc(-c4cccc(F)c4F)cc23)CC1] | 313 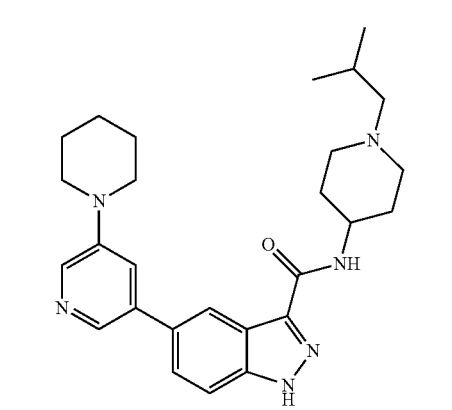 [SMILES: CC(C)CN1CCC(NC(=O)c2n[nH]c3ccc(-c4cncc(N5CCCCC5)c4)cc23)CC1] |

TABLE 1-continued
314
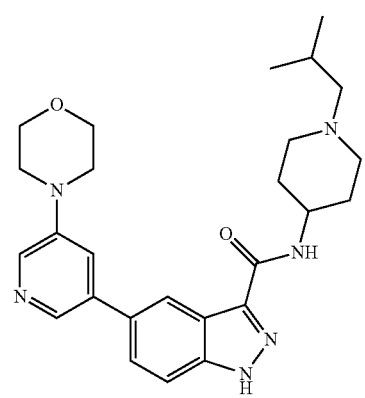 [SMILES: CC(C)CN1CCC(NC(=O)c2n[nH]c3ccc(-c4cncc(N5CCOCC5)c4)cc23)CC1]
315
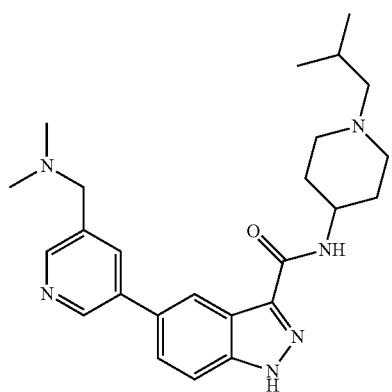 [SMILES: CC(C)CN1CCC(NC(=O)c2n[nH]c3ccc(-c4cncc(CN(C)C)c4)cc23)CC1]
316
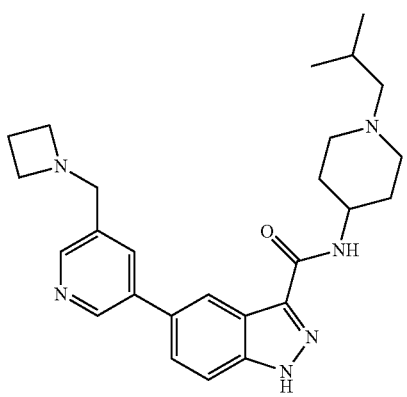 [SMILES: CC(C)CN1CCC(NC(=O)c2n[nH]c3ccc(-c4cncc(CN5CCC5)c4)cc23)CC1]
317
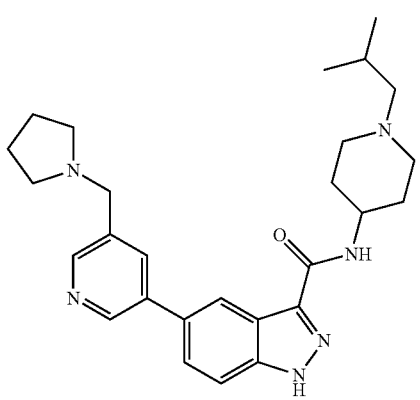 [SMILES: CC(C)CN1CCC(NC(=O)c2n[nH]c3ccc(-c4cncc(CN5CCCC5)c4)cc23)CC1]
TABLE 1-continued
318
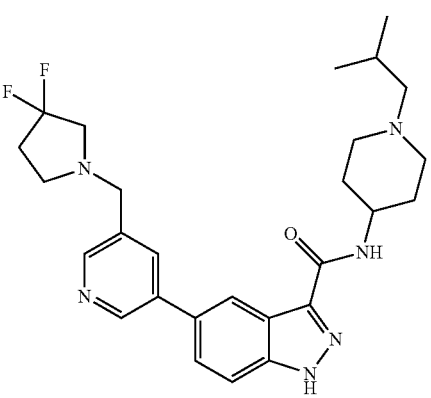 [SMILES: CC(C)CN1CCC(NC(=O)c2n[nH]c3ccc(-c4cncc(CN5CCC(F)(F)C5)c4)cc23)CC1]
319
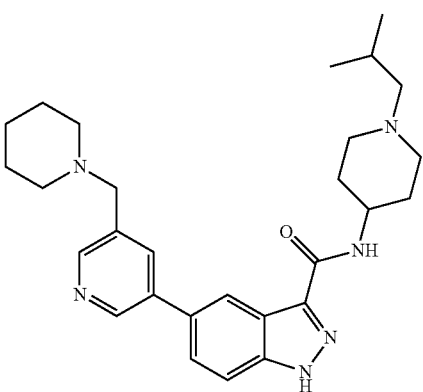 [SMILES: CC(C)CN1CCC(NC(=O)c2n[nH]c3ccc(-c4cncc(CN5CCCCC5)c4)cc23)CC1]
320
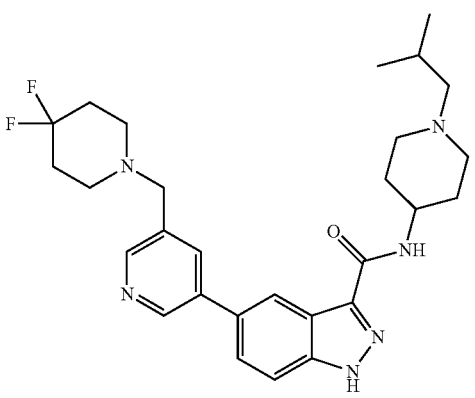 [SMILES: CC(C)CN1CCC(NC(=O)c2n[nH]c3ccc(-c4cncc(CN5CCC(F)(F)CC5)c4)cc23)CC1]
321
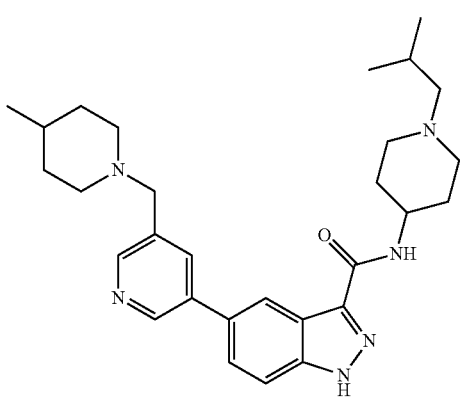 [SMILES: CC(C)CN1CCC(NC(=O)c2n[nH]c3ccc(-c4cncc(CN5CCC(C)CC5)c4)cc23)CC1]

TABLE 1-continued
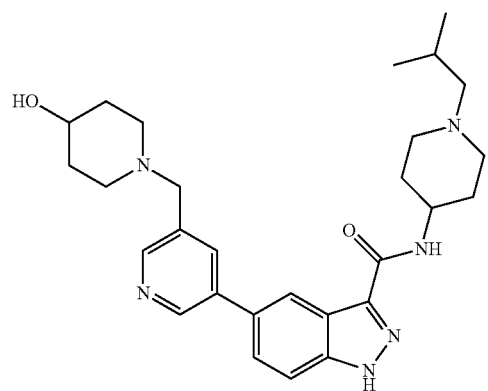 [SMILES: CC(C)CN1CCC(NC(=O)c2n[nH]c3ccc(-c4cncc(CN5CCC(O)CC5)c4)cc23)CC1] 322
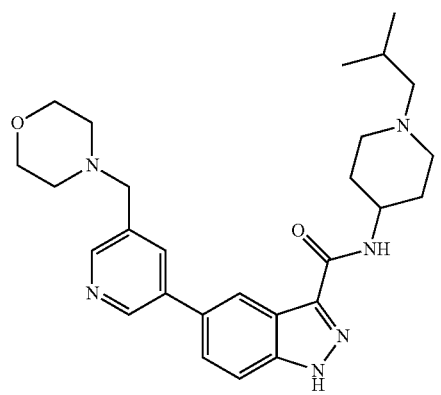 [SMILES: CC(C)CN1CCC(NC(=O)c2n[nH]c3ccc(-c4cncc(CN5CCOCC5)c4)cc23)CC1] 323
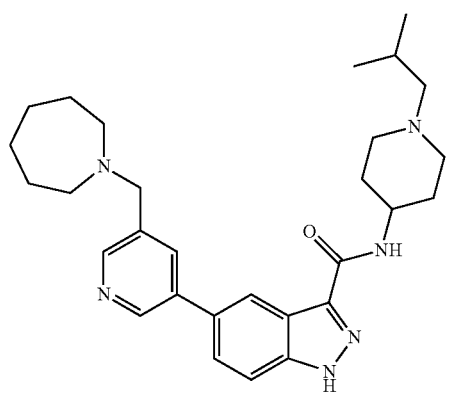 [SMILES: CC(C)CN1CCC(NC(=O)c2n[nH]c3ccc(-c4cncc(CN5CCCCCC5)c4)cc23)CC1] 324
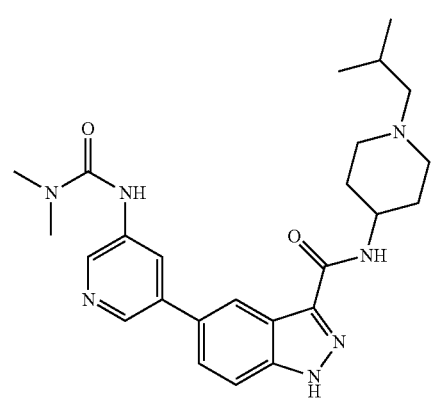 [SMILES: CC(C)CN1CCC(NC(=O)c2n[nH]c3ccc(-c4cncc(NC(=O)N(C)C)c4)cc23)CC1] 325
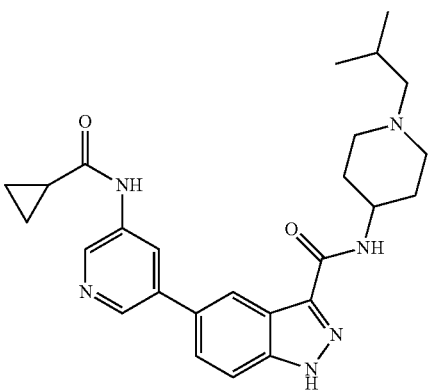 [SMILES: CC(C)CN1CCC(NC(=O)c2n[nH]c3ccc(-c4cncc(NC(=O)C5CC5)c4)cc23)CC1] 326
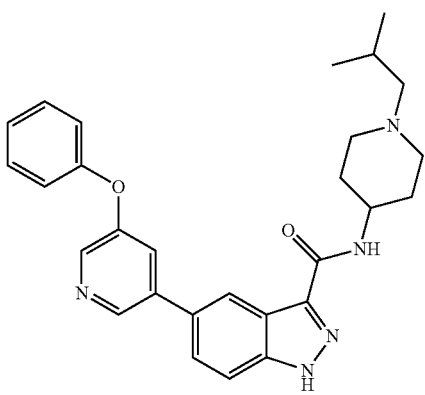 [SMILES: CC(C)CN1CCC(NC(=O)c2n[nH]c3ccc(-c4cncc(Oc5ccccc5)c4)cc23)CC1] 327
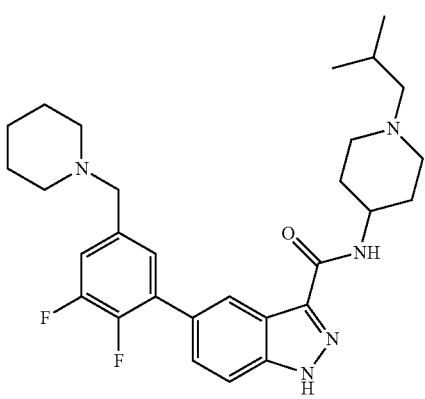 [SMILES: CC(C)CN1CCC(NC(=O)c2n[nH]c3ccc(-c4cc(CN5CCCCC5)cc(F)c4F)cc23)CC1] 328
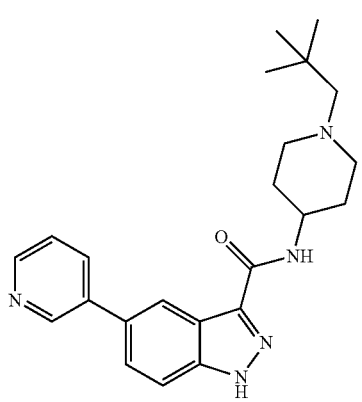 [SMILES: CC(C)(C)CN1CCC(NC(=O)c2n[nH]c3ccc(-c4cccnc4)cc23)CC1] 329

TABLE 1-continued
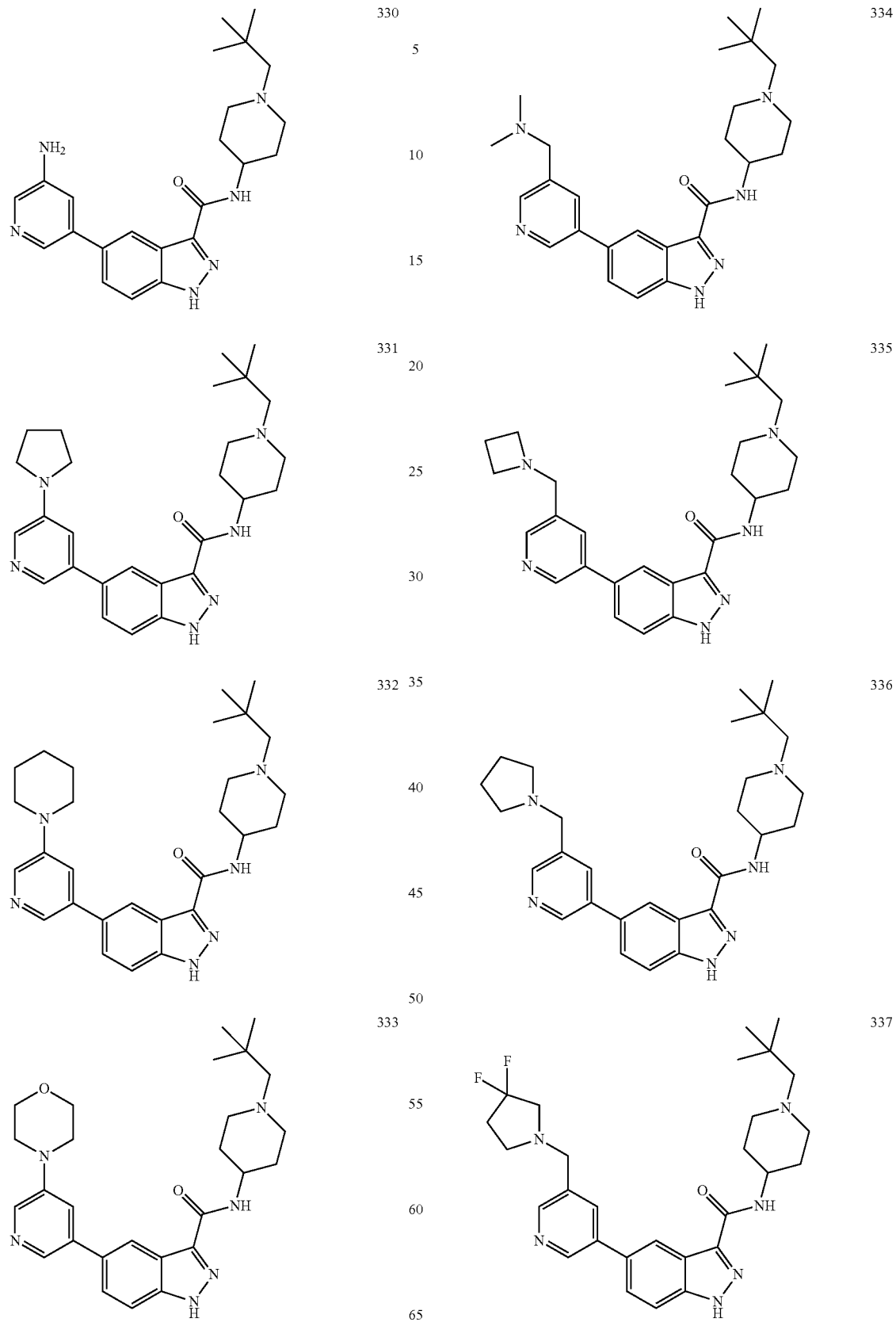

TABLE 1-continued
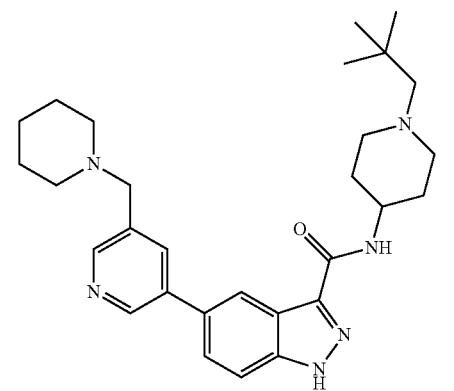 [SMILES: CC(C)(C)CN1CCC(NC(=O)c2n[nH]c3ccc(-c4cncc(CN5CCCCC5)c4)cc23)CC1]
338
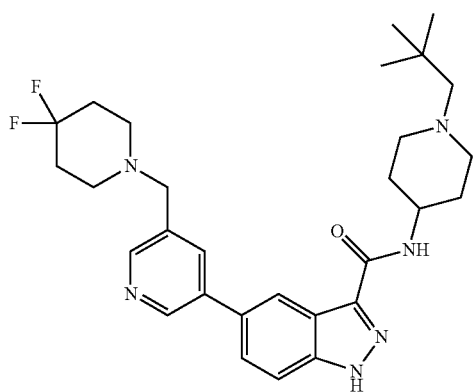 [SMILES: CC(C)(C)CN1CCC(NC(=O)c2n[nH]c3ccc(-c4cncc(CN5CCC(F)(F)CC5)c4)cc23)CC1]
339
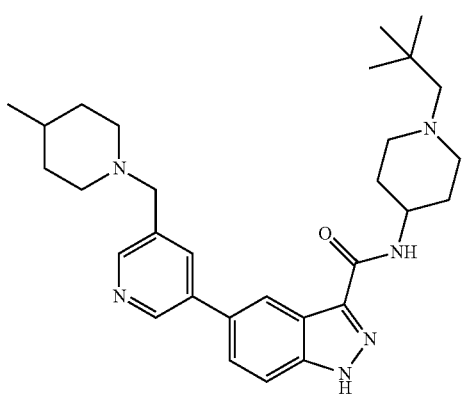 [SMILES: CC1CCN(Cc2cncc(-c3ccc4[nH]nc(C(=O)NC5CCN(CC(C)(C)C)CC5)c4c3)c2)CC1]
340
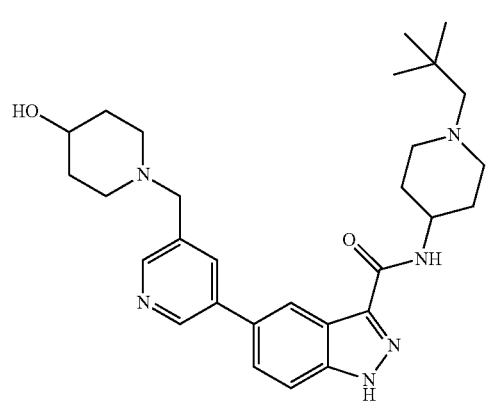 [SMILES: CC(C)(C)CN1CCC(NC(=O)c2n[nH]c3ccc(-c4cncc(CN5CCC(O)CC5)c4)cc23)CC1]
341
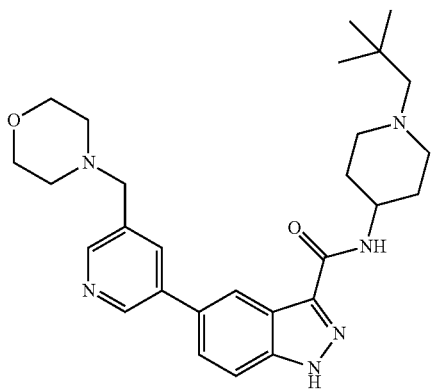 [SMILES: CC(C)(C)CN1CCC(NC(=O)c2n[nH]c3ccc(-c4cncc(CN5CCOCC5)c4)cc23)CC1]
342
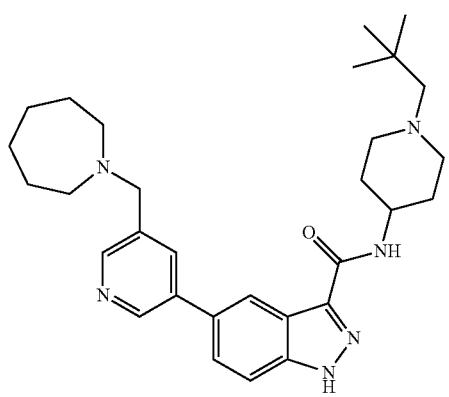 [SMILES: CC(C)(C)CN1CCC(NC(=O)c2n[nH]c3ccc(-c4cncc(CN5CCCCCC5)c4)cc23)CC1]
343
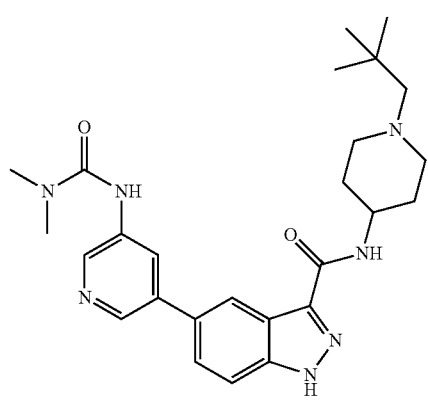 [SMILES: CN(C)C(=O)Nc1cncc(-c2ccc3[nH]nc(C(=O)NC4CCN(CC(C)(C)C)CC4)c3c2)c1]
344
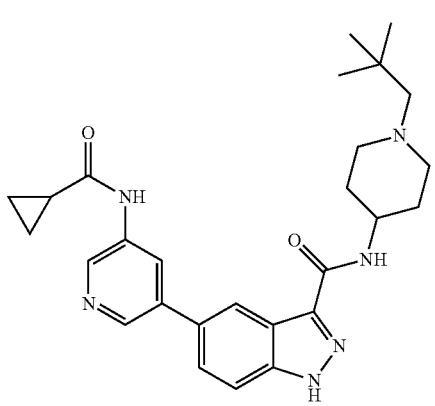 [SMILES: CC(C)(C)CN1CCC(NC(=O)c2n[nH]c3ccc(-c4cncc(NC(=O)C5CC5)c4)cc23)CC1]
345

TABLE 1-continued
| | |
|---|---|
| 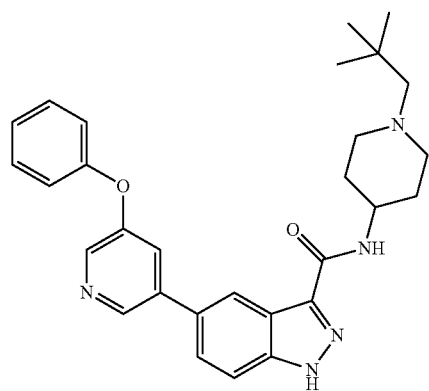 [SMILES: CC(C)(C)CN1CCC(NC(=O)c2n[nH]c3ccc(-c4cncc(Oc5ccccc5)c4)cc23)CC1] 346 | 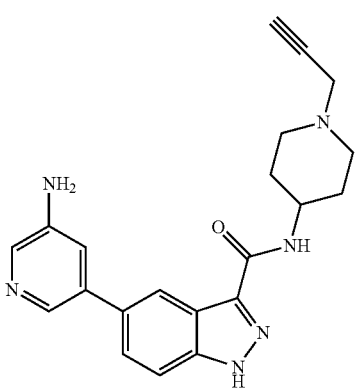 350 |
| 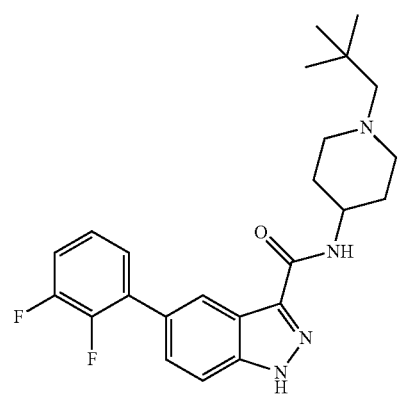 [SMILES: CC(C)(C)CN1CCC(NC(=O)c2n[nH]c3ccc(-c4cccc(F)c4F)cc23)CC1] 347 | 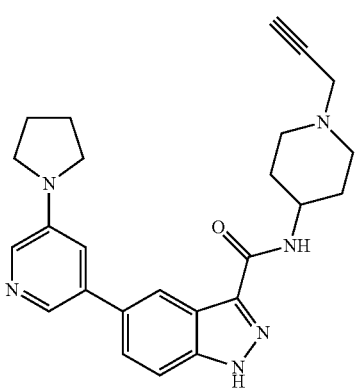 351 |
| 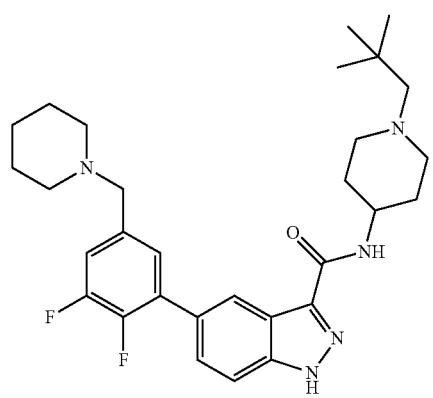 [SMILES: CC(C)(C)CN1CCC(NC(=O)c2n[nH]c3ccc(-c4cc(CN5CCCCC5)cc(F)c4F)cc23)CC1] 348 | 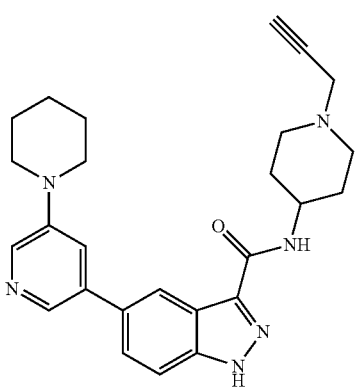 352 |
| 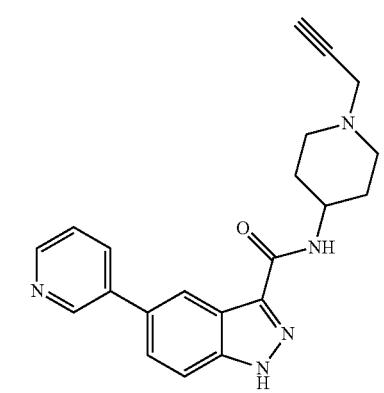 [SMILES: C#CCN1CCC(NC(=O)c2n[nH]c3ccc(-c4cccnc4)cc23)CC1] 349 | 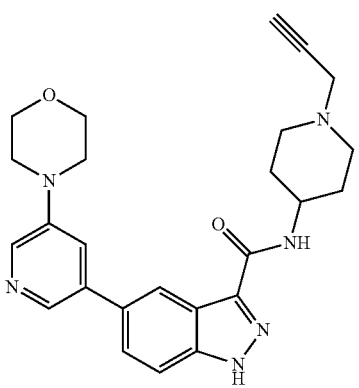 [SMILES: C#CCN1CCC(NC(=O)c2n[nH]c3ccc(-c4cncc(N5CCOCC5)c4)cc23)CC1] 353 |

TABLE 1-continued
354 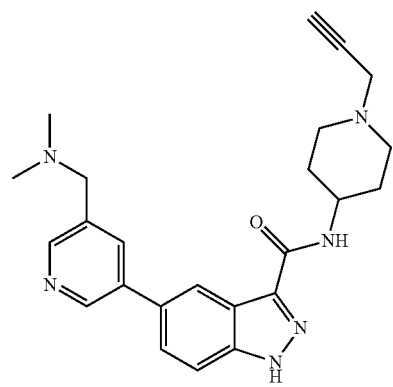 [SMILES: C#CCN1CCC(NC(=O)c2n[nH]c3ccc(-c4cncc(CN(C)C)c4)cc23)CC1]
355 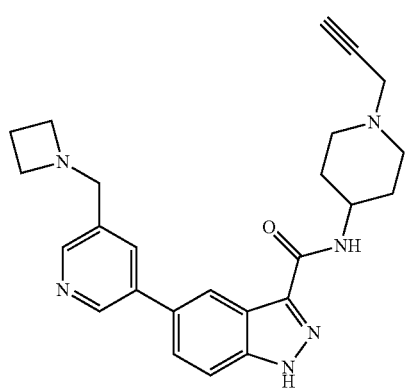 [SMILES: C#CCN1CCC(NC(=O)c2n[nH]c3ccc(-c4cncc(CN5CCC5)c4)cc23)CC1]
356 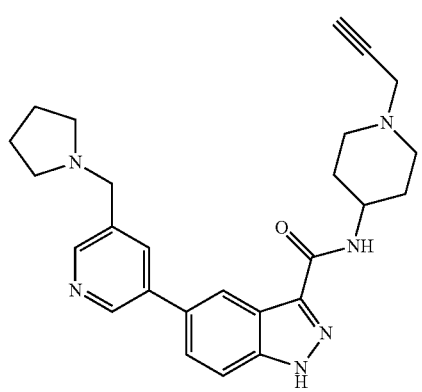 [SMILES: C#CCN1CCC(NC(=O)c2n[nH]c3ccc(-c4cncc(CN5CCCC5)c4)cc23)CC1]
357 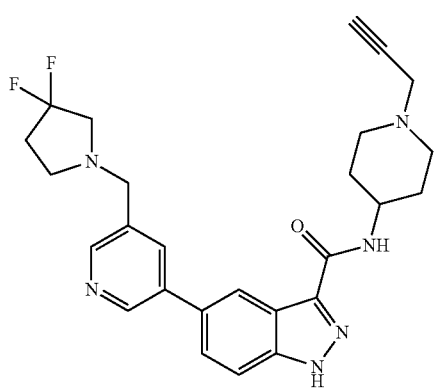 [SMILES: C#CCN1CCC(NC(=O)c2n[nH]c3ccc(-c4cncc(CN5CCC(F)(F)C5)c4)cc23)CC1]
TABLE 1-continued
358 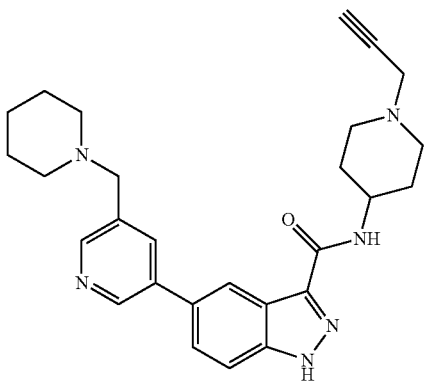 [SMILES: C#CCN1CCC(NC(=O)c2n[nH]c3ccc(-c4cncc(CN5CCCCC5)c4)cc23)CC1]
359 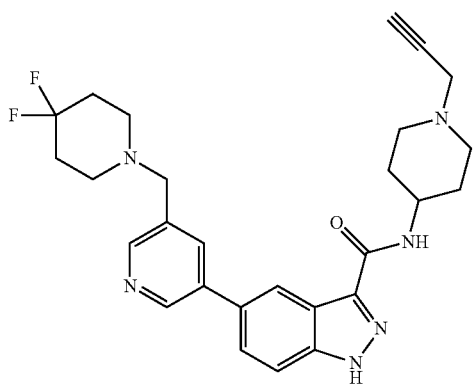 [SMILES: C#CCN1CCC(NC(=O)c2n[nH]c3ccc(-c4cncc(CN5CCC(F)(F)CC5)c4)cc23)CC1]
360 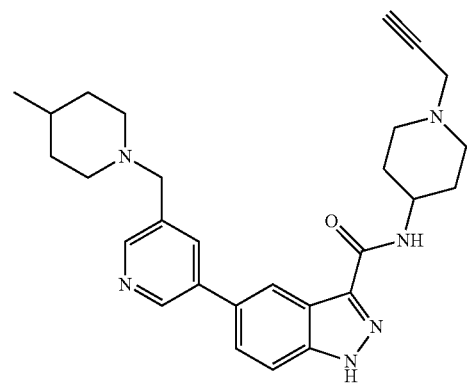 [SMILES: C#CCN1CCC(NC(=O)c2n[nH]c3ccc(-c4cncc(CN5CCC(C)CC5)c4)cc23)CC1]
361 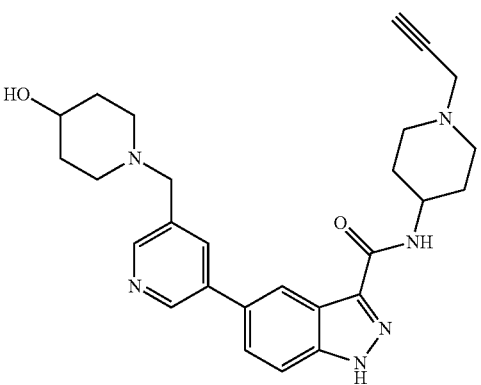 [SMILES: C#CCN1CCC(NC(=O)c2n[nH]c3ccc(-c4cncc(CN5CCC(O)CC5)c4)cc23)CC1]

TABLE 1-continued
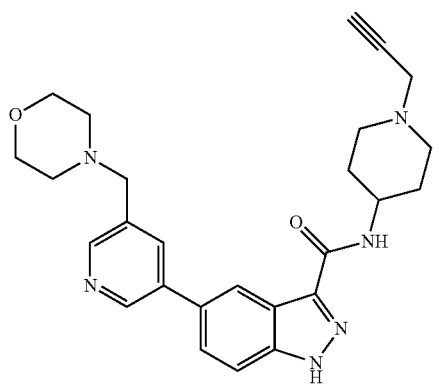 [SMILES: C#CCN1CCC(NC(=O)c2n[nH]c3ccc(-c4cncc(CN5CCOCC5)c4)cc23)CC1]
362
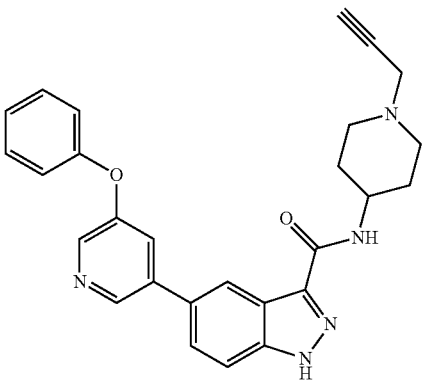
366
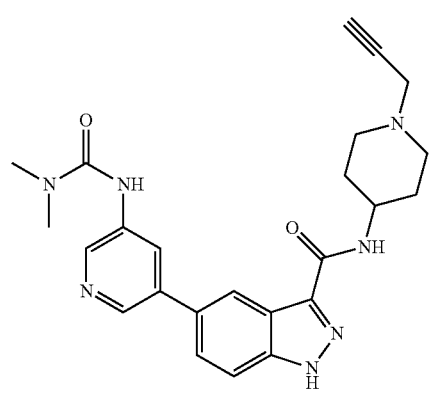 [SMILES: C#CCN1CCC(NC(=O)c2n[nH]c3ccc(-c4cncc(NC(=O)N(C)C)c4)cc23)CC1]
363
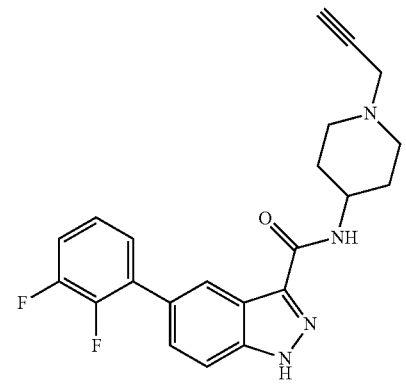
367
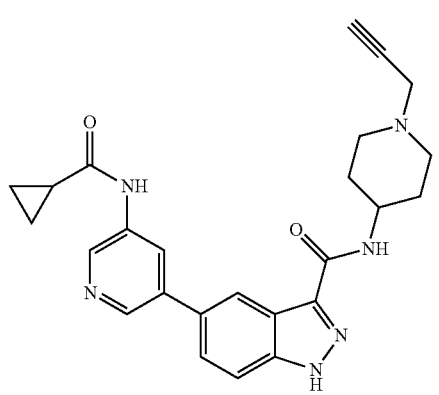 [SMILES: C#CCN1CCC(NC(=O)c2n[nH]c3ccc(-c4cncc(NC(=O)C5CC5)c4)cc23)CC1]
364
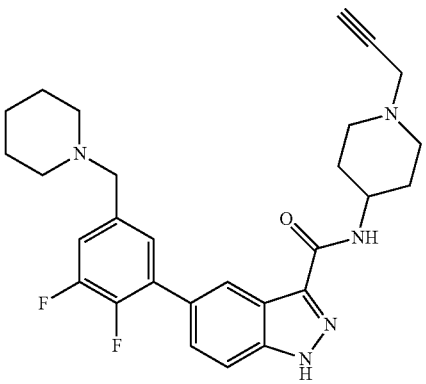 [SMILES: C#CCN1CCC(NC(=O)c2n[nH]c3ccc(-c4cc(CN5CCCCC5)cc(F)c4F)cc23)CC1]
368
365
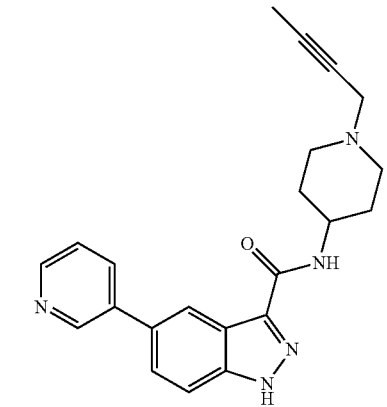 [SMILES: CC#CCN1CCC(NC(=O)c2n[nH]c3ccc(-c4cccnc4)cc23)CC1]
369

TABLE 1-continued
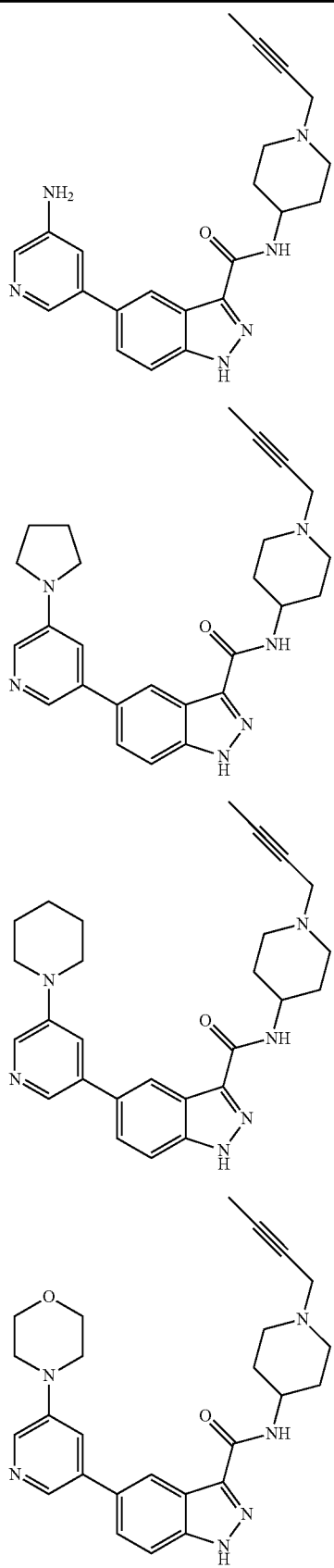
370
371
372
373
TABLE 1-continued
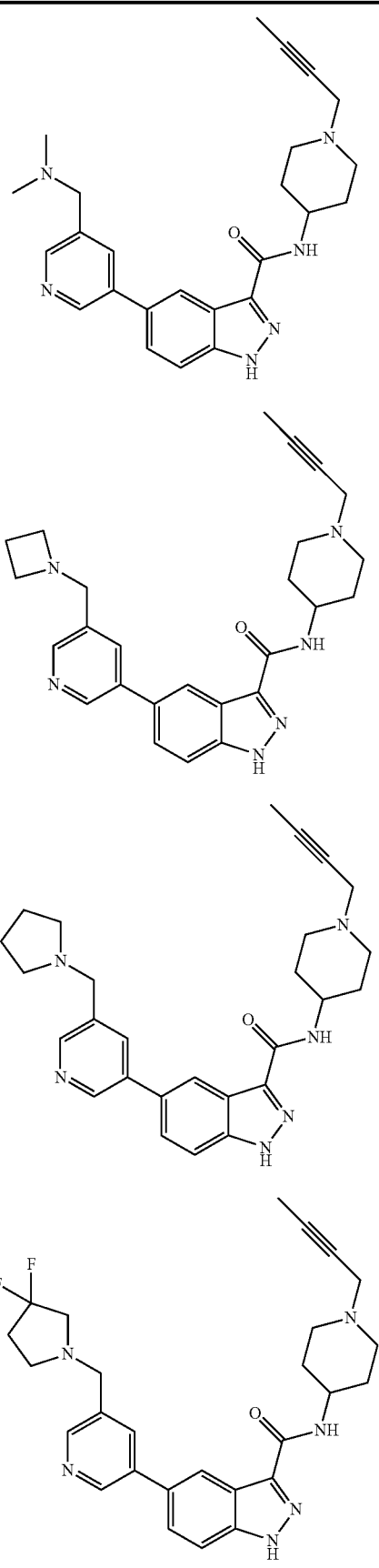
374
375
376
377

TABLE 1-continued
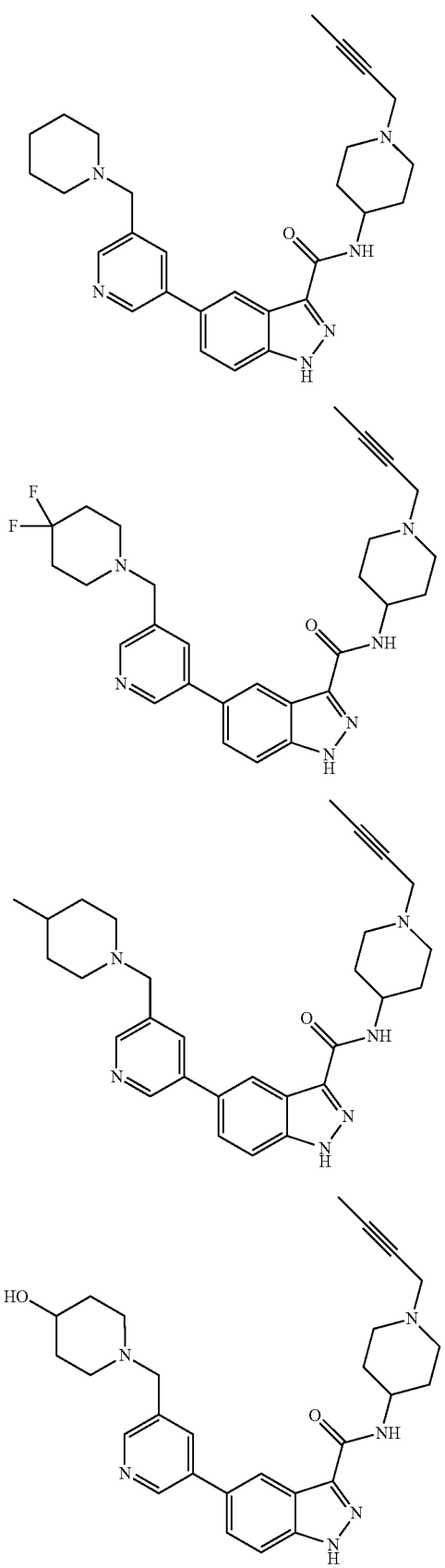
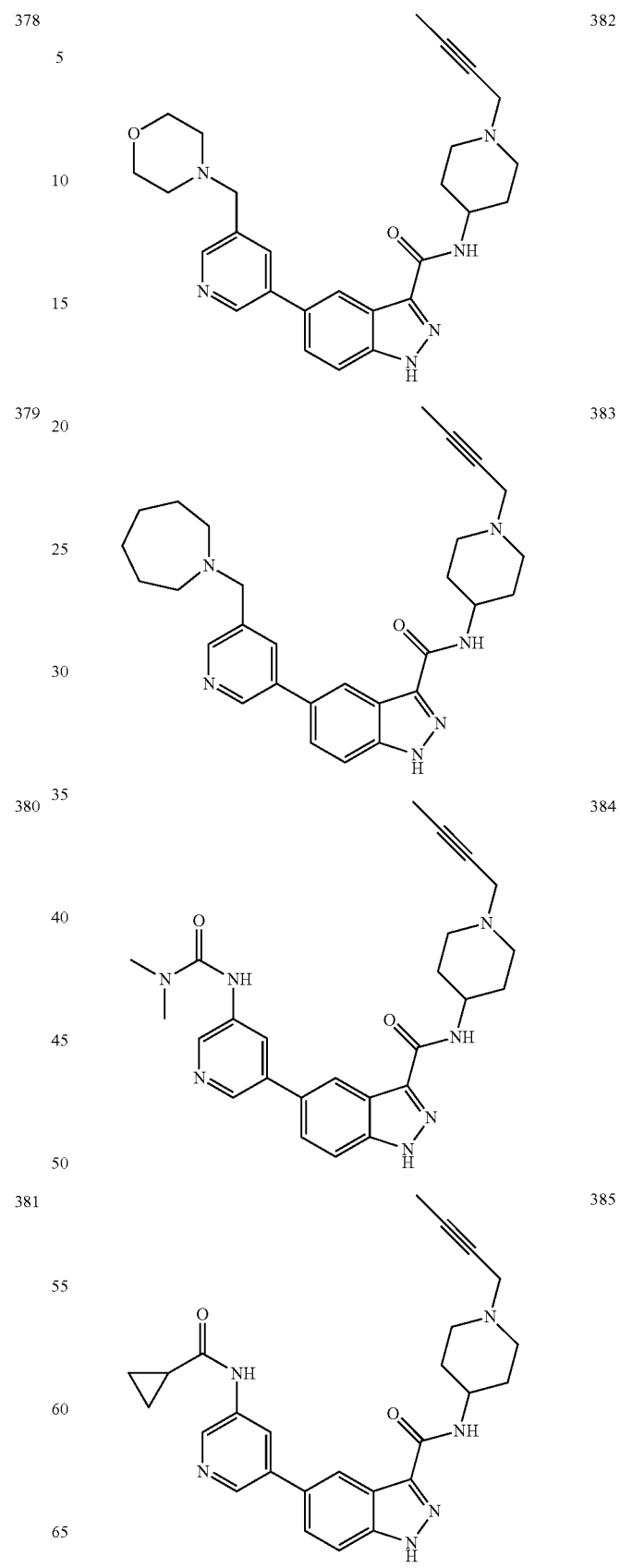

TABLE 1-continued
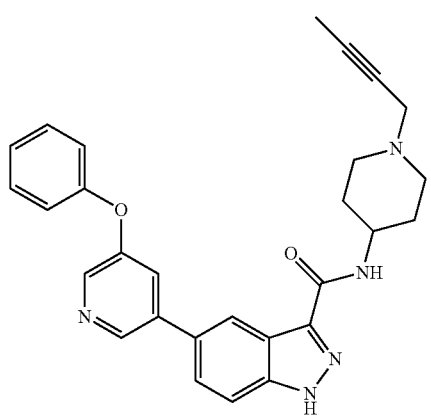 [SMILES: CC#CCN1CCC(NC(=O)c2n[nH]c3ccc(-c4cncc(Oc5ccccc5)c4)cc23)CC1]
386
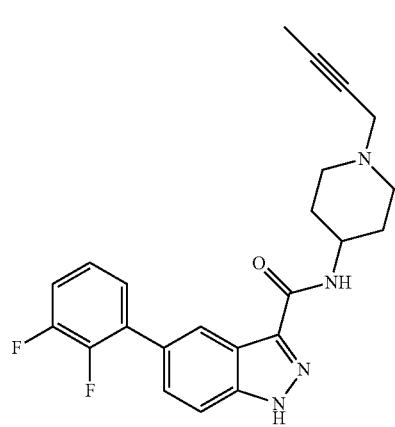 [SMILES: CC#CCN1CCC(NC(=O)c2n[nH]c3ccc(-c4cccc(F)c4F)cc23)CC1]
387
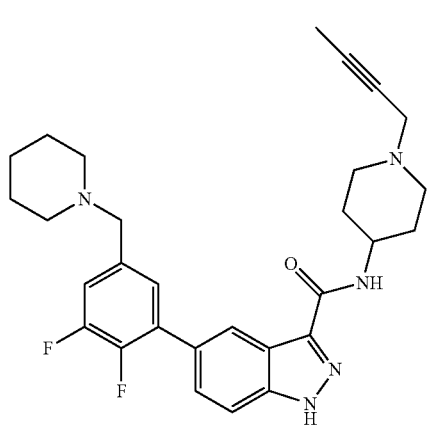 [SMILES: CC#CCN1CCC(NC(=O)c2n[nH]c3ccc(-c4cc(CN5CCCCC5)cc(F)c4F)cc23)CC1]
388
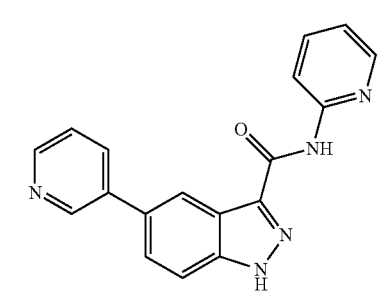 [SMILES: O=C(Nc1ccccn1)c1n[nH]c2ccc(-c3cccnc3)cc12]
389
TABLE 1-continued
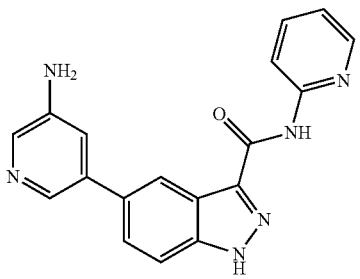 [SMILES: Nc1cncc(-c2ccc3[nH]nc(C(=O)Nc4ccccn4)c3c2)c1]
390
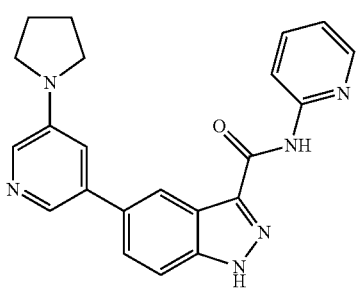 [SMILES: O=C(Nc1ccccn1)c1n[nH]c2ccc(-c3cncc(N4CCCC4)c3)cc12]
391
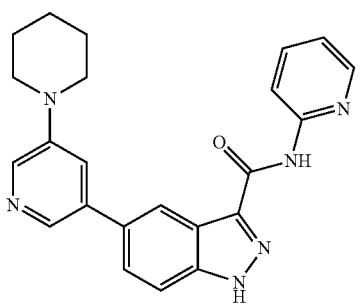 [SMILES: O=C(Nc1ccccn1)c1n[nH]c2ccc(-c3cncc(N4CCCCC4)c3)cc12]
392
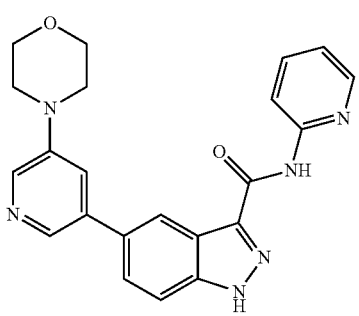 [SMILES: O=C(Nc1ccccn1)c1n[nH]c2ccc(-c3cncc(N4CCOCC4)c3)cc12]
393
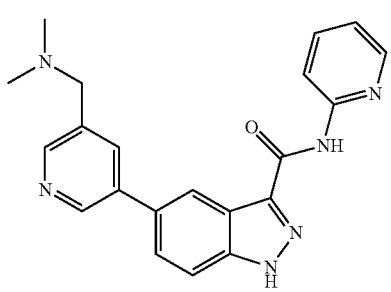 [SMILES: CN(C)Cc1cncc(-c2ccc3[nH]nc(C(=O)Nc4ccccn4)c3c2)c1]
394

TABLE 1-continued
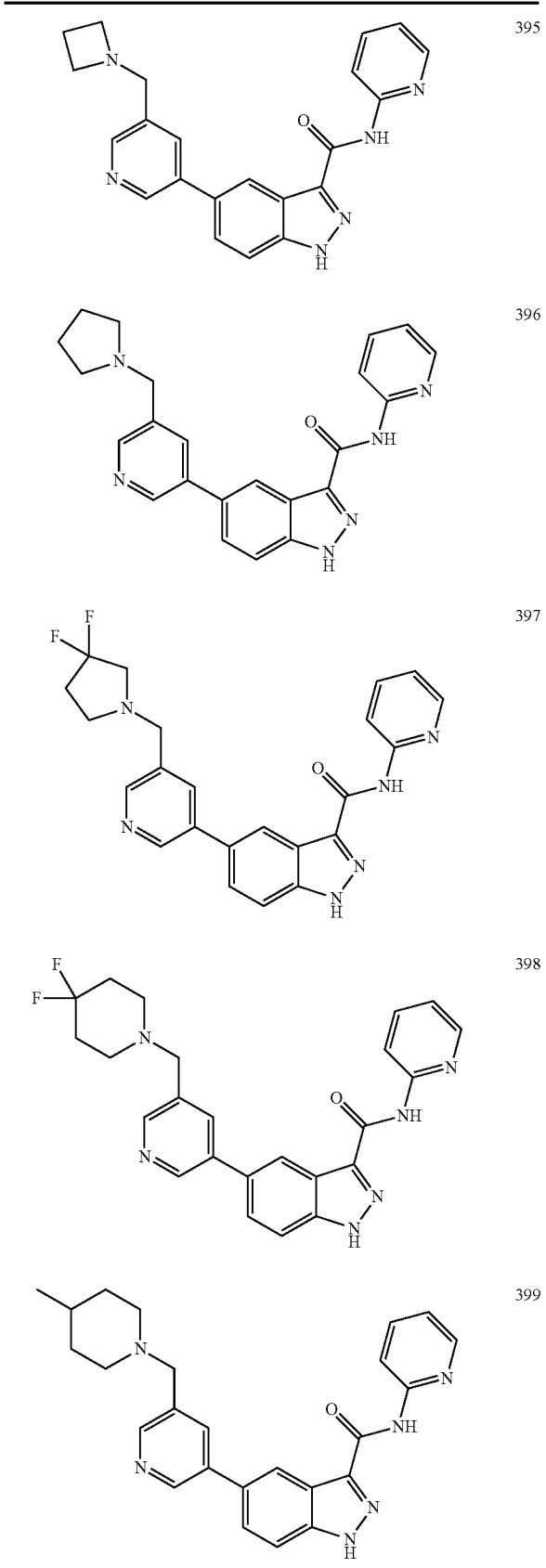
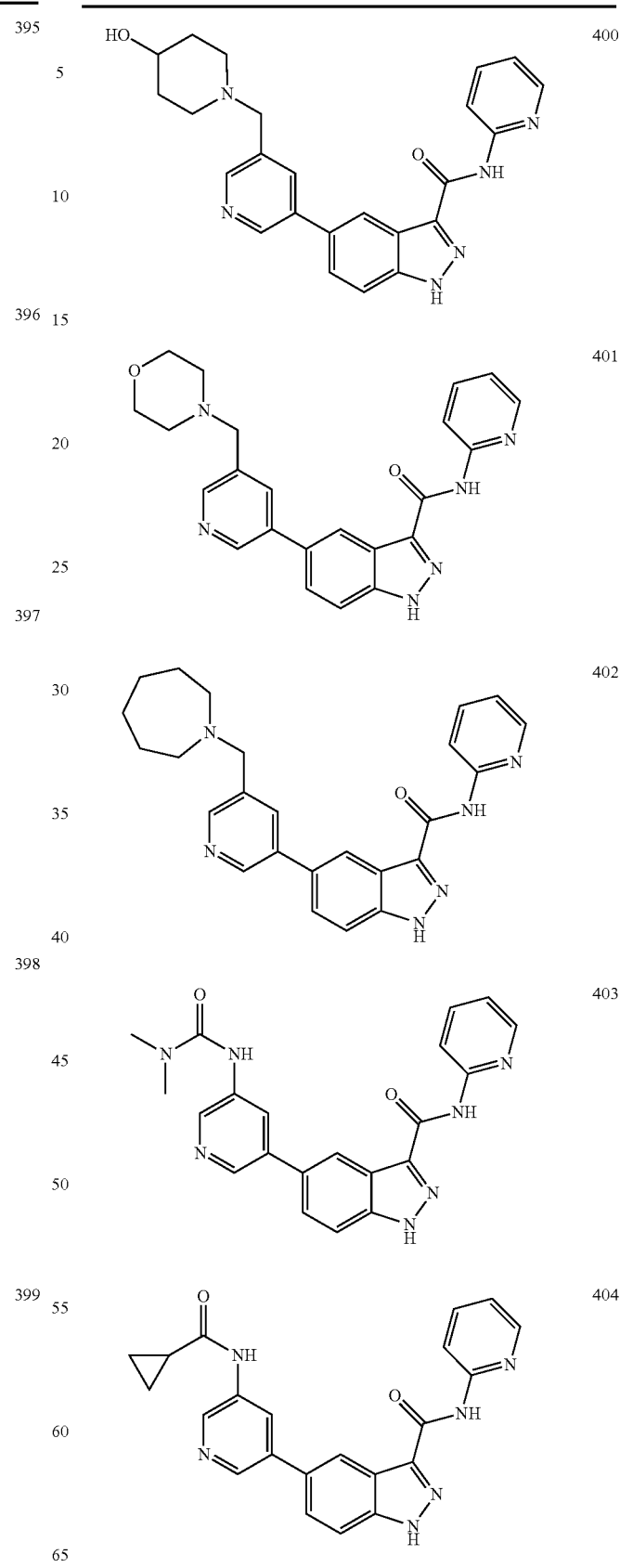

TABLE 1-continued
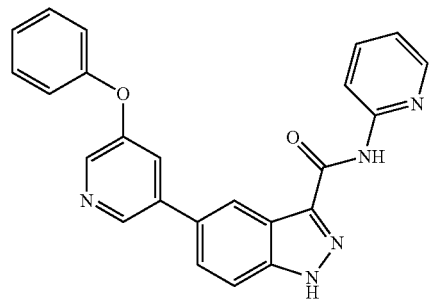 [SMILES: O=C(Nc1ccccn1)c1n[nH]c2ccc(-c3cncc(Oc4ccccc4)c3)cc12] 405
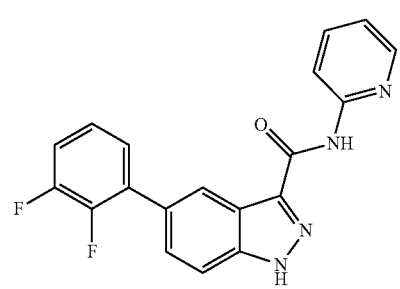 [SMILES: O=C(Nc1ccccn1)c1n[nH]c2ccc(-c3cccc(F)c3F)cc12] 406
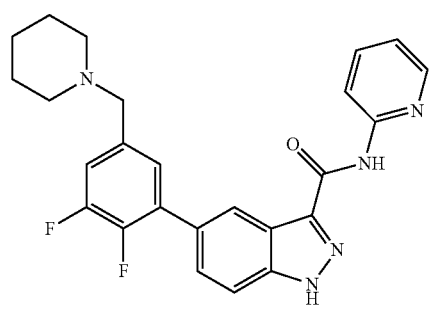 [SMILES: O=C(Nc1ccccn1)c1n[nH]c2ccc(-c3cc(CN4CCCCC4)cc(F)c3F)cc12] 407
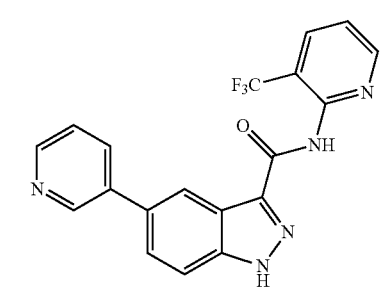 [SMILES: O=C(Nc1ncccc1C(F)(F)F)c1n[nH]c2ccc(-c3cccnc3)cc12] 408
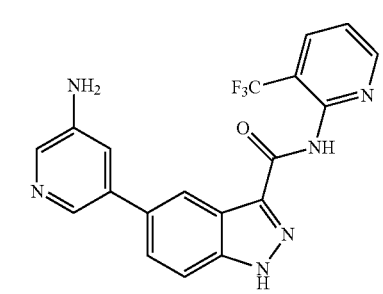 [SMILES: Nc1cncc(-c2ccc3[nH]nc(C(=O)Nc4ncccc4C(F)(F)F)c3c2)c1] 409
TABLE 1-continued
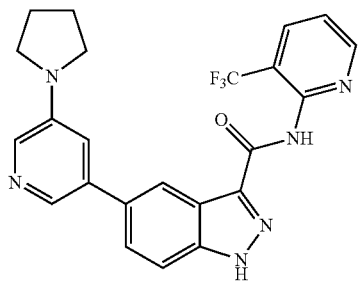 [SMILES: O=C(Nc1ncccc1C(F)(F)F)c1n[nH]c2ccc(-c3cncc(N4CCCC4)c3)cc12] 410
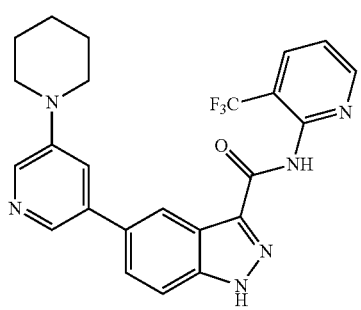 [SMILES: O=C(Nc1ncccc1C(F)(F)F)c1n[nH]c2ccc(-c3cncc(N4CCCCC4)c3)cc12] 411
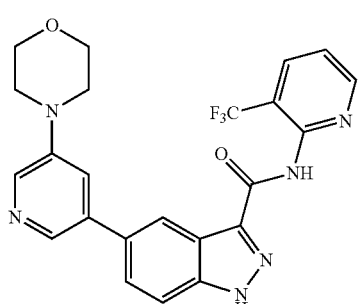 412
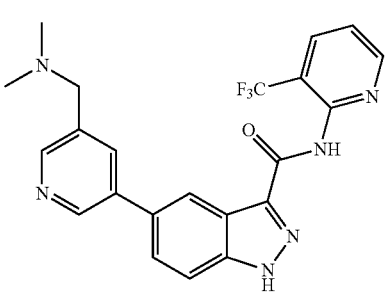 [SMILES: CN(C)Cc1cncc(-c2ccc3[nH]nc(C(=O)Nc4ncccc4C(F)(F)F)c3c2)c1] 413
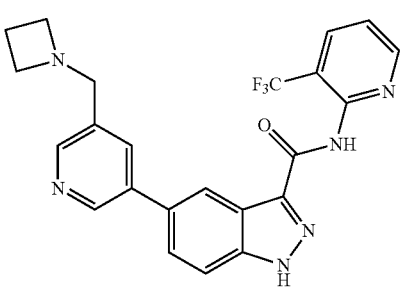 [SMILES: O=C(Nc1ncccc1C(F)(F)F)c1n[nH]c2ccc(-c3cncc(CN4CCC4)c3)cc12] 414

169
TABLE 1-continued
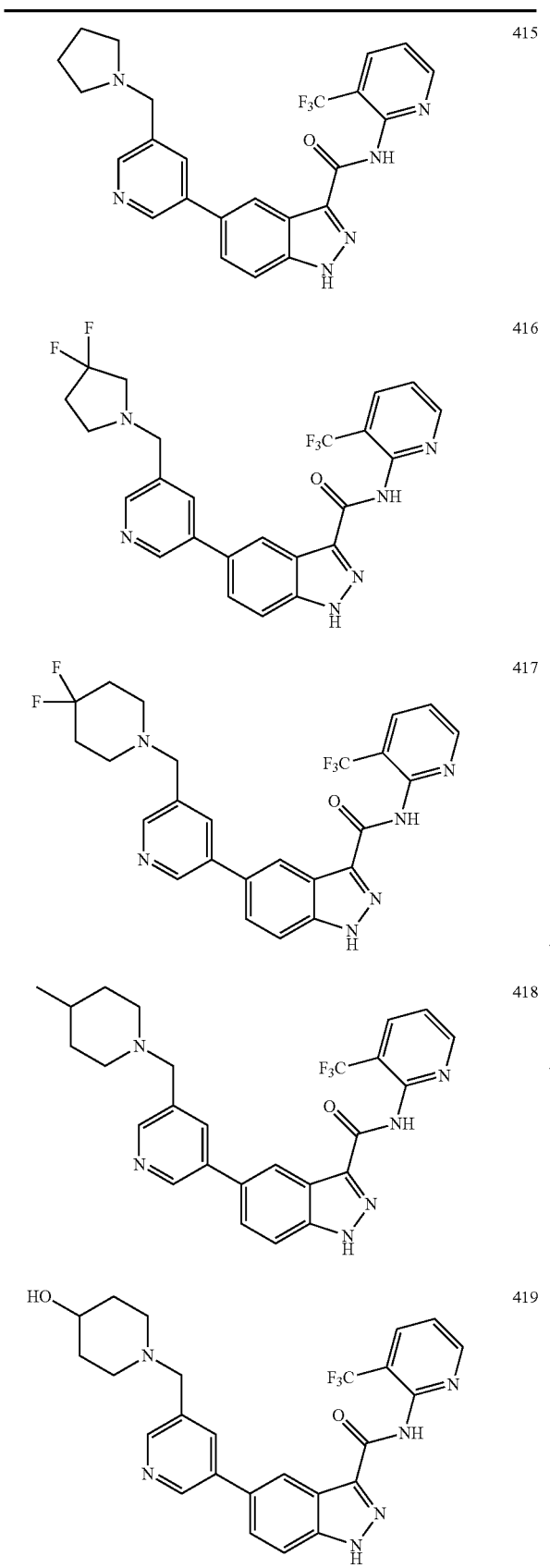
170
TABLE 1-continued
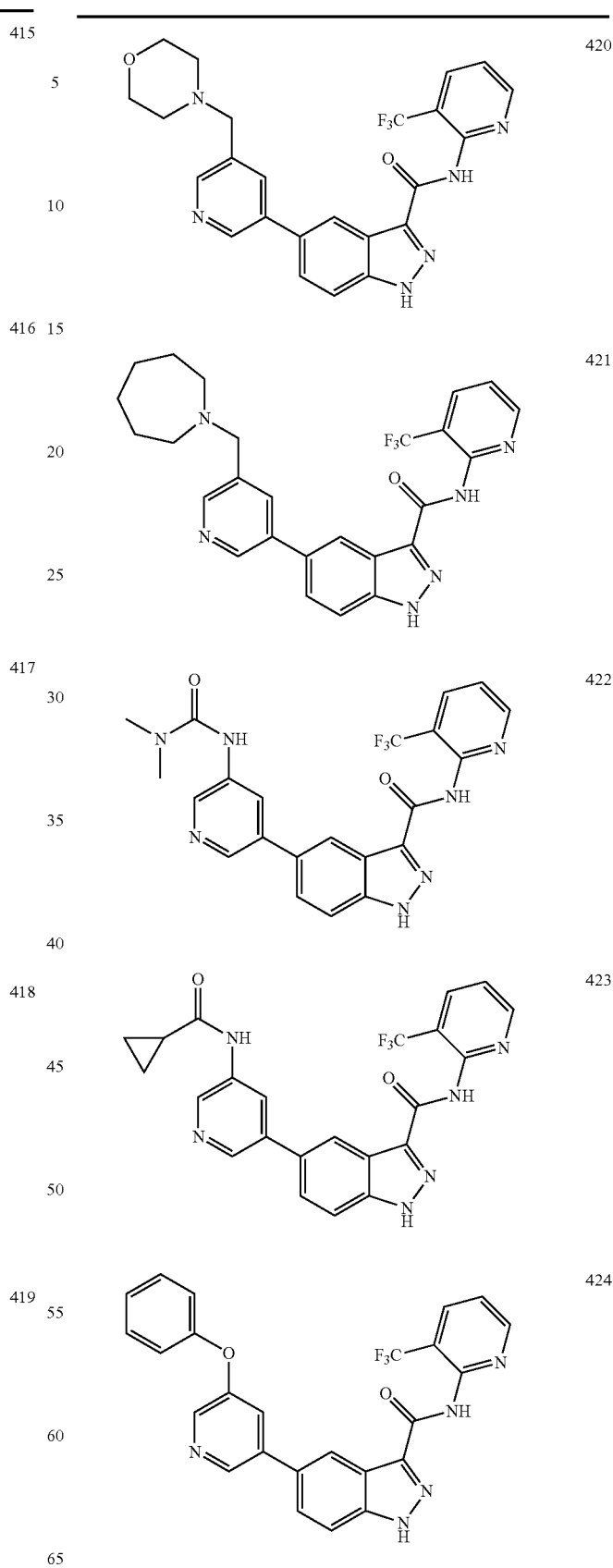

TABLE 1-continued
| | |
|---|---|
| 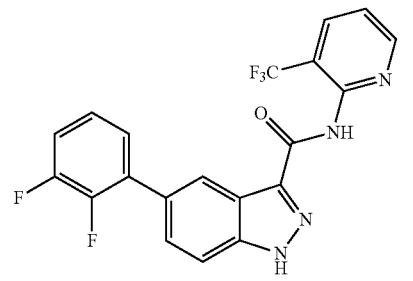 [SMILES: O=C(Nc1ncccc1C(F)(F)F)c1n[nH]c2ccc(-c3cccc(F)c3F)cc12] | 425 |
| 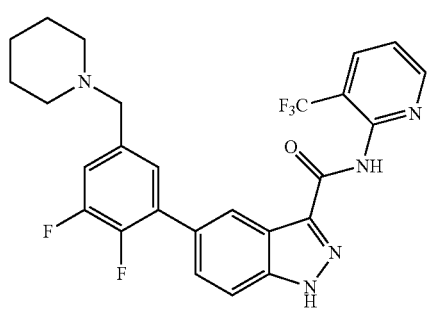 [SMILES: O=C(Nc1ncccc1C(F)(F)F)c1n[nH]c2ccc(-c3cc(CN4CCCCC4)cc(F)c3F)cc12] | 426 |
| 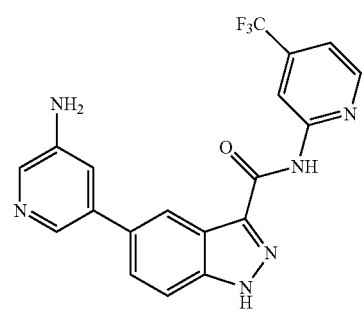 [SMILES: Nc1cncc(-c2ccc3[nH]nc(C(=O)Nc4cc(C(F)(F)F)ccn4)c3c2)c1] | 427 |
| 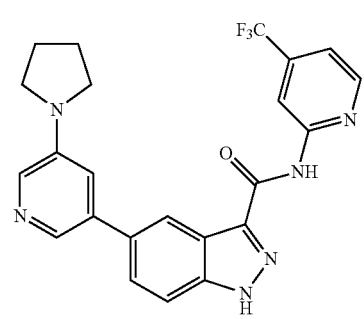 [SMILES: O=C(Nc1cc(C(F)(F)F)ccn1)c1n[nH]c2ccc(-c3cncc(N4CCCC4)c3)cc12] | 428 |
| 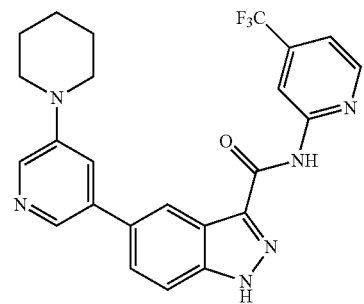 | 429 |
TABLE 1-continued
| | |
|---|---|
| 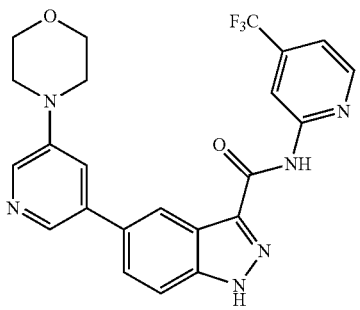 [SMILES: O=C(Nc1cc(C(F)(F)F)ccn1)c1n[nH]c2ccc(-c3cncc(N4CCOCC4)c3)cc12] | 430 |
| 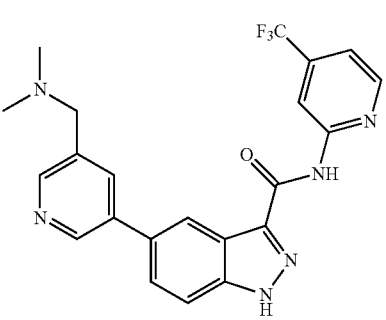 [SMILES: CN(C)Cc1cncc(-c2ccc3[nH]nc(C(=O)Nc4cc(C(F)(F)F)ccn4)c3c2)c1] | 431 |
| 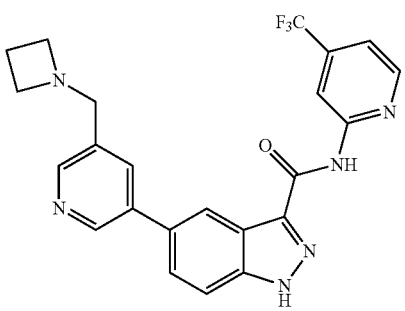 [SMILES: O=C(Nc1cc(C(F)(F)F)ccn1)c1n[nH]c2ccc(-c3cncc(CN4CCC4)c3)cc12] | 432 |
| 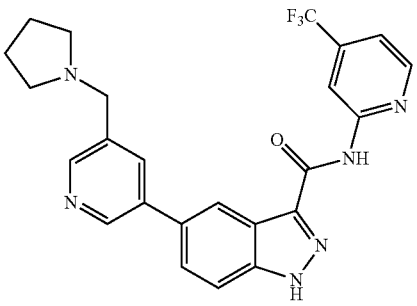 [SMILES: O=C(Nc1cc(C(F)(F)F)ccn1)c1n[nH]c2ccc(-c3cncc(CN4CCCC4)c3)cc12] | 433 |
| 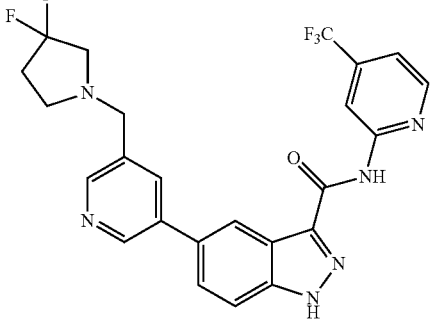 | 434 |

TABLE 1-continued
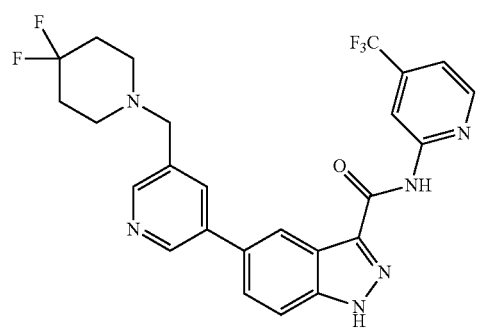 [SMILES: O=C(Nc1cc(C(F)(F)F)ccn1)c1n[nH]c2ccc(-c3cncc(CN4CCC(F)(F)CC4)c3)cc12] 435
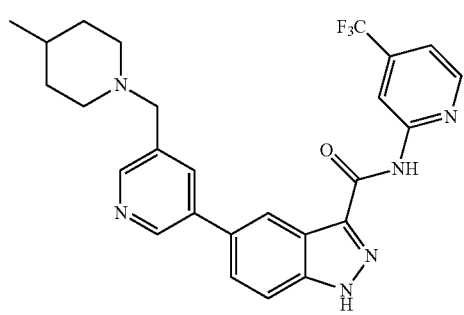 [SMILES: CC1CCN(Cc2cncc(-c3ccc4[nH]nc(C(=O)Nc5cc(C(F)(F)F)ccn5)c4c3)c2)CC1] 436
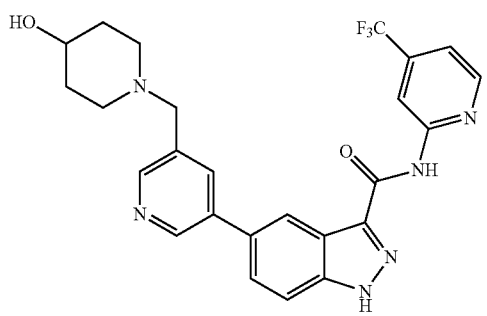 [SMILES: O=C(Nc1cc(C(F)(F)F)ccn1)c1n[nH]c2ccc(-c3cncc(CN4CCC(O)CC4)c3)cc12] 437
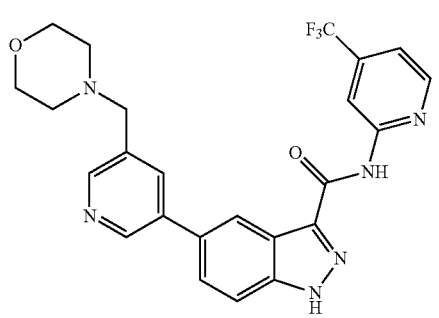 [SMILES: O=C(Nc1cc(C(F)(F)F)ccn1)c1n[nH]c2ccc(-c3cncc(CN4CCOCC4)c3)cc12] 438
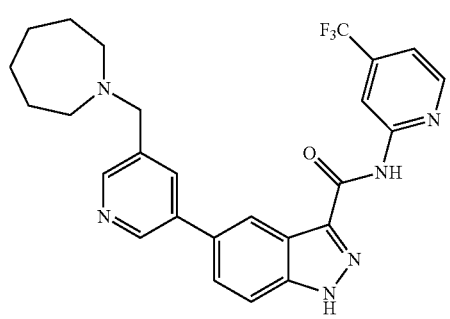 [SMILES: O=C(Nc1cc(C(F)(F)F)ccn1)c1n[nH]c2ccc(-c3cncc(CN4CCCCCC4)c3)cc12] 439
TABLE 1-continued
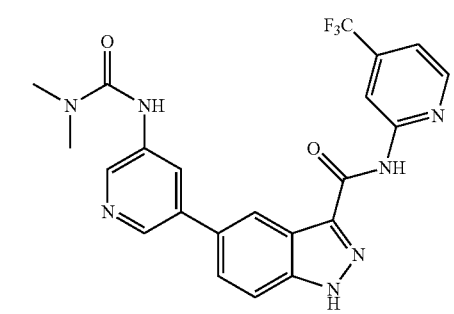 [SMILES: CN(C)C(=O)Nc1cncc(-c2ccc3[nH]nc(C(=O)Nc4cc(C(F)(F)F)ccn4)c3c2)c1] 440
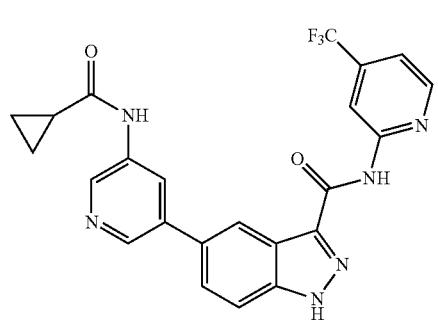 [SMILES: O=C(Nc1cc(C(F)(F)F)ccn1)c1n[nH]c2ccc(-c3cncc(NC(=O)C4CC4)c3)cc12] 441
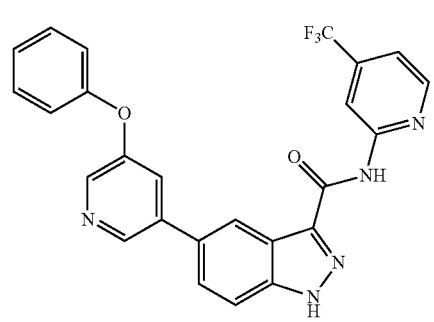 442
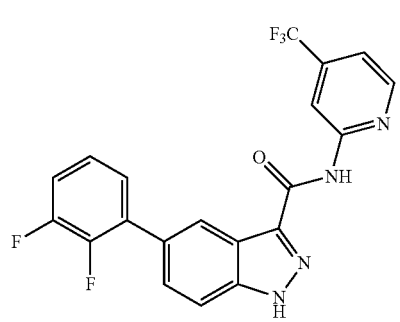 [SMILES: O=C(Nc1cc(C(F)(F)F)ccn1)c1n[nH]c2ccc(-c3cccc(F)c3F)cc12] 443
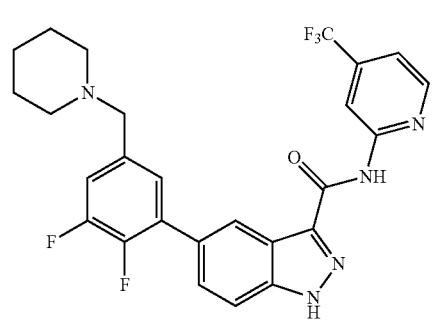 [SMILES: O=C(Nc1cc(C(F)(F)F)ccn1)c1n[nH]c2ccc(-c3cc(CN4CCCCC4)cc(F)c3F)cc12] 444

TABLE 1-continued
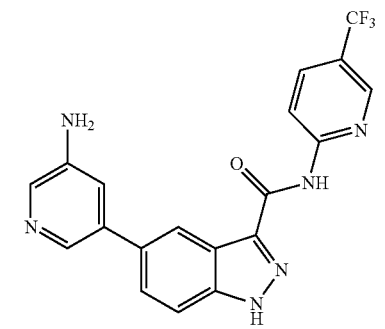 [SMILES: Nc1cncc(-c2ccc3[nH]nc(C(=O)Nc4ccc(C(F)(F)F)cn4)c3c2)c1] 445
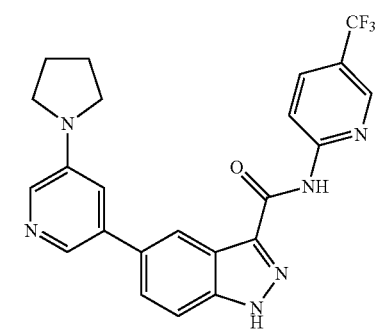 [SMILES: O=C(Nc1ccc(C(F)(F)F)cn1)c1n[nH]c2ccc(-c3cncc(N4CCCC4)c3)cc12] 446
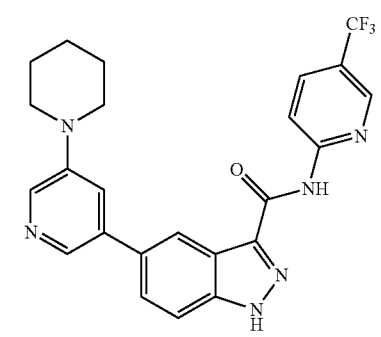 [SMILES: O=C(Nc1ccc(C(F)(F)F)cn1)c1n[nH]c2ccc(-c3cncc(N4CCCCC4)c3)cc12] 447
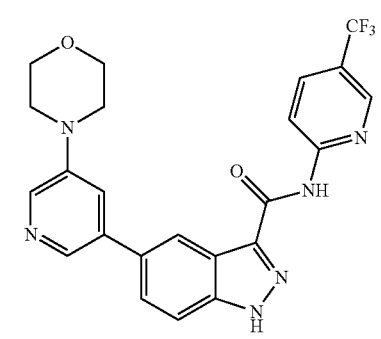 [SMILES: O=C(Nc1ccc(C(F)(F)F)cn1)c1n[nH]c2ccc(-c3cncc(N4CCOCC4)c3)cc12] 448
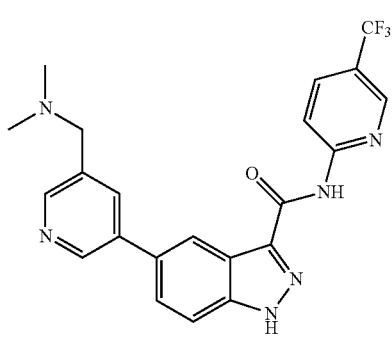 [SMILES: CN(C)Cc1cncc(-c2ccc3[nH]nc(C(=O)Nc4ccc(C(F)(F)F)cn4)c3c2)c1] 449
TABLE 1-continued
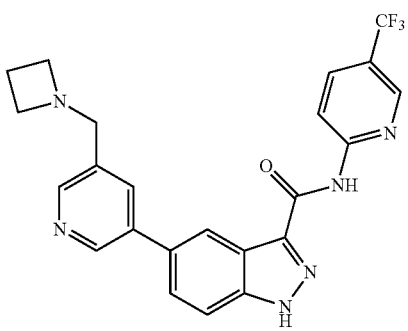 [SMILES: O=C(Nc1ccc(C(F)(F)F)cn1)c1n[nH]c2ccc(-c3cncc(CN4CCC4)c3)cc12] 450
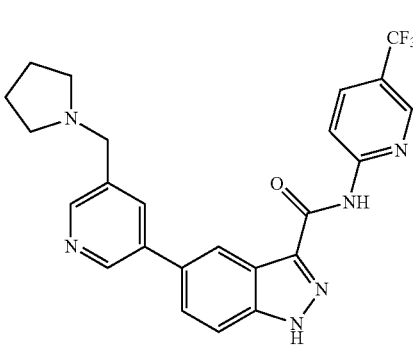 451
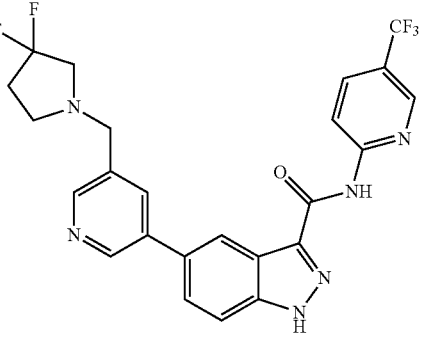 452
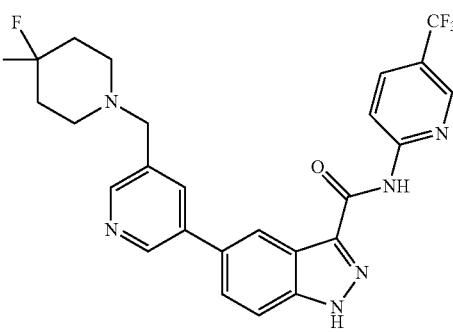 453

TABLE 1-continued
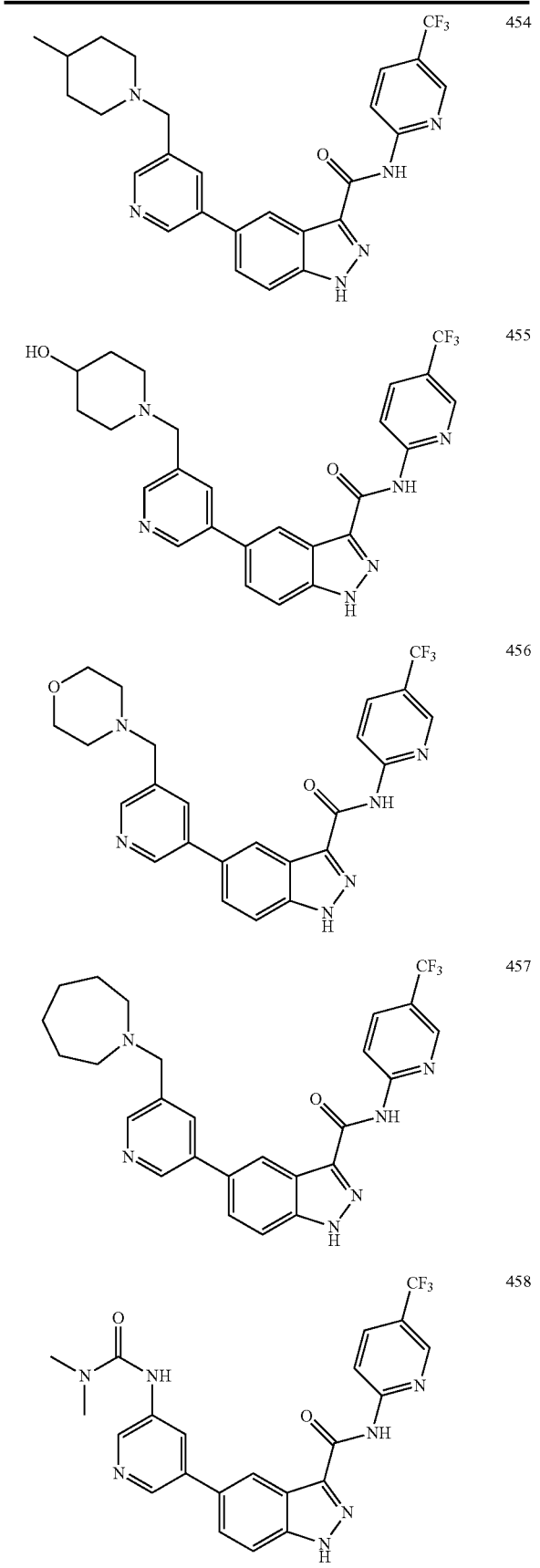
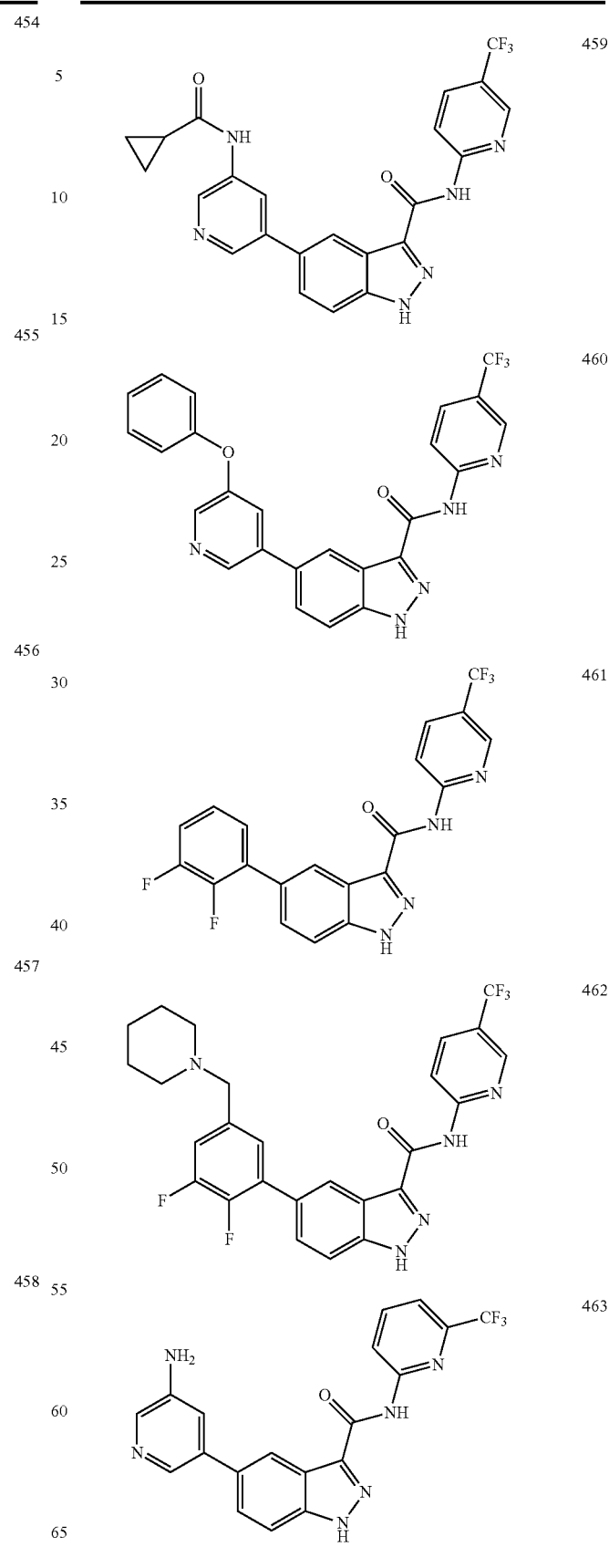

TABLE 1-continued
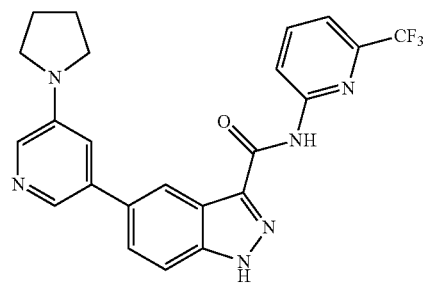 [SMILES: O=C(Nc1cccc(C(F)(F)F)n1)c1n[nH]c2ccc(-c3cncc(N4CCCC4)c3)cc12] 464
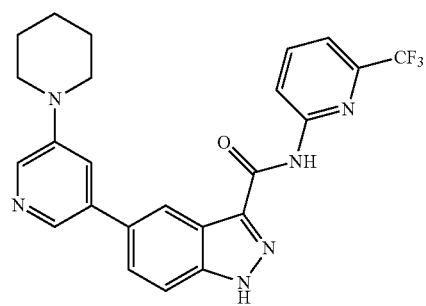 [SMILES: O=C(Nc1cccc(C(F)(F)F)n1)c1n[nH]c2ccc(-c3cncc(N4CCCCC4)c3)cc12] 465
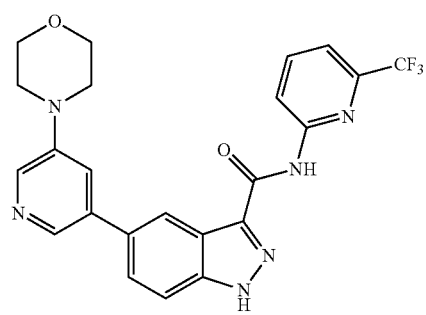 [SMILES: O=C(Nc1cccc(C(F)(F)F)n1)c1n[nH]c2ccc(-c3cncc(N4CCOCC4)c3)cc12] 466
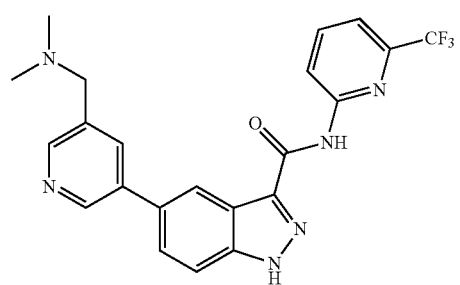 [SMILES: CN(C)Cc1cncc(-c2ccc3[nH]nc(C(=O)Nc4cccc(C(F)(F)F)n4)c3c2)c1] 467
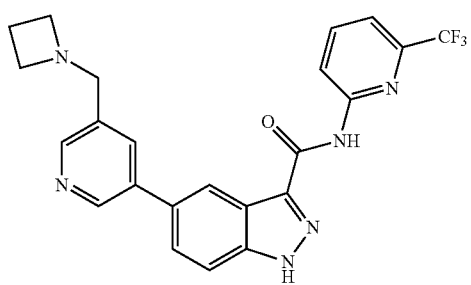 [SMILES: O=C(Nc1cccc(C(F)(F)F)n1)c1n[nH]c2ccc(-c3cncc(CN4CCC4)c3)cc12] 468
TABLE 1-continued
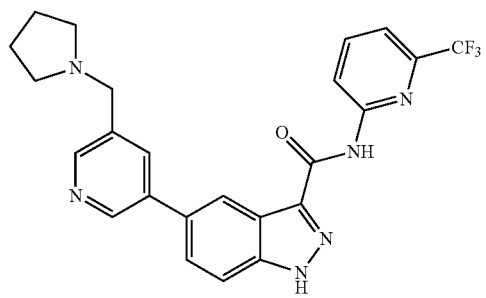 [SMILES: O=C(Nc1cccc(C(F)(F)F)n1)c1n[nH]c2ccc(-c3cncc(CN4CCCC4)c3)cc12] 469
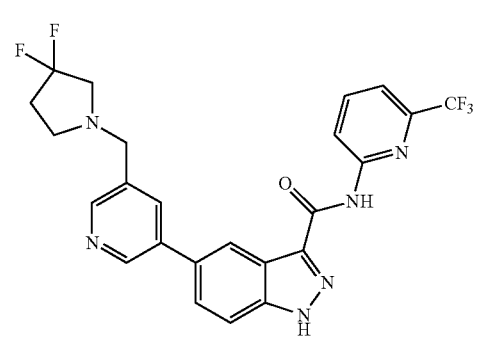 [SMILES: O=C(Nc1cccc(C(F)(F)F)n1)c1n[nH]c2ccc(-c3cncc(CN4CCC(F)(F)C4)c3)cc12] 470
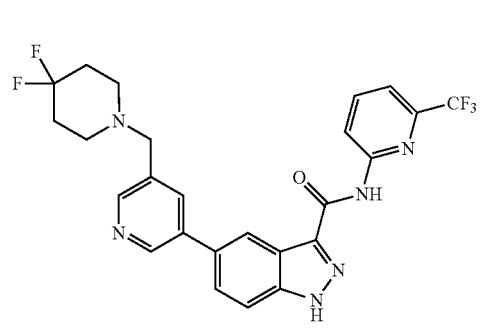 [SMILES: O=C(Nc1cccc(C(F)(F)F)n1)c1n[nH]c2ccc(-c3cncc(CN4CCC(F)(F)CC4)c3)cc12] 471
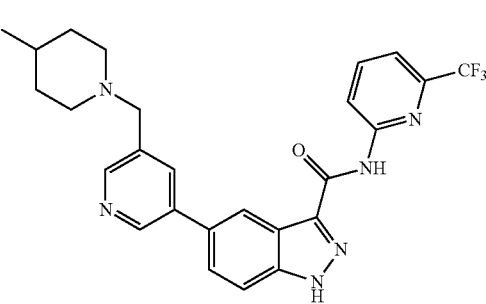 [SMILES: CC1CCN(Cc2cncc(-c3ccc4[nH]nc(C(=O)Nc5cccc(C(F)(F)F)n5)c4c3)c2)CC1] 472
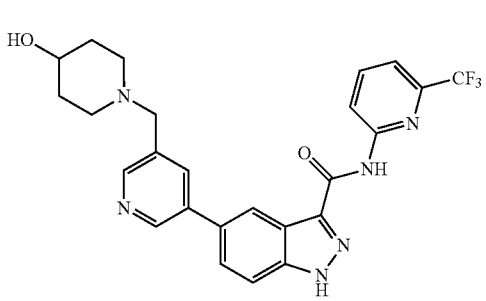 [SMILES: O=C(Nc1cccc(C(F)(F)F)n1)c1n[nH]c2ccc(-c3cncc(CN4CCC(O)CC4)c3)cc12] 473

TABLE 1-continued
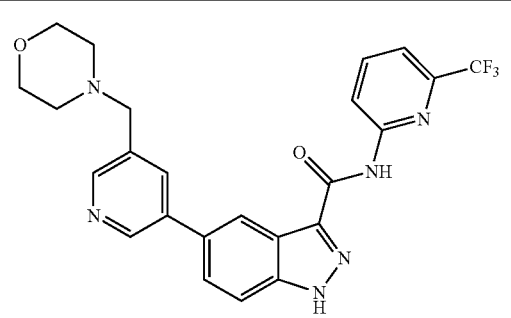 474
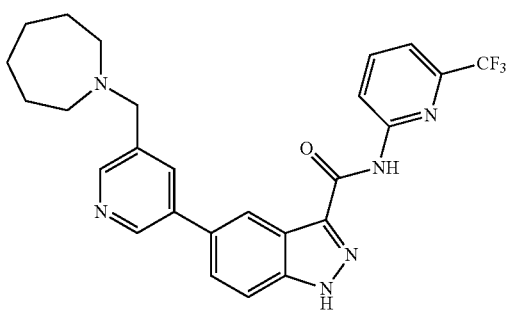 [SMILES: O=C(Nc1cccc(C(F)(F)F)n1)c1n[nH]c2ccc(-c3cncc(CN4CCCCCC4)c3)cc12] 475
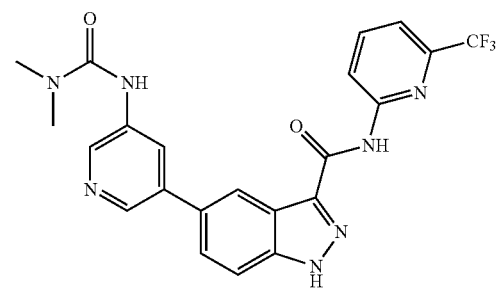 [SMILES: CN(C)C(=O)Nc1cncc(-c2ccc3[nH]nc(C(=O)Nc4cccc(C(F)(F)F)n4)c3c2)c1] 476
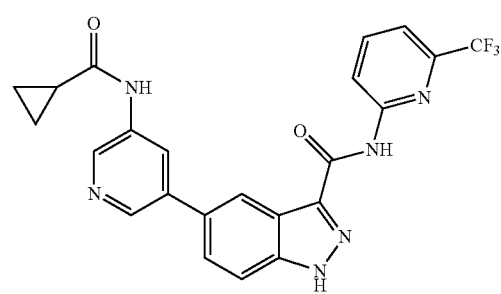 [SMILES: O=C(Nc1cccc(C(F)(F)F)n1)c1n[nH]c2ccc(-c3cncc(NC(=O)C4CC4)c3)cc12] 477
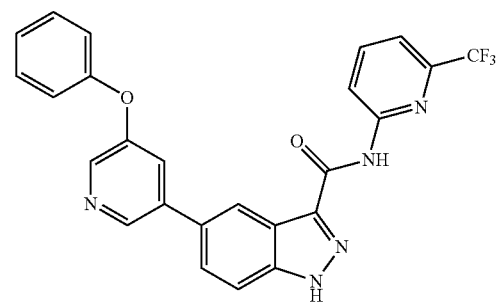 [SMILES: O=C(Nc1cccc(C(F)(F)F)n1)c1n[nH]c2ccc(-c3cncc(Oc4ccccc4)c3)cc12] 478
TABLE 1-continued
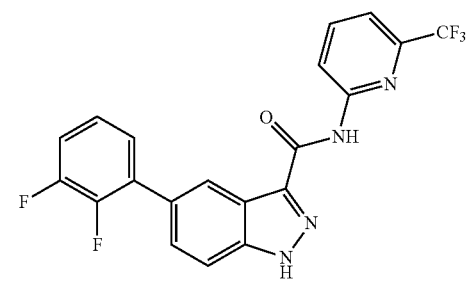 [SMILES: O=C(Nc1cccc(C(F)(F)F)n1)c1n[nH]c2ccc(-c3cccc(F)c3F)cc12] 479
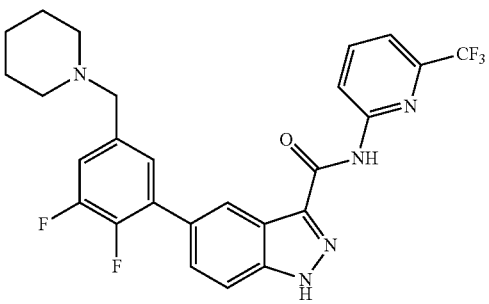 [SMILES: O=C(Nc1cccc(C(F)(F)F)n1)c1n[nH]c2ccc(-c3cc(CN4CCCCC4)cc(F)c3F)cc12] 480
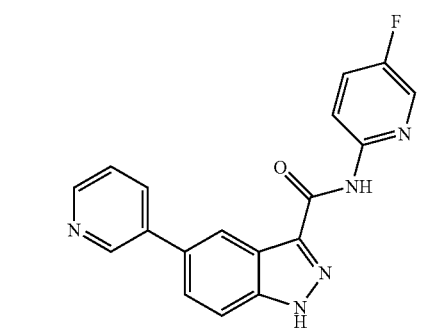 [SMILES: O=C(Nc1ccc(F)cn1)c1n[nH]c2ccc(-c3cccnc3)cc12] 481
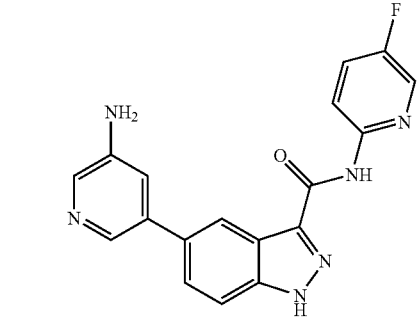 [SMILES: Nc1cncc(-c2ccc3[nH]nc(C(=O)Nc4ccc(F)cn4)c3c2)c1] 482
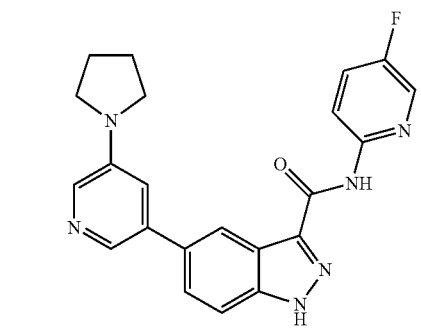 [SMILES: O=C(Nc1ccc(F)cn1)c1n[nH]c2ccc(-c3cncc(N4CCCC4)c3)cc12] 483

TABLE 1-continued
| | |
|---|---|
| 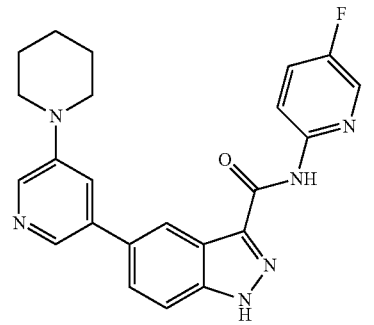 [SMILES: O=C(Nc1ccc(F)cn1)c1n[nH]c2ccc(-c3cncc(N4CCCCC4)c3)cc12] | 484 |
| 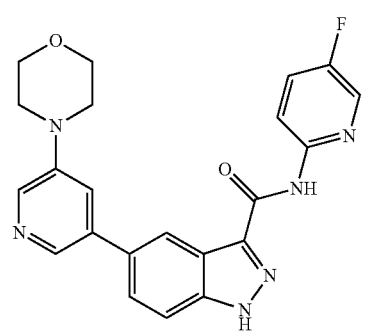 [SMILES: O=C(Nc1ccc(F)cn1)c1n[nH]c2ccc(-c3cncc(N4CCOCC4)c3)cc12] | 485 |
| 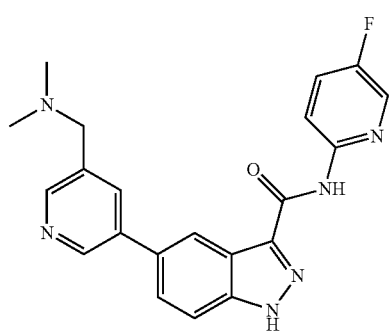 [SMILES: CN(C)Cc1cncc(-c2ccc3[nH]nc(C(=O)Nc4ccc(F)cn4)c3c2)c1] | 486 |
|  | 487 |
| 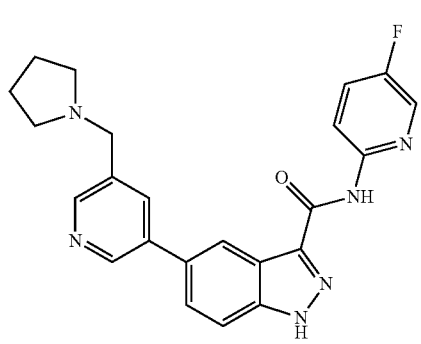 [SMILES: O=C(Nc1ccc(F)cn1)c1n[nH]c2ccc(-c3cncc(CN4CCCC4)c3)cc12] | 488 |
TABLE 1-continued
| | |
|---|---|
| 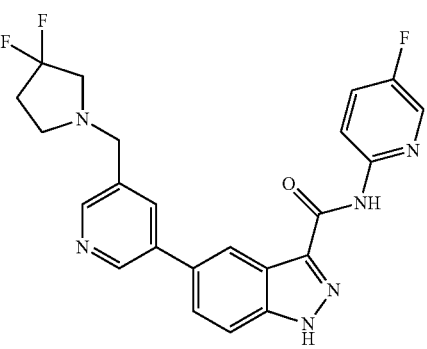 [SMILES: O=C(Nc1ccc(F)cn1)c1n[nH]c2ccc(-c3cncc(CN4CCC(F)(F)C4)c3)cc12] | 489 |
| 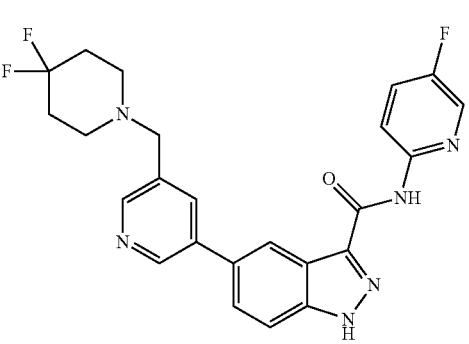 [SMILES: O=C(Nc1ccc(F)cn1)c1n[nH]c2ccc(-c3cncc(CN4CCC(F)(F)CC4)c3)cc12] | 490 |
| 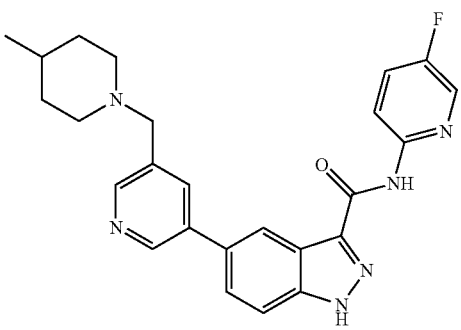 [SMILES: CC1CCN(Cc2cncc(-c3ccc4[nH]nc(C(=O)Nc5ccc(F)cn5)c4c3)c2)CC1] | 491 |
| 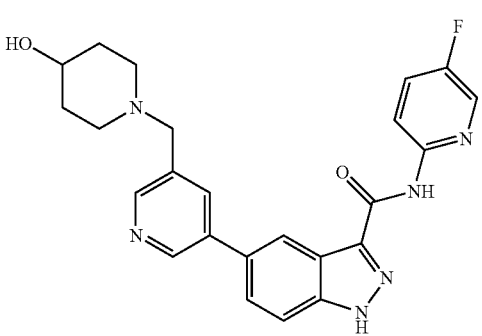 [SMILES: O=C(Nc1ccc(F)cn1)c1n[nH]c2ccc(-c3cncc(CN4CCC(O)CC4)c3)cc12] | 492 |

TABLE 1-continued
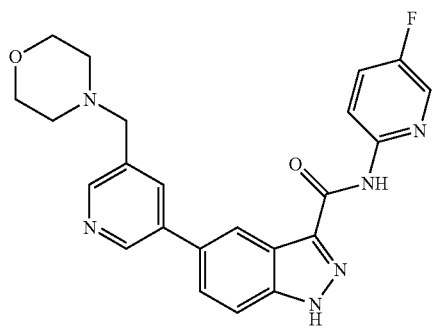 [SMILES: O=C(Nc1ccc(F)cn1)c1n[nH]c2ccc(-c3cncc(CN4CCOCC4)c3)cc12]
493
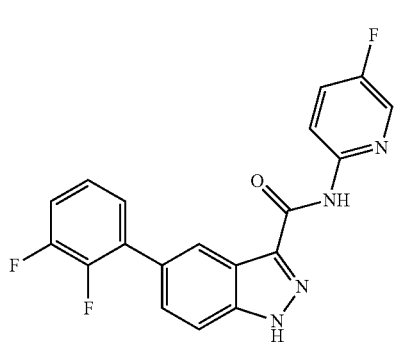 [SMILES: O=C(Nc1ccc(F)cn1)c1n[nH]c2ccc(-c3cccc(F)c3F)cc12]
498
494
499
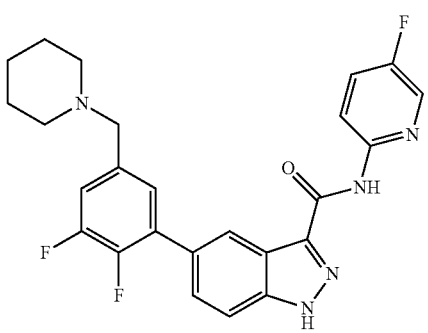 [SMILES: O=C(Nc1ccc(F)cn1)c1n[nH]c2ccc(-c3cc(CN4CCCCC4)cc(F)c3F)cc12]
495
500
496

501
497

502
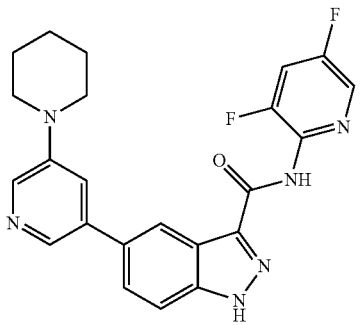

TABLE 1-continued
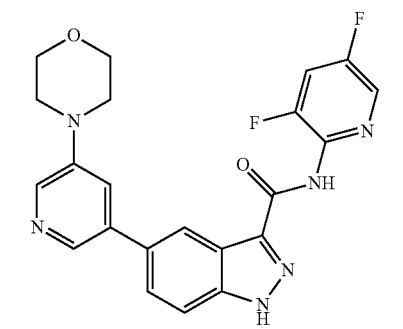 [SMILES: O=C(Nc1ncc(F)cc1F)c1n[nH]c2ccc(-c3cncc(N4CCOCC4)c3)cc12] 503
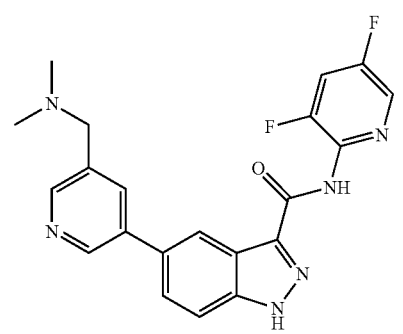 [SMILES: CN(C)Cc1cncc(-c2ccc3[nH]nc(C(=O)Nc4ncc(F)cc4F)c3c2)c1] 504
 505
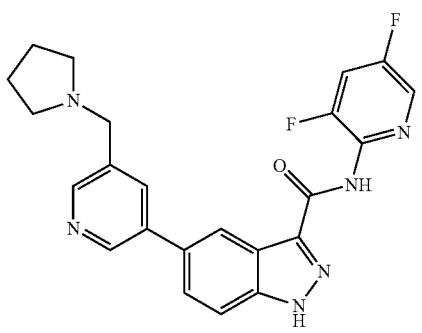 [SMILES: O=C(Nc1ncc(F)cc1F)c1n[nH]c2ccc(-c3cncc(CN4CCCC4)c3)cc12] 506
TABLE 1-continued
 507
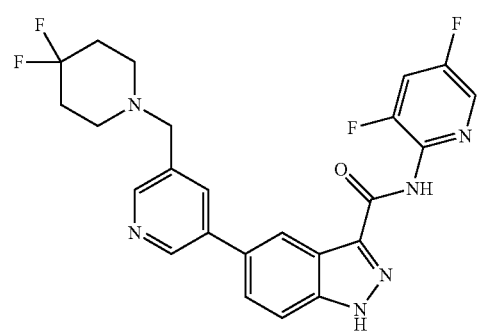 [SMILES: O=C(Nc1ncc(F)cc1F)c1n[nH]c2ccc(-c3cncc(CN4CCC(F)(F)CC4)c3)cc12] 508
 509
 510
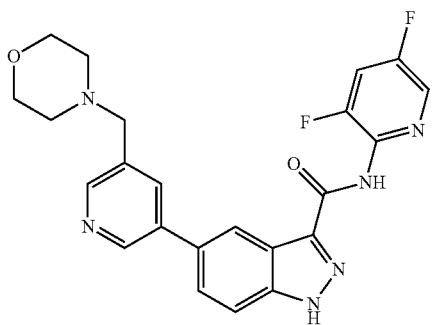 [SMILES: O=C(Nc1ncc(F)cc1F)c1n[nH]c2ccc(-c3cncc(CN4CCOCC4)c3)cc12] 511

TABLE 1-continued
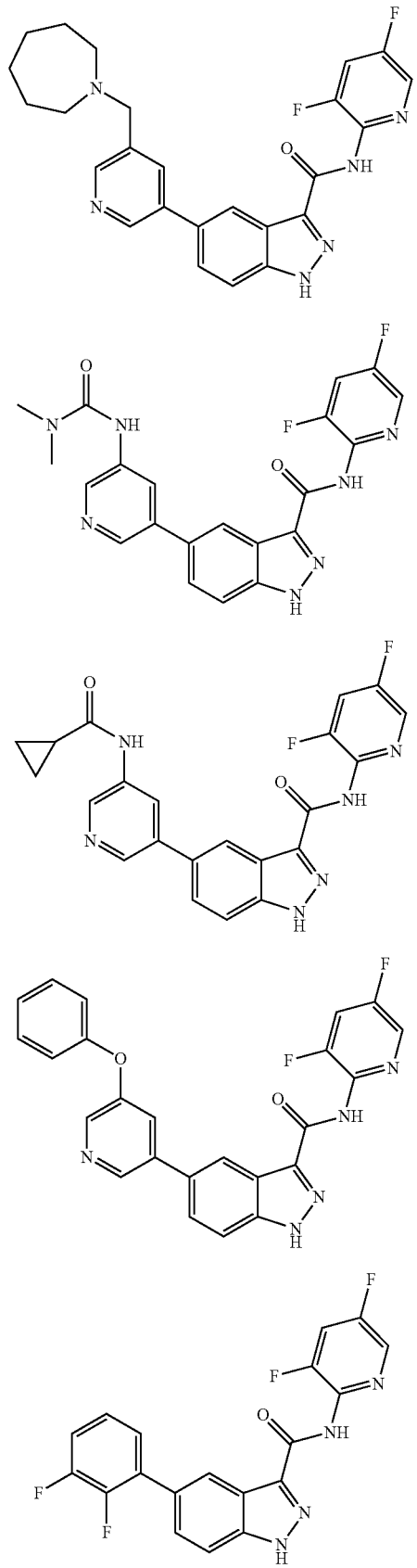
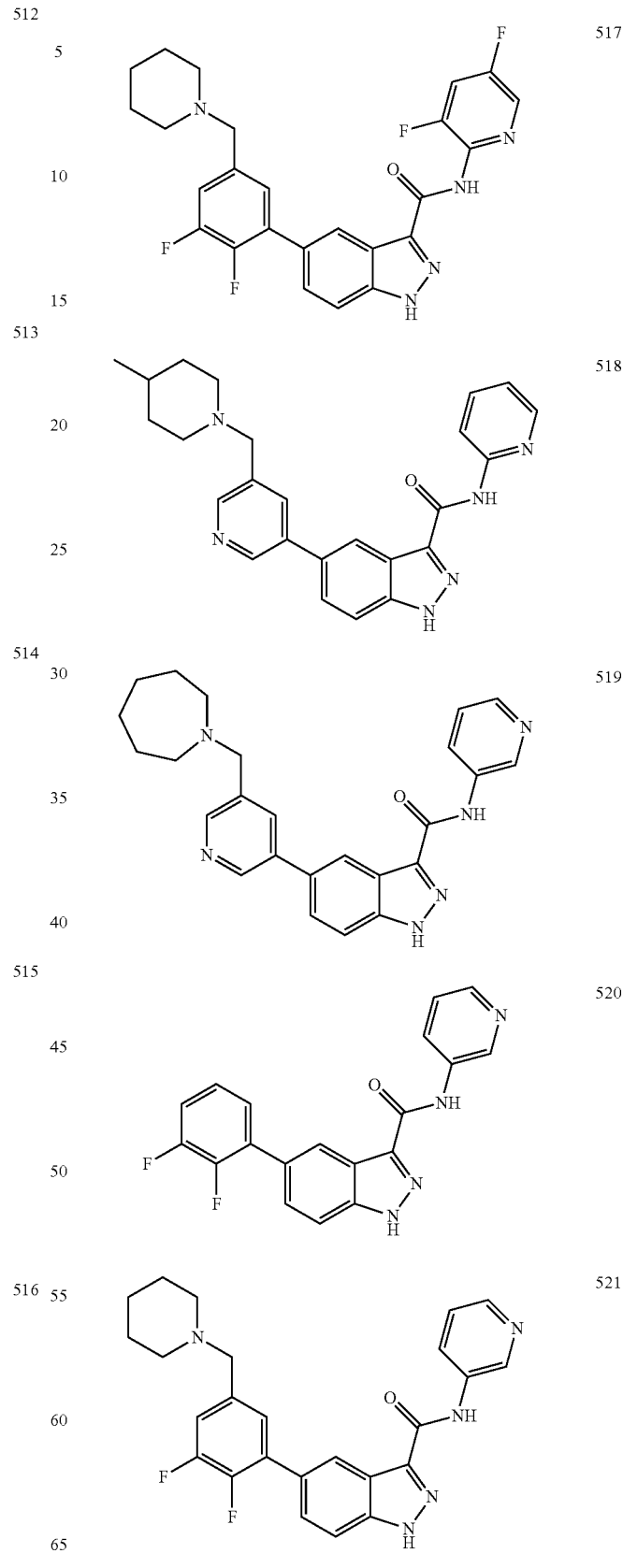

TABLE 1-continued
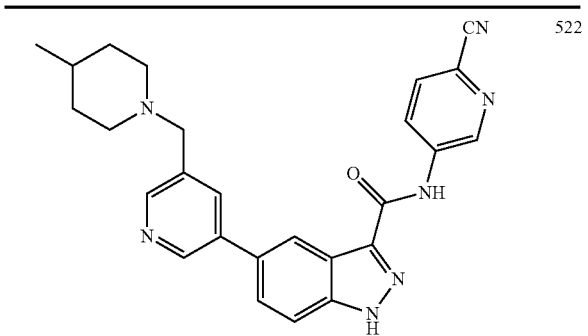 522
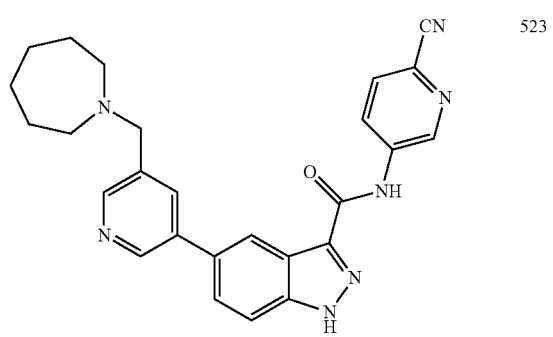 523
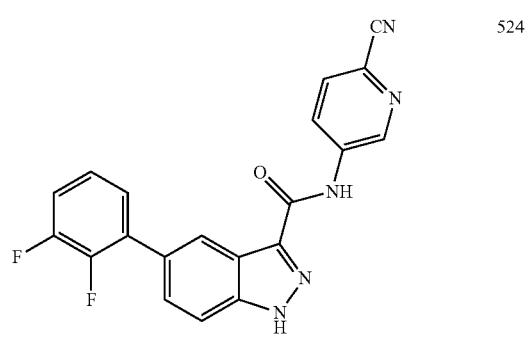 524
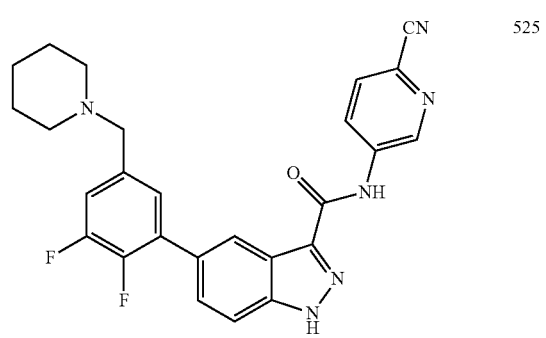 525
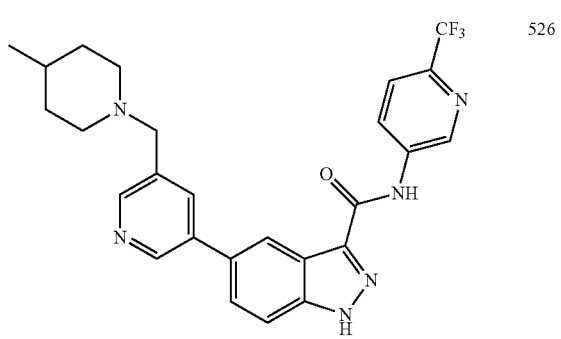 526
TABLE 1-continued
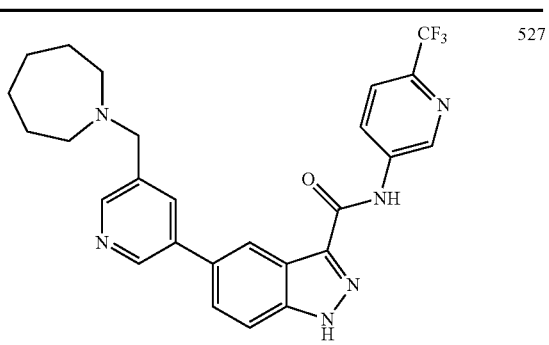 527
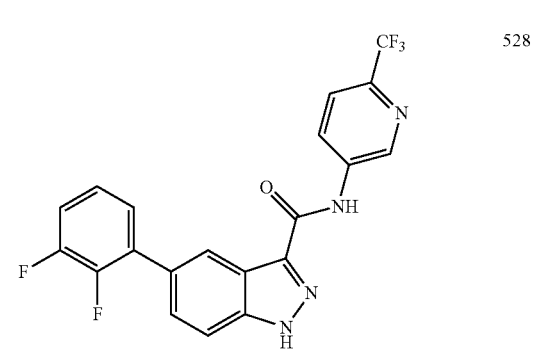 528
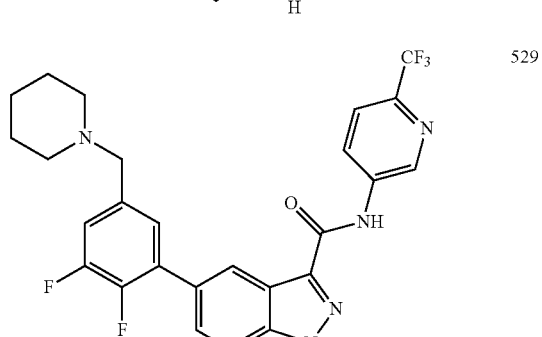 529
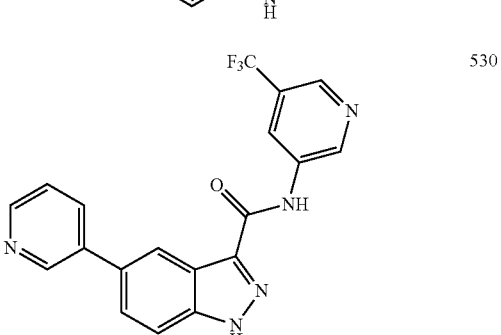 530
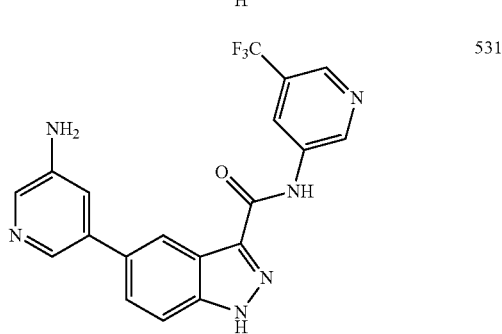 531

TABLE 1-continued

TABLE 1-continued
| | |
|---|---|
| 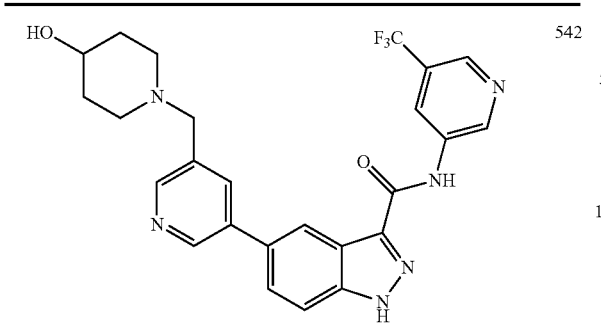 | 542 |
| 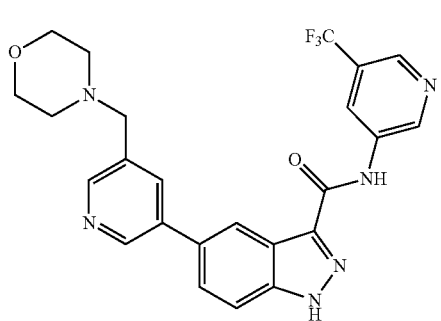 [SMILES: O=C(Nc1cncc(C(F)(F)F)c1)c1n[nH]c2ccc(-c3cncc(CN4CCOCC4)c3)cc12] | 543 |
| 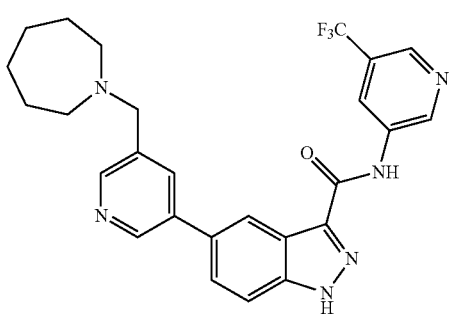 | 544 |
| 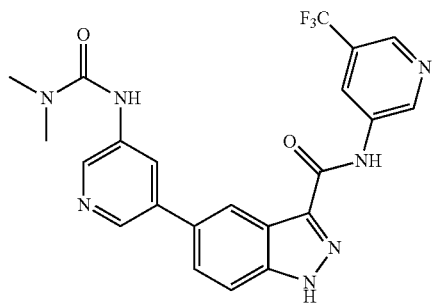 [SMILES: CN(C)C(=O)Nc1cncc(-c2ccc3[nH]nc(C(=O)Nc4cncc(C(F)(F)F)c4)c3c2)c1] | 545 |
| 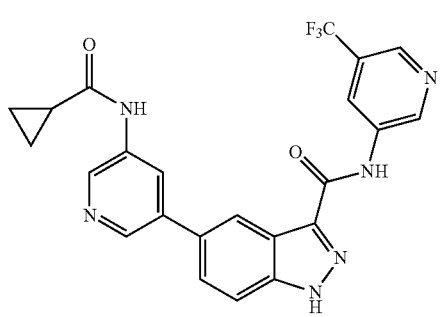 [SMILES: O=C(Nc1cncc(C(F)(F)F)c1)c1n[nH]c2ccc(-c3cncc(NC(=O)C4CC4)c3)cc12] | 546 |
TABLE 1-continued
| | |
|---|---|
| 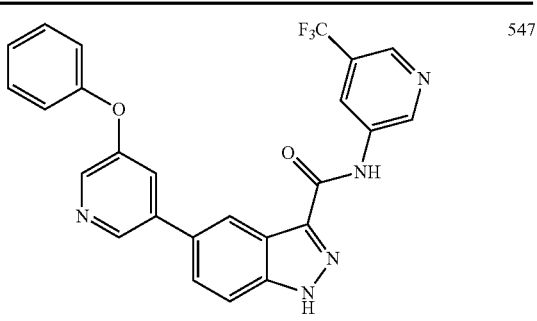 | 547 |
| 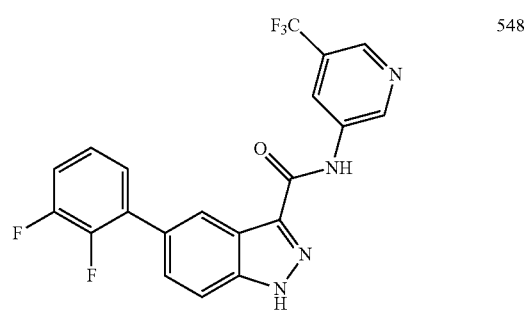 | 548 |
| 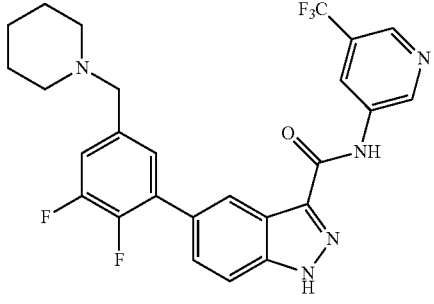 [SMILES: O=C(Nc1cncc(C(F)(F)F)c1)c1n[nH]c2ccc(-c3cc(CN4CCCCC4)cc(F)c3F)cc12] | 549 |
| 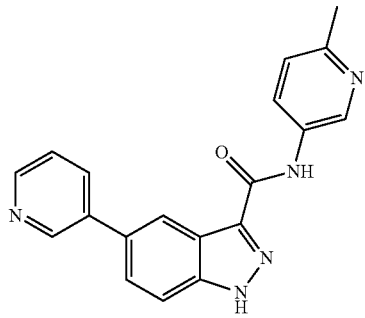 [SMILES: Cc1ccc(NC(=O)c2n[nH]c3ccc(-c4cccnc4)cc23)cn1] | 550 |
| 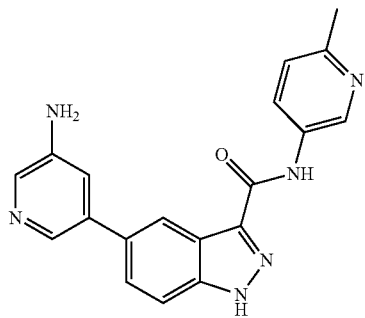 | 551 |

TABLE 1-continued
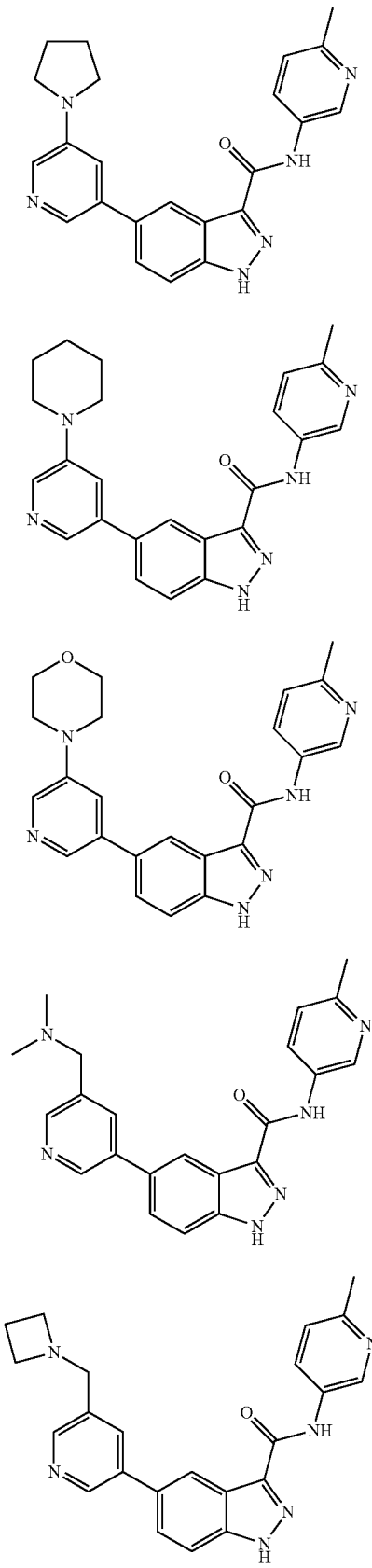
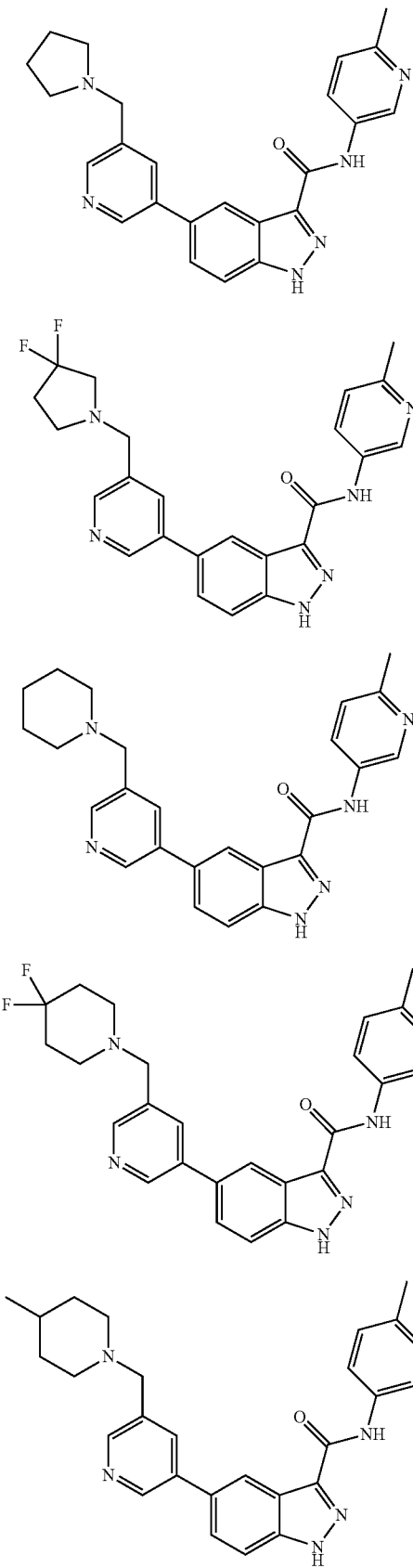

TABLE 1-continued
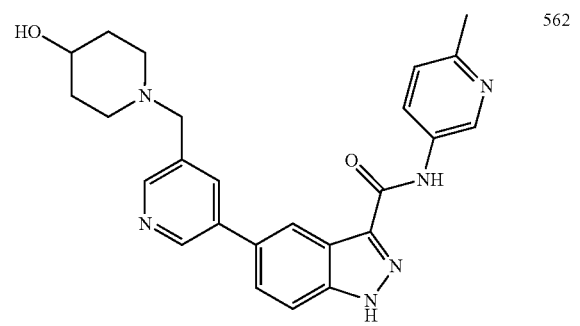 562
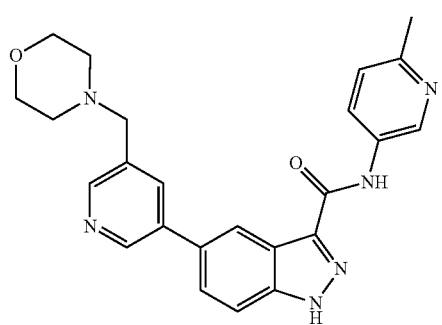 [SMILES: Cc1ccc(NC(=O)c2n[nH]c3ccc(-c4cncc(CN5CCOCC5)c4)cc23)cn1] 563
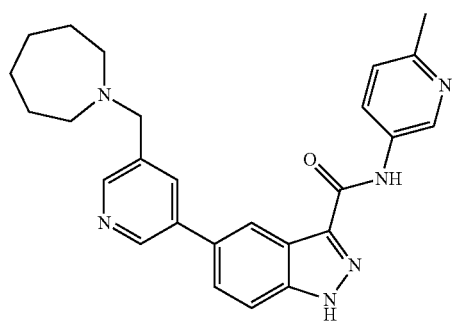 564
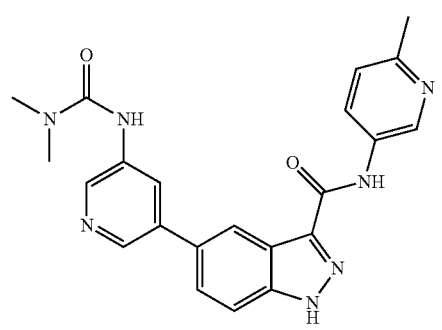 565
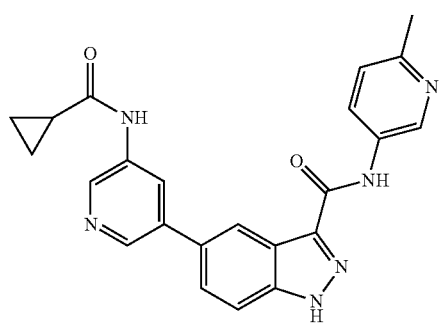 [SMILES: Cc1ccc(NC(=O)c2n[nH]c3ccc(-c4cncc(NC(=O)C5CC5)c4)cc23)cn1] 566
TABLE 1-continued
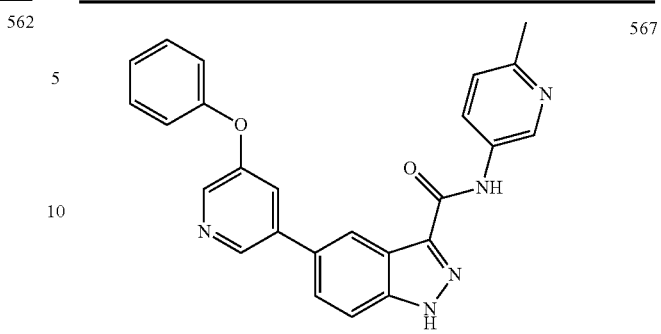 567
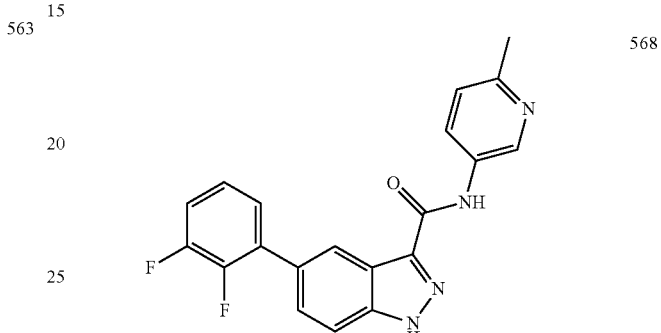 568
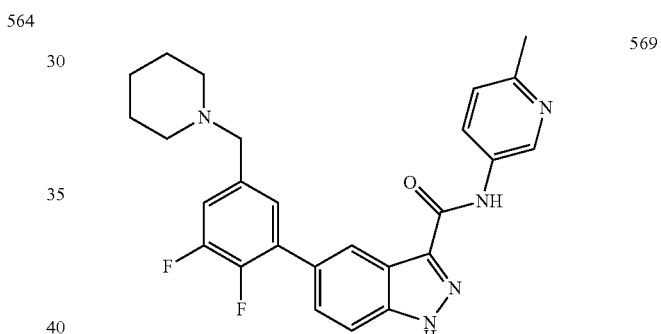 569
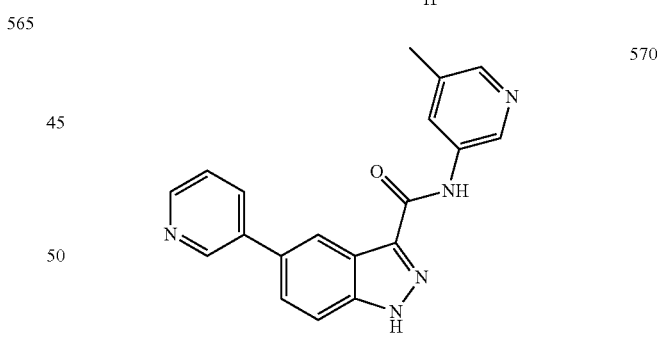 570
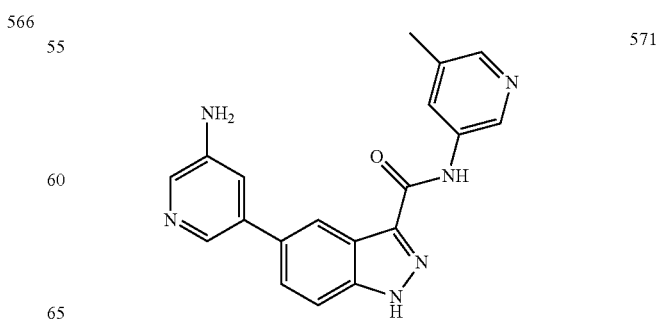 571

TABLE 1-continued
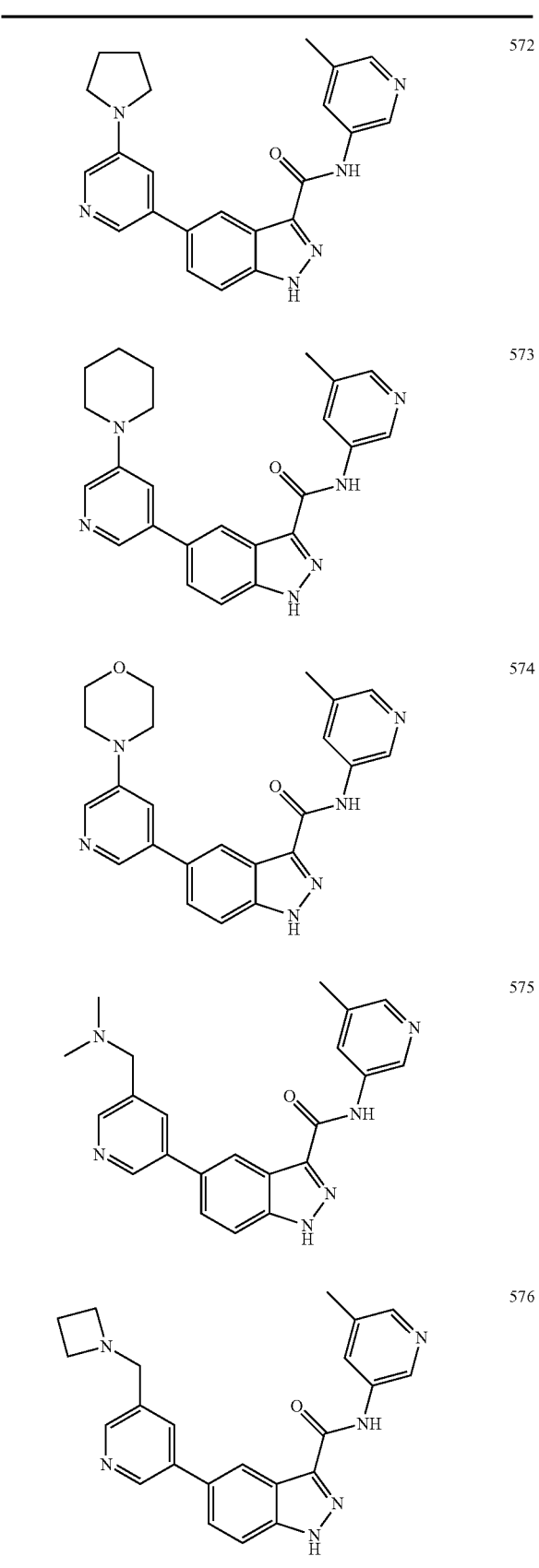
572
573
574
575
576
TABLE 1-continued
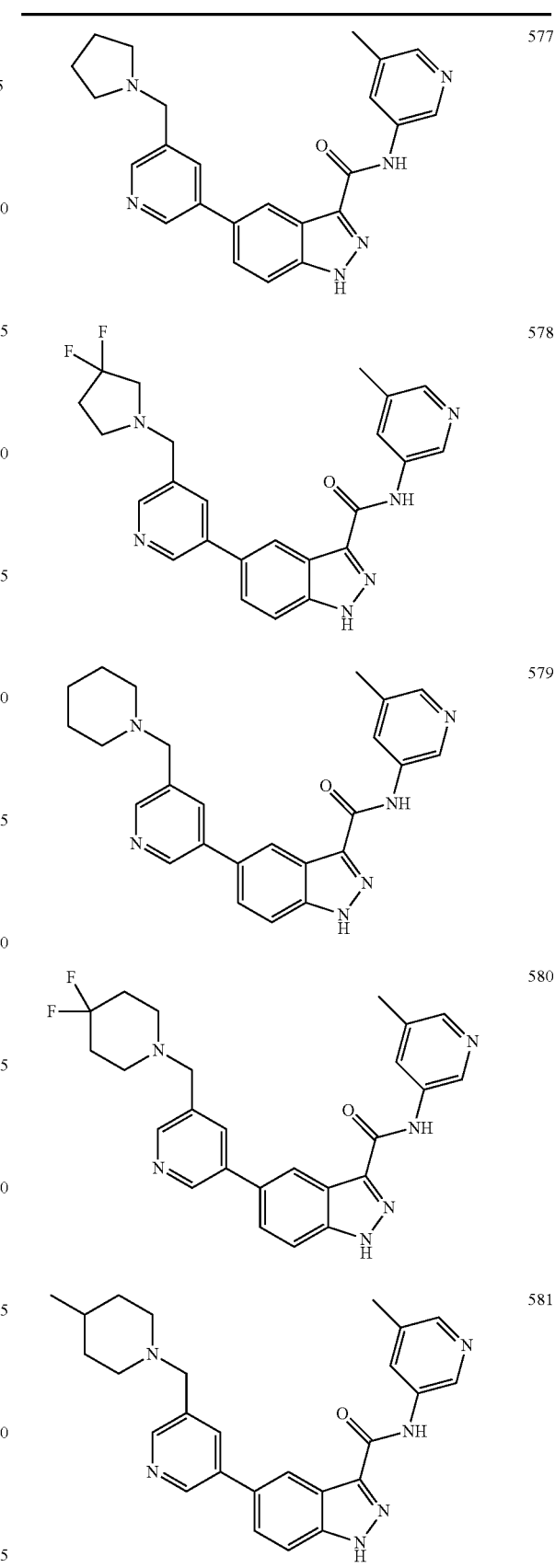
577
578
579
580
581

TABLE 1-continued
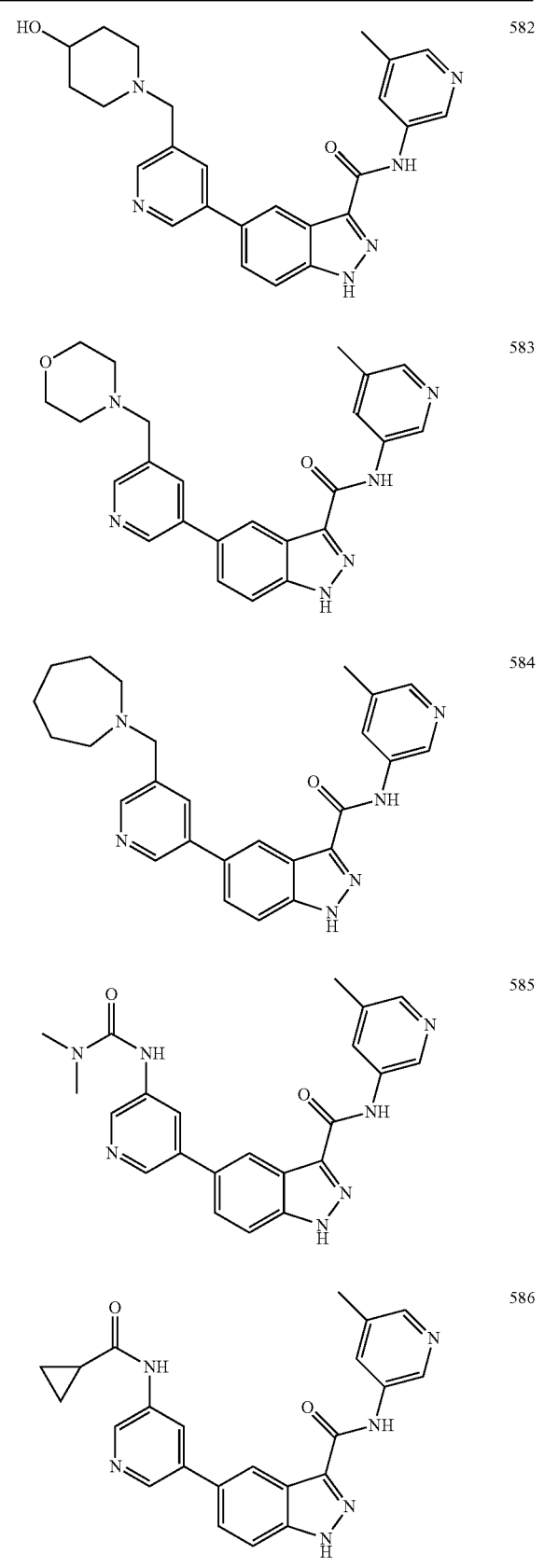
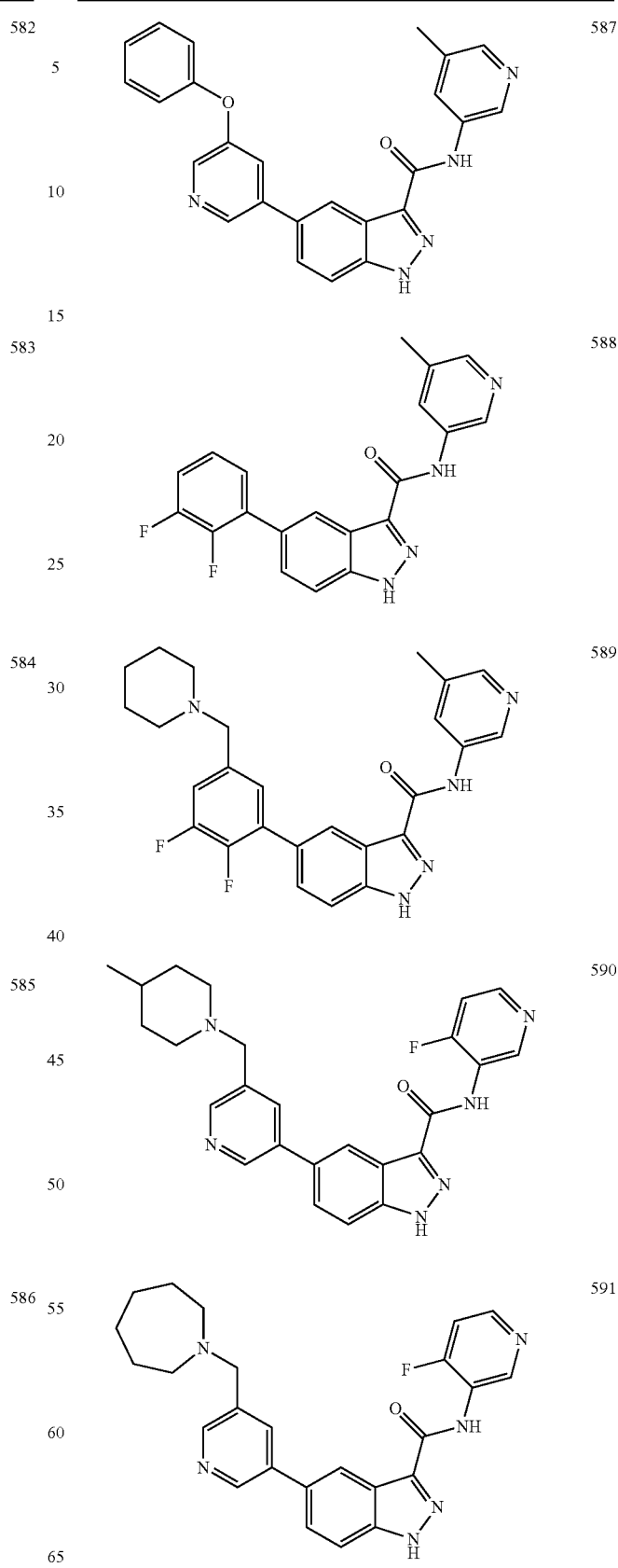

TABLE 1-continued
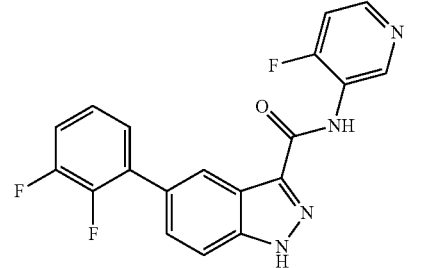 [SMILES: O=C(Nc1cnccc1F)c1n[nH]c2ccc(-c3cccc(F)c3F)cc12] 592
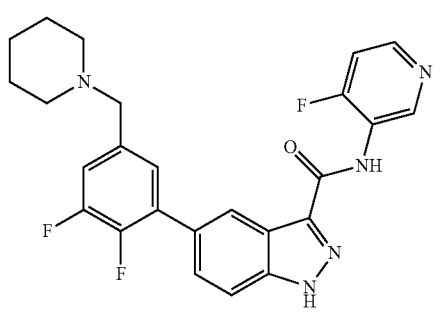 [SMILES: O=C(Nc1cnccc1F)c1n[nH]c2ccc(-c3cc(CN4CCCCC4)cc(F)c3F)cc12] 593
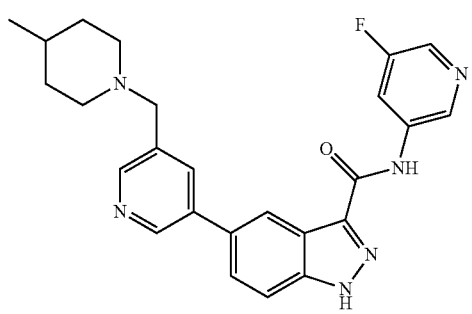 [SMILES: CC1CCN(Cc2cncc(-c3ccc4[nH]nc(C(=O)Nc5cncc(F)c5)c4c3)c2)CC1] 594
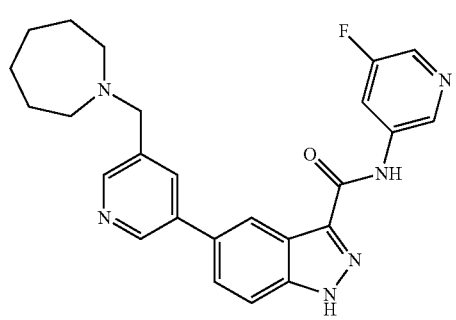 595
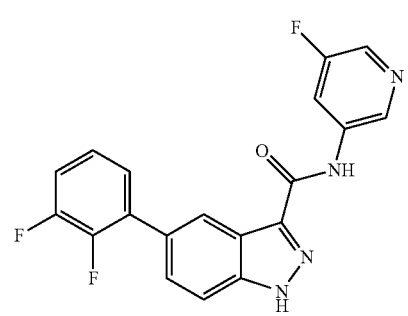 [SMILES: O=C(Nc1cncc(F)c1)c1n[nH]c2ccc(-c3cccc(F)c3F)cc12] 596
TABLE 1-continued
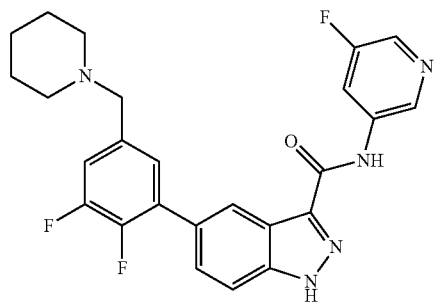 [SMILES: O=C(Nc1cncc(F)c1)c1n[nH]c2ccc(-c3cc(CN4CCCCC4)cc(F)c3F)cc12] 597
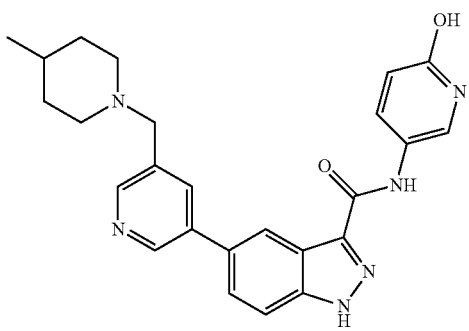 598
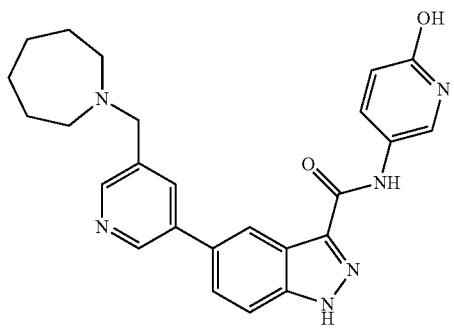 [SMILES: O=C(Nc1ccc(O)nc1)c1n[nH]c2ccc(-c3cncc(CN4CCCCCC4)c3)cc12] 599
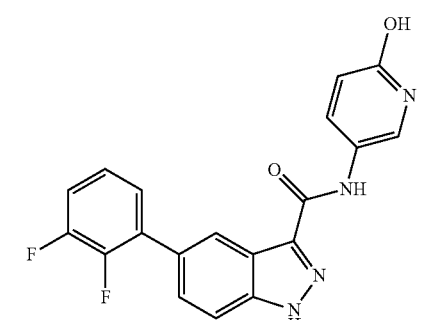 600
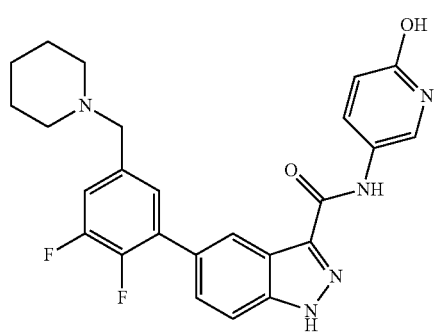 [SMILES: O=C(Nc1ccc(O)nc1)c1n[nH]c2ccc(-c3cc(CN4CCCCC4)cc(F)c3F)cc12] 601

TABLE 1-continued
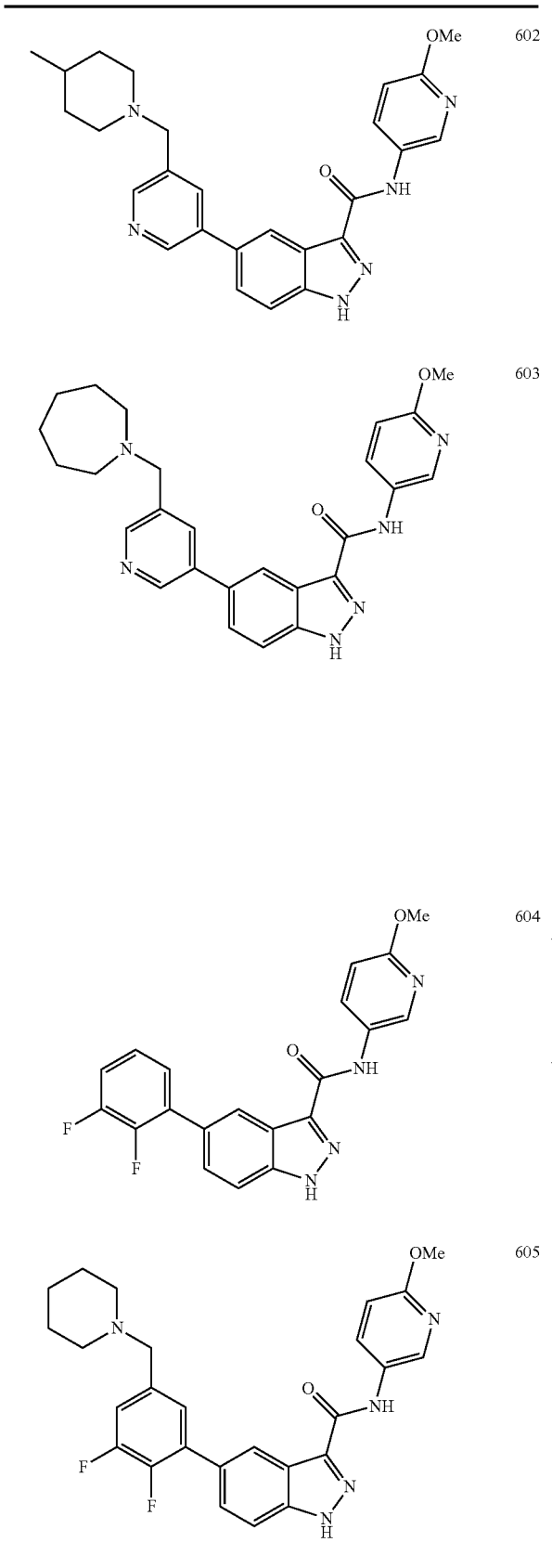
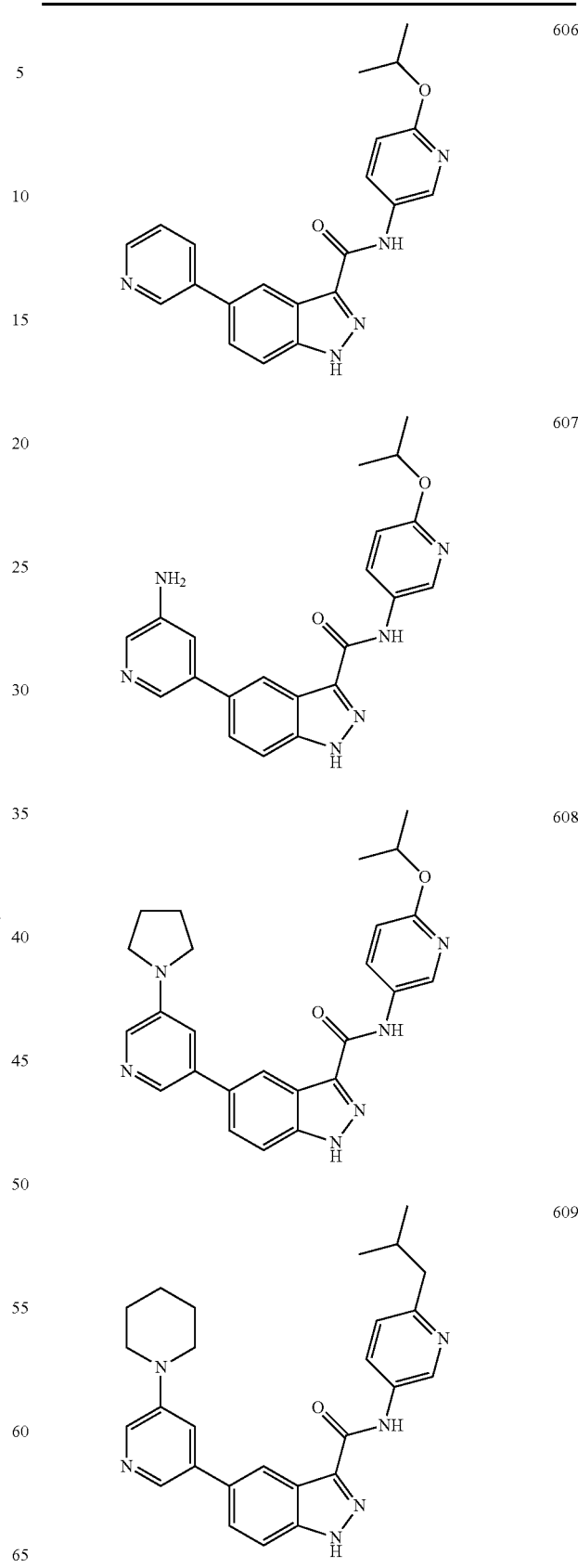

TABLE 1-continued
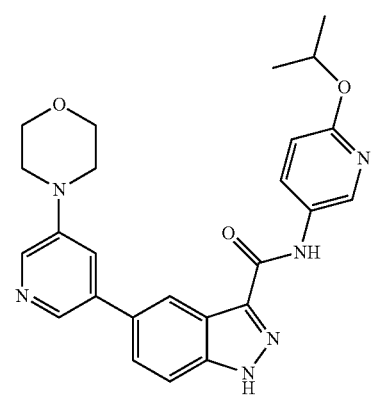 [SMILES: CC(C)Oc1ccc(NC(=O)c2n[nH]c3ccc(-c4cncc(N5CCOCC5)c4)cc23)cn1] 610
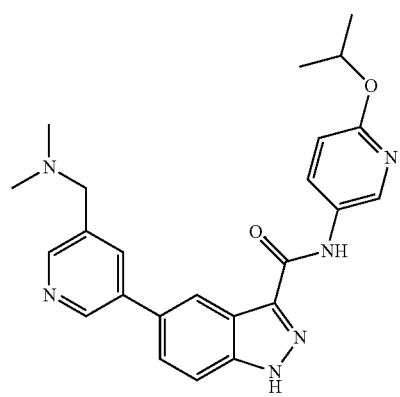 [SMILES: CC(C)Oc1ccc(NC(=O)c2n[nH]c3ccc(-c4cncc(CN(C)C)c4)cc23)cn1] 611
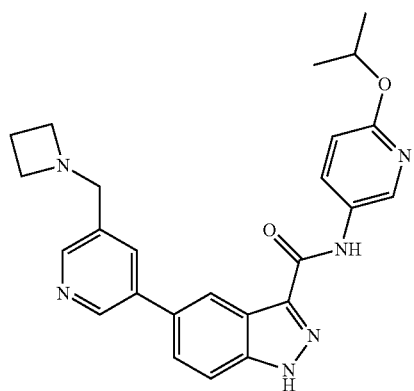 [SMILES: CC(C)Oc1ccc(NC(=O)c2n[nH]c3ccc(-c4cncc(CN5CCC5)c4)cc23)cn1] 612
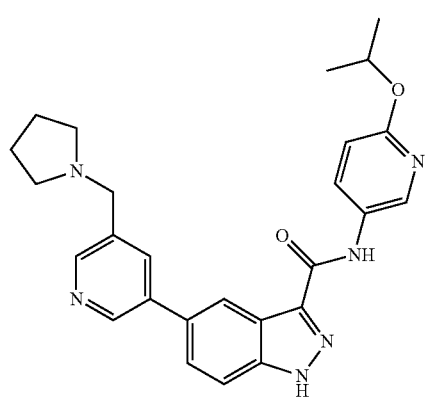 [SMILES: CC(C)Oc1ccc(NC(=O)c2n[nH]c3ccc(-c4cncc(CN5CCCC5)c4)cc23)cn1] 613
TABLE 1-continued
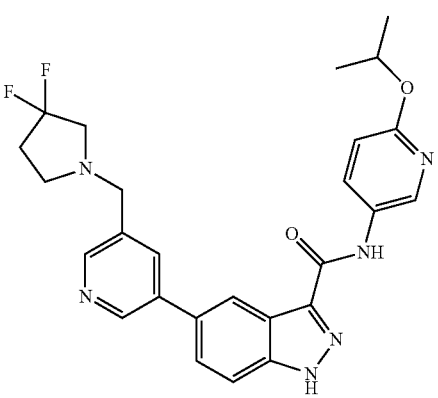 [SMILES: CC(C)Oc1ccc(NC(=O)c2n[nH]c3ccc(-c4cncc(CN5CCC(F)(F)C5)c4)cc23)cn1] 614
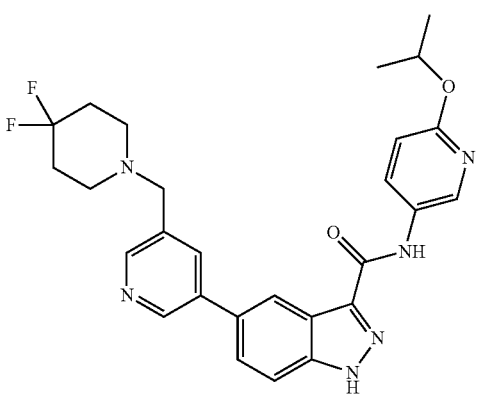 [SMILES: CC(C)Oc1ccc(NC(=O)c2n[nH]c3ccc(-c4cncc(CN5CCC(F)(F)CC5)c4)cc23)cn1] 615
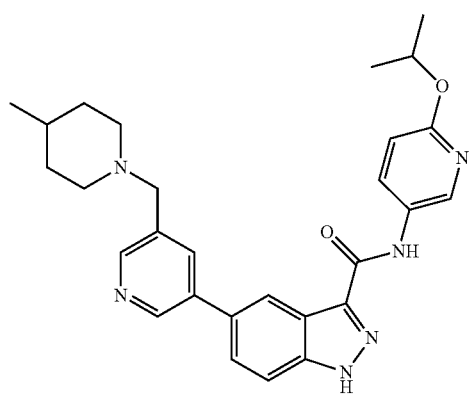 [SMILES: CC1CCN(Cc2cncc(-c3ccc4[nH]nc(C(=O)Nc5ccc(OC(C)C)nc5)c4c3)c2)CC1] 616
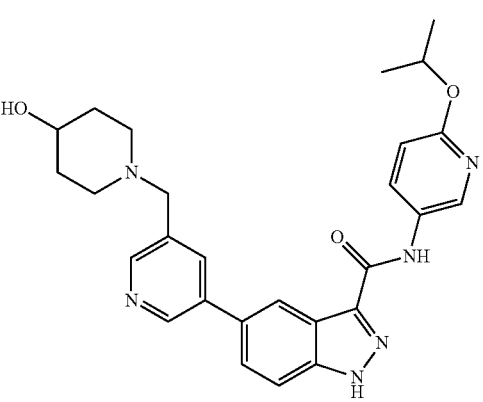 [SMILES: CC(C)Oc1ccc(NC(=O)c2n[nH]c3ccc(-c4cncc(CN5CCC(O)CC5)c4)cc23)cn1] 617

TABLE 1-continued
618
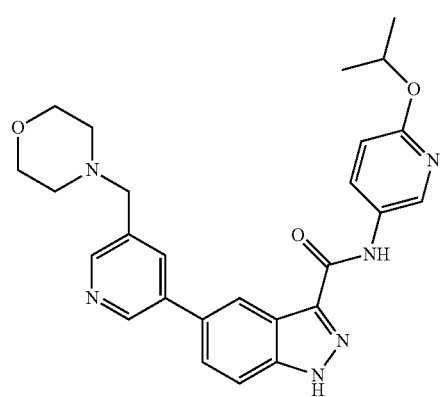 [SMILES: CC(C)Oc1ccc(NC(=O)c2n[nH]c3ccc(-c4cncc(CN5CCOCC5)c4)cc23)cn1]
619
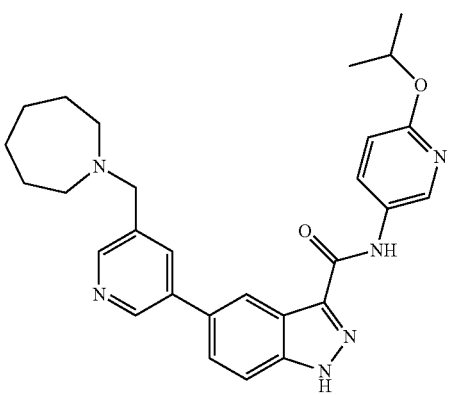
620
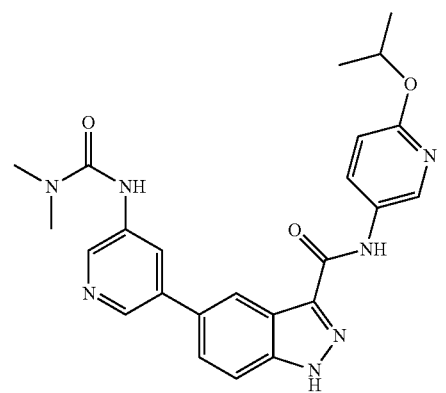 [SMILES: CC(C)Oc1ccc(NC(=O)c2n[nH]c3ccc(-c4cncc(NC(=O)N(C)C)c4)cc23)cn1]
621
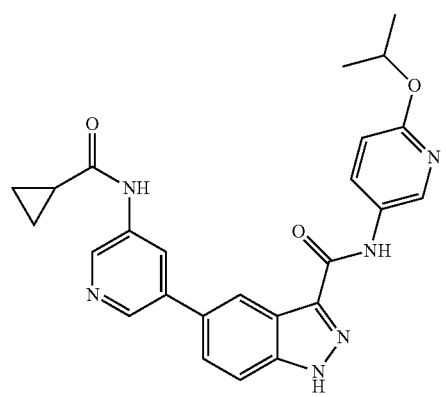 [SMILES: CC(C)Oc1ccc(NC(=O)c2n[nH]c3ccc(-c4cncc(NC(=O)C5CC5)c4)cc23)cn1]
TABLE 1-continued
622
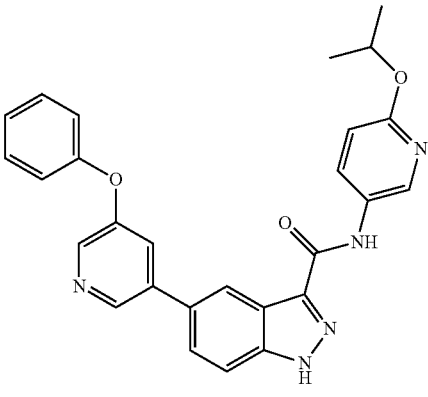 [SMILES: CC(C)Oc1ccc(NC(=O)c2n[nH]c3ccc(-c4cncc(Oc5ccccc5)c4)cc23)cn1]
623
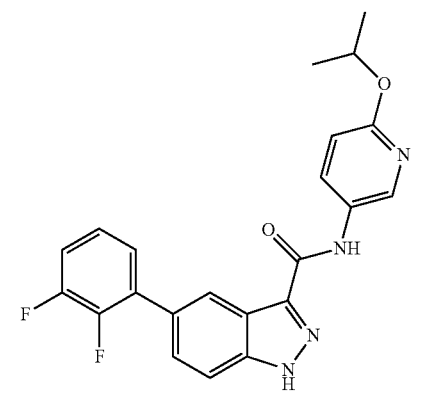 [SMILES: CC(C)Oc1ccc(NC(=O)c2n[nH]c3ccc(-c4cccc(F)c4F)cc23)cn1]
624
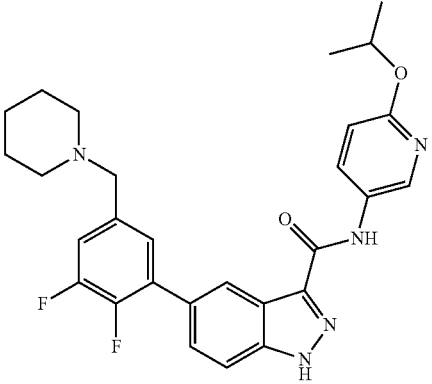 [SMILES: CC(C)Oc1ccc(NC(=O)c2n[nH]c3ccc(-c4cc(CN5CCCCC5)cc(F)c4F)cc23)cn1]
625
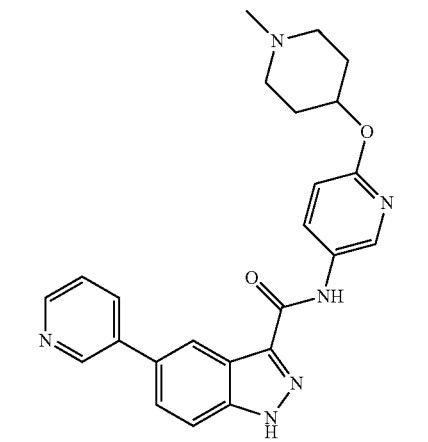 [SMILES: CN1CCC(Oc2ccc(NC(=O)c3n[nH]c4ccc(-c5cccnc5)cc34)cn2)CC1]

TABLE 1-continued
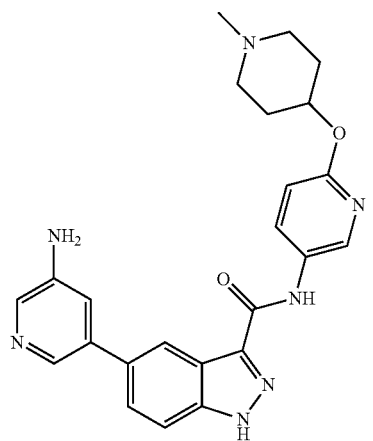 [SMILES: CN1CCC(Oc2ccc(NC(=O)c3n[nH]c4ccc(-c5cncc(N)c5)cc34)cn2)CC1]
626
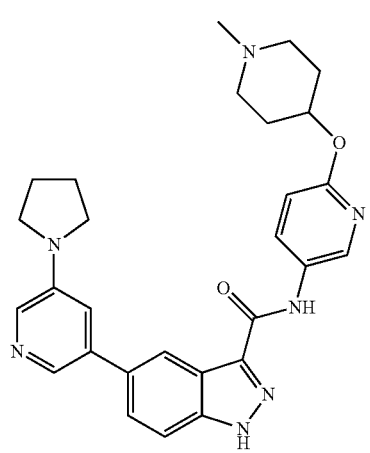 [SMILES: CN1CCC(Oc2ccc(NC(=O)c3n[nH]c4ccc(-c5cncc(N6CCCC6)c5)cc34)cn2)CC1]
627
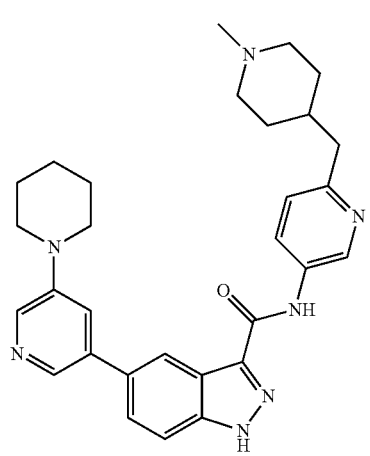 [SMILES: CN1CCC(Cc2ccc(NC(=O)c3n[nH]c4ccc(-c5cncc(N6CCCCC6)c5)cc34)cn2)CC1]
628
TABLE 1-continued
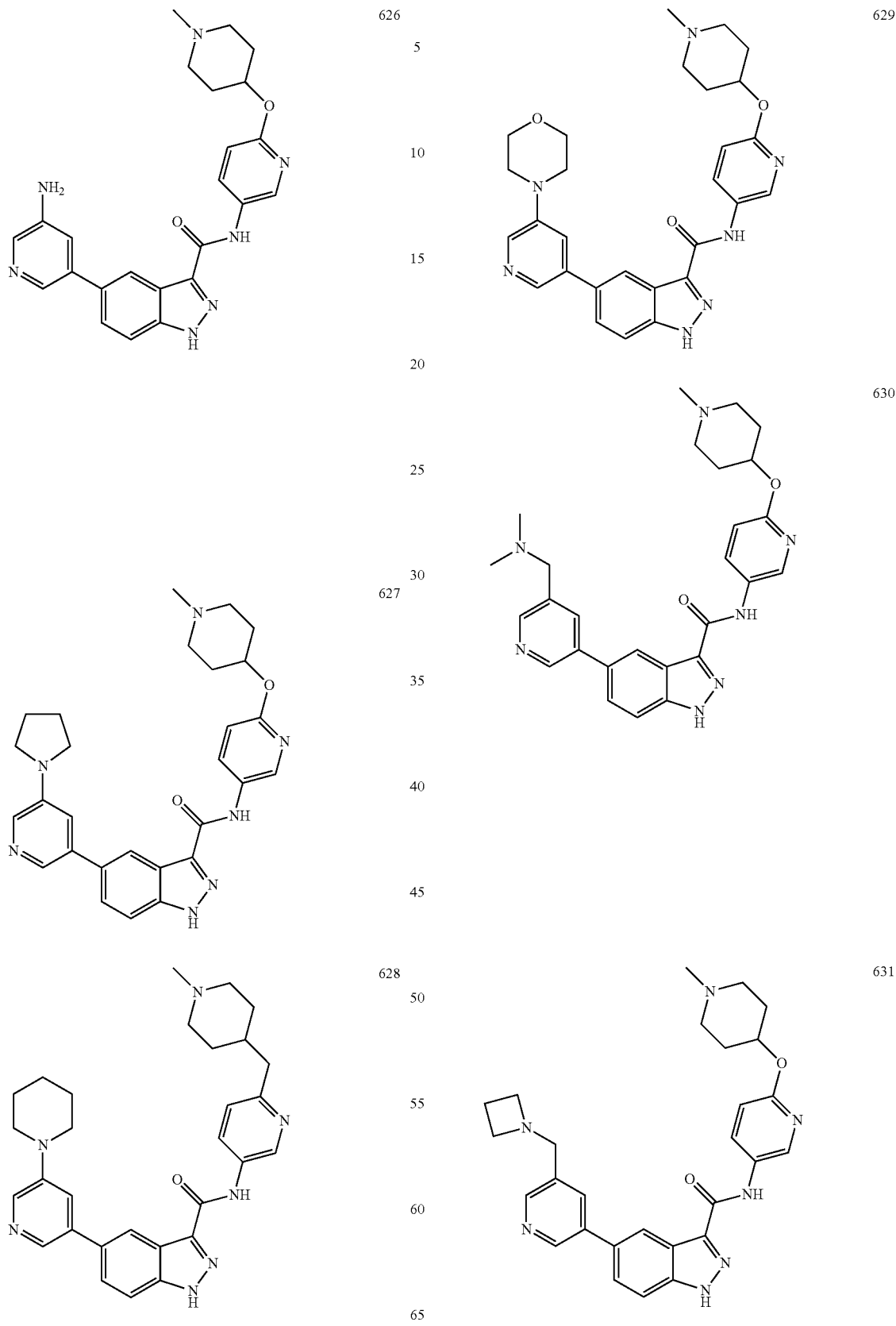

TABLE 1-continued
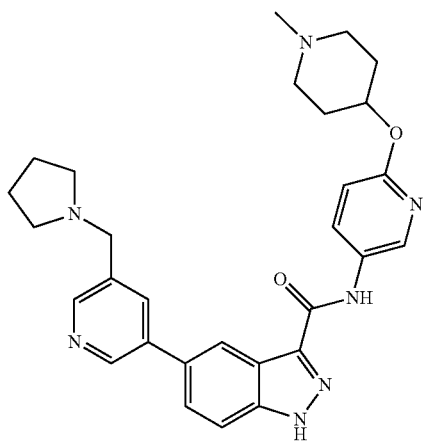 [SMILES: CN1CCC(Oc2ccc(NC(=O)c3n[nH]c4ccc(-c5cncc(CN6CCCC6)c5)cc34)cn2)CC1]
632
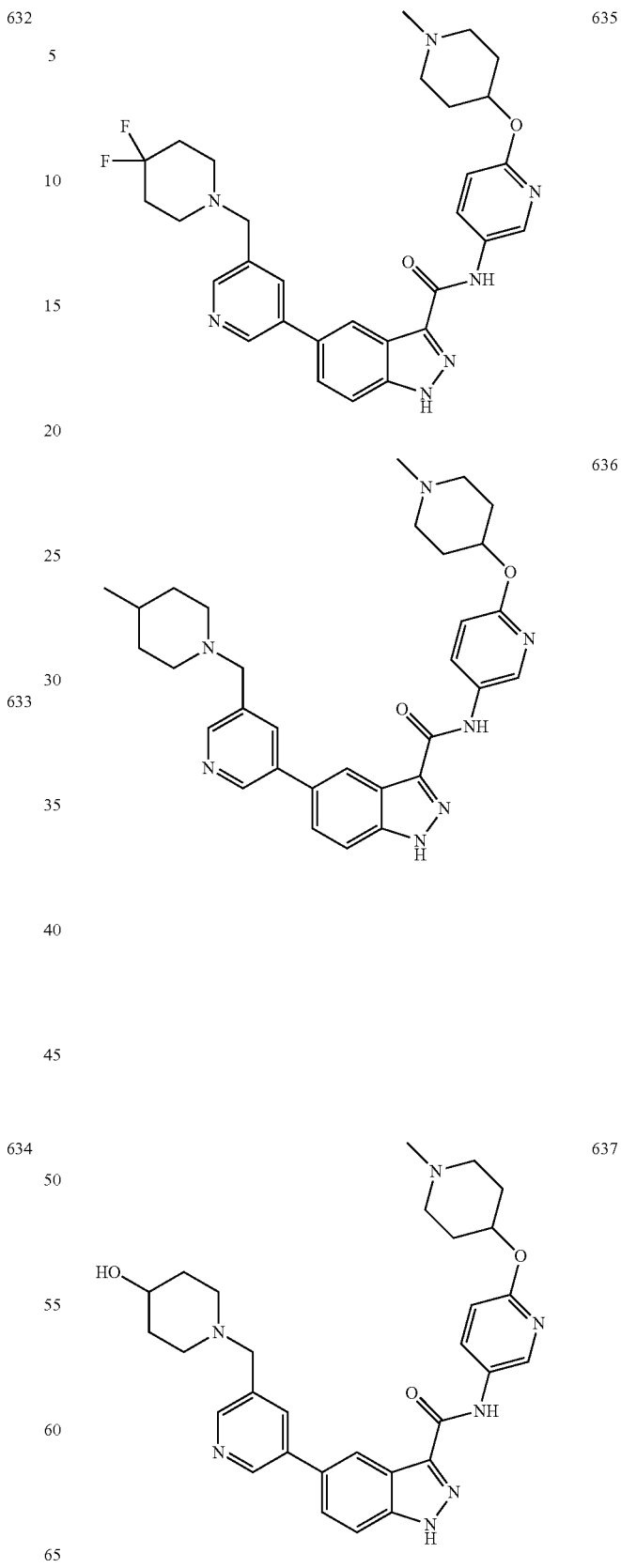

TABLE 1-continued
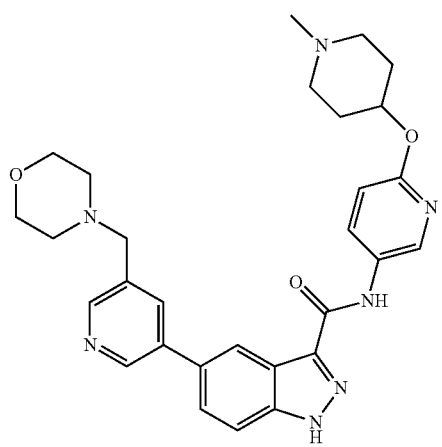 [SMILES: CN1CCC(Oc2ccc(NC(=O)c3n[nH]c4ccc(-c5cncc(CN6CCOCC6)c5)cc34)cn2)CC1]
638
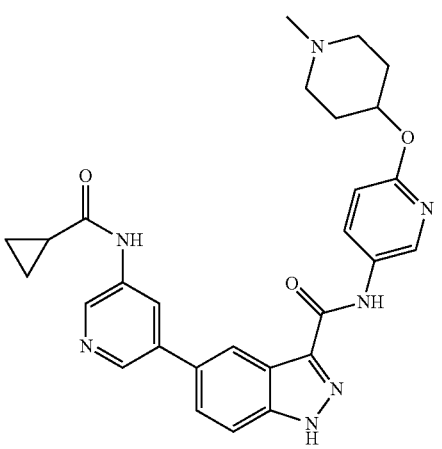
641
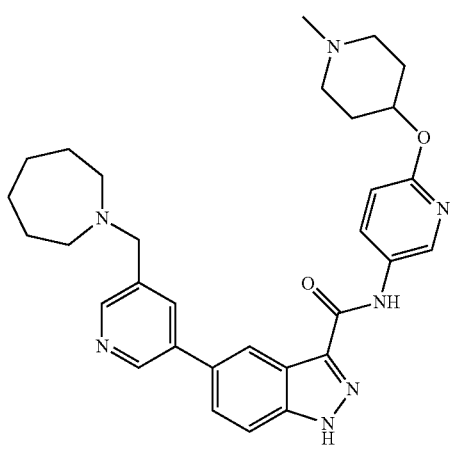 [SMILES: CN1CCC(Oc2ccc(NC(=O)c3n[nH]c4ccc(-c5cncc(CN6CCCCCC6)c5)cc34)cn2)CC1]
639
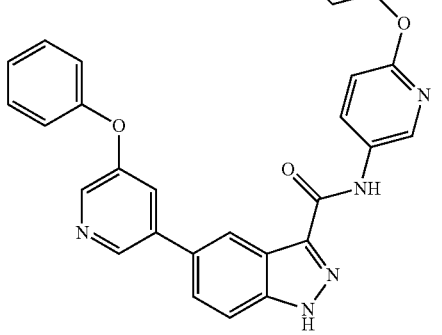
642
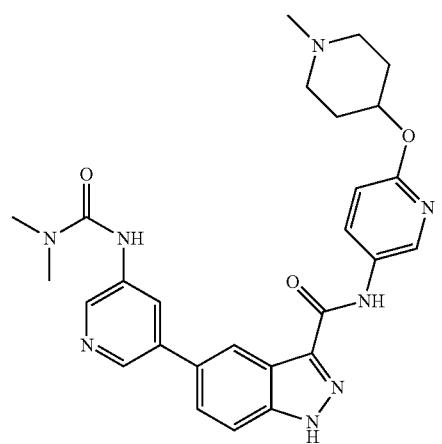 [SMILES: CN1CCC(Oc2ccc(NC(=O)c3n[nH]c4ccc(-c5cncc(NC(=O)N(C)C)c5)cc34)cn2)CC1]
640
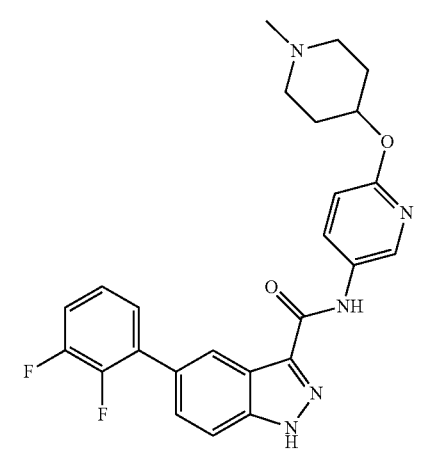 [SMILES: CN1CCC(Oc2ccc(NC(=O)c3n[nH]c4ccc(-c5cccc(F)c5F)cc34)cn2)CC1]
643

TABLE 1-continued
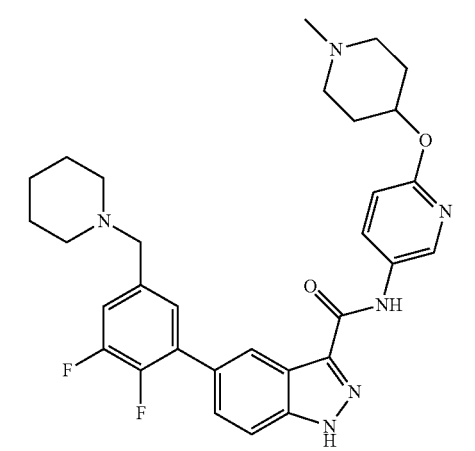 [SMILES: CN1CCC(Oc2ccc(NC(=O)c3n[nH]c4ccc(-c5cc(CN6CCCCC6)cc(F)c5F)cc34)cn2)CC1]
644
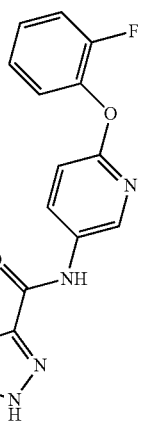
645
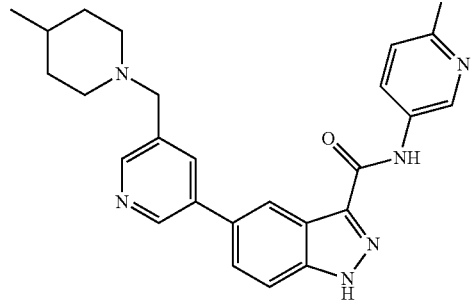
646
TABLE 1-continued
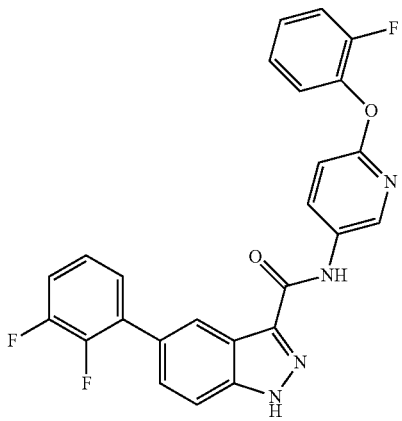 [SMILES: O=C(Nc1ccc(Oc2ccccc2F)nc1)c1n[nH]c2ccc(-c3cccc(F)c3F)cc12]
647
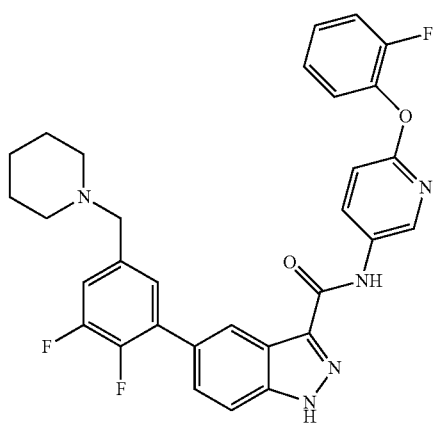 [SMILES: O=C(Nc1ccc(Oc2ccccc2F)nc1)c1n[nH]c2ccc(-c3cc(CN4CCCCC4)cc(F)c3F)cc12]
648
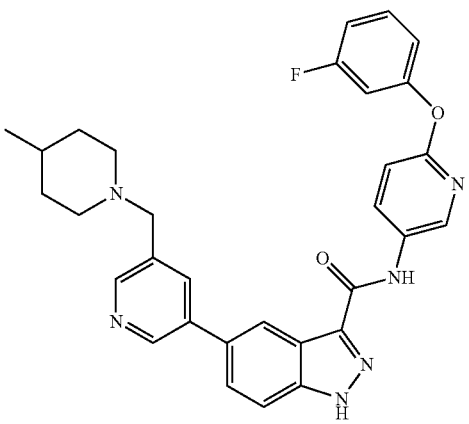 [SMILES: CC1CCN(Cc2cncc(-c3ccc4[nH]nc(C(=O)Nc5ccc(Oc6cccc(F)c6)nc5)c4c3)c2)CC1]
649

TABLE 1-continued
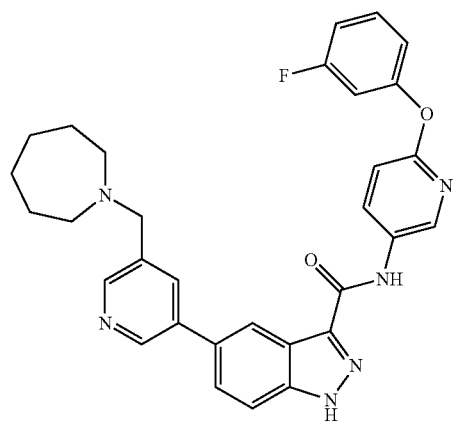 [SMILES: O=C(Nc1ccc(Oc2cccc(F)c2)nc1)c1n[nH]c2ccc(-c3cncc(CN4CCCCCC4)c3)cc12]
650
651
652
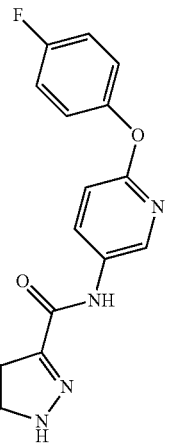
653
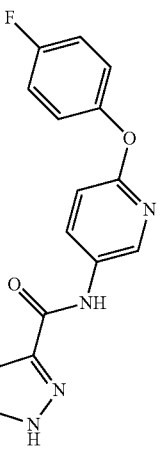
654
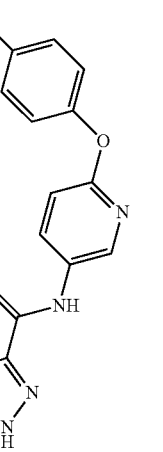
655

TABLE 1-continued
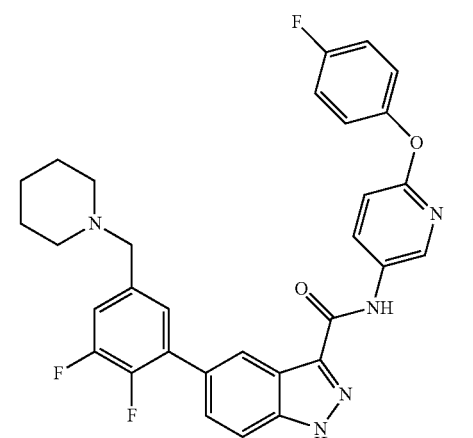
656
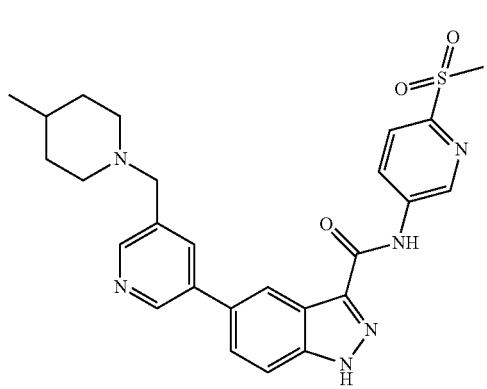
657
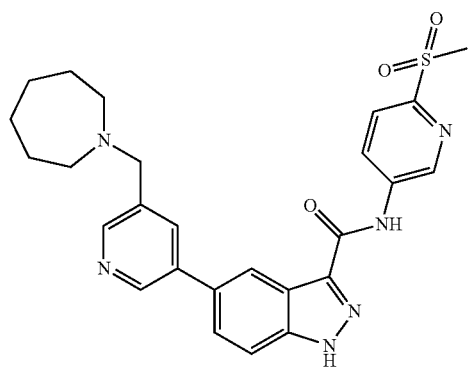 [SMILES: CS(=O)(=O)c1ccc(NC(=O)c2n[nH]c3ccc(-c4cncc(CN5CCCCCC5)c4)cc23)cn1]
658
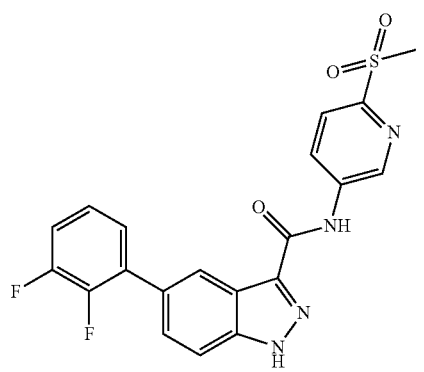 [SMILES: CS(=O)(=O)c1ccc(NC(=O)c2n[nH]c3ccc(-c4cccc(F)c4F)cc23)cn1]
659
TABLE 1-continued
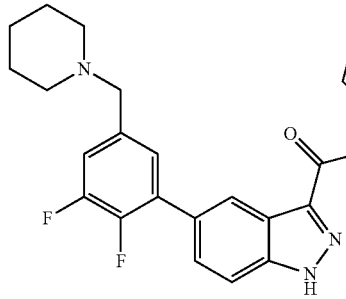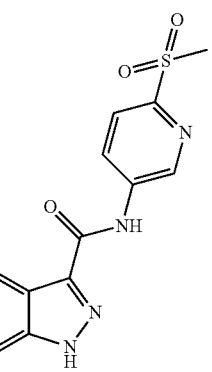
660
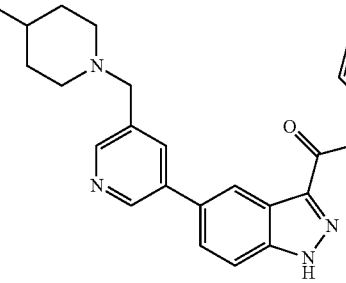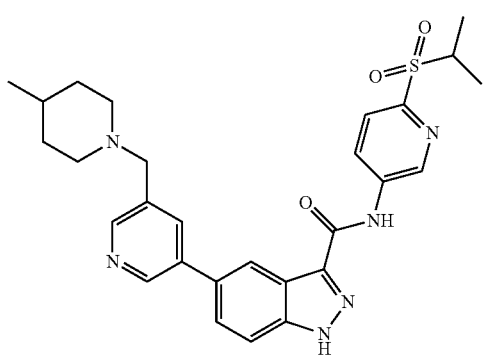 [SMILES: CC1CCN(Cc2cncc(-c3ccc4[nH]nc(C(=O)Nc5ccc(S(=O)(=O)C(C)C)nc5)c4c3)c2)CC1]
661
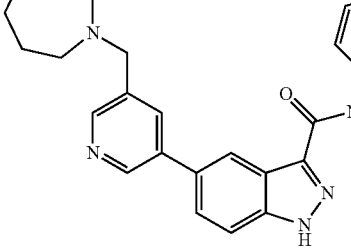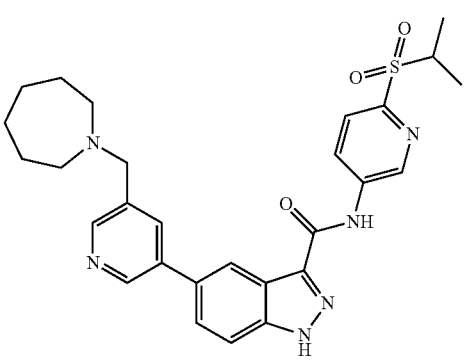 [SMILES: CC(C)S(=O)(=O)c1ccc(NC(=O)c2n[nH]c3ccc(-c4cncc(CN5CCCCCC5)c4)cc23)cn1]
662
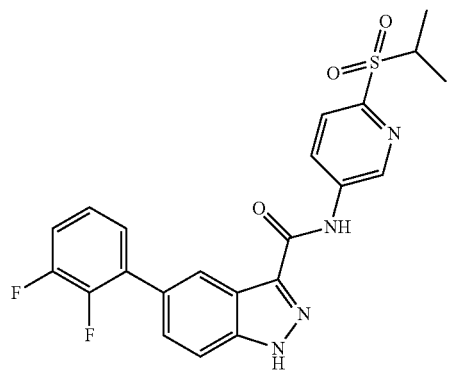 [SMILES: CC(C)S(=O)(=O)c1ccc(NC(=O)c2n[nH]c3ccc(-c4cccc(F)c4F)cc23)cn1]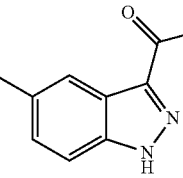
663

TABLE 1-continued
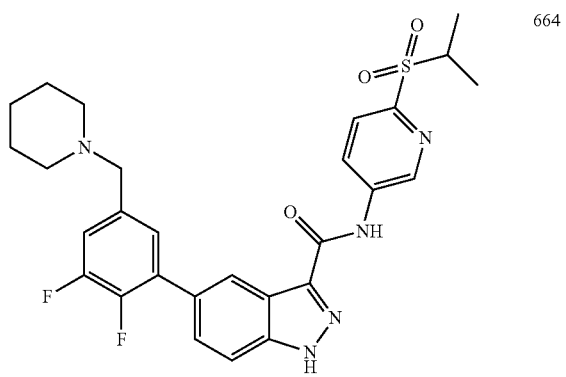
664
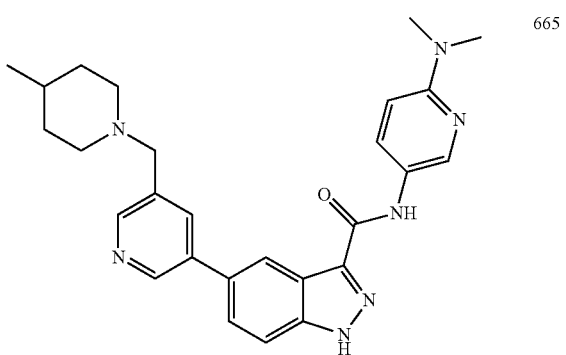
665
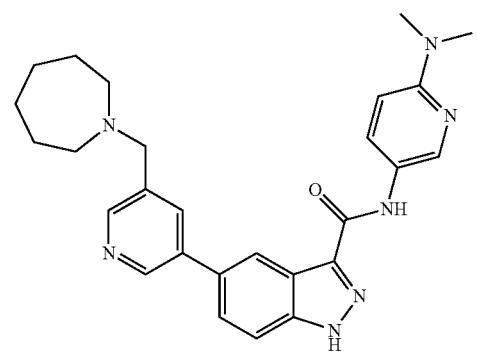 [SMILES: CN(C)c1ccc(NC(=O)c2n[nH]c3ccc(-c4cncc(CN5CCCCCC5)c4)cc23)cn1]
666
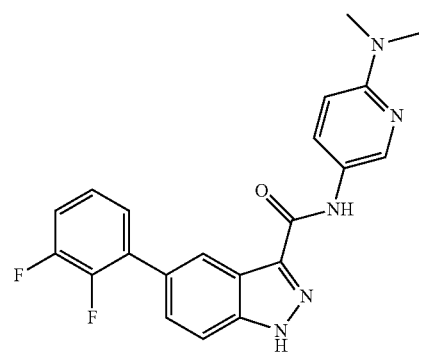 [SMILES: CN(C)c1ccc(NC(=O)c2n[nH]c3ccc(-c4cccc(F)c4F)cc23)cn1]
667
TABLE 1-continued
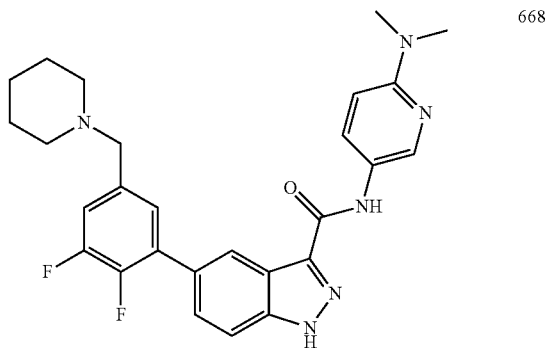
668
669
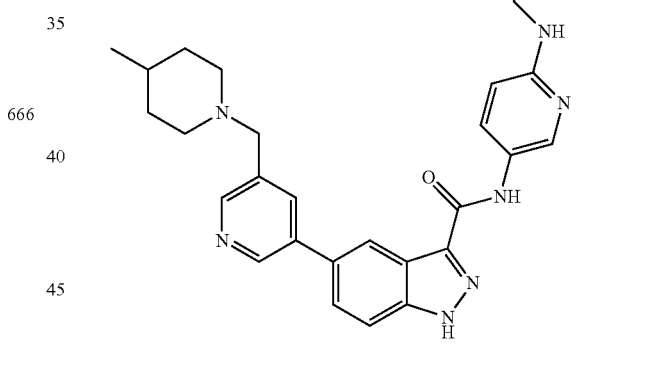
670

TABLE 1-continued
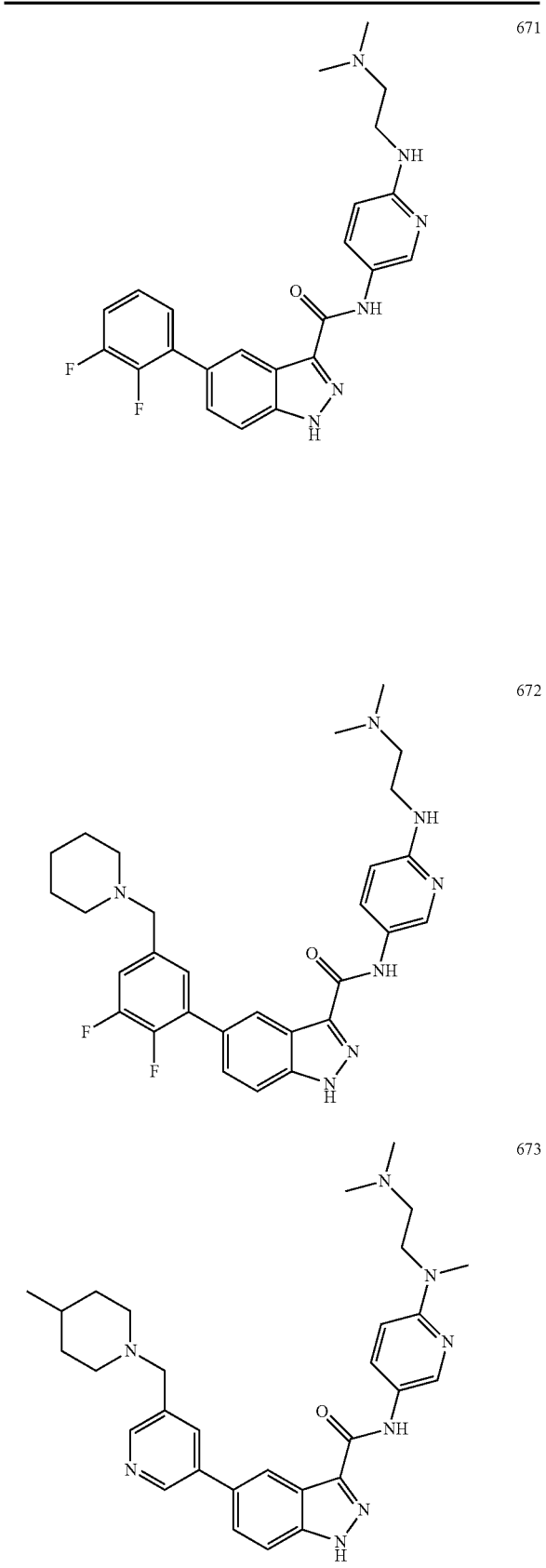
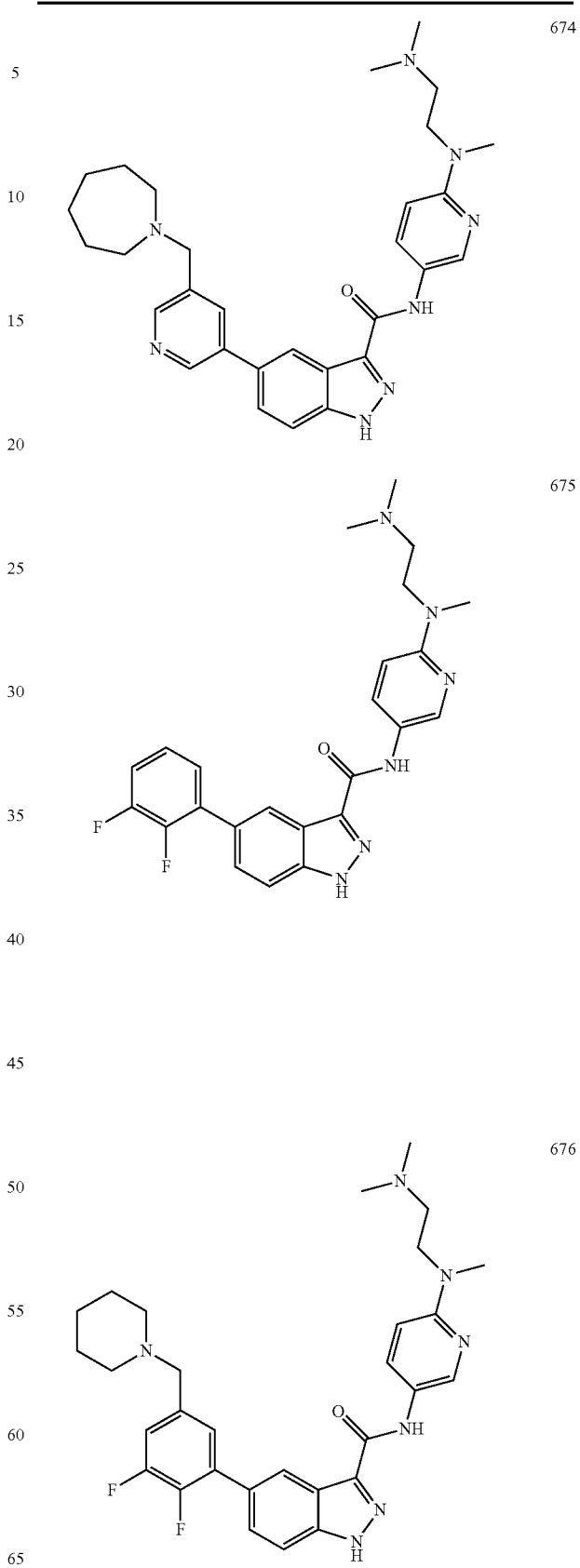

TABLE 1-continued
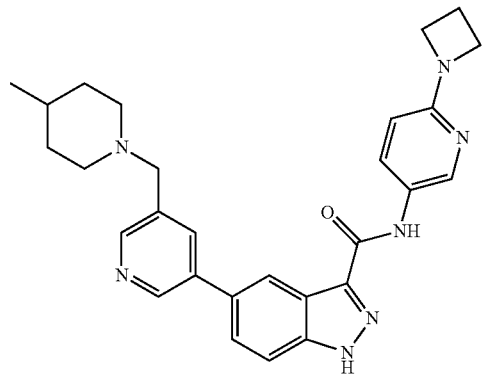 [SMILES: CC1CCN(Cc2cncc(-c3ccc4[nH]nc(C(=O)Nc5ccc(N6CCC6)nc5)c4c3)c2)CC1]
677
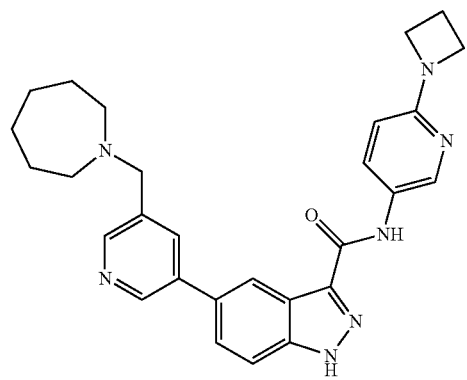 [SMILES: O=C(Nc1ccc(N2CCC2)nc1)c1n[nH]c2ccc(-c3cncc(CN4CCCCCC4)c3)cc12]
678
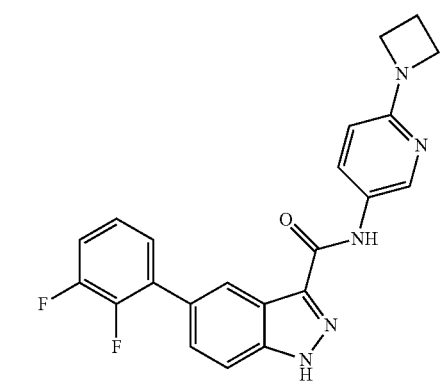 [SMILES: O=C(Nc1ccc(N2CCC2)nc1)c1n[nH]c2ccc(-c3cccc(F)c3F)cc12]
679
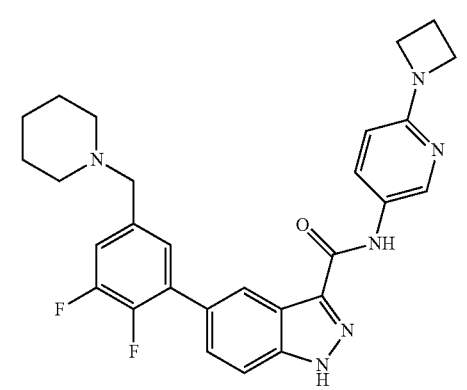 [SMILES: O=C(Nc1ccc(N2CCC2)nc1)c1n[nH]c2ccc(-c3cc(CN4CCCCC4)cc(F)c3F)cc12]
680
TABLE 1-continued
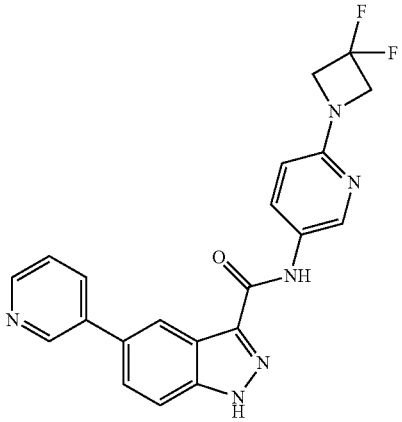 [SMILES: O=C(Nc1ccc(N2CC(F)(F)C2)nc1)c1n[nH]c2ccc(-c3cccnc3)cc12]
681
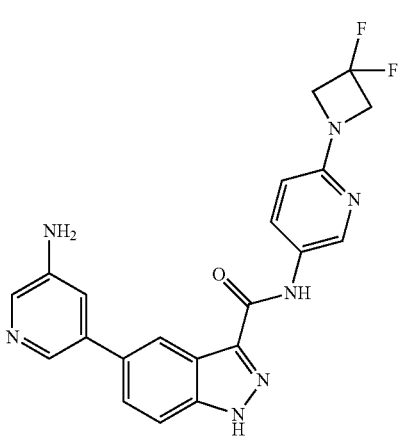 [SMILES: Nc1cncc(-c2ccc3[nH]nc(C(=O)Nc4ccc(N5CC(F)(F)C5)nc4)c3c2)c1]
682
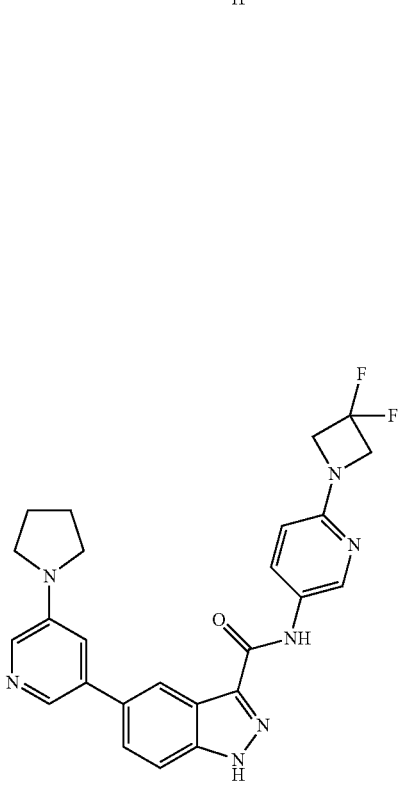
683

TABLE 1-continued
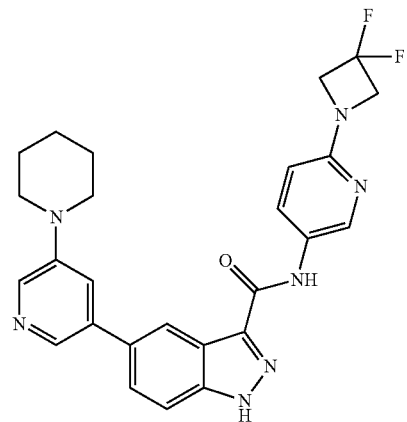 [SMILES: O=C(Nc1ccc(N2CC(F)(F)C2)nc1)c1n[nH]c2ccc(-c3cncc(N4CCCCC4)c3)cc12]
684
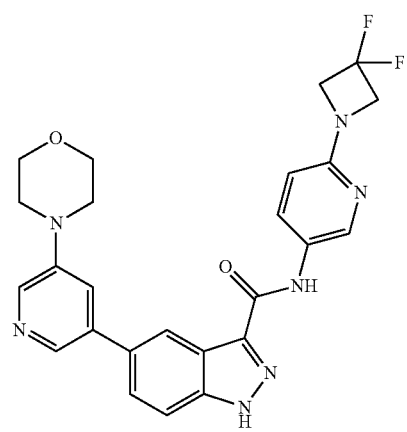 [SMILES: O=C(Nc1ccc(N2CC(F)(F)C2)nc1)c1n[nH]c2ccc(-c3cncc(N4CCOCC4)c3)cc12]
685
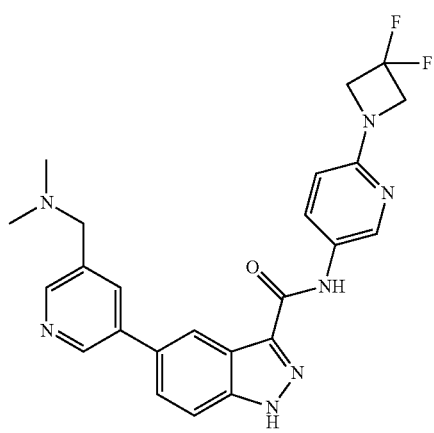 [SMILES: CN(C)Cc1cncc(-c2ccc3[nH]nc(C(=O)Nc4ccc(N5CC(F)(F)C5)nc4)c3c2)c1]
686
TABLE 1-continued
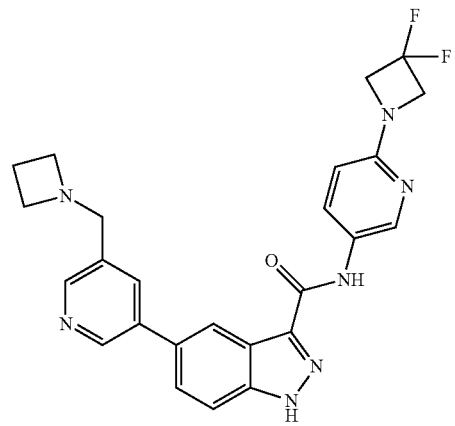 [SMILES: O=C(Nc1ccc(N2CC(F)(F)C2)nc1)c1n[nH]c2ccc(-c3cncc(CN4CCC4)c3)cc12]
687
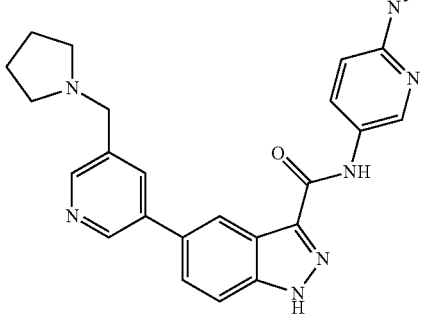
688
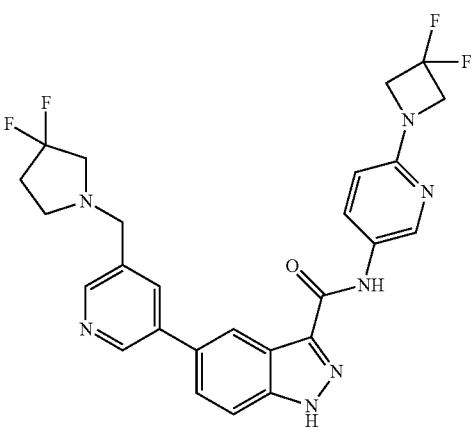 [SMILES: O=C(Nc1ccc(N2CC(F)(F)C2)nc1)c1n[nH]c2ccc(-c3cncc(CN4CCC(F)(F)C4)c3)cc12]
689

TABLE 1-continued
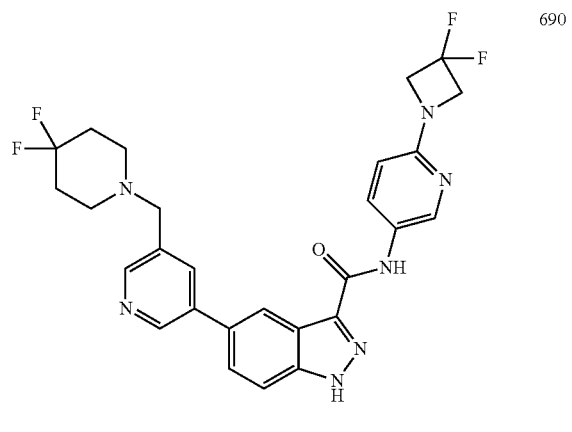 690
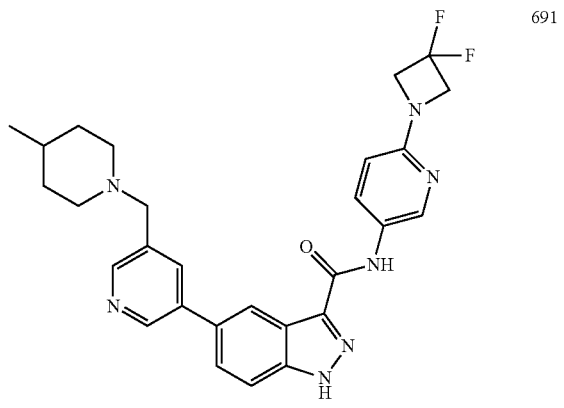 691
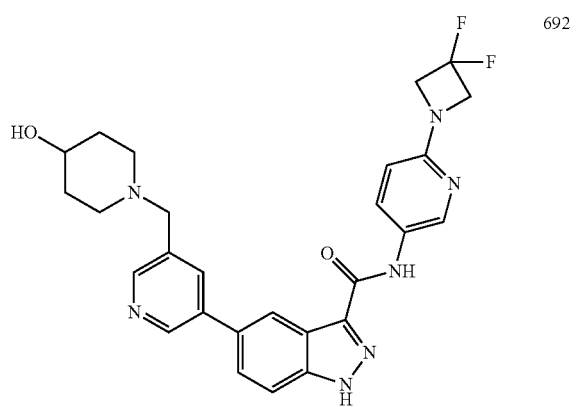 692
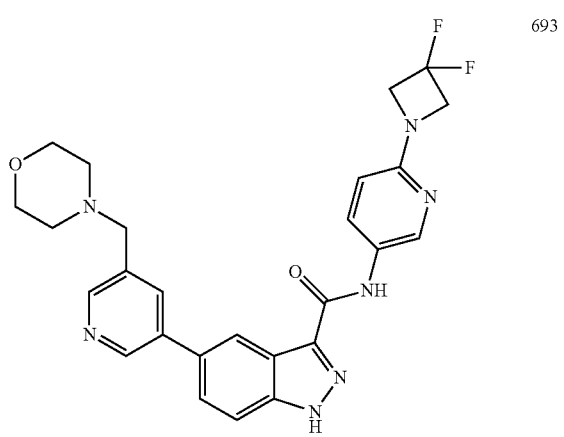 693
TABLE 1-continued
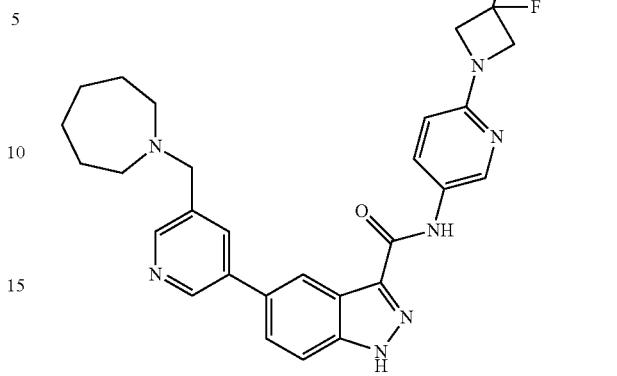 694
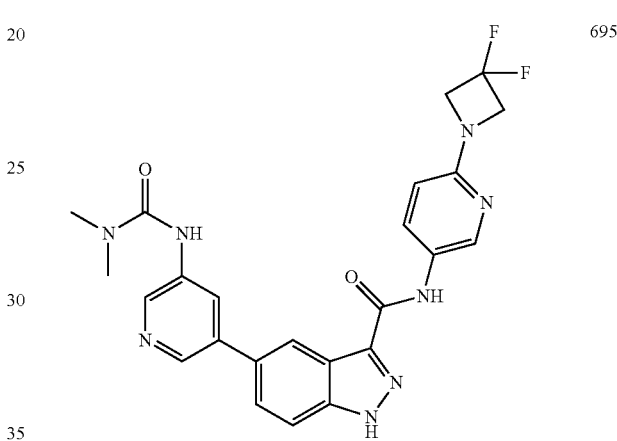 695
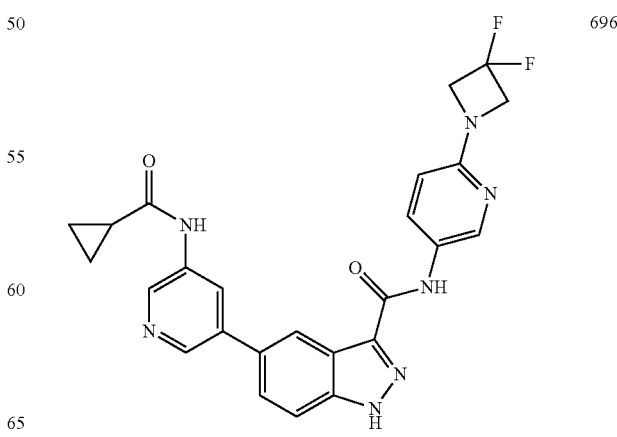 696

TABLE 1-continued
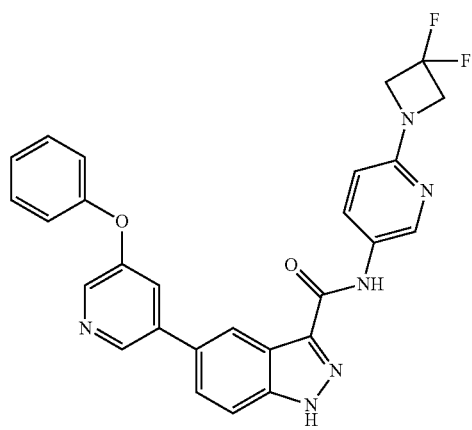 [SMILES: O=C(Nc1ccc(N2CC(F)(F)C2)nc1)c1n[nH]c2ccc(-c3cncc(Oc4ccccc4)c3)cc12] 697
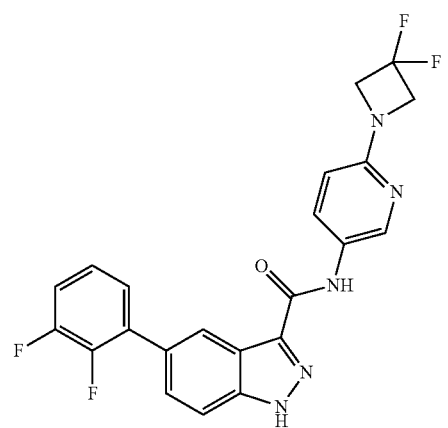 [SMILES: O=C(Nc1ccc(N2CC(F)(F)C2)nc1)c1n[nH]c2ccc(-c3cccc(F)c3F)cc12] 698
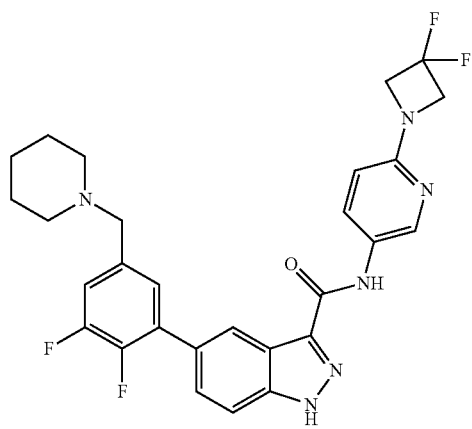 [SMILES: O=C(Nc1ccc(N2CC(F)(F)C2)nc1)c1n[nH]c2ccc(-c3cc(CN4CCCCC4)cc(F)c3F)cc12] 699
TABLE 1-continued
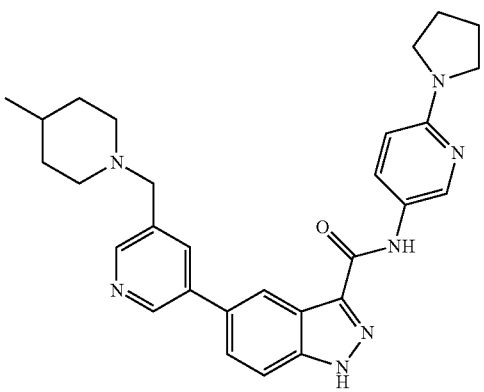 [SMILES: CC1CCN(Cc2cncc(-c3ccc4[nH]nc(C(=O)Nc5ccc(N6CCCC6)nc5)c4c3)c2)CC1] 700
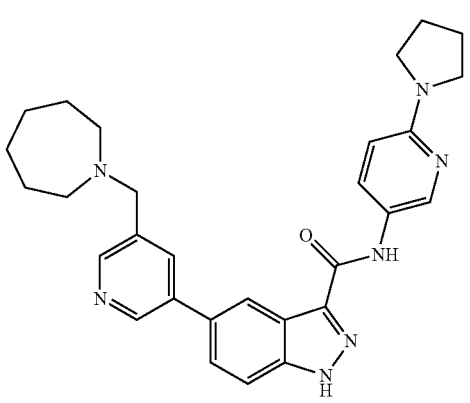 [SMILES: O=C(Nc1ccc(N2CCCC2)nc1)c1n[nH]c2ccc(-c3cncc(CN4CCCCCC4)c3)cc12] 701
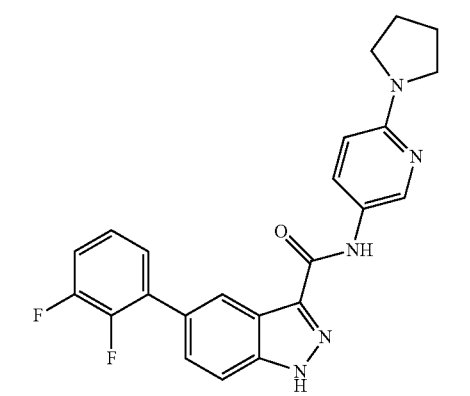 [SMILES: O=C(Nc1ccc(N2CCCC2)nc1)c1n[nH]c2ccc(-c3cccc(F)c3F)cc12] 702
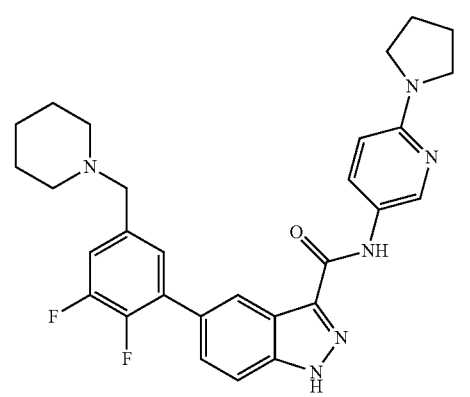 [SMILES: O=C(Nc1ccc(N2CCCC2)nc1)c1n[nH]c2ccc(-c3cc(CN4CCCCC4)cc(F)c3F)cc12] 703

TABLE 1-continued
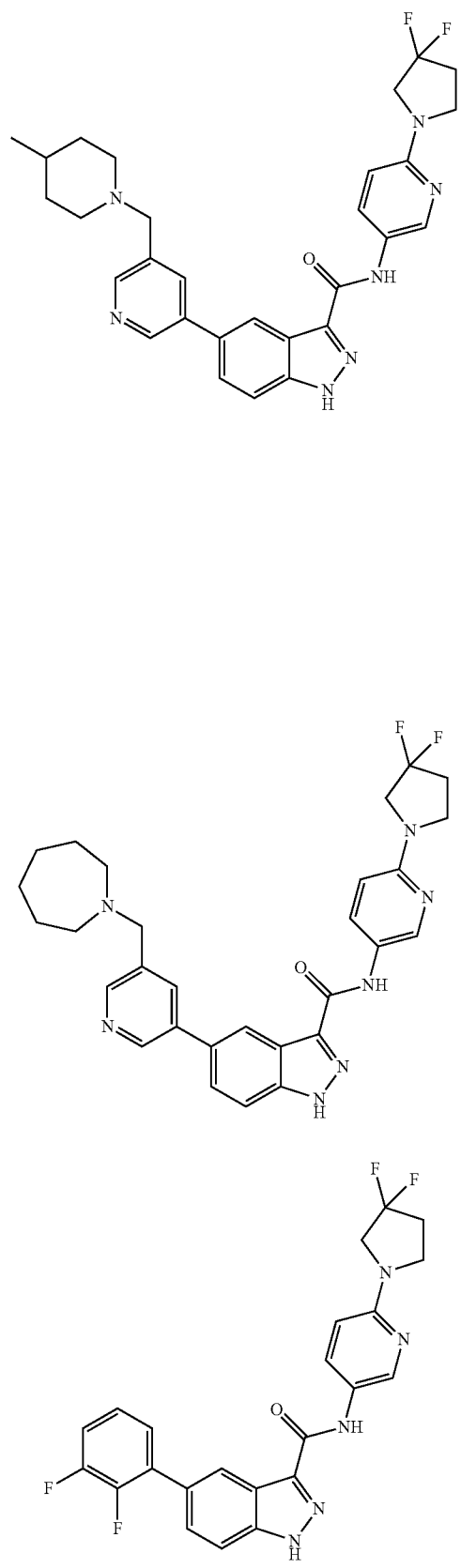
TABLE 1-continued
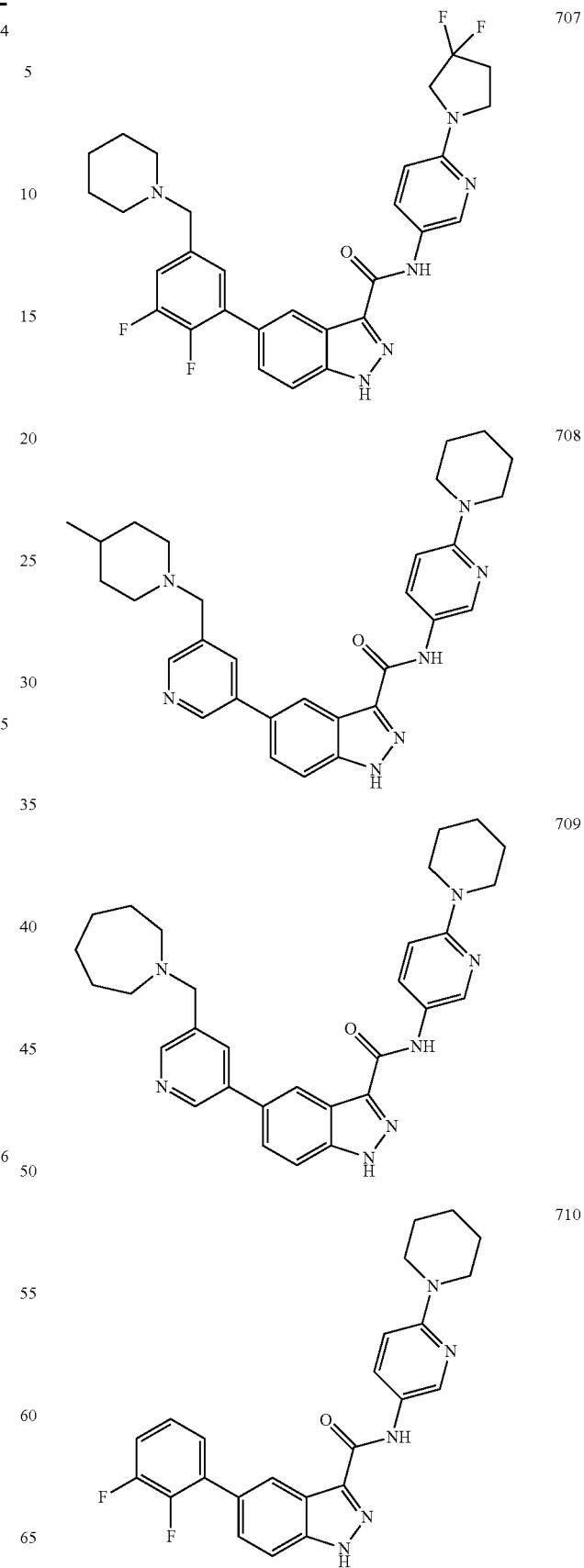

TABLE 1-continued
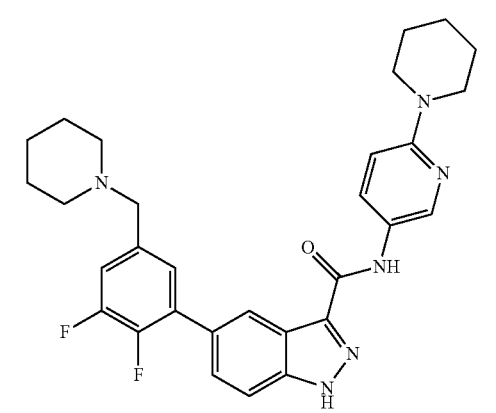 [SMILES: O=C(Nc1ccc(N2CCCCC2)nc1)c1n[nH]c2ccc(-c3cc(CN4CCCCC4)cc(F)c3F)cc12]
711
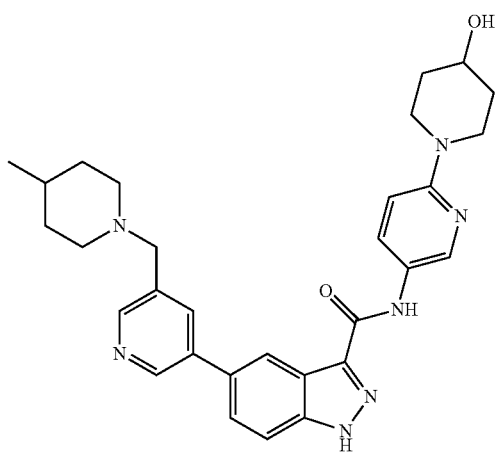 [SMILES: CC1CCN(Cc2cncc(-c3ccc4[nH]nc(C(=O)Nc5ccc(N6CCC(O)CC6)nc5)c4c3)c2)CC1]
712
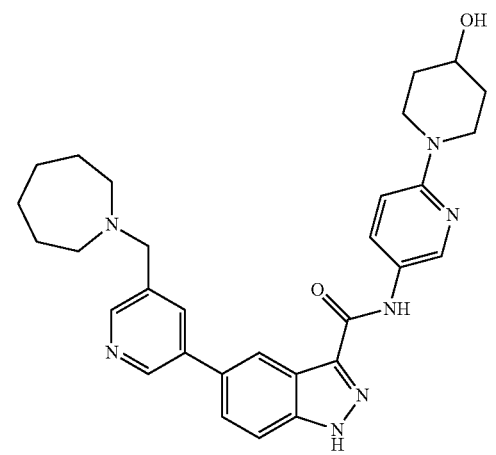 [SMILES: O=C(Nc1ccc(N2CCC(O)CC2)nc1)c1n[nH]c2ccc(-c3cncc(CN4CCCCCC4)c3)cc12]
713
TABLE 1-continued
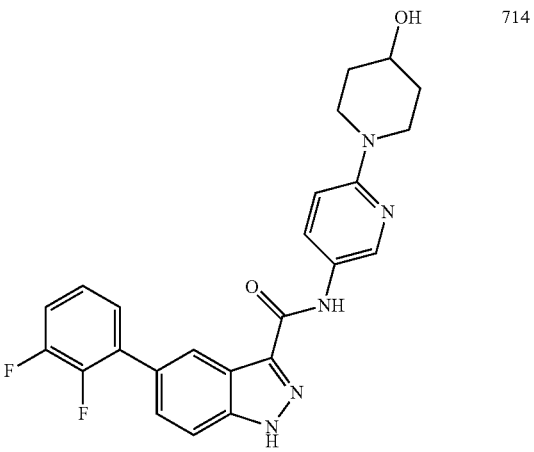
714
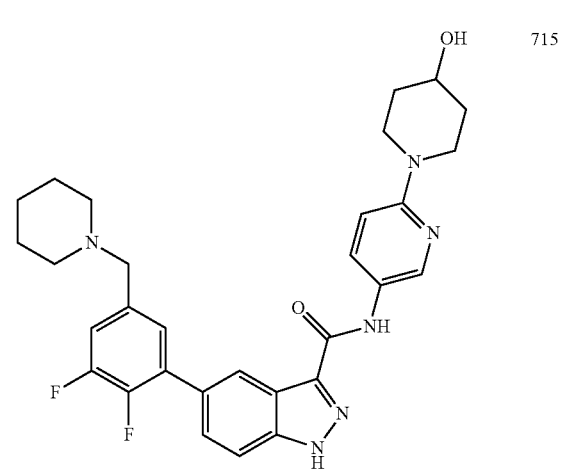
715
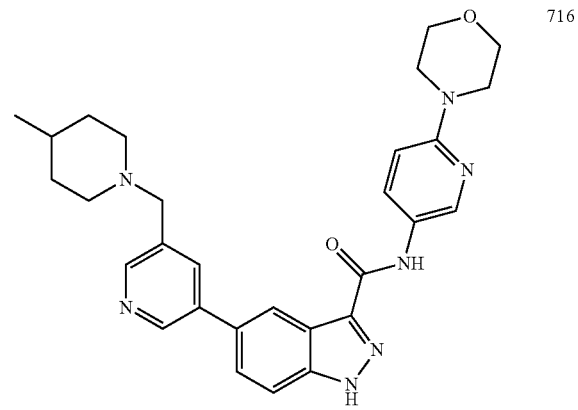
716

241
TABLE 1-continued
242
TABLE 1-continued
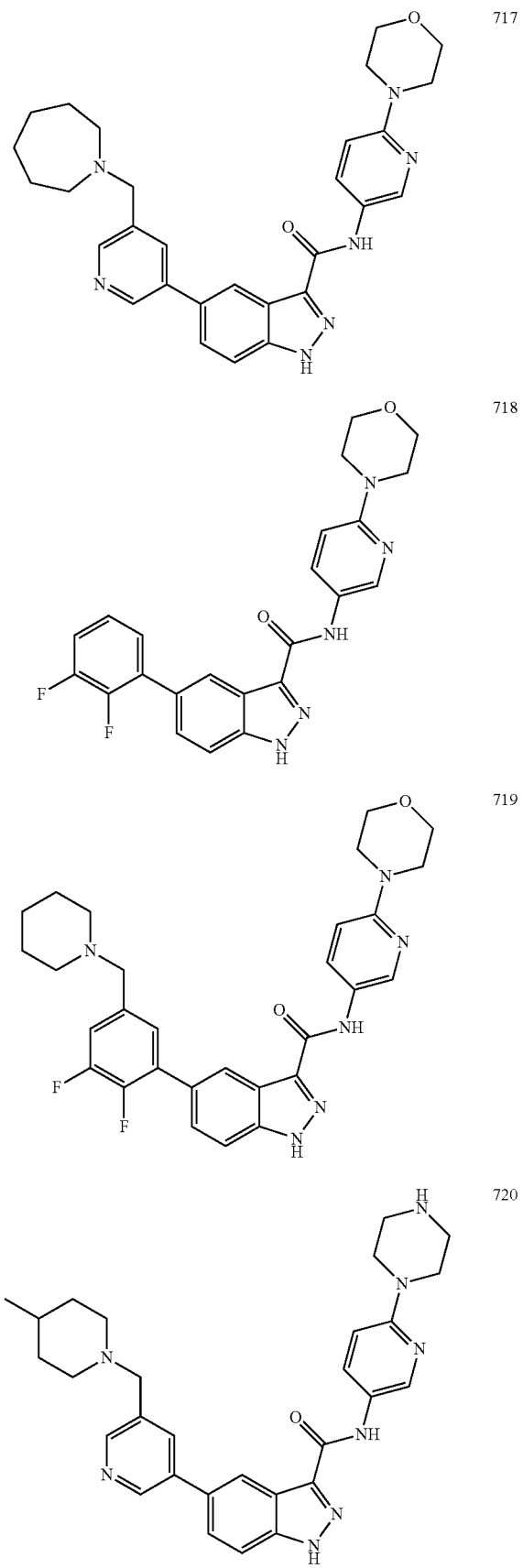
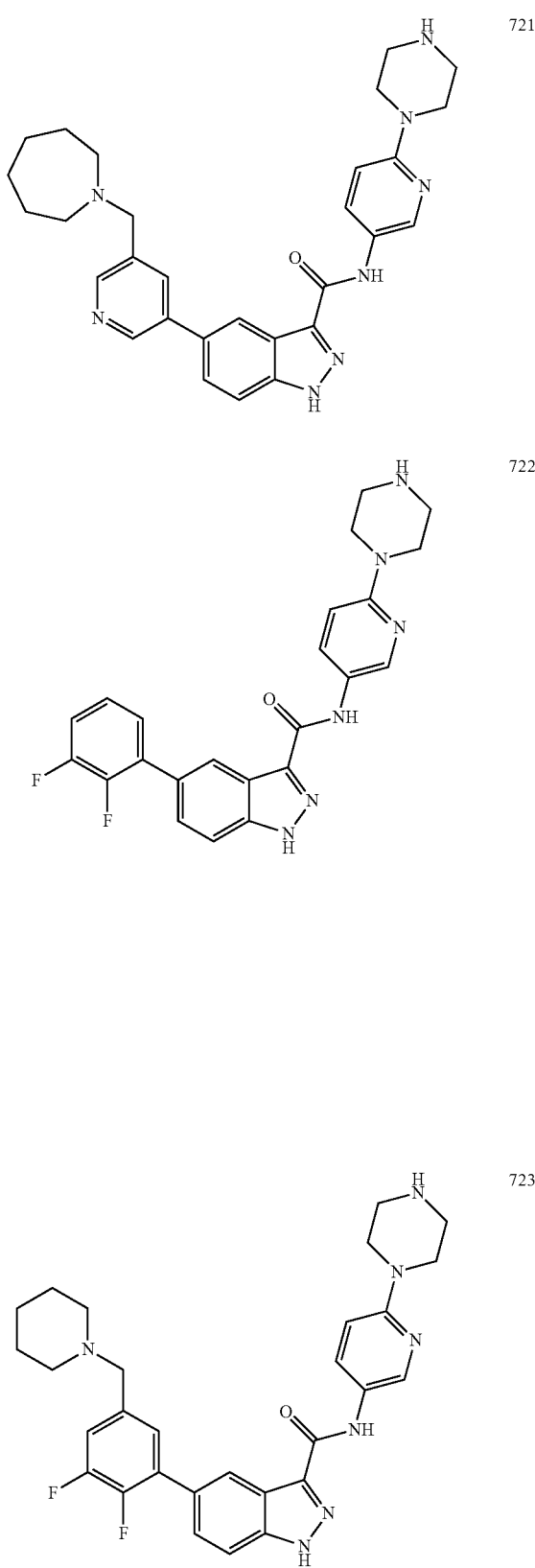

TABLE 1-continued
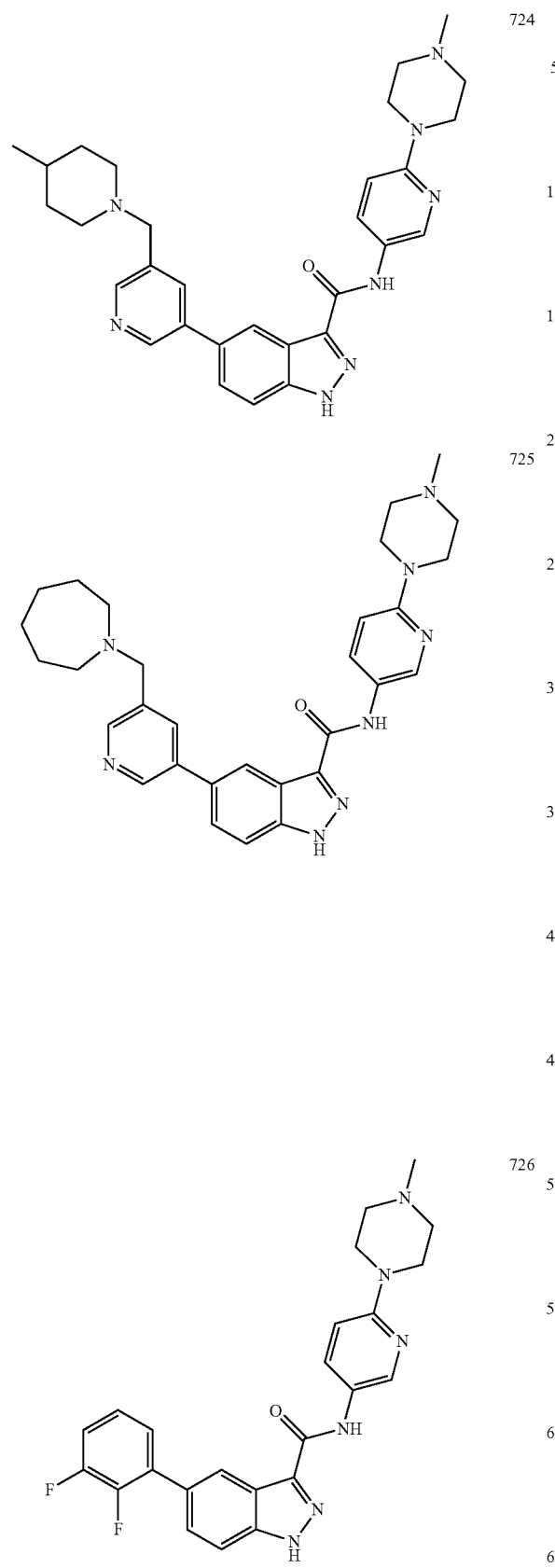
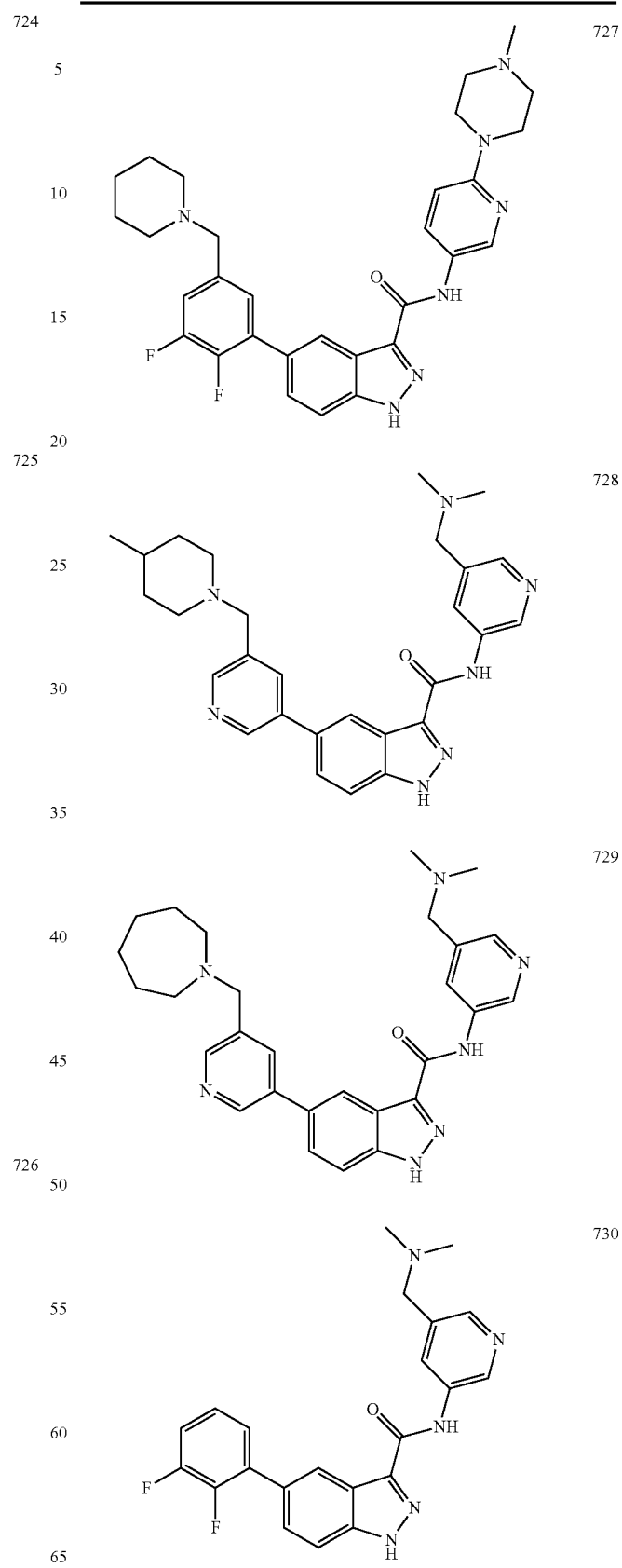

TABLE 1-continued
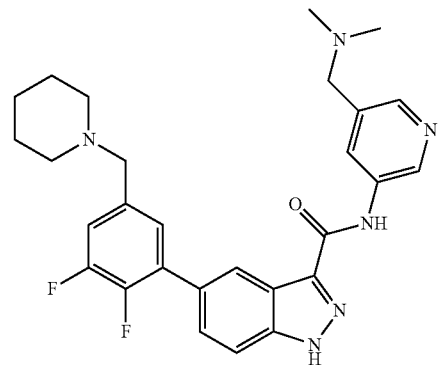 [SMILES: CN(C)Cc1cncc(NC(=O)c2n[nH]c3ccc(-c4cc(CN5CCCCC5)cc(F)c4F)cc23)c1] 731
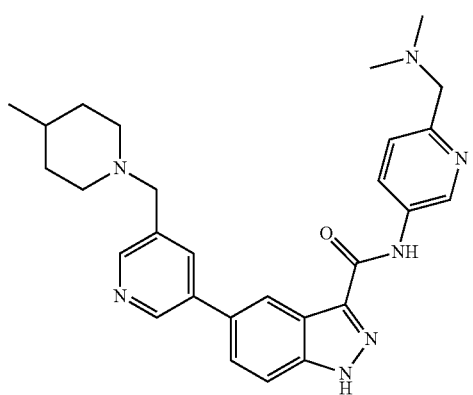 [SMILES: CC1CCN(Cc2cncc(-c3ccc4[nH]nc(C(=O)Nc5ccc(CN(C)C)nc5)c4c3)c2)CC1] 732
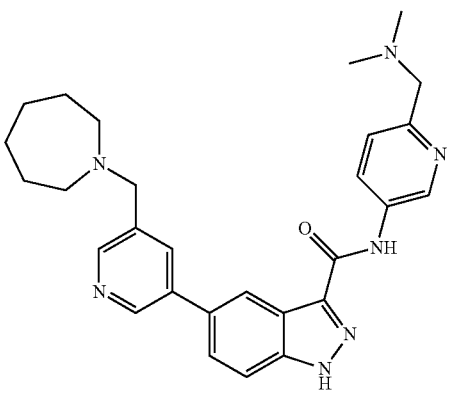 [SMILES: CN(C)Cc1ccc(NC(=O)c2n[nH]c3ccc(-c4cncc(CN5CCCCCC5)c4)cc23)cn1] 733
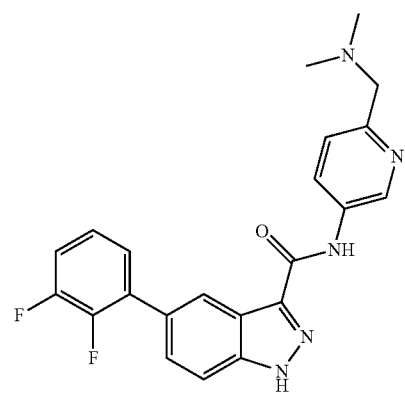 [SMILES: CN(C)Cc1ccc(NC(=O)c2n[nH]c3ccc(-c4cccc(F)c4F)cc23)cn1] 734
TABLE 1-continued
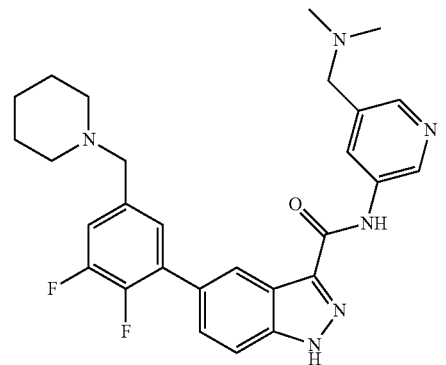 735
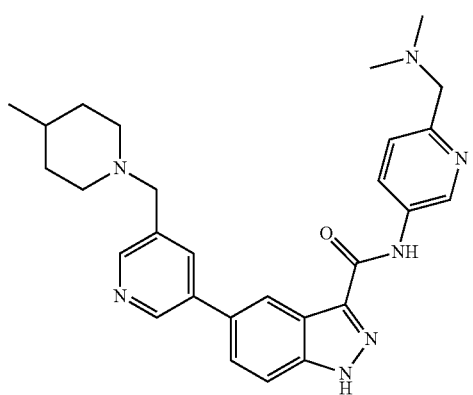 [SMILES: CC1CCN(Cc2cncc(-c3ccc4[nH]nc(C(=O)Nc5ccc(CN(C)C)nc5)c4c3)c2)CC1] 736
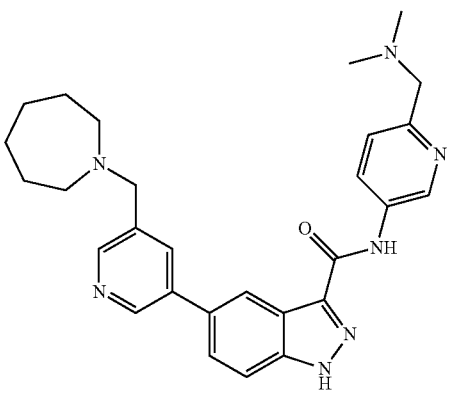 [SMILES: CN(C)Cc1ccc(NC(=O)c2n[nH]c3ccc(-c4cncc(CN5CCCCCC5)c4)cc23)cn1] 737
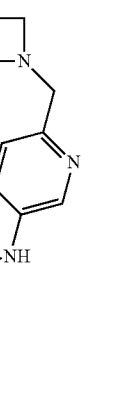 738

TABLE 1-continued
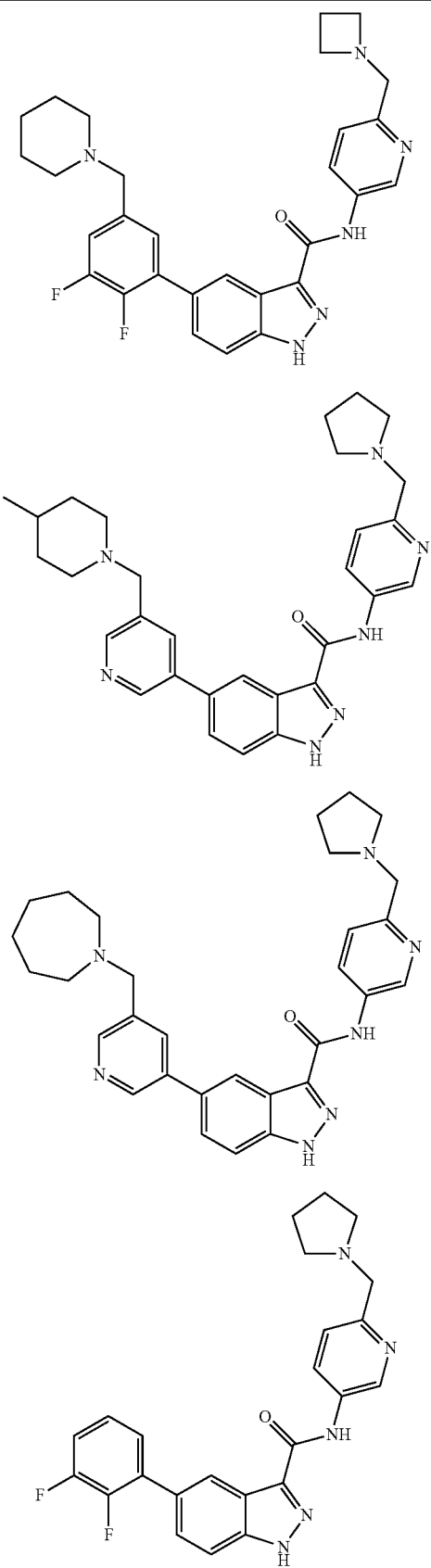
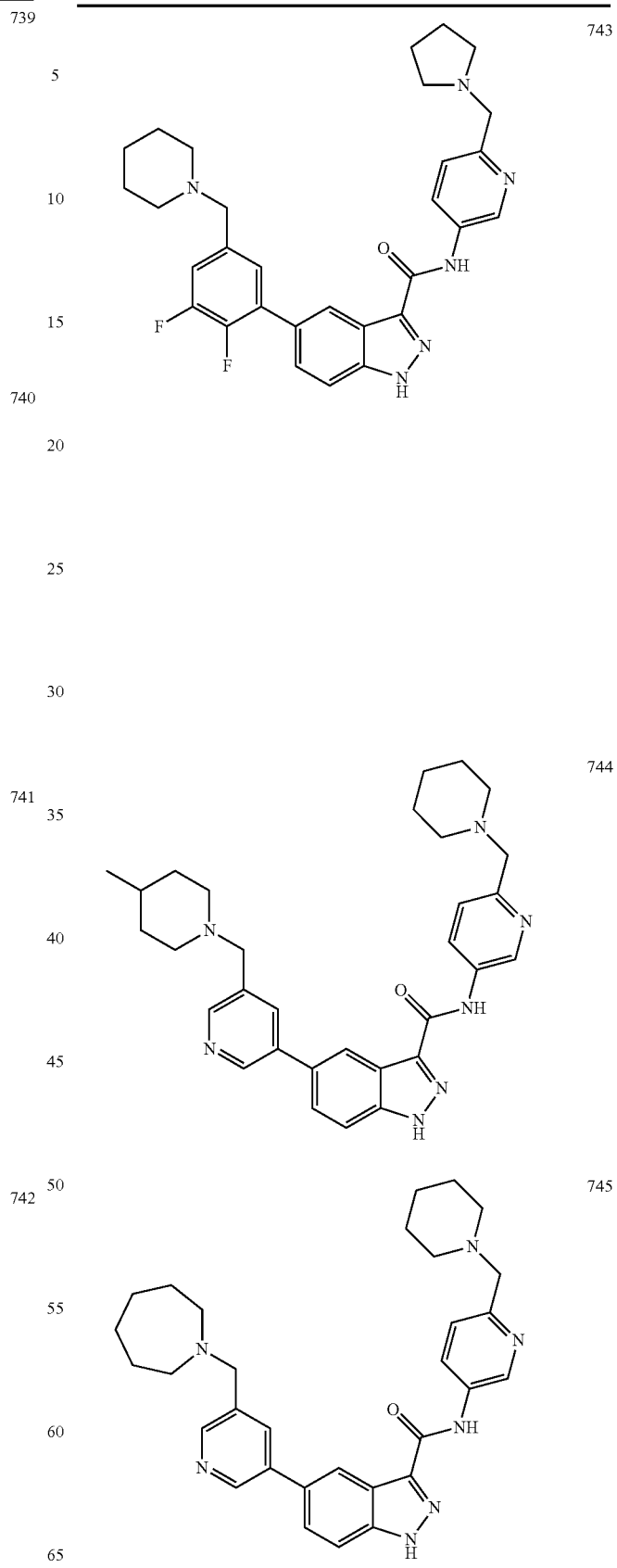

TABLE 1-continued
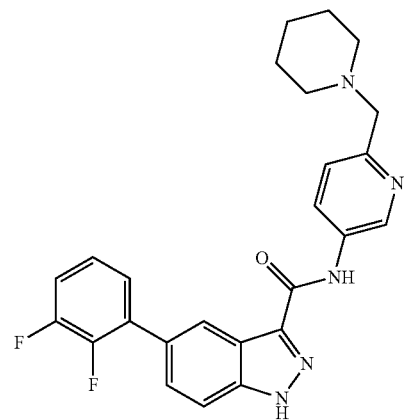
746
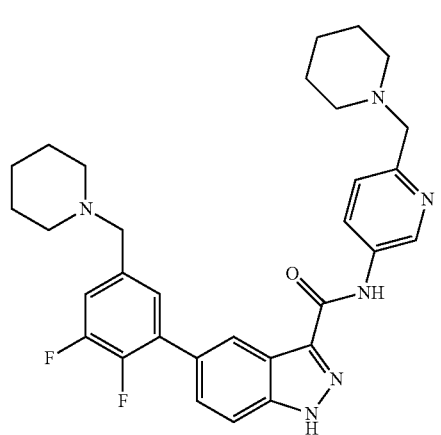
747
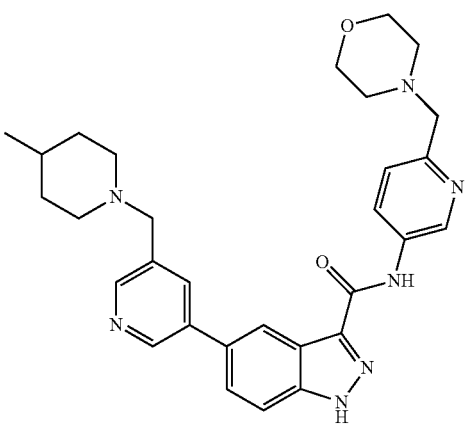
748
TABLE 1-continued
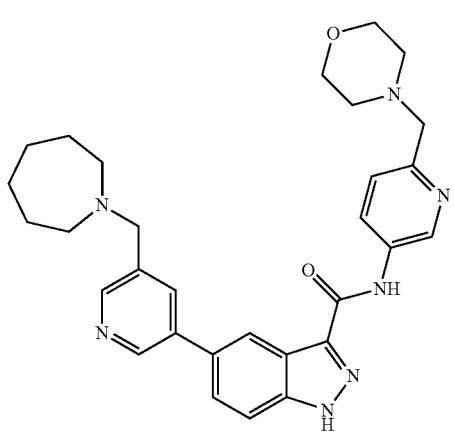 [SMILES: O=C(Nc1ccc(CN2CCCCC2)nc1)c1n[nH]c2ccc(-c3cncc(CN4CCCCCC4)c3)cc12]
749
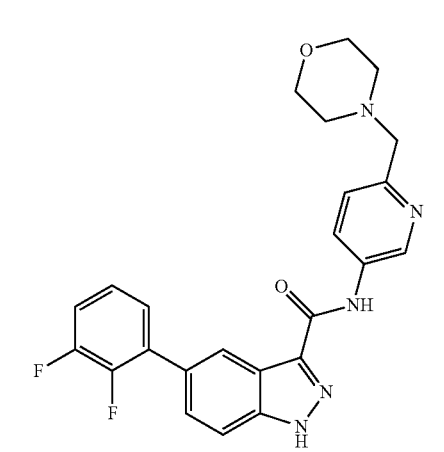 [SMILES: O=C(Nc1ccc(CN2CCCCC2)nc1)c1n[nH]c2ccc(-c3cccc(F)c3F)cc12]
750
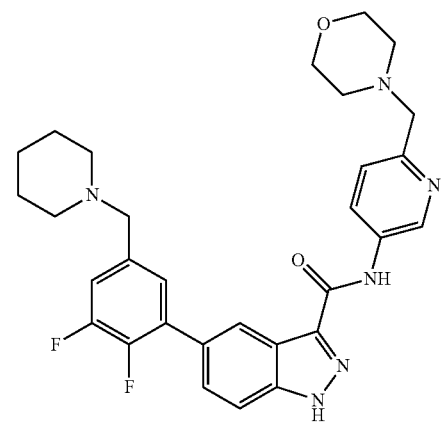 [SMILES: O=C(Nc1ccc(CN2CCCCC2)nc1)c1n[nH]c2ccc(-c3cc(CN4CCCCC4)cc(F)c3F)cc12]
751

TABLE 1-continued
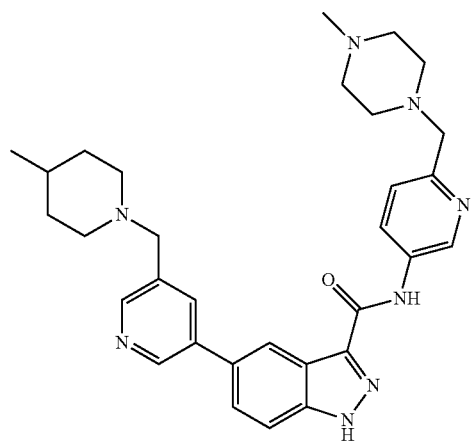 [SMILES: CC1CCN(Cc2cncc(-c3ccc4[nH]nc(C(=O)Nc5ccc(CN6CCN(C)CC6)nc5)c4c3)c2)CC1]
752
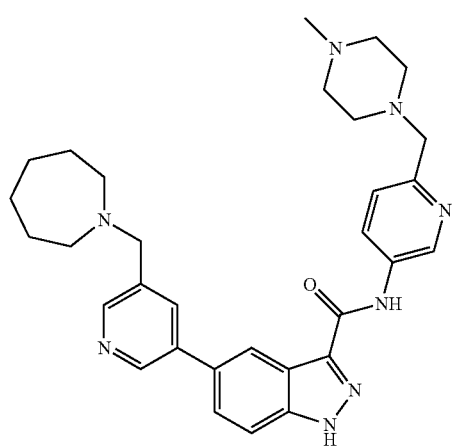
753
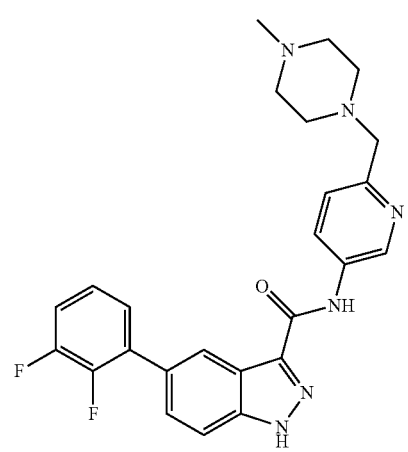 [SMILES: CN1CCN(Cc2ccc(NC(=O)c3n[nH]c4ccc(-c5cccc(F)c5F)cc34)cn2)CC1]
754
TABLE 1-continued
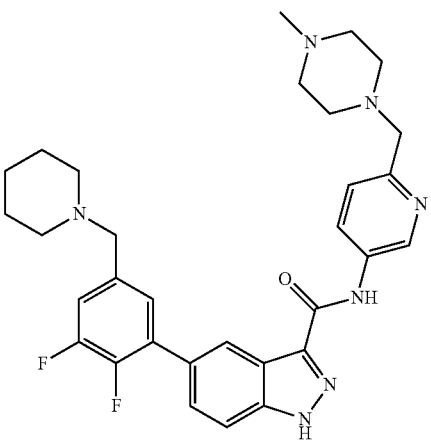 [SMILES: CN1CCN(Cc2ccc(NC(=O)c3n[nH]c4ccc(-c5cc(CN6CCCCC6)cc(F)c5F)cc34)cn2)CC1]
755
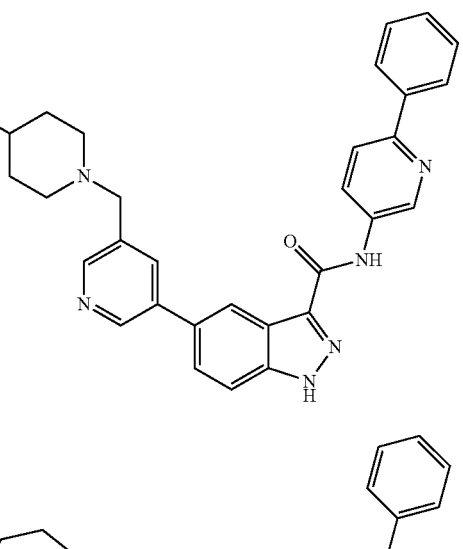
756
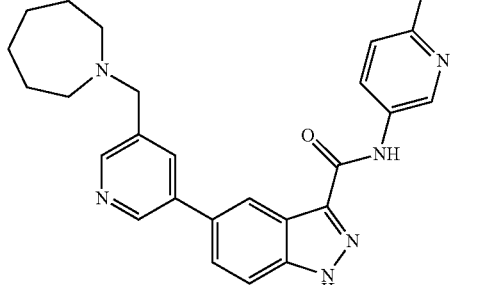
757
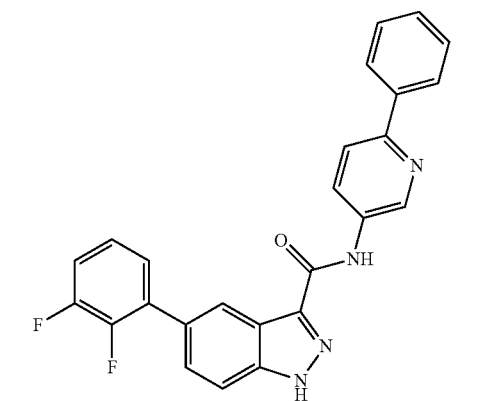 [SMILES: O=C(Nc1ccc(-c2ccccc2)nc1)c1n[nH]c2ccc(-c3cccc(F)c3F)cc12]
758

TABLE 1-continued
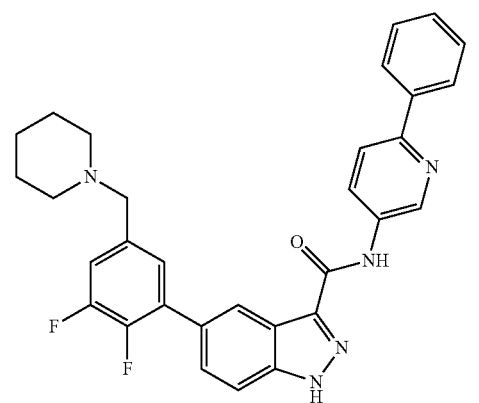 [SMILES: O=C(Nc1ccc(-c2ccccc2)nc1)c1n[nH]c2ccc(-c3cc(CN4CCCCC4)cc(F)c3F)cc12]
759
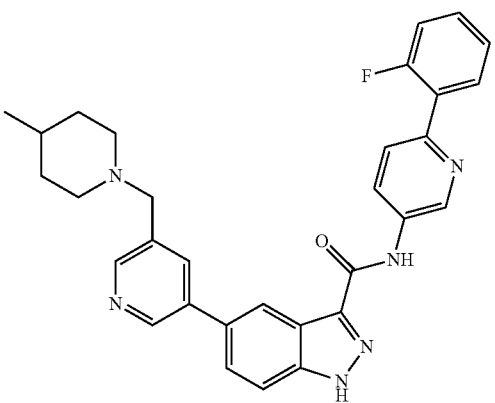 [SMILES: CC1CCN(Cc2cncc(-c3ccc4[nH]nc(C(=O)Nc5ccc(-c6ccccc6F)nc5)c4c3)c2)CC1]
760
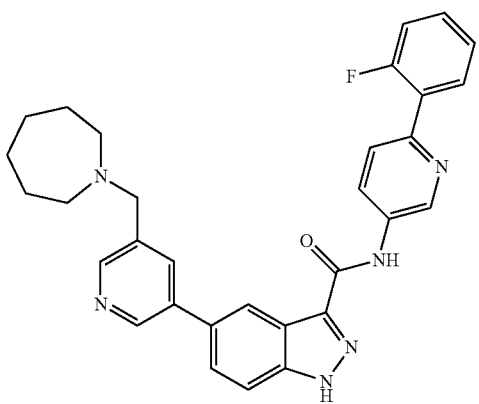 [SMILES: O=C(Nc1ccc(-c2ccccc2F)nc1)c1n[nH]c2ccc(-c3cncc(CN4CCCCCC4)c3)cc12]
761
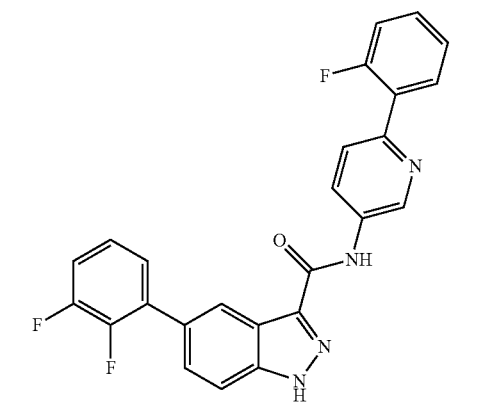 [SMILES: O=C(Nc1ccc(-c2ccccc2F)nc1)c1n[nH]c2ccc(-c3cccc(F)c3F)cc12]
762
TABLE 1-continued
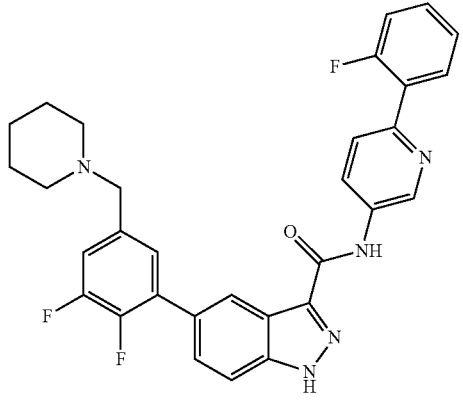 [SMILES: O=C(Nc1ccc(-c2ccccc2F)nc1)c1n[nH]c2ccc(-c3cc(CN4CCCCC4)cc(F)c3F)cc12]
763
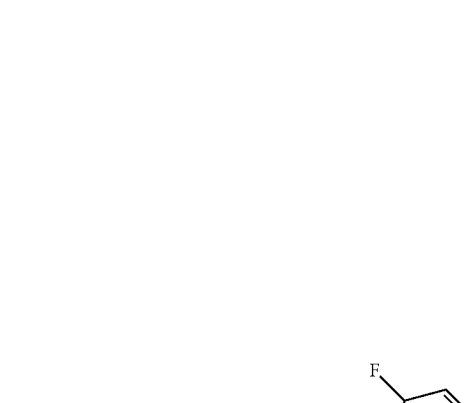
764
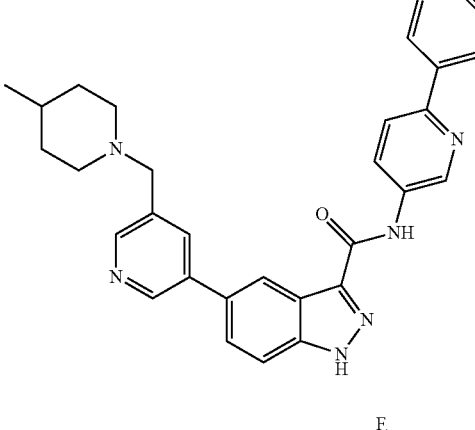
765

TABLE 1-continued
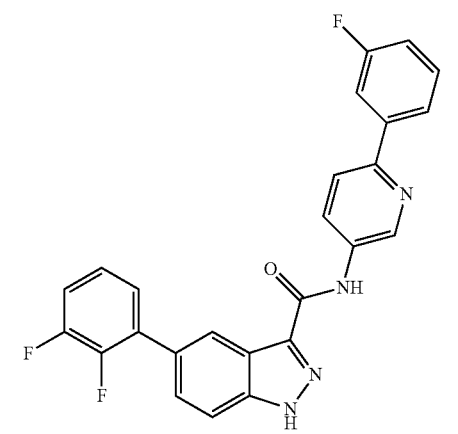 [SMILES: O=C(Nc1ccc(-c2cccc(F)c2)nc1)c1n[nH]c2ccc(-c3cccc(F)c3F)cc12]
766
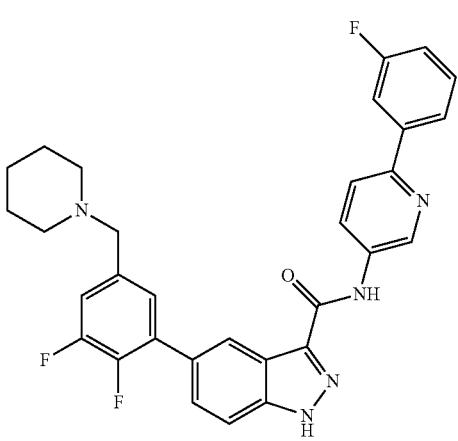 [SMILES: O=C(Nc1ccc(-c2cccc(F)c2)nc1)c1n[nH]c2ccc(-c3cc(CN4CCCCC4)cc(F)c3F)cc12]
767
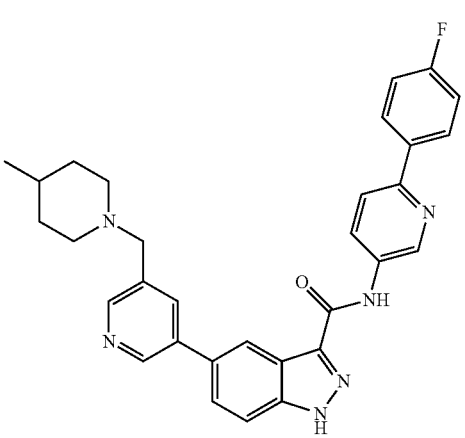 [SMILES: CC1CCN(Cc2cncc(-c3ccc4[nH]nc(C(=O)Nc5ccc(-c6ccc(F)cc6)nc5)c4c3)c2)CC1]
768
TABLE 1-continued
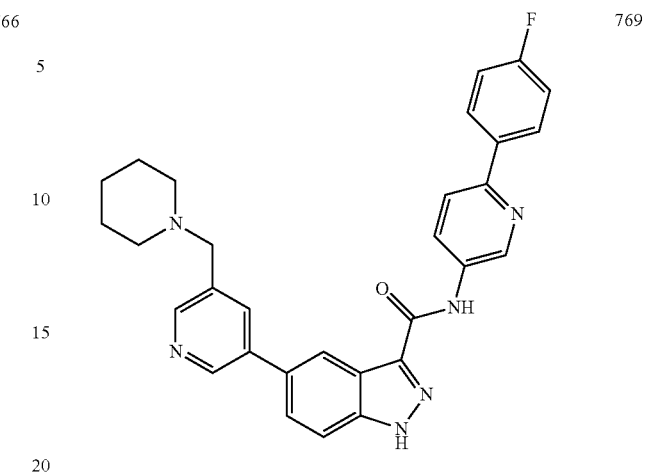
769
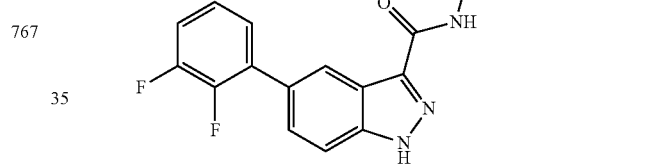
770
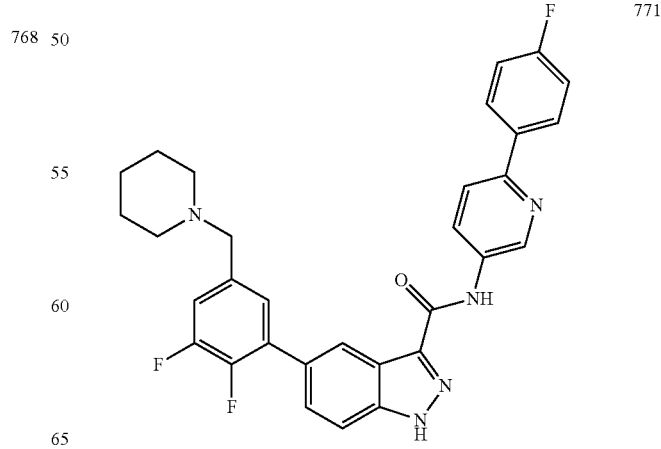
771

TABLE 1-continued
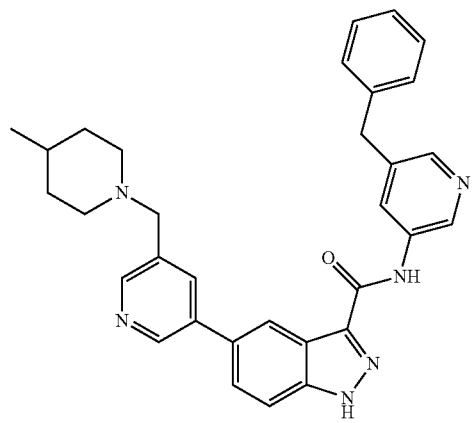 [SMILES: CC1CCN(Cc2cncc(-c3ccc4[nH]nc(C(=O)Nc5cncc(Cc6ccccc6)c5)c4c3)c2)CC1]
772
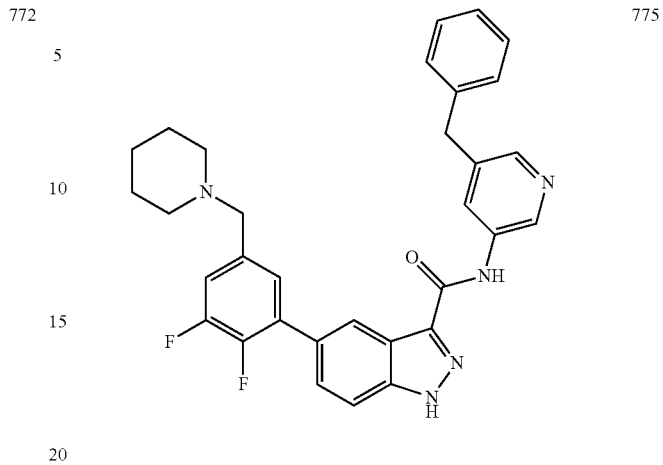
775
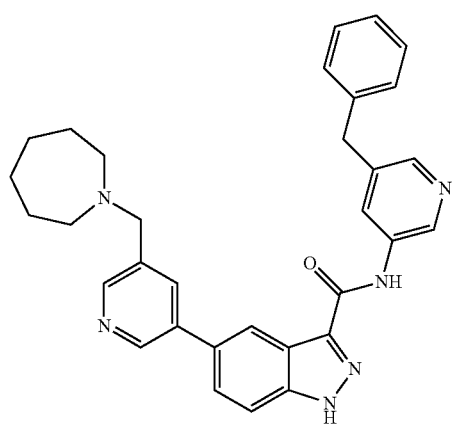 [SMILES: O=C(Nc1cncc(Cc2ccccc2)c1)c1n[nH]c2ccc(-c3cncc(CN4CCCCCC4)c3)cc12]
773
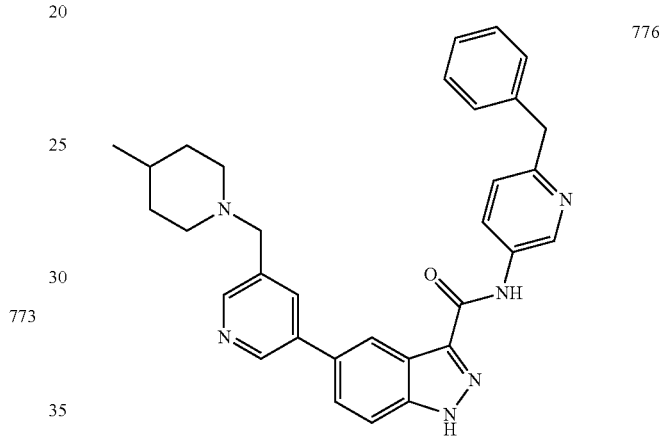
776
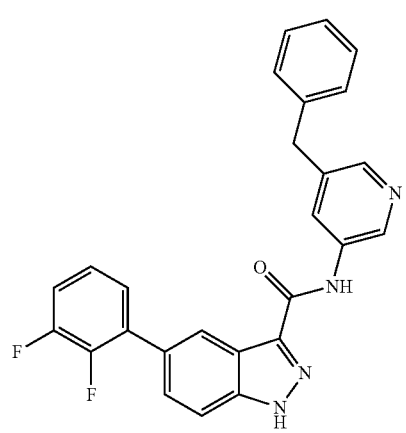 [SMILES: O=C(Nc1cncc(Cc2ccccc2)c1)c1n[nH]c2ccc(-c3cccc(F)c3F)cc12]
774
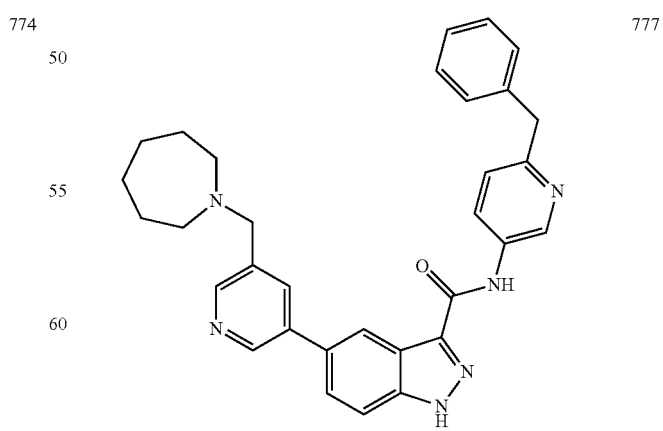
777

TABLE 1-continued
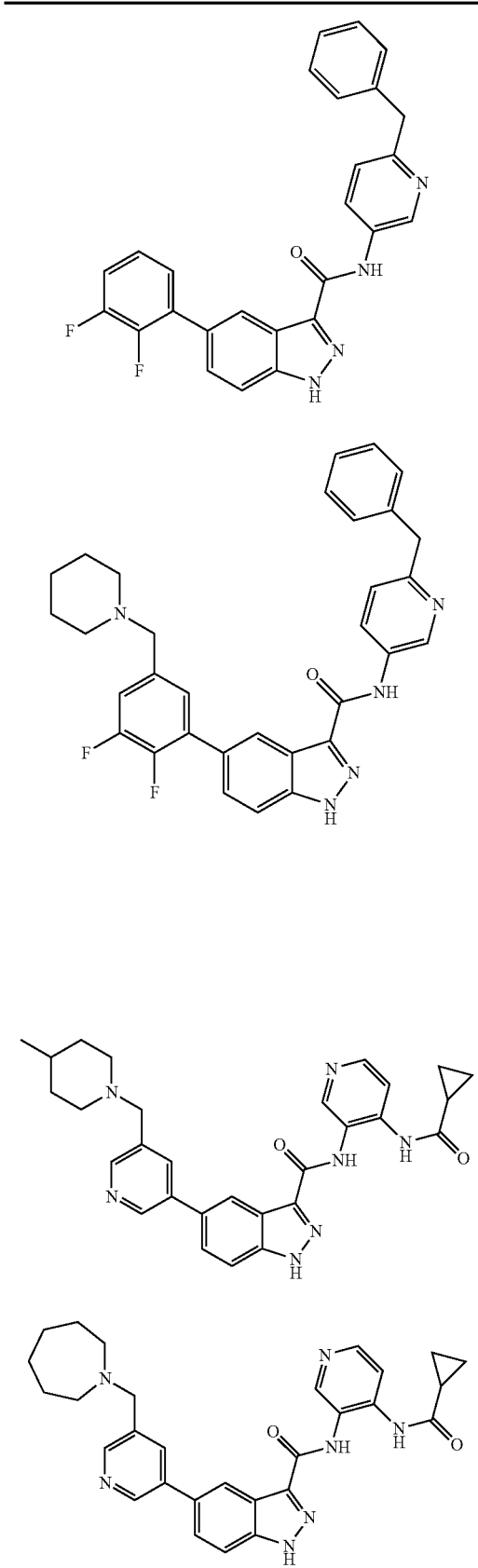
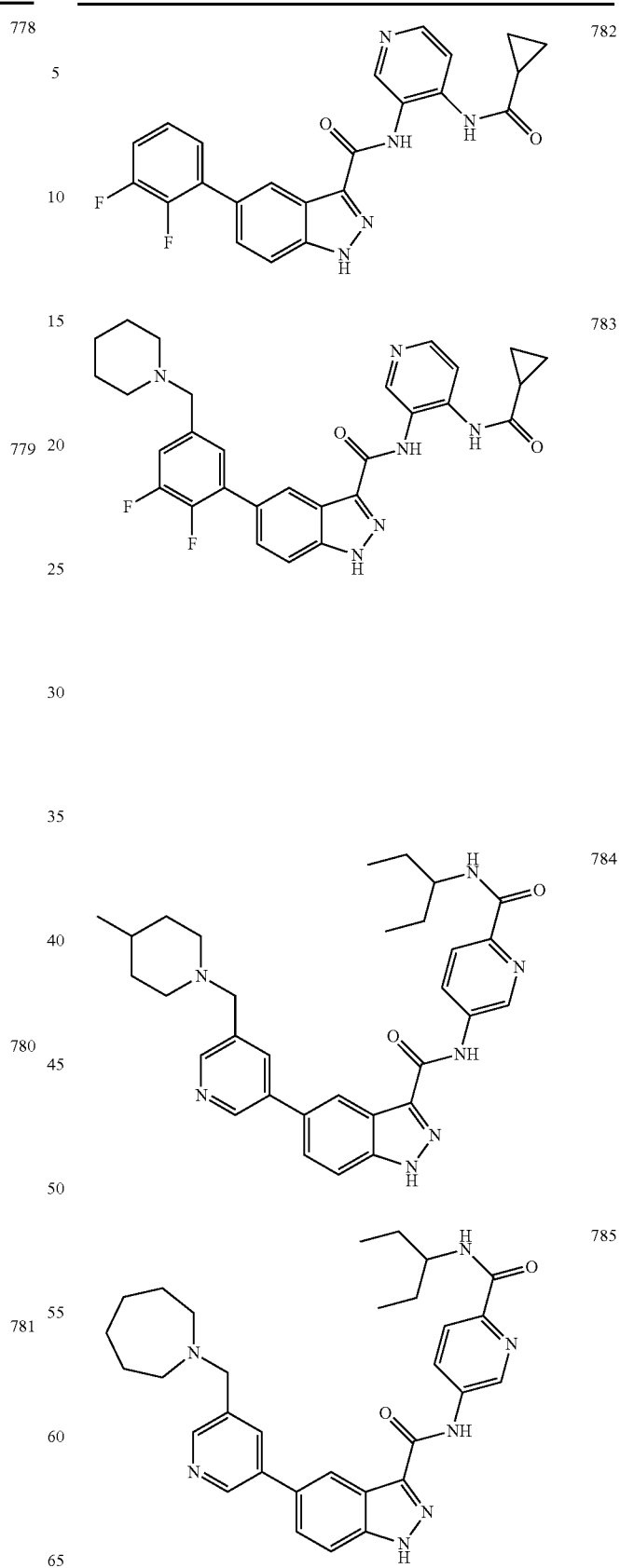

TABLE 1-continued
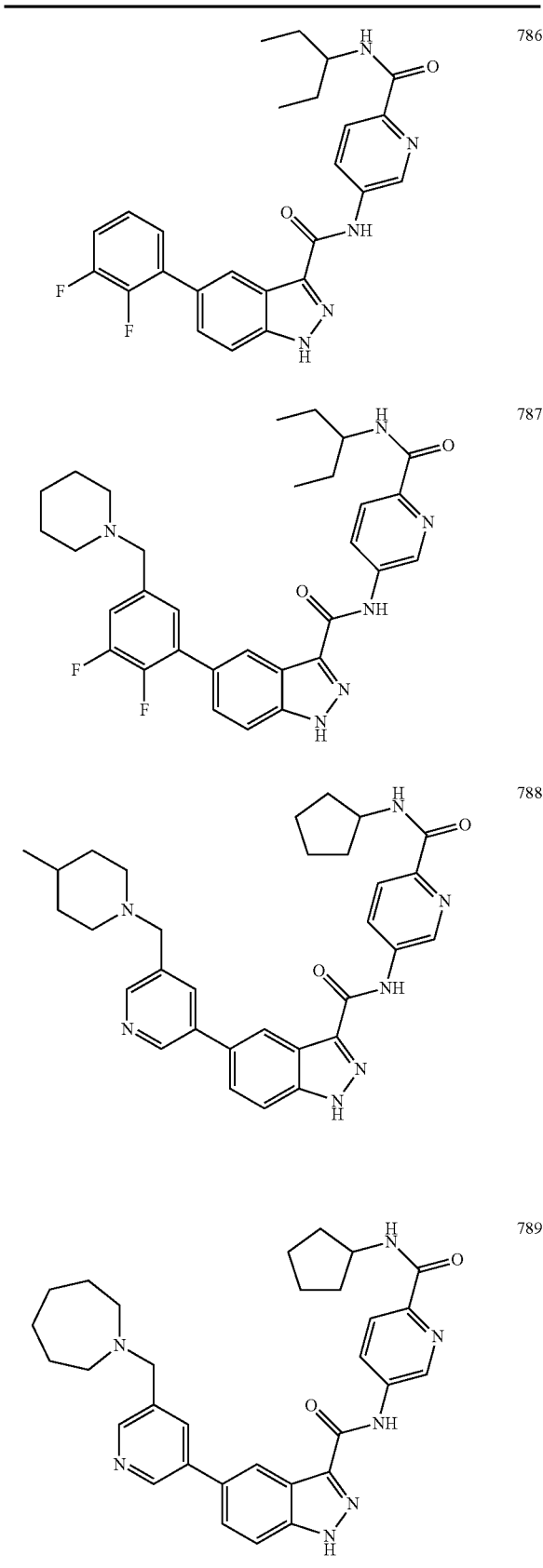
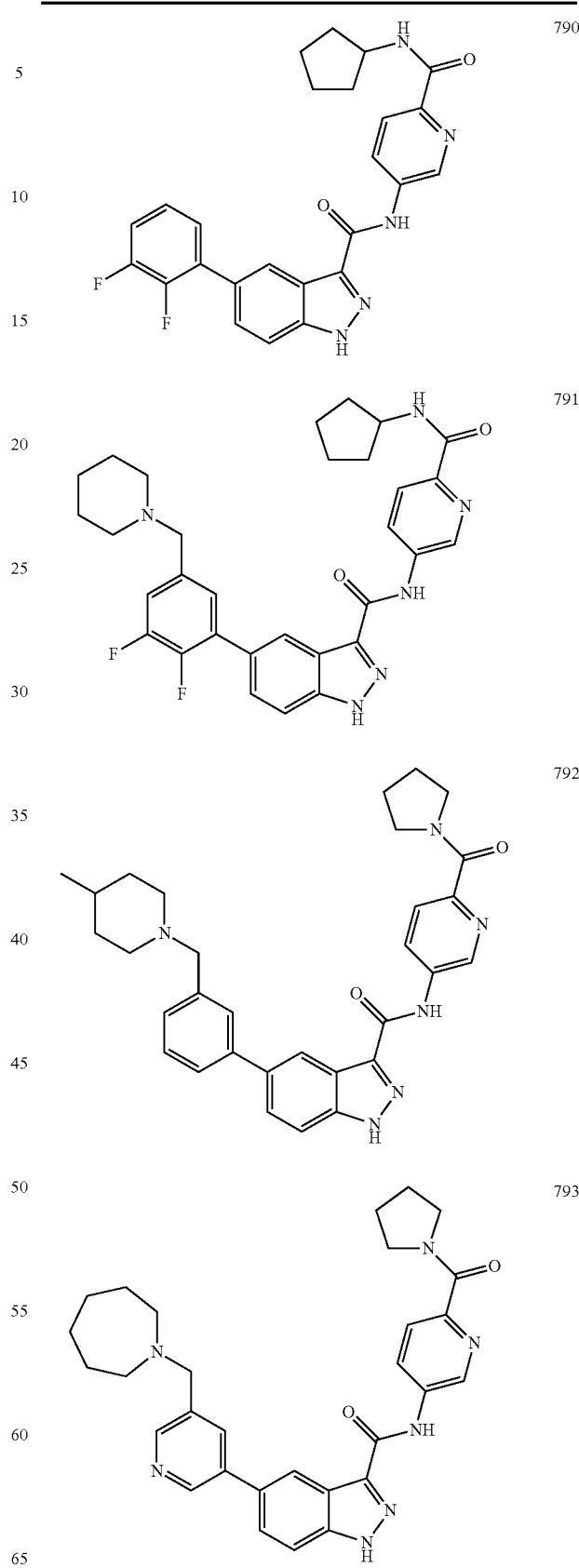

TABLE 1-continued
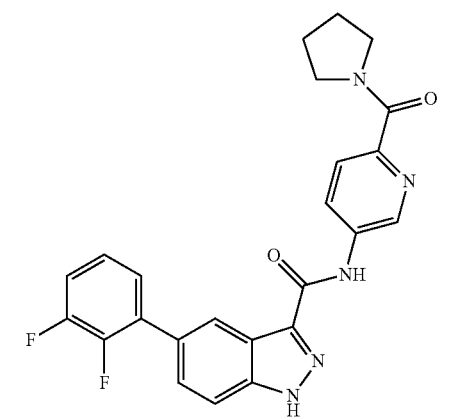 [SMILES: O=C(Nc1ccc(C(=O)N2CCCC2)nc1)c1n[nH]c2ccc(-c3cccc(F)c3F)cc12]
794
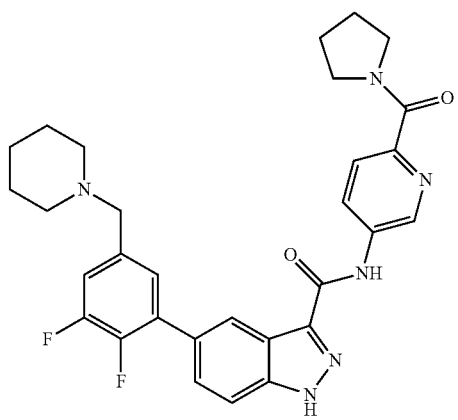 [SMILES: O=C(Nc1ccc(C(=O)N2CCCC2)nc1)c1n[nH]c2ccc(-c3cc(CN4CCCCC4)cc(F)c3F)cc12]
795
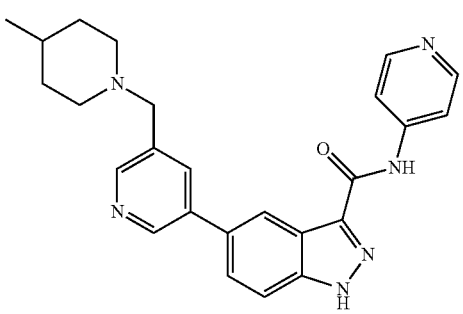 [SMILES: CC1CCN(Cc2cncc(-c3ccc4[nH]nc(C(=O)Nc5ccncc5)c4c3)c2)CC1]
796
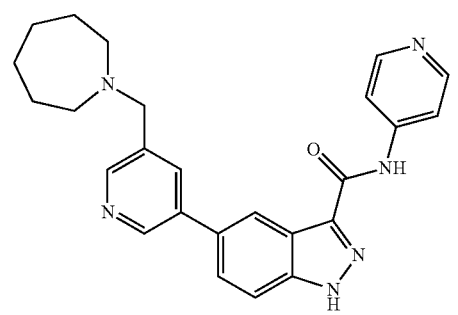 [SMILES: O=C(Nc1ccncc1)c1n[nH]c2ccc(-c3cncc(CN4CCCCCC4)c3)cc12]
797
TABLE 1-continued
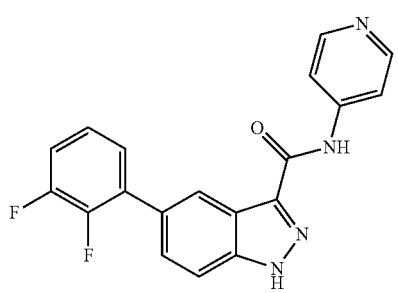 [SMILES: O=C(Nc1ccncc1)c1n[nH]c2ccc(-c3cccc(F)c3F)cc12]
798
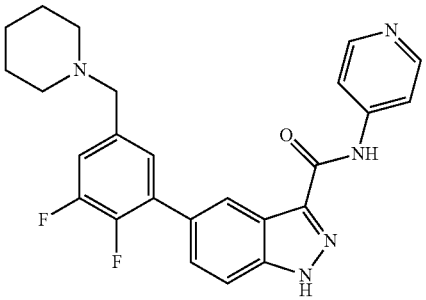 [SMILES: O=C(Nc1ccncc1)c1n[nH]c2ccc(-c3cc(CN4CCCCC4)cc(F)c3F)cc12]
799
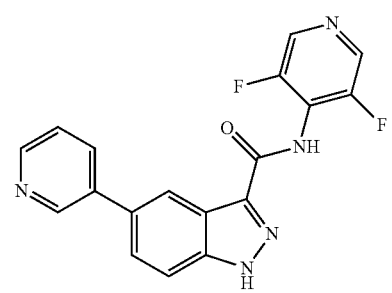 [SMILES: O=C(Nc1c(F)cncc1F)c1n[nH]c2ccc(-c3cccnc3)cc12]
800
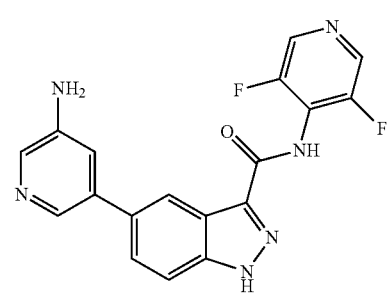 [SMILES: Nc1cncc(-c2ccc3[nH]nc(C(=O)Nc4c(F)cncc4F)c3c2)c1]
801
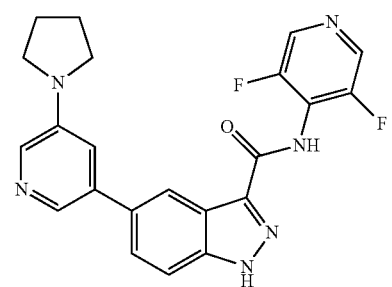 [SMILES: O=C(Nc1c(F)cncc1F)c1n[nH]c2ccc(-c3cncc(N4CCCC4)c3)cc12]
802

TABLE 1-continued
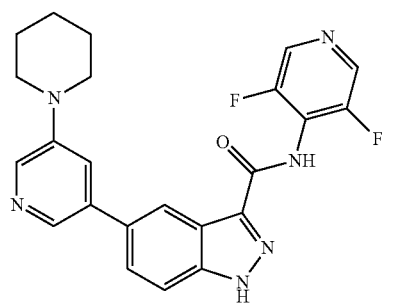 [SMILES: O=C(Nc1c(F)cncc1F)c1n[nH]c2ccc(-c3cncc(N4CCCCC4)c3)cc12] 803
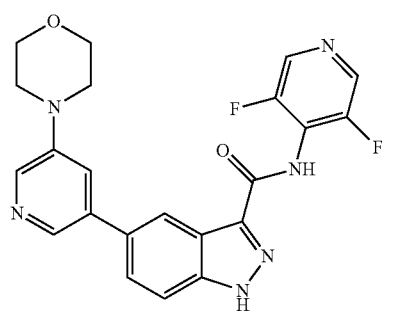 [SMILES: O=C(Nc1c(F)cncc1F)c1n[nH]c2ccc(-c3cncc(N4CCOCC4)c3)cc12] 804
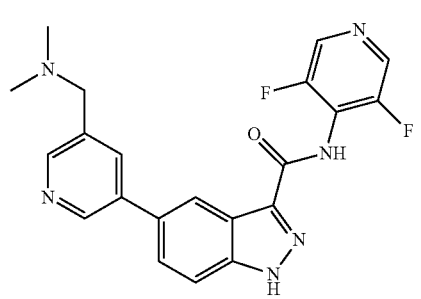 [SMILES: CN(C)Cc1cncc(-c2ccc3[nH]nc(C(=O)Nc4c(F)cncc4F)c3c2)c1] 805
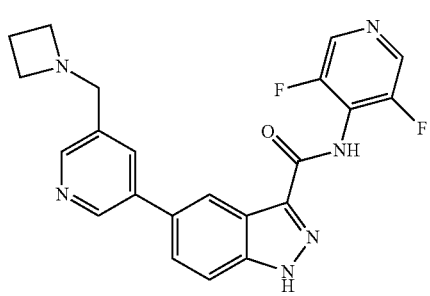 [SMILES: O=C(Nc1c(F)cncc1F)c1n[nH]c2ccc(-c3cncc(CN4CCC4)c3)cc12] 806
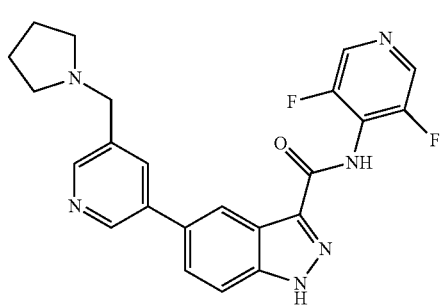 [SMILES: O=C(Nc1c(F)cncc1F)c1n[nH]c2ccc(-c3cncc(CN4CCCC4)c3)cc12] 807
TABLE 1-continued
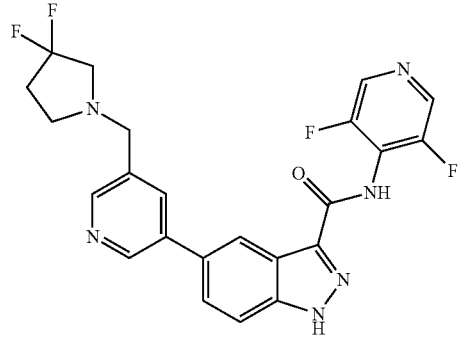 [SMILES: O=C(Nc1c(F)cncc1F)c1n[nH]c2ccc(-c3cncc(CN4CCC(F)(F)C4)c3)cc12] 808
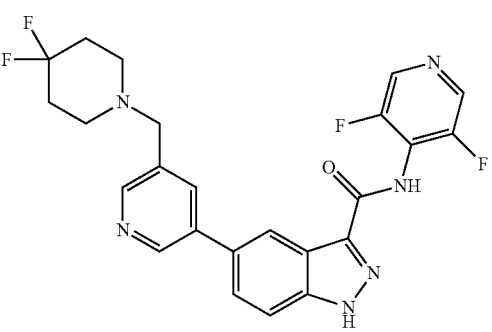 [SMILES: O=C(Nc1c(F)cncc1F)c1n[nH]c2ccc(-c3cncc(CN4CCC(F)(F)CC4)c3)cc12] 809
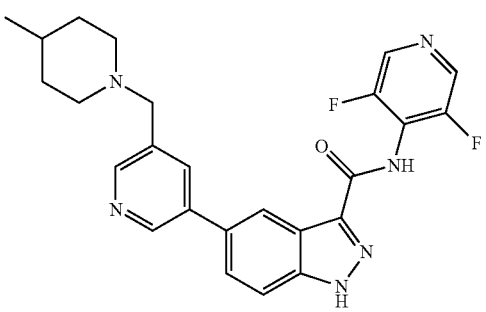 [SMILES: CC1CCN(Cc2cncc(-c3ccc4[nH]nc(C(=O)Nc5c(F)cncc5F)c4c3)c2)CC1] 810
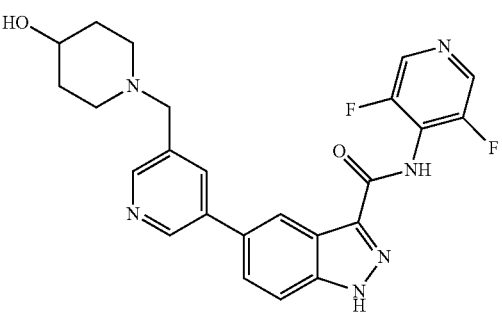 [SMILES: O=C(Nc1c(F)cncc1F)c1n[nH]c2ccc(-c3cncc(CN4CCC(O)CC4)c3)cc12] 811
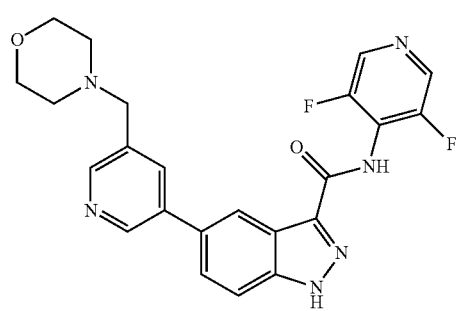 [SMILES: O=C(Nc1c(F)cncc1F)c1n[nH]c2ccc(-c3cncc(CN4CCOCC4)c3)cc12] 812

TABLE 1-continued
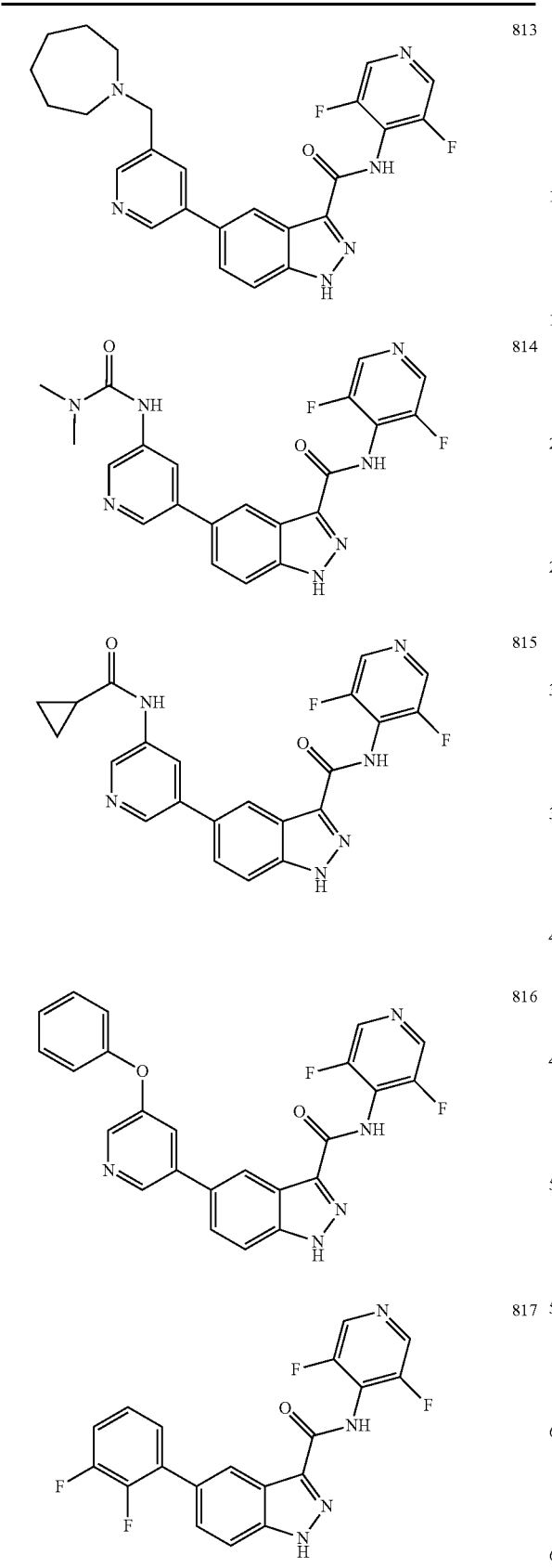
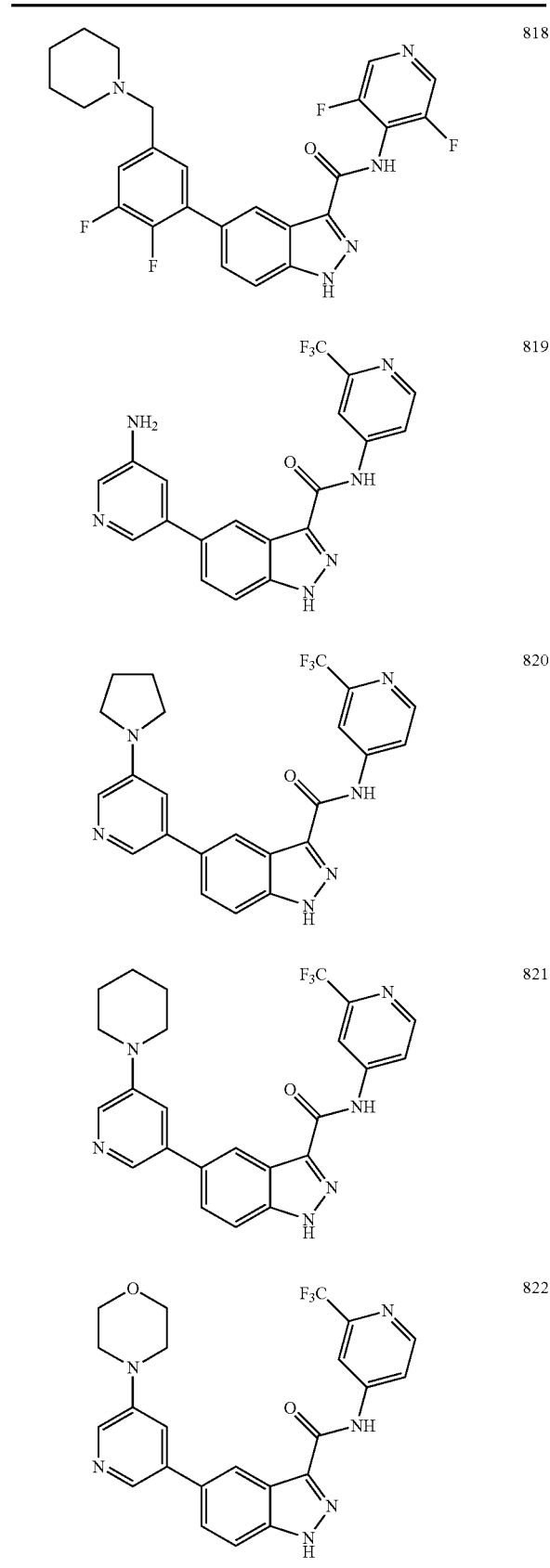

TABLE 1-continued
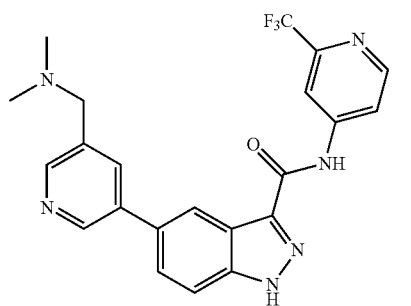 [SMILES: CN(C)Cc1cncc(-c2ccc3[nH]nc(C(=O)Nc4ccnc(C(F)(F)F)c4)c3c2)c1]
823
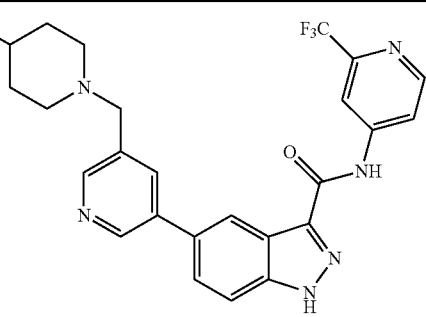
828
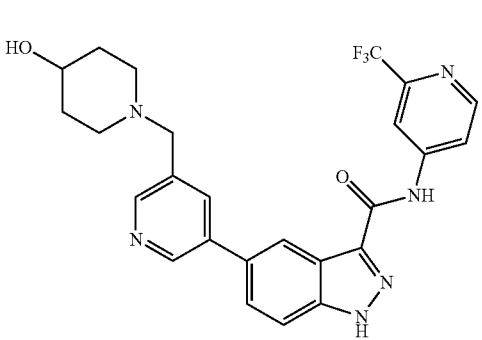 [SMILES: O=C(Nc1ccnc(C(F)(F)F)c1)c1n[nH]c2ccc(-c3cncc(CN4CCC(O)CC4)c3)cc12]
824
829
825
830
826
831
827
832

TABLE 1-continued
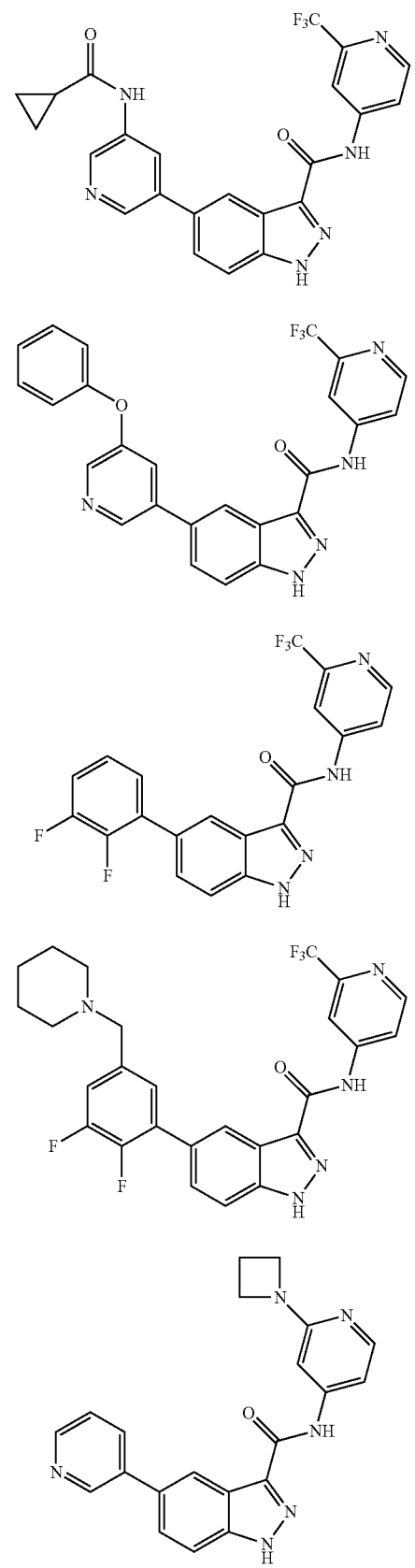
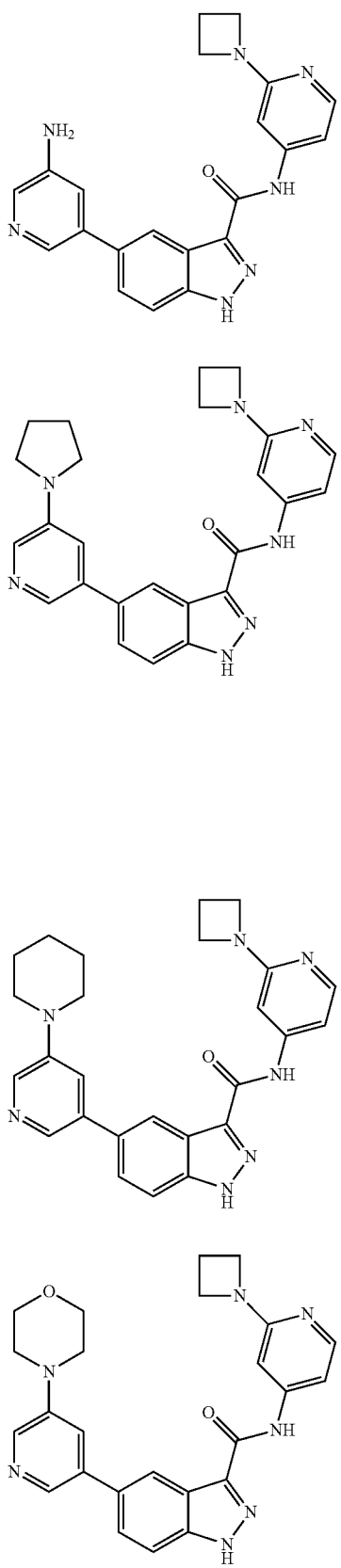

TABLE 1-continued
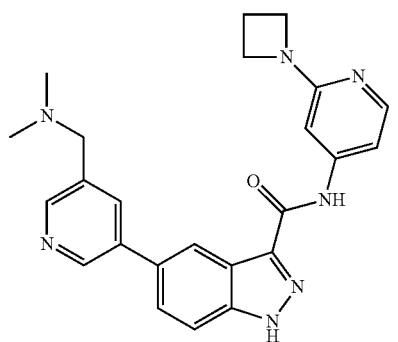 [SMILES: CN(C)Cc1cncc(-c2ccc3[nH]nc(C(=O)Nc4ccnc(N5CCC5)c4)c3c2)c1]
842
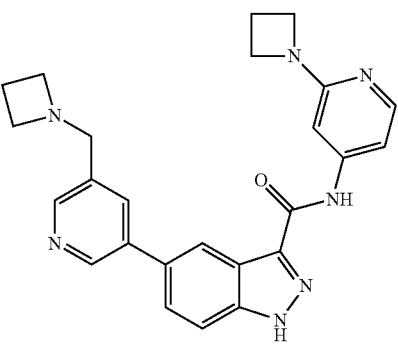 [SMILES: O=C(Nc1ccnc(N2CCC2)c1)c1n[nH]c2ccc(-c3cncc(CN4CCC4)c3)cc12]
843
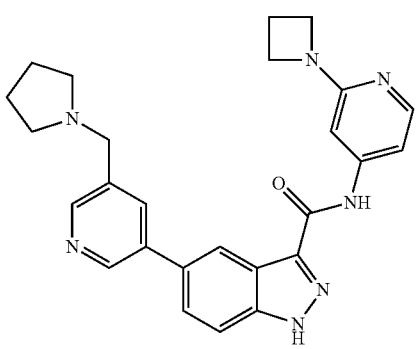 [SMILES: O=C(Nc1ccnc(N2CCC2)c1)c1n[nH]c2ccc(-c3cncc(CN4CCCC4)c3)cc12]
844
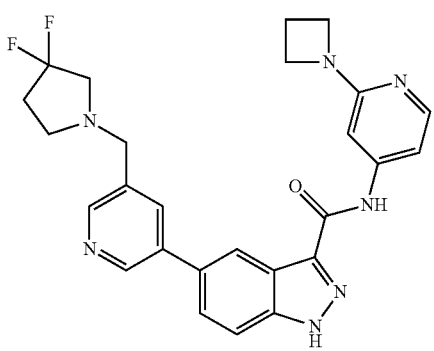 [SMILES: O=C(Nc1ccnc(N2CCC2)c1)c1n[nH]c2ccc(-c3cncc(CN4CCC(F)(F)C4)c3)cc12]
845
TABLE 1-continued
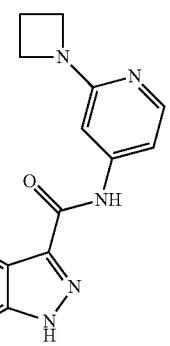
846
847
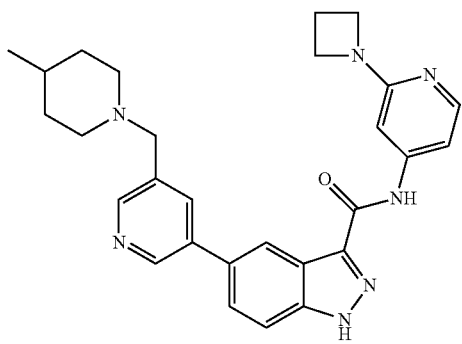 [SMILES: CC1CCN(Cc2cncc(-c3ccc4[nH]nc(C(=O)Nc5ccnc(N6CCC6)c5)c4c3)c2)CC1]
848
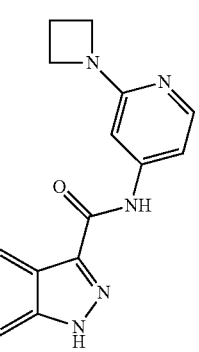
849

TABLE 1-continued
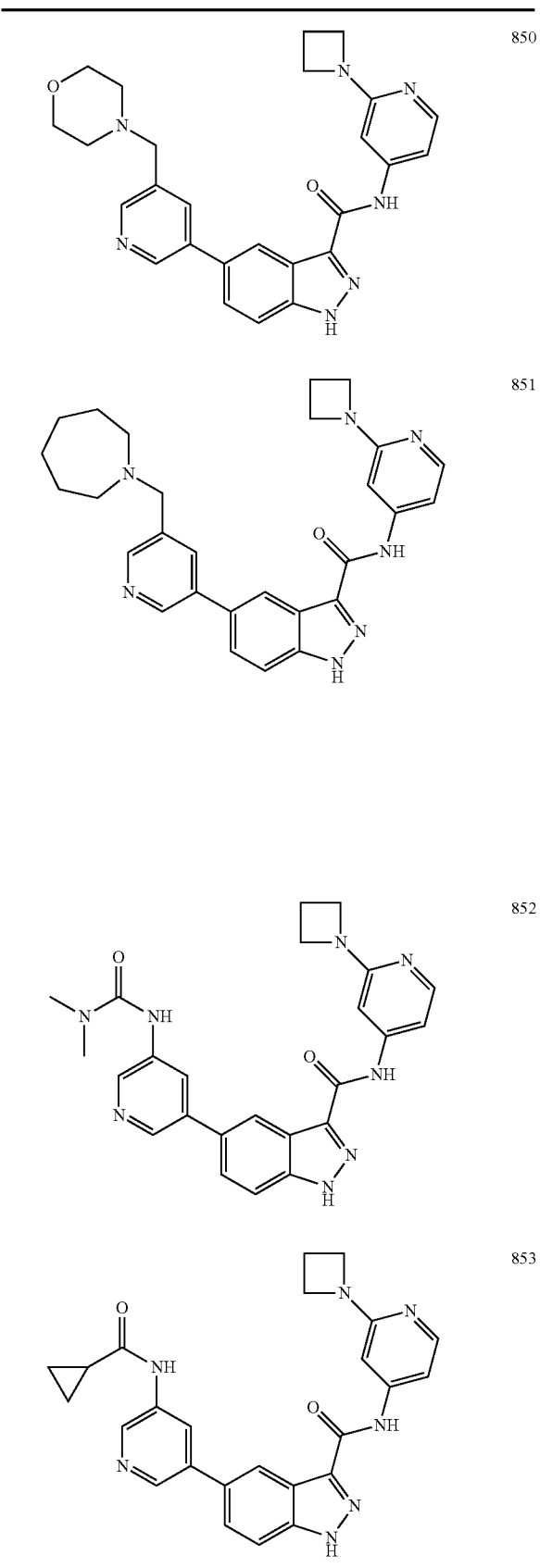
850
851
852
853
TABLE 1-continued
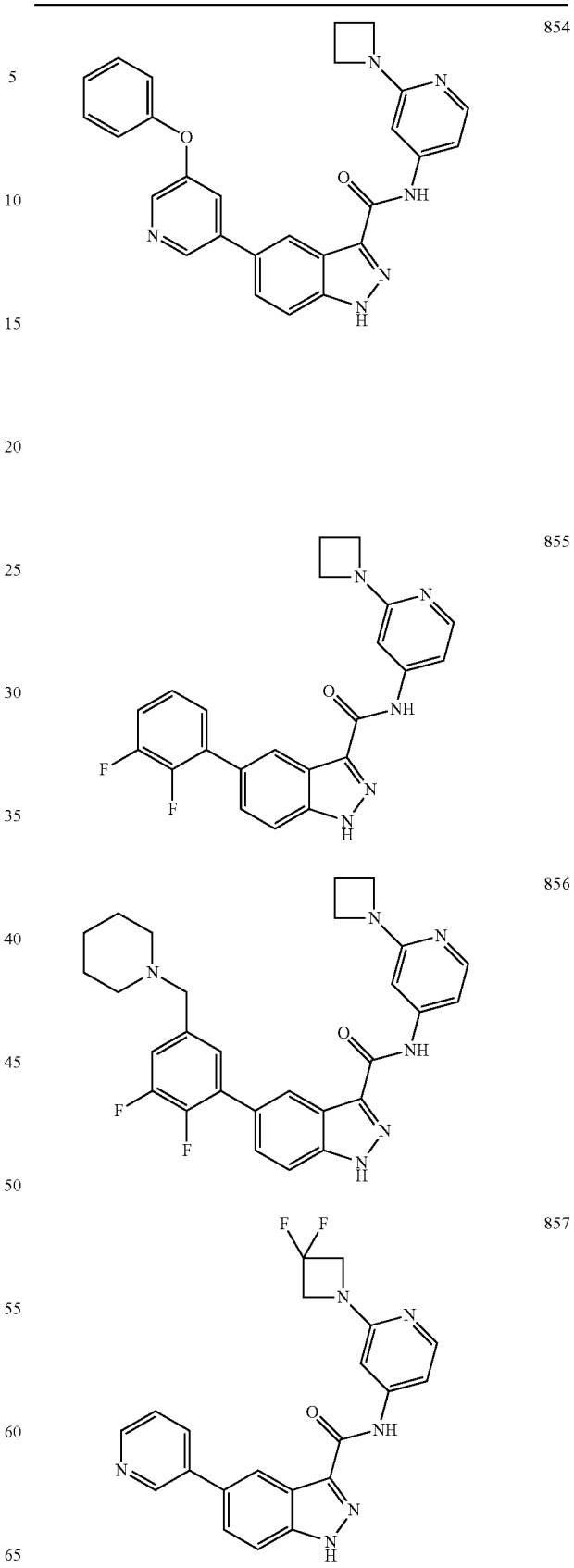
854
855
856
857

TABLE 1-continued
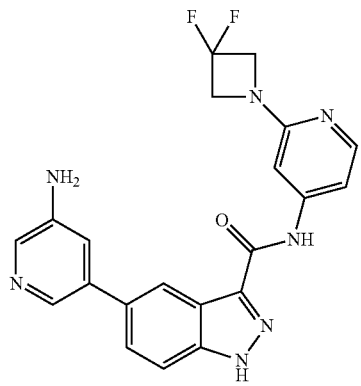 [SMILES: Nc1cncc(-c2ccc3[nH]nc(C(=O)Nc4ccnc(N5CC(F)(F)C5)c4)c3c2)c1] 858
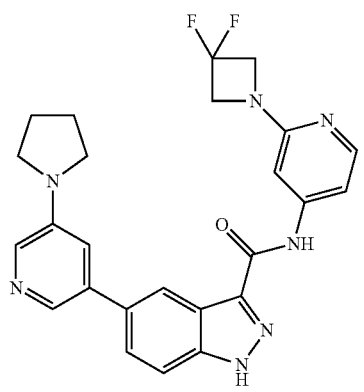 [SMILES: O=C(Nc1ccnc(N2CC(F)(F)C2)c1)c1n[nH]c2ccc(-c3cncc(N4CCCC4)c3)cc12] 859
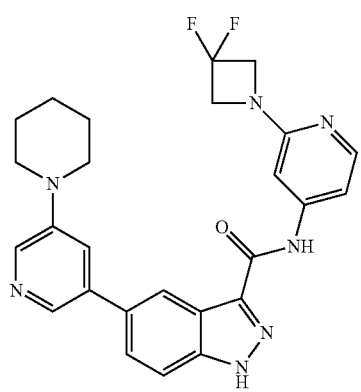 [SMILES: O=C(Nc1ccnc(N2CC(F)(F)C2)c1)c1n[nH]c2ccc(-c3cncc(N4CCCCC4)c3)cc12] 860
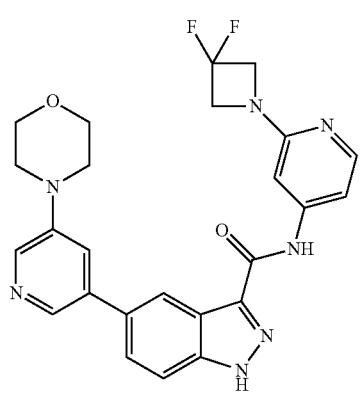 861
TABLE 1-continued
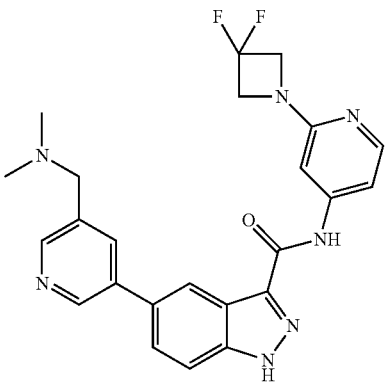 [SMILES: CN(C)Cc1cncc(-c2ccc3[nH]nc(C(=O)Nc4ccnc(N5CC(F)(F)C5)c4)c3c2)c1] 862
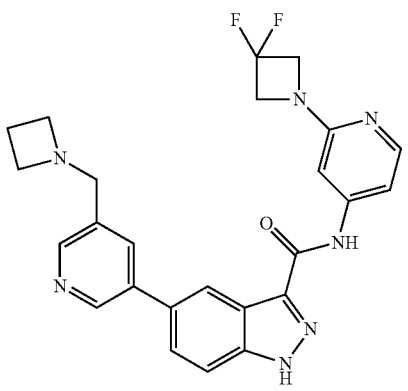 [SMILES: O=C(Nc1ccnc(N2CC(F)(F)C2)c1)c1n[nH]c2ccc(-c3cncc(CN4CCC4)c3)cc12] 863
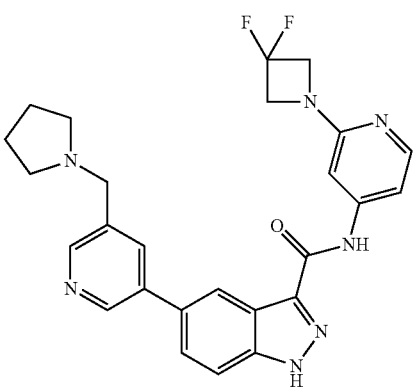 [SMILES: O=C(Nc1ccnc(N2CC(F)(F)C2)c1)c1n[nH]c2ccc(-c3cncc(CN4CCCC4)c3)cc12] 864
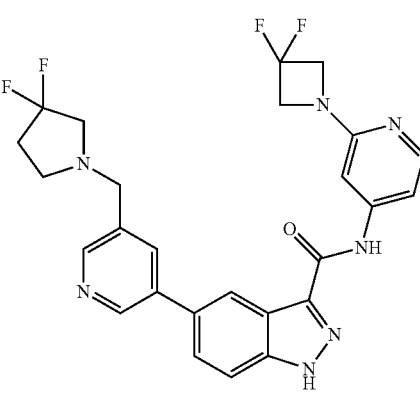 865

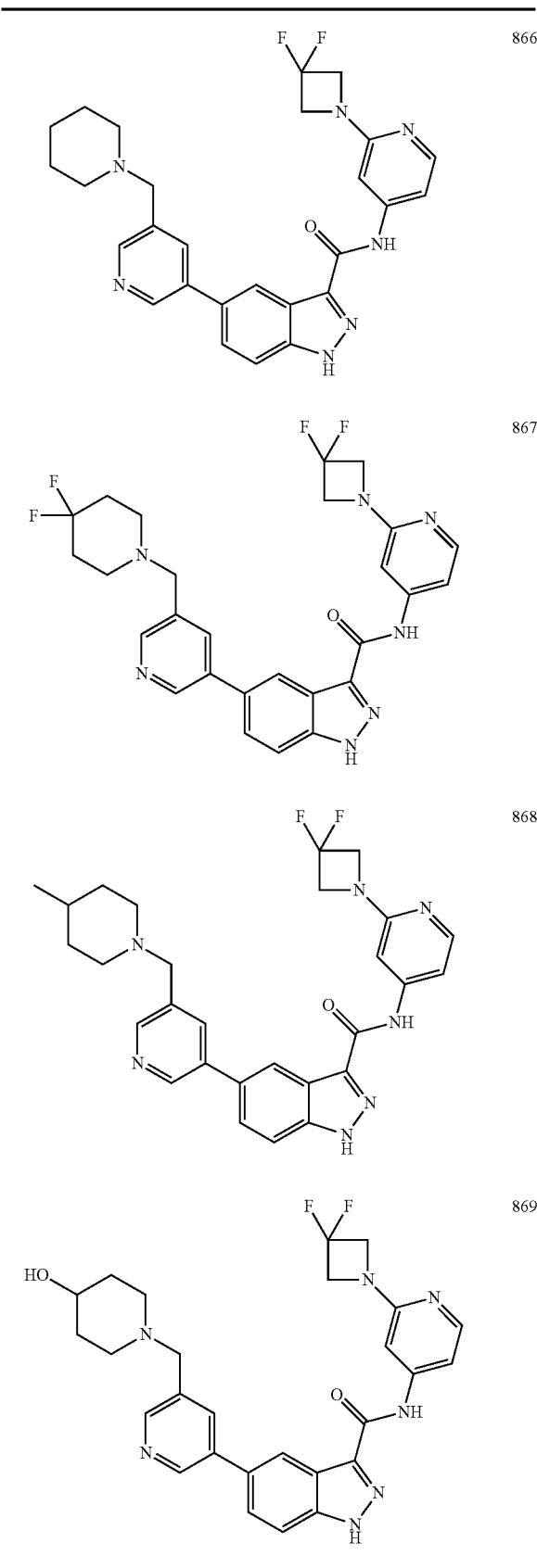

TABLE 1-continued
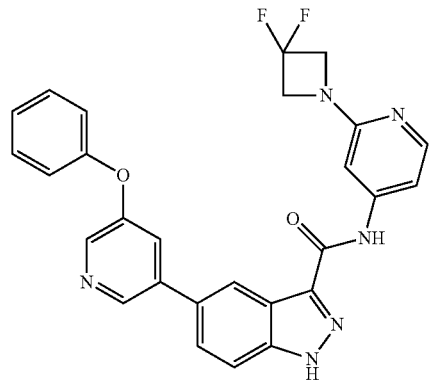 [SMILES: O=C(Nc1ccnc(N2CC(F)(F)C2)c1)c1n[nH]c2ccc(-c3cncc(Oc4ccccc4)c3)cc12] 874
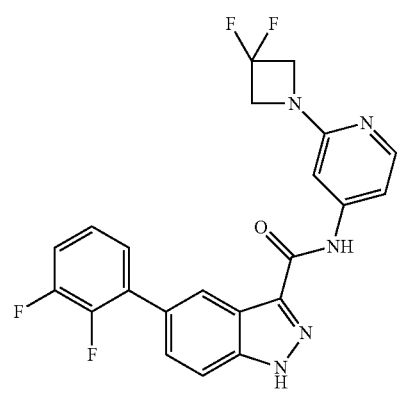 [SMILES: O=C(Nc1ccnc(N2CC(F)(F)C2)c1)c1n[nH]c2ccc(-c3cccc(F)c3F)cc12] 875
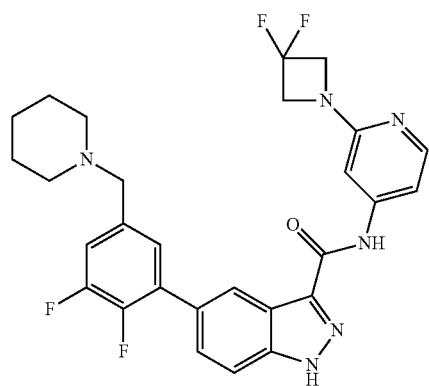 [SMILES: O=C(Nc1ccnc(N2CC(F)(F)C2)c1)c1n[nH]c2ccc(-c3cc(CN4CCCCC4)cc(F)c3F)cc12] 876
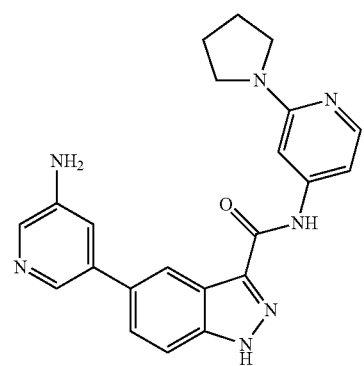 [SMILES: Nc1cncc(-c2ccc3[nH]nc(C(=O)Nc4ccnc(N5CCCC5)c4)c3c2)c1] 877
TABLE 1-continued
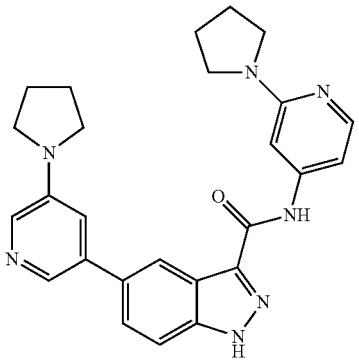 [SMILES: O=C(Nc1ccnc(N2CCCC2)c1)c1n[nH]c2ccc(-c3cncc(N4CCCC4)c3)cc12] 878
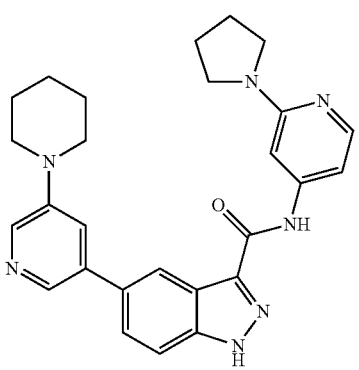 [SMILES: O=C(Nc1ccnc(N2CCCC2)c1)c1n[nH]c2ccc(-c3cncc(N4CCCCC4)c3)cc12] 879
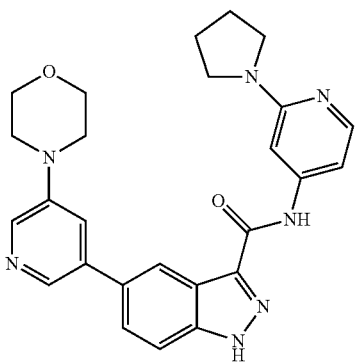 [SMILES: O=C(Nc1ccnc(N2CCCC2)c1)c1n[nH]c2ccc(-c3cncc(N4CCOCC4)c3)cc12] 880
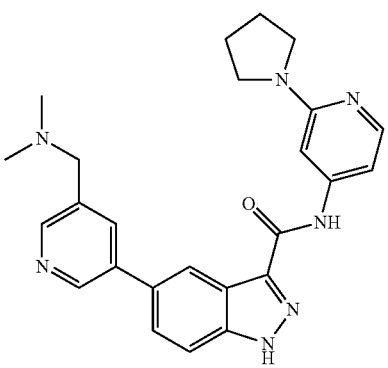 [SMILES: CN(C)Cc1cncc(-c2ccc3[nH]nc(C(=O)Nc4ccnc(N5CCCC5)c4)c3c2)c1] 881

TABLE 1-continued
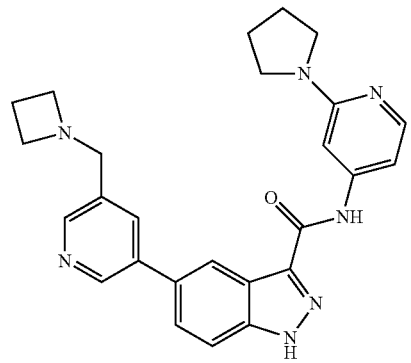 [SMILES: O=C(Nc1ccnc(N2CCCC2)c1)c1n[nH]c2ccc(-c3cncc(CN4CCC4)c3)cc12]
882
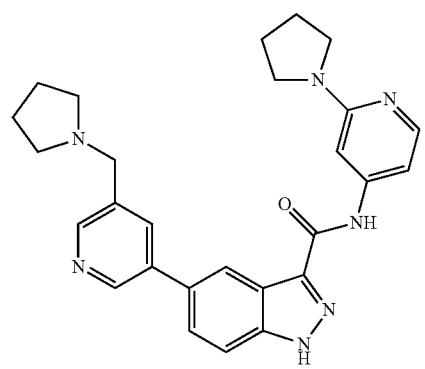 [SMILES: O=C(Nc1ccnc(N2CCCC2)c1)c1n[nH]c2ccc(-c3cncc(CN4CCCC4)c3)cc12]
883
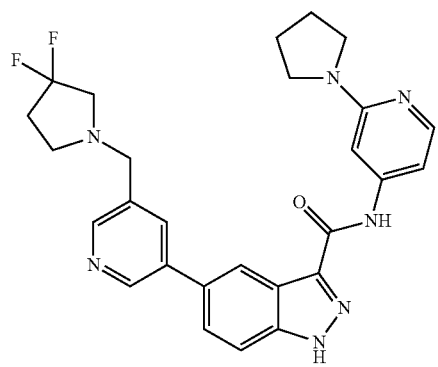 [SMILES: O=C(Nc1ccnc(N2CCCC2)c1)c1n[nH]c2ccc(-c3cncc(CN4CCC(F)(F)C4)c3)cc12]
884
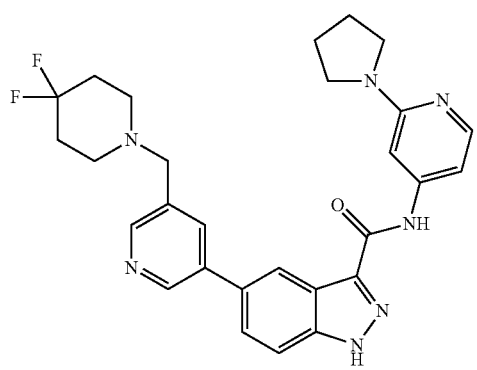 [SMILES: O=C(Nc1ccnc(N2CCCC2)c1)c1n[nH]c2ccc(-c3cncc(CN4CCC(F)(F)CC4)c3)cc12]
885
TABLE 1-continued
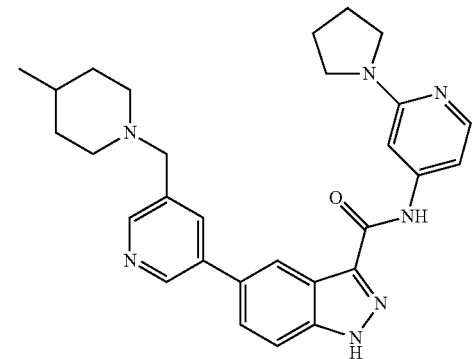 [SMILES: CC1CCN(Cc2cncc(-c3ccc4[nH]nc(C(=O)Nc5ccnc(N6CCCC6)c5)c4c3)c2)CC1]
886
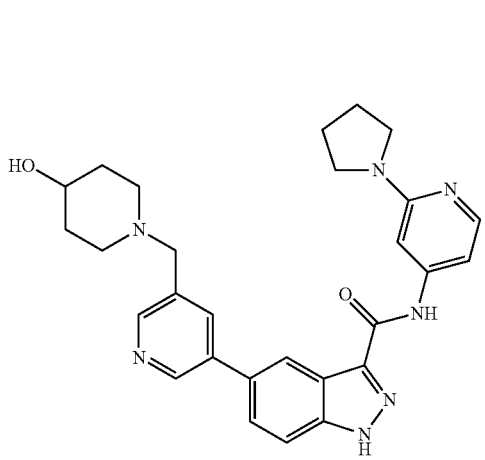 [SMILES: O=C(Nc1ccnc(N2CCCC2)c1)c1n[nH]c2ccc(-c3cncc(CN4CCC(O)CC4)c3)cc12]
887
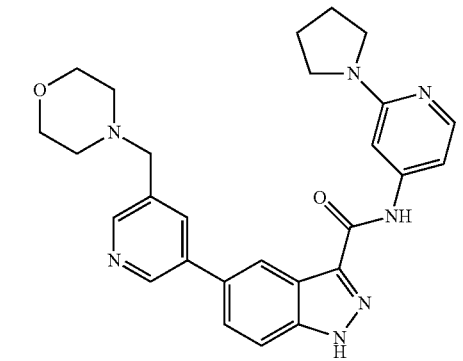 [SMILES: O=C(Nc1ccnc(N2CCCC2)c1)c1n[nH]c2ccc(-c3cncc(CN4CCOCC4)c3)cc12]
888
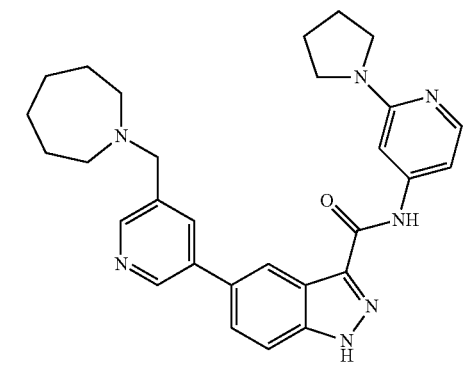 [SMILES: O=C(Nc1ccnc(N2CCCC2)c1)c1n[nH]c2ccc(-c3cncc(CN4CCCCCC4)c3)cc12]
889

TABLE 1-continued

TABLE 1-continued
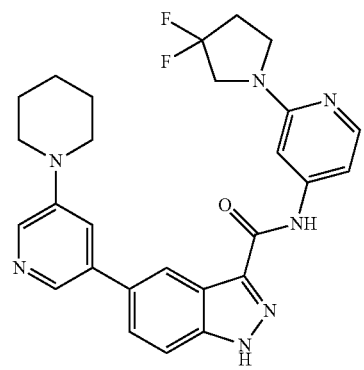 [SMILES: O=C(Nc1ccnc(N2CCC(F)(F)C2)c1)c1n[nH]c2ccc(-c3cncc(N4CCCCC4)c3)cc12] 898
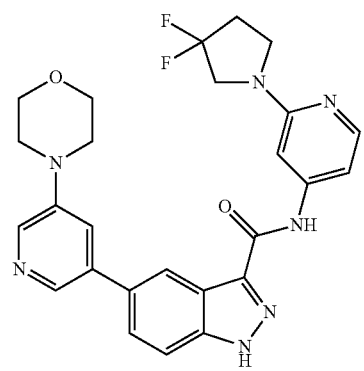 [SMILES: O=C(Nc1ccnc(N2CCC(F)(F)C2)c1)c1n[nH]c2ccc(-c3cncc(N4CCOCC4)c3)cc12] 899
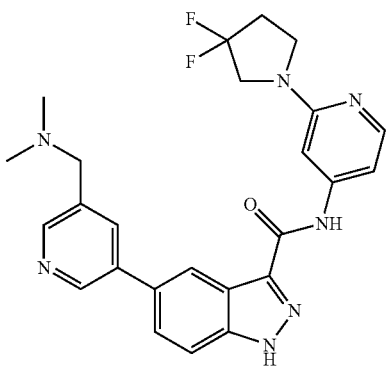 [SMILES: CN(C)Cc1cncc(-c2ccc3[nH]nc(C(=O)Nc4ccnc(N5CCC(F)(F)C5)c4)c3c2)c1] 900
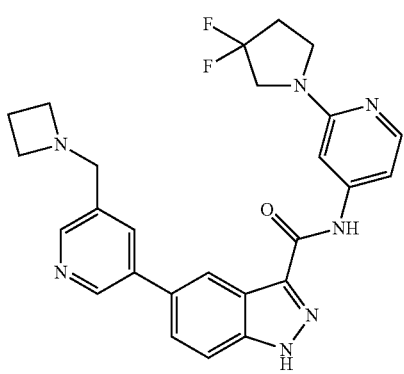 [SMILES: O=C(Nc1ccnc(N2CCC(F)(F)C2)c1)c1n[nH]c2ccc(-c3cncc(CN4CCC4)c3)cc12] 901
TABLE 1-continued
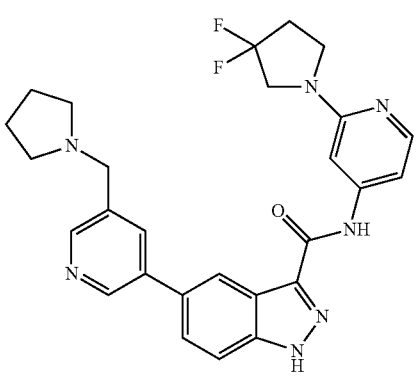 [SMILES: O=C(Nc1ccnc(N2CCC(F)(F)C2)c1)c1n[nH]c2ccc(-c3cncc(CN4CCCC4)c3)cc12] 902
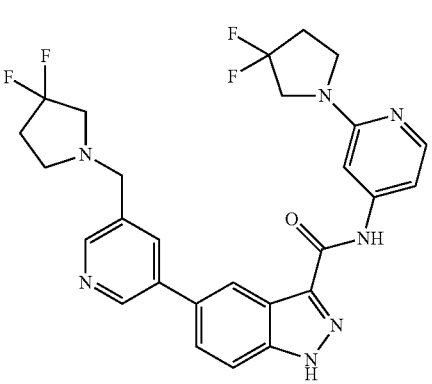 [SMILES: O=C(Nc1ccnc(N2CCC(F)(F)C2)c1)c1n[nH]c2ccc(-c3cncc(CN4CCC(F)(F)C4)c3)cc12] 903
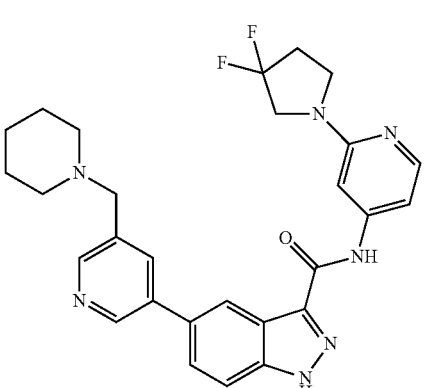 904
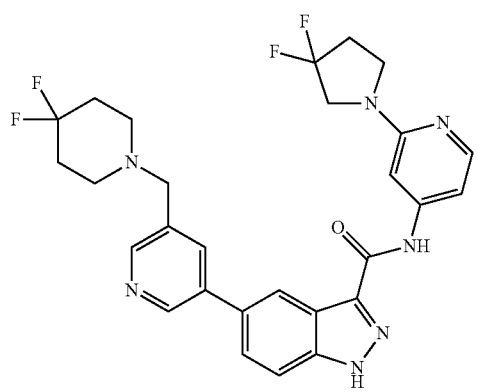 [SMILES: O=C(Nc1ccnc(N2CCC(F)(F)C2)c1)c1n[nH]c2ccc(-c3cncc(CN4CCC(F)(F)CC4)c3)cc12] 905

TABLE 1-continued
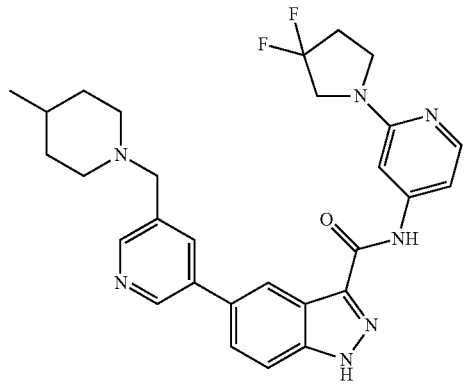 [SMILES: CC1CCN(Cc2cncc(-c3ccc4[nH]nc(C(=O)Nc5ccnc(N6CCC(F)(F)C6)c5)c4c3)c2)CC1] 906
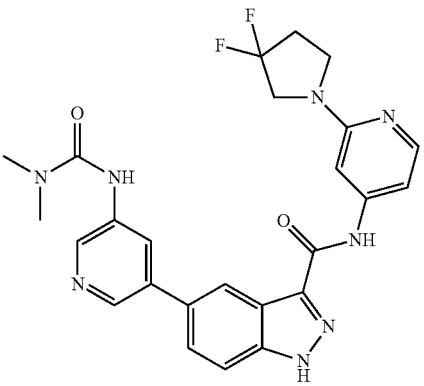 910
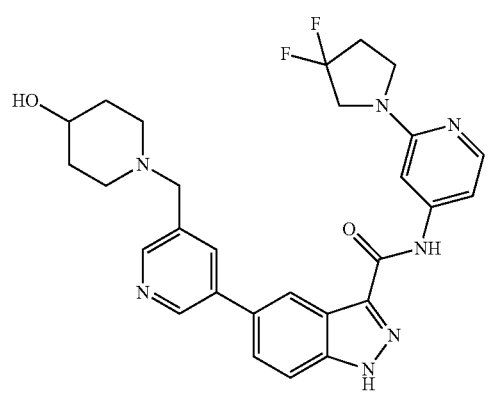 [SMILES: O=C(Nc1ccnc(N2CCC(F)(F)C2)c1)c1n[nH]c2ccc(-c3cncc(CN4CCC(O)CC4)c3)cc12] 907
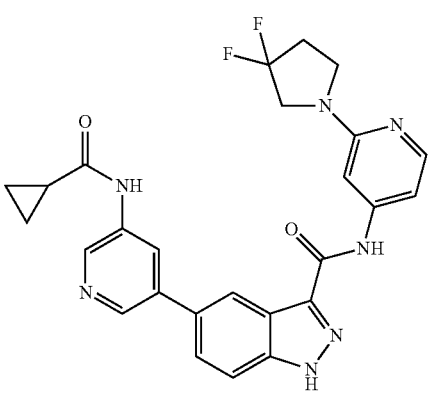 911
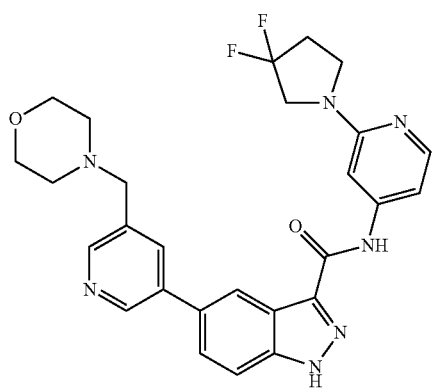 [SMILES: O=C(Nc1ccnc(N2CCC(F)(F)C2)c1)c1n[nH]c2ccc(-c3cncc(CN4CCOCC4)c3)cc12] 908
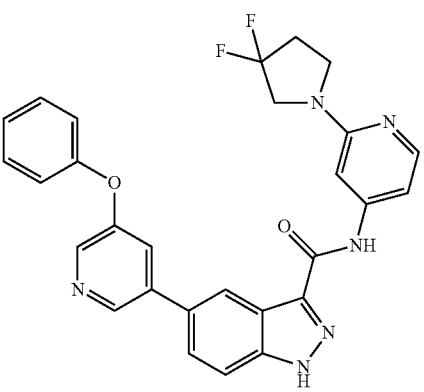 912
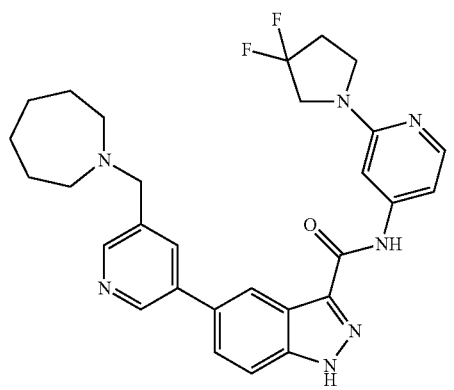 [SMILES: O=C(Nc1ccnc(N2CCC(F)(F)C2)c1)c1n[nH]c2ccc(-c3cncc(CN4CCCCCC4)c3)cc12] 909
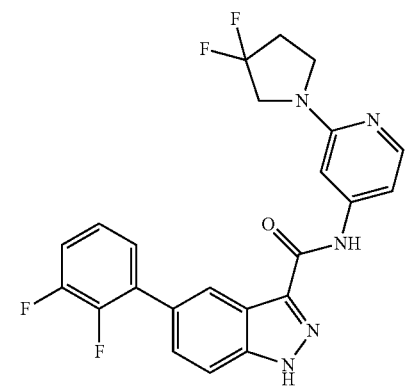 [SMILES: O=C(Nc1ccnc(N2CCC(F)(F)C2)c1)c1n[nH]c2ccc(-c3cccc(F)c3F)cc12] 913

TABLE 1-continued
| | |
|---|---|
| 914 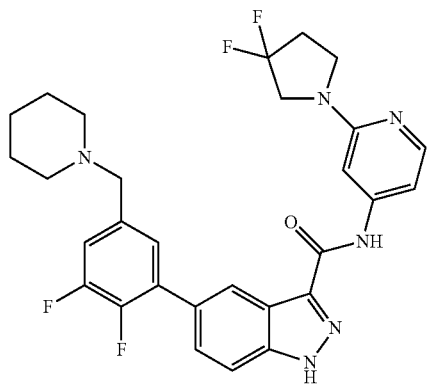 [SMILES: O=C(Nc1ccnc(N2CCC(F)(F)C2)c1)c1n[nH]c2ccc(-c3cc(CN4CCCCC4)cc(F)c3F)cc12] | 918 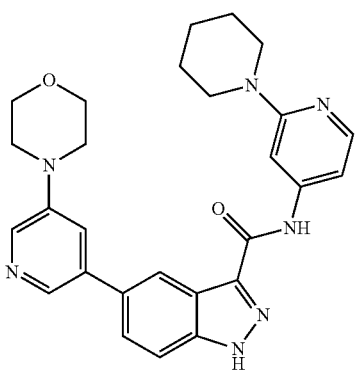 |
| 915 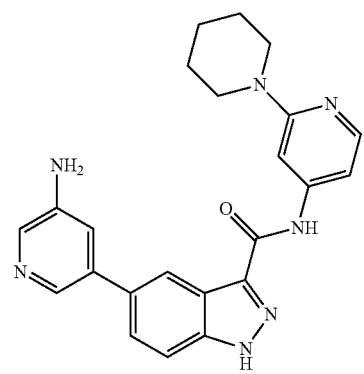 [SMILES: Nc1cncc(-c2ccc3[nH]nc(C(=O)Nc4ccnc(N5CCCCC5)c4)c3c2)c1] | 919 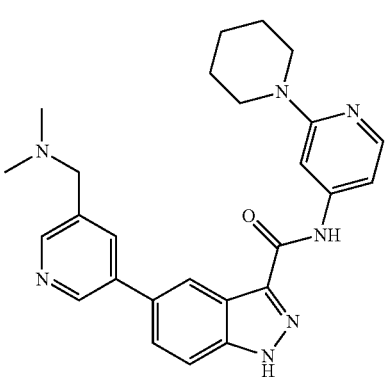 |
| 916 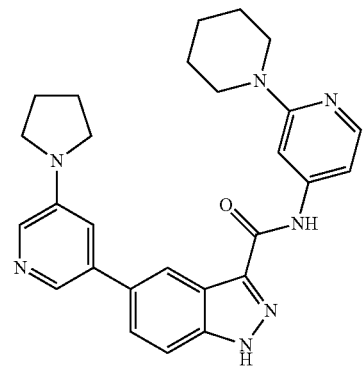 [SMILES: O=C(Nc1ccnc(N2CCCCC2)c1)c1n[nH]c2ccc(-c3cncc(N4CCCC4)c3)cc12] | 920 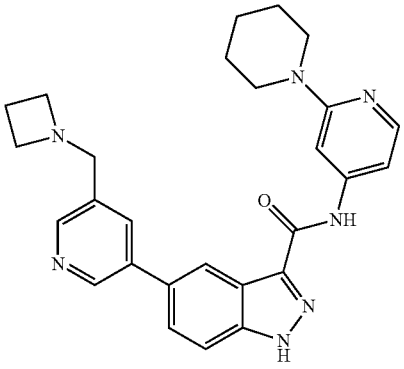 |
| 917 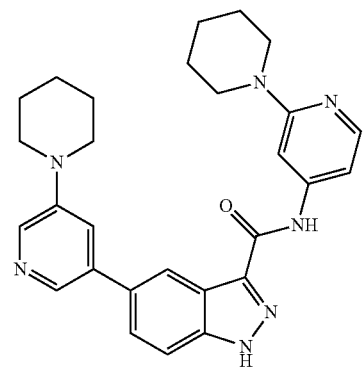 [SMILES: O=C(Nc1ccnc(N2CCCCC2)c1)c1n[nH]c2ccc(-c3cncc(N4CCCCC4)c3)cc12] | 921 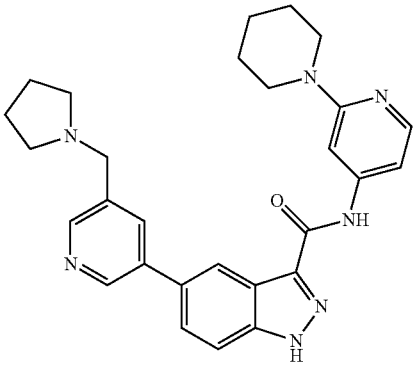 [SMILES: O=C(Nc1ccnc(N2CCCCC2)c1)c1n[nH]c2ccc(-c3cncc(CN4CCCC4)c3)cc12] |

TABLE 1-continued
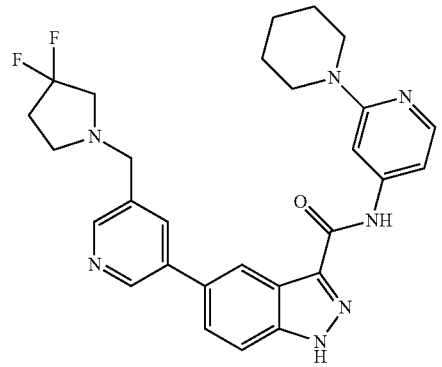 [SMILES: O=C(Nc1ccnc(N2CCCCC2)c1)c1n[nH]c2ccc(-c3cncc(CN4CCC(F)(F)C4)c3)cc12]
922
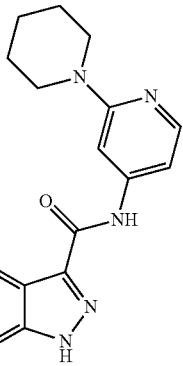
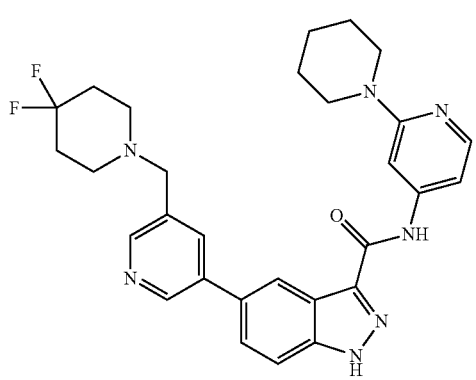 [SMILES: O=C(Nc1ccnc(N2CCCCC2)c1)c1n[nH]c2ccc(-c3cncc(CN4CCC(F)(F)CC4)c3)cc12]
923
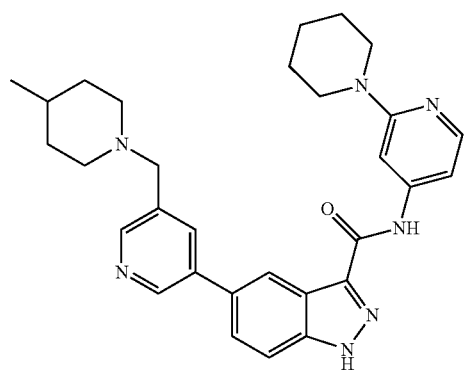 [SMILES: CC1CCN(Cc2cncc(-c3ccc4[nH]nc(C(=O)Nc5ccnc(N6CCCCC6)c5)c4c3)c2)CC1]
924
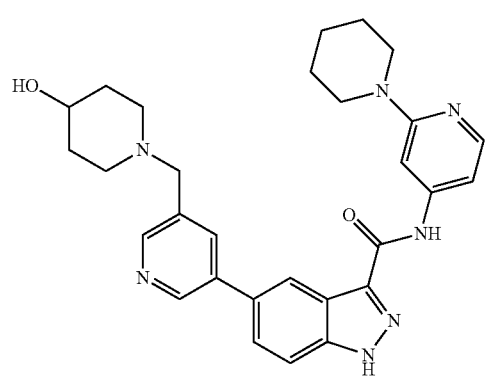 [SMILES: O=C(Nc1ccnc(N2CCCCC2)c1)c1n[nH]c2ccc(-c3cncc(CN4CCC(O)CC4)c3)cc12]
925
TABLE 1-continued
926
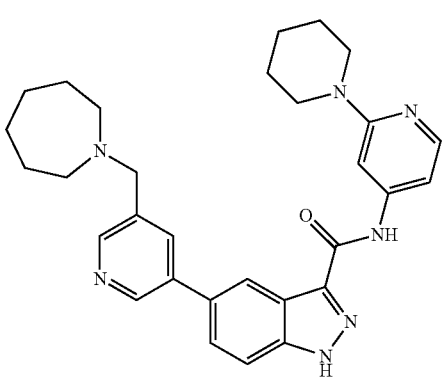 [SMILES: O=C(Nc1ccnc(N2CCCCC2)c1)c1n[nH]c2ccc(-c3cncc(CN4CCCCCC4)c3)cc12]
927
928
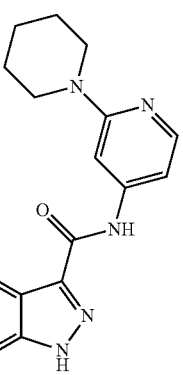
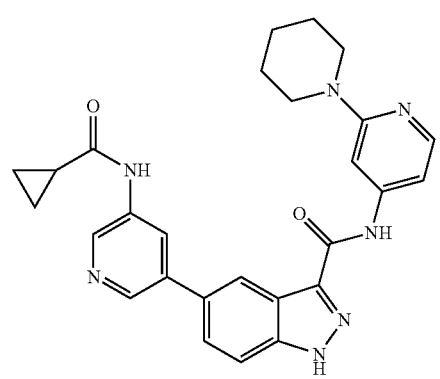 [SMILES: O=C(Nc1ccnc(N2CCCCC2)c1)c1n[nH]c2ccc(-c3cncc(NC(=O)C4CC4)c3)cc12]
929

TABLE 1-continued
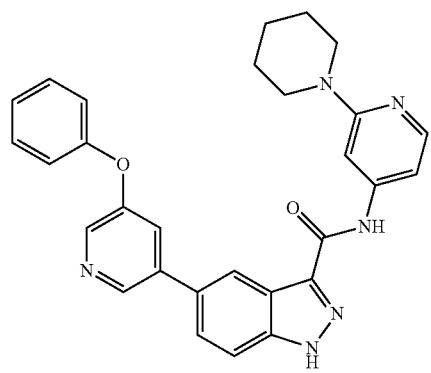 [SMILES: O=C(Nc1ccnc(N2CCCCC2)c1)c1n[nH]c2ccc(-c3cncc(Oc4ccccc4)c3)cc12]
930
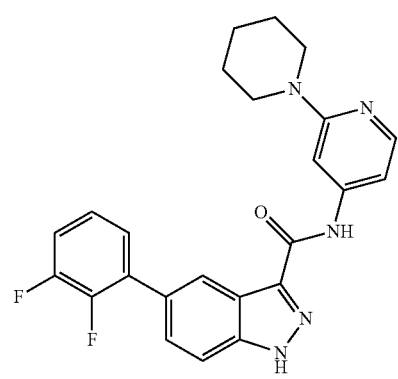 [SMILES: O=C(Nc1ccnc(N2CCCCC2)c1)c1n[nH]c2ccc(-c3cccc(F)c3F)cc12]
931
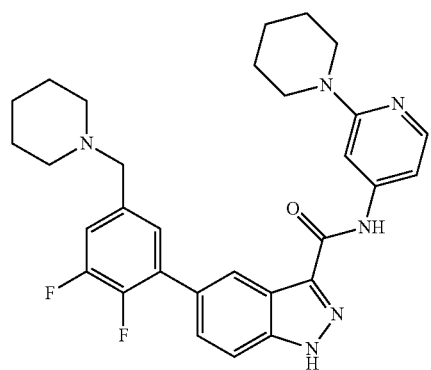 [SMILES: O=C(Nc1ccnc(N2CCCCC2)c1)c1n[nH]c2ccc(-c3cc(CN4CCCCC4)cc(F)c3F)cc12]
932
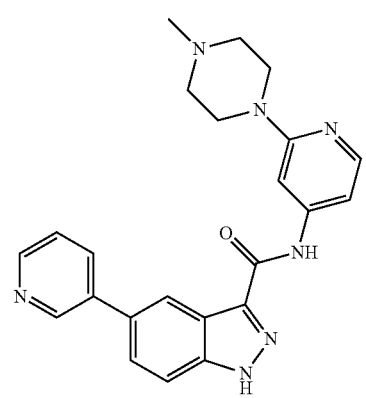 [SMILES: CN1CCN(c2cc(NC(=O)c3n[nH]c4ccc(-c5cccnc5)cc34)ccn2)CC1]
933
TABLE 1-continued
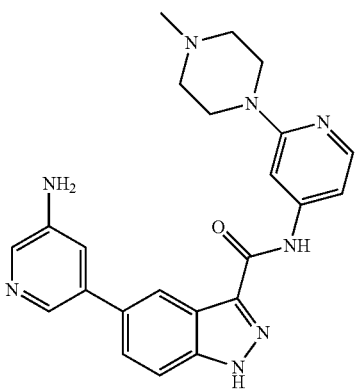 [SMILES: CN1CCN(c2cc(NC(=O)c3n[nH]c4ccc(-c5cncc(N)c5)cc34)ccn2)CC1]
934
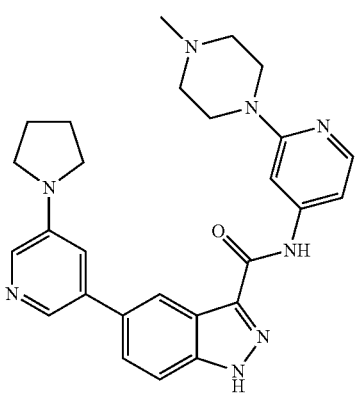 [SMILES: CN1CCN(c2cc(NC(=O)c3n[nH]c4ccc(-c5cncc(N6CCCC6)c5)cc34)ccn2)CC1]
935
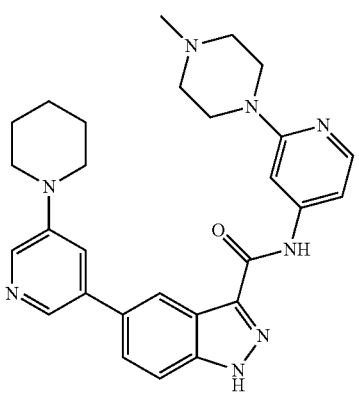 [SMILES: CN1CCN(c2cc(NC(=O)c3n[nH]c4ccc(-c5cncc(N6CCCCC6)c5)cc34)ccn2)CC1]
936
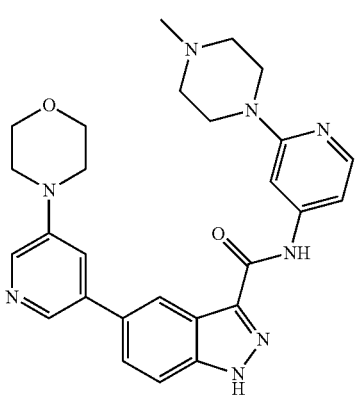 [SMILES: CN1CCN(c2cc(NC(=O)c3n[nH]c4ccc(-c5cncc(N6CCOCC6)c5)cc34)ccn2)CC1]
937

TABLE 1-continued
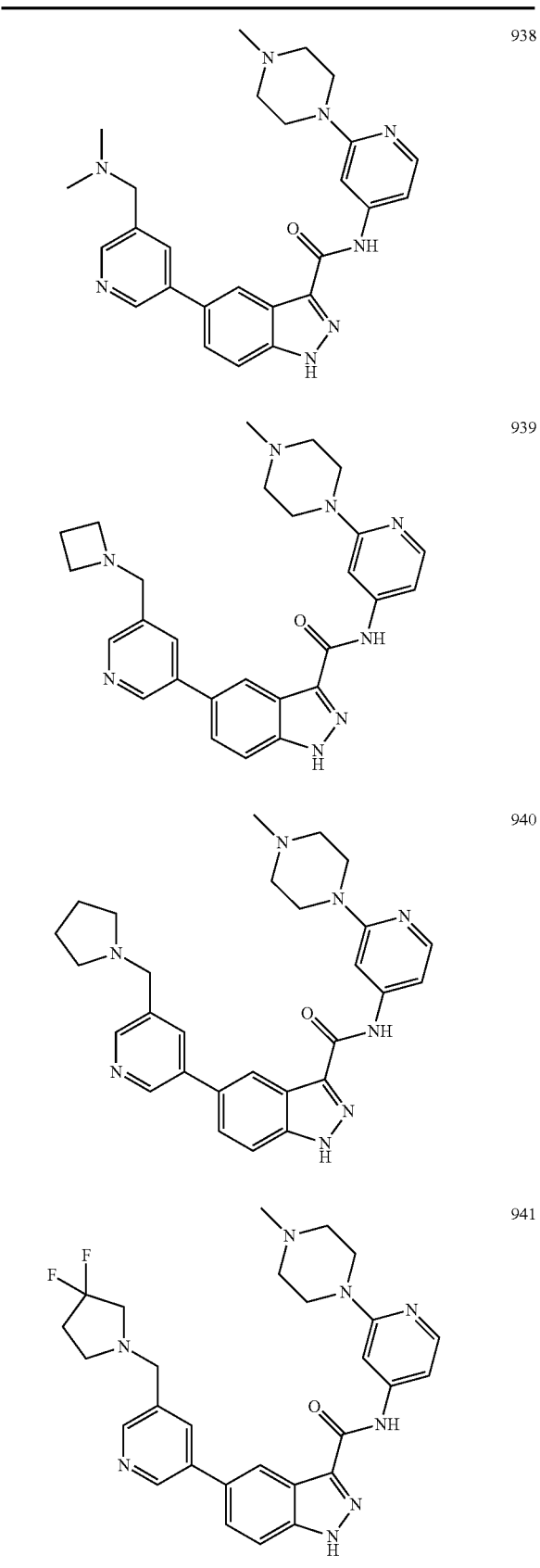
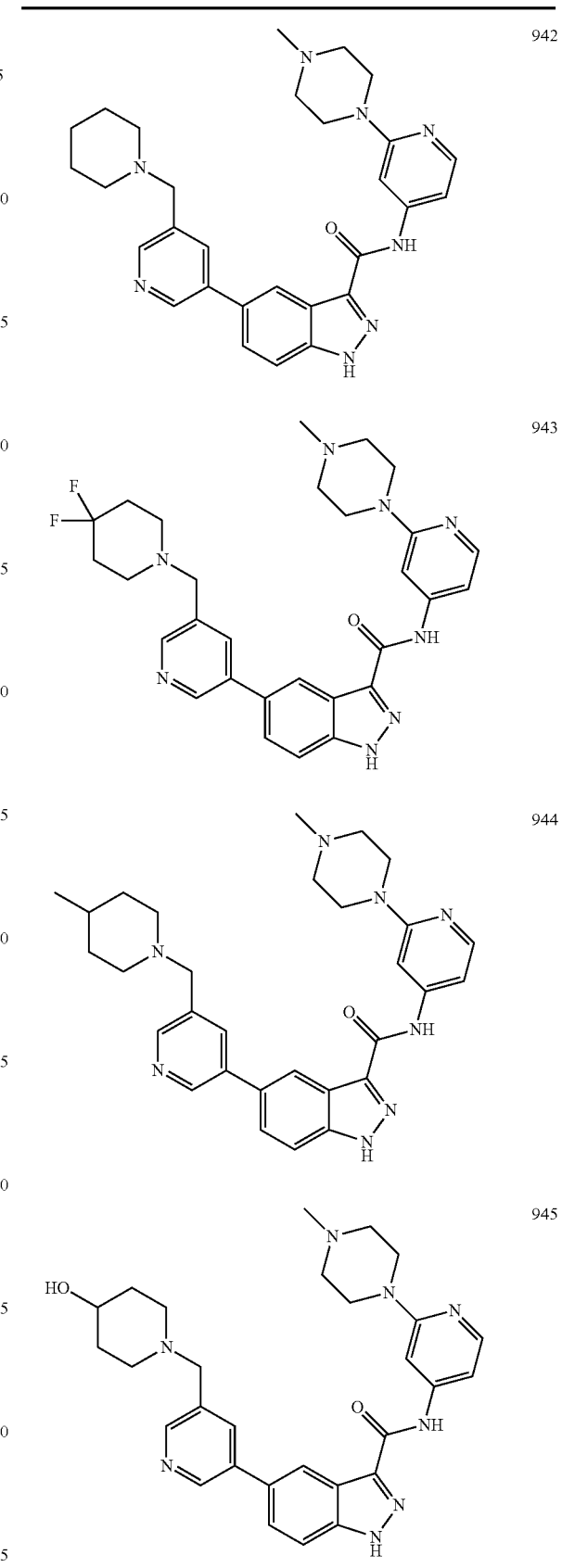

TABLE 1-continued
946
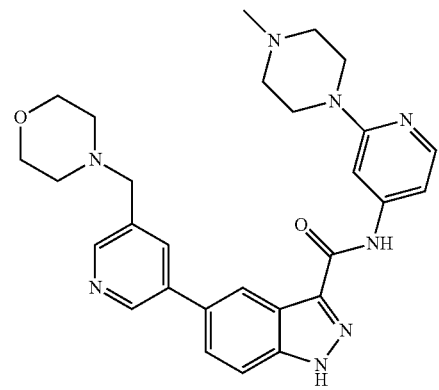 [SMILES: CN1CCN(c2cc(NC(=O)c3n[nH]c4ccc(-c5cncc(CN6CCOCC6)c5)cc34)ccn2)CC1]
947
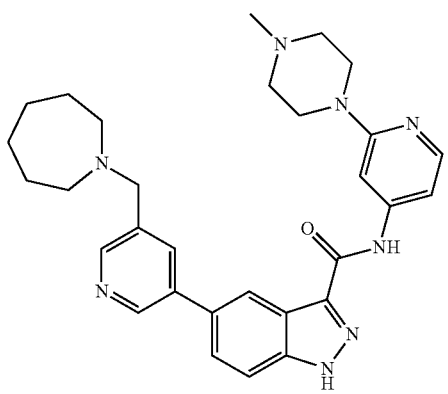 [SMILES: CN1CCN(c2cc(NC(=O)c3n[nH]c4ccc(-c5cncc(CN6CCCCCC6)c5)cc34)ccn2)CC1]
948
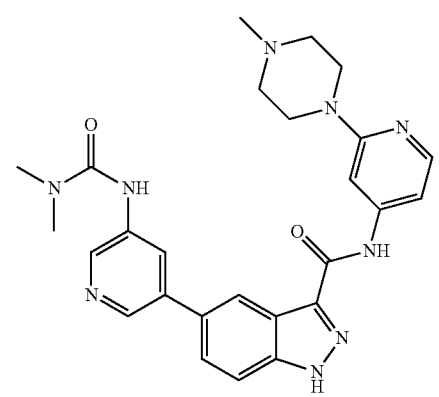 [SMILES: CN1CCN(c2cc(NC(=O)c3n[nH]c4ccc(-c5cncc(NC(=O)N(C)C)c5)cc34)ccn2)CC1]
949
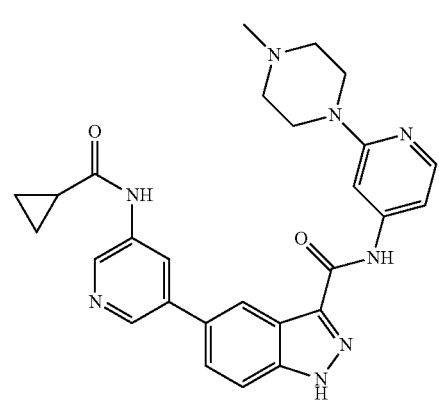 [SMILES: CN1CCN(c2cc(NC(=O)c3n[nH]c4ccc(-c5cncc(NC(=O)C6CC6)c5)cc34)ccn2)CC1]
TABLE 1-continued
950
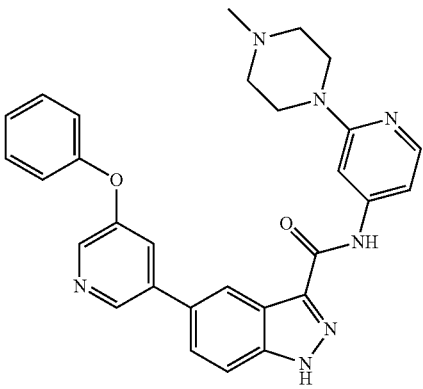 [SMILES: CN1CCN(c2cc(NC(=O)c3n[nH]c4ccc(-c5cncc(Oc6ccccc6)c5)cc34)ccn2)CC1]
951
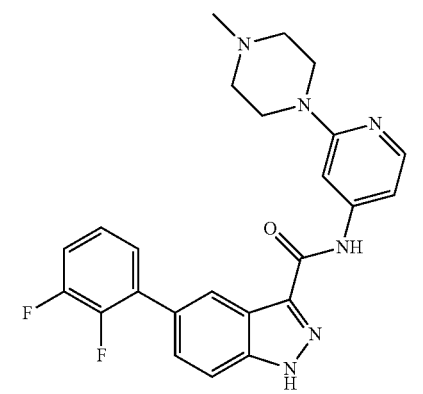 [SMILES: CN1CCN(c2cc(NC(=O)c3n[nH]c4ccc(-c5cccc(F)c5F)cc34)ccn2)CC1]
952
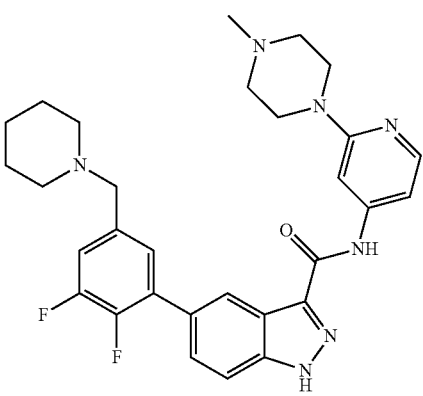 [SMILES: CN1CCN(c2cc(NC(=O)c3n[nH]c4ccc(-c5cc(CN6CCCCC6)cc(F)c5F)cc34)ccn2)CC1]
953
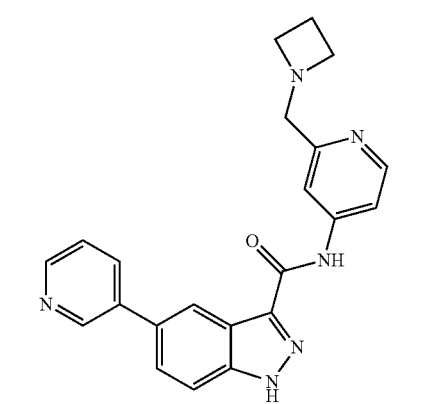 [SMILES: O=C(Nc1ccnc(CN2CCC2)c1)c1n[nH]c2ccc(-c3cccnc3)cc12]

TABLE 1-continued
954 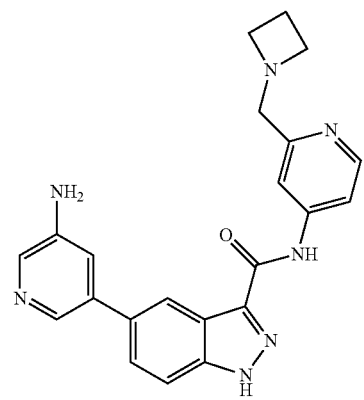 [SMILES: Nc1cncc(-c2ccc3[nH]nc(C(=O)Nc4ccnc(CN5CCC5)c4)c3c2)c1]
955 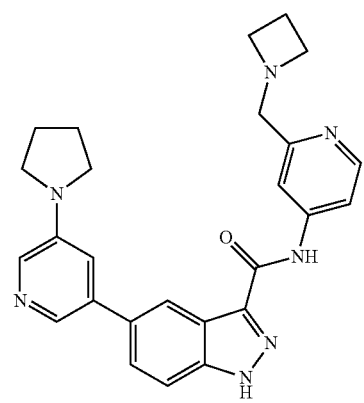 [SMILES: O=C(Nc1ccnc(CN2CCC2)c1)c1n[nH]c2ccc(-c3cncc(N4CCCC4)c3)cc12]
956 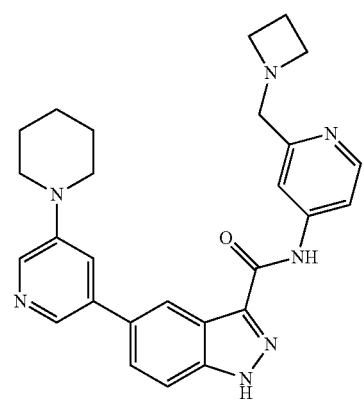 [SMILES: O=C(Nc1ccnc(CN2CCC2)c1)c1n[nH]c2ccc(-c3cncc(N4CCCCC4)c3)cc12]
957 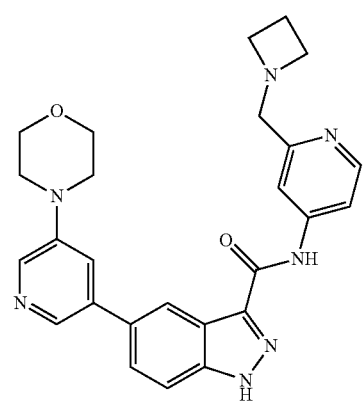 [SMILES: O=C(Nc1ccnc(CN2CCC2)c1)c1n[nH]c2ccc(-c3cncc(N4CCOCC4)c3)cc12]
TABLE 1-continued
958 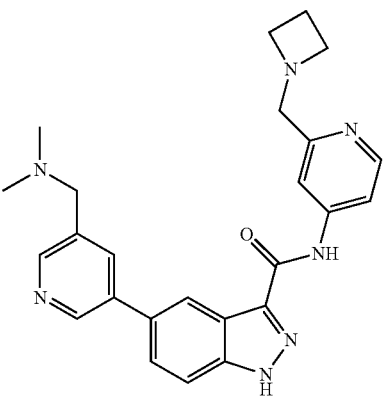 [SMILES: CN(C)Cc1cncc(-c2ccc3[nH]nc(C(=O)Nc4ccnc(CN5CCC5)c4)c3c2)c1]
959 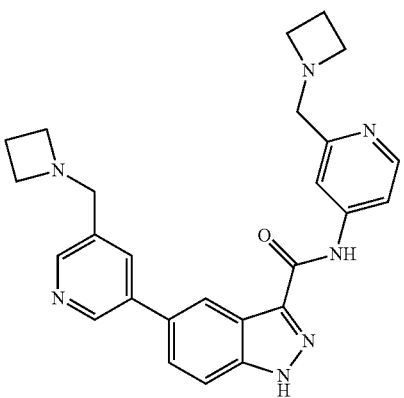 [SMILES: O=C(Nc1ccnc(CN2CCC2)c1)c1n[nH]c2ccc(-c3cncc(CN4CCC4)c3)cc12]
960 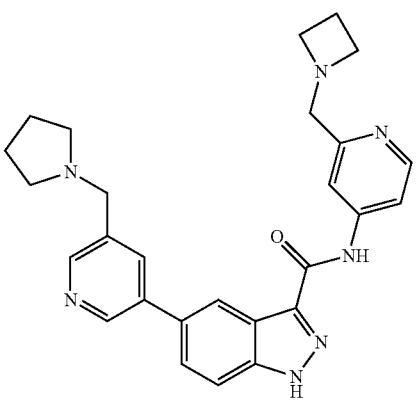 [SMILES: O=C(Nc1ccnc(CN2CCC2)c1)c1n[nH]c2ccc(-c3cncc(CN4CCCC4)c3)cc12]
961 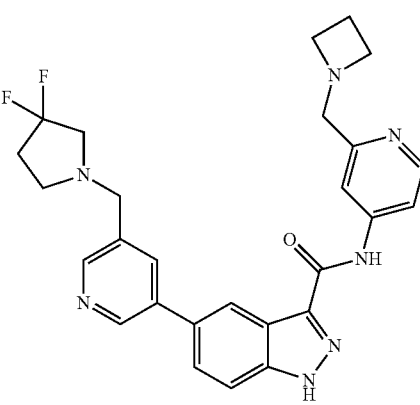

TABLE 1-continued
962 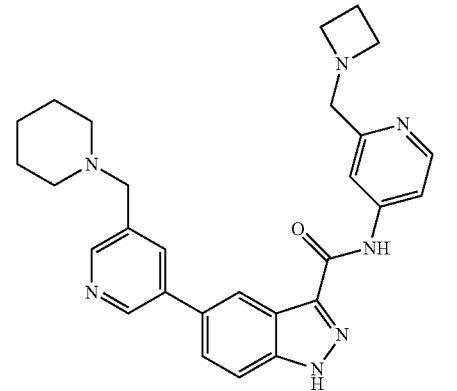 [SMILES: O=C(Nc1ccnc(CN2CCC2)c1)c1n[nH]c2ccc(-c3cncc(CN4CCCCC4)c3)cc12]
963 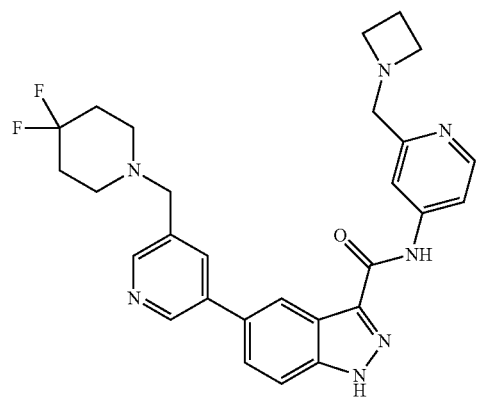 [SMILES: O=C(Nc1ccnc(CN2CCC2)c1)c1n[nH]c2ccc(-c3cncc(CN4CCC(F)(F)CC4)c3)cc12]
964 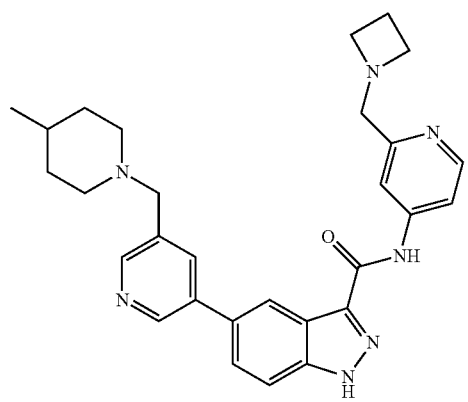 [SMILES: CC1CCN(Cc2cncc(-c3ccc4[nH]nc(C(=O)Nc5ccnc(CN6CCC6)c5)c4c3)c2)CC1]
965 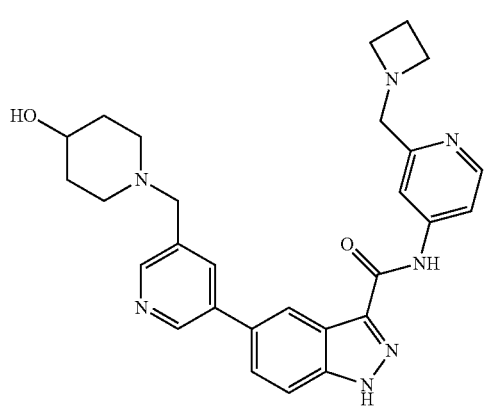 [SMILES: O=C(Nc1ccnc(CN2CCC2)c1)c1n[nH]c2ccc(-c3cncc(CN4CCC(O)CC4)c3)cc12]
TABLE 1-continued
966 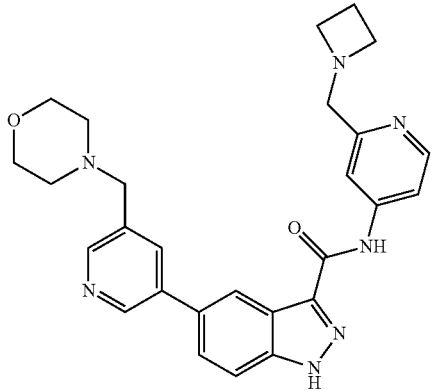 [SMILES: O=C(Nc1ccnc(CN2CCC2)c1)c1n[nH]c2ccc(-c3cncc(CN4CCOCC4)c3)cc12]
967 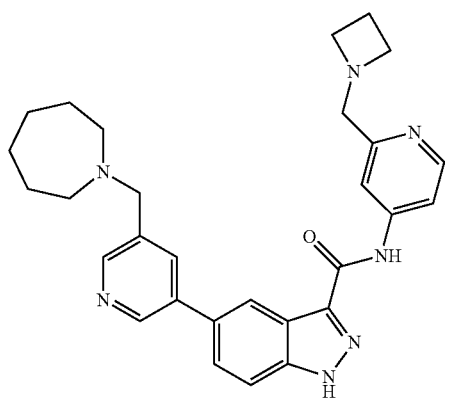 [SMILES: O=C(Nc1ccnc(CN2CCC2)c1)c1n[nH]c2ccc(-c3cncc(CN4CCCCCC4)c3)cc12]
968 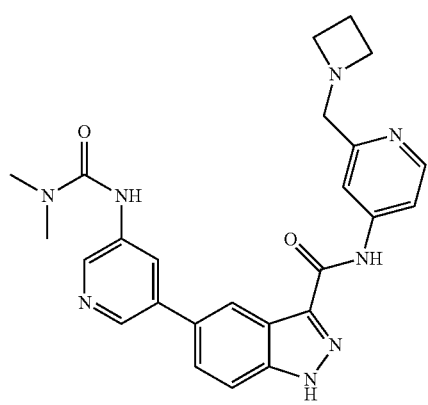 [SMILES: CN(C)C(=O)Nc1cncc(-c2ccc3[nH]nc(C(=O)Nc4ccnc(CN5CCC5)c4)c3c2)c1]
969 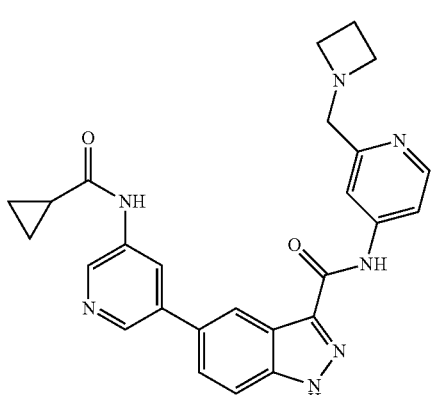

TABLE 1-continued
970 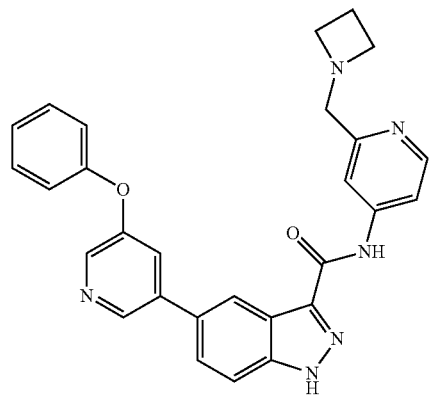 [SMILES: O=C(Nc1ccnc(CN2CCC2)c1)c1n[nH]c2ccc(-c3cncc(Oc4ccccc4)c3)cc12]
971 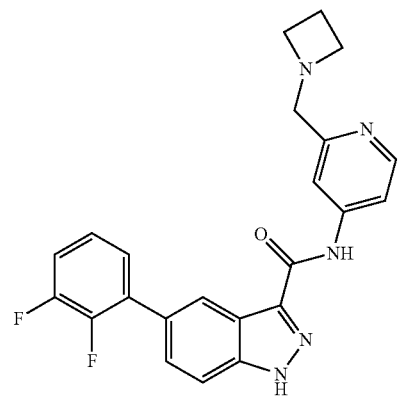 [SMILES: O=C(Nc1ccnc(CN2CCC2)c1)c1n[nH]c2ccc(-c3cccc(F)c3F)cc12]
972 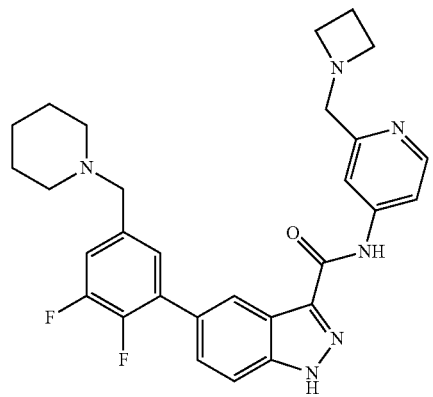 [SMILES: O=C(Nc1ccnc(CN2CCC2)c1)c1n[nH]c2ccc(-c3cc(CN4CCCCC4)cc(F)c3F)cc12]
973 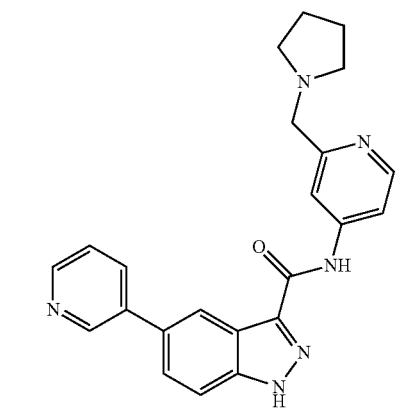 [SMILES: O=C(Nc1ccnc(CN2CCCC2)c1)c1n[nH]c2ccc(-c3cccnc3)cc12]
TABLE 1-continued
974 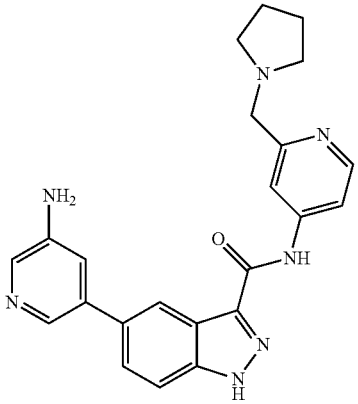 [SMILES: Nc1cncc(-c2ccc3[nH]nc(C(=O)Nc4ccnc(CN5CCCC5)c4)c3c2)c1]
975 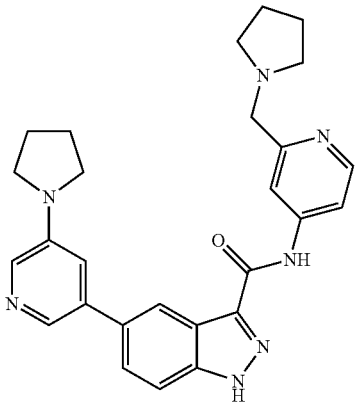 [SMILES: O=C(Nc1ccnc(CN2CCCC2)c1)c1n[nH]c2ccc(-c3cncc(N4CCCC4)c3)cc12]
976 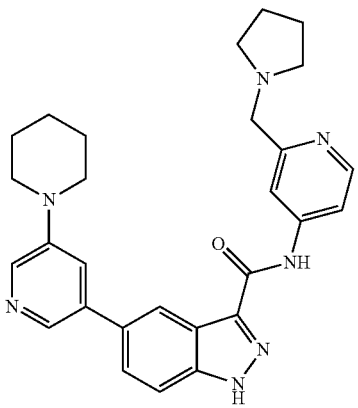 [SMILES: O=C(Nc1ccnc(CN2CCCC2)c1)c1n[nH]c2ccc(-c3cncc(N4CCCCC4)c3)cc12]
977 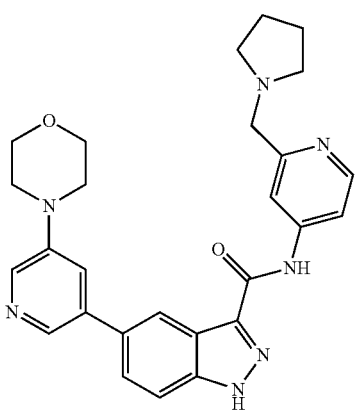 [SMILES: O=C(Nc1ccnc(CN2CCCC2)c1)c1n[nH]c2ccc(-c3cncc(N4CCOCC4)c3)cc12]

TABLE 1-continued

TABLE 1-continued
986 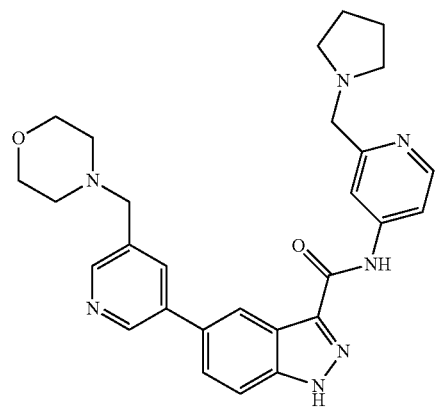 [SMILES: O=C(Nc1ccnc(CN2CCCC2)c1)c1n[nH]c2ccc(-c3cncc(CN4CCOCC4)c3)cc12]
987 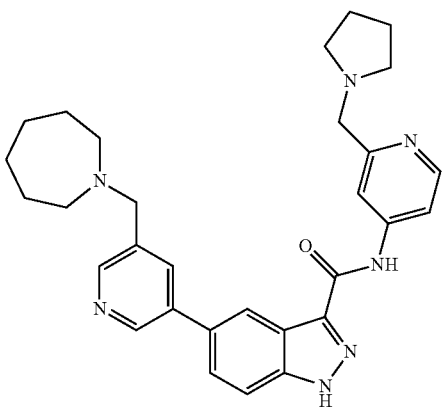 [SMILES: O=C(Nc1ccnc(CN2CCCC2)c1)c1n[nH]c2ccc(-c3cncc(CN4CCCCCC4)c3)cc12]
988 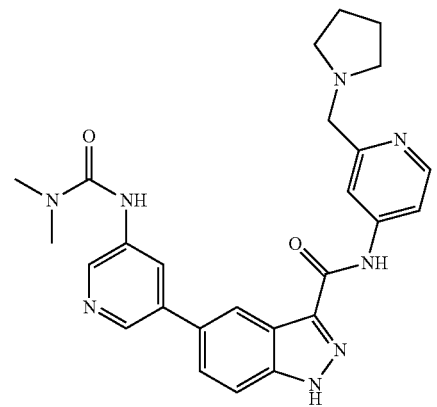 [SMILES: CN(C)C(=O)Nc1cncc(-c2ccc3[nH]nc(C(=O)Nc4ccnc(CN5CCCC5)c4)c3c2)c1]
989 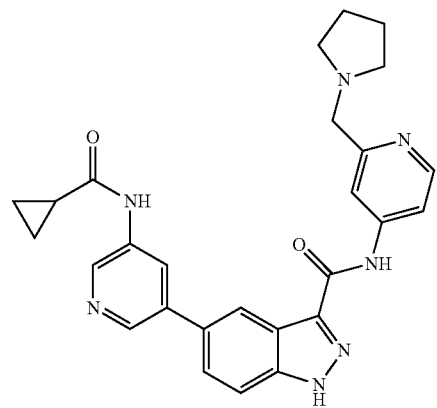 [SMILES: O=C(Nc1ccnc(CN2CCCC2)c1)c1n[nH]c2ccc(-c3cncc(NC(=O)C4CC4)c3)cc12]
TABLE 1-continued
990 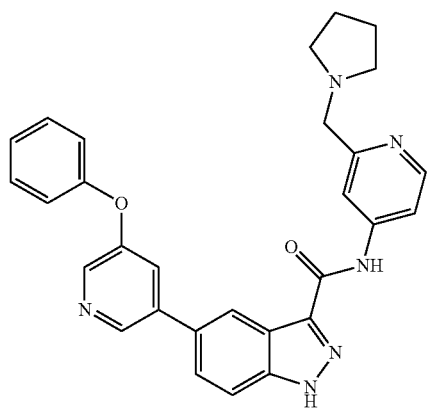 [SMILES: O=C(Nc1ccnc(CN2CCCC2)c1)c1n[nH]c2ccc(-c3cncc(Oc4ccccc4)c3)cc12]
991 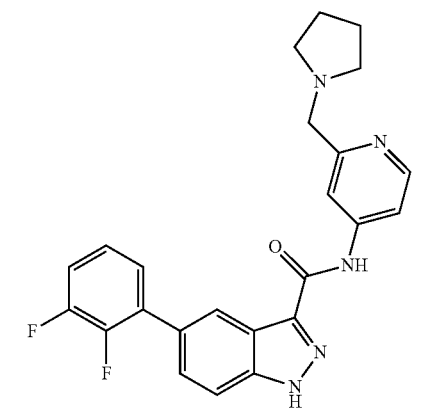 [SMILES: O=C(Nc1ccnc(CN2CCCC2)c1)c1n[nH]c2ccc(-c3cccc(F)c3F)cc12]
992 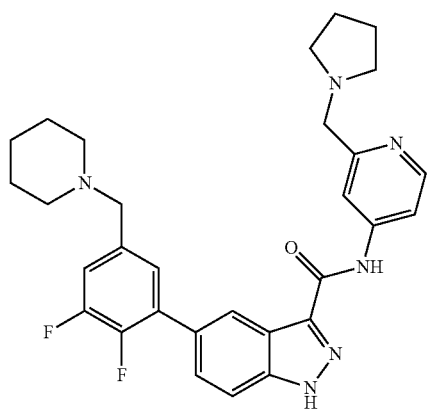 [SMILES: O=C(Nc1ccnc(CN2CCCC2)c1)c1n[nH]c2ccc(-c3cc(CN4CCCCC4)cc(F)c3F)cc12]
993 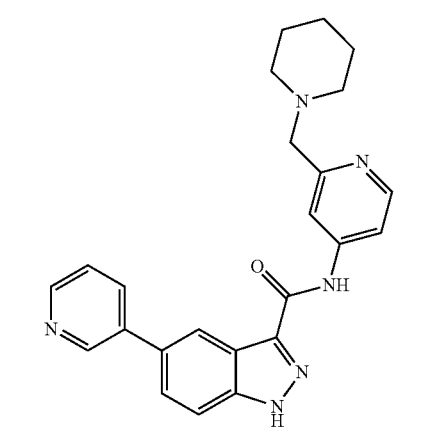 [SMILES: O=C(Nc1ccnc(CN2CCCCC2)c1)c1n[nH]c2ccc(-c3cccnc3)cc12]

TABLE 1-continued
994
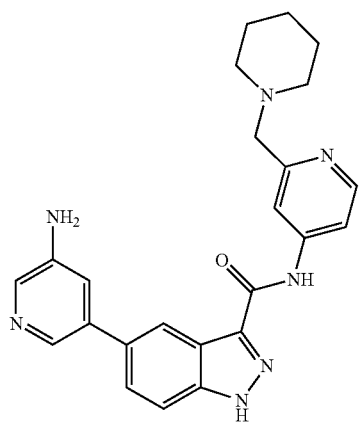 [SMILES: Nc1cncc(-c2ccc3[nH]nc(C(=O)Nc4ccnc(CN5CCCCC5)c4)c3c2)c1]
995
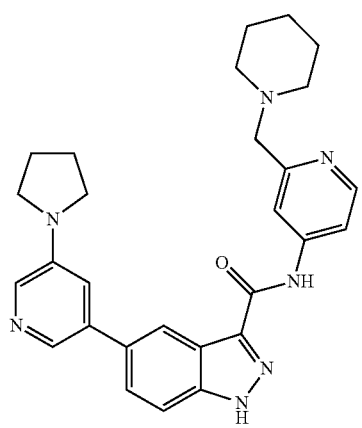 [SMILES: O=C(Nc1ccnc(CN2CCCCC2)c1)c1n[nH]c2ccc(-c3cncc(N4CCCC4)c3)cc12]
996
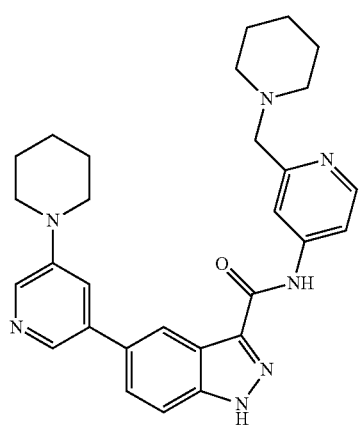 [SMILES: O=C(Nc1ccnc(CN2CCCCC2)c1)c1n[nH]c2ccc(-c3cncc(N4CCCCC4)c3)cc12]
TABLE 1-continued
997
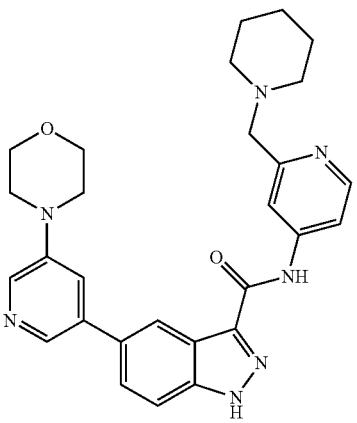 [SMILES: O=C(Nc1ccnc(CN2CCCCC2)c1)c1n[nH]c2ccc(-c3cncc(N4CCOCC4)c3)cc12]
998
999
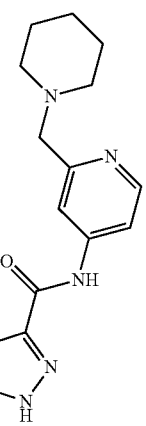

TABLE 1-continued
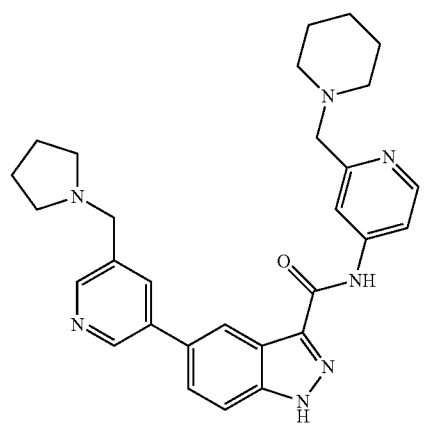 [SMILES: O=C(Nc1ccnc(CN2CCCCC2)c1)c1n[nH]c2ccc(-c3cncc(CN4CCCC4)c3)cc12]
1000
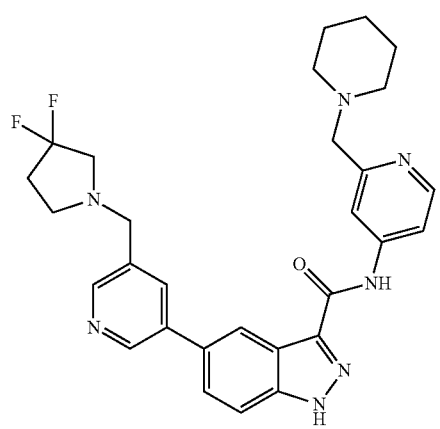 [SMILES: O=C(Nc1ccnc(CN2CCCCC2)c1)c1n[nH]c2ccc(-c3cncc(CN4CCC(F)(F)C4)c3)cc12]
1001
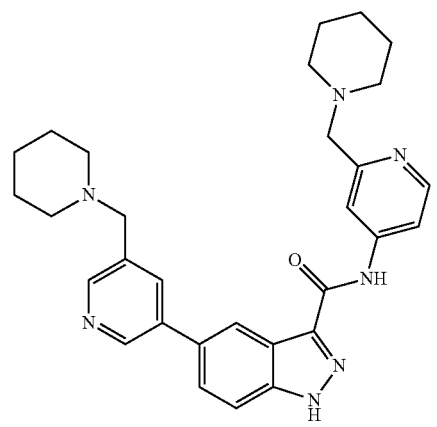 [SMILES: O=C(Nc1ccnc(CN2CCCCC2)c1)c1n[nH]c2ccc(-c3cncc(CN4CCCCC4)c3)cc12]
1002
TABLE 1-continued
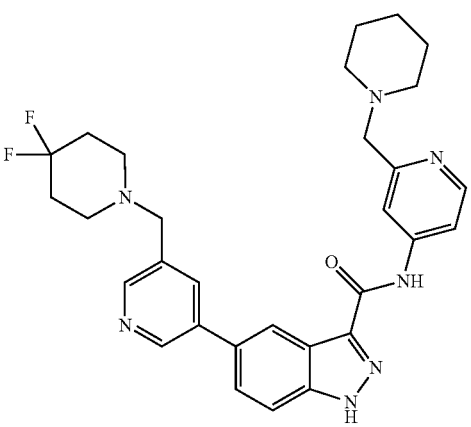 [SMILES: O=C(Nc1ccnc(CN2CCCCC2)c1)c1n[nH]c2ccc(-c3cncc(CN4CCC(F)(F)CC4)c3)cc12]
1003
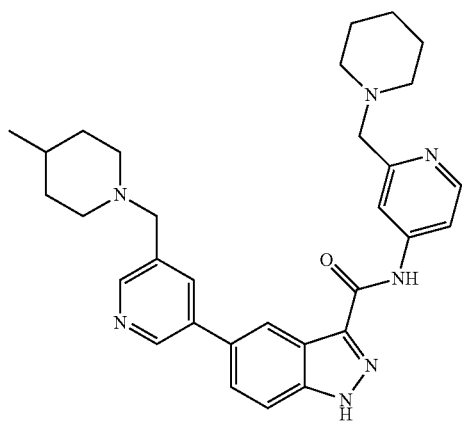 [SMILES: CC1CCN(Cc2cncc(-c3ccc4[nH]nc(C(=O)Nc5ccnc(CN6CCCCC6)c5)c4c3)c2)CC1]
1004
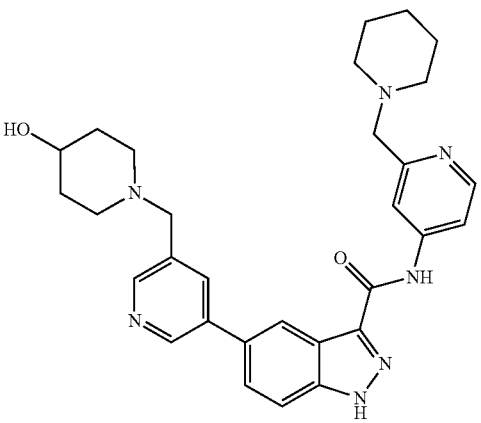 [SMILES: O=C(Nc1ccnc(CN2CCCCC2)c1)c1n[nH]c2ccc(-c3cncc(CN4CCC(O)CC4)c3)cc12]
1005

TABLE 1-continued
1006
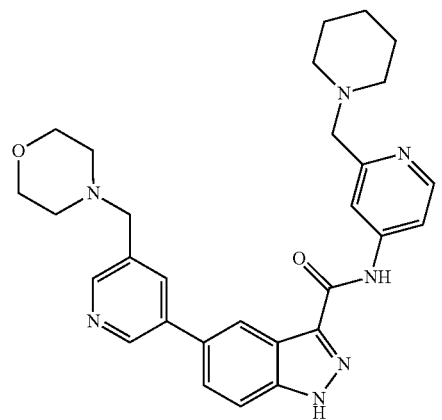 [SMILES: O=C(Nc1ccnc(CN2CCCCC2)c1)c1n[nH]c2ccc(-c3cncc(CN4CCOCC4)c3)cc12]
1007
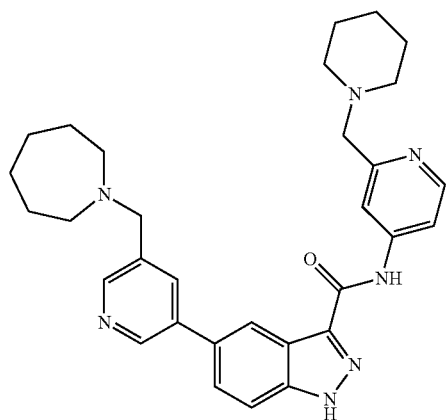 [SMILES: O=C(Nc1ccnc(CN2CCCCC2)c1)c1n[nH]c2ccc(-c3cncc(CN4CCCCCC4)c3)cc12]
1008
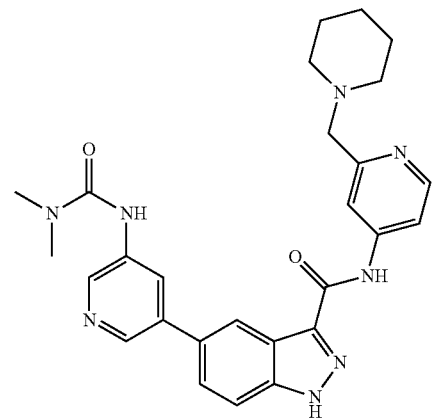 [SMILES: CN(C)C(=O)Nc1cncc(-c2ccc3[nH]nc(C(=O)Nc4ccnc(CN5CCCCC5)c4)c3c2)c1]
TABLE 1-continued
1009
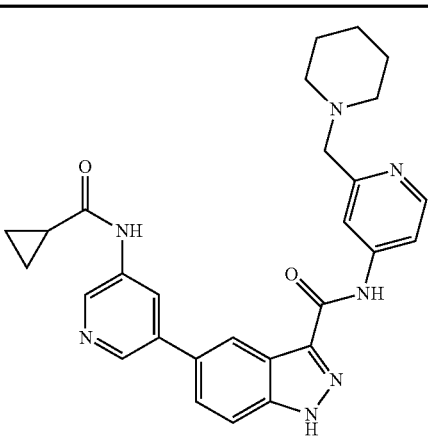
1010
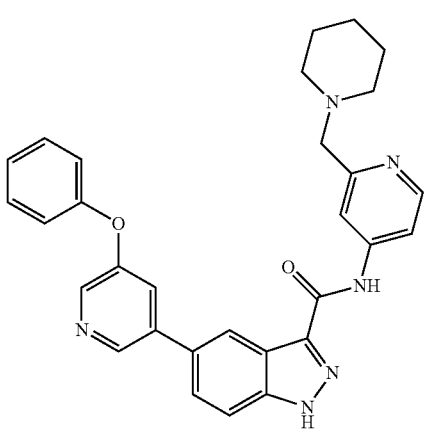 [SMILES: O=C(Nc1ccnc(CN2CCCCC2)c1)c1n[nH]c2ccc(-c3cncc(Oc4ccccc4)c3)cc12]
1011
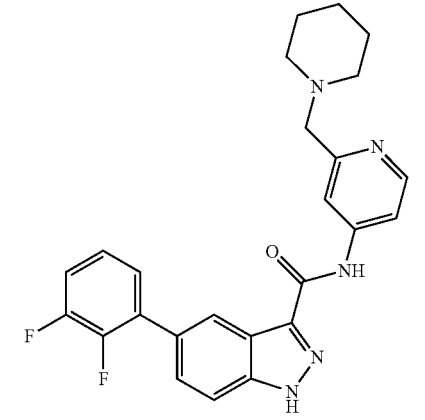 [SMILES: O=C(Nc1ccnc(CN2CCCCC2)c1)c1n[nH]c2ccc(-c3cccc(F)c3F)cc12]

TABLE 1-continued
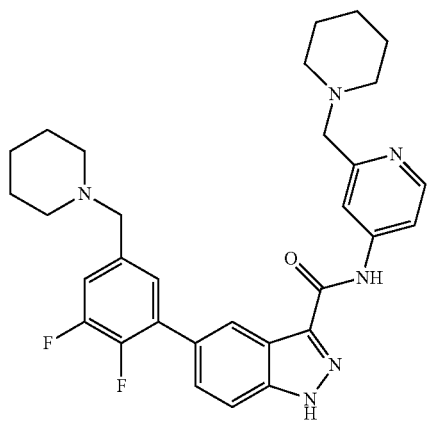 [SMILES: O=C(Nc1ccnc(CN2CCCCC2)c1)c1n[nH]c2ccc(-c3cc(CN4CCCCC4)cc(F)c3F)cc12]
1012
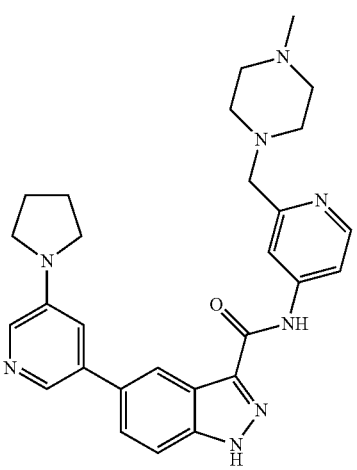
1015
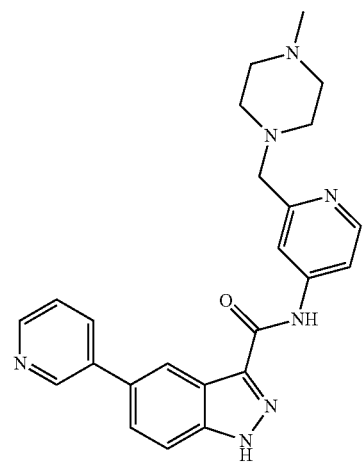 [SMILES: CN1CCN(Cc2cc(NC(=O)c3n[nH]c4ccc(-c5cccnc5)cc34)ccn2)CC1]
1013
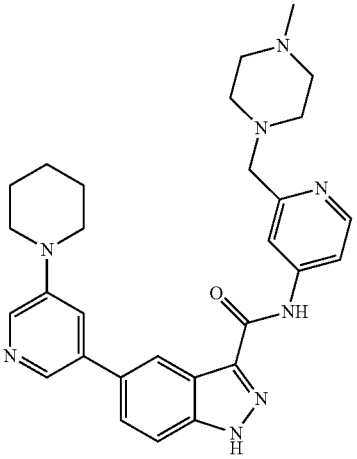
1016
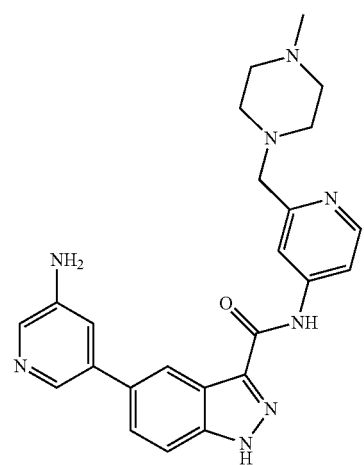 [SMILES: CN1CCN(Cc2cc(NC(=O)c3n[nH]c4ccc(-c5cncc(N)c5)cc34)ccn2)CC1]
1014
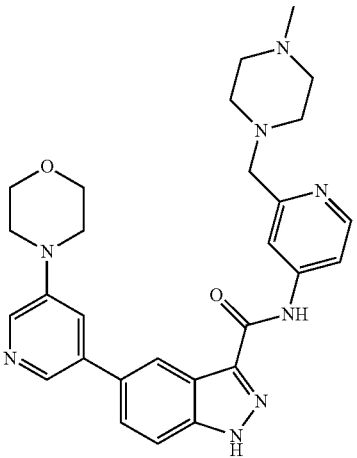 [SMILES: CN1CCN(Cc2cc(NC(=O)c3n[nH]c4ccc(-c5cncc(N6CCOCC6)c5)cc34)ccn2)CC1]
1017

TABLE 1-continued
1018
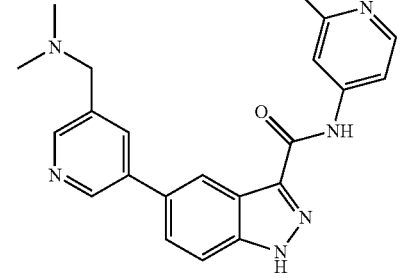
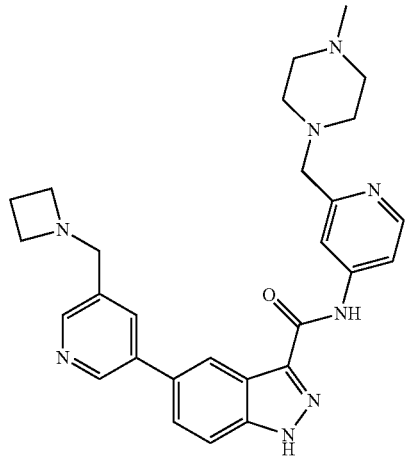 [SMILES: CN1CCN(Cc2cc(NC(=O)c3n[nH]c4ccc(-c5cncc(CN6CCC6)c5)cc34)ccn2)CC1]
1019
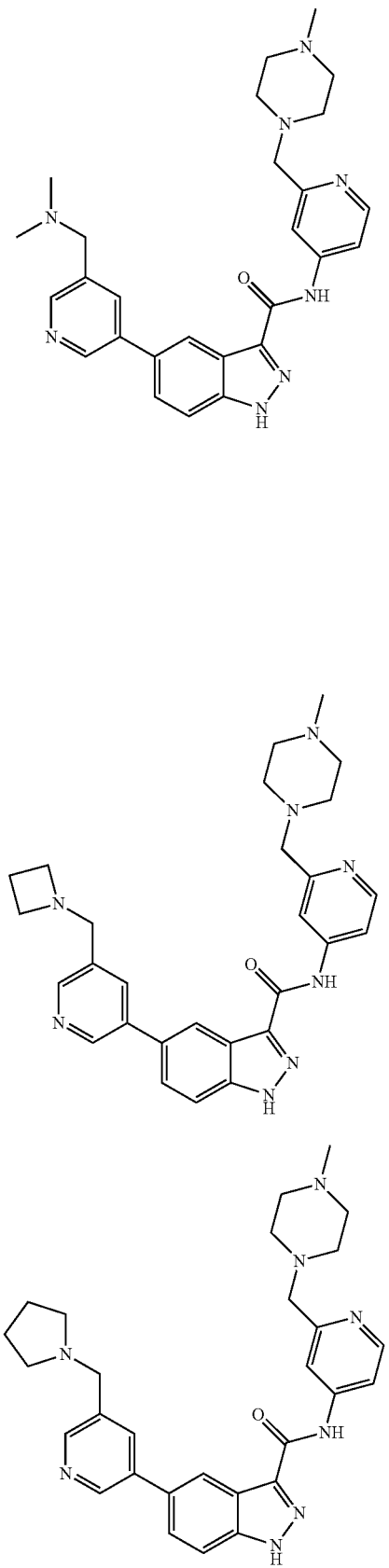
1020
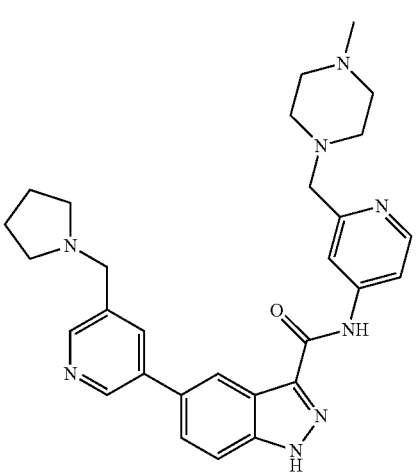 [SMILES: CN1CCN(Cc2cc(NC(=O)c3n[nH]c4ccc(-c5cncc(CN6CCCC6)c5)cc34)ccn2)CC1]
TABLE 1-continued
1021
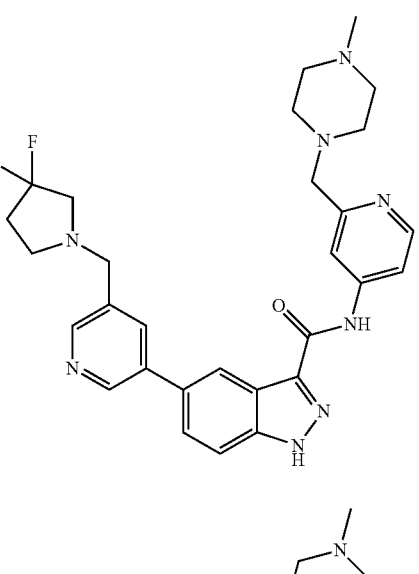
1022
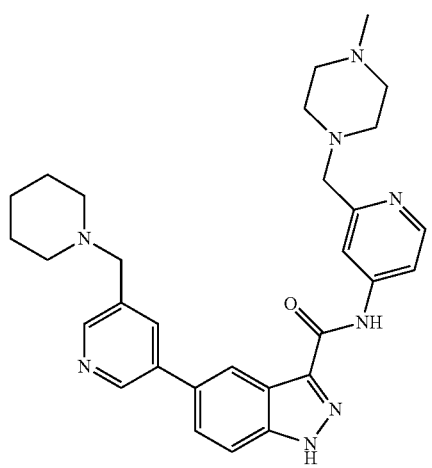 [SMILES: CN1CCN(Cc2cc(NC(=O)c3n[nH]c4ccc(-c5cncc(CN6CCCCC6)c5)cc34)ccn2)CC1]
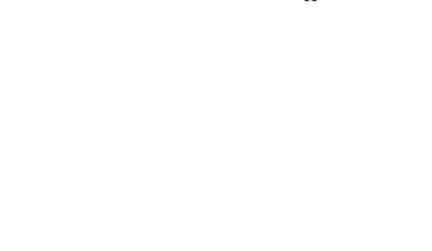
1023
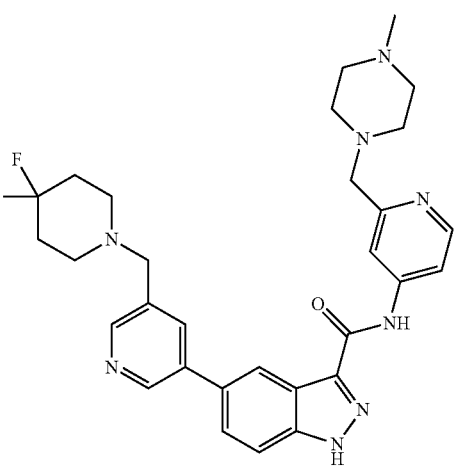

TABLE 1-continued
1024
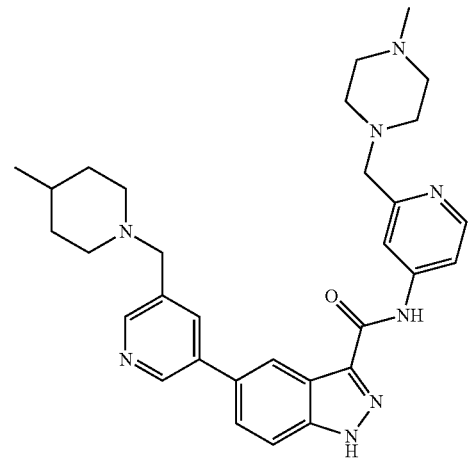 [SMILES: CC1CCN(Cc2cncc(-c3ccc4[nH]nc(C(=O)Nc5ccnc(CN6CCN(C)CC6)c5)c4c3)c2)CC1]
1025
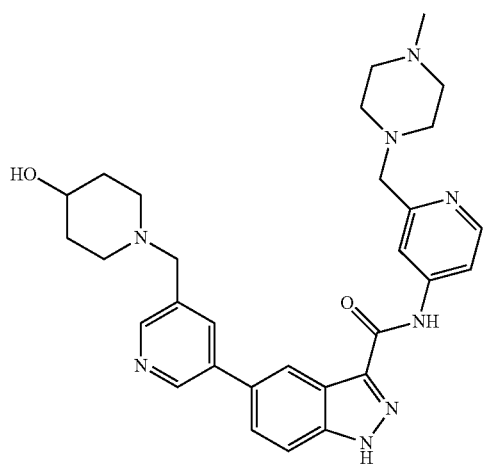 [SMILES: CN1CCN(Cc2cc(NC(=O)c3n[nH]c4ccc(-c5cncc(CN6CCC(O)CC6)c5)cc34)ccn2)CC1]
1026
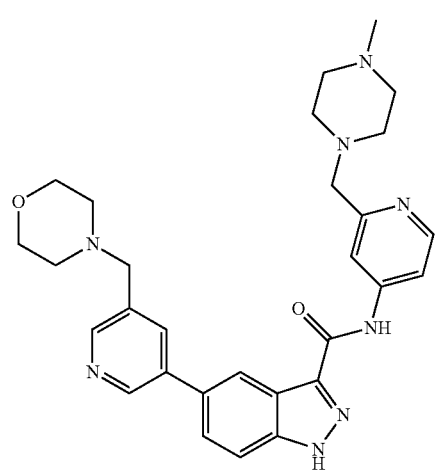 [SMILES: CN1CCN(Cc2cc(NC(=O)c3n[nH]c4ccc(-c5cncc(CN6CCOCC6)c5)cc34)ccn2)CC1]
TABLE 1-continued
1027
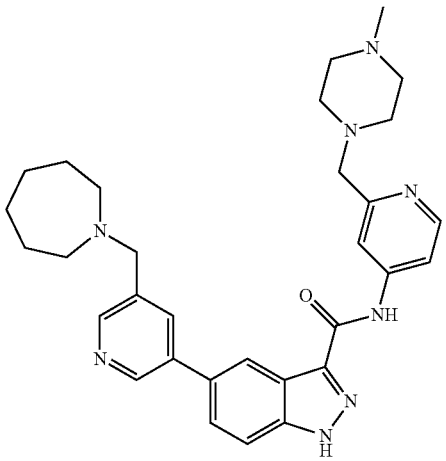 [SMILES: CN1CCN(Cc2cc(NC(=O)c3n[nH]c4ccc(-c5cncc(CN6CCCCCC6)c5)cc34)ccn2)CC1]
1028
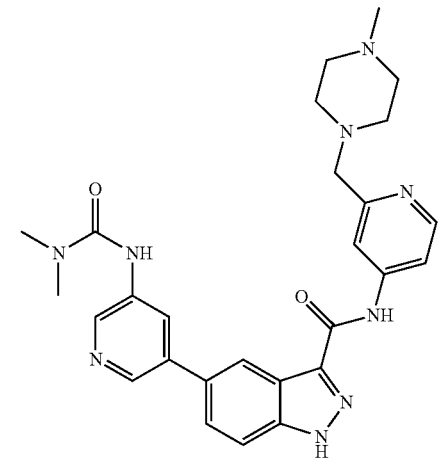 [SMILES: CN1CCN(Cc2cc(NC(=O)c3n[nH]c4ccc(-c5cncc(NC(=O)N(C)C)c5)cc34)ccn2)CC1]
1029
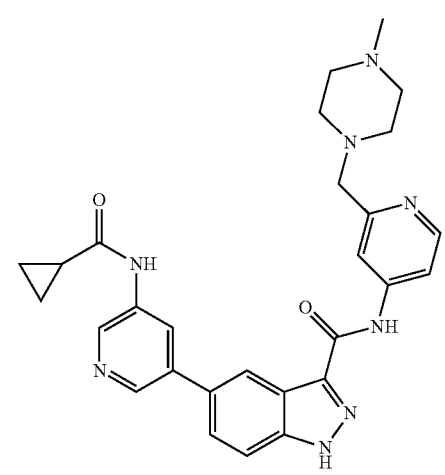 [SMILES: CN1CCN(Cc2cc(NC(=O)c3n[nH]c4ccc(-c5cncc(NC(=O)C6CC6)c5)cc34)ccn2)CC1]

TABLE 1-continued
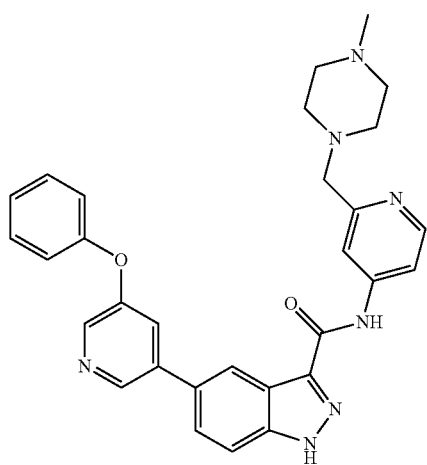 [SMILES: CN1CCN(Cc2cc(NC(=O)c3n[nH]c4ccc(-c5cncc(Oc6ccccc6)c5)cc34)ccn2)CC1] 1030
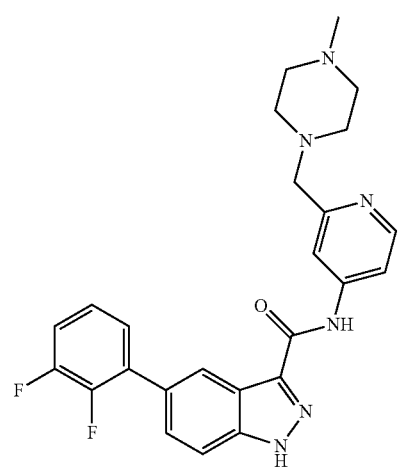 [SMILES: CN1CCN(Cc2cc(NC(=O)c3n[nH]c4ccc(-c5cccc(F)c5F)cc34)ccn2)CC1] 1031
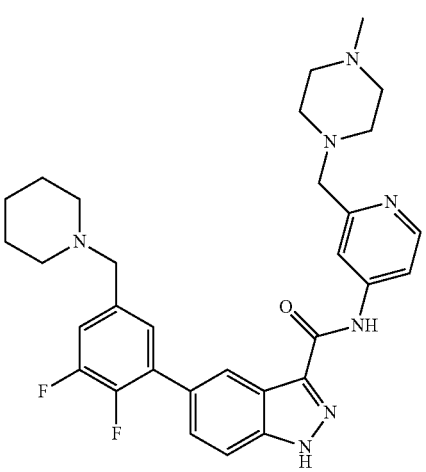 [SMILES: CN1CCN(Cc2cc(NC(=O)c3n[nH]c4ccc(-c5cc(CN6CCCCC6)cc(F)c5F)cc34)ccn2)CC1] 1032
TABLE 1-continued
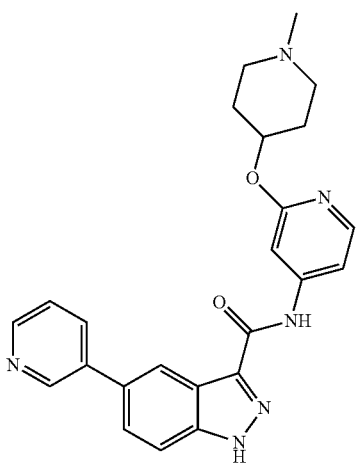 [SMILES: CN1CCC(Oc2cc(NC(=O)c3n[nH]c4ccc(-c5cccnc5)cc34)ccn2)CC1] 1033
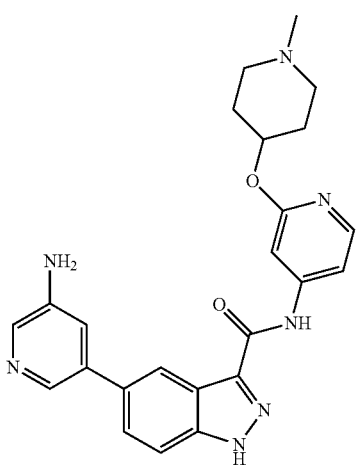 [SMILES: CN1CCC(Oc2cc(NC(=O)c3n[nH]c4ccc(-c5cncc(N)c5)cc34)ccn2)CC1] 1034
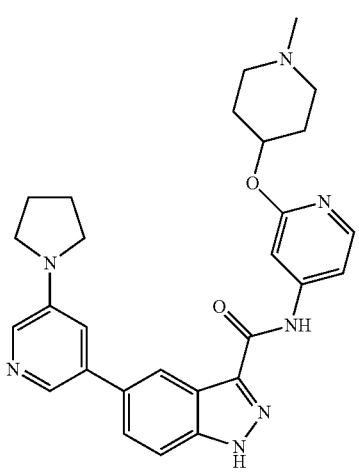 [SMILES: CN1CCC(Oc2cc(NC(=O)c3n[nH]c4ccc(-c5cncc(N6CCCC6)c5)cc34)ccn2)CC1] 1035

TABLE 1-continued
1036 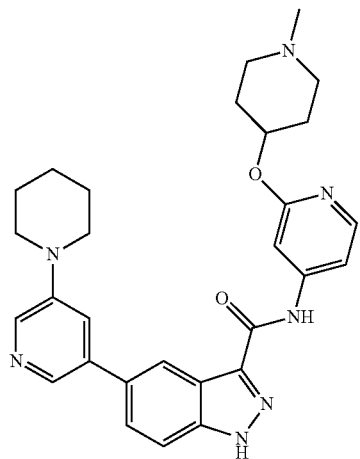 [SMILES: CN1CCC(Oc2cc(NC(=O)c3n[nH]c4ccc(-c5cncc(N6CCCCC6)c5)cc34)ccn2)CC1]
1037 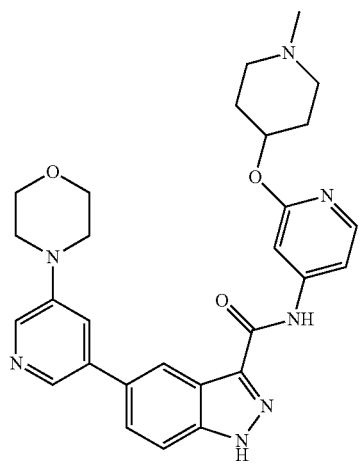 [SMILES: CN1CCC(Oc2cc(NC(=O)c3n[nH]c4ccc(-c5cncc(N6CCOCC6)c5)cc34)ccn2)CC1]
1038 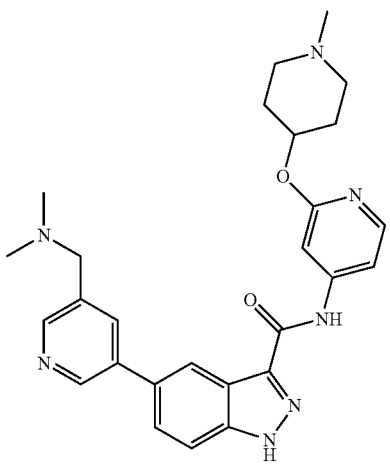 [SMILES: CN(C)Cc1cncc(-c2ccc3[nH]nc(C(=O)Nc4ccnc(OC5CCN(C)CC5)c4)c3c2)c1]
1039 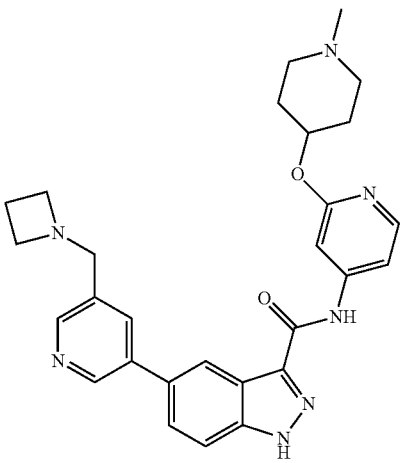 [SMILES: CN1CCC(Oc2cc(NC(=O)c3n[nH]c4ccc(-c5cncc(CN6CCC6)c5)cc34)ccn2)CC1]
1040 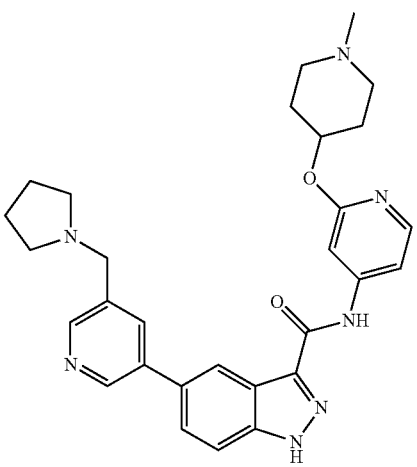 [SMILES: CN1CCC(Oc2cc(NC(=O)c3n[nH]c4ccc(-c5cncc(CN6CCCC6)c5)cc34)ccn2)CC1]
1041 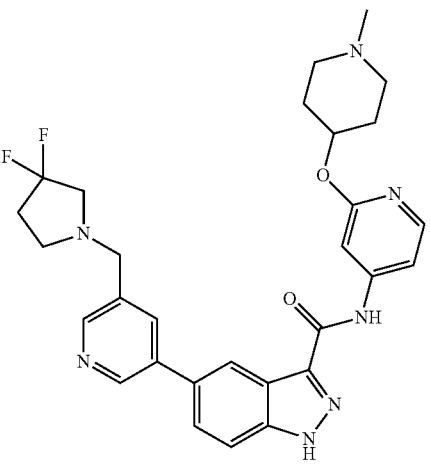 [SMILES: CN1CCC(Oc2cc(NC(=O)c3n[nH]c4ccc(-c5cncc(CN6CCC(F)(F)C6)c5)cc34)ccn2)CC1]

TABLE 1-continued
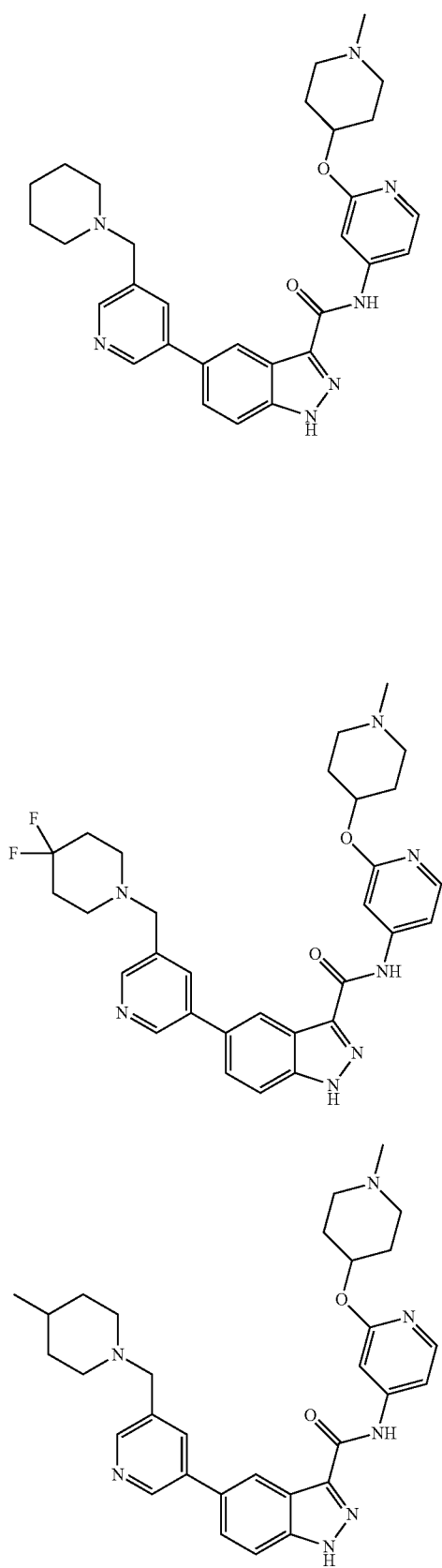
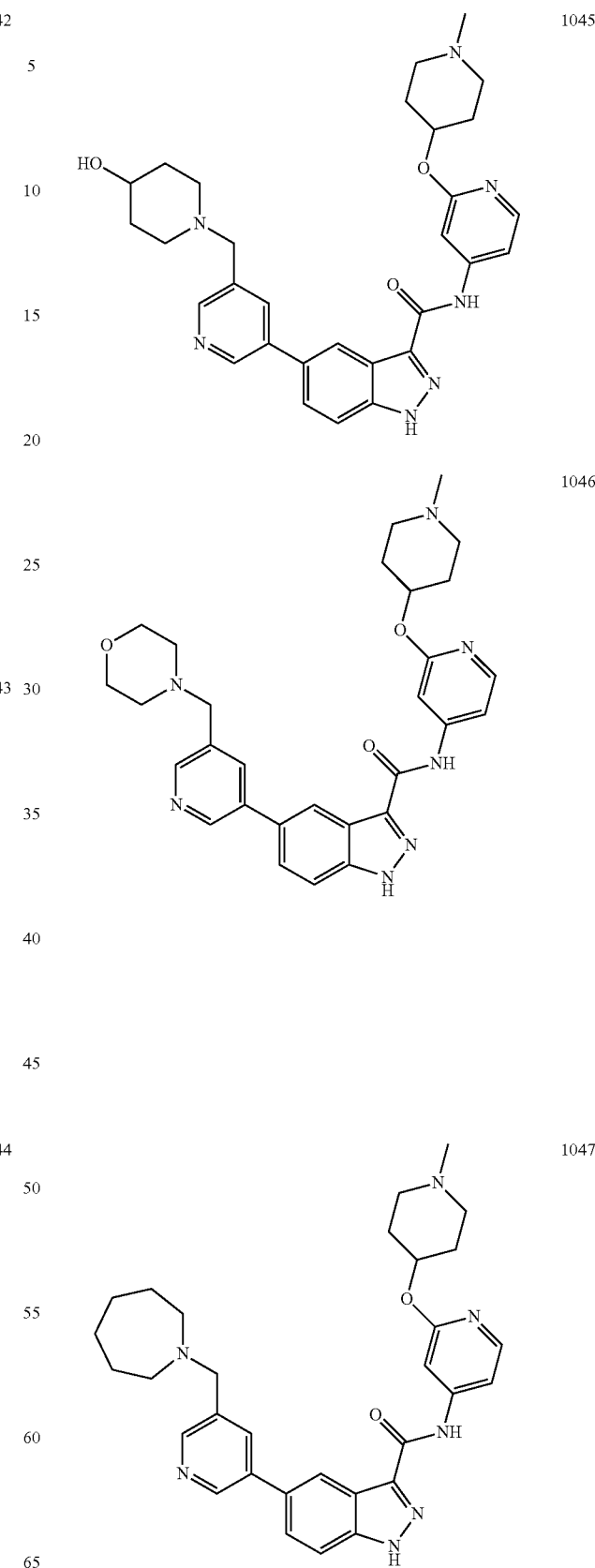

TABLE 1-continued
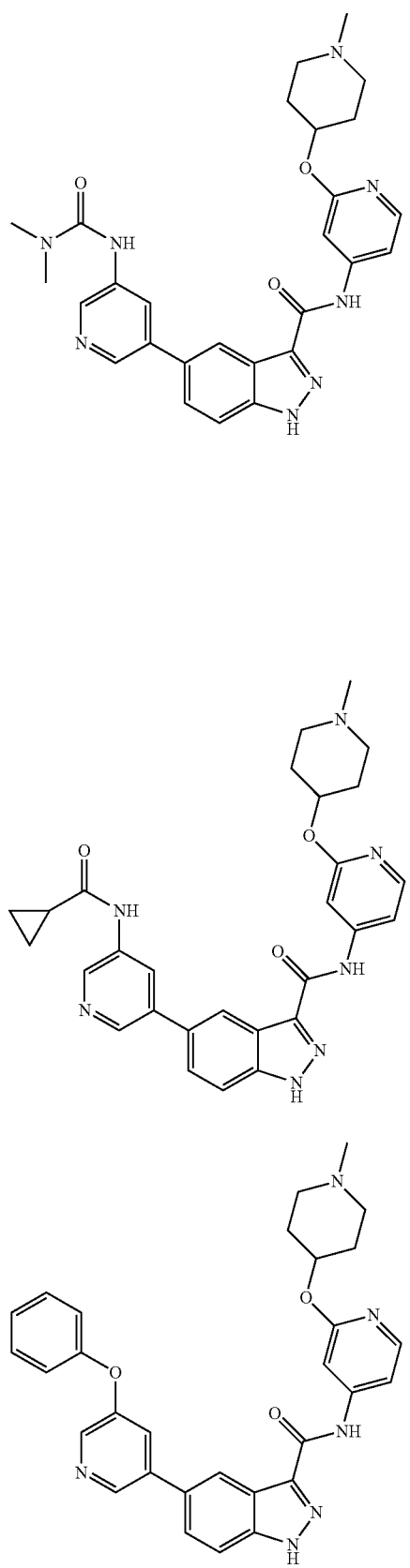
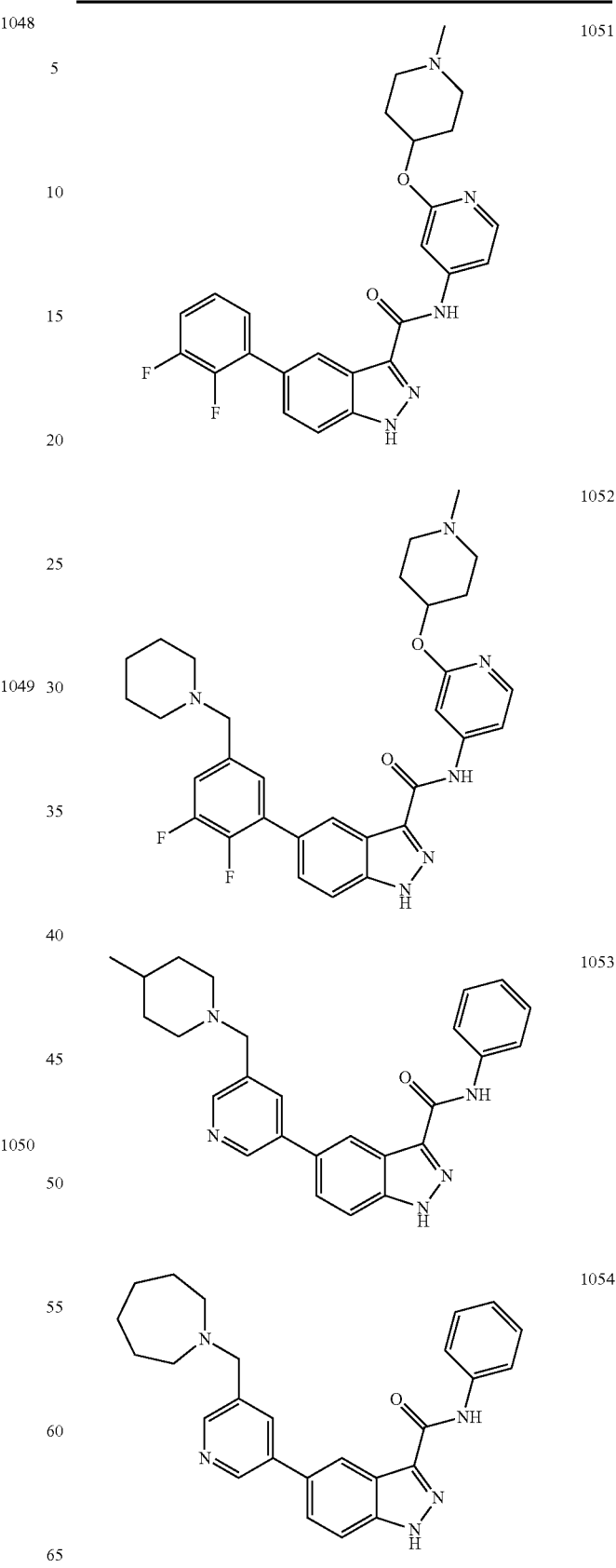

331
TABLE 1-continued
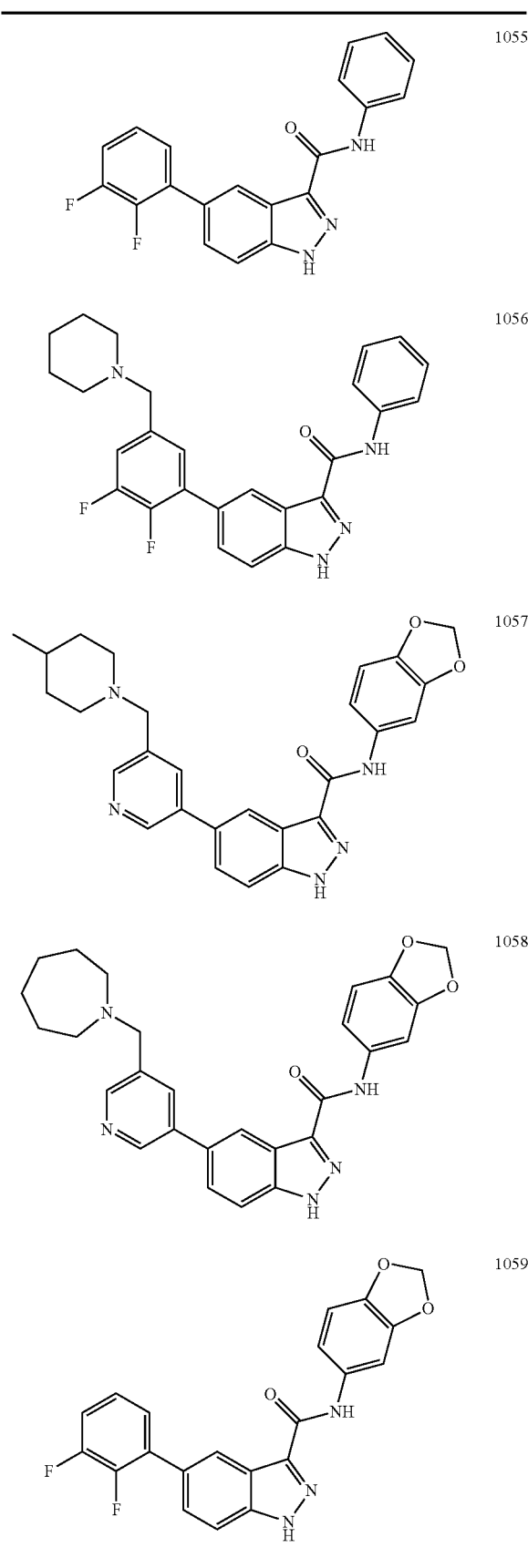
332
TABLE 1-continued
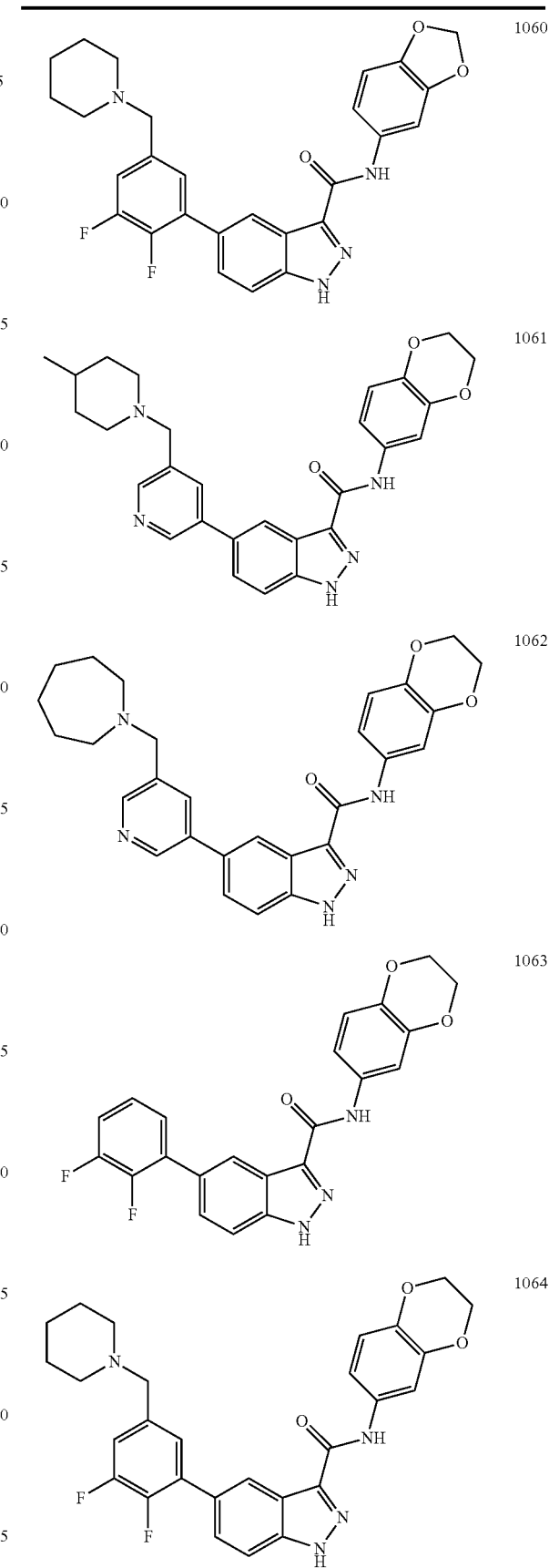

TABLE 1-continued
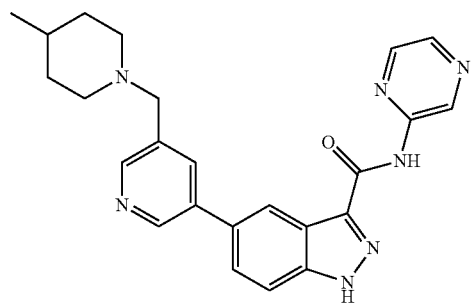 [SMILES: CC1CCN(Cc2cncc(-c3ccc4[nH]nc(C(=O)Nc5cnccn5)c4c3)c2)CC1] 1065
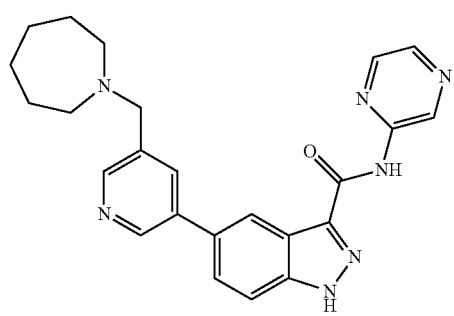 [SMILES: O=C(Nc1cnccn1)c1n[nH]c2ccc(-c3cncc(CN4CCCCCC4)c3)cc12] 1066
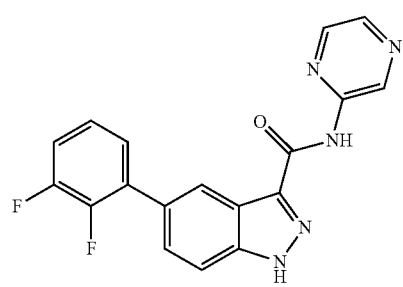 [SMILES: O=C(Nc1cnccn1)c1n[nH]c2ccc(-c3cccc(F)c3F)cc12] 1067
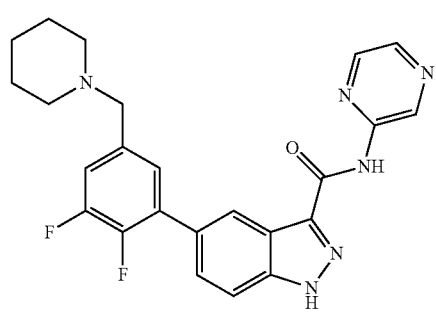 [SMILES: O=C(Nc1cnccn1)c1n[nH]c2ccc(-c3cc(CN4CCCCC4)cc(F)c3F)cc12] 1068
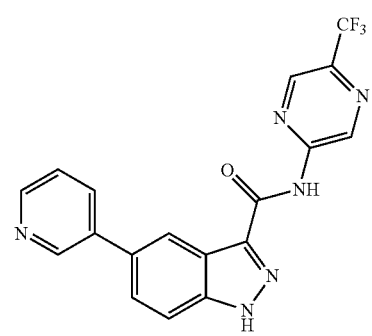 [SMILES: O=C(Nc1cnc(C(F)(F)F)cn1)c1n[nH]c2ccc(-c3cccnc3)cc12] 1069
TABLE 1-continued
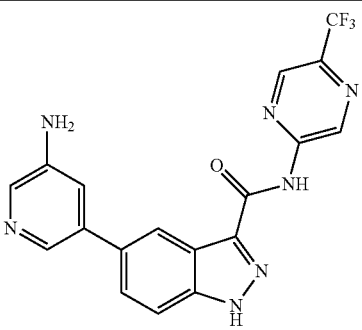 1070
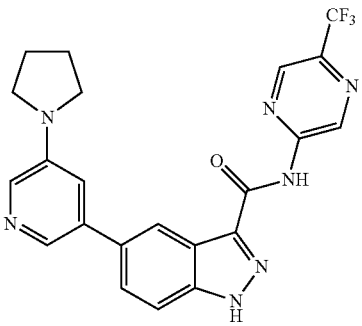 [SMILES: O=C(Nc1cnc(C(F)(F)F)cn1)c1n[nH]c2ccc(-c3cncc(N4CCCC4)c3)cc12] 1071
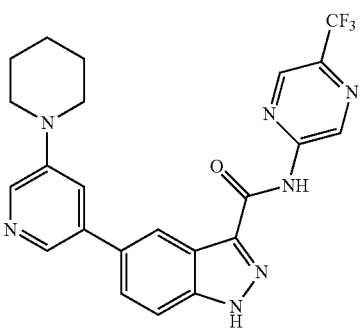 [SMILES: O=C(Nc1cnc(C(F)(F)F)cn1)c1n[nH]c2ccc(-c3cncc(N4CCCCC4)c3)cc12] 1072
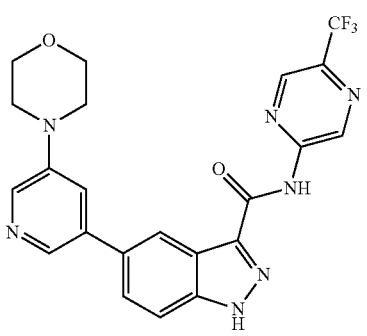 [SMILES: O=C(Nc1cnc(C(F)(F)F)cn1)c1n[nH]c2ccc(-c3cncc(N4CCOCC4)c3)cc12] 1073
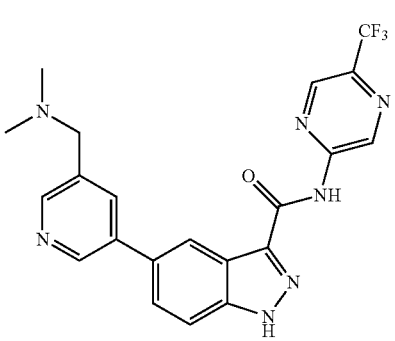 [SMILES: CN(C)Cc1cncc(-c2ccc3[nH]nc(C(=O)Nc4cnc(C(F)(F)F)cn4)c3c2)c1] 1074

TABLE 1-continued
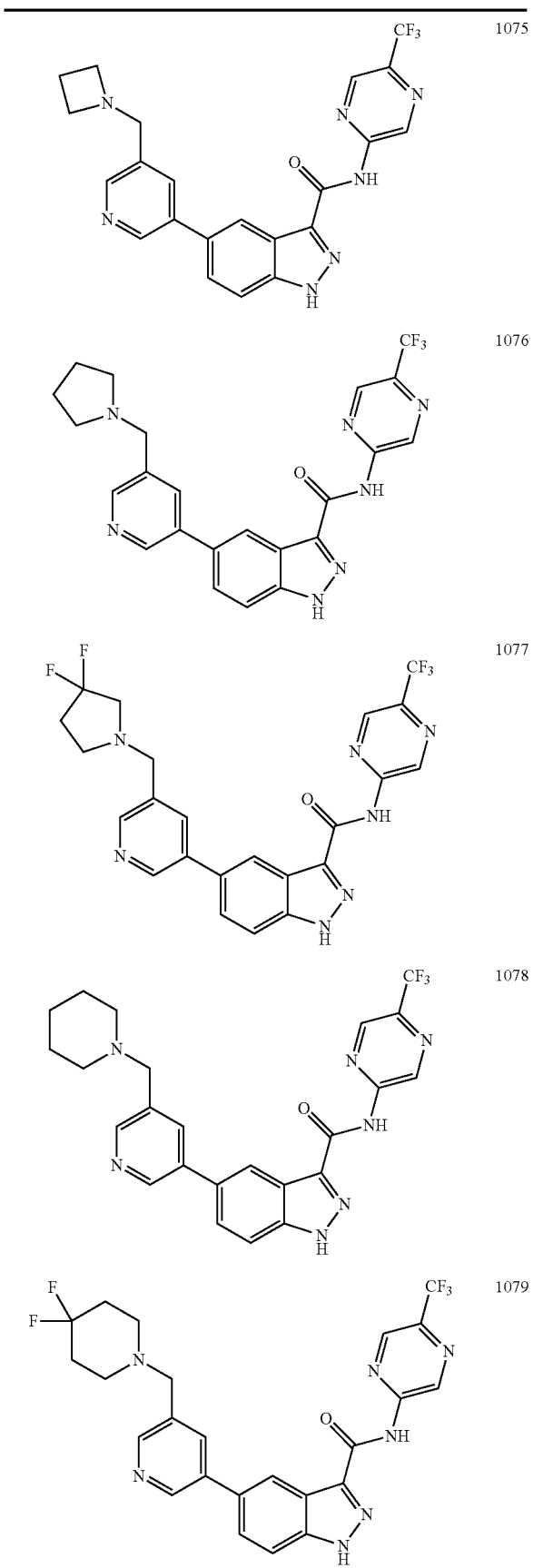
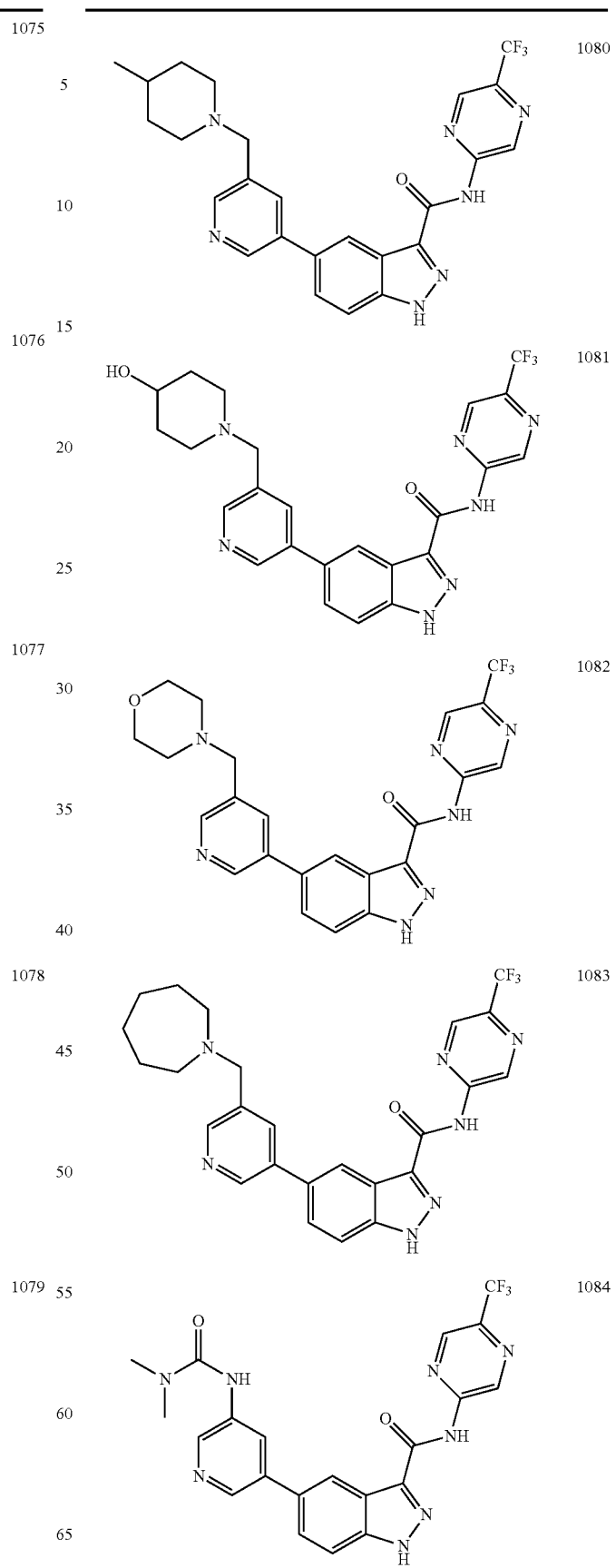

TABLE 1-continued
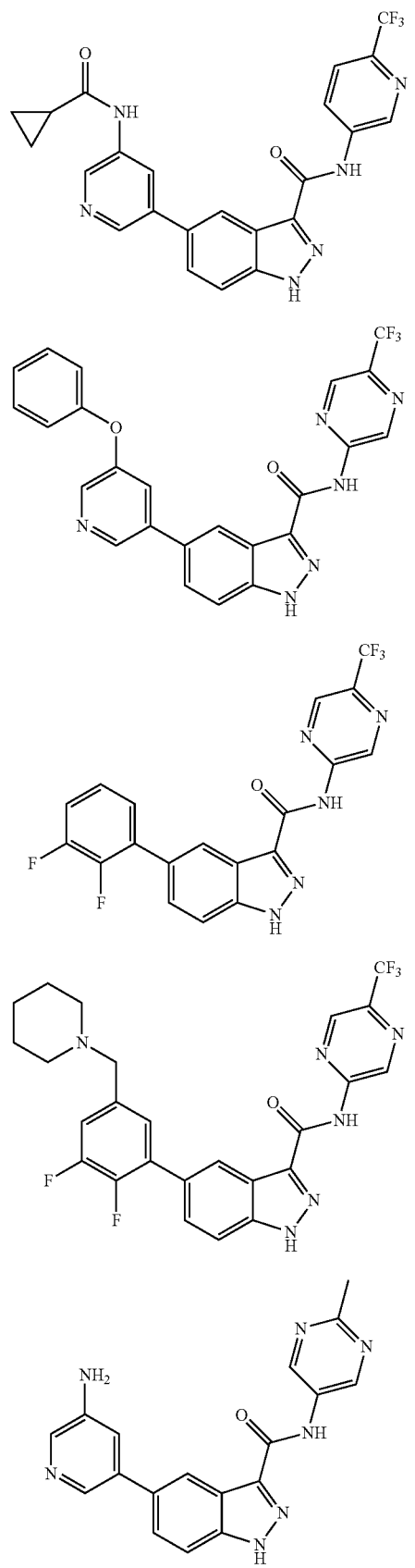
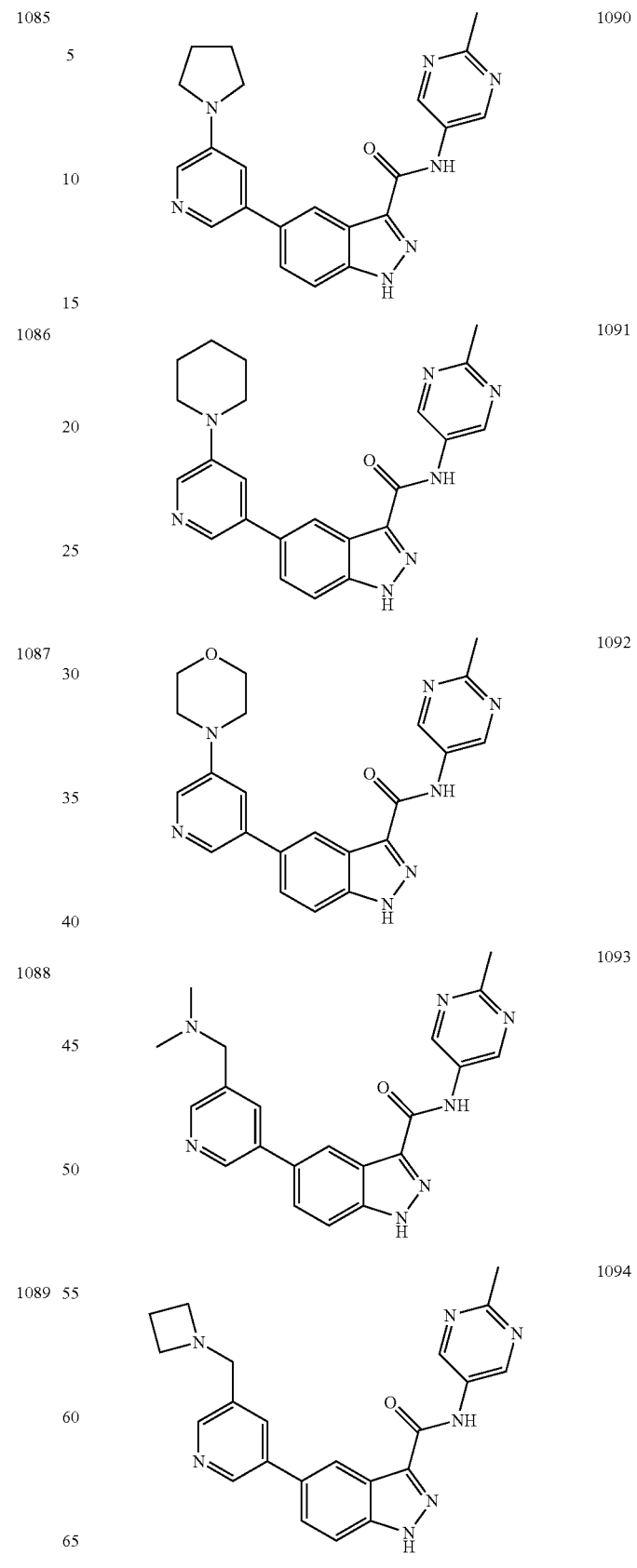

TABLE 1-continued
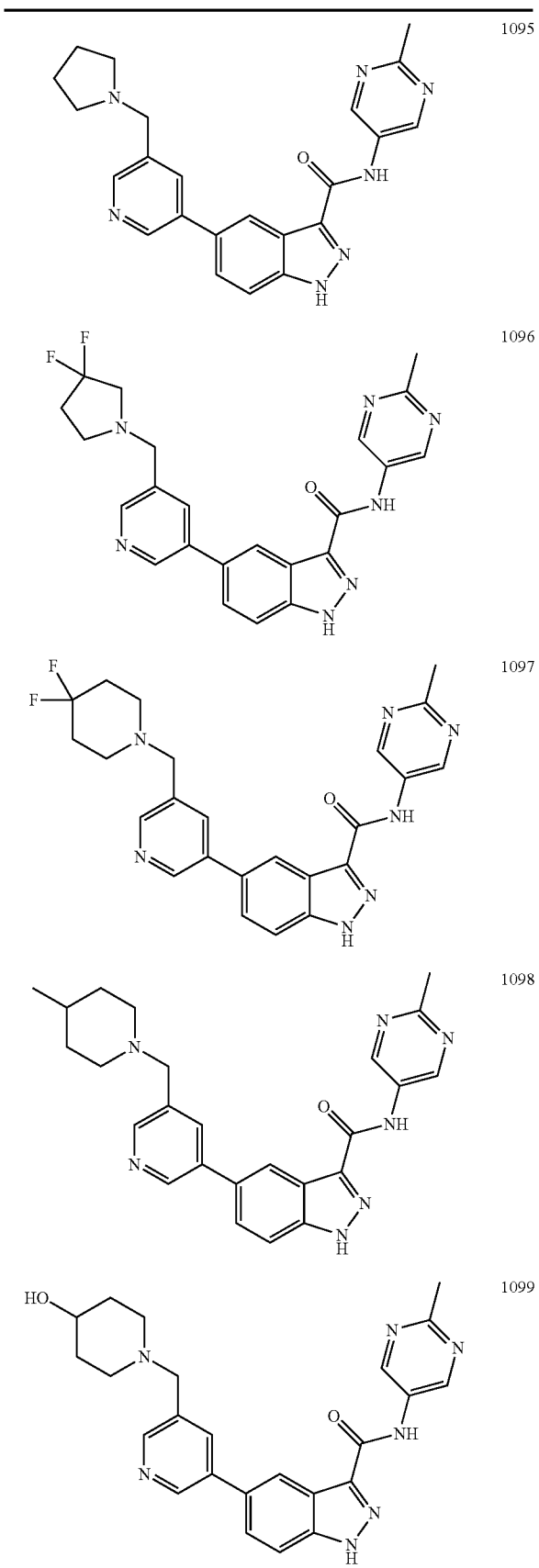
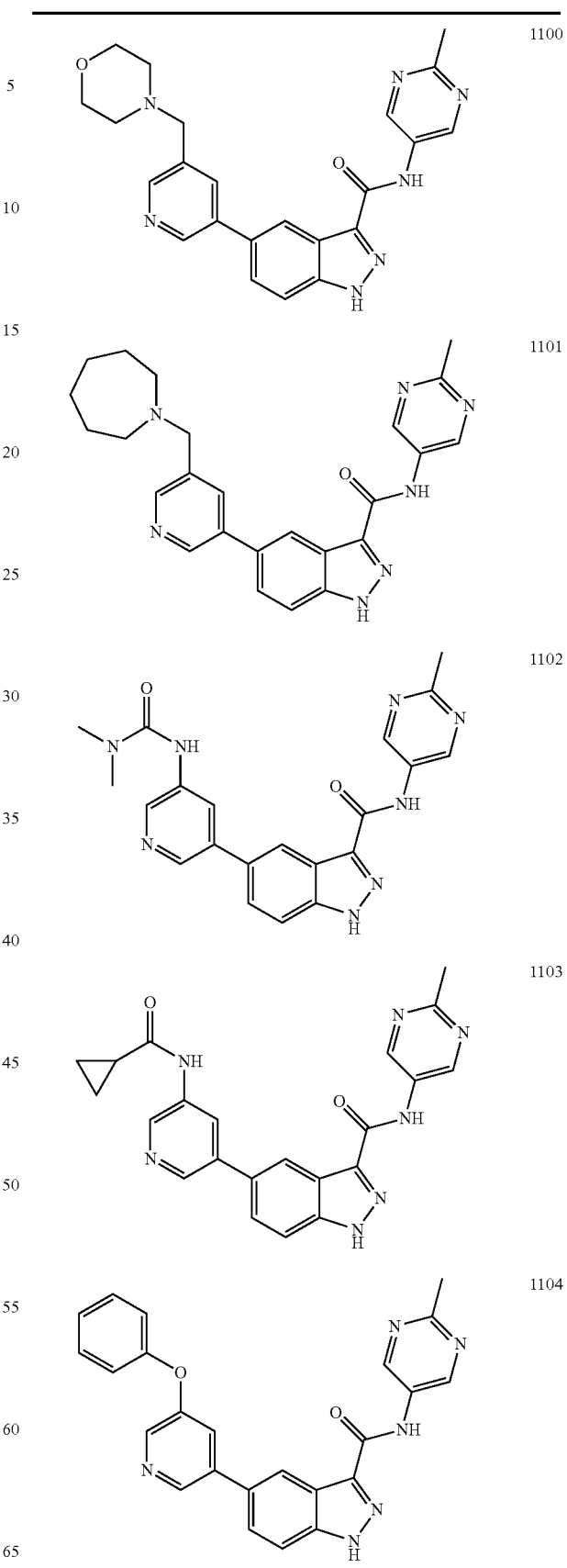

TABLE 1-continued
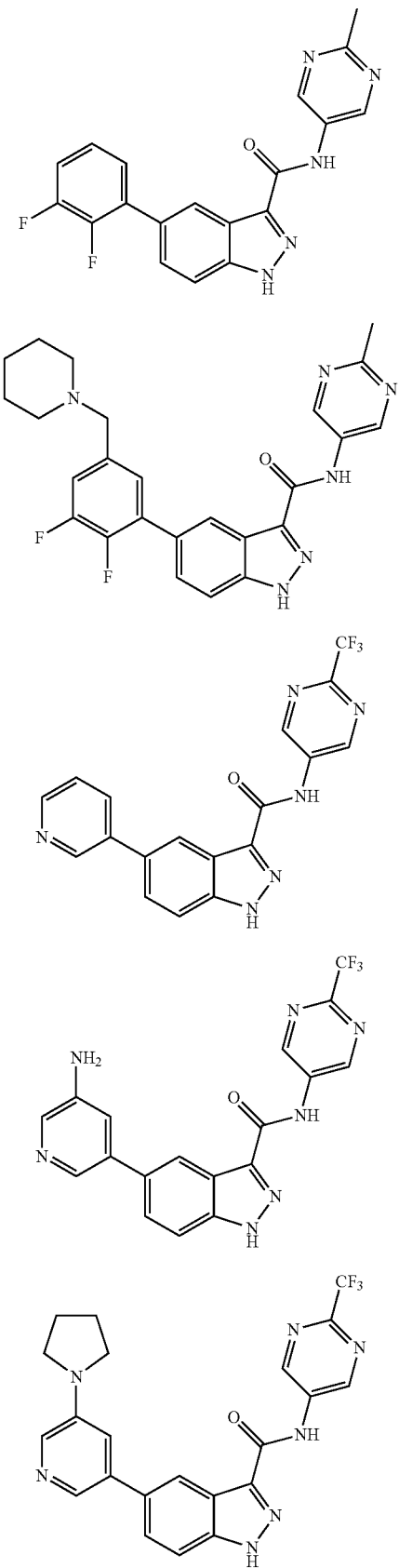
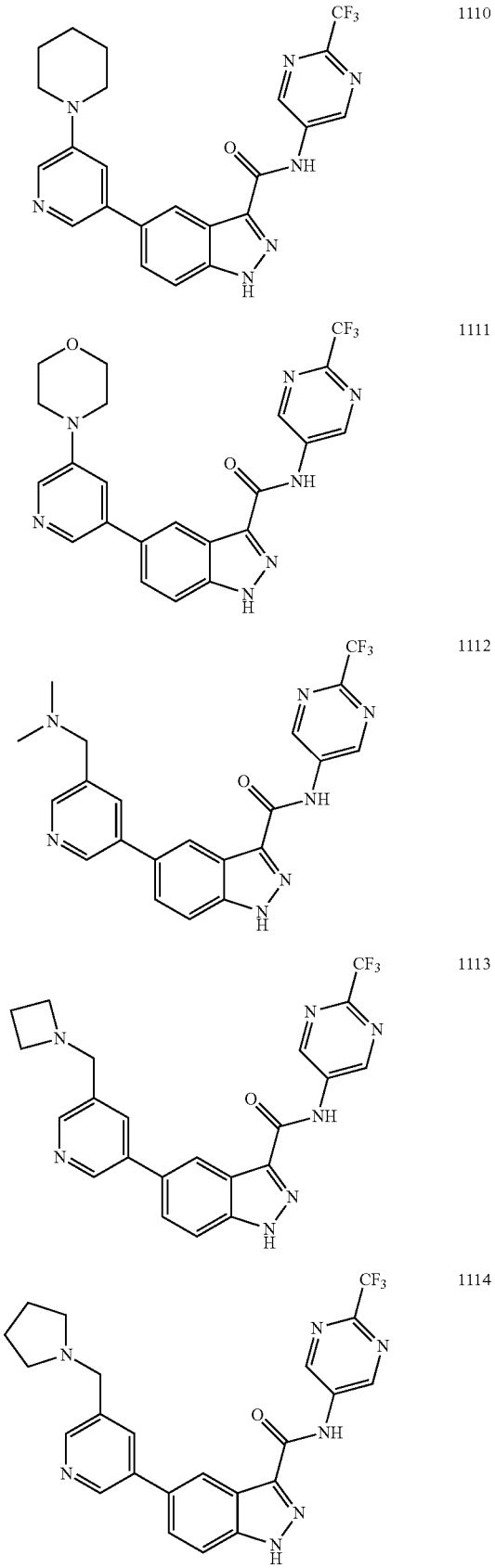

TABLE 1-continued
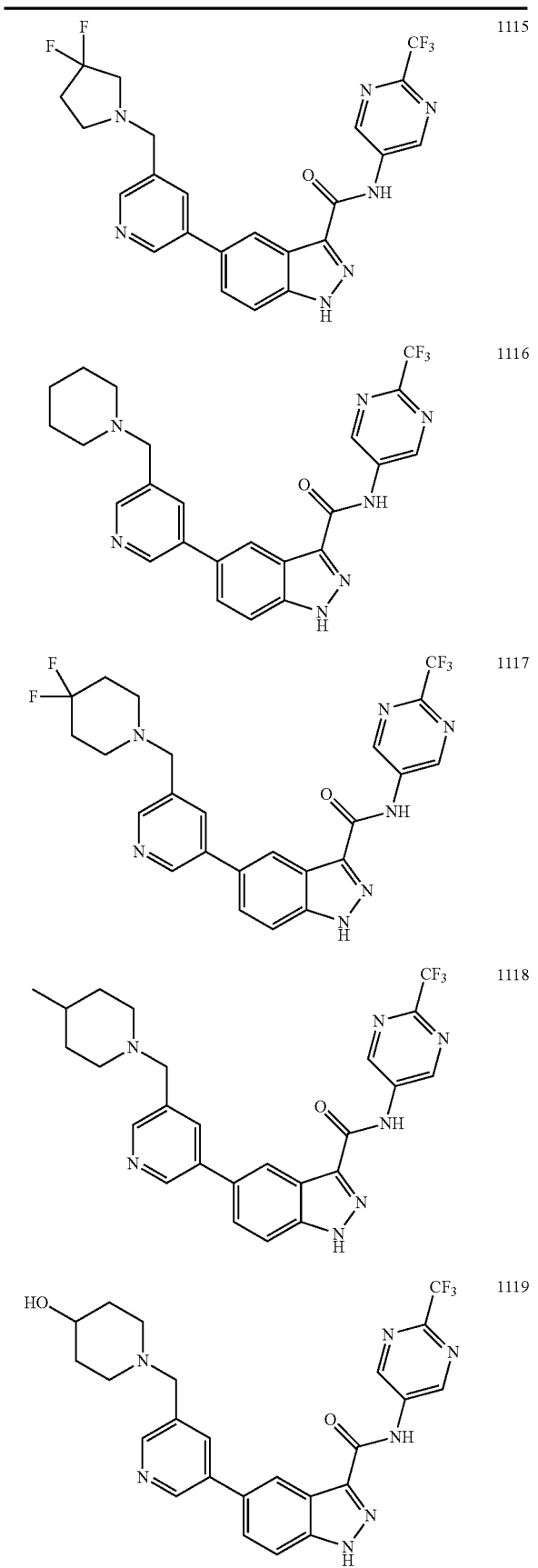
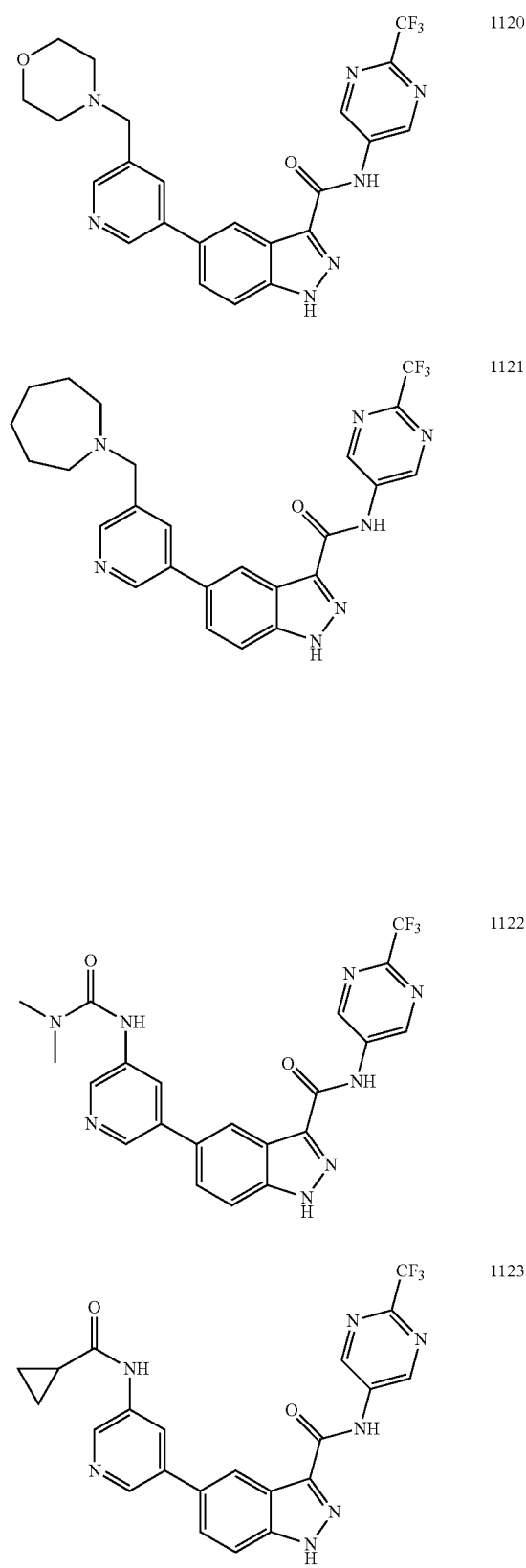

TABLE 1-continued
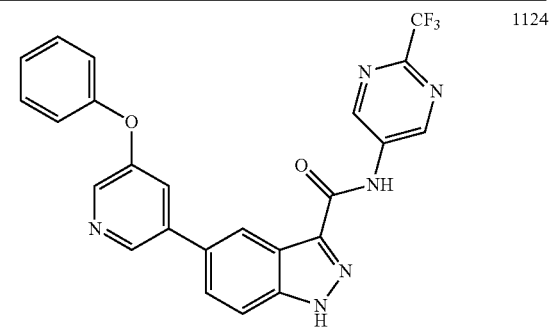
1124
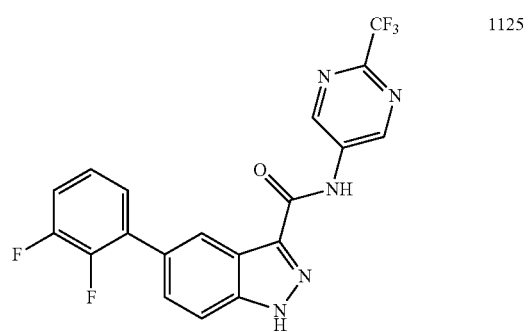
1125
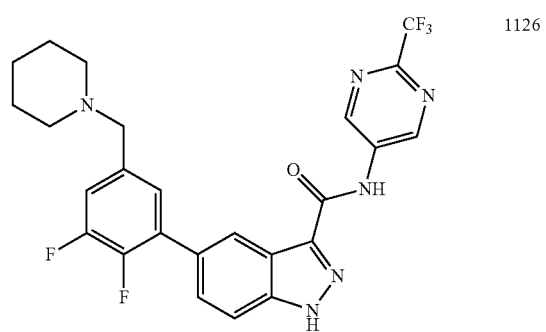
1126
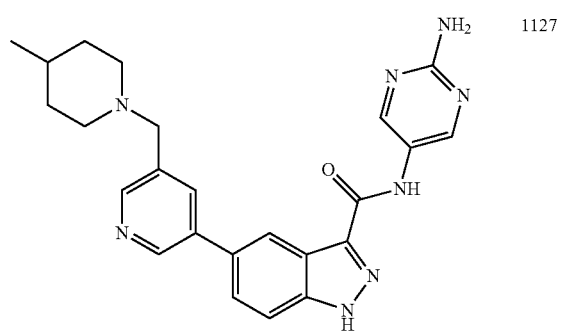
1127
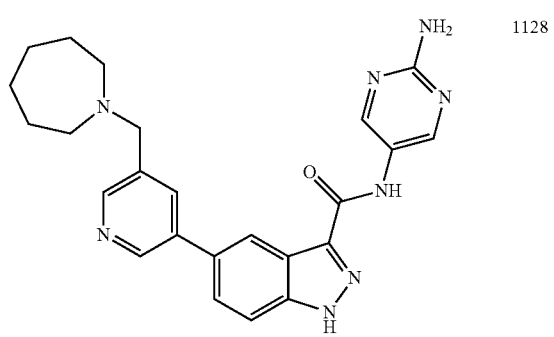
1128
TABLE 1-continued
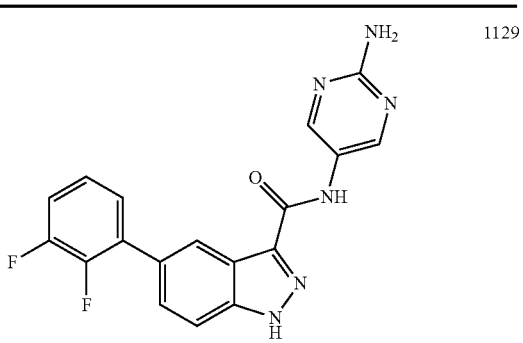
1129
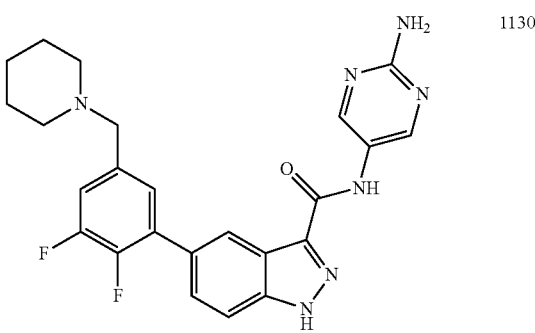
1130
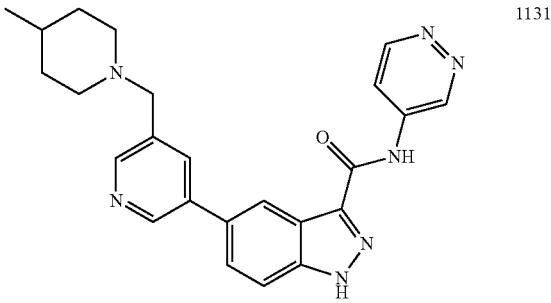
1131
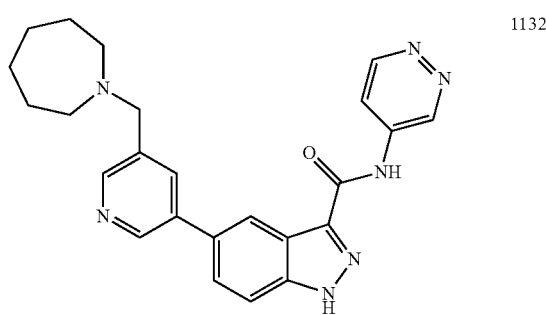
1132
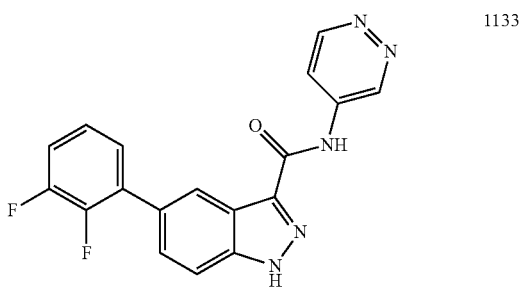
1133

TABLE 1-continued
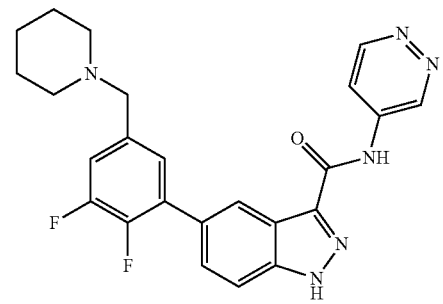 [SMILES: O=C(Nc1ccnnc1)c1n[nH]c2ccc(-c3cc(CN4CCCCC4)cc(F)c3F)cc12]
1134
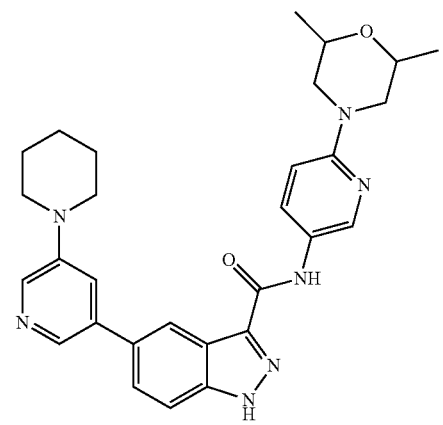 [SMILES: CC1CN(c2ccc(NC(=O)c3n[nH]c4ccc(-c5cncc(N6CCCCC6)c5)cc34)cn2)CC(C)O1]
1135
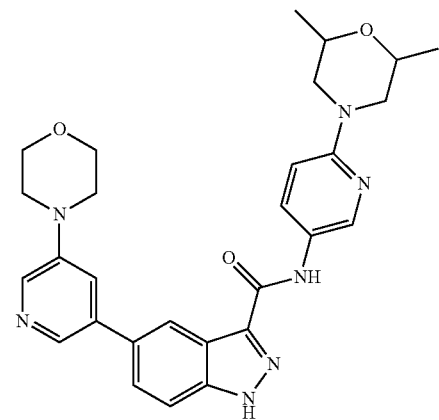 [SMILES: CC1CN(c2ccc(NC(=O)c3n[nH]c4ccc(-c5cncc(N6CCOCC6)c5)cc34)cn2)CC(C)O1]
1136
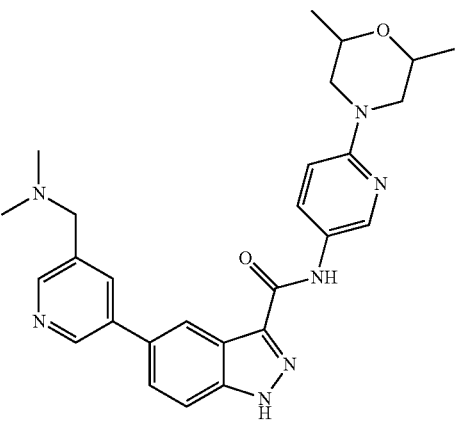
1137
TABLE 1-continued
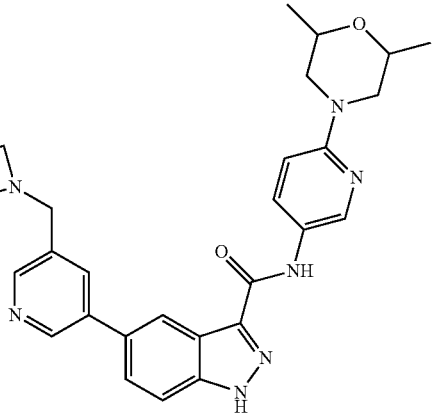
1138
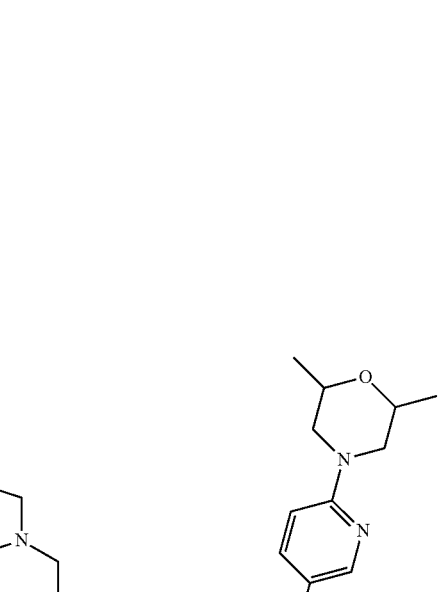
1139
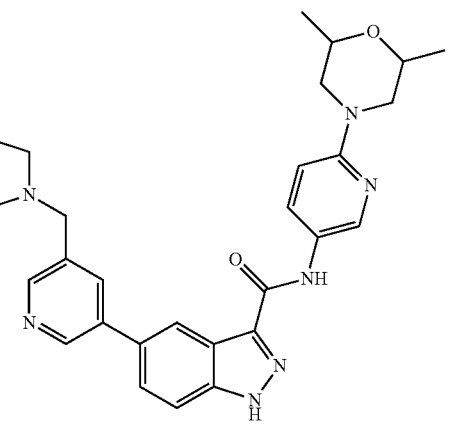
1140

TABLE 1-continued
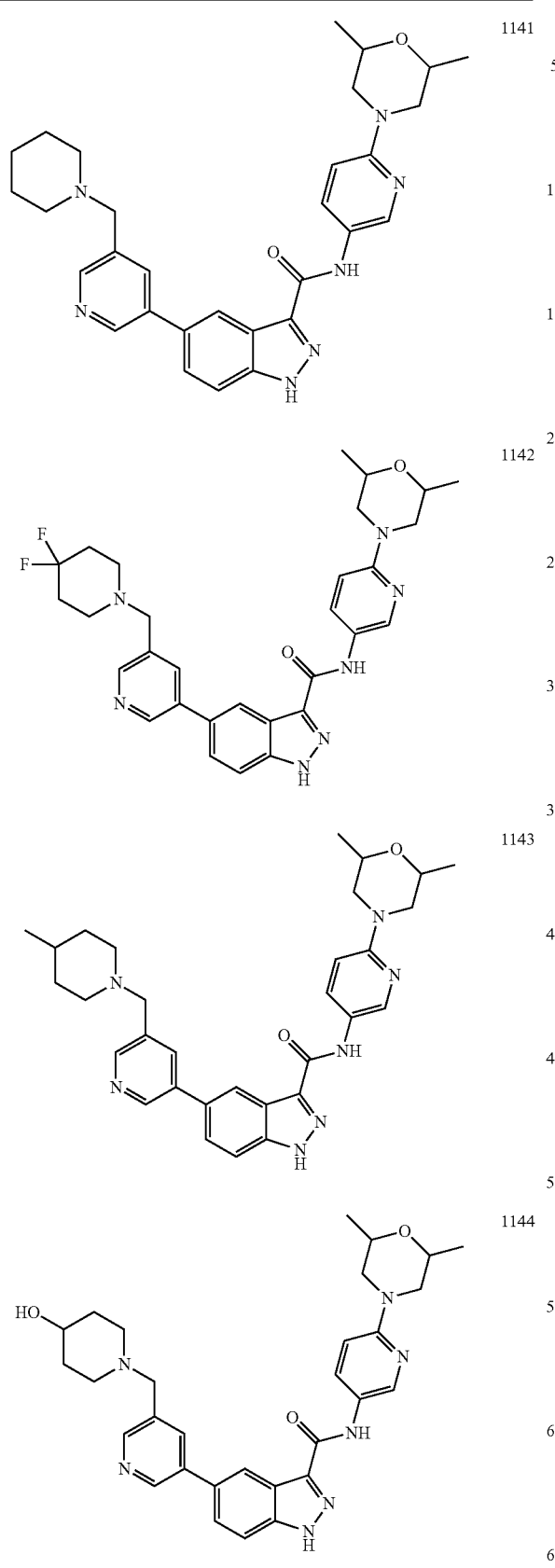
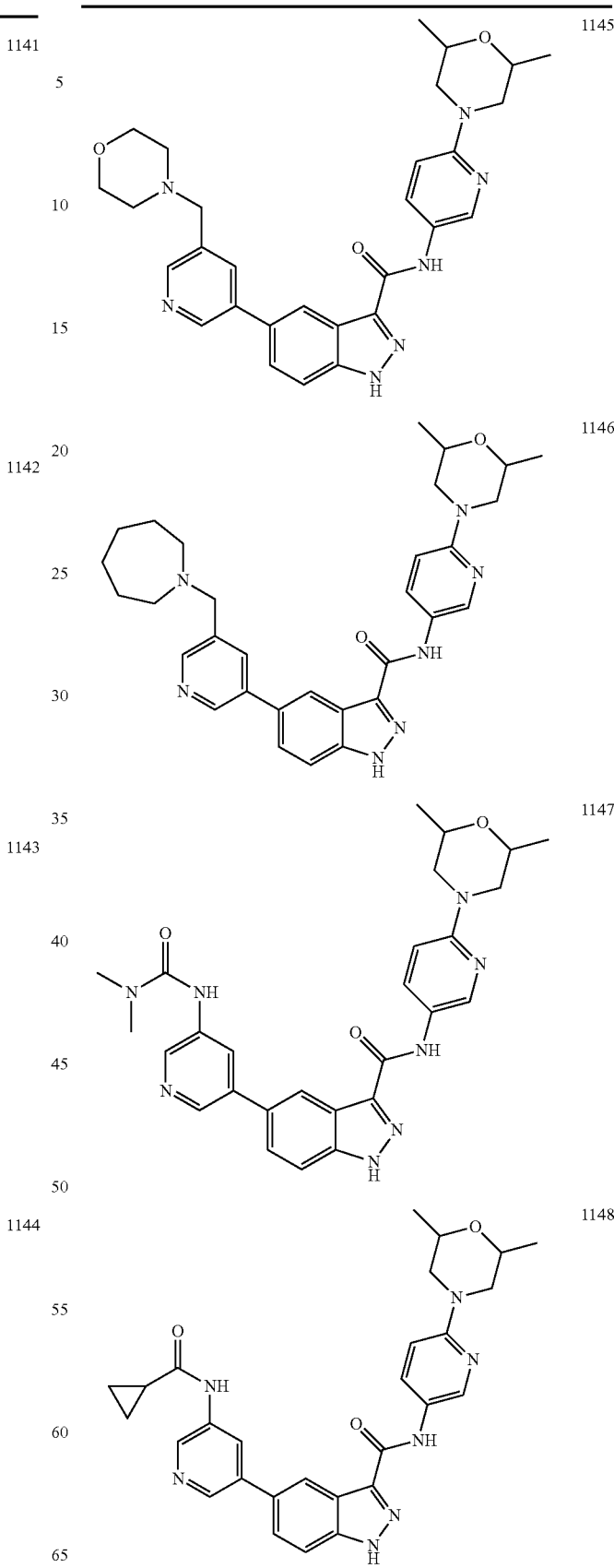

TABLE 1-continued
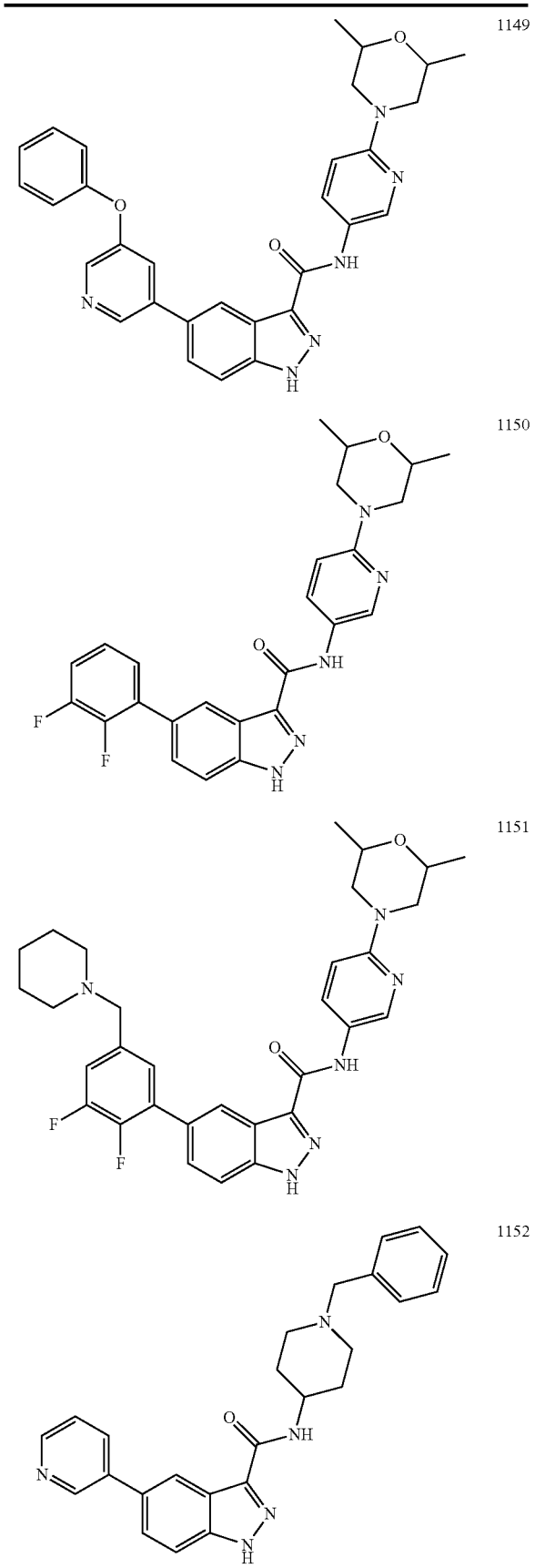
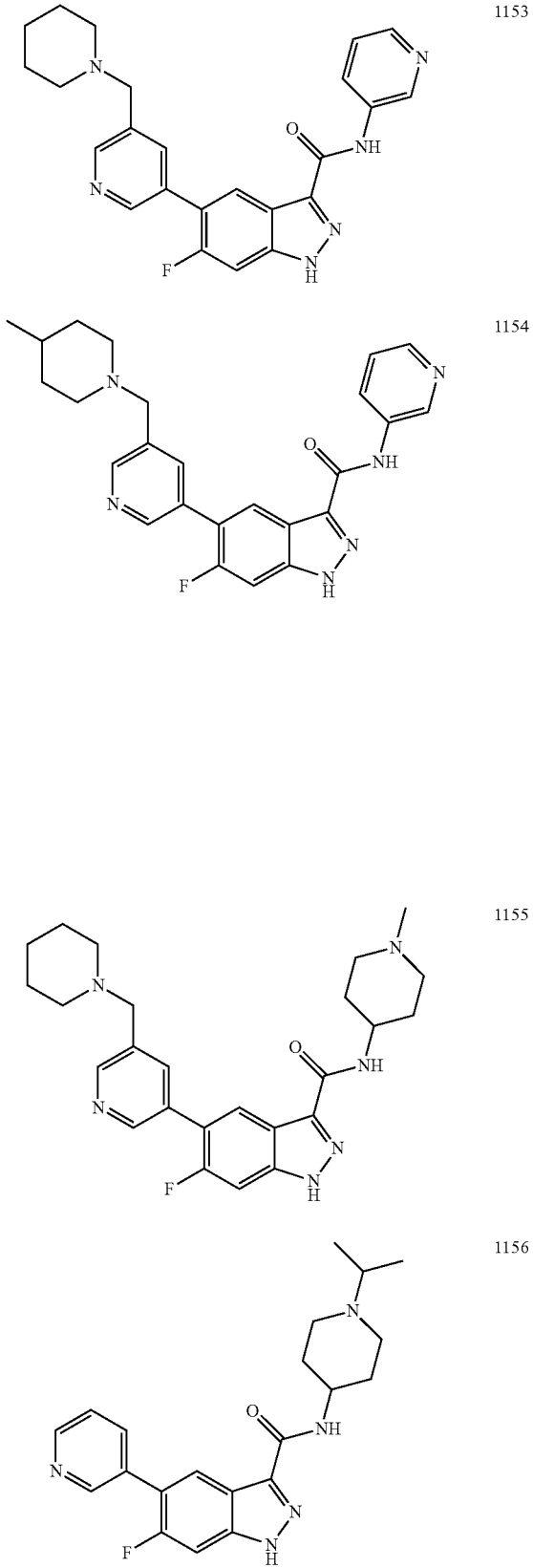

TABLE 1-continued
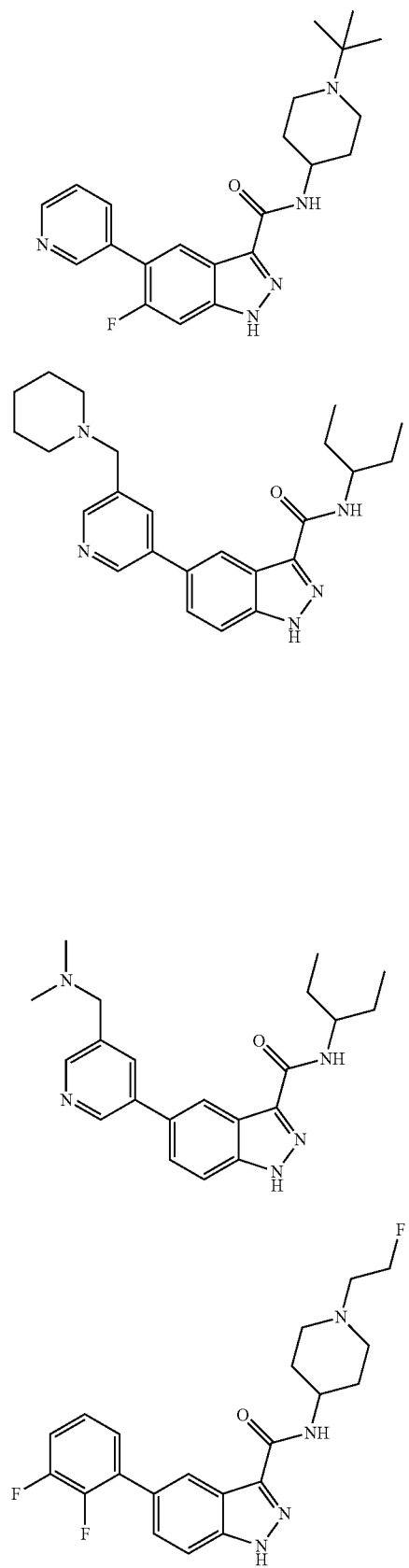
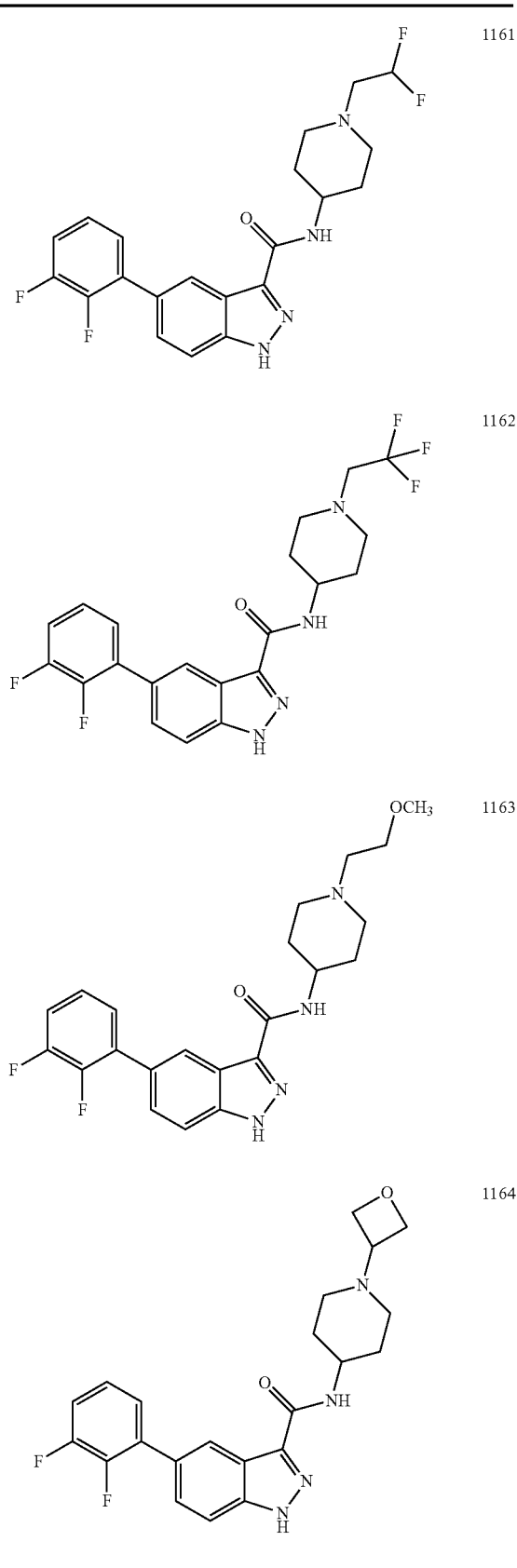

TABLE 1-continued
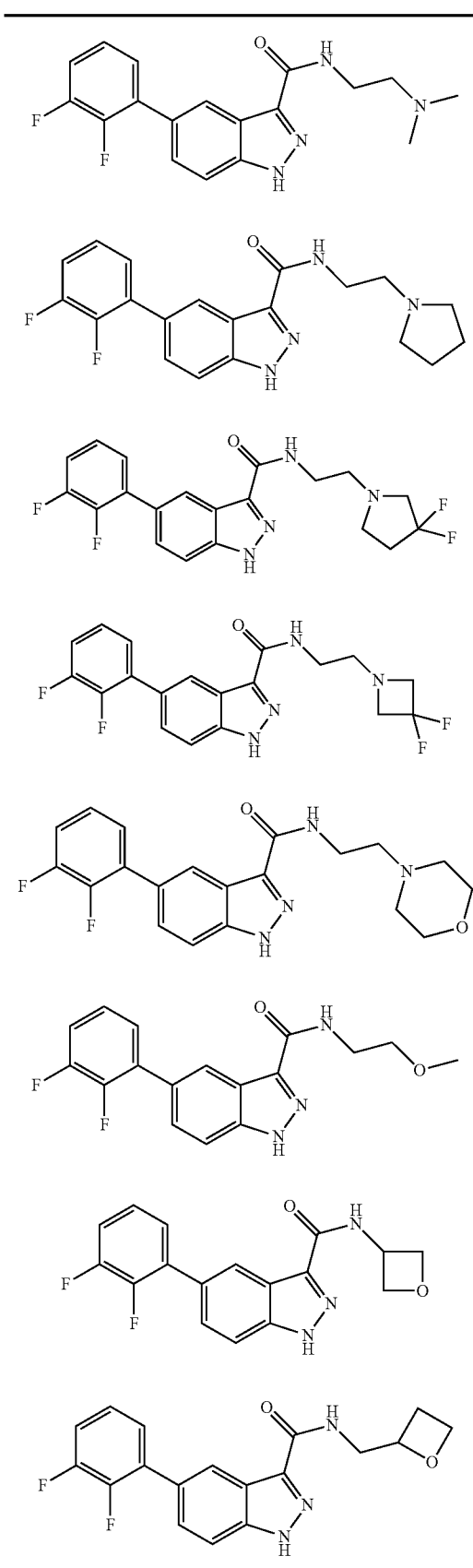
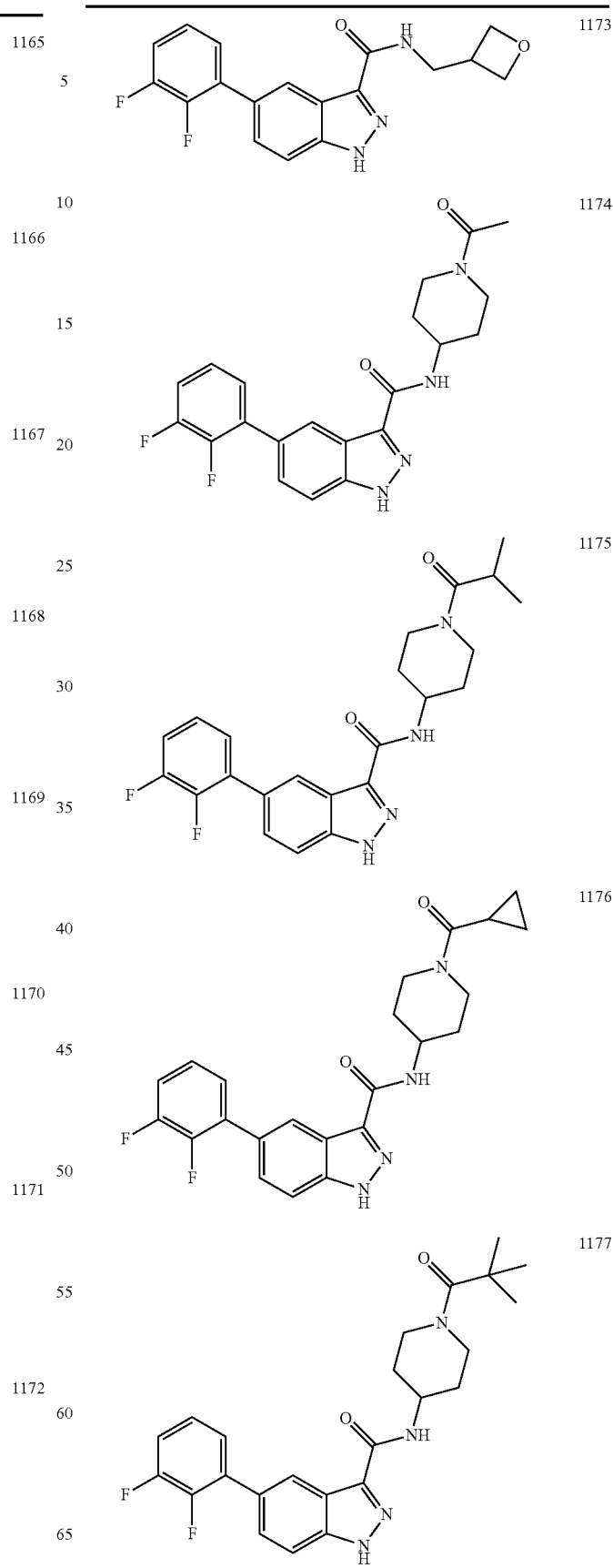

TABLE 1-continued
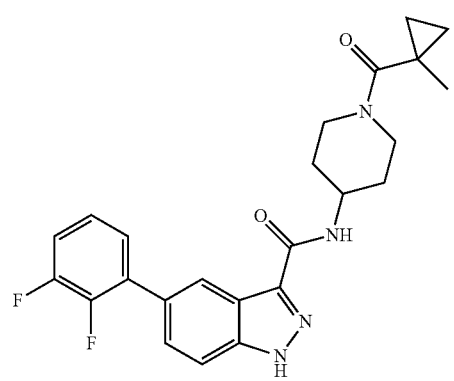 [SMILES: CC1(C(=O)N2CCC(NC(=O)c3n[nH]c4ccc(-c5cccc(F)c5F)cc34)CC2)CC1] 1178
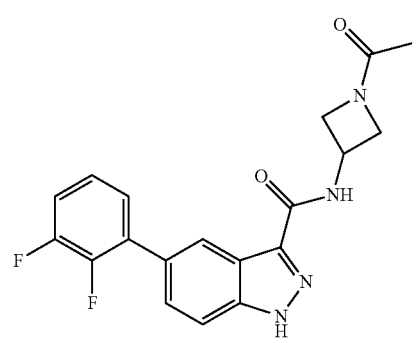 [SMILES: CC(=O)N1CC(NC(=O)c2n[nH]c3ccc(-c4cccc(F)c4F)cc23)C1] 1179
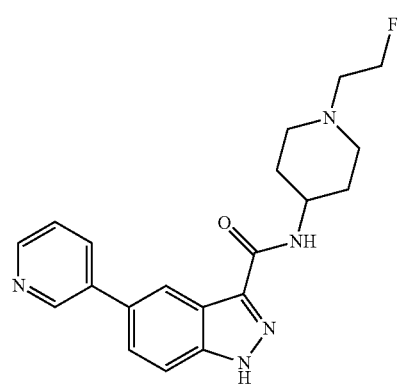 [SMILES: O=C(NC1CCN(CCF)CC1)c1n[nH]c2ccc(-c3cccnc3)cc12] 1180
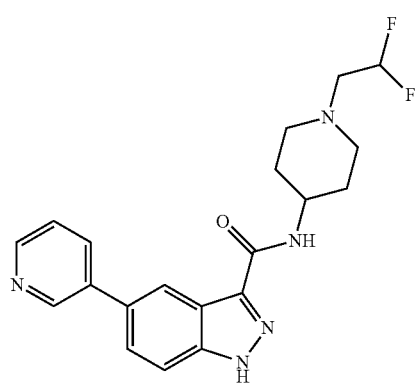 [SMILES: O=C(NC1CCN(CC(F)F)CC1)c1n[nH]c2ccc(-c3cccnc3)cc12] 1181
TABLE 1-continued
 1182
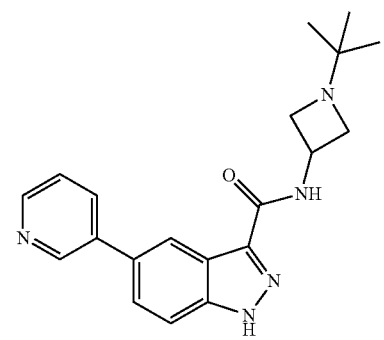 [SMILES: CC(C)(C)N1CC(NC(=O)c2n[nH]c3ccc(-c4cccnc4)cc23)C1] 1183
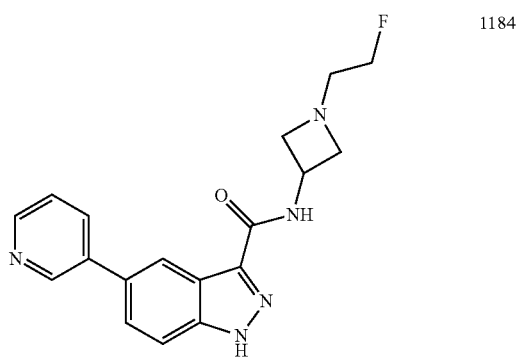 1184
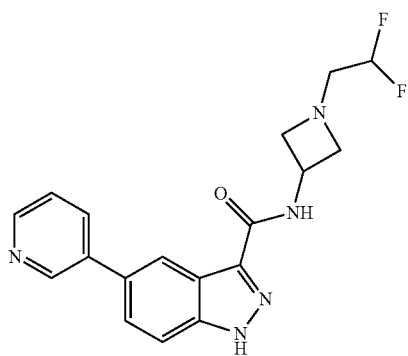 [SMILES: O=C(NC1CN(CC(F)F)C1)c1n[nH]c2ccc(-c3cccnc3)cc12] 1185

TABLE 1-continued
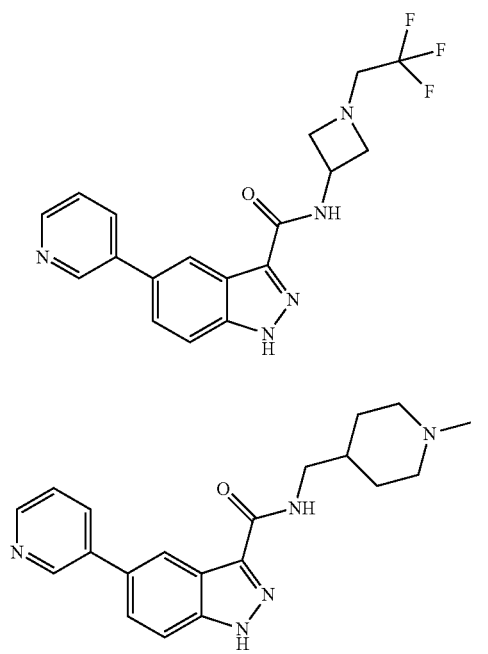
1186
1187
1188
1189
1190
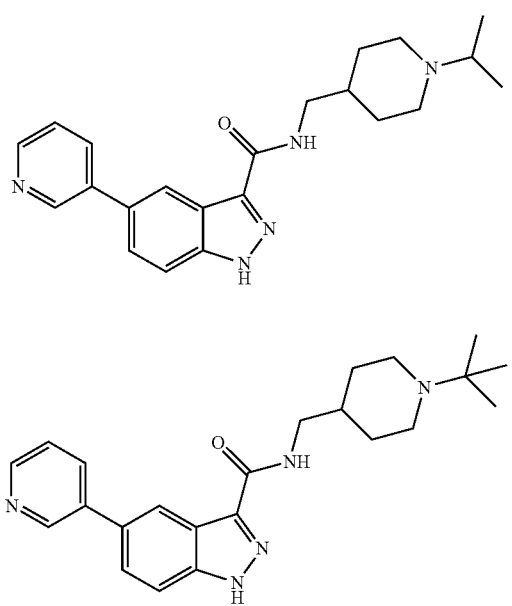
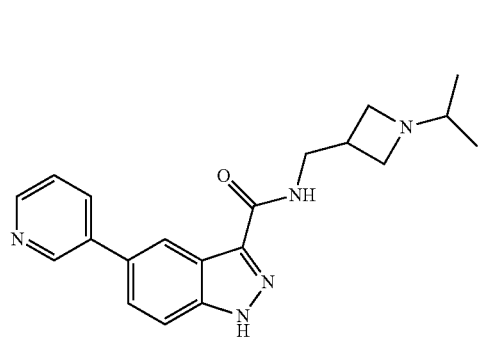 [SMILES: CC(C)N1CC(CNC(=O)c2n[nH]c3ccc(-c4cccnc4)cc23)C1]
TABLE 1-continued
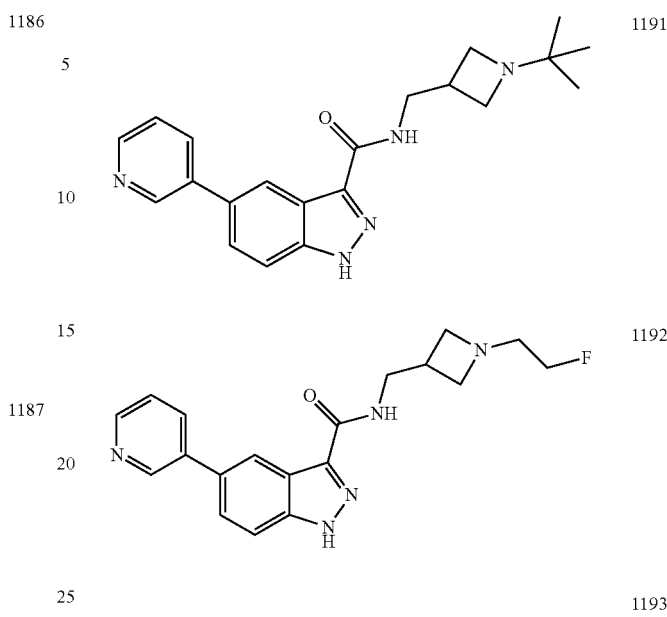
1191
1192
1193
1194
1195
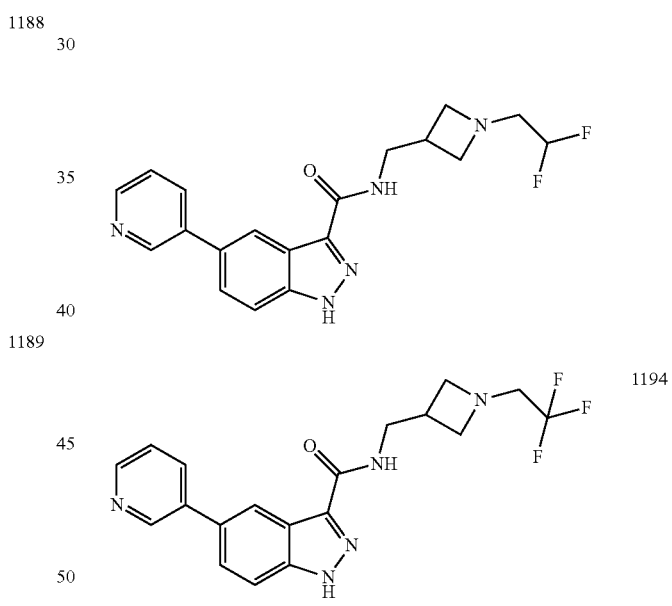
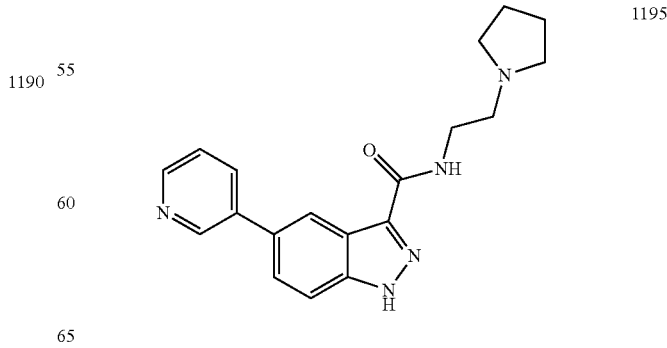

TABLE 1-continued
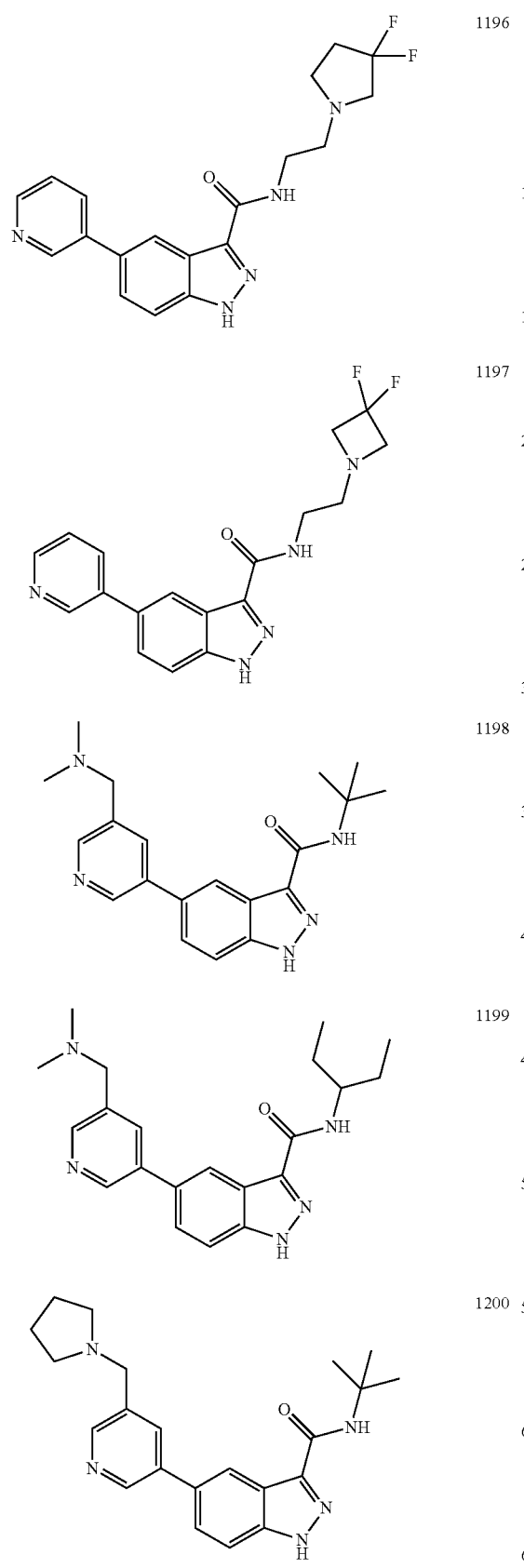
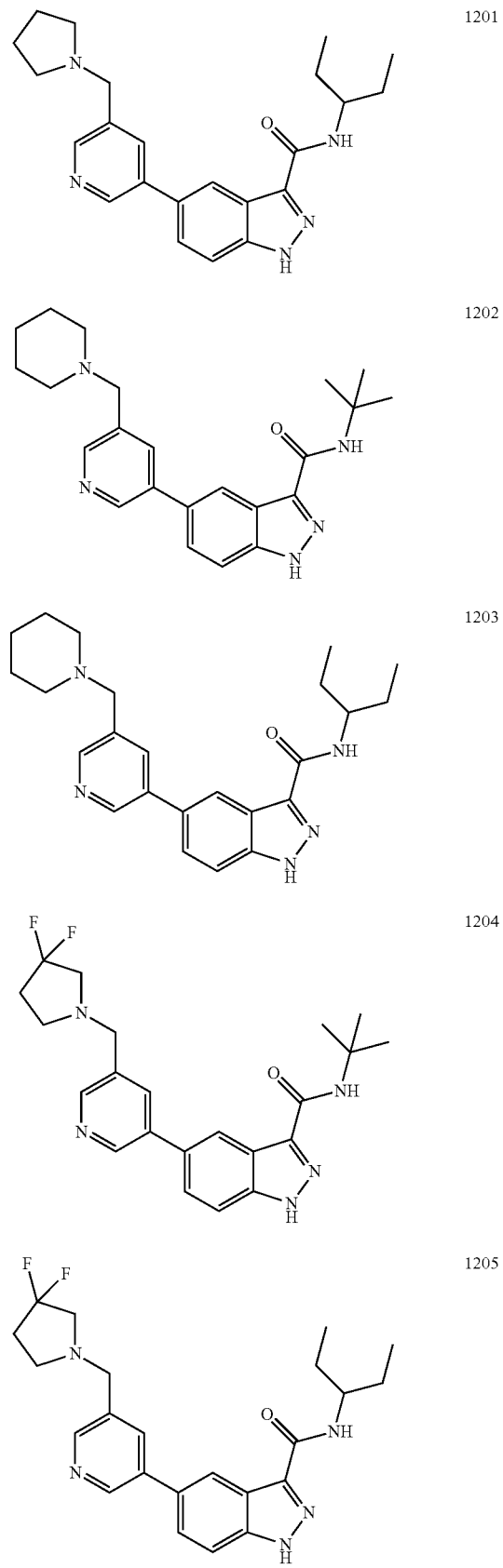

TABLE 1-continued
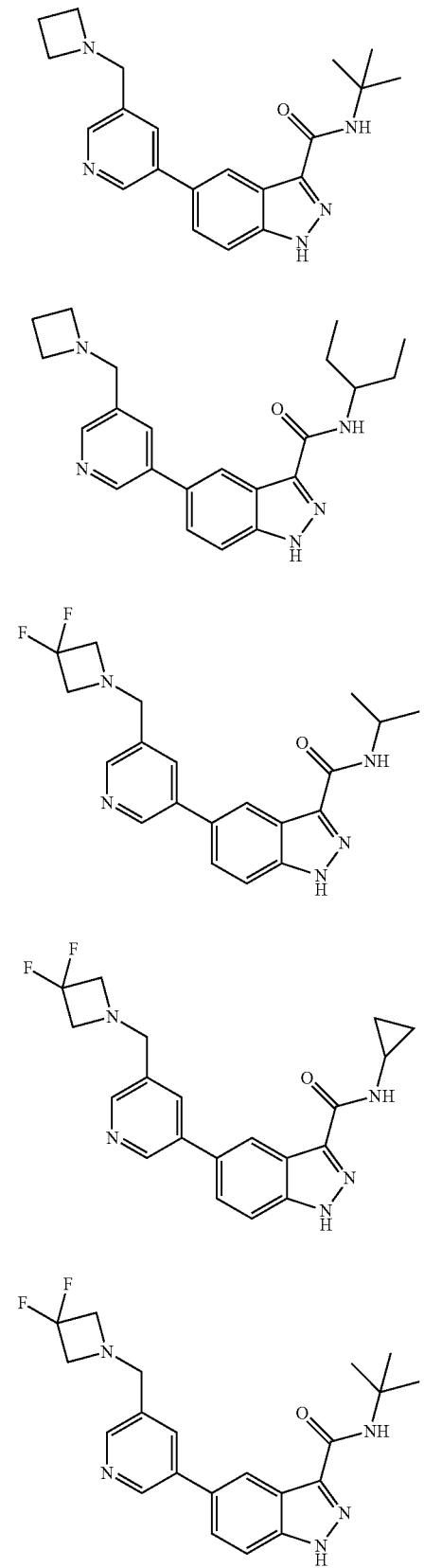
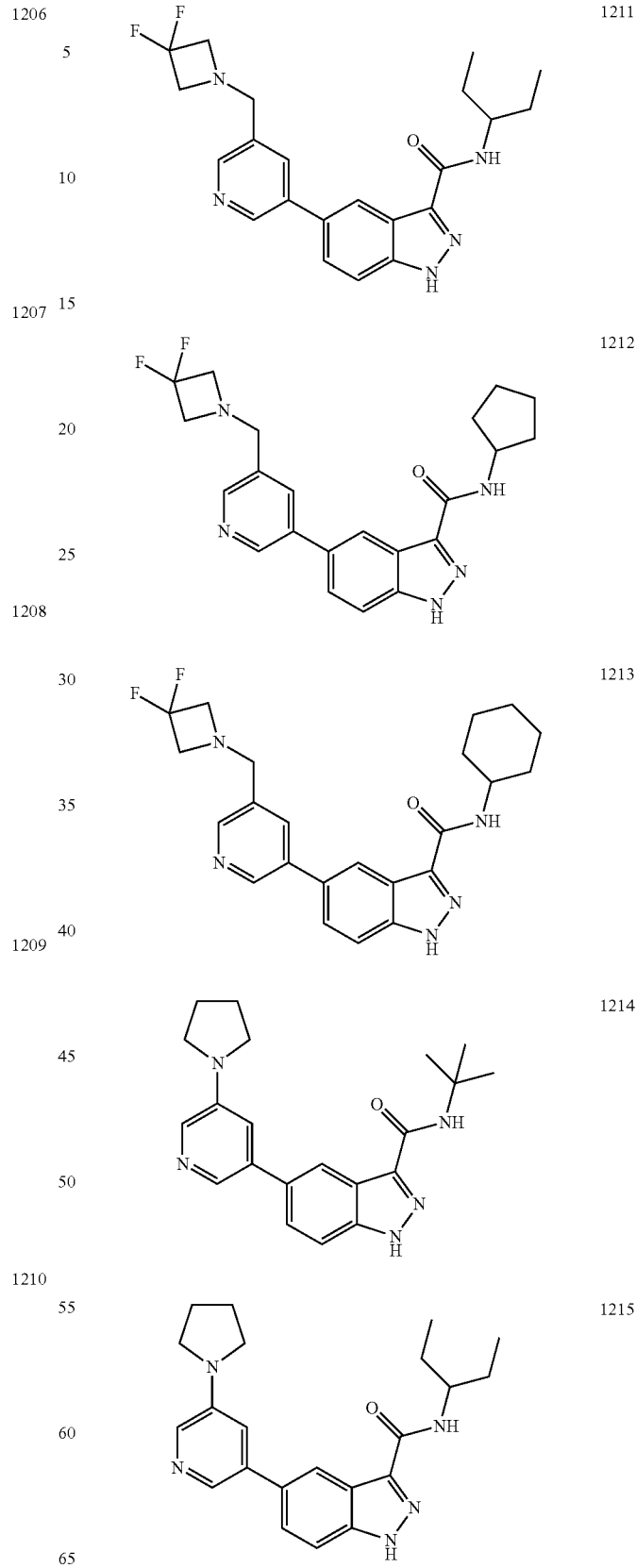

TABLE 1-continued
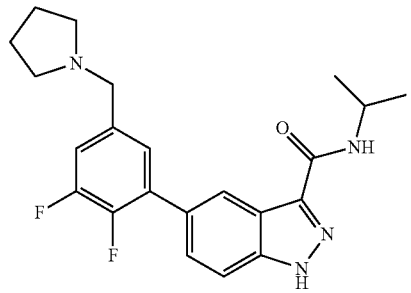 [SMILES: CC(C)NC(=O)c1n[nH]c2ccc(-c3cc(CN4CCCC4)cc(F)c3F)cc12] 1216
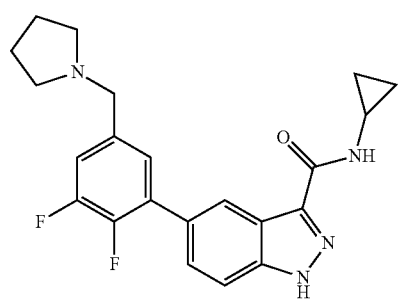 [SMILES: O=C(NC1CC1)c1n[nH]c2ccc(-c3cc(CN4CCCC4)cc(F)c3F)cc12] 1217
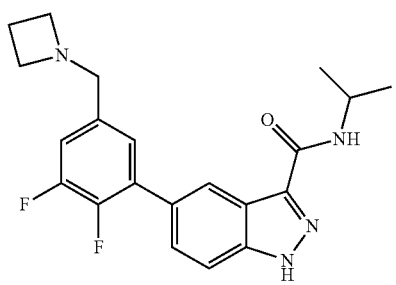 [SMILES: CC(C)NC(=O)c1n[nH]c2ccc(-c3cc(CN4CCC4)cc(F)c3F)cc12] 1218
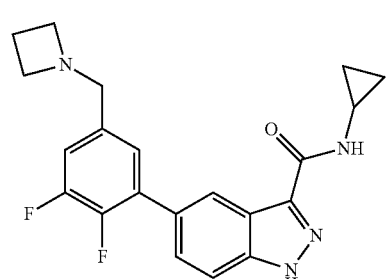 1219
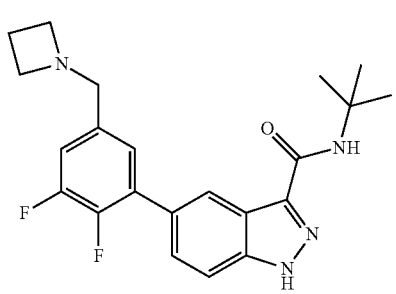 [SMILES: CC(C)(C)NC(=O)c1n[nH]c2ccc(-c3cc(CN4CCC4)cc(F)c3F)cc12] 1220
TABLE 1-continued
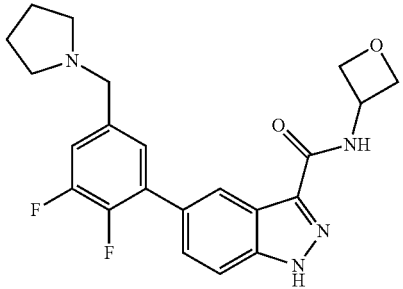 [SMILES: O=C(NC1COC1)c1n[nH]c2ccc(-c3cc(CN4CCCC4)cc(F)c3F)cc12] 1221
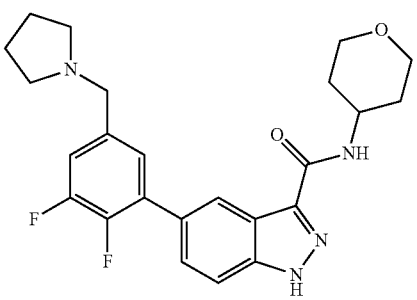 [SMILES: O=C(NC1CCOCC1)c1n[nH]c2ccc(-c3cc(CN4CCCC4)cc(F)c3F)cc12] 1222
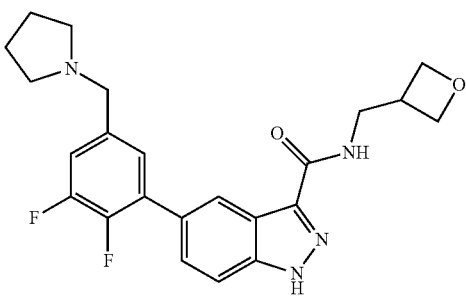 [SMILES: O=C(NCC1COC1)c1n[nH]c2ccc(-c3cc(CN4CCCC4)cc(F)c3F)cc12] 1223
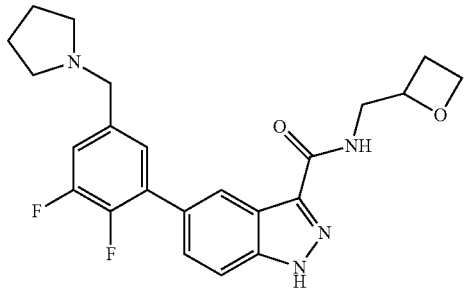 [SMILES: O=C(NCC1CCO1)c1n[nH]c2ccc(-c3cc(CN4CCCC4)cc(F)c3F)cc12] 1224
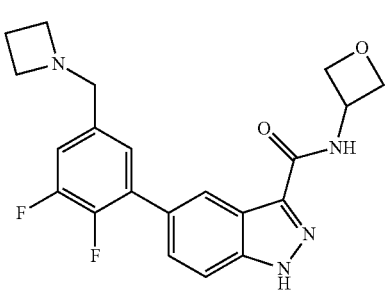 [SMILES: O=C(NC1COC1)c1n[nH]c2ccc(-c3cc(CN4CCC4)cc(F)c3F)cc12] 1225

TABLE 1-continued
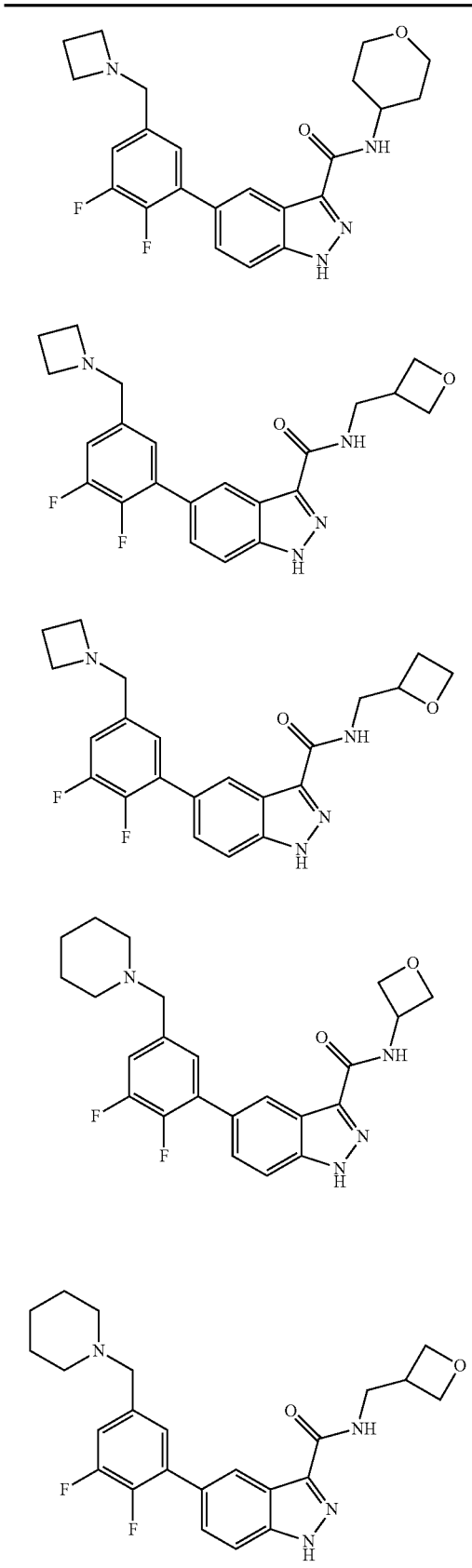
TABLE 1-continued
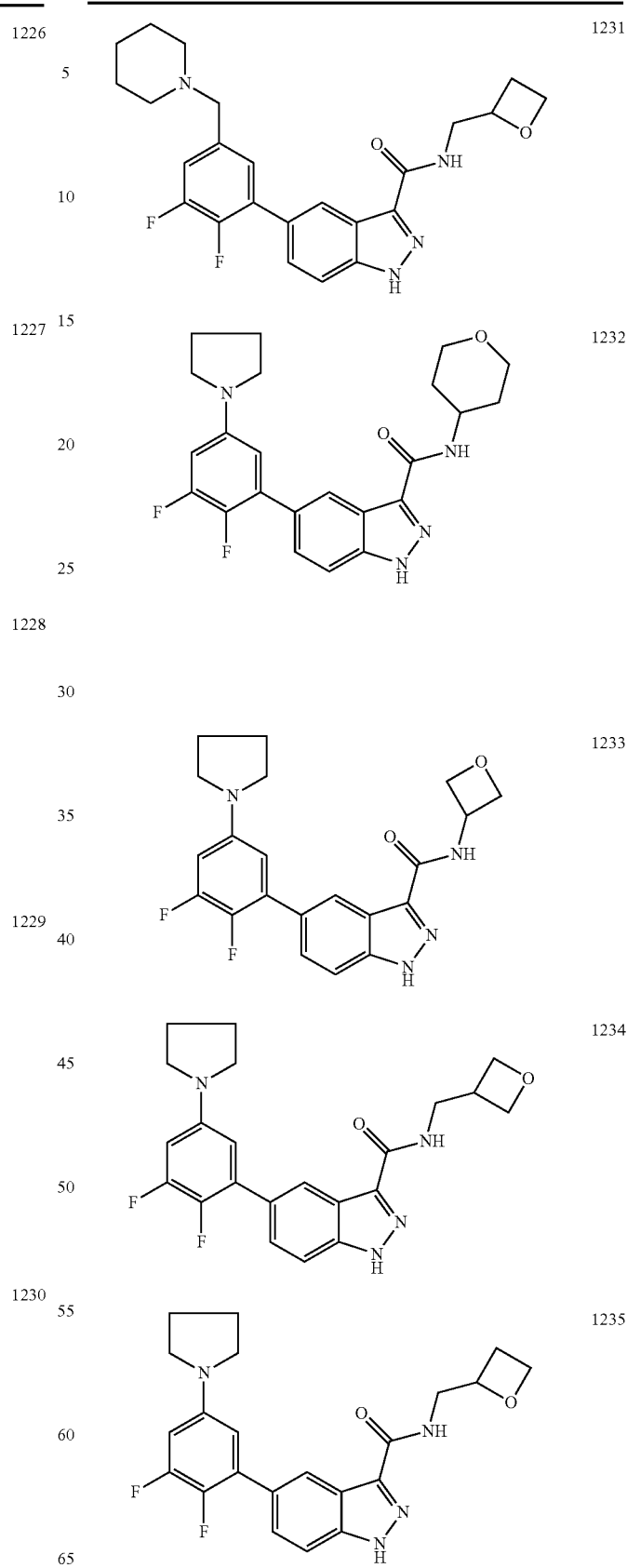

TABLE 1-continued
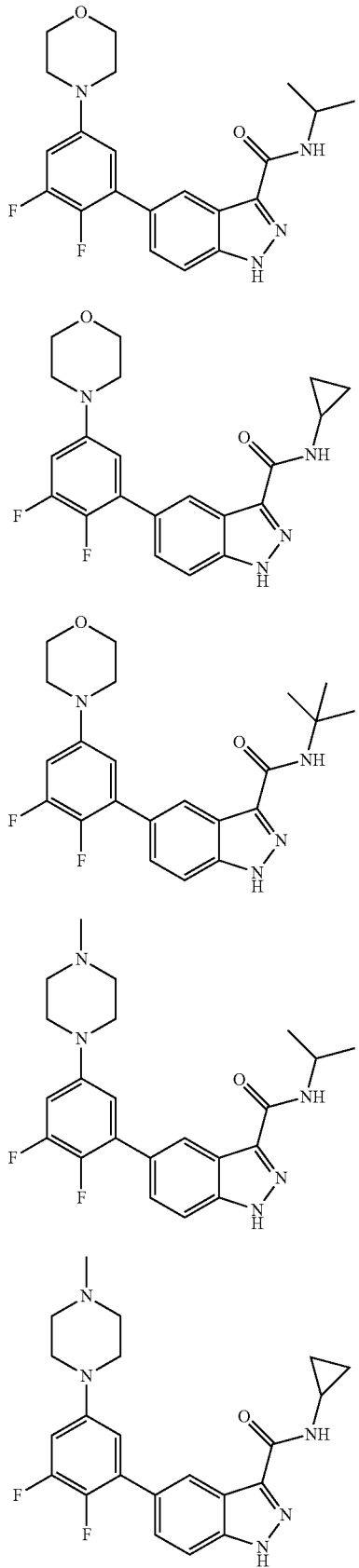
1236
1237
1238
1239
1240
TABLE 1-continued
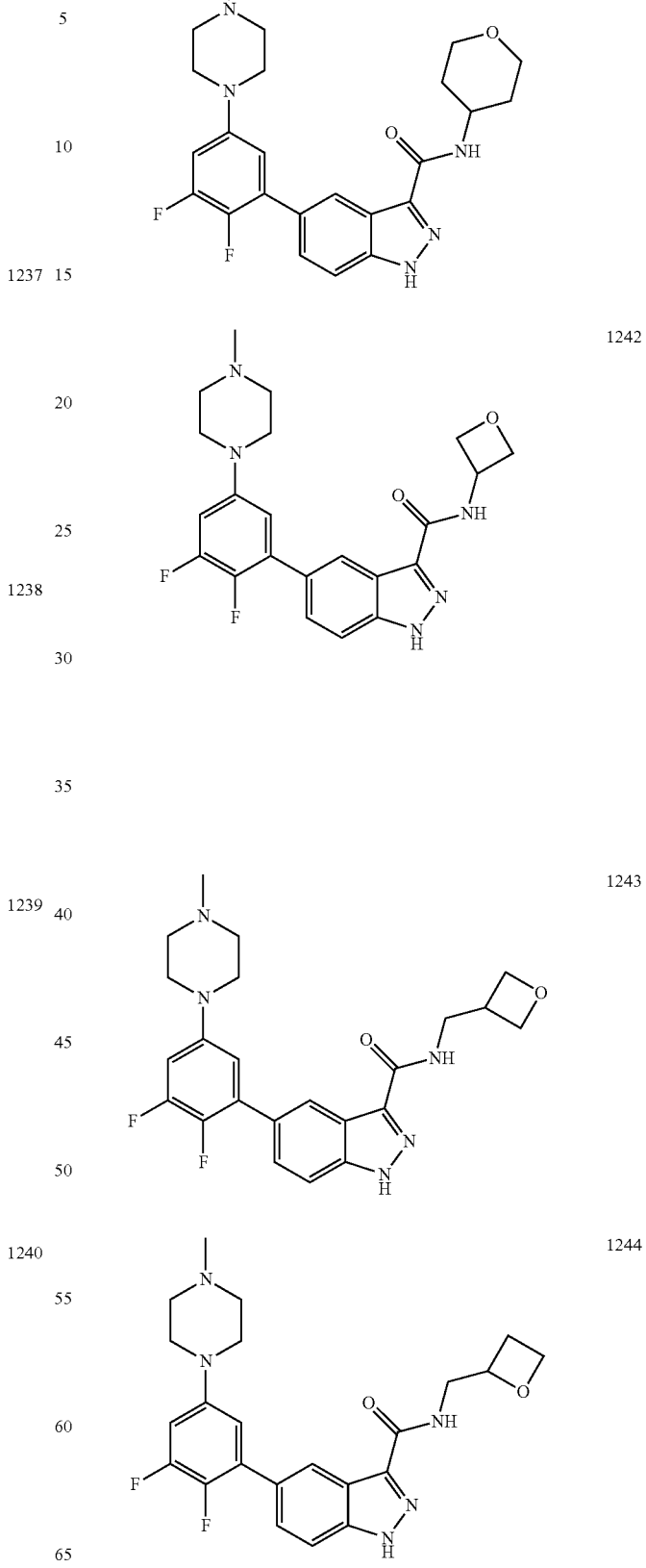
1241
1242
1243
1244

TABLE 1-continued
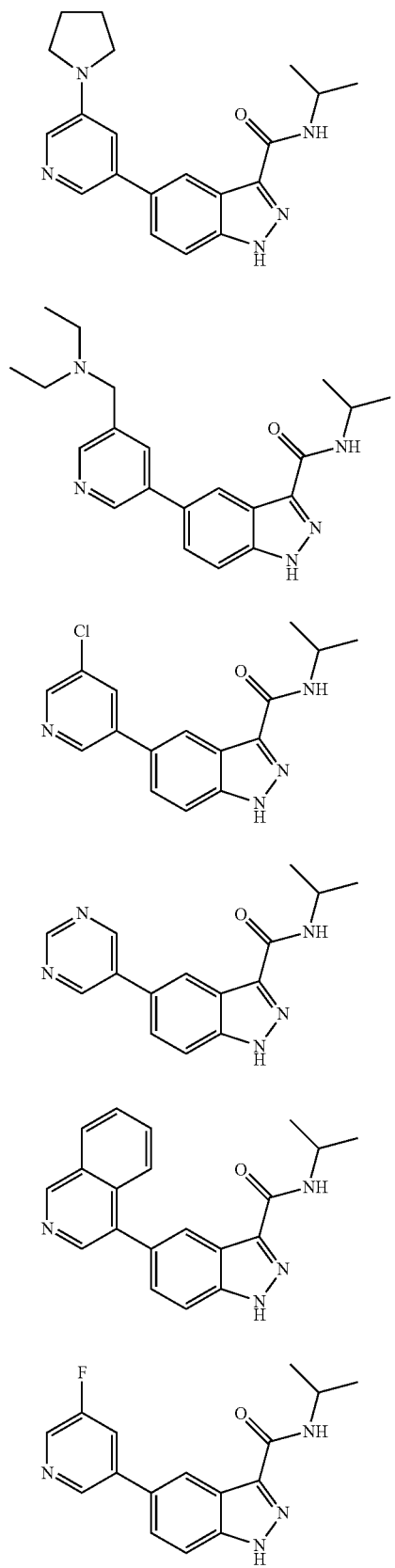
TABLE 1-continued
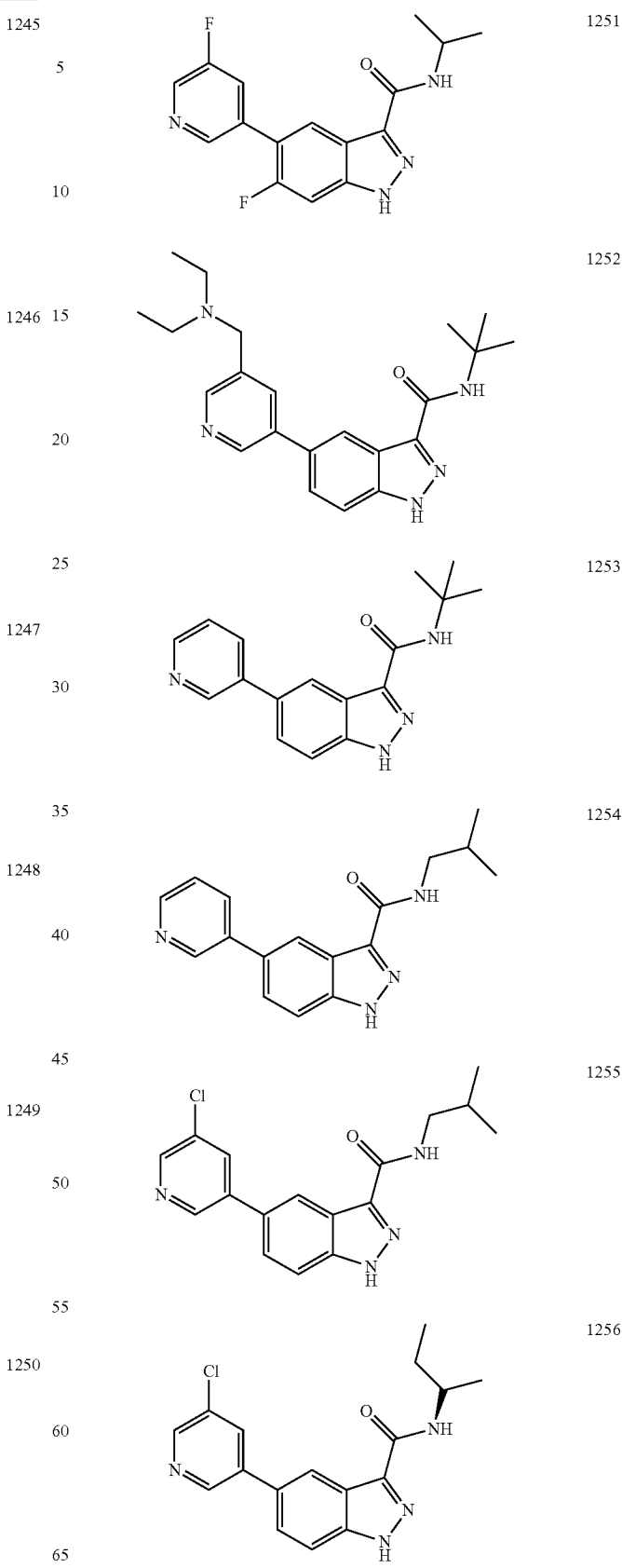

TABLE 1-continued
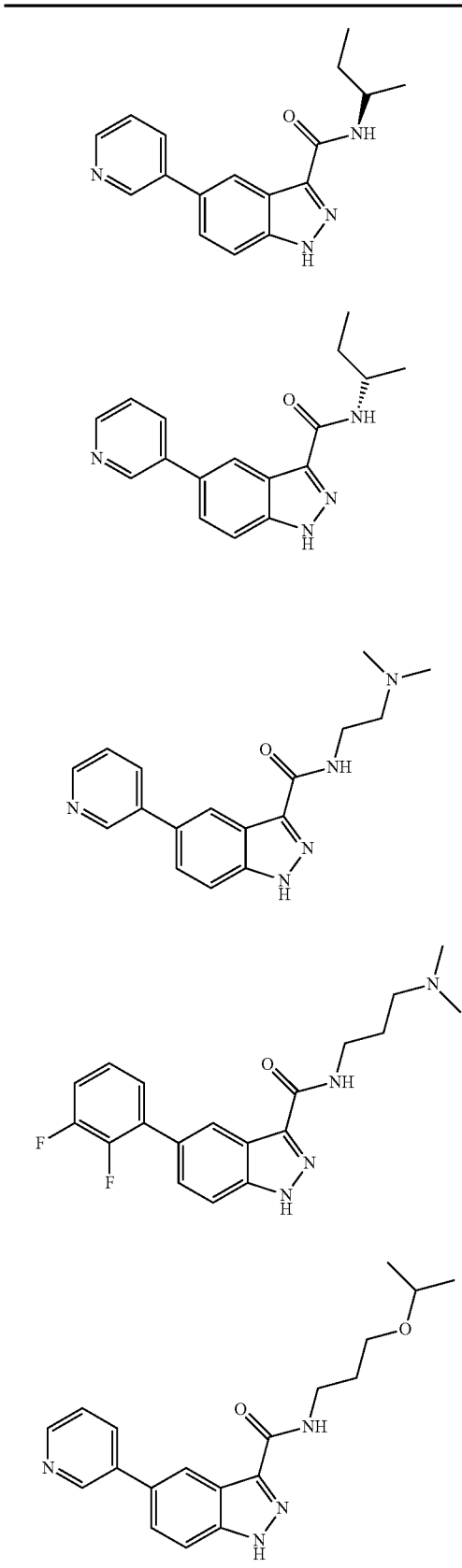
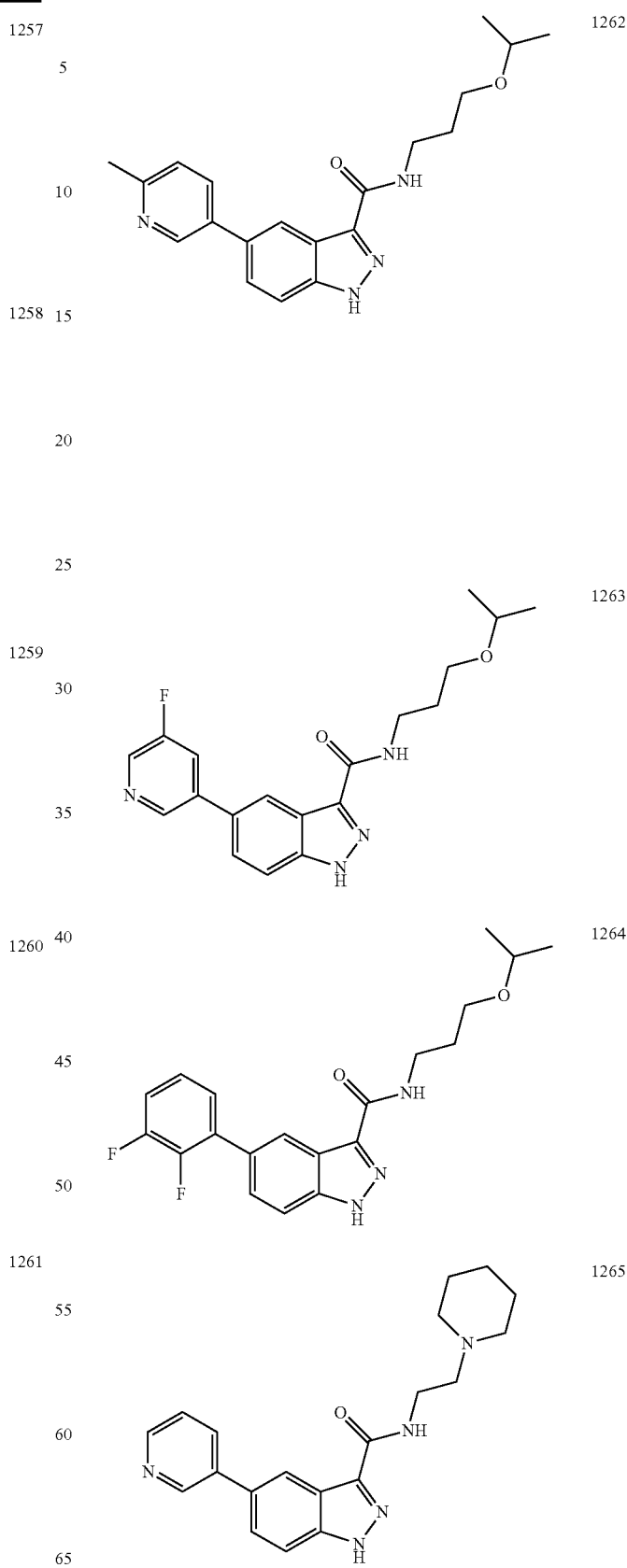

TABLE 1-continued
1266 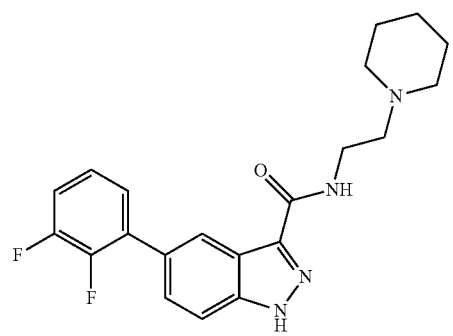 [SMILES: O=C(NCCN1CCCCC1)c1n[nH]c2ccc(-c3cccc(F)c3F)cc12]
1267 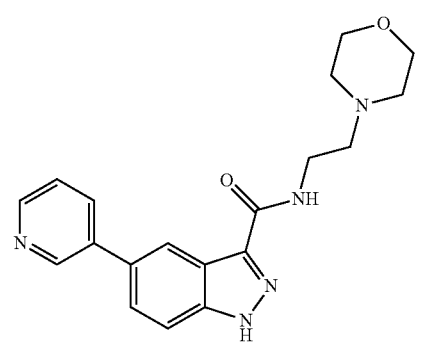 [SMILES: O=C(NCCN1CCOCC1)c1n[nH]c2ccc(-c3cccnc3)cc12]
1268 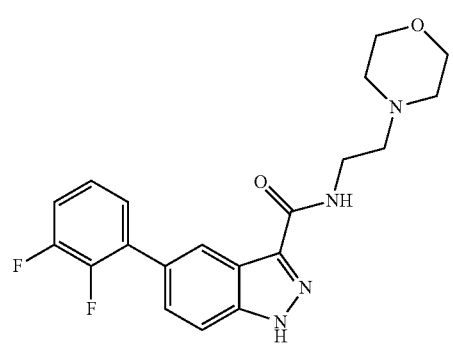 [SMILES: O=C(NCCN1CCOCC1)c1n[nH]c2ccc(-c3cccc(F)c3F)cc12]
1269 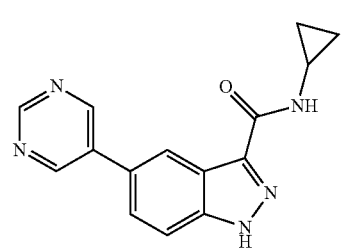 [SMILES: O=C(NC1CC1)c1n[nH]c2ccc(-c3cncnc3)cc12]
1270 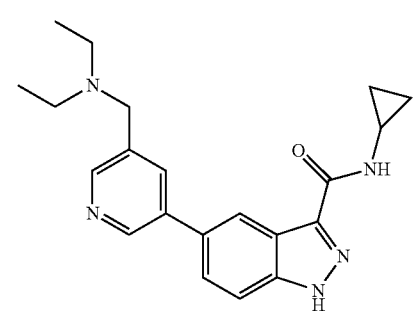 [SMILES: CCN(CC)Cc1cncc(-c2ccc3[nH]nc(C(=O)NC4CC4)c3c2)c1]
TABLE 1-continued
1271 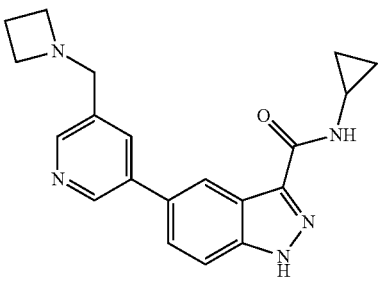 [SMILES: O=C(NC1CC1)c1n[nH]c2ccc(-c3cncc(CN4CCC4)c3)cc12]
1272 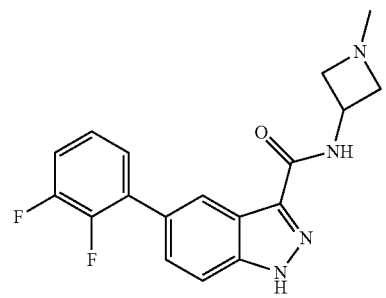 [SMILES: CN1CC(NC(=O)c2n[nH]c3ccc(-c4cccc(F)c4F)cc23)C1]
1273 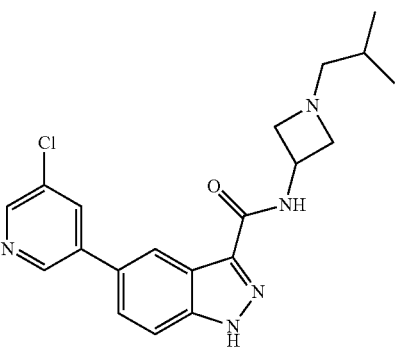 [SMILES: CC(C)CN1CC(NC(=O)c2n[nH]c3ccc(-c4cncc(Cl)c4)cc23)C1]
1274 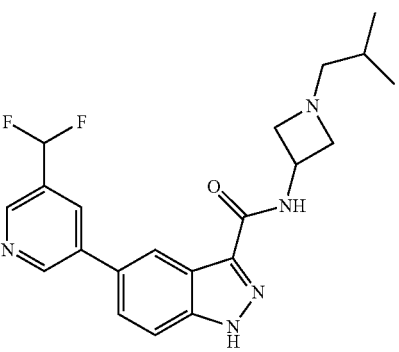 [SMILES: CC(C)CN1CC(NC(=O)c2n[nH]c3ccc(-c4cncc(C(F)F)c4)cc23)C1]
1275 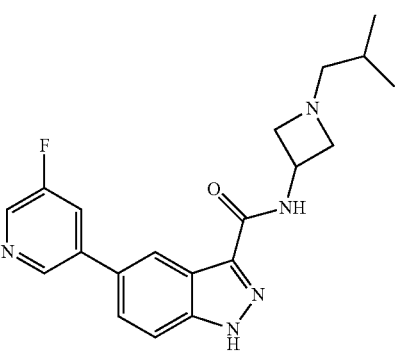 [SMILES: CC(C)CN1CC(NC(=O)c2n[nH]c3ccc(-c4cncc(F)c4)cc23)C1]

TABLE 1-continued
| | |
|---|---|
| 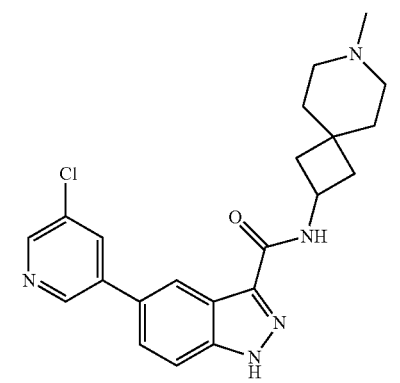 [SMILES: CN1CCC2(CC1)CC(NC(=O)c1n[nH]c3ccc(-c4cncc(Cl)c4)cc13)C2] | 1276 |
| 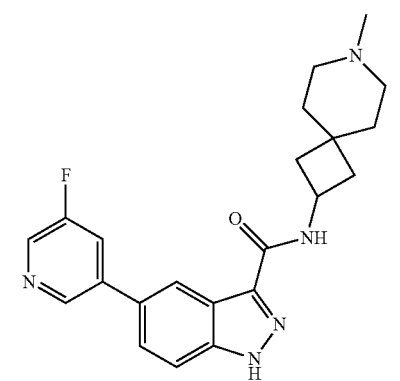 [SMILES: CN1CCC2(CC1)CC(NC(=O)c1n[nH]c3ccc(-c4cncc(F)c4)cc13)C2] | 1277 |
| 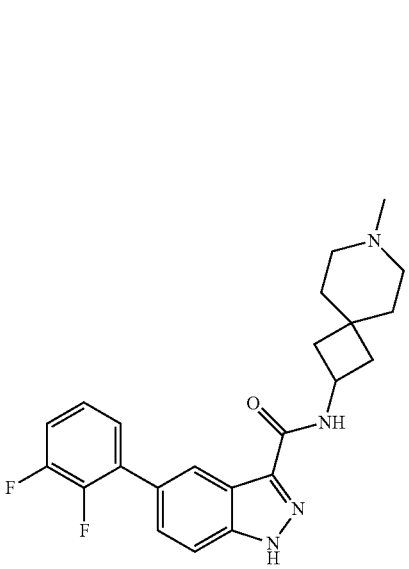 [SMILES: CN1CCC2(CC1)CC(NC(=O)c1n[nH]c3ccc(-c4cccc(F)c4F)cc13)C2] | 1278 |
| 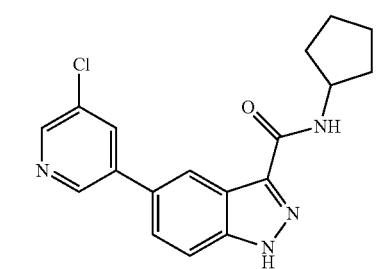 | 1279 |
TABLE 1-continued
| | |
|---|---|
| 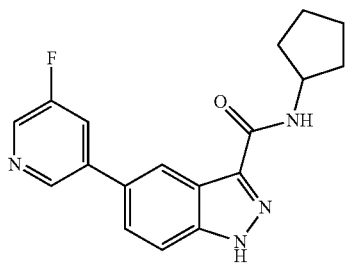 [SMILES: O=C(NC1CCCC1)c1n[nH]c2ccc(-c3cncc(F)c3)cc12] | 1280 |
| 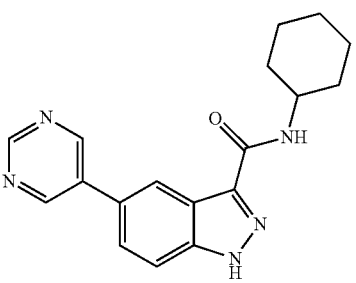 [SMILES: O=C(NC1CCCCC1)c1n[nH]c2ccc(-c3cncnc3)cc12] | 1281 |
| 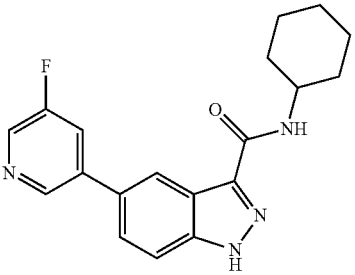 [SMILES: O=C(NC1CCCCC1)c1n[nH]c2ccc(-c3cncc(F)c3)cc12] | 1282 |
| 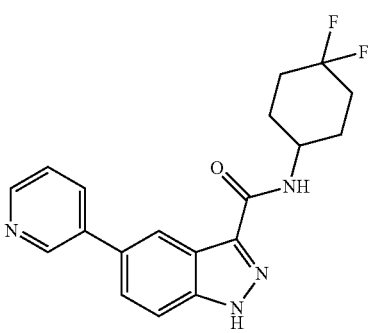 [SMILES: O=C(NC1CCC(F)(F)CC1)c1n[nH]c2ccc(-c3cccnc3)cc12] | 1283 |
| 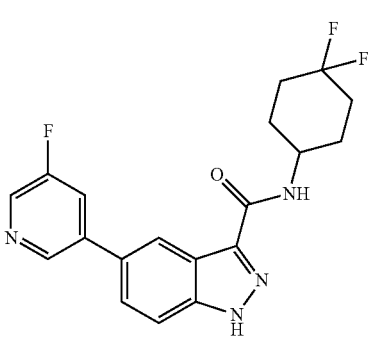 [SMILES: O=C(NC1CCC(F)(F)CC1)c1n[nH]c2ccc(-c3cncc(F)c3)cc12] | 1284 |

TABLE 1-continued
1285
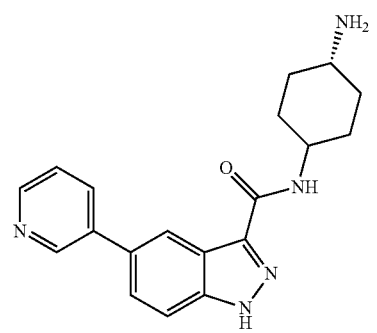
1286
1287
1288
TABLE 1-continued
1289
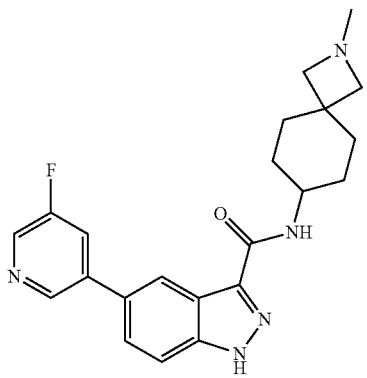 [SMILES: CN1CC2(CCC(NC(=O)c3n[nH]c4ccc(-c5cncc(F)c5)cc34)CC2)C1]
1290
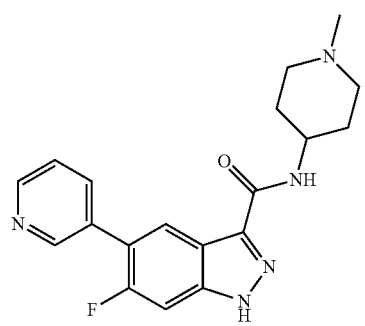 [SMILES: CN1CCC(NC(=O)c2n[nH]c3cc(F)c(-c4cccnc4)cc23)CC1]
1291
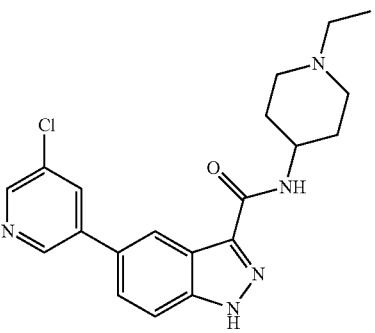 [SMILES: CCN1CCC(NC(=O)c2n[nH]c3ccc(-c4cncc(Cl)c4)cc23)CC1]
1292
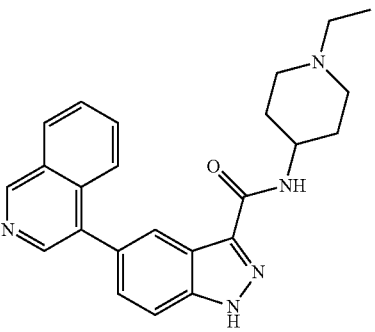 [SMILES: CCN1CCC(NC(=O)c2n[nH]c3ccc(-c4cncc5ccccc45)cc23)CC1]

TABLE 1-continued
| 1293 | 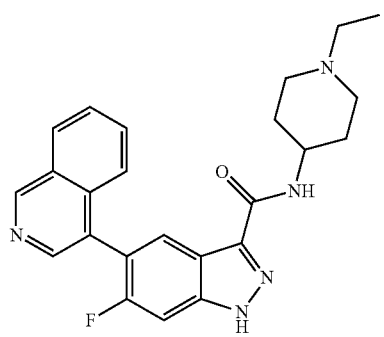 [SMILES: CCN1CCC(NC(=O)c2n[nH]c3cc(F)c(-c4cncc5ccccc45)cc23)CC1] |
| 1294 | 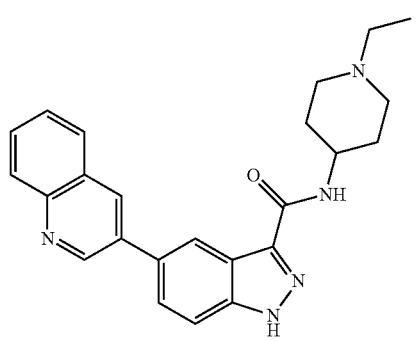 [SMILES: CCN1CCC(NC(=O)c2n[nH]c3ccc(-c4cnc5ccccc5c4)cc23)CC1] |
| 1295 | 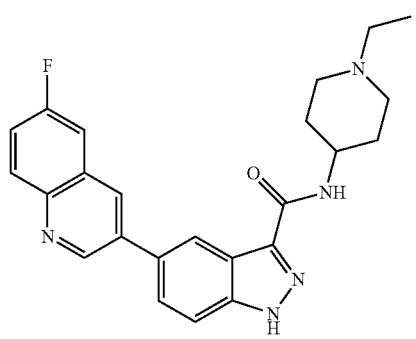 [SMILES: CCN1CCC(NC(=O)c2n[nH]c3ccc(-c4cnc5ccc(F)cc5c4)cc23)CC1] |
| 1296 | 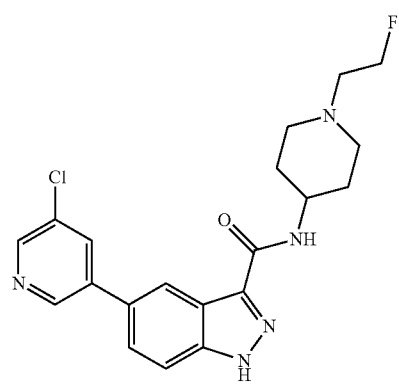 [SMILES: O=C(NC1CCN(CCF)CC1)c1n[nH]c2ccc(-c3cncc(Cl)c3)cc12] |
TABLE 1-continued
| 1297 | 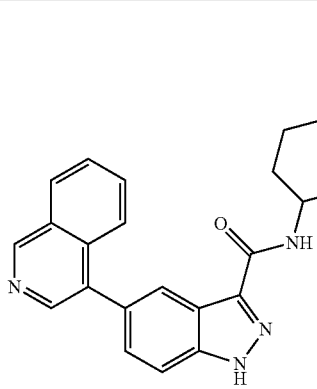 |
| 1298 | 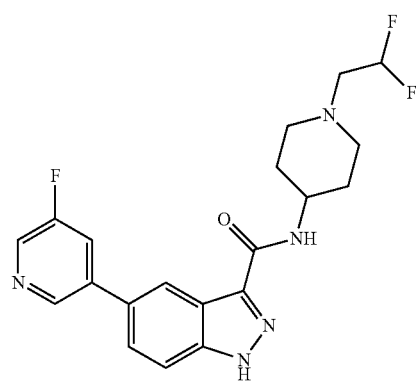 |
| 1299 | 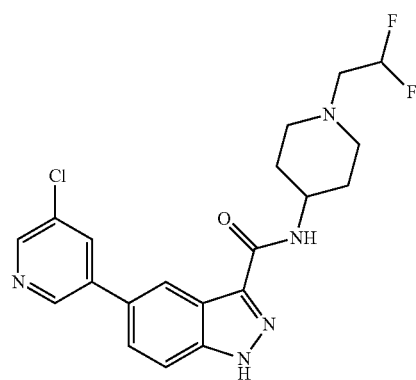 [SMILES: O=C(NC1CCN(CC(F)F)CC1)c1n[nH]c2ccc(-c3cncc(F)c3)cc12] |
| 1300 | 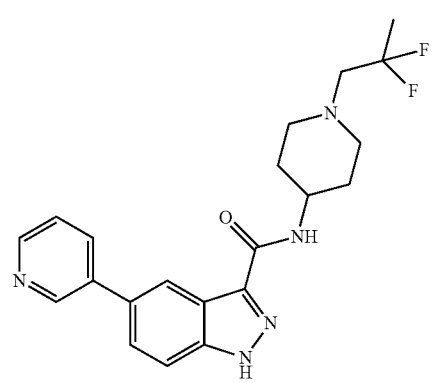 [SMILES: CC(F)(F)CN1CCC(NC(=O)c2n[nH]c3ccc(-c4cccnc4)cc23)CC1] |

TABLE 1-continued
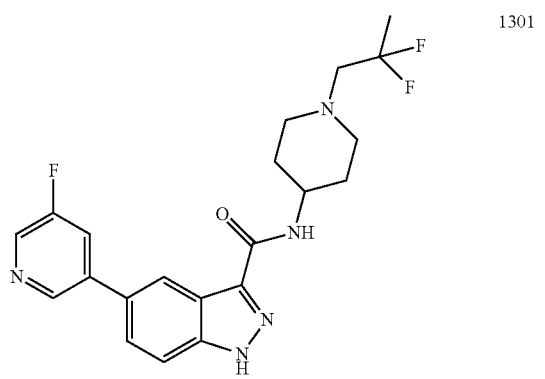
1301
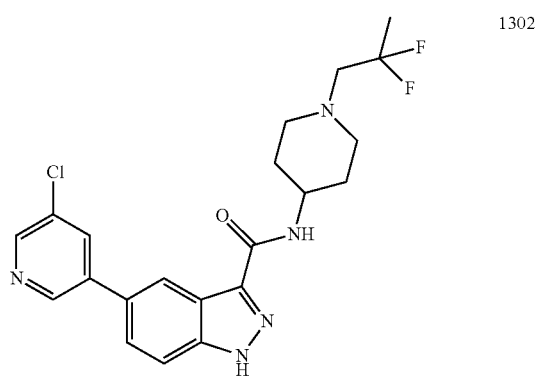
1302
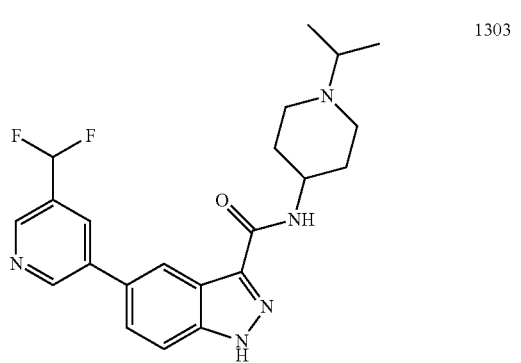
1303
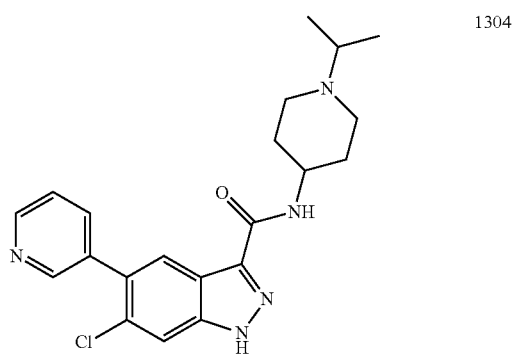
1304
TABLE 1-continued
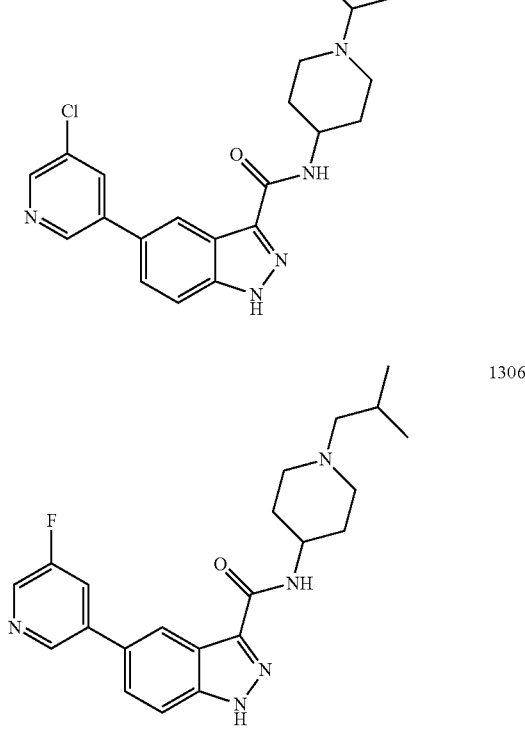
1305
1306
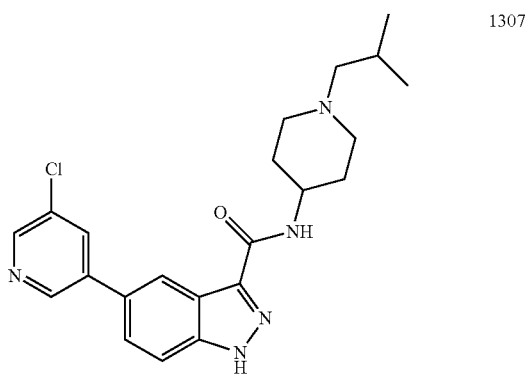
1307
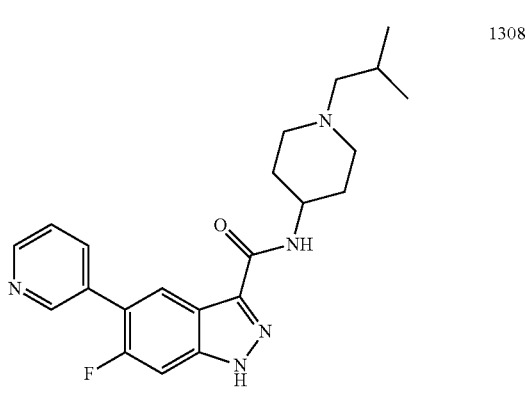
1308

TABLE 1-continued
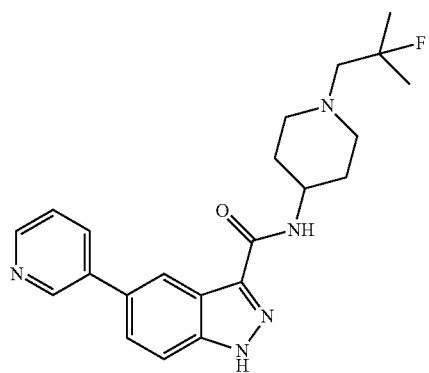
1309
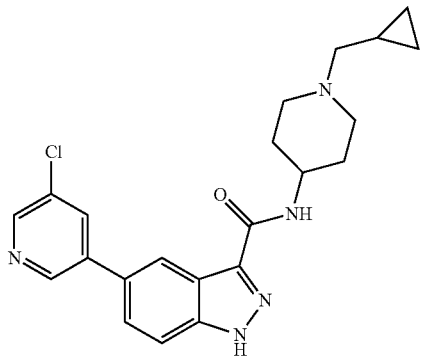
1313
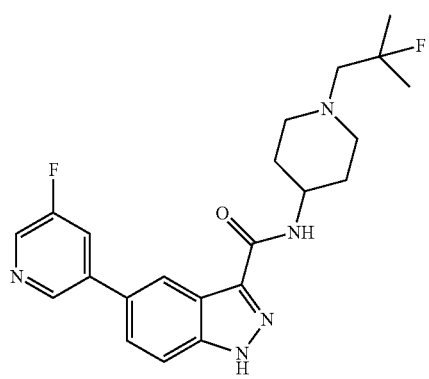 [SMILES: CC(C)(F)CN1CCC(NC(=O)c2n[nH]c3ccc(-c4cncc(F)c4)cc23)CC1]
1310
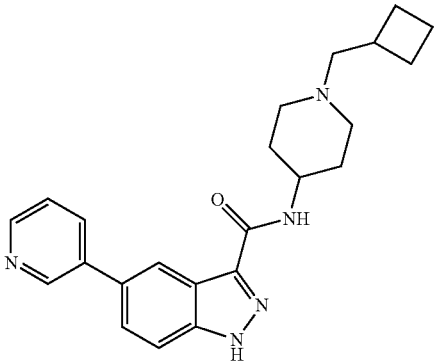 [SMILES: O=C(NC1CCN(CC2CCC2)CC1)c1n[nH]c2ccc(-c3cccnc3)cc12]
1314
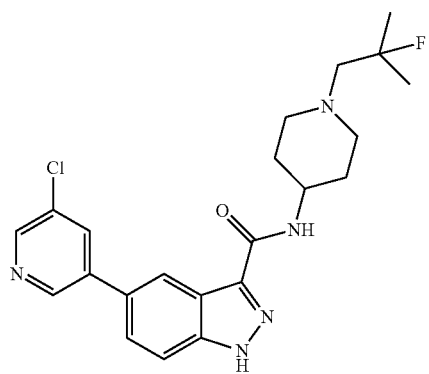
1311
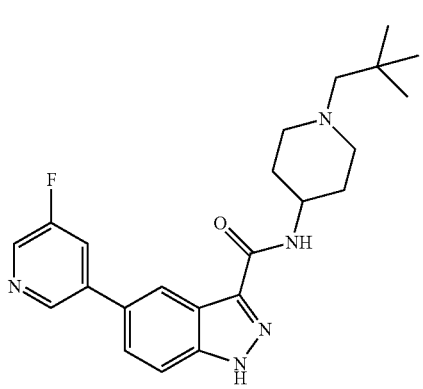 [SMILES: CC(C)(C)CN1CCC(NC(=O)c2n[nH]c3ccc(-c4cncc(F)c4)cc23)CC1]
1315
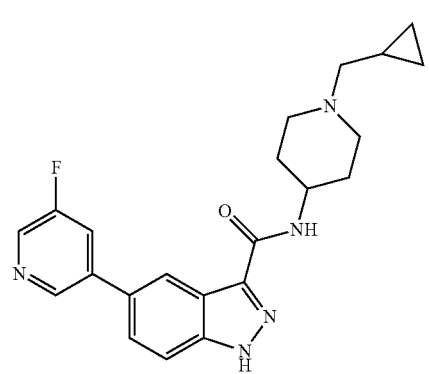
1312
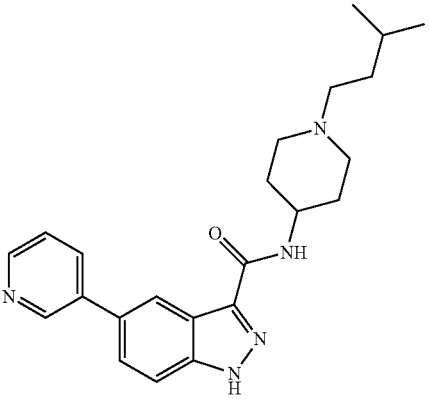 [SMILES: CC(C)CCN1CCC(NC(=O)c2n[nH]c3ccc(-c4cccnc4)cc23)CC1]
1316

TABLE 1-continued
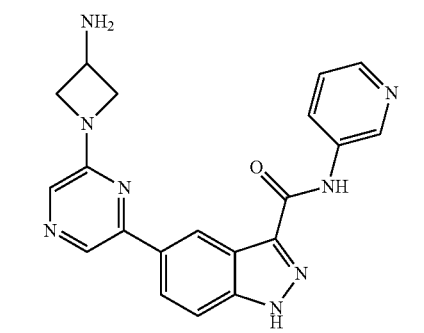 [SMILES: NC1CN(c2cncc(-c3ccc4[nH]nc(C(=O)Nc5cccnc5)c4c3)n2)C1]
1317
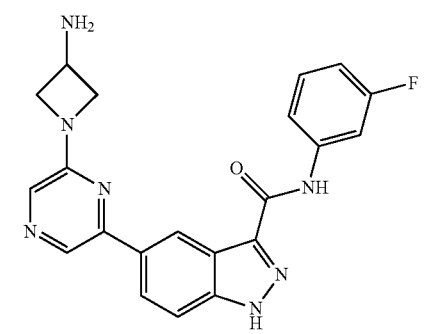 [SMILES: NC1CN(c2cncc(-c3ccc4[nH]nc(C(=O)Nc5cccc(F)c5)c4c3)n2)C1]
1318
1319
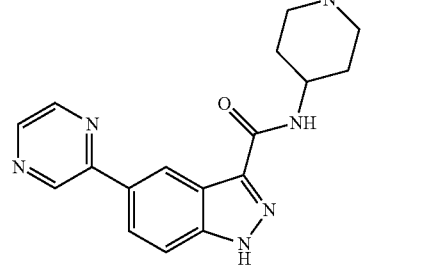
1320
TABLE 1-continued
1321
1322
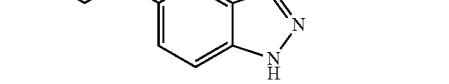
1323
1324

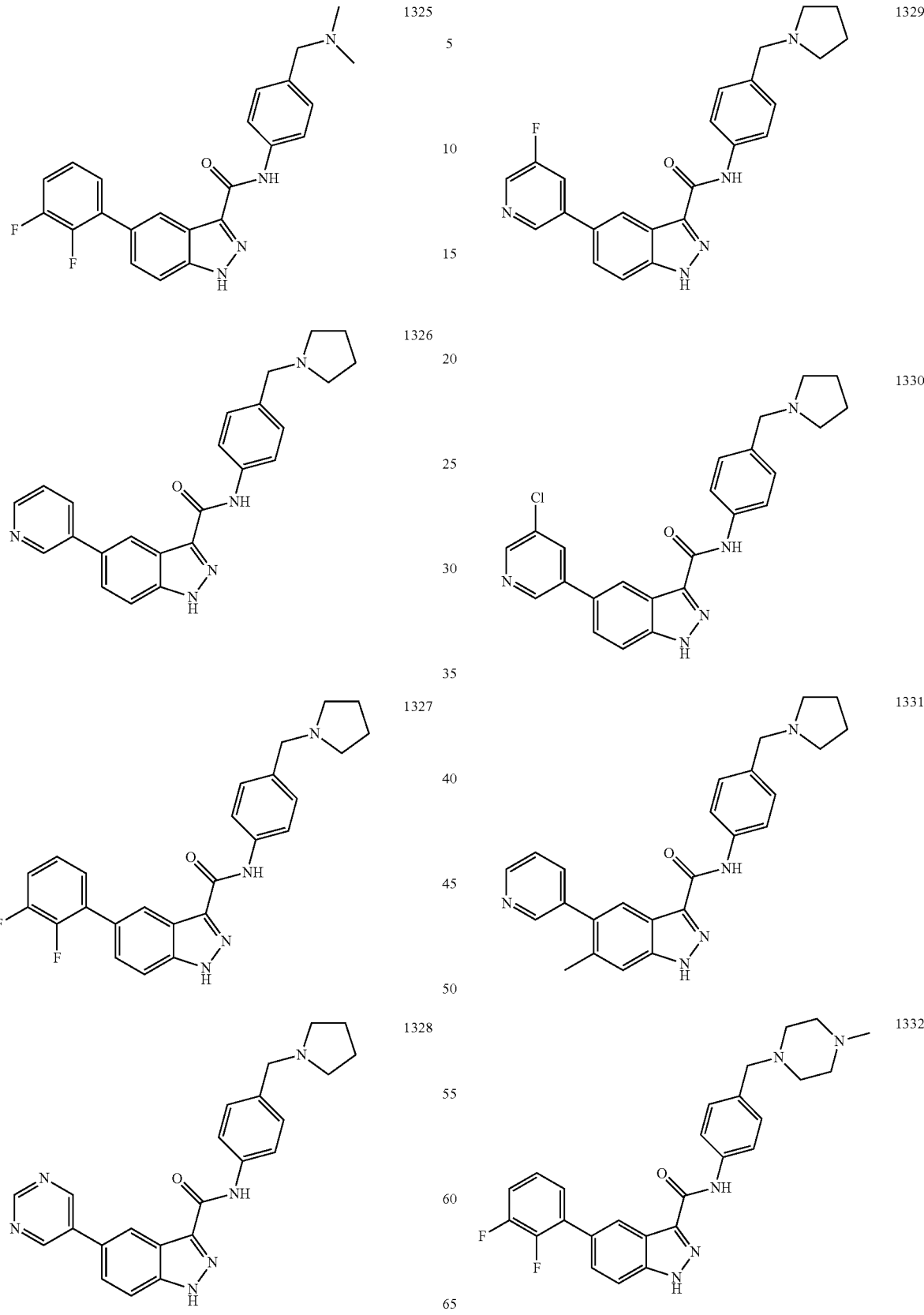

TABLE 1-continued
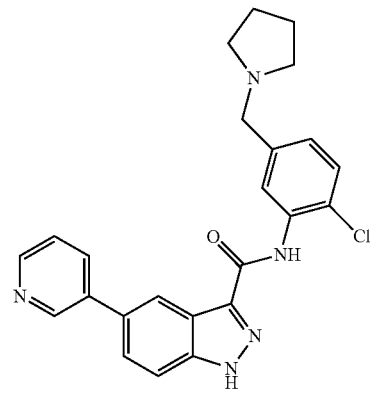 [SMILES: O=C(Nc1cc(CN2CCCC2)ccc1Cl)c1n[nH]c2ccc(-c3cccnc3)cc12]
1333
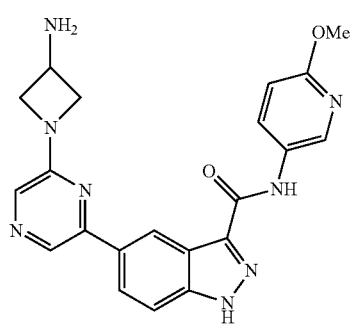 [SMILES: COc1ccc(NC(=O)c2n[nH]c3ccc(-c4cncc(N5CC(N)C5)n4)cc23)cn1]
1334
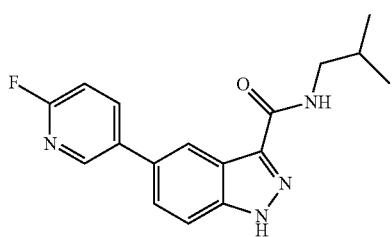 [SMILES: CC(C)CNC(=O)c1n[nH]c2ccc(-c3ccc(F)nc3)cc12]
1335
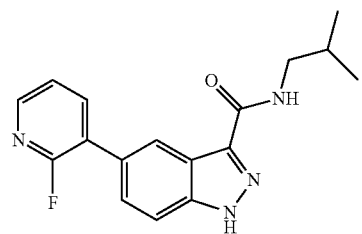 [SMILES: CC(C)CNC(=O)c1n[nH]c2ccc(-c3cccnc3F)cc12]
1336
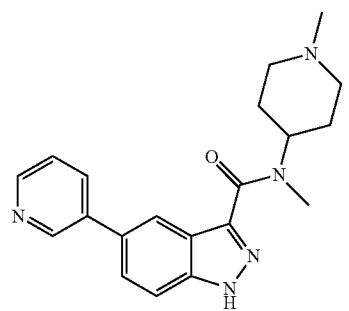 [SMILES: CN1CCC(N(C)C(=O)c2n[nH]c3ccc(-c4cccnc4)cc23)CC1]
1337
TABLE 1-continued
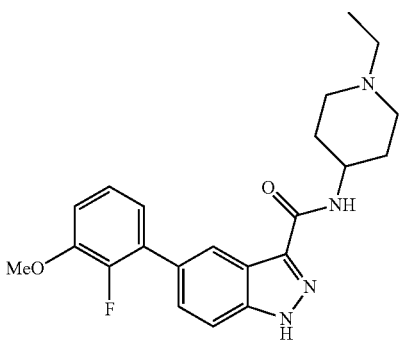 [SMILES: CCN1CCC(NC(=O)c2n[nH]c3ccc(-c4cccc(OC)c4F)cc23)CC1]
1338
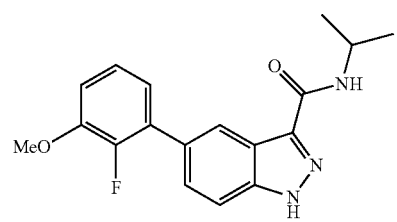 [SMILES: COc1cccc(-c2ccc3[nH]nc(C(=O)NC(C)C)c3c2)c1F]
1339
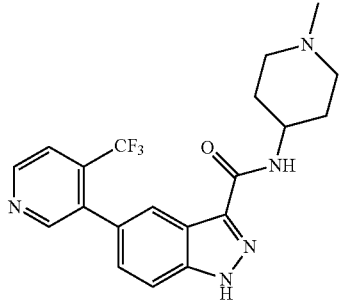 [SMILES: CN1CCC(NC(=O)c2n[nH]c3ccc(-c4cnccc4C(F)(F)F)cc23)CC1]
1340
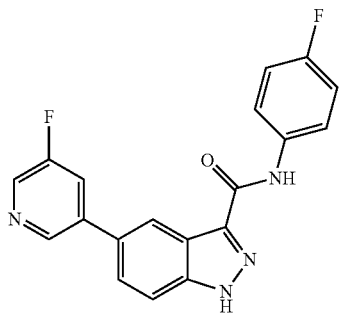 [SMILES: O=C(Nc1ccc(F)cc1)c1n[nH]c2ccc(-c3cncc(F)c3)cc12]
1341
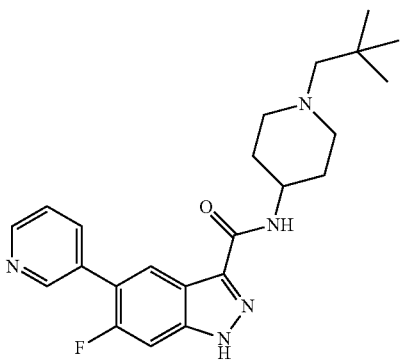 [SMILES: CC(C)(C)CN1CCC(NC(=O)c2n[nH]c3cc(F)c(-c4cccnc4)cc23)CC1]
1342

TABLE 1-continued
1343 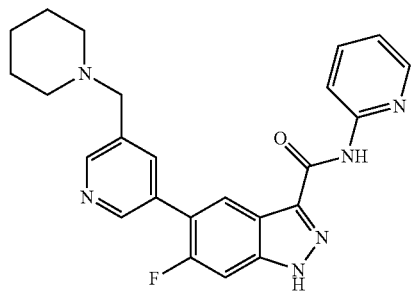 [SMILES: O=C(Nc1ccccn1)c1n[nH]c2cc(F)c(-c3cncc(CN4CCCCC4)c3)cc12]
1344 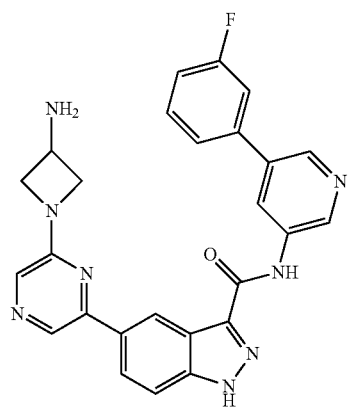 [SMILES: NC1CN(c2cncc(-c3ccc4[nH]nc(C(=O)Nc5cncc(-c6cccc(F)c6)c5)c4c3)n2)C1]
1345 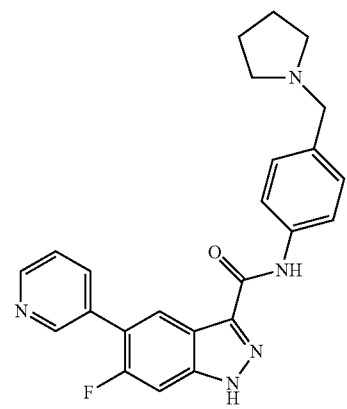 [SMILES: O=C(Nc1ccc(CN2CCCC2)cc1)c1n[nH]c2cc(F)c(-c3cccnc3)cc12]
1346 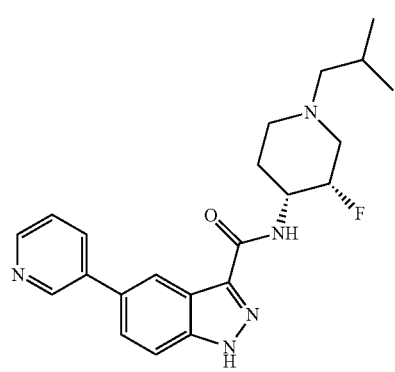 [SMILES: CC(C)CN1CC[C@@H](NC(=O)c2n[nH]c3ccc(-c4cccnc4)cc23)[C@@H](F)C1]
TABLE 1-continued
1347 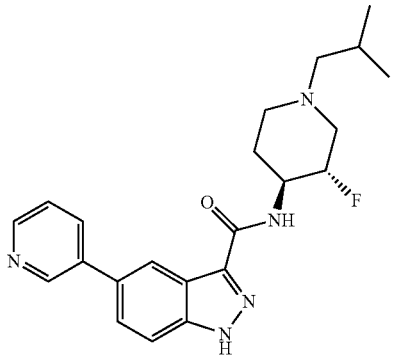 [SMILES: CC(C)CN1CC[C@H](NC(=O)c2n[nH]c3ccc(-c4cccnc4)cc23)[C@@H](F)C1]
1348 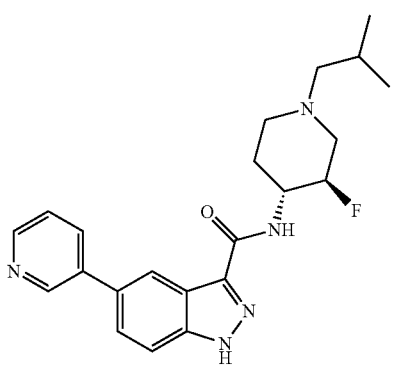 [SMILES: CC(C)CN1CC[C@@H](NC(=O)c2n[nH]c3ccc(-c4cccnc4)cc23)[C@H](F)C1]
1349 
1350 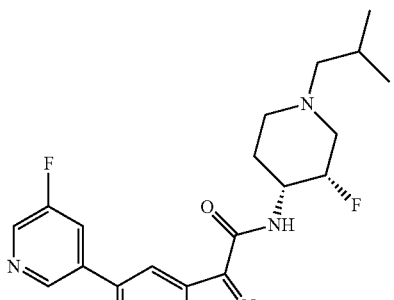

TABLE 1-continued
1351 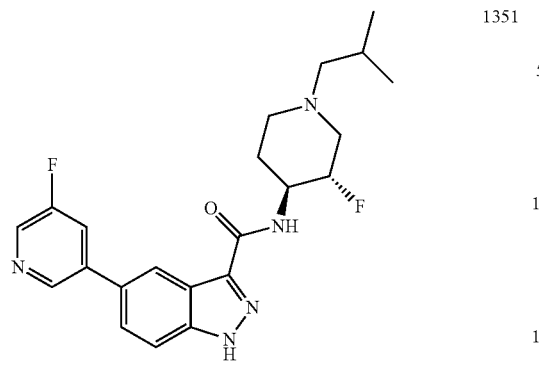
1352 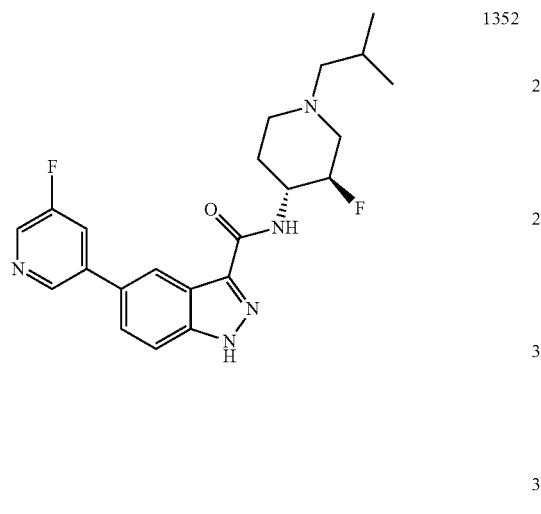
1353 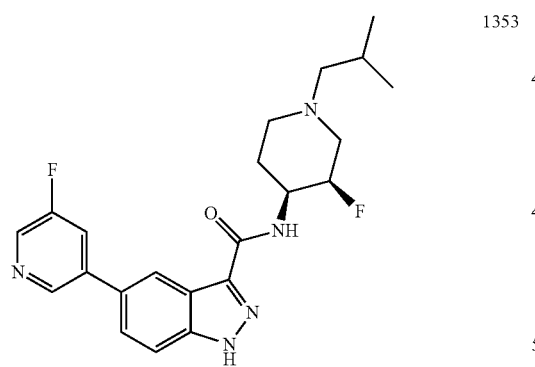
1354 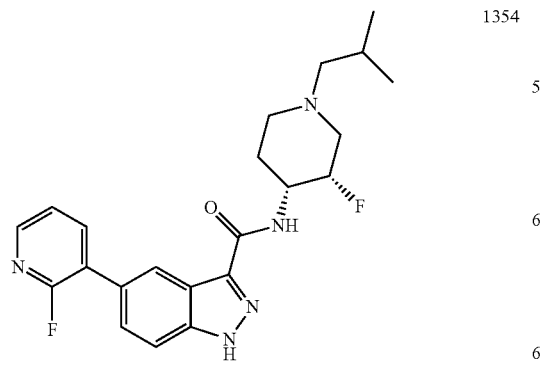
TABLE 1-continued
1355 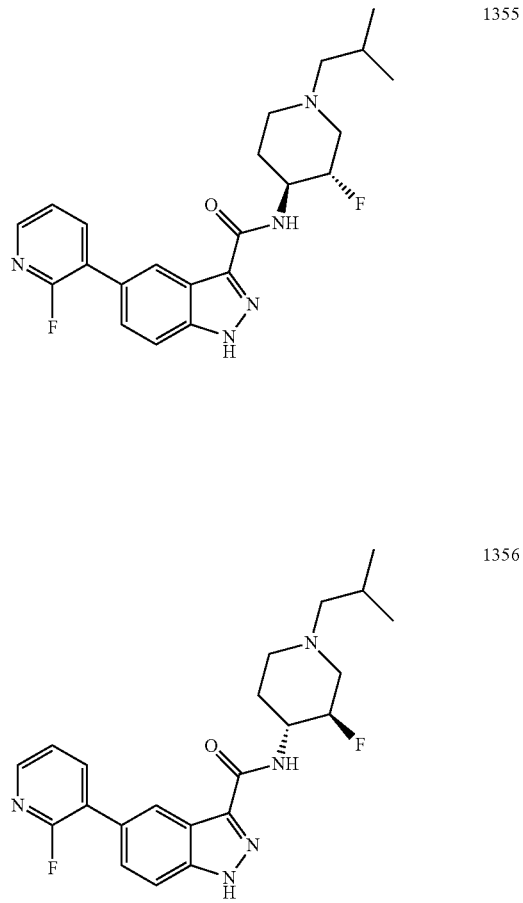
1356
1357
1358 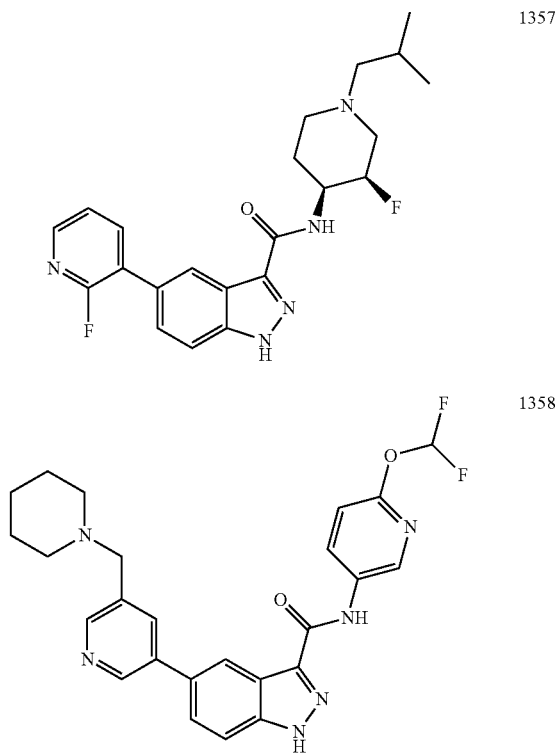

TABLE 1-continued
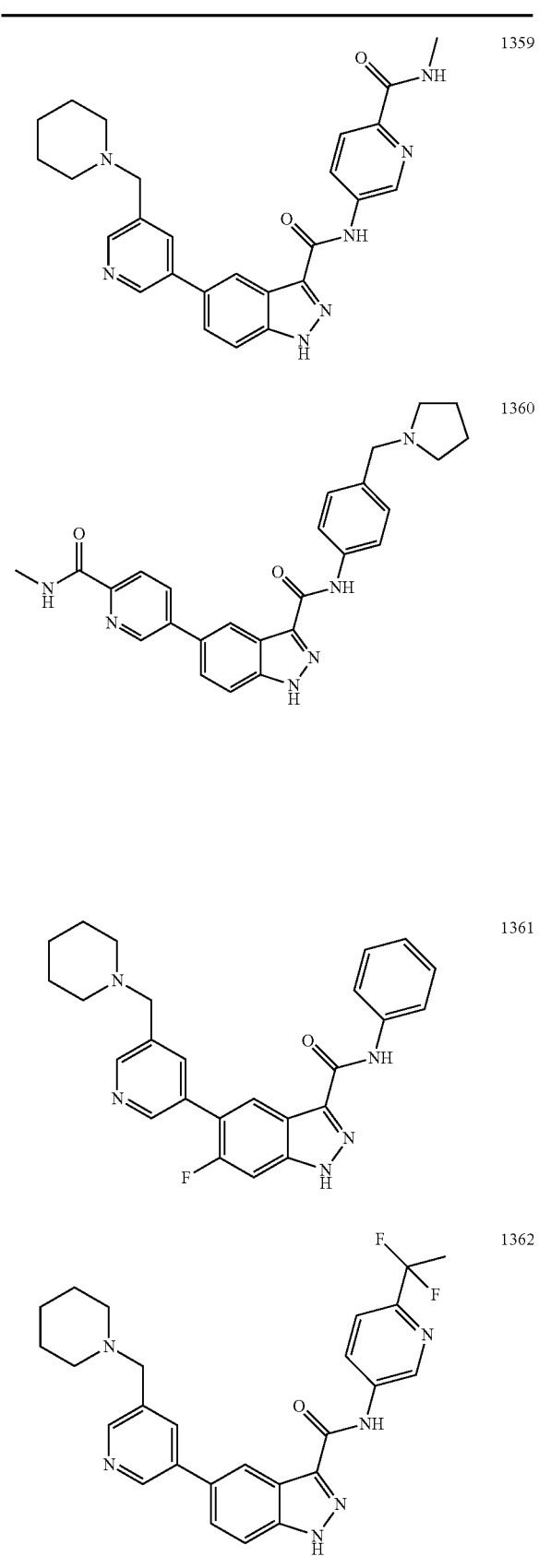
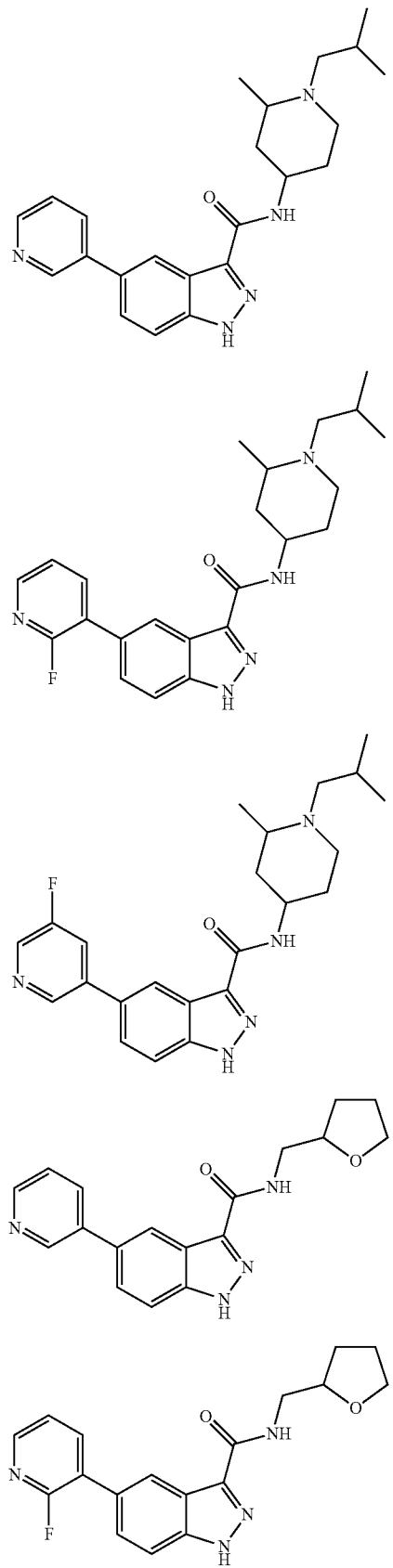

TABLE 1-continued

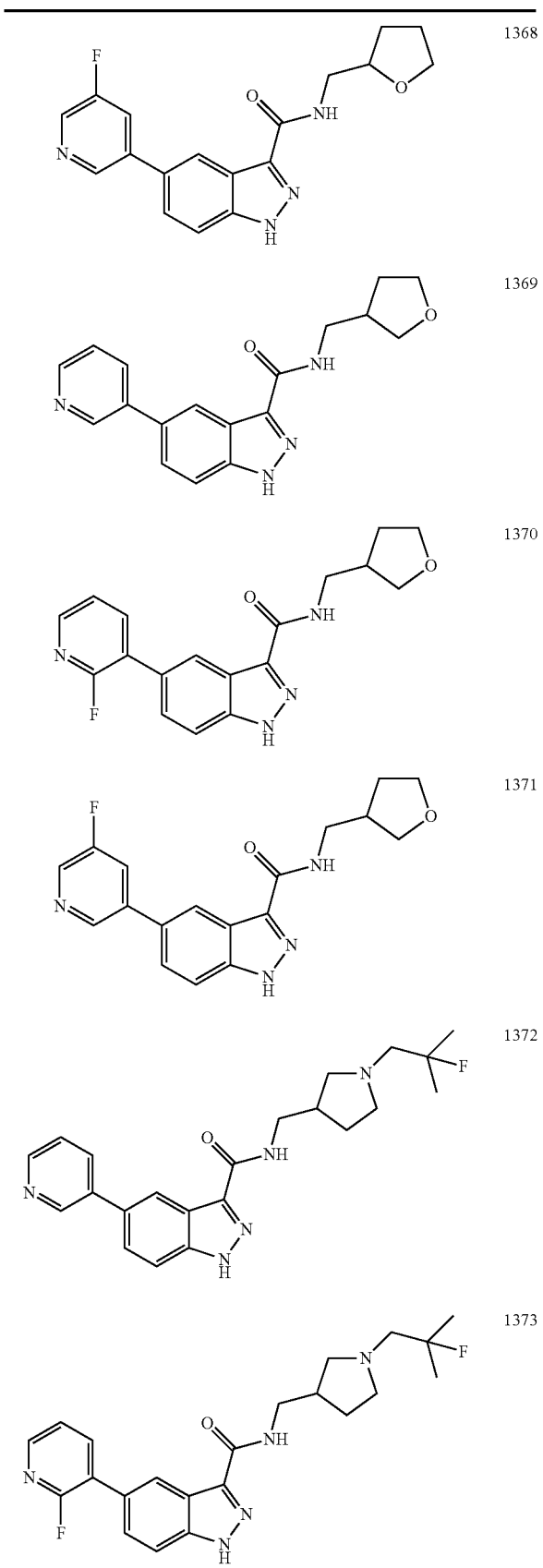

TABLE 1-continued

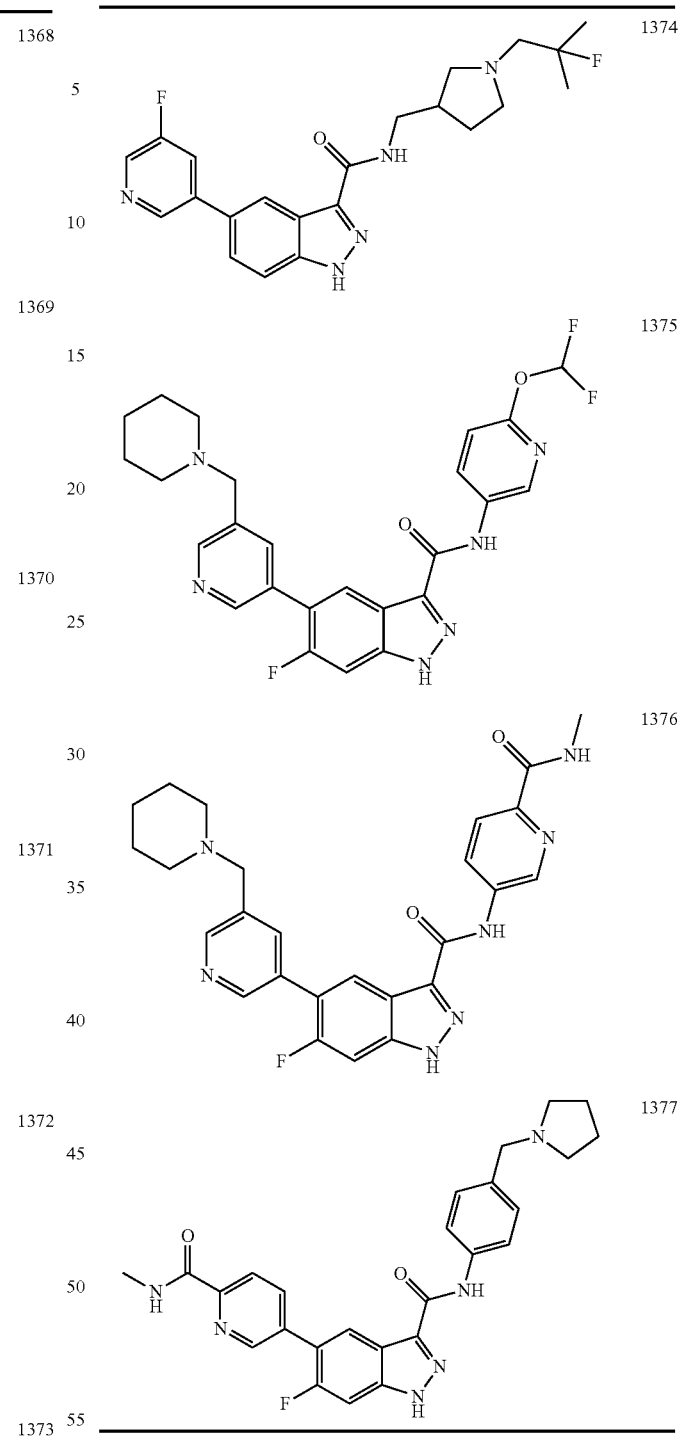

Administration and Pharmaceutical Compositions

Some embodiments include pharmaceutical compositions comprising: (a) a therapeutically effective amount of a compound provided herein, or its corresponding enantiomer, diastereoisomer or tautomer, or pharmaceutically acceptable salt; and (b) a pharmaceutically acceptable carrier.

The compounds provided herein may also be useful in combination (administered together or sequentially) with other active agents.

Non-limiting examples of diseases which can be treated with a combination of a compound of Formulas I, II, III, IV, V, VI, VII, VIII, IX and/or X and other another active agent are colorectal cancer, ovarian cancer, chronic inflammation, diabetic retinopathy, pulmonary fibrosis, and osteoarthritis. For example, a compound of Formulas I, II, III, IV, V, VI, VII, VIII, IX and/or X can be combined with one or more chemotherapeutic compounds.

In some embodiments, colorectal cancer can be treated with a combination of a compound of Formulas I, II, III, IV, V, VI, VII, VIII, IX and/or X and one or more of the following drugs: 5-Fluorouracil (5-FU), which can be administered with the vitamin-like drug leucovorin (also called folinic acid); capecitabine (XELODA®), irinotecan (CAMPTOSAR®), oxaliplatin (ELOXATIN®). Examples of combinations of these drugs which could be further combined with a compound of Formulas I, II, III, IV, V, VI, VII, VIII, IX and/or X are FOLFOX (5-FU, leucovorin, and oxaliplatin), FOLFIRI (5-FU, leucovorin, and irinotecan), FOLFOXIRI (leucovorin, 5-FU, oxaliplatin, and irinotecan) and CapeOx (Capecitabine and oxaliplatin). For rectal cancer, chemo with 5-FU or capecitabine combined with radiation may be given before surgery (neoadjuvant treatment).

In some embodiments, ovarian cancer can be treated with a combination of a compound of Formulas I, II, III, IV, V, VI, VII, VIII, IX and/or X and one or more of the following drugs: Topotecan, Liposomal doxorubicin (DOXIL®), Gemcitabine (GEMZAR®), Cyclophosphamide (CYTOXAN®), Vinorelbine (NAVELBINE®), Ifosfamide (IFEX®), Etoposide (VP-16), Altretamine (HEXALEN®), Capecitabine (XELODA®), Irinotecan (CPT-11, CAMPTOSAR®), Melphalan, Pemetrexed (ALIMTA®) and Albumin bound paclitaxel (nab-paclitaxel, ABRAXANE®). Examples of combinations of these drugs which could be further combined with a compound of Formulas I, II, III, IV, V, VI, VII, VIII, IX and/or X are TIP (paclitaxel [Taxol], ifosfamide, and cisplatin), VeIP (vinblastine, ifosfamide, and cisplatin) and VIP (etoposide [VP-16], ifosfamide, and cisplatin).

In some embodiments, a compound of Formulas I, II, III, IV, V, VI, VII, VIII, IX and/or X can be used to treat cancer in combination with any of the following methods: (a) Hormone therapy such as aromatase inhibitors, LHRH [luteinizing hormone-releasing hormone] analogs and inhibitors, and others; (b) Ablation or embolization procedures such as radiofrequency ablation (RFA), ethanol (alcohol) ablation, microwave thermotherapy and cryosurgery (cryotherapy); (c) Chemotherapy using alkylating agents such as cisplatin and carboplatin, oxaliplatin, mechlorethamine, cyclophosphamide, chlorambucil and ifosfamide; (d) Chemotherapy using anti-metabolites such as azathioprine and mercaptopurine; (e) Chemotherapy using plant alkaloids and terpenoids such as vinca alkaloids (i.e. Vincristine, Vinblastine, Vinorelbine and Vindesine) and taxanes; (f) Chemotherapy using podophyllotoxin, etoposide, teniposide and docetaxel; (g) Chemotherapy using topoisomerase inhibitors such as irinotecan, topotecan, amsacrine, etoposide, etoposide phosphate, and teniposide; (h) Chemotherapy using cytotoxic antibiotics such as actinomycin, anthracyclines, doxorubicin, daunorubicin, valrubicin, idarubicin, epirubicin, bleomycin, plicamycin and mitomycin; (i) Chemotherapy using tyrosine-kinase inhibitors such as Imatinib mesylate (GLEEVEC®, also known as STI-571), Gefitinib (Iressa, also known as ZD1839), Erlotinib (marketed as TARCEVA®), Bortezomib (VELCADE®), tamoxifen, tofacitinib, crizotinib, Bcl-2 inhibitors (e.g. obatoclax in clinical trials, ABT-263, and Gossypol), PARP inhibitors (e.g. Iniparib, Olaparib in clinical trials), PI3K inhibitors (eg. perifosine in a phase III trial), VEGF Receptor 2 inhibitors (e.g. Apatinib), AN-152, (AEZS-108), Braf inhibitors (e.g. vemurafenib, dabrafenib and LGX818), MEK inhibitors (e.g. trametinib and MEK162), CDK inhibitors, (e.g. PD-0332991), salinomycin and Sorafenib; (j) Chemotherapy using monoclonal antibodies such as Rituximab (marketed as MABTHERA® or RITUXAN®), Trastuzumab (Herceptin also known as ErbB2), Cetuximab (marketed as ERBITUX®), and Bevacizumab (marketed as AVASTIN®); and (k) radiation therapy.

In some embodiments, diabetic retinopathy can be treated with a combination of a compound of Formulas I, II, III, IV, V, VI, VII, VIII, IX and/or X and one or more of natural supplements, for example: Bilberry, Butcher's broom, Ginkgo, Grape seed extract, and Pycnogenol (Pine bark).

In some embodiments, a compound of Formulas I, II, III, IV, V, VI, VII, VIII, IX and/or X can be used to treat pulmonary fibrosis in combination with any of the following methods: oxygen therapy, pulmonary rehabilitation, and surgery.

In some embodiments, a compound of Formulas I, II, III, IV, V, VI, VII, VIII, IX and/or X can be used to treat osteoarthritis in combination with any of the following methods: (a) Nonsteroidal anti-inflammatory drugs (NSAIDs) such as ibuprofen, naproxen and acetaminophen; (b) physical therapy; (c) injections of corticosteroid medications; and (d) injections of hyaluronic acid derivatives (e.g. Hyalgan, Synvisc).

Administration of the compounds disclosed herein or the pharmaceutically acceptable salts thereof can be via any of the accepted modes of administration, including, but not limited to, orally, subcutaneously, intravenously, intranasally, topically, transdermally, intraperitoneally, intramuscularly, intrapulmonarily, vaginally, rectally, ontologically, neuro-otologically, intraocularly, subconjuctivally, via anterior eye chamber injection, intravitreally, intraperitoneally, intrathecally, intracystically, intrapleurally, via wound irrigation, intrabuccally, intra-abdominally, intra-articularly, intra-aurally, intrabronchially, intracapsularly, intrameningeally, via inhalation, via endotracheal or endobronchial instillation, via direct instillation into pulmonary cavities, intraspinally, intrasynovially, intrathoracically, via thoracostomy irrigation, epidurally, intratympanically, intracisternally, intravascularly, intraventricularly, intraosseously, via irrigation of infected bone, or via application as part of any admixture with a prosthetic devices. In some embodiments, the administration method includes oral or parenteral administration.

Compounds provided herein intended for pharmaceutical use may be administered as crystalline or amorphous products. Pharmaceutically acceptable compositions may be solid, semi-solid, liquid, solutions, colloidal, liposomes, emulsions, suspensions, complexes, coacervates, and aerosols. Dosage forms, such as, e.g., tablets, capsules, powders, liquids, suspensions, suppositories, aerosols, implants, controlled release or the like are provided herein. They may be obtained, for example, as solid plugs, powders, or films by methods such as precipitation, crystallization, milling, grinding, supercritical fluid processing, coacervation, complex coacervation, encapsulation, emulsification, complexation, freeze drying, spray drying, or evaporative drying. Microwave or radio frequency drying may be used for this purpose. The compounds can also be administered in sustained or controlled release dosage forms, including depot injections, osmotic pumps, pills (tablets and or capsules), transdermal (including electrotransport) patches, implants, and the like, for prolonged and/or timed, pulsed administration at a predetermined rate.

The compounds can be administered either alone or in combination with a conventional pharmaceutical carrier, excipient or the like. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens, poloxamers or other similar polymeric delivery matrices, serum proteins, such as human serum albumin, buffer substances such as phosphates, tris, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β, and γ-cyclodextrin, or chemically modified derivatives such as hydroxyalkylcyclodextrins, including 2- and 3-hydroxypropyl-β-cyclodextrins, or other solubilized derivatives can also be used to enhance delivery of compounds described herein. Dosage forms or compositions containing a compound as described herein in the range of 0.005% to 100% with the balance made up from non-toxic carrier may be prepared. The contemplated compositions may contain 0.001%-100% of a compound provided herein, in one embodiment 0.1-95%, in another embodiment 75-85%, in a further embodiment 20-80%. Actual methods of preparing such dosage forms are known, or will be apparent, to those skilled in this art; for example, see *Remington: The Science and Practice of Pharmacy,* 22$^{nd}$ Edition (Pharmaceutical Press, London, UK. 2012).

In one embodiment, the compositions will take the form of a unit dosage form such as a pill or tablet and thus the composition may contain, along with a compound provided herein, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils, PEG's, poloxamer 124 or triglycerides) is encapsulated in a capsule (gelatin or cellulose base capsule). Unit dosage forms in which one or more compounds provided herein or additional active agents are physically separated are also contemplated; e.g., capsules with granules (or tablets in a capsule) of each drug; two-layer tablets; two-compartment gel caps, etc. Enteric coated or delayed release oral dosage forms are also contemplated.

Liquid pharmaceutically administrable compositions can, for example, be prepared by dissolving, dispersing, etc. a compound provided herein and optional pharmaceutical adjuvants in a carrier (e.g., water, saline, aqueous dextrose, glycerol, glycols, ethanol or the like) to form a solution, colloid, liposome, emulsion, complexes, coacervate or suspension. If desired, the pharmaceutical composition can also contain minor amounts of nontoxic auxiliary substances such as wetting agents, emulsifying agents, co-solvents, solubilizing agents, pH buffering agents and the like (e.g., sodium acetate, sodium citrate, cyclodextrine derivatives, sorbitan monolaurate, triethanolamine acetate, triethanolamine oleate, and the like).

In some embodiments, the unit dosage of compounds of Formulas I, II, III, IV, V, VI, VII, VIII, IX and/or X is about 0.25 mg/Kg to about 50 mg/Kg in humans.

In some embodiments, the unit dosage of compounds of Formulas I, II, III, IV, V, VI, VII, VIII, IX and/or X is about 0.25 mg/Kg to about 20 mg/Kg in humans.

In some embodiments, the unit dosage of compounds of Formulas I, II, III, IV, V, VI, VII, VIII, IX and/or X is about 0.50 mg/Kg to about 19 mg/Kg in humans.

In some embodiments, the unit dosage of compounds of Formulas I, II, III, IV, V, VI, VII, VIII, IX and/or X is about 0.75 mg/Kg to about 18 mg/Kg in humans.

In some embodiments, the unit dosage of compounds of Formulas I, II, III, IV, V, VI, VII, VIII, IX and/or X is about 1.0 mg/Kg to about 17 mg/Kg in humans.

In some embodiments, the unit dosage of compounds of Formulas I, II, III, IV, V, VI, VII, VIII, IX and/or X is about 1.25 mg/Kg to about 16 mg/Kg in humans.

In some embodiments, the unit dosage of compounds of Formulas I, II, III, IV, V, VI, VII, VIII, IX and/or X is about 1.50 mg/Kg to about 15 mg/Kg in humans.

In some embodiments, the unit dosage of compounds of Formulas I, II, III, IV, V, VI, VII, VIII, IX and/or X is about 1.75 mg/Kg to about 14 mg/Kg in humans.

In some embodiments, the unit dosage of compounds of Formulas I, II, III, IV, V, VI, VII, VIII, IX and/or X is about 2.0 mg/Kg to about 13 mg/Kg in humans.

In some embodiments, the unit dosage of compounds of Formulas I, II, III, IV, V, VI, VII, VIII, IX and/or X is about 3.0 mg/Kg to about 12 mg/Kg in humans.

In some embodiments, the unit dosage of compounds of Formulas I, II, III, IV, V, VI, VII, VIII, IX and/or X is about 4.0 mg/Kg to about 11 mg/Kg in humans.

In some embodiments, the unit dosage of compounds of Formulas I, II, III, IV, V, VI, VII, VIII, IX and/or X is about 5.0 mg/Kg to about 10 mg/Kg in humans.

In some embodiments, the compositions are provided in unit dosage forms suitable for single administration.

In some embodiments, the compositions are provided in unit dosage forms suitable for twice a day administration.

In some embodiments, the compositions are provided in unit dosage forms suitable for three times a day administration.

Injectables can be prepared in conventional forms, either as liquid solutions, colloid, liposomes, complexes, coacervate or suspensions, as emulsions, or in solid forms suitable for reconstitution in liquid prior to injection. The percentage of a compound provided herein contained in such parenteral compositions is highly dependent on the specific nature thereof, as well as the activity of the compound and the needs of the patient. However, percentages of active ingredient or active agent (e.g., a compound of Formulas I, II, III, IV, V, VI, VII, VIII, IX and/or X) of 0.01% to 10% in solution are employable, and could be higher if the composition is a solid or suspension, which could be subsequently diluted to the above percentages.

In some embodiments, the composition will comprise about 0.1-10% of the active agent in solution.

In some embodiments, the composition will comprise about 0.1-5% of the active agent in solution.

In some embodiments, the composition will comprise about 0.1-4% of the active agent in solution.

In some embodiments, the composition will comprise about 0.15-3% of the active agent in solution.

In some embodiments, the composition will comprise about 0.2-2% of the active agent in solution.

In some embodiments, the compositions are provided in dosage forms suitable for continuous dosage by intravenous infusion over a period of about 1-96 hours.

In some embodiments, the compositions are provided in dosage forms suitable for continuous dosage by intravenous infusion over a period of about 1-72 hours.

In some embodiments, the compositions are provided in dosage forms suitable for continuous dosage by intravenous infusion over a period of about 1-48 hours.

In some embodiments, the compositions are provided in dosage forms suitable for continuous dosage by intravenous infusion over a period of about 1-24 hours.

In some embodiments, the compositions are provided in dosage forms suitable for continuous dosage by intravenous infusion over a period of about 1-12 hours.

In some embodiments, the compositions are provided in dosage forms suitable for continuous dosage by intravenous infusion over a period of about 1-6 hours.

In some embodiments, these compositions can be administered by intravenous infusion to humans at doses of about 5 mg/m$^2$ to about 300 mg/m$^2$.

In some embodiments, these compositions can be administered by intravenous infusion to humans at doses of about 5 mg/m$^2$ to about 200 mg/m$^2$.

In some embodiments, these compositions can be administered by intravenous infusion to humans at doses of about 5 mg/m$^2$ to about 100 mg/m$^2$.

In some embodiments, these compositions can be administered by intravenous infusion to humans at doses of about 10 mg/m$^2$ to about 50 mg/m$^2$.

In some embodiments, these compositions can be administered by intravenous infusion to humans at doses of about 50 mg/m$^2$ to about 200 mg/m$^2$.

In some embodiments, these compositions can be administered by intravenous infusion to humans at doses of about 75 mg/m$^2$ to about 175 mg/m$^2$.

In some embodiments, these compositions can be administered by intravenous infusion to humans at doses of about 100 mg/m$^2$ to about 150 mg/m$^2$.

It is to be noted that concentrations and dosage values may also vary depending on the specific compound and the severity of the condition to be alleviated. It is to be further understood that for any particular patient, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

In one preferred embodiment, the compositions can be administered to the respiratory tract (including nasal and pulmonary) e.g., through a nebulizer, metered-dose inhalers, atomizer, mister, aerosol, dry powder inhaler, insufflator, liquid instillation or other suitable device or technique.

In some embodiments, aerosols intended for delivery to the nasal mucosa are provided for inhalation through the nose. For optimal delivery to the nasal cavities, inhaled particle sizes of about 5 to about 100 microns are useful, with particle sizes of about 10 to about 60 microns being preferred. For nasal delivery, a larger inhaled particle size may be desired to maximize impaction on the nasal mucosa and to minimize or prevent pulmonary deposition of the administered formulation. In some embodiments, aerosols intended for delivery to the lung are provided for inhalation through the nose or the mouth. For delivery to the lung, inhaled aerodynamic particle sizes of about less than 10 µm are useful (e.g., about 1 to about 10 microns). Inhaled particles may be defined as liquid droplets containing dissolved drug, liquid droplets containing suspended drug particles (in cases where the drug is insoluble in the suspending medium), dry particles of pure drug substance, drug substance incorporated with excipients, liposomes, emulsions, colloidal systems, coacervates, aggregates of drug nanoparticles, or dry particles of a diluent which contain embedded drug nanoparticles.

In some embodiments, compounds of Formulas I, II, III, IV, V, VI, VII, VIII, IX and/or X disclosed herein intended for respiratory delivery (either systemic or local) can be administered as aqueous formulations, as non-aqueous solutions or suspensions, as suspensions or solutions in halogenated hydrocarbon propellants with or without alcohol, as a colloidal system, as emulsions, coacervates, or as dry powders. Aqueous formulations may be aerosolized by liquid nebulizers employing either hydraulic or ultrasonic atomization or by modified micropump systems (like the soft mist inhalers, the AERODOSE® or the AERX® systems). Propellant-based systems may use suitable pressurized metered-dose inhalers (pMDIs). Dry powders may use dry powder inhaler devices (DPIs), which are capable of dispersing the drug substance effectively. A desired particle size and distribution may be obtained by choosing an appropriate device.

In some embodiments, the compositions of Formulas I, II, III, IV, V, VI, VII, VIII, IX and/or X disclosed herein can be administered to the ear by various methods. For example, a round window catheter (e.g., U.S. Pat. Nos. 6,440,102 and 6,648,873) can be used.

Alternatively, formulations can be incorporated into a wick for use between the outer and middle ear (e.g., U.S. Pat. No. 6,120,484) or absorbed to collagen sponge or other solid support (e.g., U.S. Pat. No. 4,164,559).

If desired, formulations of the disclosure can be incorporated into a gel formulation (e.g., U.S. Pat. Nos. 4,474,752 and 6,911,211).

In some embodiments, compounds of Formulas I, II, III, IV, V, VI, VII, VIII, IX and/or X disclosed herein intended for delivery to the ear can be administered via an implanted pump and delivery system through a needle directly into the middle or inner ear (cochlea) or through a cochlear implant stylet electrode channel or alternative prepared drug delivery channel such as but not limited to a needle through temporal bone into the cochlea.

Other options include delivery via a pump through a thin film coated onto a multichannel electrode or electrode with a specially imbedded drug delivery channel (pathways) carved into the thin film for this purpose. In other embodiments, the acidic or basic solid gacyclidine can be delivered from the reservoir of an external or internal implanted pumping system.

Formulations of the disclosure also can be administered to the ear by intratympanic injection into the middle ear, inner ear, or cochlea (e.g., U.S. Pat. No. 6,377,849 and Ser. No. 11/337,815).

Intratympanic injection of therapeutic agents is the technique of injecting a therapeutic agent behind the tympanic membrane into the middle and/or inner ear. In one embodiment, the formulations described herein are administered directly onto the round window membrane via transtympanic injection. In another embodiment, the ion channel modulating agent auris-acceptable formulations described herein are administered onto the round window membrane via a non-transtympanic approach to the inner ear. In additional embodiments, the formulation described herein is administered onto the round window membrane via a surgical approach to the round window membrane comprising modification of the crista fenestrae cochleae.

In some embodiments, the compounds of Formulas I, II, III, IV, V, VI, VII, VIII, IX and/or X are formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG (like PEG ointments), and the like.

Suppositories for rectal administration of the drug (either as a solution, colloid, suspension or a complex) can be prepared by mixing a compound provided herein with a suitable non-irritating excipient that is solid at ordinary temperatures but liquid at the rectal temperature and will therefore melt or erode/dissolve in the rectum and release the compound. Such materials include cocoa butter, glycerinated gelatin, hydrogenated vegetable oils, poloxamers, mixtures of polyethylene glycols of various molecular weights and fatty acid esters of polyethylene glycol. In suppository forms of the compositions, a low-melting wax such as, but not limited to, a mixture of fatty acid glycerides, optionally in combination with cocoa butter, is first melted.

Solid compositions can be provided in various different types of dosage forms, depending on the physicochemical properties of the compound provided herein, the desired dissolution rate, cost considerations, and other criteria. In one of the embodiments, the solid composition is a single unit. This implies that one unit dose of the compound is comprised in a single, physically shaped solid form or article. In other words, the solid composition is coherent, which is in contrast to a multiple unit dosage form, in which the units are incoherent.

Examples of single units which may be used as dosage forms for the solid composition include tablets, such as compressed tablets, film-like units, foil-like units, wafers, lyophilized matrix units, and the like. In one embodiment, the solid composition is a highly porous lyophilized form. Such lyophilizates, sometimes also called wafers or lyophilized tablets, are particularly useful for their rapid disintegration, which also enables the rapid dissolution of the compound.

On the other hand, for some applications the solid composition may also be formed as a multiple unit dosage form as defined above. Examples of multiple units are powders, granules, microparticles, pellets, mini-tablets, beads, lyophilized powders, and the like. In one embodiment, the solid composition is a lyophilized powder. Such a dispersed lyophilized system comprises a multitude of powder particles, and due to the lyophilization process used in the formation of the powder, each particle has an irregular, porous microstructure through which the powder is capable of absorbing water very rapidly, resulting in quick dissolution. Effervescent compositions are also contemplated to aid the quick dispersion and absorption of the compound.

Another type of multiparticulate system which is also capable of achieving rapid drug dissolution is that of powders, granules, or pellets from water-soluble excipients which are coated with a compound provided herein so that the compound is located at the outer surface of the individual particles. In this type of system, the water-soluble low molecular weight excipient may be useful for preparing the cores of such coated particles, which can be subsequently coated with a coating composition comprising the compound and, for example, one or more additional excipients, such as a binder, a pore former, a saccharide, a sugar alcohol, a film-forming polymer, a plasticizer, or other excipients used in pharmaceutical coating compositions.

Also provided herein are kits. Typically, a kit includes one or more compounds or compositions as described herein. In certain embodiments, a kit can include one or more delivery systems, e.g., for delivering or administering a compound as provided herein, and directions for use of the kit (e.g., instructions for treating a patient). In another embodiment, the kit can include a compound or composition as described herein and a label that indicates that the contents are to be administered to a patient with cancer. In another embodiment, the kit can include a compound or composition as described herein and a label that indicates that the contents are to be administered to a patient with one or more of hepatocellular carcinoma, colon cancer, leukemia, lymphoma, sarcoma, ovarian cancer, chronic inflammation, diabetic retinopathy, pulmonary fibrosis, rheumatoid arthritis, sepsis, anklyosing spondylitism, psoriasis, scleroderma, mycotic and viral infections, bone and cartilage diseases, Alzheimer's disease, lung disease, osteoarthritis, articular cartilage (chondral) defects, degenerative disc disease (or intervertebral disc degeneration), polyposis coli, bone density and vascular defects in the eye (Osteoporosis-pseudoglioma Syndrome, OPPG), familial exudative vitreoretinopathy, retinal angiogenesis, early coronary disease, tetra-amelia, Müllerian-duct regression and virilization, SERKAL syndrome, type II diabetes, Fuhrmann syndrome, Al-Awadi/Raas-Rothschild/Schinzel phocomelia syndrome, odonto-onycho-dermal dysplasia, obesity, split-hand/foot malformation, caudal duplication, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman's syndrome, Prader-Willi syndrome, Beckwith-Wiedemann Syndrome, Norrie disease, and Rett syndrome.

Methods of Treatment

The compounds and compositions provided herein can be used as inhibitors and/or modulators of one or more components of the Wnt pathway, which may include one or more Wnt proteins, and thus can be used to treat a variety of disorders and diseases in which aberrant Wnt signaling is implicated, such as cancer and other diseases associated with abnormal angiogenesis, cellular proliferation, and cell cycling. Accordingly, the compounds and compositions provided herein can be used to treat cancer, to reduce or inhibit angiogenesis, to reduce or inhibit cellular proliferation, to correct a genetic disorder, and/or to treat a neurological condition/disorder/disease due to mutations or dysregulation of the Wnt pathway and/or of one or more of Wnt signaling components. Non-limiting examples of diseases which can be treated with the compounds and compositions provided herein include a variety of cancers, chronic inflammation, diabetic retinopathy, pulmonary fibrosis, rheumatoid arthritis, sepsis, anklyosing spondylitism, psoriasis, scleroderma, mycotic and viral infections, bone and cartilage diseases, neurological conditions/diseases such as Alzheimer's disease, amyotrophic lateral sclerosis (ALS), motor neurone disease, multiple sclerosis or autism, lung disease, osteoarthritis, articular cartilage (chondral) defects, degenerative disc disease (or intervertebral disc degeneration), polyposis coli, bone density and vascular defects in the eye (Osteoporosis-pseudoglioma Syndrome, OPPG), familial exudative vitreoretinopathy, retinal angiogenesis, early coronary disease, tetra-amelia, Müllerian-duct regression and virilization, SERKAL syndrome, type II diabetes, Fuhrmann syndrome, Al-Awadi/Raas-Rothschild/Schinzel phocomelia syndrome, odonto-onycho-dermal dysplasia, obesity, split-hand/foot malformation, caudal duplication, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman's syndrome, Prader-Willi syndrome, Beckwith-Wiedemann Syndrome, Norrie disease, and Rett syndrome.

With respect to cancer, the Wnt pathway is known to be constitutively activated in a variety of cancers including, for example, colon cancer, hepatocellular carcinoma, lung cancer, ovarian cancer, prostate cancer, pancreatic cancer and leukemias such as CML, CLL and T-ALL. Accordingly, the compounds and compositions described herein may be used to treat these cancers in which the Wnt pathway is constitutively activated. In certain embodiments, the cancer is chosen from hepatocellular carcinoma, colon cancer, leukemia, lymphoma, sarcoma and ovarian cancer.

Other cancers can also be treated with the compounds and compositions described herein.

More particularly, cancers that may be treated by the compound, compositions and methods described herein include, but are not limited to, the following:

1) Breast cancers, including, for example ER breast cancer, $ER^-$ breast cancer, her2$^-$ breast cancer, her2$^+$ breast cancer, stromal tumors such as fibroadenomas, phyllodes tumors, and sarcomas, and epithelial tumors such as large duct papillomas; carcinomas of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma; and miscellaneous malignant neoplasms.

Further examples of breast cancers can include luminal A, luminal B, basal A, basal B, and triple negative breast cancer, which is estrogen receptor negative ($ER^-$), progesterone receptor negative, and her2 negative (her2$^-$). In some embodiments, the breast cancer may have a high risk Oncotype score.

2) Cardiac cancers, including, for example sarcoma, e.g., angiosarcoma, fibrosarcoma, rhabdomyosarcoma, and liposarcoma; myxoma; rhabdomyoma; fibroma; lipoma and teratoma.

3) Lung cancers, including, for example, bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; and mesothelioma.

4) Gastrointestinal cancer, including, for example, cancers of the esophagus, e.g., squamous cell carcinoma, adenocarcinoma, leiomyosarcoma, and lymphoma; cancers of the stomach, e.g., carcinoma, lymphoma, and leiomyosarcoma; cancers of the pancreas, e.g., ductal adenocarcinoma, insulinoma, glucagonoma, gastrinoma, carcinoid tumors, and vipoma; cancers of the small bowel, e.g., adenocarcinoma, lymphoma, carcinoid tumors, Kaposi's sarcoma, leiomyoma, hemangioma, lipoma, neurofibroma, and fibroma; cancers of the large bowel, e.g., adenocarcinoma, tubular adenoma, villous adenoma, hamartoma, and leiomyoma.

5) Genitourinary tract cancers, including, for example, cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma.

6) Liver cancers, including, for example, hepatoma, e.g., hepatocellular carcinoma; cholangiocarcinoma; hepatoblastoma; angiosarcoma; hepatocellular adenoma; and hemangioma.

7) Bone cancers, including, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors.

8) Nervous system cancers, including, for example, cancers of the skull, e.g., osteoma, hemangioma, granuloma, xanthoma, and osteitis deformans; cancers of the meninges, e.g., meningioma, meningiosarcoma, and gliomatosis; cancers of the brain, e.g., astrocytoma, medulloblastoma, glioma, ependymoma, germinoma (pinealoma), glioblastoma multiform, oligodendroglioma, schwannoma, retinoblastoma, and congenital tumors; and cancers of the spinal cord, e.g., neurofibroma, meningioma, glioma, and sarcoma.

9) Gynecological cancers, including, for example, cancers of the uterus, e.g., endometrial carcinoma; cancers of the cervix, e.g., cervical carcinoma, and pre tumor cervical dysplasia; cancers of the ovaries, e.g., ovarian carcinoma, including serous cystadenocarcinoma, mucinous cystadenocarcinoma, unclassified carcinoma, granulosa theca cell tumors, Sertoli Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma.

10) Hematologic cancers, including, for example, cancers of the blood, e.g., acute myeloid leukemia, chronic myeloid leukemia, acute lymphoblastic leukemia, chronic lymphocytic leukemia, myeloproliferative diseases, multiple myeloma, and myelodysplastic syndrome, Hodgkin's lymphoma, non-Hodgkin's lymphoma (malignant lymphoma) and Waldenström's macroglobulinemia.

11) Skin cancers and skin disorders, including, for example, malignant melanoma, basal cell carcinoma, squamous cell carcinoma, Kaposi's sarcoma, moles dysplastic nevi, lipoma, angioma, dermatofibroma, keloids, and scleroderma.

12) Adrenal gland cancers, including, for example, neuroblastoma.

Cancers may be solid tumors that may or may not be metastatic. Cancers may also occur, as in leukemia, as a diffuse tissue. Thus, the term "tumor cell," as provided herein, includes a cell afflicted by any one of the above identified disorders.

A method of treating cancer using a compound or composition as described herein may be combined with existing methods of treating cancers, for example by chemotherapy, irradiation, or surgery (e.g., oophorectomy). In some embodiments, a compound or composition can be administered before, during, or after another anticancer agent or treatment.

The compounds and compositions described herein can be used as anti-angiogenesis agents and as agents for modulating and/or inhibiting the activity of protein kinases, thus providing treatments for cancer and other diseases associated with cellular proliferation mediated by protein kinases. Accordingly, provided herein is a method of treating cancer or preventing or reducing angiogenesis through kinase inhibition.

In addition, and including treatment of cancer, the compounds and compositions described herein can function as cell-cycle control agents for treating proliferative disorders in a patient. Disorders associated with excessive proliferation include, for example, cancers, scleroderma, immunological disorders involving undesired proliferation of leukocytes, and restenosis and other smooth muscle disorders. Furthermore, such compounds may be used to prevent de-differentiation of post-mitotic tissue and/or cells.

Diseases or disorders associated with uncontrolled or abnormal cellular proliferation include, but are not limited to, the following:

a variety of cancers, including, but not limited to, carcinoma, hematopoietic tumors of lymphoid lineage, hematopoietic tumors of myeloid lineage, tumors of mesenchymal origin, tumors of the central and peripheral nervous system and other tumors including melanoma, seminoma, and Kaposi's sarcoma.

a disease process which features abnormal cellular proliferation, e.g., benign prostatic hyperplasia, familial adenomatosis polyposis, neurofibromatosis, atherosclerosis, arthritis, glomerulonephritis, restenosis following angioplasty or vascular surgery, inflammatory bowel disease, transplantation rejection, endotoxic shock, and fungal infections. Fibrotic disorders such as skin fibrosis; scleroderma; progressive systemic fibrosis; lung fibrosis; muscle fibrosis; kidney fibrosis; glomerulosclerosis; glomerulonephritis; hypertrophic scar formation; uterine fibrosis; renal fibrosis; cirrhosis of the liver, liver fibrosis; adhesions, such as those occurring in the abdomen, pelvis, spine or tendons; chronic obstructive pulmonary disease; fibrosis following myocardial infarction; pulmonary fibrosis; fibrosis and scarring associated with diffuse/interstitial lung disease; central nervous system fibrosis, such as fibrosis following stroke; fibrosis associated with neuro-degenerative disorders such as Alzheimer's Disease or multiple sclerosis; fibrosis associated with proliferative vitreoretinopathy (PVR); restenosis; endometriosis; ischemic disease and radiation fibrosis.

defective apoptosis-associated conditions, such as cancers (including but not limited to those types mentioned herein), viral infections (including but not limited to herpesvirus, poxvirus, Epstein-Barr virus, Sindbis virus and adenovirus), prevention of AIDS development in HIV-infected individuals, autoimmune diseases (including but not limited to systemic lupus erythematosus, rheumatoid arthritis, sepsis, anklyosing spondylitism, psoriasis, scleroderma, autoimmune mediated glomerulonephritis, inflammatory bowel disease and autoimmune diabetes mellitus), neuro-degenerative disorders (including but not limited to Alzheimer's disease, lung disease, amyotrophic lateral sclerosis, retinitis pigmentosa, Parkinson's disease, AIDS-related dementia, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis), aspirin-sensitive rhinosinusitis, cystic fibrosis, multiple sclerosis, kidney diseases and cancer pain.

genetic diseases due to mutations in Wnt signaling components, such as polyposis coli, bone density and vascular defects in the eye (Osteoporosis-pseudoglioma Syndrome, OPPG), familial exudative vitreoretinopathy, retinal angiogenesis, early coronary disease, tetra-amelia, Müllerian-duct regression and virilization, SERKAL syndrome, type II diabetes, Fuhrmann syndrome, Al-Awadi/Raas-Rothschild/Schinzel phocomelia syndrome, odonto-onycho-dermal dysplasia, obesity, split-hand/foot malformation, caudal duplication, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman's syndrome, Prader-Willi syndrome, Beckwith-Wiedemann Syndrome, Norrie disease and Rett syndrome.

The compounds and compositions provided herein have been found to possess immunomodulatory activities and are expected to control the innate immune system (e.g. macrophages and T cells) and suppress pro-inflammatory cytokine release (e.g. TNF, IL-6) which is well known to be involved in chronic inflammation in a wide variety of disease areas. Therefore compounds and compositions provided herein can used to treat chronic inflammation associated with disorders and diseases including but not limited to eye disorders, joint pain, arthritis (rheumatoid, osteo, psoriatic gout), cancers (colon, breast, lung, pancreas, and others), gastrointestinal disorders (ulcerative colitis and inflammatory bowel diseases), pulmonary disorders (chronic obstructive pulmonary disorder and asthma), allergies, skin disorders (atopic dermatitis and psoriasis), diabetes, pancreatitis, tendonitis, hepatitis, heart disease, myocarditis, stroke, lupus, and neurological disorders such as multiple sclerosis, Parkinson's and dementia including Alzheimer's disease.

The compounds and compositions provided herein can be used as inhibitors and/or modulators of the enzyme DYRK1A, and thus can be used to treat a variety of disorders and diseases associated with tau protein, amyloid or alpha-synuclein pathology including, but not limited to, Alzheimer's Disease, Amyotrophic Lateral Sclerosis, Down Syndrome, Frontotemporal Dementia with Parkinsonism-17 (FTDP-17), Lewy body dementia, Parkinson's Disease, Pick's Disease, and additional diseases with pronounced neurodegeneration such as Autism, Dementia, Epilepsy, Huntington's Disease, Multiple Sclerosis; diseases and disorders associated with acquired brain injury such as Chronic Traumatic Encephalopathy, Traumatic Brain Injury, Tumor, and Stroke.

Non-limiting examples of neurological disorders (e.g., neurological conditions and neurological diseases) which can be treated with the compounds and compositions provided herein include Alzheimer's disease, aphasia, apraxia, arachnoiditis, ataxia telangiectasia, attention deficit hyperactivity disorder, auditory processing disorder, autism, alcoholism, Bell's palsy, bipolar disorder, brachial plexus injury, Canavan disease, carpal tunnel syndrome, causalgia, central pain syndrome, central pontine myelinolysis, centronuclear myopathy, cephalic disorder, cerebral aneurysm, cerebral arteriosclerosis, cerebral atrophy, cerebral gigantism, cerebral palsy, cerebral vasculitis, cervical spinal stenosis, Charcot-Marie-Tooth disease, Chiari malformation, chronic fatigue syndrome, chronic inflammatory demyelinating polyneuropathy (CIDP), chronic pain, Coffin-Lowry syndrome, complex regional pain syndrome, compression neuropathy, congenital facial diplegia, corticobasal degeneration, cranial arteritis, craniosynostosis, Creutzfeldt-Jakob disease, cumulative trauma disorder, Cushing's syndrome, cytomegalic inclusion body disease (CIBD), Dandy-Walker syndrome, Dawson disease, De Morsier's syndrome, Dejerine-Klumpke palsy, Dejerine-Sottas disease, delayed sleep phase syndrome, dementia, dermatomyositis, developmental dyspraxia, diabetic neuropathy, diffuse sclerosis, Dravet syndrome, dysautonomia, dyscalculia, dysgraphia, dyslexia, dystonia, empty sella syndrome, encephalitis, encephalocele, encephalotrigeminal angiomatosis, encopresis, epilepsy, Erb's palsy, erythromelalgia, essential tremor, Fabry's disease, Fahr's syndrome, familial spastic paralysis, febrile seizure, Fisher syndrome, Friedreich's ataxia, fibromyalgia, Foville's syndrome, Gaucher's disease, Gerstmann's syndrome, giant cell arteritis, giant cell inclusion disease, globoid cell leukodystrophy, gray matter heterotopia, Guillain-Barré syndrome, HTLV-1 associated myelopathy, Hallervorden-Spatz disease, hemifacial spasm, hereditary spastic paraplegia, heredopathia atactica polyneuritiformis, herpes zoster oticus, herpes zoster, Hirayama syndrome, holoprosencephaly, Huntington's disease, hydranencephaly, hydrocephalus, hypercortisolism, hypoxia, immune-mediated encephalomyelitis, inclusion body myositis, incontinentia pigmenti, infantile phytanic acid storage disease, infantile Refsum disease, infantile spasms, inflammatory myopathy, intracranial cyst, intracranial hypertension, Joubert syndrome, Karak syndrome, Kearns-Sayre syndrome, Kennedy disease, Kinsbourne syndrome, Klippel Feil syndrome, Krabbe disease, Kugelberg-Welander disease, kuru, Lafora disease, Lambert-Eaton myasthenic syndrome, Landau-Kleffner syndrome, lateral medullary (Wallenberg) syndrome, Leigh's disease, Lennox-Gastaut syndrome, Lesch-Nyhan syndrome, leukodystrophy, Lewy body dementia, lissencephaly, locked-in syndrome, Lou Gehrig's disease, lumbar disc disease, lumbar spinal stenosis, Lyme disease, Machado-Joseph disease (Spinocerebellar ataxia type 3), macrencephaly, macropsia, megalencephaly, Melkersson-Rosenthal syndrome, Menieres disease, meningitis, Menkes disease, etachromatic leukodystrophy, microcephaly, micropsia, Miller Fisher syndrome, misophonia, mitochondrial myopathy, Mobius syndrome, monomelic amyotrophy, motor neurone disease, motor skills disorder, Moyamoya disease, mucopolysaccharidoses, multi-infarct dementia, multifocal motor neuropathy, multiple sclerosis, multiple system atrophy, muscular dystrophy, myalgic encephalomyelitis, myasthenia gravis, myelinoclastic diffuse sclerosis, myoclonic Encephalopathy of infants, myoclonus, myopathy, myotubular myopathy, myotonia congenital, narcolepsy, neurofibromatosis, neuroleptic malignant syndrome, lupus erythematosus, neuromyotonia, neuronal ceroid lipofuscinosis, Niemann-Pick disease, O'Sullivan-McLeod syndrome, occipital Neuralgia, occult Spinal Dysraphism Sequence, Ohtahara syndrome, olivopontocerebellar atrophy, opsoclonus myoclonus syndrome, optic neuritis, orthostatic hypotension, palinopsia, paresthesia, Parkinson's disease, paramyotonia Congenita, paraneoplastic diseases, paroxysmal attacks, Parry-Romberg syndrome, Pelizaeus-Merzbacher disease, periodic paralyses, peripheral neuropathy, photic sneeze reflex, phytanic acid storage disease, Pick's disease, polymicrogyria (PMG), polymyositis, porencephaly, post-polio syndrome, postherpetic neuralgia (PHN), postural hypotension, Prader-Willi syndrome, primary lateral sclerosis, prion diseases, progressive hemifacial atrophy, progressive multifocal leukoencephalopathy, progressive supranuclear palsy, pseudotumor cerebri, Ramsay Hunt syndrome type I, Ramsay Hunt syndrome type II, Ramsay Hunt syndrome type III, Rasmussen's encephalitis, reflex neurovascular dystrophy, Refsum disease, restless legs syndrome, retrovirus-associated myelopathy, Rett syndrome, Reye's syndrome, rhythmic movement disorder, Romberg syndrome, Saint Vitus dance, Sandhoff disease, schizophrenia, Schilder's disease, schizencephaly, sensory integration dysfunction, septo-optic dysplasia, Shy-Drager syndrome, Sjögren's syndrome, snatiation, Sotos syndrome, spasticity, spina bifida, spinal cord tumors, spinal muscular atrophy, spinocerebellar ataxia, Steele-Richardson-Olszewski syndrome, Stiff-person syndrome, stroke, Sturge-Weber syndrome, subacute sclerosing panencephalitis, subcortical arteriosclerotic encephalopathy, superficial siderosis, Sydenham's chorea, syncope, synesthesia, syringomyelia, tarsal tunnel syndrome, tardive dyskinesia, tardive dysphrenia, Tarlov cyst, Tay-Sachs disease, temporal arteritis, tetanus, tethered spinal cord syndrome, Thomsen disease, thoracic outlet syndrome, tic douloureux, Todd's paralysis, Tourette syndrome, toxic encephalopathy, transient ischemic attack, transmissible spongiform encephalopathies, transverse myelitis, tremor, trigeminal neuralgia, tropical spastic paraparesis, trypanosomiasis, tuberous sclerosis, ubisiosis, Von Hippel-Lindau disease (VHL), Viliuisk Encephalomyelitis (VE), Wallenberg's syndrome, Werdnig, Hoffman disease, west syndrome, Williams syndrome, Wilson's disease, and Zellweger syndrome.

The compounds and compositions may also be useful in the inhibition of the development of invasive cancer, tumor angiogenesis and metastasis.

In some embodiments, the disclosure provides a method for treating a disease or disorder associated with aberrant cellular proliferation by administering to a patient in need of such treatment an effective amount of one or more of the compounds of Formulas I, II, III, IV, V, VI, VII, VIII, IX and/or X, in combination (simultaneously or sequentially) with at least one other agent.

In some embodiments, the pharmaceutical composition comprises a therapeutically effective amount of a compound of Formulas I, II, III, IV, V, VI, VII, VIII, IX and/or X, or a pharmaceutically acceptable salt thereof, and a pharmaceutically acceptable excipient.

In some embodiments, the method of treating a disorder or disease in which aberrant Wnt signaling is implicated in a patient is provided herein, the method comprises administering to the patient a therapeutically effective amount of a compound of Formulas I, II, III, IV, V, VI, VII, VIII, IX and/or X, or a pharmaceutically acceptable salt thereof.

In some embodiments, the disorder or disease is the pain and inflammation associated with cancer.

In some embodiments, the disorder or disease is the pain and inflammation associated with a joint.

In some embodiments, the disorder or disease is the pain and inflammation associated with the knee.

In some embodiments, the disorder or disease is the pain and inflammation associated with the hip.

In some embodiments, the disorder or disease is the pain and inflammation associated with the shoulder.

In some embodiments, the disorder or disease is the pain and inflammation associated with arthritis.

In some embodiments, the disorder or disease is the pain and inflammation associated with gastrointestinal disorders.

In some embodiments, the disorder or disease is the pain and inflammation associated with pulmonary disorders.

In some embodiments, the disorder or disease is the pain and inflammation associated with allergies.

In some embodiments, the disorder or disease is the pain and inflammation associated with skin disorders.

In some embodiments, the disorder or disease is the pain and inflammation associated with diabetes.

In some embodiments, the disorder or disease is the pain and inflammation associated with pancreatitis.

In some embodiments, the disorder or disease is the pain and inflammation associated with tendonitis.

In some embodiments, the disorder or disease is the pain and inflammation associated with heart disease.

In some embodiments, the disorder or disease is the pain and inflammation associated with lupus.

In some embodiments, the disorder or disease is the pain and inflammation associated with a neurological disorder.

In some embodiments, the disorder or disease is the pain and inflammation associated with multiple sclerosis.

In some embodiments, the disorder or disease is the pain and inflammation associated with Parkinson's.

In some embodiments, the disorder or disease is cancer.

In some embodiments, the disorder or disease is diabetic retinopathy.

In some embodiments, chronic inflammation is associated with the disorder or disease.

In some embodiments, the disorder or disease is pulmonary fibrosis.

In some embodiments, the disorder or disease is rheumatoid arthritis.

In some embodiments, the disorder or disease is scleroderma.

In some embodiments, the disorder or disease is a mycotic or viral infection.

In some embodiments, the disorder or disease is a bone or cartilage disease.

In some embodiments, the disorder or disease is Alzheimer's disease.

In some embodiments, the disorder or disease is osteoarthritis.

In some embodiments, the disorder or disease is lung disease

In some embodiments, the disorder or disease is a genetic disease caused by mutations in Wnt signaling components, wherein the genetic disease is selected from: polyposis coli, osteoporosis-pseudoglioma syndrome, familial exudative vitreoretinopathy, retinal angiogenesis, early coronary disease, tetra-amelia syndrome, Müllerian-duct regression and virilization, SERKAL syndrome, diabetes mellitus type 2, Fuhrmann syndrome, Al-Awadi/Raas-Rothschild/Schinzel phocomelia syndrome, odonto-onycho-dermal dysplasia, obesity, split-hand/foot malformation, caudal duplication syndrome, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman syndrome, Prader-Willi syndrome, Beckwith-Wiedemann Syndrome, Norrie disease, and Rett syndrome.

In some embodiments, the patient is a human.

In some embodiments, the cancer is chosen from: hepatocellular carcinoma, colon cancer, breast cancer, pancreatic cancer, chronic myeloid leukemia (CML), chronic myelomonocytic leukemia, chronic lymphocytic leukemia (CLL), acute myeloid leukemia, acute lymphocytic leukemia, Hodgkin lymphoma, lymphoma, sarcoma, and ovarian cancer.

In some embodiments, the cancer is chosen from: lung cancer—non-small cell, lung cancer—small cell, multiple myeloma, nasopharyngeal cancer, neuroblastoma, osteosarcoma, penile cancer, pituitary tumors, prostate cancer, retinoblastoma, rhabdomyosarcoma, salivary gland cancer, skin cancer—basal and squamous cell, skin cancer—melanoma, small intestine cancer, stomach cancers, testicular cancer, thymus cancer, thyroid cancer, uterine sarcoma, vaginal cancer, vulvar cancer, laryngeal or hypopharyngeal cancer, kidney cancer, Kaposi sarcoma, gestational trophoblastic disease, gastrointestinal stromal tumor, gastrointestinal carcinoid tumor, gallbladder cancer, eye cancer (melanoma and lymphoma), Ewing tumor, esophagus cancer, endometrial cancer, colorectal cancer, cervical cancer, brain or spinal cord tumor, bone metastasis, bone cancer, bladder cancer, bile duct cancer, anal cancer, and adrenal cortical cancer.

In some embodiments, the cancer is hepatocellular carcinoma.

In some embodiments, the cancer is colon cancer.

In some embodiments, the cancer is breast cancer.

In some embodiments, the cancer is pancreatic cancer.

In some embodiments, the cancer is chronic myeloid leukemia (CML).

In some embodiments, the cancer is chronic myelomonocytic leukemia.

In some embodiments, the cancer is chronic lymphocytic leukemia (CLL).

In some embodiments, the cancer is acute myeloid leukemia.

In some embodiments, the cancer is acute lymphocytic leukemia.

In some embodiments, the cancer is Hodgkin lymphoma.

In some embodiments, the cancer is lymphoma.

In some embodiments, the cancer is sarcoma.

In some embodiments, the cancer is ovarian cancer.

In some embodiments, the cancer is lung cancer—non-small cell.

In some embodiments, the cancer is lung cancer—small cell.

In some embodiments, the cancer is multiple myeloma.

In some embodiments, the cancer is nasopharyngeal cancer.

In some embodiments, the cancer is neuroblastoma.

In some embodiments, the cancer is osteosarcoma.

In some embodiments, the cancer is penile cancer.

In some embodiments, the cancer is pituitary tumors.

In some embodiments, the cancer is prostate cancer.

In some embodiments, the cancer is retinoblastoma.

In some embodiments, the cancer is rhabdomyosarcoma.

In some embodiments, the cancer is salivary gland cancer.

In some embodiments, the cancer is skin cancer—basal and squamous cell.

In some embodiments, the cancer is skin cancer—melanoma.

In some embodiments, the cancer is small intestine cancer.

In some embodiments, the cancer is stomach cancers.

In some embodiments, the cancer is testicular cancer.

In some embodiments, the cancer is thymus cancer.

In some embodiments, the cancer is thyroid cancer.

In some embodiments, the cancer is uterine sarcoma.

In some embodiments, the cancer is vaginal cancer.

In some embodiments, the cancer is vulvar cancer.

In some embodiments, the cancer is Wilms tumor.

In some embodiments, the cancer is laryngeal or hypopharyngeal cancer.

In some embodiments, the cancer is kidney cancer.

In some embodiments, the cancer is Kaposi sarcoma.

In some embodiments, the cancer is gestational trophoblastic disease.

In some embodiments, the cancer is gastrointestinal stromal tumor.

In some embodiments, the cancer is gastrointestinal carcinoid tumor.

In some embodiments, the cancer is gallbladder cancer.

In some embodiments, the cancer is eye cancer (melanoma and lymphoma).

In some embodiments, the cancer is Ewing tumor.

In some embodiments, the cancer is esophagus cancer.

In some embodiments, the cancer is endometrial cancer.

In some embodiments, the cancer is colorectal cancer.

In some embodiments, the cancer is cervical cancer.

In some embodiments, the cancer is brain or spinal cord tumor.

In some embodiments, the cancer is bone metastasis.

In some embodiments, the cancer is bone cancer.

In some embodiments, the cancer is bladder cancer.

In some embodiments, the cancer is bile duct cancer.

In some embodiments, the cancer is anal cancer.

In some embodiments, the cancer is adrenal cortical cancer.

In some embodiments, the disorder or disease is a neurological condition, disorder or disease, wherein the neurological condition/disorder/disease is selected from: Alzheimer's disease, frontotemporal dementias, dementia with lewy bodies, prion diseases, Parkinson's disease, Huntington's disease, progressive supranuclear palsy, corticobasal degeneration, multiple system atrophy, amyotrophic lateral sclerosis (ALS), inclusion body myositis, autism, degenerative myopathies, diabetic neuropathy, other metabolic neuropathies, endocrine neuropathies, orthostatic hypotension, multiple sclerosis, and Charcot-Marie-Tooth disease.

In some embodiments, the disorder or disease is a neurological disease or disorder associated with tau protein, amyloid or alpha-synuclein pathology.

In some embodiments, the disorder or disease is selected from the group consisting of: Alzheimer's Disease, Amyotrophic Lateral Sclerosis, Down Syndrome, Frontotemporal Dementia with Parkinsonism-17 (FTDP-17), Lewy body dementia, Parkinson's Disease, Pick's Disease, and additional diseases with pronounced neurodegeneration such as Autism, Dementia, Epilepsy, Huntington's Disease, Multiple Sclerosis; diseases and disorders associated with acquired brain injury such as Chronic Traumatic Encephalopathy, Traumatic Brain Injury, Tumor, and Stroke.

In some embodiments, a compound of Formulas I, II, III, IV, V, VI, VII, VIII, IX and/or X inhibits DYRK1A.

In some embodiments, a compound of Formulas I, II, III, IV, V, VI, VII, VIII, IX and/or X inhibits one or more proteins in the Wnt pathway.

In some embodiments, a compound of Formulas I, II, III, IV, V, VI, VII, VIII, IX and/or X inhibits signaling induced by one or more Wnt proteins.

In some embodiments, the Wnt proteins are chosen from: WNT1, WNT2, WNT2B, WNT3, WNT3A, WNT4, WNT5A, WNT5B, WNT6, WNT7A, WNT7B, WNT8A, WNT8B, WNT9A, WNT9B, WNT10A, WNT10B, WNT1, and WNT16.

In some embodiments, a compound of Formulas I, II, III, IV, V, VI, VII, VIII, IX and/or X inhibit a kinase activity.

In some embodiments, a method for treating a disease or disorder mediated by the Wnt pathway in a patient is provided, the method comprising administering to the patient a therapeutically effective amount of a compound (or compounds) of Formulas I, II, III, IV, V, VI, VII, VIII, IX and/or X, or a pharmaceutically acceptable salt thereof.

In some embodiments, a compound of Formulas I, II, III, IV, V, VI, VII, VIII, IX and/or X inhibit one or more Wnt proteins.

In some embodiments, a method for treating a disease or disorder mediated by kinase activity in a patient is provided, the method comprises administering to the patient a therapeutically effective amount of a compound (or compounds) of Formulas I, II, III, IV, V, VI, VII, VIII, IX and/or X, or a pharmaceutically acceptable salt thereof.

In some embodiments, the disease or disorder comprises tumor growth, cell proliferation, or angiogenesis.

In some embodiments, the method inhibits the activity of a protein kinase receptor, the method comprises contacting the receptor with an effective amount of a compound (or compounds) of Formulas I, II, III, IV, V, VI, VII, VIII, IX and/or X, or a pharmaceutically acceptable salt thereof.

In some embodiments, a method for treating a disease or disorder associated with aberrant cellular proliferation in a patient is provided, the method comprises administering to the patient a therapeutically effective amount of a compound (or compounds) of Formulas I, II, III, IV, V, VI, VII, VIII, IX and/or X, or a pharmaceutically acceptable salt thereof.

In some embodiments, the method prevents or reduces angiogenesis in a patient; the method comprises administering to the patient a therapeutically effective amount of a compound (or compounds) of Formulas I, II, III, IV, V, VI, VII, VIII, IX and/or X, or a pharmaceutically acceptable salt thereof.

In some embodiments, the method prevents or reduces abnormal cellular proliferation in a patient; the method comprises administering to the patient a therapeutically effective amount of a compound (or compounds) of Formulas I, II, III, IV, V, VI, VII, VIII, IX and/or X, or a pharmaceutically acceptable salt thereof.

In some embodiments, a method for treating a disease or disorder associated with aberrant cellular proliferation in a patient is provided, the method comprises administering to the patient a pharmaceutical composition comprising one or more of the compounds of Formulas I, II, III, IV, V, VI, VII, VIII, IX and/or X in combination with a pharmaceutically acceptable carrier and one or more other agents.

Moreover, the compounds and compositions, for example, as inhibitors of the cyclin-dependent kinases (CDKs), can modulate the level of cellular RNA and DNA synthesis and therefore are expected to be useful in the treatment of viral infections such as HIV, human papilloma virus, herpes virus, Epstein-Barr virus, adenovirus, Sindbis virus, pox virus, and the like.

Compounds and compositions described herein can inhibit the kinase activity of, for example, CDK/cyclin complexes, such as those active in the Go or GI stage of the cell cycle, e.g., CDK2, CDK4, and/or CDK6 complexes.

Evaluation of Biological Activity

The biological activity of the compounds described herein can be tested using any suitable assay known to those of skill in the art, see e.g., WO 2001/053268 and WO 2005/009997. For example, the activity of a compound may be tested using one or more of the test methods outlined below.

In one example, tumor cells may be screened for Wnt independent growth. In such a method, tumor cells of interest are contacted with a compound (i.e. inhibitor) of interest, and the proliferation of the cells, e.g. by uptake of tritiated thymidine, is monitored. In some embodiments, tumor cells may be isolated from a candidate patient who has been screened for the presence of a cancer that is associated with a mutation in the Wnt signaling pathway. Candidate cancers include, without limitation, those listed above.

In another example, in vitro assays for Wnt biological activity may be used, e.g. stabilization of β-catenin and promoting growth of stem cells. Assays for biological activity of Wnt include stabilization of β-catenin, which can be measured, for example, by serial dilutions of a candidate inhibitor composition. An exemplary assay for Wnt biological activity contacts a Wnt composition in the presence of a candidate inhibitor with cells, e.g. mouse L cells. The cells are cultured for a period of time sufficient to stabilize β-catenin, usually at least about 1 hour, and lysed. The cell lysate is resolved by SDS PAGE, then transferred to nitrocellulose and probed with antibodies specific for β-catenin.

In a further example, the activity of a candidate compound can be measured in a *Xenopus* secondary axis bioassay [Leyns, L. et al. *Cell* (1997), 88(6), 747-756].

In another example, in vitro assays for DYRK1A biological activity may be used, e.g. regulation of microtubule-associated protein tau (MAPT/Tau) phosphorylation in neuronal cell line such as the human SH-SY5Y neuroblastoma cell line. Assays for DYRK1a-regulated level of phosphorylation can include monitoring levels of basal pSer396 Tau, which can be measured, for example, by serial dilutions of a candidate inhibitor composition using a ten micromolar top concentration and detected by ELISA or Western Blotting. An exemplary assay for DYRK-1a-regulated phosphorylation uses the SH-SY5Y cells cultured in a 96 well plate format for a period of time sufficient to stabilize microtubules and Tau phosphorylation, usually at least 2 days, then treated with a ⅓ serial dilution of compounds overnight and lysed. The cell lysate is resolved by SDS PAGE, then transferred to nitrocellulose and probed with an antibody specific for pSer396 Tau. The chemoluminescence signal for HRP-linked antibodies used in western blotting is detected using a Carestream Image Station and blot densitometry for pSer396 and beta-actin are analyzed using ImageJ (NIH).

In a further example, the activity of a candidate compound can be measured by ELISA by adding the lysate mentioned above onto total Tau-coated plates and detected with a specific pSer396 antibody. Colorimetric detection of ELISA signal is performed by Cytation3 plate reader (Biotek).

To further illustrate this disclosure, the following examples are included. The examples should not, of course, be construed as specifically limiting the disclosure. Variations of these examples within the scope of the claims are within the purview of one skilled in the art and are considered to fall within the scope of the invention as described and claimed herein. The reader will recognize that the skilled artisan, armed with the present disclosure and skill in the art is able to prepare and use the invention without exhaustive examples.

EXAMPLES

Compound Preparation

The starting materials used in preparing the compounds of the disclosure are known, made by known methods, or are commercially available. It will be apparent to the skilled artisan that methods for preparing precursors and functionality related to the compounds claimed herein are generally described in the literature. The skilled artisan given the literature and this disclosure is well equipped to prepare any of the compounds.

It is recognized that the skilled artisan in the art of organic chemistry can readily carry out manipulations without further direction, that is, it is well within the scope and practice of the skilled artisan to carry out these manipulations. These include reduction of carbonyl compounds to their corresponding alcohols, oxidations, acylations, aromatic substitutions, both electrophilic and nucleophilic, etherifications, esterification and saponification and the like. These manipulations are discussed in standard texts such as *March's Advanced Organic Chemistry: Reactions, Mechanisms, and Structure* $7^{th}$ Ed., John Wiley & Sons (2013), Carey and Sundberg, *Advanced Organic Chemistry: Part B: Reaction and Synthesis* $5^{th}$ Ed., Springer (2007), *Comprehensive Organic Transformations: A Guide to Functional Group Transformations*, $2^{nd}$ Ed., John Wiley & Sons (1999) and the like.

The skilled artisan will readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in P. Wuts *Greene's Protective Groups in Organic Synthesis*, 5th Ed., John Wiley & Sons (2014).

Trademarks used herein are examples only and reflect illustrative materials used at the time of filing the present disclosure. The skilled artisan will recognize that variations in lot, manufacturing processes, and the like, are expected. Hence the examples, and the trademarks used in them are non-limiting, and they are not intended to be limiting, but are merely an illustration of how a skilled artisan may choose to perform one or more of the embodiments of the disclosure.

($^1$H) nuclear magnetic resonance spectra (NMR) were measured in the indicated solvents on a Bruker NMR spectrometer (Avance TM DRX300, 300 MHz for $^1$H or Avance TM DRX500, 500 MHz for $^1$H) or Varian NMR spectrometer (Mercury 400BB, 400 MHz for $^1$H). Peak positions are expressed in parts per million (ppm) downfield from tetramethylsilane. The peak multiplicities are denoted as follows, s, singlet; d, doublet; t, triplet; q, quartet; ABq, AB quartet; quin, quintet; sex, sextet; sep, septet; non, nonet; dd, doublet of doublets; d/ABq, doublet of AB quartet; dt, doublet of triplets; td, triplet of doublets; dq, doublet of quartets; m, multiplet.

The following abbreviations have the indicated meanings:
brine=saturated aqueous sodium chloride
$CDCl_3$=deuterated chloroform
DAST=diethylaminosulfur trifluoride
DCE=dichloroethane
DCM=dichloromethane
DHP=3,4-dihydro-2H-pyran
DIPEA=N,N-diisopropylethylamine
DMF=N,N-dimethylformamide
DMSO-$d_6$=deuterated dimethylsulfoxide
ESIMS=electron spray mass spectrometry
EtOAc=ethyl acetate
$Et_3SiH$=triethylsilane
HATU=1-[bis(dimethylamino)methylene]-1H-1,2,3-triazolo[4,5-b]pyridinium 3-oxide hexafluorophosphate
HCl=hydrochloric acid
HOAc=acetic acid
KOAc=potassium acetate
$K_3PO_4$=potassium phosphate
LAH=lithium aluminum hydride
MeOH=methanol
$MgSO_4$=magnesium sulfate
MsCl=methanesulfonyl chloride (mesyl chloride)
$NaBD_4$=sodium borodeuteride NaBH(OAc)$_3$=sodium triacetoxy borohydride
NaHCO$_3$=sodium bicarbonate
NMR=nuclear magnetic resonance
ON=overnight
Pd/C=palladium on carbon
PdCl$_2$(dppf)$_2$=1,1'-bis(diphenylphosphino)ferrocene-palladium(II)dichloride
Pd(PPh$_3$)$_2$Cl$_2$=dichloro-bis(triphenylphosphine)palladium (II)
Pd(PPh$_3$)$_4$=tetrakis(triphenylphosphine)palladium(0)
PPTS=pyridinium p-toluenesulfonate
r.t.=room temperature
SEM=2-(trimethylsilyl)ethoxymethyl
TEA=triethylamine
TFA=trifluoroacetic acid
THF=tetrahydrofuran
TLC=thin layer chromatography The following example schemes are provided for the guidance of the reader, and collectively represent an example method for making the compounds provided herein. Furthermore, other methods for preparing compounds of the disclosure will be readily apparent to the person of ordinary skill in the art in light of the following reaction schemes and examples. The skilled artisan is thoroughly equipped to prepare these compounds by those methods given the literature and this disclosure. The compound numberings used in the synthetic schemes depicted below are meant for those specific schemes only, and should not be construed as or confused with same numberings in other sections of the application. Unless otherwise indicated, all variables are as defined above.

General Procedures

Compounds of Formulas I, II, III, IV, V, VI, VII, VIII, IX and/or X of the present disclosure can be prepared as depicted in Scheme 1.

Scheme 1

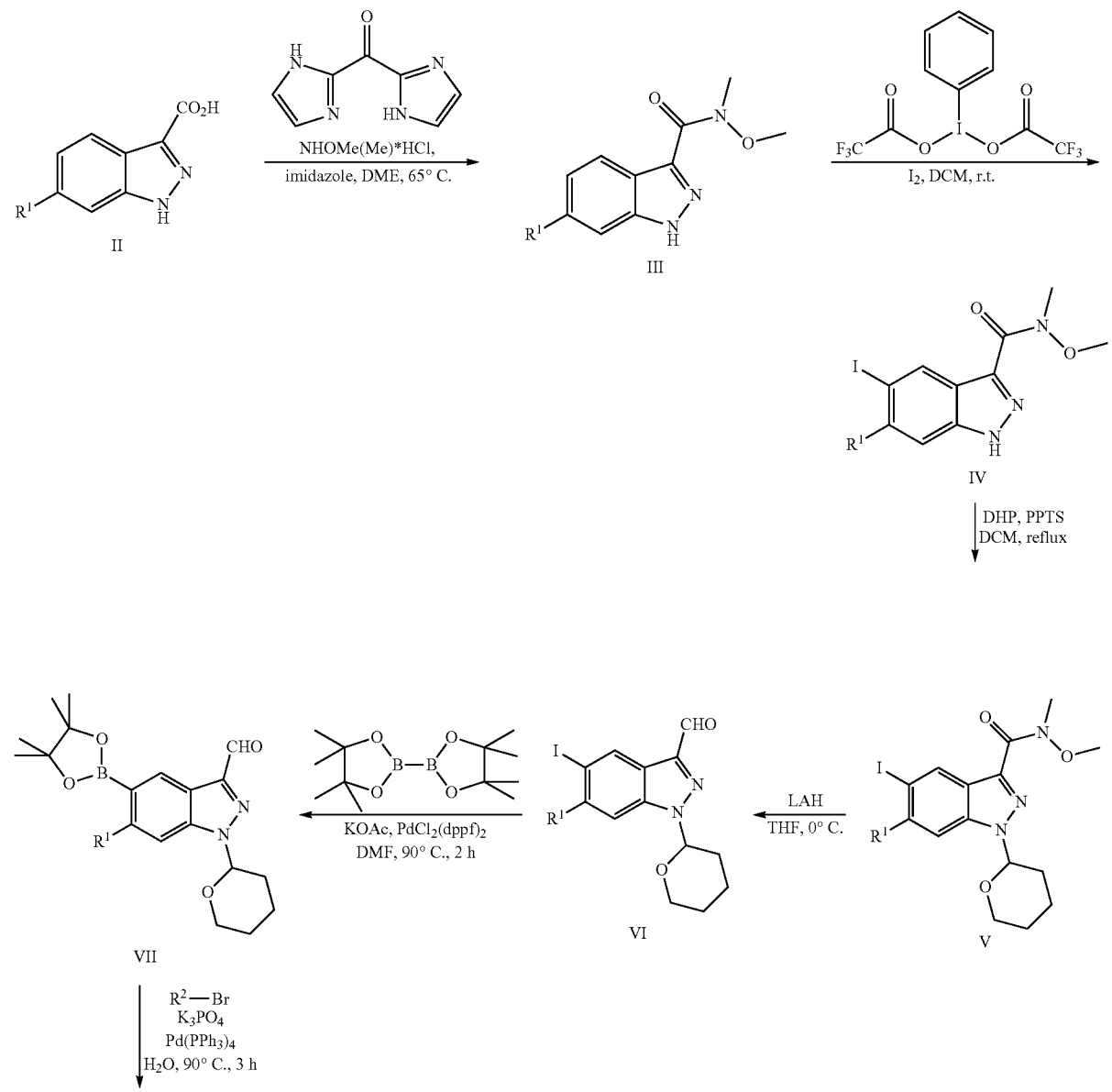

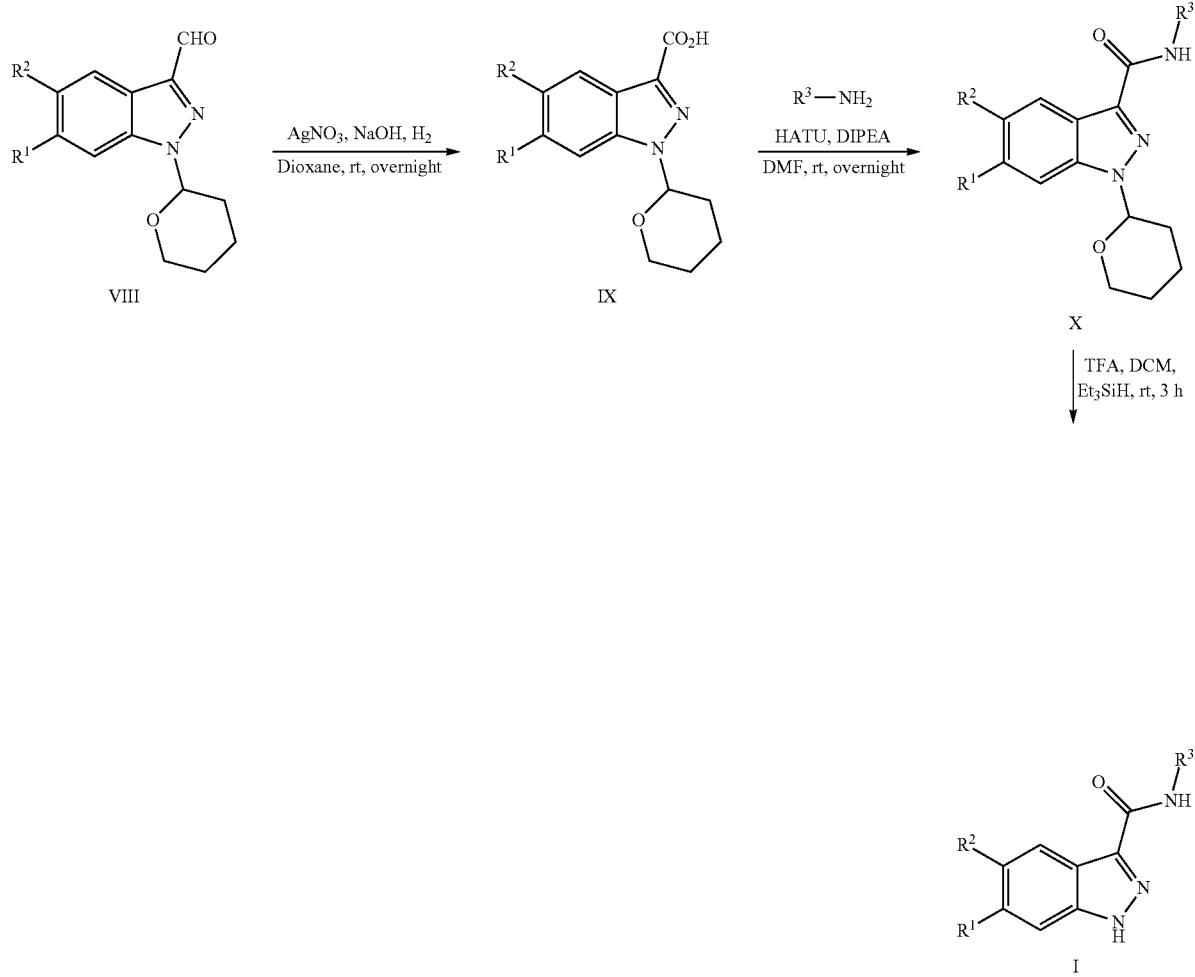

Scheme 1 describes a method for preparation of indazole-3-carboxamide derivatives (I) by first forming the Weinreb amide (III) of a 1H-indazole-3-carboxylic acid (II). The Weinreb amide (III) is reacted with (bis(trifluoroacetoxy) iodo)benzene to produce the 5-iodo-1H-indazole-3-carboxylic acid (IV) followed by THP protection of the indazole nitrogen. The Weinreb amide of protected indazole V is reduced to aldehyde VI followed by reaction with bis(pinacolato)diboron to give the pinacol ester (VII). Suzuki coupling with a variety of aromatic and nonaromatic bromides yields the $R^2$ substituted indazole VIII. Oxidation of the aldehyde to the acid (IX) followed by HATU mediated coupling of a variety of amines and sequent deprotection produces the desired indazole-3-carboxamide derivatives (I).

Compounds of Formulas I, II, III, IV, V, VI, VII, VIII, IX and/or X of the present invention can also be prepared as depicted in Scheme 2.

Scheme 2

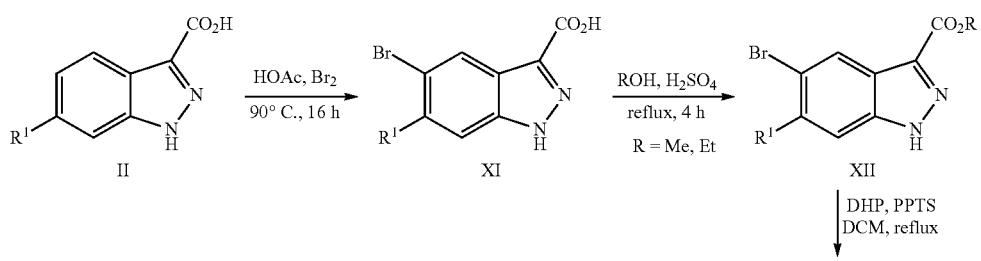

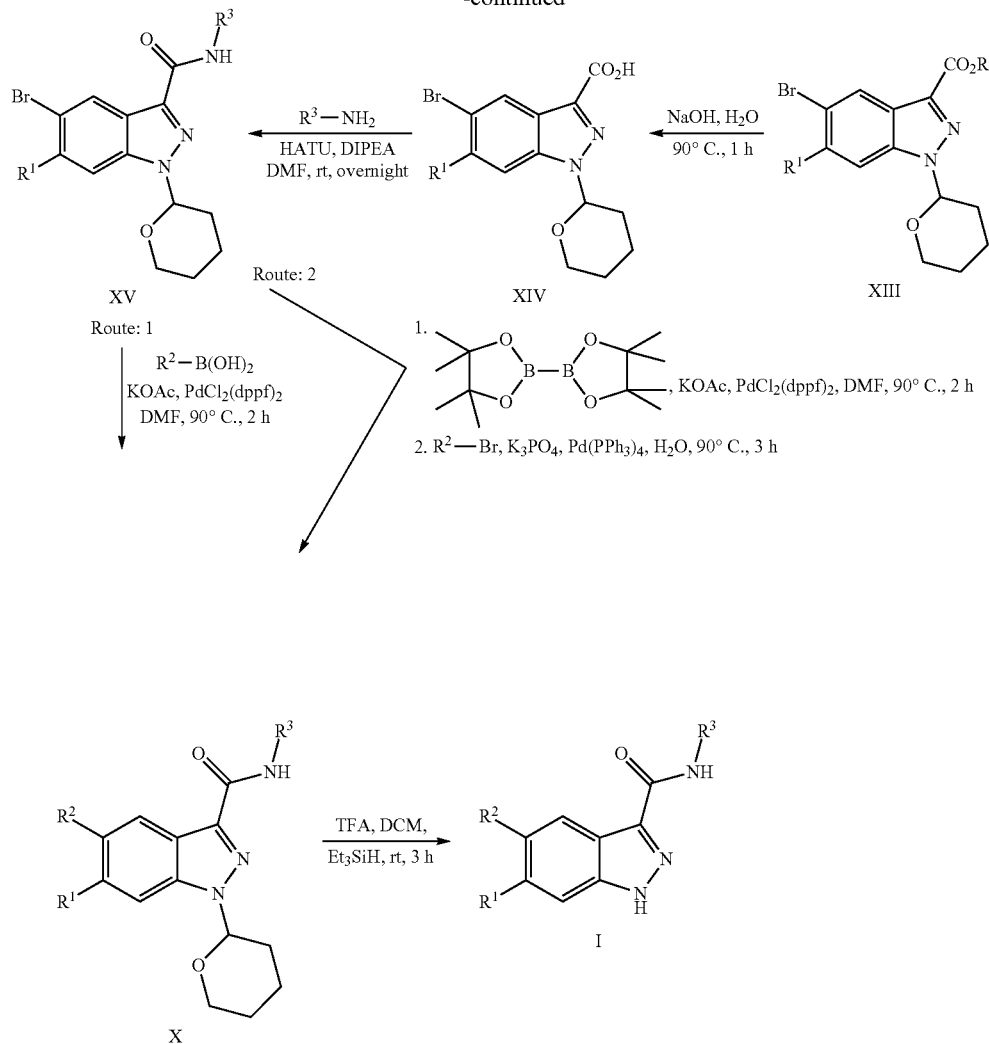

Scheme 2 describes an alternative method for preparation of indazole-3-carboxamide derivatives (I) by bromination of the indazole 5-position followed by esterification to form ester XII. The indazole nitrogen is THP protected and the ester is hydrolyzed to acid XIV. The acid is coupled with a variety of amines to produce amide XV which is then coupled with a variety of boronic acids (Route 1) to give X. Alternatively, XV can be converted to the boronate ester and then couple to a variety of bromides (Route 2) to yield X. Final deprotection of the indazole nitrogen yields the desired indazole-3-carboxamide derivatives (I).

Compounds of Formulas I, II, III, IV, V, VI, VII, VIII, IX and/or X of the present invention can also be prepared as depicted in Scheme 3.

Scheme 3

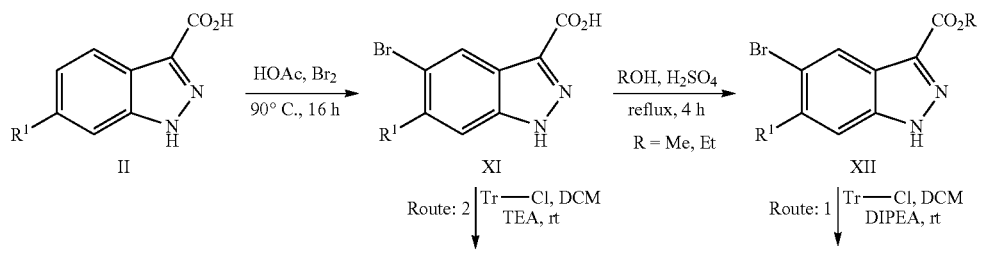

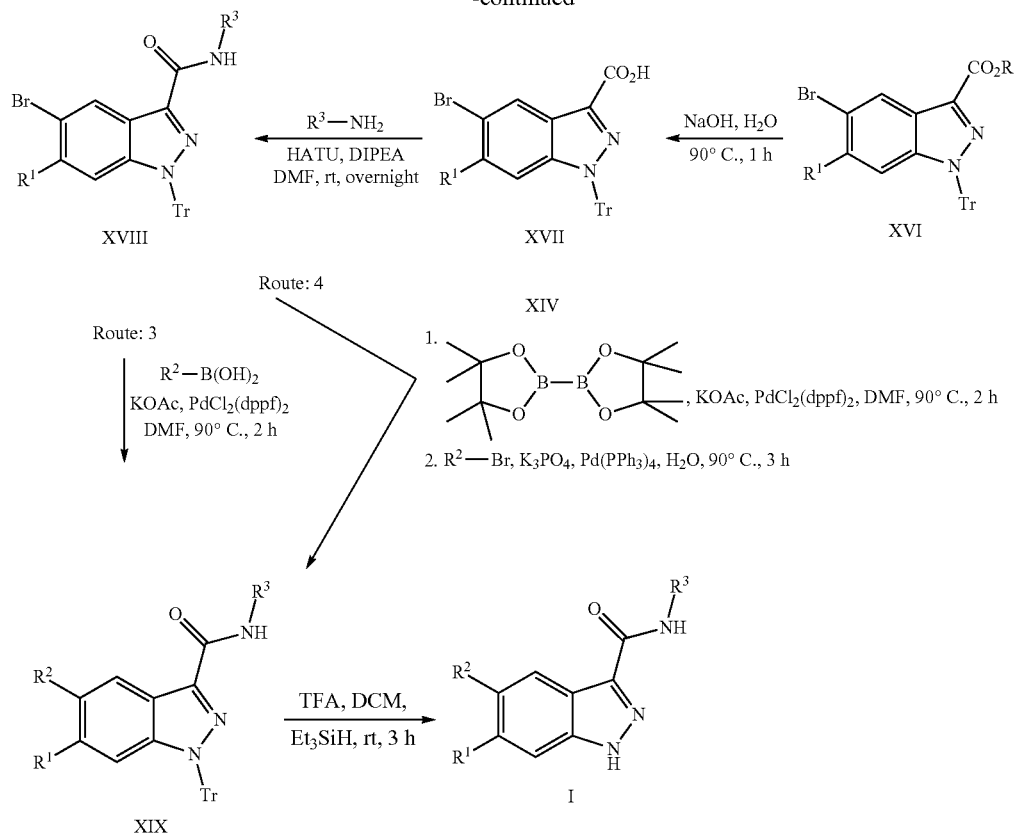

Scheme 3 describes another alternative method for preparation of indazole-3-carboxamide derivatives (I) by bromination of the indazole 5-position followed by either Route 1: esterification to form ester XII, then trityl protection of the indazole nitrogen and then finally hydrolyzed of the ester to acid XVII; or Route 2: trityl protection of the indazole nitrogen directly to acid XVII. The acid is coupled with a variety of amines to produce amide XVIII which is then coupled with a variety of boronic acids (Route 3) to give XIX. Alternatively, XVIII can be converted to the boronate ester and then couple to a variety of bromides (Route 4) to yield XIX. Final deprotection of the indazole nitrogen yields the desired indazole-3-carboxamide derivatives (I).

Illustrative Compound Examples

Preparation of intermediate N-(5-bromopyridin-3-yl)-2,4-difluorobenzamide (XXIII) is depicted below in Scheme 4.

Scheme 4

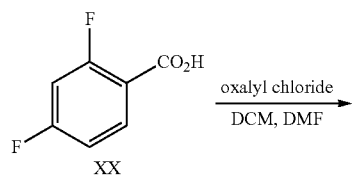

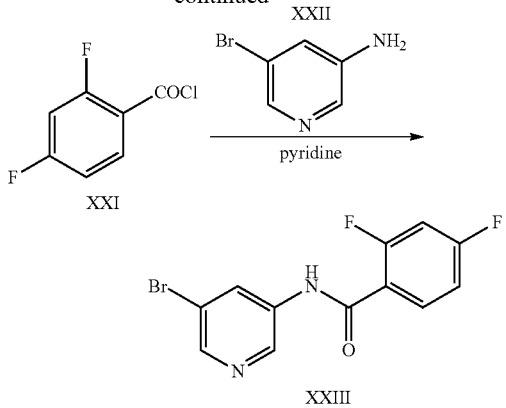

Step 1

To a solution of 2,4-difluorobenzoic acid (XX) (2.00 g, 12.65 mmol, 1 eq) in DCM (50 mL) was added oxalyl chloride (1.3 mL, 15.18 mmol, 1.2 eq) followed by catalytic DMF. This mixture was stirred at room temperature for 2 h. The solvent was concentrated in vacuo to produce 2,4-difluorobenzoyl chloride (XXI) which was used without further purification.

Step 2

To a solution of 2,4-difluorobenzoyl chloride (XXI) in pyridine (20 mL) then 3-amino-5-bromopyridine (XXII) (2.63 g, 15.18 mmol, 1.21 eq) was added and stirred at room temperature for 16 h. The reaction was then quenched with water (10 mL) and the the solvent was concentrated in vacuo. The residue was purified by chromatography on silica gel (Hexanes:EtOAc=4:1) to afford N-(5-bromopyridin-3-yl)-2,4-difluorobenzamide (XXIII) (3.3 g, 10.6 mmol, 84.0% yield) as a tan solid. ESIMS found for $C_{12}H_7BrF_2N_2O$ m/z 312.8 (M+H).

The following intermediates were prepared in accordance with the procedure described in the above Scheme 4.

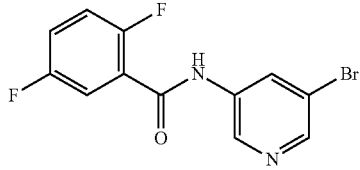

XXIV

N-(5-Bromopyridin-3-yl)-2,5-difluorobenzamide (XXIV): Tan solid (01.66 g, 5.3 mmol, 41.9% yield). ESIMS found for $C_{12}H_7BrF_2N_2O$ m/z 312.8 (M+H).

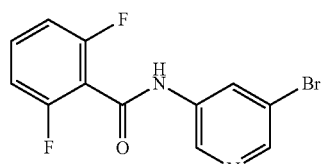

XXV

N-(5-Bromopyridin-3-yl)-2,6-difluorobenzamide (XXV): Beige solid (2.72 g, 8.7 mmol, 68.7% yield). ESIMS found for $C_{12}H_7BrF_2N_2O$ m/z 312.9 (M+H).

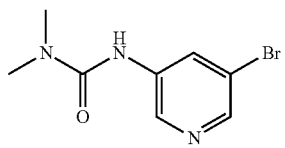

XXVI 3-(5-Bromopyridin-3-yl)-1,1-dimethylurea (XXVI): Brown solid (1.24 g, 5.09 mmol, 88% yield). 1H NMR (DMSO-$d_6$) δ ppm 8.67-8.64 (m, 2H), 8.23 (d, J=7.8 Hz, 1H), 2.93 (s, 6H); ESIMS found for $C_8H_{10}BrN_3O$ m/z 245.05 (M+H).

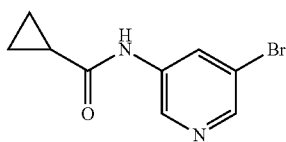

XXVII

N-(5-Bromopyridin-3-yl)cyclopropanecarboxamide (XXVII): Off white solid, (83% yield), $^1$H NMR (CDCl$_3$, 400 MHz) δ ppm 8.46-8.39 (m, 3H), 7.54 (bs, 1H), 1.56-1.50 (m, 1H), 1.13-1.07 (m, 2H), 0.96-0.90 (m, 2H); ESIMS found for $C_9H_9BrN_2O$ m/z 240.85 (M+H).

Preparation of intermediate (XXIX) is depicted below in Scheme 5.

Scheme 5

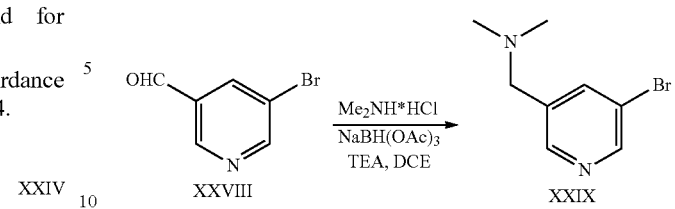

Step 1

To a solution of 5-bromonicotinaldehyde (XXVIII) (5.0 g, 26.9 mmol) in DCE (108 mL) was added dimethylamine-HCl (4.39 g, 53.8 mmol) and TEA (7.5 g, 53.8 mmol). The reaction was stirred at room temperature for 1 h. NaBH(OAc)$_3$ was added and the reaction was stirred overnight at room temperature. The reaction was diluted with DCM and sat. aq. NaHCO$_3$. The organic layer was separated, washed with water, brine, dried and concentrated under vacuum to produce 1-(5-bromopyridin-3-yl)-N,N-dimethylmethanamine (XXIX) as a brown liquid (92.6% yield). $^1$H NMR (CDCl$_3$) δ ppm 2.15 (s, 6H), 3.43 (s, 2H), 7.94 (s, 1H), 8.47 (d, J=2 Hz, 1H), 8.59 (d, J=3 Hz, 1H); ESIMS found for $C_8H_{11}BrN_2$ m/z 215 ($M^{Br79}$+H) and 217 ($M^{Br81}$+H).

The following intermediates were prepared in accordance with the procedure described in the above Scheme 5.

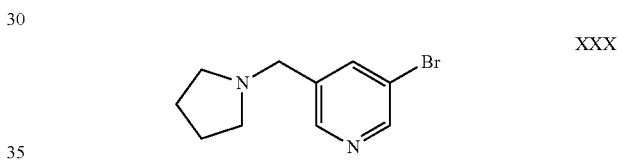

XXX

3-Bromo-5-(pyrrolidin-1-ylmethyl)pyridine (XXX): Golden liquid (1.35 g, 97% yield). $^1$H NMR (DMSO-$d_6$) 1.68-1.71 (m, 4H), 2.42-2.44 (m, 4H), 3.60 (s, 2H), 7.96 (s, 1H), 8.48 (d, J=2 Hz, 1H), 8.58 (d, J=3 Hz, 1H); ESIMS found for $C_{10}H_{13}BrN_2$ m/z 242 (M+H).

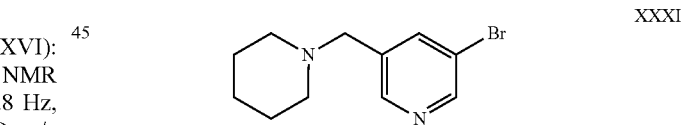

XXXI

3-Bromo-5-(piperidin-1-ylmethyl)pyridine (XXXI): Brown liquid (13.1 g, 94% yield). $^1$H NMR (DMSO-$d_6$) 1.36-1.39 (m, 2H), 1.46-1.51 (m, 4H), 2.31-2.32 (m, 4H), 3.46 (s, 2H), 7.94 (s, 1H), 8.47 (d, J=2 Hz, 1H), 8.58 (d, J=3 Hz, 1H); ESIMS found for $C_{11}H_{15}BrN_2$ m/z 257 (M+H).

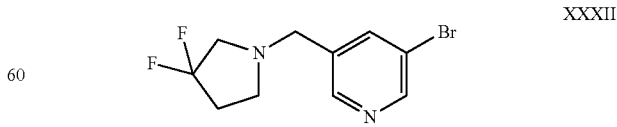

XXXII

3-Bromo-5-((3,3-difluoropyrrolidin-1-yl)methyl)pyridine (XXXII): Brown liquid (7.38 g, 26.64 mmol, 94.9% yield). $^1$H NMR (DMSO-$d_6$) 2.21-2.30 (m, 2H), 2.70 (t, J=7 Hz, 2H), 2.89 (t, J=13 Hz, 2H), 3.66 (s, 2H), 7.95-7.98 (m, 1H), 8.57 (d, J=1.7 Hz, 1H), 8.61 (d, J=2.2 Hz, 1H); ESIMS found for $C_{10}H_{11}BrF_2N_2$ m/z 276 (M+H).

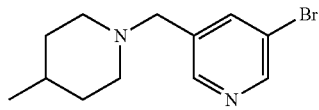

XXXIII

3-Bromo-5-((4-methylpiperidin-1-yl)methyl)pyridine (XXXIII): Brown oil (2.93 g, 10.88 mmol, 97.8% yield). ESIMS found for $C_{12}H_{17}BrN_2$ m/z 271.1 ($^{81}$BrM+H).

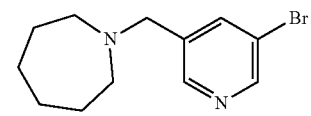

XXXIV 1-((5-Bromopyridin-3-yl)methyl)azepane (XXXIV): Brown liquid (2.80 g, 10.4 mmol, 95.3% yield). ESIMS found for $C_{12}H_{17}BrN_2$ m/z 271.0 ($^{81}$BrM+H).

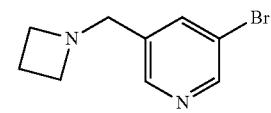

XXXV 3-(Azetidin-1-ylmethyl)-5-bromopyridine (XXXV): Brown oil (300 mg, 1.32 mmol, 12.2% yield). ESIMS found for $C_9H_{11}BrN_2$ m/z 226.9 ($^{79}$BrM+H).

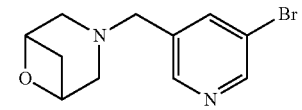

XXXVI 3-((5-Bromopyridin-3-yl)methyl)-6-oxa-3-azabicyclo[3.1.1]heptane (XXXVI): Brown solid (1.35 g, 5.0 mmol, 79.8% yield). ESIMS found for $C_{11}H_{13}BrN_2O$ m/z 270.7 ($^{81}$BrM+H).

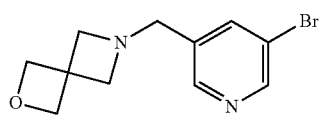

XXXVII 6-((5-Bromopyridin-3-yl)methyl)-2-oxa-6-azaspiro[3.3]heptane (XXXVII): Brown oil (0.852 g, 3.16 mmol, 71.8% yield). ESIMS found for $C_{11}H_{13}BrN_2O$ m/z 270.9 ($^{81}$BrM+H).

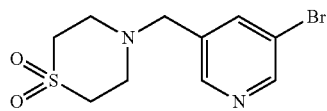

XXXVIII 4-((5-Bromopyridin-3-yl)methyl)thiomorpholine 1,1-dioxide (XXXVIII): Brown oil (588 mg, 1.93 mmol, 33.0% yield). ESIMS found for $C_{11}H_{13}BrN_2O$ m/z 306.6 ($^{81}$BrM+H).

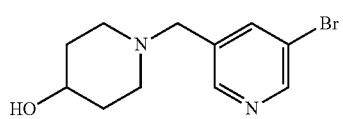

XXXIX 1-(5-Bromopyridin-3-yl)piperidin-4-ol (XXXIX): Brown oil (2.15 g, 7.93 mmol, 72.7% yield). $^1$H NMR (DMSO-$d_6$) 1.34-1.41 (m, 2H), 1.67-1.71 (m, 2H), 2.03-2.07 (m, 2H), 2.62-2.64 (m, 2H), 3.42-3.46 (m, 1H), 3.47 (s, 2H), 4.55 (d, J=4.2 Hz, 1H), 7.93-7.94 (m, 1H), 8.46 (d, J=1.6 Hz, 1H), 8.58 (d, J=2.2 Hz, 1H); ESIMS found for $C_{11}H_{15}BrN_2O$ m/z 272 (M+H).

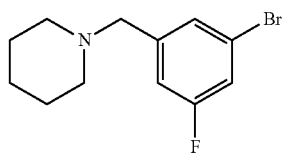

XL 1-(3-Bromo-5-fluorobenzyl)piperidine (XL): Clear liquid (2.83 g, 10.4 mmol, 100% yield). ESIMS found for $C_{12}H_{15}BrFN$ m/z 272.0 ($^{79}$BrM+H).

Preparation of 3-bromo-5-(piperidin-1-ylmethyl-d2)pyridine (XLV) is depicted below in Scheme 6.

Scheme 6

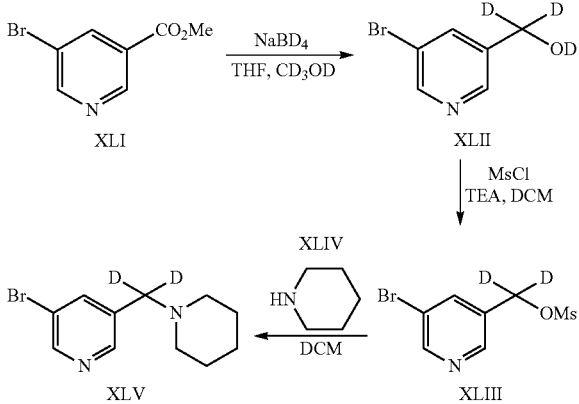

Step 1

To a solution of methyl 5-bromopyridine-3-carboxylate (XLI) (2.00 g, 9.25 mmol, 1 eq) in THF (45 mL) was added sodium borodeuteride (0.77 g, 18.5 mmol, 2 eq) batchwise with stirring. CD$_3$OD (5 mL) was then added and the mixture was heated to reflux for 16 h. The reaction was quenched by pouring onto ice. The aqueous layer was extracted with EtOAc, the organic layer was dried over MgSO$_4$, filtered and concentrated in vacuo. The resultant residue was purified by chromatography on silica gel (hexanes:EtOAc=4:1) to afford (5-bromopyridin-3-yl)methan-d$_2$-ol-d (XLII) (0.58 g, 3.1 mmol, 33% yield) as a brown oil. ESIMS found for C$_6$H$_3$D$_3$BrNO m/z 291.9 ($^{81}$BrM+H).

Step 2-3

To a solution of (5-bromopyridin-3-yl)methan-d$_2$-ol-d (XLII) (0.58 g, 3.1 mmol, 1 eq) in DCM (30 mL) was added TEA (1.28 mL, 9.15 mmol, 3 eq). Methane sulfonyl chloride (0.26 mL, 3.35 mmol, 1.1 eq) was added at 0° C. The reaction was stirred for 3 h before adding piperidine (XLIV) (0.90 mL, 9.15 mmol, 3 eq) and the reaction was stirred at room temperature for 16 h. This mixture then poured into water, the aqueous layer was extracted with EtOAc and the organic layer was dried over MgSO$_4$, filtered and concentrated in vacuo. The resultant residue was purified by chromatography on silica gel (hexanes:EtOAc=1:1) to afford 3-bromo-5-(piperidin-1-ylmethyl-d2)pyridine (XLV) (0.59 g, 3.1 mmol, 73.9% yield) as a brown oil. ESIMS found for C$_{11}$H$_{13}$D$_2$BrN$_2$ m/z 256.8 ($^{79}$BrM+H).

Preparation of tert-butyl(1-(6-chloropyrazin-2-yl)azetidin-3-yl)carbamate (XLVIII) is depicted below in Scheme 7.

Scheme 7

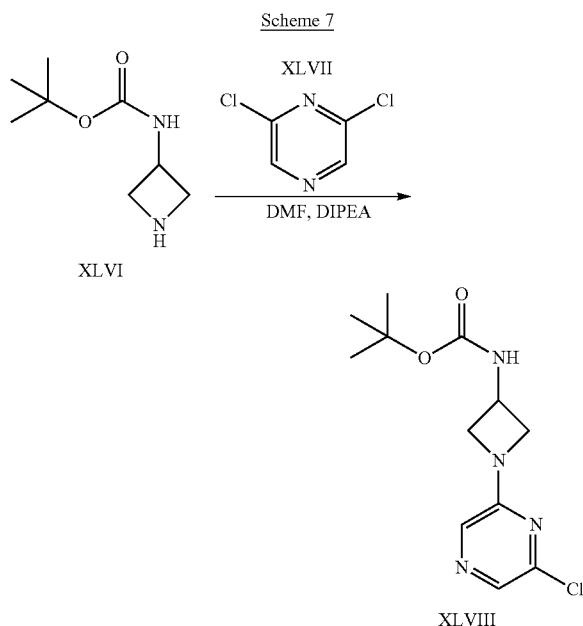

Step 1

To a solution of tert-butyl azetidin-3-ylcarbamate hydrochloride (XLVI) (2 g, 9.58 mmol) in dry DMF (19.2 mL) was added DIPEA (8.37 ml, 47.9 mmol). To this mixture was added 2,6-dichloropyrazine (XLVII) (1.428 g, 9.58 mmol) and the reaction was stirred at 95° C. for 3 hours. The reaction was quenched with water (20 mL) and extracted with EtOAc. The organic layer was dried over anhydrous Na$_2$SO$_4$, filtered and concentrated. The residue was purified by silica gel column chromatography (40 g) (100% hexanes→hexanes:EtOAc 1:1) to yield tert-butyl(1-(6-chloropyrazin-2-yl)azetidin-3-yl)carbamate (XLVIII) (2.2882 g, 8.04 mmol, 84% yield) as a white solid. ESIMS found for C$_{12}$H$_{17}$ClN$_4$O$_2$ m/z 285.1 (M+H).

Preparation of 3-bromo-5-(pyrrolidin-1-yl)pyridine (LI) is depicted below in Scheme 8.

Scheme 8

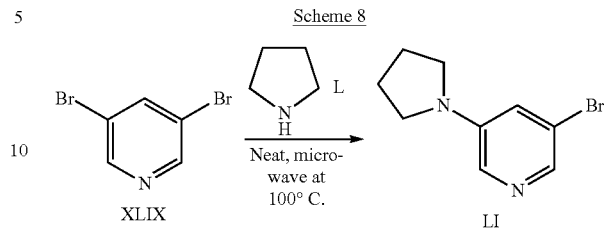

Step 1

To a microwave vial was added 3,5-dibromopyridine (XLIX) (2.0 g, 8.44 mmol) and pyrrolidine (L) (3.0 g, 42.2 mmol). The reaction was microwaved at 100° C. for 16 h. The crude mixture was purified by chromatography on silica gel (hexanes:EtOAc=4:1) to afford 3-bromo-5-(pyrrolidin-1-yl)pyridine (LI) (1.41 g, 6.21 mmol, 73.6% yield) as a white solid. ESIMS found for C$_9$H$_{11}$BrN$_2$ m/z 228.9 (M+H).

Preparation of 3-bromo-5-(difluoromethyl)pyridine (LIII) is depicted below in Scheme 9.

Scheme 9

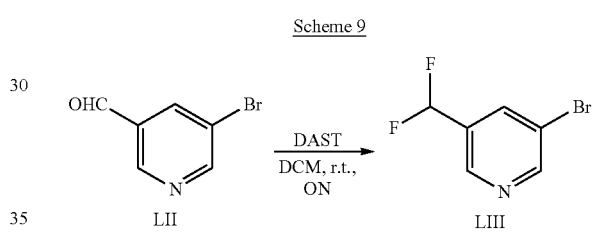

Step 1

To a solution of 5-bromonicotinaldehyde (LII) (1.3 g, 7.0 mmol) in dry DCM (20 mL) was added DAST (1.73 mL, 14.0 mmol) under argon. The reaction was stirred at room temperature overnight. The mixture was slowly added to aq, sat. NaHCO$_3$ solution. The organic phase was separated, washed with brine, dried over anhydrous Na$_2$SO$_4$ and evaporated under vacuum. The crude mixture was purified by chromatography on silica gel (hexanes:EtOAc=1:1) to produce 3-bromo-5-(difluoromethyl)pyridine (LIII) (814 mg, 3.91 mmol, 55.9% yield) as a solid. $^1$H NMR (DMSO-d$_6$, 500 MHz) δ ppm 7.14 (t, J=55.0 Hz, 1H), 8.31 (s, 1H), 8.79 (d, J=1.37 Hz, 1H), 8.91 (t, J=0.95 Hz, 1H); ESIMS found for C$_6$H$_4$BrF$_2$N m/z 207.9 (M+H).

Preparation of 1-(3-bromo-4,5-difluorobenzyl)piperidine (LVI) is depicted below in Scheme 10.

Scheme 10

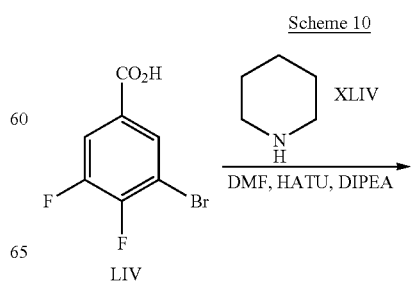

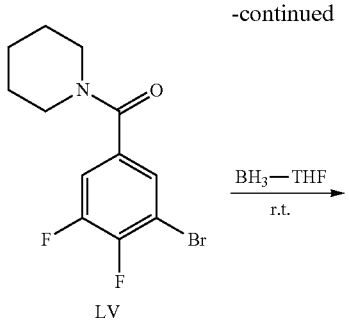 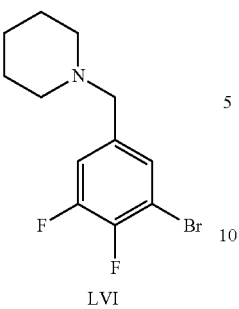

LV → LVI (BH₃—THF, r.t.)

Step 1

To a solution of 3-bromo-4,5-difluorobenzoic acid (LIV) (2.4 g, 10.1 mmol) in DMF (20 mL) was added piperdine (XLIV) (1.2 mL, 12.1 mmol), HATU (3.84 g, 10.1 mmol) and DIPEA (3.6 mL, 20.2 mmol). The reaction was stirred at room temperature overnight. To the reaction was added EtOAc and aq, sat. NaHCO₃. The organic phase was separated, washed with brine, dried over anhydrous Na₂SO₄ and evaporated under vacuum. The crude mixture was purified by chromatography on silica gel (100% hexanes→hexanes: EtOAc=1:1) to produce (3-bromo-4,5-difluorophenyl)(piperidin-1-yl)methanone (LV) (2.6 g, 8.55 mmol, 84.6% yield) as a yellow oil. ESIMS found for $C_{12}H_{12}BrF_2NO$ m/z 304.1 (M+H).

Step 2

(3-Bromo-4,5-difluorophenyl)(piperidin-1-yl)methanone (LV) (872 mg, 2.86 mmol) was dissolved in BH₃-THF (6 mL, 5.74 mmol) and stirred at room temperature overnight. To the reaction was then added EtOAc and aq, sat. NaHCO₃. The organic phase was separated, washed with brine, dried over anhydrous Na₂SO₄ and evaporated under vacuum. The crude mixture was purified by chromatography on silica gel (100% hexanes→hexanes:EtOAc=1:3) to 1-(3-bromo-4,5-difluorobenzyl)piperidine (LVI) (650 mg, 2.24 mmol, 78.3% yield) as a yellow solid. ESIMS found for $C_{12}H_{14}BrF_2N$ m/z 290.0 (M+H).

Preparation of intermediate 6-(4-methylpiperazin-1-yl)pyridin-3-amine (LX) is depicted below in Scheme 11.

Scheme 11

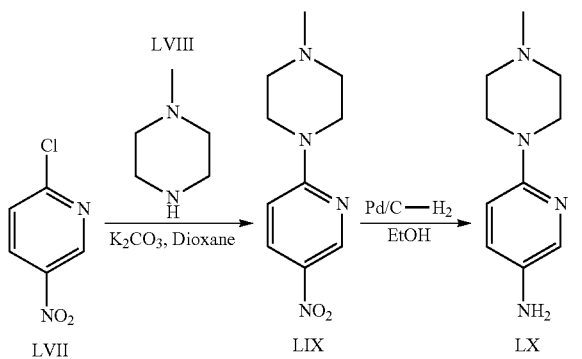

Step 1

To a solution of 2-chloro-5-nitropyridine (LVII) (3.17 g, 20.0 mmol) in dioaxane (50 mL) was added 1-methylpiperazine (LVIII) (4.00 g, 40.0 mmol) and potassium carbonate. The reaction was refluxed overnight, cooled to room temperature and concentrated under vacuum. The residue was treated with water and sonicated followed by stirring for 30 min. The solid was filtered, washed with cold water and dried to give 1-methyl-4-(5-nitropyridin-2-yl)piperazine (LIX) as a yellow solid (3.85 g, 17.3 mmol, 86.6% yield). ESIMS found for $C_{10}H_{14}N_4O_2$ m/z 223.1 (M+H).

Step 2

10% Palladium on carbon (40 mg) was added to a solution of 1-methyl-4-(5-nitropyridin-2-yl)piperazine (LIX) (3.80 g, 17.09 mmol) in EtOH (50.0 mL). The flask was evacuated and replaced with a hydrogen atmosphere. The solution was stirred at room temperature for 6 h under hydrogen. The catalyst was filtered through a pad of Celite, and the solvent was removed under reduced pressure to afford 6-(4-methylpiperazin-1-yl)pyridin-3-amine (LX) as a brown viscous oil which solidified under vacuum (3.30 g, 17.1 mmol, quantitative). ESIMS found for $C_{10}H_{16}N_4$ m/z 193.0 (M+H).

The following intermediates were prepared in accordance with the procedure described in the above Scheme 11.

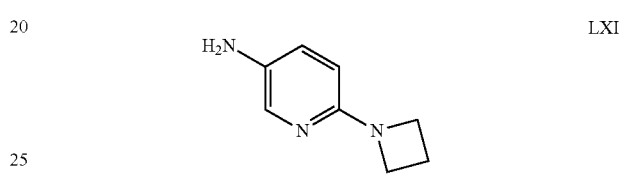

6-(Azetidin-1-yl)pyridin-3-amine (LXI): Burgundy solid (1.45 g, 9.70 mmol, 99.3% yield). ESIMS found for $C_8H_{11}N_3$ m/z 149.0 (M+H).

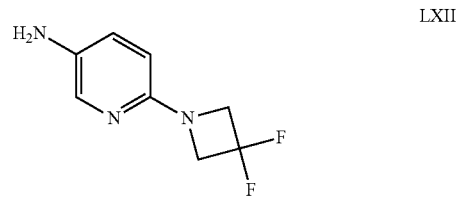 [SMILES: Nc1ccc(N2CC(F)(F)C2)nc1]

6-(3,3-Difluoroazetidin-1-yl)pyridin-3-amine (LXII): Purple solid (820 mg, 4.43 mmol, 89.9% yield). ESIMS found for $C_8H_9F_2N_3$ m/z 186.0 (M+H).

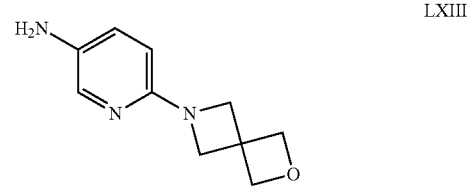 [SMILES: Nc1ccc(N2CC3(COC3)C2)nc1]

6-(2-Oxa-6-azaspiro[3.3]heptan-6-yl)pyridin-3-amine (LXIII): Purple viscous oil (562 mg, 2.94 mmol, 72.4% yield). ESIMS found for $C_{10}H_{13}N_3O$ m/z 192.0 (M+H).

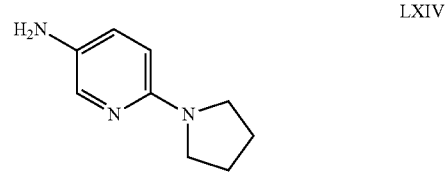 [SMILES: Nc1ccc(N2CCCC2)nc1]

6-(Pyrrolidin-1-yl)pyridin-3-amine (LXIV): Deep purple oil (1.43 g, 8.77 mmol, 100% yield). ESIMS found for $C_9H_{13}N_3$ m/z 164 (M+H).

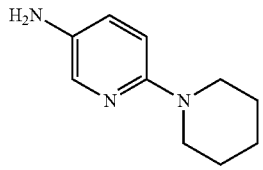
LXV 6-(Piperidin-1-yl)pyridin-3-amine (LXV): Dark red viscous oil (4.93 g, 27.81 mmol, 95.9% yield). $^1$H NMR (DMSO-$d_6$) δ ppm 1.48-1.71 (m, 8H), 3.42-3.53 (m, 2H), 4.48 (brs, 2H), 6.59 (d, J=9 Hz, 1H), 6.89 (dd, J=9 Hz, J=3 Hz, 1H), 7.58 (d, J=3 Hz, 1H); ESIMS found for $C_{10}H_{15}N_3$ m/z 178.0 (M+H).

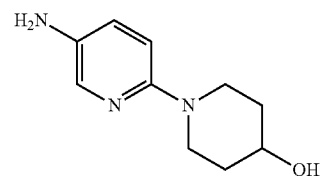
LXVI 1-(5-Aminopyridin-2-yl)piperidin-4-ol (LXVI): Dark brown oil (5.7 g, 29.5 mmol, 99.5% yield). $^1$H NMR (DMSO-$d_6$) δ ppm 1.36 (tq, J=13 Hz, J=4 Hz, 2H), 1.72-1.76 (m, 2H), 2.79 (dt, J=13 Hz, J=3 Hz, 2H), 3.54-3.61 (m, 1H), 3.70-3.78 (m, 2H), 4.49 (s, 2H), 4.61 (d, J=4 Hz, 1H), 6.61 (d, J=9 Hz, 1H), 6.88 (dd, J=9 Hz, J=3 Hz, 1H), 7.57 (d, J=3 Hz, 1H); ESIMS found for $C_{10}H_{15}N_3O$ m/z 194.1 (M+H).

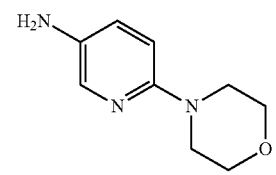
LXVII

6-Morpholinopyridin-3-amine (LXVII): Purple solid (782 mg, 4.36 mmol, 95% yield). ESIMS found for $C_9H_{13}N_3O$ m/z 180 (M+H).

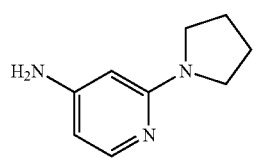
LXVIII 2-(Pyrrolidin-1-yl)pyridin-4-amine (LXVIII): Light orange solid (803 mg, 4.92 mmol, 63.2% yield). ESIMS found for $C_9H_{13}N_3$ m/z 164.0 (M+H).

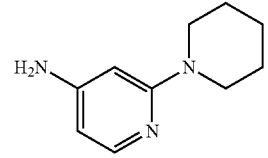
LXIX 2-(Piperidin-1-yl)pyridin-4-amine (LXIX): Light orange solid (821 mg, 4.63 mmol, 59.5% yield). ESIMS found for $C_{10}H_{15}N_3$ m/z 178.1 (M+H).

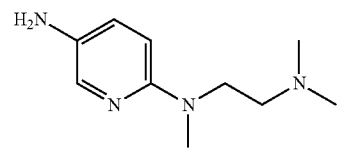
LXX $N^2$-(2-(Dimethylamino)ethyl)-$N^2$-methylpyridine-2,5-diamine (LXX): Deep purple oil (1.55 g, 7.98 mmol, 96% yield). ESIMS found for $C_{10}H_{18}N_4$ m/z 195 (M+H).

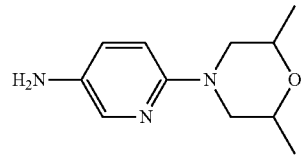
LXXI 6-(2,6-Dimethylmorpholino)pyridin-3-amine (LXXI): Deep red oil (1.2 g, 5.79 mmol, 92.0% yield). ESIMS found for $C_{11}H_{17}N_3O$ m/z 208.1 (M+H).

Preparation of intermediate tert-butyl 4-(5-aminopyridin-2-yl)piperazine-1-carboxylate (LXXIV) is depicted below in Scheme 12.

Scheme 12

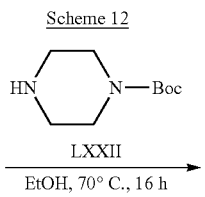
LVII

LXXII
EtOH, 70° C., 16 h

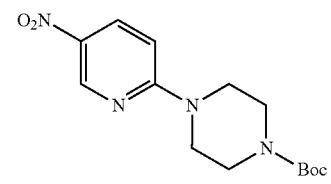
LXXIII

Pd/C—$H_2$
EtOH, 6 h, rt

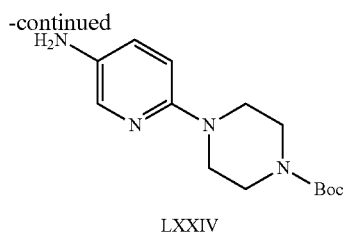

LXXIV

Step 1

To a solution of 2-chloro-5-nitropyridine (LVII) (2.0 g, 12.6 mmol) in EtOH (20 mL) was added tert-butyl piperazine-1-carboxylate (LXXII) (7.05 g, 37.9 mmol). The reaction was headed at 70° C. for 16 h. The reaction was concentrated under vacuum and then dissolved in EtOAc. The EtOAc was washed with 1 M NaOH, brine and then dried over MgSO$_4$ to give tert-butyl 4-(5-nitropyridin-2-yl)piperazine-1-carboxylate (LXXIII) as a yellow solid (4.94 g). ESIMS found for $C_{14}H_{20}N_4O_4$ m/z 309.0 (M+H).

Step 2

Preparation of intermediate tert-butyl 4-(5-aminopyridin-2-yl)piperazine-1-carboxylate (LXXIV) was performed following the procedure listed in Scheme 11, Step 2. Purple solid (990 mg, 3.56 mmol, quantitative). ESIMS found for $C_{14}H_{22}N_4O_2$ m/z 278.8 (M+H).

Preparation of intermediate N-(3-aminopyridin-4-yl)cyclopropanecarboxamide (LXXVIII) is depicted below in Scheme 13.

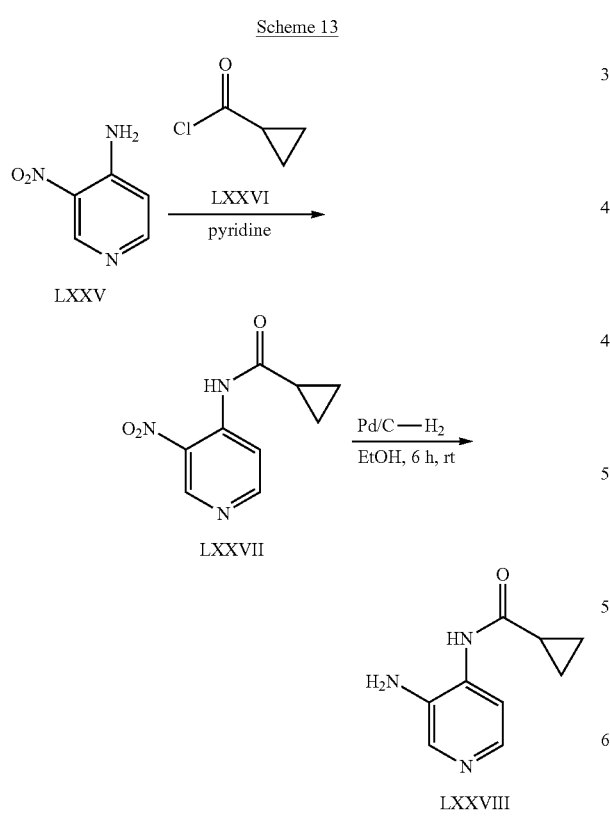

Step 1

To a solution of 3-nitropyridin-4-amine (LXXV) (500 mg, 3.59 mmol) was in pyridine was added cyclopropanecarbonyl chloride (LXXVI) (413 mg, 3.95 mmol). The reaction mixture was stirred at room temperature for 3 h. The solution was concentrated under vacuum and the residue was dissolved in EtOAc. The EtOAc solution was washed with water, brine, dried over MgSO4 and concentrated to a residue to afford N-(3-nitropyridin-4-yl)cyclopropanecarboxamide (LXXVII) as a light yellow solid (740 mg, 3.57 mmol, 99.5% yield). ESIMS found for $C_9H_9N_3O_3$ m/z 207.7 (M+H).

Step 2

Preparation of intermediate N-(3-aminopyridin-4-yl)cyclopropanecarboxamide (LXXVIII) was performed following the procedure listed in Scheme 11, Step 2. Dark grey solid (632 mg, 3.57 mmol, quantitative). ESIMS found for $C_9H_{11}N_3O$ m/z 178.0 (M+H).

The following intermediate was prepared in accordance with the procedure described in the above Scheme 13.

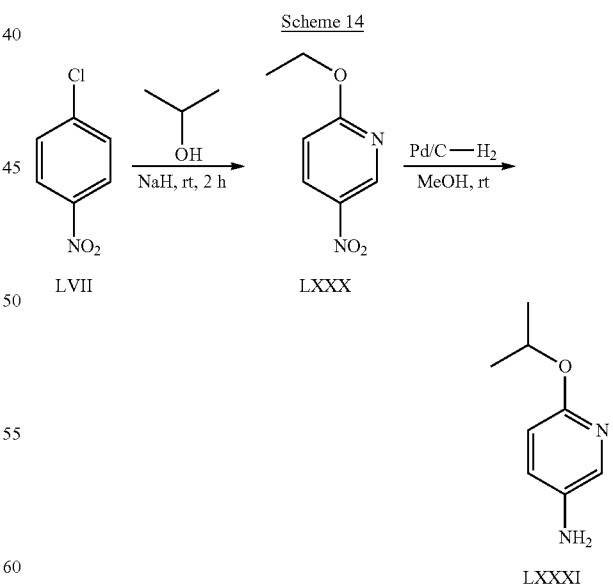

N-(3-Aminopyridin-4-yl)-3-methylbutanamide (LXXIX): Orange solid (692 mg, 3.58 mmol, 100% yield). ESIMS found for $C_{10}H_{15}N_3O$ m/z 194.0 (M+H).

Preparation of intermediate 6-isopropoxypyridin-3-amine (LXXXI) is depicted below in Scheme 14.

Step 1

To a suspension of 2-chloro-5-nitropyridine (LVII) (1.58 g, 10.0 mmol) in isopropanol (20 mL) was added NaH (60% in mineral oil) (800 mg, 20 mmol) in portions. The solution was stirred under Ar at room temperature for 2 h. The reaction was then quenched by adding dropwise addition of water. The solution was concentrated under vacuum and the residue was partitioned between CHCl₃ and water. The organic layer was separated and the aqueous phase was washed with CHCl₃. The combined CHCl₃ were washed with water, brine, dried over MgSO₄ and concentrated under vacuum. The residue was purified on a silica column (5:1 EtOAc:hexane) to yield 2-chloro-5-nitropyridine (LXXX) as a yellow solid (880 mg, 4.83 mmol, 48.3% yield). ¹H NMR (DMSO-d₆, 500 MHz) δ ppm 1.34 (d, J=6.5 Hz, 6H), 5.38 (sep, J=6.5 Hz, 1H), 6.96 (d, J=9.5 Hz, 1H), 8.44 (dd, J=2.5 Hz, J=9 Hz, 1H), 9.07 (d, J=3 Hz, 1H); ESIMS found for C₈H₁₀N₂O₃ m/z 183.1 (M+H).

Step 2

Preparation of intermediate 6-isopropoxypyridin-3-amine (LXXXI) was performed following the procedure listed in Scheme 11, Step 2. Brown oil (735 mg, 4.83 mmol, 100% yield). ¹H NMR (DMSO-d₆, 500 MHz) δ ppm 1.21 (d, J=6 Hz, 6H), 4.68 (s, 2H), 5.01 (sep, J=6 Hz, 1H), 6.45 (d, J=8.5 Hz, 1H), 6.97 (dd, J=2.5 Hz, J=8.5 Hz, 1H), 7.48 (d, J=3 Hz, 1H); ESIMS found for C₈H₁₂N₂O m/z 153.1 (M+H).

The following intermediates were prepared in accordance with the procedure described in the above Scheme 14.

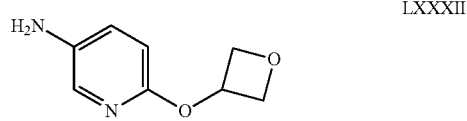 [SMILES: Nc1ccc(OC2COC2)nc1]

6-(Oxetan-3-yloxy)pyridin-3-amine (LXXXII): Yellow solid (1.69 g, 10.0 mmol, 100% yield). ¹H NMR (DMSO-d₆, 500 MHz) δ ppm 4.49 (dd, J=5.5 Hz, J=7.5 Hz, 2H), 4.75-4.85 (m, 4H), 5.38 (quin, J=5.5 Hz, 1H), 6.60 (d, J=8.5 Hz, 1H), 7.02 (dd, J=2.5 Hz, J=8.5 Hz, 1H), 7.42 (d, J=2.5 Hz, 1H); ESIMS found for C₈H₁₀N₂O₂ m/z 167.0 (M+H).

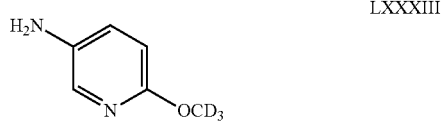

6-(Methoxy-d3)pyridin-3-amine (LXXXIII): Blue oil (1.21 g, 9.5 mmol, 99.8% yield). ¹H NMR (DMSO-d₆, 500 MHz) δ ppm 4.72 (s, 2H), 6.53 (d, J=8.5 Hz, 1H), 6.99 (dd, J=2.5 Hz, J=8.5 Hz, 1H), 7.49 (d, J=2.5 Hz, 1H); ESIMS found for C₆H₅D₃N₂O m/z 128.2 (M+H).

Preparation of intermediate 6-(2-fluorophenoxy)pyridin-3-amine (LXXXVI) is depicted below in Scheme 15.

Scheme 15

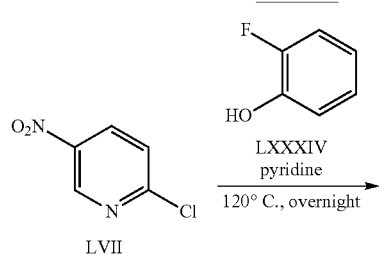

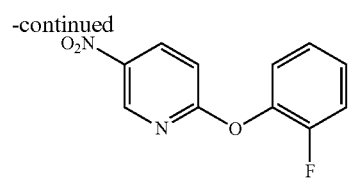

LXXXV

Pd/C—H₂
EtOH, 6 h, rt

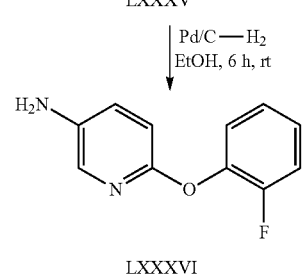

LXXXVI

Step 1

A solution of 2-chloro-5-nitropyridine (LVII) (682 mg, 4.30 mmol) and 2-fluorophenol (LXXXIV) (482 mg, 4.30 mmol) in pyridine (20 mL) was heated in a microwave reactor at 180° C. for 1 h. The solution was cooled to room temperature and concentrated under vacuum. The residue was dissolved in EtOAc, washed with water, brine, dried over MgSO₄ and evaporated. The residue was purified by silica gel column chromatography (100% hexane→2:98 EtOAc:hexane) to give 2-(2-fluorophenoxy)-5-nitropyridine (LXXXV) as a yellow oil (7.70 mg, 3.29 mmol, 76.5% yield). ESIMS found for C₁₁H₇FN₂O₃ m/z 234.9 (M+H).

Step 2

Preparation of intermediate 6-(2-fluorophenoxy)pyridin-3-amine (LXXXVI) was performed following the procedure listed in Scheme 11, Step 2. Dark brown oil (611 mg, 2.99 mmol, 91.2% yield). ESIMS found for C₁₁H₉FN₂O m/z 204.9 (M+H).

The following intermediates were prepared in accordance with the procedure described in the above Scheme 15.

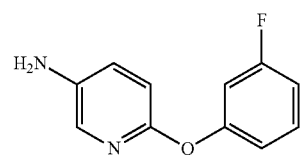

6-(3-Fluorophenoxy)pyridin-3-amine (LXXXVII): Yellow viscous oil (2.27 g, 9.7 mmol, 77% yield). ¹H NMR (DMSO-d₆) δ ppm 7.11 (dd, J=8 Hz, J=2 Hz, 1H), 7.17 (dt, J=8 Hz, J=6 Hz, 1H), 7.23 (td, J=10 Hz, J=2 Hz, 1H), 7.31 (d, J=9 Hz, 1H), 7.52 (q, J=9 Hz, 1H), 8.64 (dd, J=9 Hz, J=3 Hz, 1H), 9.05 (d, J=3 Hz, 1H); ESIMS found for C₁₁H₇FN₂O₃ m/z 234.9 (M+H).

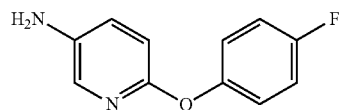

6-(4-Fluorophenoxy)pyridin-3-amine (LXXXVIII): Dark brown oil (870 mg, 4.3 mmol, 100% yield). ¹H NMR (DMSO-d$_6$) δ ppm 5.08 (brs, 2H), 6.75 (d, J=15 Hz, 1H), 6.90-7.01 (m, 2H), 7.07 (dd, J=9 Hz, J=3 Hz, 1H), 7.16 (t, 9 Hz, 1H), 7.26-7.30 (m, 1H), 7.73 (d, J=3 Hz, 1H); ESIMS found for C$_{11}$H$_9$FN$_2$O m/z 204.9 (M+H).

Preparation of intermediate 6-phenylpyridin-3-amine (XCII) is depicted below in Scheme 16.

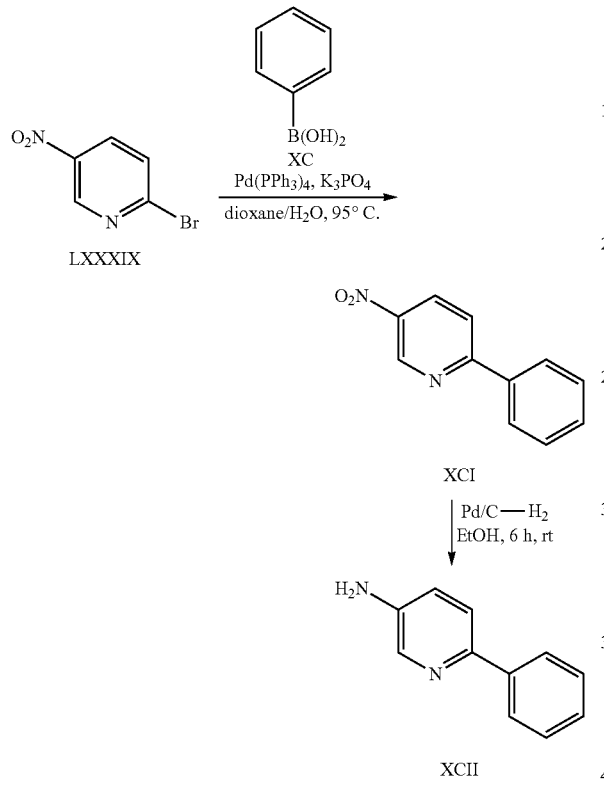

Step 1

To a solution of 2-bromo-5-nitropyridine (LXXXIX) (302 mg, 1.49 mmol) in a mixture of dioxane (14 mL) and water (3 mL) was added phenylboronic acid (XC) (199 mg, 1.64 mmol), Pd(PPh$_3$)$_4$ (86 mg, 0.74 mmol) and K$_3$PO$_4$ (473 mg, 2.23 mmol). The reaction was microwaved at 95° C. for 1 h. The reaction was cooled and the organic phase was separated, dried over MgSO$_4$ and evaporated under vacuum. The residue was purified by silica gel column chromatography (100% hexane→5:95 EtOAc:hexane) to give 5-nitro-2-phenylpyridine (XCI) as off-white needles (254 mg, 1.27 mmol, 85% yield). ESIMS found for C$_{11}$H$_8$N$_2$O$_2$ m/z 200.9 (M+H).

Step 2

Preparation of intermediate 6-phenylpyridin-3-amine (XCII) was performed following the procedure listed in Scheme 11, Step 2. Black green viscous oil (211 mg, 1.24 mmol, 98% yield). $^1$H NMR (DMSO-d$_6$) δ ppm 5.45 (s, 2H), 6.99 (dd, J=11 Hz, J=3 Hz, 1H), 7.25-7.28 (m, 1H), 7.38-7.40 (m, 2H), 7.62 (d, J=11 Hz, 1H0, 7.89-7.91 (m, 1H), 8.02 (d, J=3 Hz, 1H); ESIMS found for C$_{11}$H$_{10}$N$_2$ m/z 171.0 (M+H).

The following intermediates were prepared in accordance with the procedure described in the above Scheme 16.

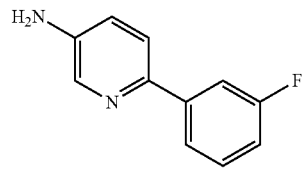

6-(3-Fluorophenyl)pyridin-3-amine (XCIII): Brown oil (252 mg, 1.34 mmol, 98% yield). ESIMS found for C$_{11}$H$_9$FN$_2$ m/z 189.0 (M+H).

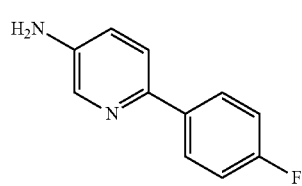

6-(4-Fluorophenyl)pyridin-3-amine (XCIV): Deep purple oil (202 mg, 1.07 mmol, 98% yield). ESIMS found for C$_{11}$H$_9$FN$_2$ m/z 189.1 (M+H).

Preparation of intermediate 5-benzylpyridin-3-amine (XCVIII) is depicted below in Scheme 17.

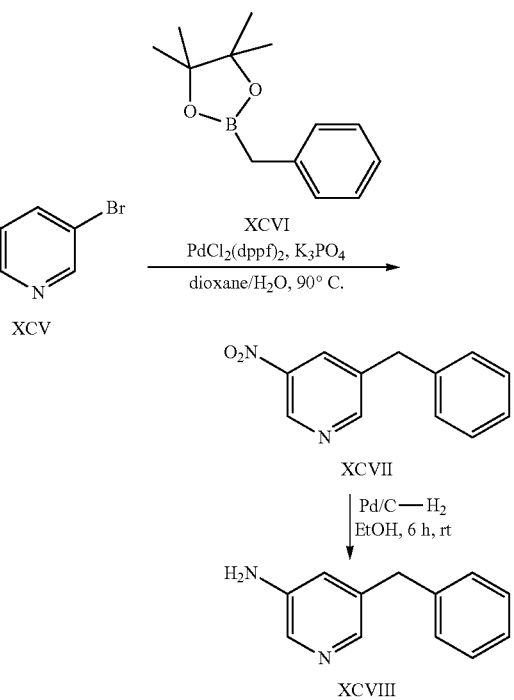

Step 1

To a solution of 3-bromo-5-nitropyridine (XCV) (295 mg, 1.45 mmol) in dioxane (14 mL) was added 2-benzyl-4,4,5,5-tetramethyl-1,3,2-dioxaborolane (XCVI) (420 μL, 1.89 mmol), PdCl$_2$(dppf)$_2$, (120 mg, 0.15 mmol) and 2M aqueous K$_3$PO$_4$ (2.2 mL, 4.36 mmol). The reaction was microwaved at 90° C. for 2 h. The reaction was cooled and the organic phase was separated, dried over MgSO$_4$ and evaporated under vacuum. The residue was purified by silica gel column chromatography (100% hexane→6:94 EtOAc:hexane) to give 3-benzyl-5-nitropyridine (XCVII) as brown oil (117 mg, 0.54 mmol, 37% yield). $^1$H NMR (DMSO-$d_6$) δ ppm 4.16 (s, 2H), 7.21-7.25 (m, 1H), 7.31-7.33 (m, 4H), 8.45-8.46 (m, 1H), 8.93 (d, J=2 Hz, 1H), 9.21 (d, J=3 Hz, 1H); ESIMS found for $C_{12}H_{10}N_2O_2$ m/z 215.0 (M+H).

Step 2

Preparation of 5-benzylpyridin-3-amine (XCVIII) was performed following the procedure listed in Scheme 11, Step 2. Black green viscous oil (139 mg, 0.75 mmol, 98% yield). ESIMS found for $C_{12}H_{12}N_2$ m/z 185.1 (M+H).

Preparation of intermediate (5-aminopyridin-2-yl)(pyrrolidin-1-yl)methanone (CI) is depicted below in Scheme 18.

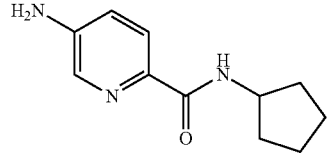

5-Amino-N-cyclopentylpicolinamide ($C_{11}$): Yellow solid (450 mg, 2.19 mmol, 93.7% yield). ESIMS found for $C_{11}H_{15}N_3O$ m/z 206.1 (M+H).

Preparation of intermediate 6-(methylsulfonyl)pyridin-3-amine (CV) is depicted below in Scheme 19.

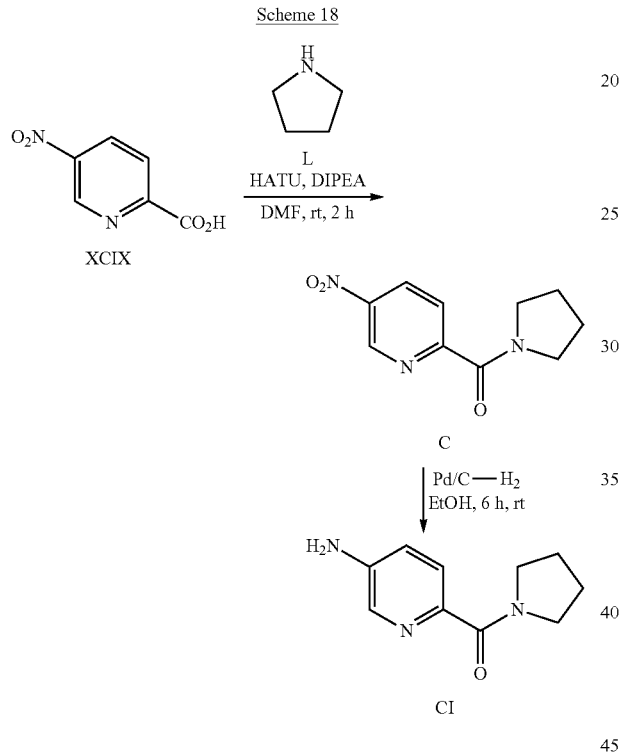

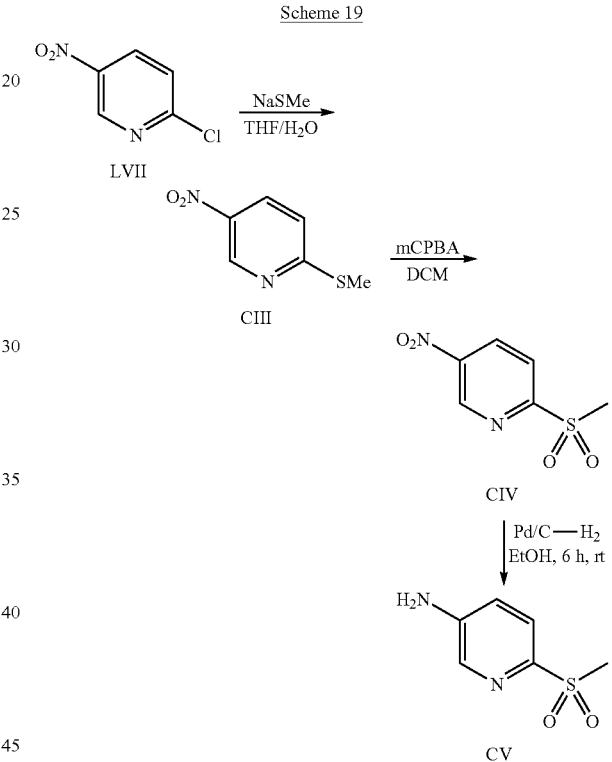

Step 1

To a solution of 5-nitropicolinic acid (XCIX) (500 mg, 2.97 mmol) in DMF (15 mL) was added pyrrolidine (L) (244 μl, 2.47 mmol) and DIPEA (1.03 mL, 5.95 mmol). The reaction was cooled at 0° C. before adding HATU (1.13 g, 2.47 mmol). The reaction was warmed to room temperature and stirred for 2 hrs. The reaction was concentrated under vacuum and then dissolved in a mixture of water and 10% iPrOH/CHCl$_3$. The organic layer was separated and the aqueous phase was washed again with 10% iPrOH/CHCl$_3$. The combined organic phases were washed with brine, dried over MgSO4 and evaporated to yield (5-nitropyridin-2-yl)(pyrrolidin-1-yl)methanone (C) as a red solid (849 mg). ESIMS found for $C_{10}H_{11}N_3O_3$ m/z 222.1 (M+H).

Step 2

Preparation of intermediate (5-aminopyridin-2-yl)(pyrrolidin-1-yl)methanone (CI) was performed following the procedure listed in Scheme 11, Step 2. Yellow solid (708 mg, 7.3 mmol, 96.4% yield). ESIMS found for $C_{10}H_{13}N_3O$ m/z 191.4 (M+H).

The following intermediate was prepared in accordance with the procedure described in the above Scheme 18.

Step 1

To a solution of sodium thiomethoxide in THF (53 mL) and H$_2$O (20 mL) cooled to 0° C. was added 2-chloro-5-nitropyridine (LVII) (5.09 g, 32.09 mmol). The reaction was warmed to room temperature and stirred for 2 hrs. The reaction was poured into ice water and stirred for 10 minutes, filtered, washed with water, dried under vacuum to yield 2-(methylthio)-5-nitropyridine (CIII) as a yellow solid (5.14 g, 30.20 mmol, 94.1%). $^1$H NMR (DMSO-$d_6$) δ ppm 2.62 (s, 3H), 7.57 (d, J=8.9 Hz, 1H), 8.38 (d, J=8.9 Hz, 1H), 9.22 (d, J=2.7 Hz, 1H); ESIMS found for $C_6H_6N_2O_2S$ m/z 171.1 (M+H).

Step 2

To a solution of 2-(methylthio)-5-nitropyridine (CIII) (502 mg, 2.95 mmol) in DCM (60 mL) was mCPBA (1.33 g, 5.90 mmol). The reaction was stirred at room temperature for 1 hr. Two additional portions of mCPBA (2×250 mg) were added at 1 hr intervals for a total reaction time of 4 hr. The reaction was poured into saturated aqueous NaHCO$_3$. The organic phase was separated and washed with water, brine and then dried over MgSO4. The solvent was removed under vacuum to produce crude 2-(methylsulfonyl)-5-nitropyridine (CIV) (854 mg) which was used without purification for step 3. ESIMS found for $C_6H_6N_2O_4S$ m/z 203.0 (M+H).

Step 3

Preparation of intermediate 6-(methylsulfonyl)pyridin-3-amine (CV) was performed following the procedure listed in Scheme 11, Step 2. The crude product was used as is without purification. ESIMS found for $C_6H_8N_2O_2S$ m/z 173.0 (M+H).

Preparation of intermediate 5-((dimethylamino)methyl)pyridin-3-amine (CIX) is depicted below in Scheme 20.

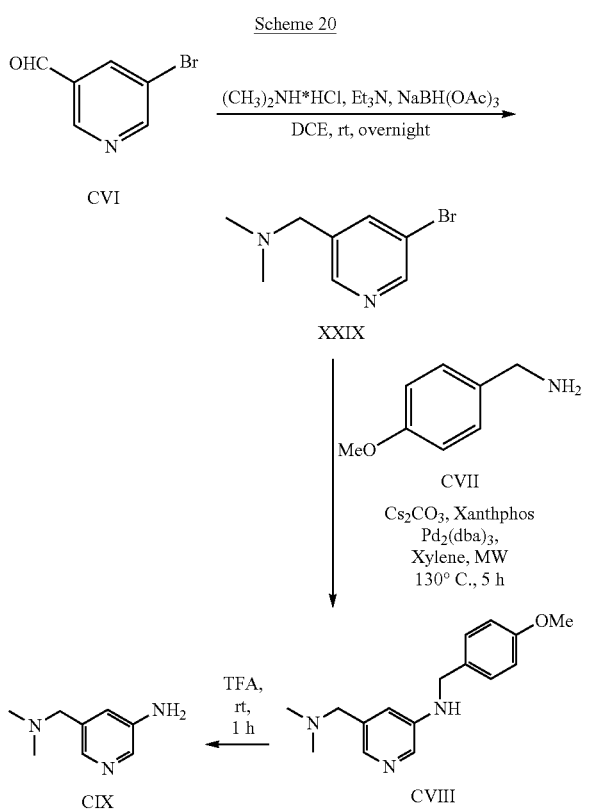

cesium carbonate (2.70 g, 8.29 mmol) and xanthphos (0.17 g, 0.30 mmol) were suspended in xylenes (12.0 mL). The solvent was degassed, and tris(dibenzylideneacetone)dipalladium(0) (0.27 g, 0.30 mmol) was added. The vessel was sealed, and the reaction was heated to 130° C. for 5 h in a microwave reactor. The solvent was decanted away from the solid material and concentrated to a residue. The residue was purified by silica gel chromatography using a 40 g Thomson normal-phase silica gel cartridge (100% $CHCl_3$→3:97 MeOH[7N $NH_3$]:$CHCl_3$) to afford 5-((dimethylamino)methyl)-N-(4-methoxybenzyl)pyridin-3-amine (CVIII) (0.68 g, 2.49 mmol, 42% yield) as a yellow solid. $^1H$ NMR (DMSO-$d_6$) δ ppm 7.84 (d, J=3 Hz, 1H), 7.64 (d, J=2 Hz, 1H), 7.27 (d, J=11 Hz, 2H), 6.88 (d, J=11 Hz, 2H), 6.83-6.82 (m, 1H), 6.35 (t, J=8 Hz, 1H), 4.20 (d, J=8 Hz, 2H), 3.72 (s, 3H), 3.24 (s, 2H), 2.08 (s, 6H); ESIMS found for $C_{16}H_{21}N_3O$ m/z 272 (M+H).

Step 3

5-((dimethylamino)methyl)-N-(4-methoxybenzyl)pyridin-3-amine (CVIII) (0.15 g, 0.56 mmol) was dissolved in TFA (2.0 mL) and stirred at room temperature for 1 h. The TFA was removed, and the residue was treated with 7N ammonia in MeOH/chloroform mixture (7/93) to neutralize the TFA and concentrated again to a residue. The residue was purified by flash silica gel chromatography utilizing a 4 g Thomson normal-phase silica gel cartridge (100% $CHCl_3$→3:97 MeOH[7N $NH_3$]:$CHCl_3$) to afford 5-((dimethylamino)methyl)pyridin-3-amine (CIX) (0.044 g, 0.29 mmol, 52% yield) as a brown oil. ESIMS found for $C_8H_{13}N_3$ m/z 152 (M+H).

Preparation of intermediate 6-(pyrrolidin-1-ylmethyl)pyridin-3-amine (CXIII) is depicted below in Scheme 21.

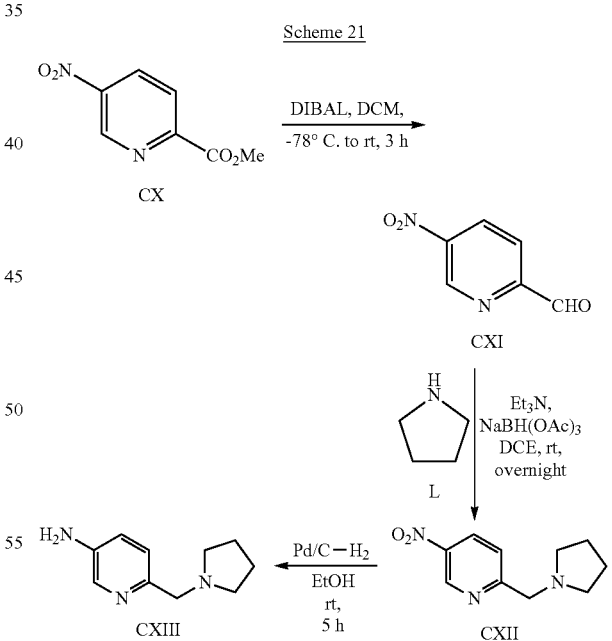

Step 1

5-Bromonicontinaldehyde (CVI) (5.01 g, 26.9 mmol) and dimethylamine hydrochloride (4.39 g, 53.8 mmol) were suspended in 1,2-dichloroethane (108 mL). Triethylamine (7.50 mL, 53.8 mmol) was added, and the reaction was stirred at room temperature for 1 h. Sodium triacetoxyborohydride (8.56 g, 40.4 mmol) was added, and the reaction was further stirred at room temperature overnight. The reaction was diluted with saturated sodium bicarbonate solution and DCM. The organic layer was separated, washed sequentially with water and brine, dried over $MgSO_4$, filtered and concentrated to give 1-(5-bromopyridin-3-yl)-N,N-dimethylmethanamine (XXIX) (1.19 g, 23.9 mmol, 89% yield) as a brown oil: $^1H$ NMR (DMSO-$d_6$) δ ppm 8.59 (d, J=3 Hz, 1H), 8.47 (d, J=2 Hz, 1H), 7.94 (s, 1H), 3.43 (s, 2H), 2.15 (s, 6H); ESIMS found for $C_8H_{11}BrN_2$ m/z 215 (M+H).

Step 2

In a 25 mL microwave vessel, 1-(5-bromopyridin-3-yl)-N,N-dimethylmethanamine (XXIX) (1.27 g, 5.92 mmol), 4-methoxybenzylamine (CVII) (0.77 mL, 5.92 mmol), Step 1

To a suspension of methyl 5-nitropicolinate (CX) (1.282 g, 7.03 mmol) in DCM (25 mL) stirred at −78° C. under argon was slowly added DIBAL (1M in toluene) (9.14 mL, 9.14 mmol). The solution was allowed to warm to room temperature over 3 h. An aqueous solution of potassium sodium tartrate was added, diluted further with water and DCM. The solution was stirred at room temperature for another 30 min before the organic layer was separated. The aqueous layer was extracted 2×DCM, combined with the organic layer, dried over MgSO4, filtered and evaporated under reduced pressure. The residue was purified by column chromatography to produce 5-nitropicolinaldehyde (CXI) as a brown oil (0.64 g, 4.2 mmol, 60% yield). $^1$H NMR (DMSO-d$_6$) δ ppm 8.17 (d, J=9 Hz, 1H), 8.81 (dd, J=9 Hz, J=2 Hz, 1H), 9.56 (d, J=2 Hz, 1H), 10.08 (s, 1H).

Step 2

Preparation of 5-nitro-2-(pyrrolidin-1-ylmethyl)pyridine (CXII) was performed following the procedure listed in Scheme 20, Step 1. Purple oil (0.41 g, 1.98 mmol, 86% yield). $^1$H NMR (DMSO-d$_6$) δ ppm 9.28 (d, J=3 Hz, 1H), 8.56 (dd, J=11 Hz, 3 Hz, 1H), 7.72 (d, J=11 Hz, 1H), 3.85 (s, 2H), 2.53-2.50 (m, 4H), 1.75-1.70 (m, 4H).

Step 3

Preparation of intermediate 6-(pyrrolidin-1-ylmethyl)pyridin-3-amine (CXIII) was performed following the procedure listed in Scheme 11, Step 2. Dark brown oil (0.35 g, 1.97 mmol, quantitative). ESIMS found for $C_{10}H_{15}N_3$ m/z 178 (M+H).

The following intermediate was prepared in accordance with the procedure described in the above Scheme 21.

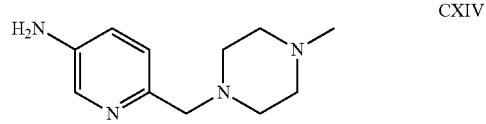

CXIV 6-((4-Methylpiperazin-1-yl)methyl)pyridin-3-amine (CXIV): Brown oil (120 mg, 0.58 mmol, 100% yield). ESIMS found for $C_{11}H_{18}N_4$ m/z 207.0 (M+H).

Preparation of intermediate 2-chloro-5-(pyrrolidin-1-ylmethyl)aniline (CXVIII) is depicted below in Scheme 22.

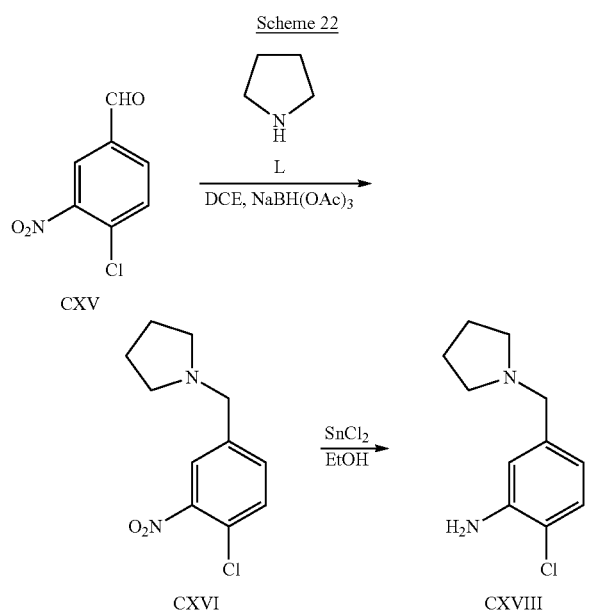

Step 1

To a stirring solution of 4-chloro-3-nitrobenzaldehyde (CXV) (1.5 g, 8.08 mmol) in DCE (40 mL) was added pyrrolidine (L) (0.664 ml, 8.08 mmol) and the mixture was stirred for 10 min. Sodium triacetoxyborohydride (3.43 g, 16.17 mmol) was then added portion wise and the mixture was stirred at room temperature for 20 hr. The reaction was quenched with aq. sat. NaHCO$_3$, diluted with DCM, organic layer separated and washed sequentially with aq. sat. NaHCO$_3$, H$_2$O and aq. sat. NaCl. The organic layer was dried over anhydrous Na$_2$SO$_4$ and concentrated in vacuo. The crude product was purified by silica gel column (100% hexanes→hexanes:EtOAc 2.5:1) to obtain 1-(4-chloro-3-nitrobenzyl)pyrrolidine (CXVI) (1.39 g, 5.78 mmol, 71.4% yield). ESIMS found for $C_{11}H_{13}ClN_2O_2$ m/z 241.0 (M+H).

Step 2

A mixture of 1-(4-chloro-3-nitrobenzyl)pyrrolidine (CXVI) (1.39 g, 5.78 mmol) and tin(II) chloride (5.48 g, 28.9 mmol) in EtOH (30 mL) was heated to reflux overnight. The solvents were concentrated in vacuo, the residue taken in water, basicified with 1N NaOH and extracted with chloroform. The organic layer was washed with water, aq. sat. NaCl, dried over anhydrous Na$_2$SO$_4$ and dried in high vacuo to obtain 2-chloro-5-(pyrrolidin-1-ylmethyl)aniline (CXVIII) (0.61 g, 2.90 mmol, 50.1% yield) which was used for next step with out purification. ESIMS found for $C_{11}H_{15}ClN_2$ m/z 211.0 (M+H).

Preparation of intermediate 1-(2-fluoro-2-methylpropyl)piperidin-4-amine (CXXII) is depicted below in Scheme 23.

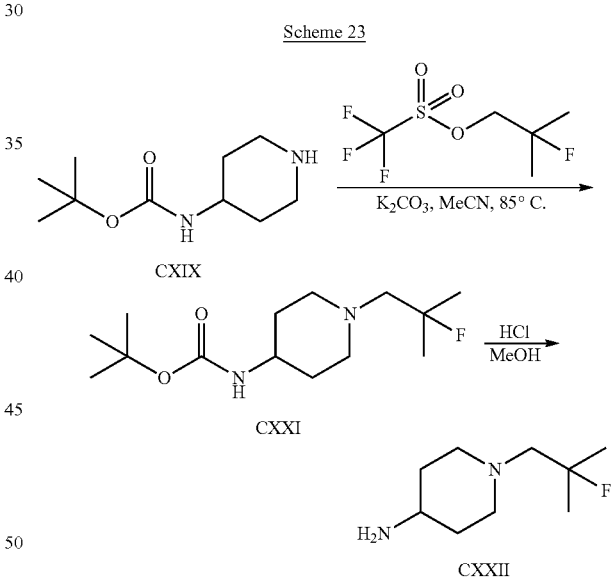

Step 1

A mixture of tert-butyl piperidin-4-ylcarbamate (CXIX) (50.0 g, 250 mmol), 2-fluoro-2-methylpropyl trifluoromethanesulfonate (CXX) (84 g, 374 mmol) and potassium carbonate (69.0 g, 499 mmol) in acetonitrile (480 mL) was heated to 85° C. overnight. The solvent was removed in vacuo, the residue partitioned between EtOAc/water, the organic layer was separated, washed with brine, dried over anhydrous Na$_2$SO$_4$, solvents removed in vacuo and the crude was purified by column chromatography using EtOAc/hexanes to obtain tert-butyl(1-(2-fluoro-2-methylpropyl)piperidin-4-yl)carbamate (CXXI) (72.9 g, 266 mmol, 106% yield) as yellow white solid. ESIMS found for $C_{14}H_{27}FN_2O_2$ m/z 274.9 (M+H).

Step 2 tert-Butyl(1-(2-fluoro-2-methylpropyl)piperidin-4-yl)carbamate (CXXI) (68.5 g, 250 mmol) was added to a solution of 12 N hydrochloric acid in MeOH (41.6 mL, 499 mmol). The reaction mixture was capped and stirred at room temperature overnight. The solvent was removed under nigh vacuum to recover a quantitative yield of 1-(2-fluoro-2-methylpropyl)piperidin-4-amine (CXXII), 2HCl (62.1 g, 251 mmol, 101% yield). Carried onto next step without further purification. ESIMS found for $C_9H_{19}FN_2$ m/z 175.1 (M+H).

The following intermediate was prepared in accordance with the procedure described in the above Scheme 23.

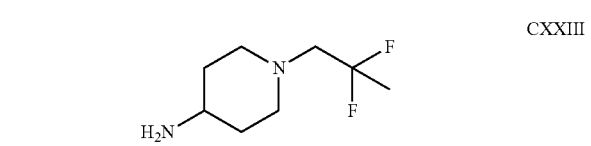

CXXIII 1-(2,2-Difluoropropyl)piperidin-4-amine (CXXIII): Brown oil (1.685 g, 6.71 mmol, 74.7% yield). ESIMS found for $C_8H_{16}F_2N_2$ m/z 179.1 (M+H).

Preparation of intermediate 1-(2-fluoroethyl)piperidin-4-amine (CXXV) is depicted below in Scheme 24.

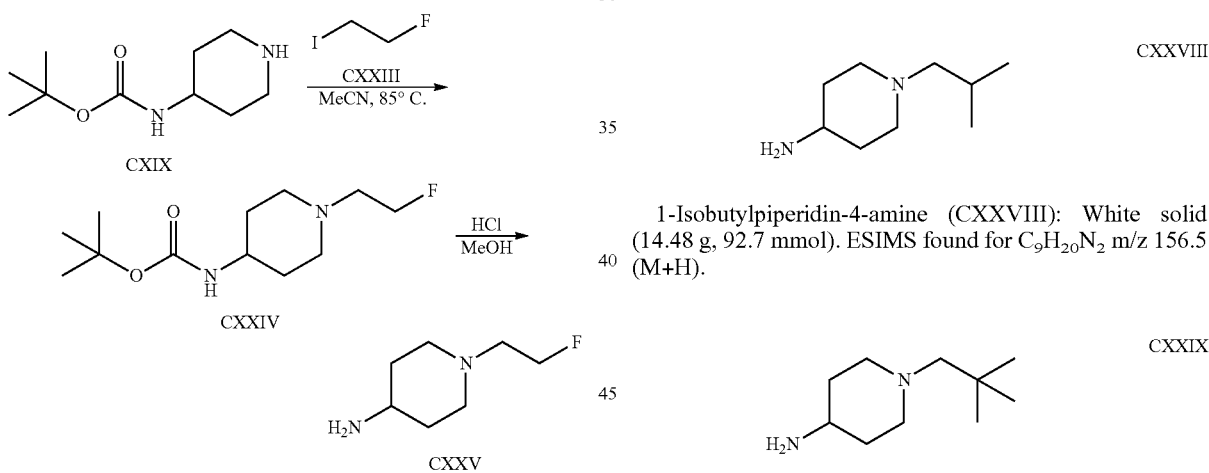

Step 1

A mixture of tert-butyl piperidin-4-ylcarbamate (CXIX) (959 mg, 4.79 mmol), 1-fluoro-2-iodoethane (CXXIII) (1.0 g, 5.75 mmol), and potassium carbonate (3.32 g, 23.95 mmol) in acetonitrile (20 mL) was heated to 85° C. overnight. The solvent was removed in vacuo, the residue partitioned between EtOAc/water, the organic layer was separated, washed with brine, dried over anhydrous $Na_2SO_4$, solvents removed in vacuo and the crude was purified by column chromatography using EtOAc/hexanes to obtain tert-butyl(1-(2-fluoroethyl)piperidin-4-yl)carbamate (CXXIV) (1.24 g, 5.0 mmol, 105% yield) as yellow white solid. ESIMS found for $C_{12}H_{23}FN_2O_2$ m/z 247.0 (M+H).

Step 2 tert-Butyl(1-(2-fluoroethyl)piperidin-4-yl)carbamate (CXXIV) (1.24 g, 4.79 mmol) was added to a solution of 4 N hydrochloric acid in dioxane (10 mL, 40 mmol). The reaction mixture was capped and stirred at room temperature overnight. The solvent was removed under nigh vacuum to recover a quantitative yield of 1-(2-fluoroethyl)piperidin-4-amine (CXXV), 2HCl (1.2 g, 5.47 mmol, 114% yield). Carried onto next step without further purification. ESIMS found for $C_7H_{15}FN_2$ m/z 147.0 (M+H).

The following intermediate was prepared in accordance with the procedure described in the above Scheme 24.

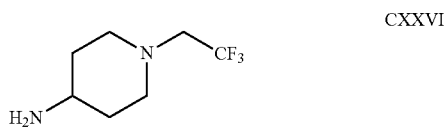

CXXVI 1-(2,2,2-Trifluoroethyl)piperidin-4-amine (CXXVI): Brown oil (2.1 g, 11.5 mmol). ESIMS found for $C_7H_{13}F_3N_2$ m/z 183.1 (M+H).

CXXVII 1-(Cyclopropylmethyl)piperidin-4-amine (CXXVII): Brown oil (1.96 g, 12.6 mmol). ESIMS found for $C_9H_{18}N_2$ m/z 155.0 (M+H).

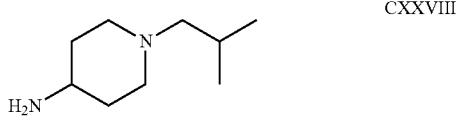

CXXVIII

1-Isobutylpiperidin-4-amine (CXXVIII): White solid (14.48 g, 92.7 mmol). ESIMS found for $C_9H_{20}N_2$ m/z 156.5 (M+H).

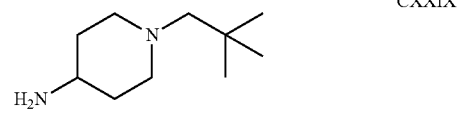

CXXIX

1-Neopentylpiperidin-4-amine (CXXIX): Orange solid (600 mg, 3.52 mmol). ESIMS found for $C_{10}H_{22}N_2$ m/z 170.9 (M+H).

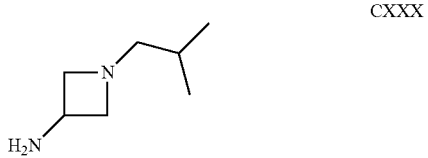

CXXX

1-Isobutylazetidin-3-amine (CXXX): White solid (0.524 g, 3.18 mmol). ESIMS found for $C_7H_{16}N_2$ m/z 129.2 (M+H).

Preparation of intermediate 5-bromo-1-(tetrahydro-2H-pyran-2-yl)-1H-indazole-3-carboxylic acid (CXXXV) is depicted below in Scheme 25.

Scheme 25

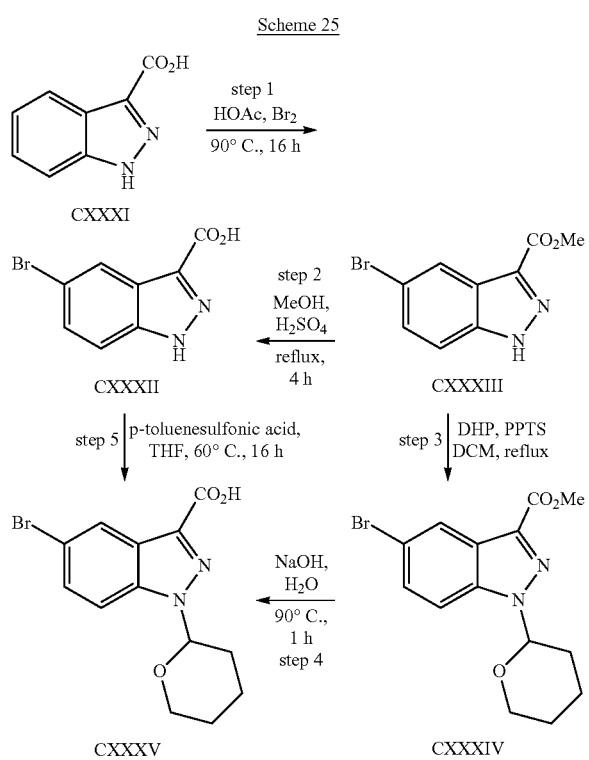

Step 1

A suspension of indazole-3-carboxylic acid (CXXXI) (1.0 g, 6.16 mmol) in glacial acetic acid (60 mL) was heated at 120° C. to get a clear solution. The solution was cooled to 90° C. A solution of bromine (0.633 mL, 12.33 mmol) in glacial acetic acid (2 mL) was added slowly to the solution while heating at 90° C. The solution was further heated 16 h at 90° C. The solution was cooled to room temperature, poured into ice water and further stirred at room temperature for 15 min. The solids formed were filtered, washed with cold water and dried under vacuum at room temperature to get 5-bromo-1H-indazole-3-carboxylic acid (CXXXII) as a white solid (1.30 g, 5.39 mmol, 87.5% yield). $^1$H NMR (DMSO-d$_6$) δ ppm 13.95 (s, 1H), 13.18 (br s, 1H), 8.21 (d, J=1.2 Hz, 1H), 7.65 (d, J=7.0 Hz, 1H), 7.56 (dd, J=7.0, 1.2 Hz, 1H); ESIMS found for $C_8H_4BrN_2O_2$ m/z 242.0 (M+H).

Step 2

Concentrated sulfuric acid (1 mL) was added to a suspension of 5-bromo-1H-indazole-3-carboxylic acid (CXXXII) (1.30 g, 5.39 mmol) in dry MeOH (50 mL) and heated to reflux for 4 h under argon. The solution was cooled to room temperature and the MeOH was evaporated under vacuum. The residue was dissolved in EtOAc and washed with water. The organic phase was dried over Na$_2$SO$_4$, filtered and concentrated to afford methyl 5-bromo-1H-indazole-3-carboxylate (CXXXIII) as a white solid (1.35 g, 5.29 mmol, 98% yield). $^1$H NMR (DMSO-d$_6$) δ ppm 14.13 (s, 1H), 8.21 (d, J=1.6 Hz, 1H), 7.67 (d, J=7.2 Hz, 1H), 7.59 (dd, J=7.2, 1.2 Hz, 1H), 3.92 (s, 3H); ESIMS found for $C_9H_7BrN_2O_2$ m/z 256.0 (M+H).

Step 3

A suspension of methyl 5-bromo-1H-indazole-3-carboxylate (CXXXIII) (1.35 g, 5.29 mmol), pyridinium p-toluenesulfonate (0.143 g, 0.56 mmol) and 3,4 dihydro-2H-pyran (1.02 mL, 11.90 mmol) in anhydrous dichloroethane (20 mL) was refluxed 5 h under argon. The suspension was turned into the clear solution. The solution was cooled and the excess solvent was evaporated under vacuum. The residue was dissolved in EtOAc and washed with dilute NaHCO$_3$ solution (sat$^d$. NaHCO$_3$ sol$^n$/H$_2$O: 1:9). The organic layer was dried over Na$_2$SO$_4$, filtered and concentrated. The residue was purified by column chromatography (100% hexanes→5:95 EtOAc:hexanes) to get methyl 5-bromo-1-(tetrahydro-2H-pyran-2-yl)-1H-indazole-3-carboxylate (CXXXIV) as a white solid (1.47 g, 4.34 mmol, 82% yield). $^1$H NMR (DMSO-d$_6$) δ ppm 8.22 (d, J=1.4 Hz, 1H), 7.89 (d, J=7.2 Hz, 1H), 7.68 (dd, J=7.2, 1.6 Hz, 1H), 6.02 (dd, J=8.0, 2.4 Hz, 1H), 3.94 (s, 3H), 3.88 (m, 1H), 3.79 (m, 1H), 2.37-2.31 (m, 1H), 2.05-1.96 (m, 2H), 1.77-1.73 (m, 1H). 1.60-1.58 (m, 2H); ESIMS found for $C_{14}H_{15}BrN_2O_3$ m/z 340.0 (M+H).

Step 4

2 N Aqueous NaOH solution (10 mL) was added to a suspension of methyl 5-bromo-1-(tetrahydro-2H-pyran-2-yl)-1H-indazole-3-carboxylate (CXXXIV) (1.30 g, 3.83 mmol) in water (20 mL) and heated at 90° C. for 1 h. The solution was cooled to room temperature, diluted with ice water and acidified to pH 3.0 with 10% aqueous HCl. The solids formed were filtered, washed with cold water and dried under vacuum at room temperature to get 5-bromo-1-(tetrahydro-2H-pyran-2-yl)-1H-indazole-3-carboxylic acid (CXXXV) as a white solid (0.87 g, 2.68 mmol, 70% yield). ESIMS found for $C_{13}H_{13}BrN_2O_3$ m/z 326.0 (M+H).

Step 5

To a solution of 5-bromo-1H-indazole-3-carboxylic acid (CXXXII) (59.8 g, 248 mmol) in THF (800 mL) under argon was added 3,4 dihydro-2H-pyran (50.6 mL, 558 mmol) and p-TsOH (4.72 g, 24.8 mmol). The reaction was heated to reflux at 60° C. for 16 h. An additional portion of p-TsOH (0.025 eq) and 3,4 dihydro-2H-pyran (0.56 eq) was added and the reflux continued for 5 h. The solution was concentrated under vacuum. EtOAc was added to the residue and the suspension was filtered and dried under high vacuum overnight to produce 5-bromo-1-(tetrahydro-2H-pyran-2-yl)-1H-indazole-3-carboxylic acid (CXXXV) as a white solid (49.07 g, 150.9 mmol, 60.8% yield). ESIMS found for $C_{13}H_{13}BrN_2O_3$ m/z 326.3 (M+H).

Preparation of intermediate 5-bromo-6-fluoro-1-(tetrahydro-2H-pyran-2-yl)-1H-indazole-3-carboxylic acid (CXL) is depicted below in Scheme 26.

Scheme 26

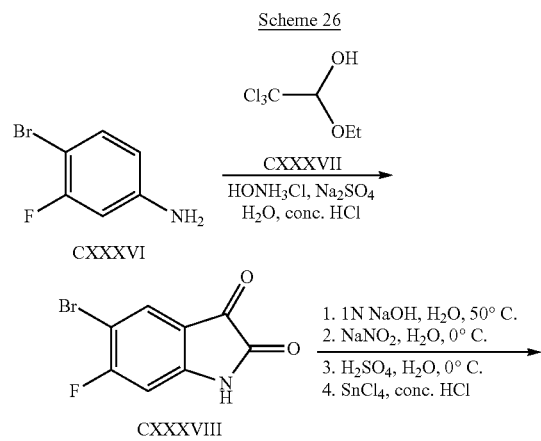

455
-continued

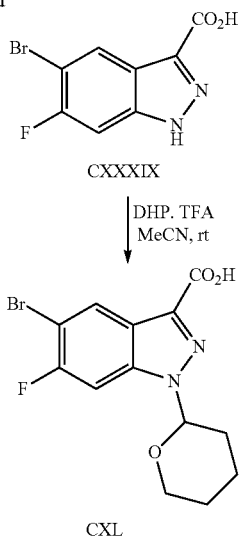

CXXXIX

CXL

Step 1

To a solution of 4-bromo-3-fluoro-aniline (CXXXXVI) (5 g, 26.3 mmol, 1 eq), hydroxylamine hydrochloride (6.58 g, 94.7 mmol, 3.6 eq), sodium sulfate (29.9 mmol, 210.5 mmol, 8 eq), conc. HCl (1.49 mL) in water (180 mL) was added 2,2,2-trichloro-1-ethoxyethanol (CXXXVII) (6.11 g, 31.6 mmol, 1.21 eq) then the mixture was heated to 55° C. for 20 h. The solids were then filtered, washed with water and dried under vacuum at 60° C. for 3 h. The solids were then added batch wise to $H_2SO_4$ (15.5 mL) at 60° C. at such a rate as to keep the temperature below 70° C. This mixture was then heated to 80° C. for 20 min and then poured over ice. The solids were filtered, washed with water and dried over vacuum at 60° C. to produce 5-bromo-6-fluoro-indoline-2,3-dione (CXXXVIII) (5.33 g, 21.8 mmol, 83% yield) as a yellow solid. $^1$H NMR (DMSO-$d_6$, 500 MHz) δ ppm 6.94 (d, J=8.78 Hz, 1H), 7.88 (d, J=7.14 Hz, 1H), 11.28 (s, 1H); ESIMS found for $C_8H_3BrFNO_2$ m/z 245.8 ($^{81}$BrM+H).

Step 2

5-Bromo-6-fluoro-indoline-2,3-dione (CXXXVIII) (4.34 g, 17.8 mmol, 1 eq) was added to 1N NaOH (19.5 mL) and heated to 50° C. for 1 h. The brownish mixture was then stirred at room temperature for 2 h. This mixture was then cooled to 0° C. and a solution of sodium nitrate (1.23 g, 17.8 mmol, 1 eq) in water (4.4 mL) was added and stirred at 0° C. for 20 min. This solution was added to a solution of $H_2SO_4$ (1.9 mL, 35.6 mmol, 2 eq) in water (37 mL) at 0° C. over 15 min, using a pastuer pipette with the tip always below the surface of the solution. This solution was stirred

456 at 0° C. for 30 min. Tin (II) chloride (8.1 g, 42.7 mmol, 2.4 eq) in conc. HCl (16.8 mL) was added at 0° C. over 30 min and the mixture was stirred for 2 h. The solids were filtered, washed with water and dried under vacuum to produce 5-bromo-6-fluoro-1H-indazole-3-carboxylic acid (CXXXIX) (4.2 g, 91.1% yield) of a brown solid which was used without further purification. $^1$H NMR (DMSO-$d_6$, 500 MHz) δ ppm 7.70 (d, J=8.78 Hz, 1H), 8.31 (d, J=6.59 Hz, 1H), 14.02 (brs, 1H); ESIMS found for $C_8H_4BrFN_2O_2$ m/z 258.6 ($^{79}$BrM+H).

Step 3

To a solution of 5-bromo-6-fluoro-1H-indazole-3-carboxylic acid (CXXXIX) (2.0 g, 7.72 mmol) in MeCN (12 mL) was added TFA (30 μL, 0.40 mmol) and DHP (2.2 mL, 15.44 mmol). The reaction was stirred at room temperature for 24 h. The solvent was removed under vacuum and the residue was purified on a silica gel column [100% $CHCl_3$ (0.1% TFA)→10% MeOH/$CHCl_3$ (0.1% TFA)] to give 5-bromo-6-fluoro-1-(tetrahydro-2H-pyran-2-yl)-1H-indazole-3-carboxylic acid (CXL) as a yellow solid (2.11 g, 6.14 mmol, 79.5% yield). $^1$H NMR (DMSO-$d_6$, 500 MHz) δ ppm 1.67-1.86 (m, 3H), 1.96-2.11 (m, 2H), 2.32-2.44 (m, 1H), 3.67-3.83 (m, 1H), 3.85-3.98 (m, 1H), 5.95 (dd, J=2.47 Hz, J=9.61 Hz, 1H), 7.99 (s, 1H), 8.32 (s, 1H).

The following intermediate was prepared in accordance with the procedure described in the above Scheme 26.

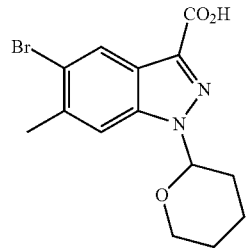

CXLI

5-Bromo-6-methyl-1-(tetrahydro-2H-pyran-2-yl)-1H-indazole-3-carboxylic acid (CXLI): Yellow solid (1.35 g, 3.98 mmol, 95.7% yield). $^1$H NMR (DMSO-$d_6$, 500 MHz) δ ppm 1.62 (s, 3H), 1.67-1.86 (m, 3H), 1.96-2.11 (m, 2H), 2.32-2.44 (m, 1H), 3.67-3.83 (m, 1H), 3.85-3.98 (m, 1H), 5.95 (dd, J=2.47 Hz, J=9.61 Hz, 1H), 7.90 (s, 1H), 8.26 (s, 1H).

Example 1

Preparation of 5-(5-((4-methylpiperidin-1-yl)methyl)pyridin-3-yl)-N-(pyrazin-2-yl)-1H-indazole-3-carboxamide (83) is depicted below in Scheme 27.

Scheme 27

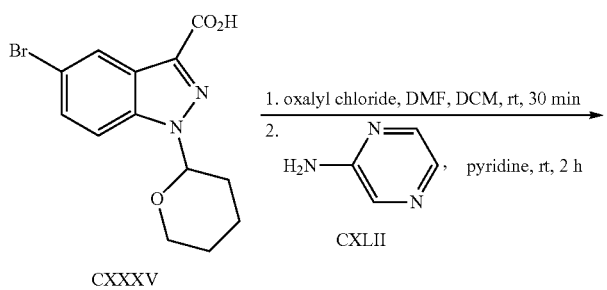

CXXXV 1. oxalyl chloride, DMF, DCM, rt, 30 min
2. CXLII, pyridine, rt, 2 h

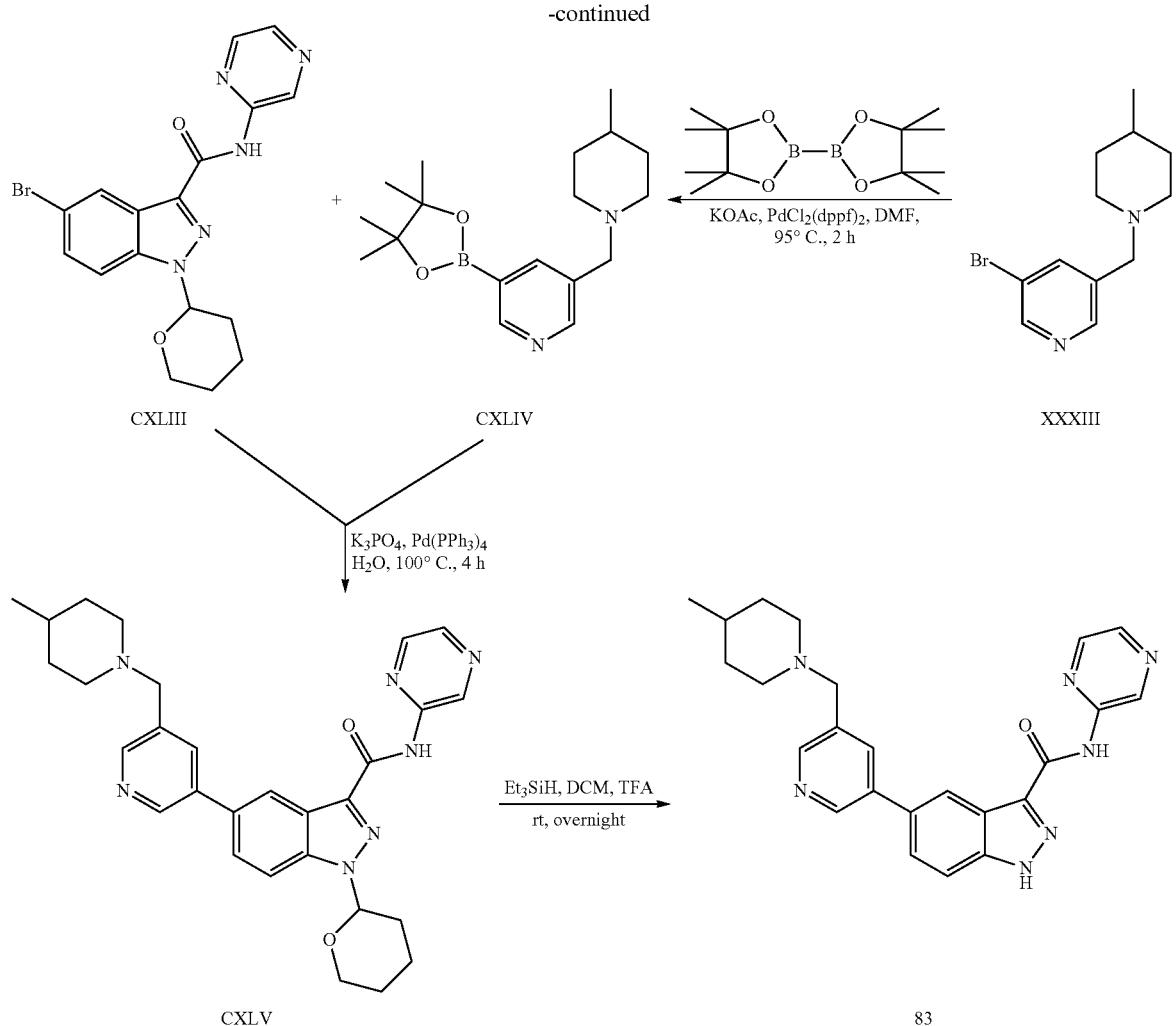

Step 1

A suspension of 5-bromo-1-(tetrahydro-2H-pyran-2-yl)-1H-indazole-3-carboxylic acid (CXXXV) (2.0 g, 6.15 mmol, 1.00 eq) in DCM (20 mL) was added oxalyl chloride (792 μL, 9.22 mmol, 1.5 eq) and dry DMF (100 μL). The reaction was stirred at room temperature for 30 min under Ar. The solvent was removed under vacuum and the residue was dissolved in dry pyridine (20 mL) under Ar before adding pyrazin-2-amine (CXLII) (643 mg, 6.76 mmol). The reaction was stirred at room temperature for 2 h before pouring into water. The mixture was basified with saturated aq. NaHCO₃ and stirred for 15 min at room temperature. The solid was filtered, washed with cold water and dried under vacuum at room temperature to produce 5-bromo-N-(pyrazin-2-yl)-1-(tetrahydro-2H-pyran-2-yl)-1H-indazole-3-carboxamide (CXLIII) (2.24 g, 5.57 mmol, 90.5% yield) as a light yellow solid. $^1$H NMR (DMSO-$d_6$, 500 MHz) δ ppm 1.58-1.68 (m, 2H), 1.72-1.85 (m, 2H), 2.03-2.13 (m, 2H), 3.75-3.84 (m, 1H), 3.87-3.95 (m, 1H), 6.06 (dd, J=2.5 Hz, J=9 Hz, 1H), 7.70 (dd, J=2 Hz, J=9 Hz, 1H), 7.91 (d, J=9 Hz, 1H), 8.37 (d, J=1.5 Hz, 1H), 8.46 (d, J=2.5 Hz, 1H), 8.50 (t, J=2 Hz, 1H), 9.46 (d, J=1.5 Hz, 1H), 10.47 (s, 1H); ESIMS found $C_{17}H_{16}BrN_5O_2$ m/z 401.9 (M+).

Step 2-3

To a solution of 3-bromo-5-((4-methylpiperidin-1-yl)methyl)pyridine (XXXIII) (269 mg, 1.0 mmol) in dry DMF (10 mL) was added bis(pinacolato)diboron (304 mg, 1.2 mmol), PdCl₂(dppf)₂ (49 mg, 0.06 mmol) and KOAc (294 mg, 3.0 mmol) and then purged with Ar. The reaction was heated at 95° C. for 2 h under Ar. The solution was cooled to room temperature before adding 5-bromo-N-(pyrazin-2-yl)-1-(tetrahydro-2H-pyran-2-yl)-1H-indazole-3-carboxamide (CXLIII) (402 mg, 1.0 mmol), Pd(PPh₃)₄ (34 mg, 0.03 mmol), K₃PO₄ (318 mg, 1.5 mmol) and water (1 mL). The reaction was purged with Ar and heated at 100° C. for 4 h under Ar. The solution was cooled to room temperature and concentrated under vacuum. The residue was partitioned between water and DCM. The organic layer was separated, dried over MgSO₄ and filtered through a bed of Celite. The filtrate was concentrated and the residue was purified on a silica gel column (100% CHCl₃→5% MeOH/CHCl₃) to give 5-(5-((4-methylpiperidin-1-yl)methyl)pyridin-3-yl)-N-(pyrazin-2-yl)-1-(tetrahydro-2H-pyran-2-yl)-1H-indazole-3-carboxamide (CXLV) as an off-white solid (220 mg, 0.43 mmol, 43.0% yield). $^1$H NMR (DMSO-$d_6$, 500 MHz) δ ppm 0.89 (d, J=6.5 Hz, 3H), 1.10-1.21 (m, 2H), 1.28-1.40 (m, 1H), 1.58 (d, J=12.5 Hz, 2H), 1.61-1.70 (m, 2H), 1.75-1.87 (m, 1H), 1.98 (t, J=1 Hz, 2H), 2.05-2.16 (m, 2H), 2.54-2.66 (m, 1H), 2.82 (d, J=11 Hz, 2H), 3.58 (s, 2H), 3.78-3.88 (m, 1H), 3.90-3.98 (m, 1H), 6.11 (dd, J=2.5 Hz. J=9.5 Hz, 1H), 7.93 (dd, J=1.5 Hz, J=9 Hz, 1H), 8.02 (s, 1H), 8.04 (d, J=8.5

Hz, 1H), 8.47 (d, J=2.5 Hz, 1H), 8.51 (t, J=2 Hz, 1H), 8.84 (d, J=2 Hz, 1H), 9.50 (d, J=1.5 Hz, 1H), 10.44 (s, 1H); ESIMS found for $C_{29}H_{33}N_7O_2$ m/z 512.3 (M+H).

Step 4

To a solution of 5-(5-((4-methylpiperidin-1-yl)methyl)pyridin-3-yl)-N-(pyrazin-2-yl)-1-(tetrahydro-2H-pyran-2-yl)-1H-indazole-3-carboxamide (CXLV) (222 mg, 0.40 mmol) in dry DCM (5 mL) was added trimethylsilane (159 µL, 1.0 mmol) and TFA (5 mL). The reaction was stirred overnight at room temperature. The solution was filtered and the filtrate was evaporated under vacuum. The residue was partitioned between $CHCl_3$ and water. The aqueous layer was separated, washed with $CHCl_3$, basified with 5N $NH_4OH$ and extracted with $CHCl_3$. The combined organic phases were washed with water, dried of $MgSO_4$, filtered and concentrated. The residue was suspended in EtOAc, boiled and cooled to room temperature. The solids were filtered, washed with cold EtOAc and dried under vacuum to yield 5-(5-((4-methylpiperidin-1-yl)methyl)pyridin-3-yl)-N-(pyrazin-2-yl)-1H-indazole-3-carboxamide (83) as a white solid (58 mg, 0.12 mmol, 31.1% yield). $^1$H NMR (DMSO-$d_6$, 500 MHz) δ ppm; $^1$H NMR (DMSO-$d_6$, 500 MHz) δ ppm 0.89 (d, J=6.5 Hz, 3H), 1.09-1.22 (m, 2H), 1.28-1.40 (m, 1H), 1.58 (brd, J=12 Hz, 2H), 1.92-2.08 (m, 2H), 2.82 (d, J=9.5 Hz, 2H), 3.58 (s, 2H), 7.84, 7.86 (ABq, $J_{AB}$=11.3 Hz, 2H), 8.01 (s, 1H), 8.45 (d, J=2.5 Hz, 1H), 8.47 (s, 1H), 8.50 (d, J=1.5 Hz, 2H), 8.83 (s, 1H), 9.50 (d, J=1 Hz, 1H), 10.36 (s, 1H), 14.11 (s, 1H); ESIMS found for $C_{24}H_{25}N_7O$ m/z 428.2 (M+1).

The following compounds were prepared in accordance with the procedure described in the above Example 1.

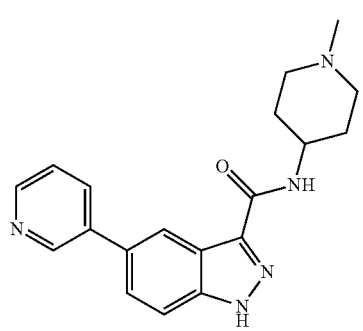

N-(1-Methylpiperidin-4-yl)-5-(pyridin-3-yl)-1H-indazole-3-carboxamide 1

White solid (53.5 mg, 0.16 mmol). $^1$H NMR (DMSO-$d_6$, 500 MHz) δ ppm 1.63-1.80 (m, 4H), 1.96 (td, J=2.5 Hz, J=11.5 Hz, 2H), 2.17 (s, 3H), 2.76 (d, J=11.5 Hz, 2H), 3.75-3.86 (m, 1H), 7.51 (ddd, J=0.5 Hz, J=5 Hz, J=8 Hz, 1H), 7.74, 7.77 (ABq, $J_{AB}$=16 Hz, 2H), 8.09 (dd, J=1.5 Hz, J=9.5 Hz, 1H), 8.21 (d, J=8.5 Hz, 1H), 8.42 (d, J=1 Hz, 1H), 8.58 (dd, J=1.5 Hz, J=9 Hz, 1H), 8.90 (d, J=1.5 Hz, 1H), 13.69 (brs, 1H); ESIMS found for $C_{19}H_{21}N_5O$ m/z 336.3 (M+1).

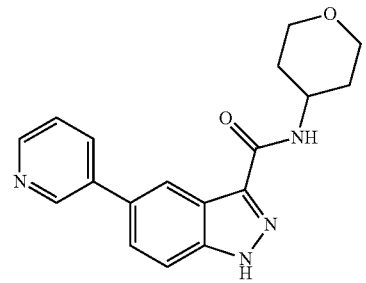

5-(Pyridin-3-yl)-N-(tetrahydro-2H-pyran-4-yl)-1H-indazole-3-carboxamide 2

White solid (81.4 mg, 0.25 mmol). $^1$H NMR (DMSO-$d_6$, 500 MHz) δ ppm 1.64-1.81 (m, 4H), 3.40 (td, J=2.5 Hz, J=11.5 Hz, 2H), 3.89 (d, J=11.5 Hz, 2H), 4.02-4.15 (m, 1H), 7.51 (dd, J=5 Hz, J=8 Hz, 1H), 7.74, 7.77 (ABq, $J_{AB}$=15.25 Hz, 2H), 8.09 (dt, J=2 Hz, J=8 Hz, 1H), 8.35 (d, J=8.5 Hz, 1H), 8.42 (s, 1H), 8.58 (dd, J=1.5 Hz, J=5 Hz, 1H), 8.90 (d, J=2 Hz, 1H), 13.70 (s, 1H); ESIMS found for $C_{18}H_{18}N_4O_2$ m/z 323.1 (M+1).

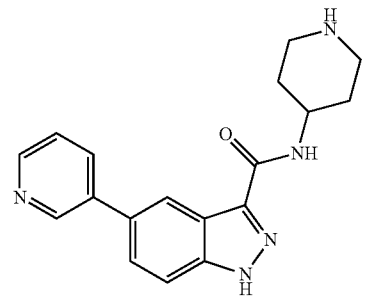

N-(Piperidin-4-yl)-5-(pyridin-3-yl)-1H-indazole-3-carboxamide 3

Beige solid (91.1 mg, 0.28 mmol). $^1$H NMR (DMSO-$d_6$, 500 MHz) δ ppm 1.51 (qd, J=3.75 Hz, J=12 Hz, 2H), 1.75 (d, J=9.5 Hz, 2H), 2.51 (qd, J=2 Hz, J=12 Hz, 2H), 2.96 (d, J=12 Hz, 2H), 3.84-3.96 (m, 1H), 7.48-7.54 (m, 1H), 7.74, 7.77 (dABq, J=2 Hz, $J_{AB}$=20.5 Hz, 2H), 8.09 (dt, J=2 Hz, J=7.5 Hz, 1H), 8.18 (d, J=8.5 Hz, 1H), 8.42 (s, 1H), 8.58 (dd, J=1.5 Hz, J=4.5 Hz, 1H), 8.90 (d, J=2 Hz, 1H); ESIMS found for $C_{18}H_{19}N_5O$ m/z 321.9 (M+1).

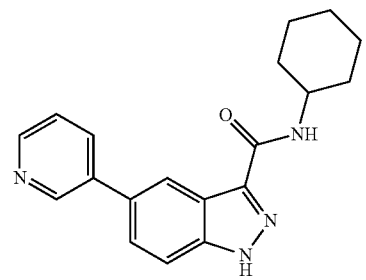

N-Cyclohexyl-5-(pyridin-3-yl)-1H-indazole-3-carboxamide 4

White solid (36.7 mg, 0.11 mmol). $^1$H NMR (DMSO-d$_6$, 500 MHz) δ ppm 1.13 (q, J=12.5 Hz, 1H), 1.33 (qd, J=3 Hz, J=12.5 Hz, 2H), 1.41 (qd, J=3 Hz, J=12 Hz, 2H), 1.60 (d, J=12.5 Hz, 1H), 1.73 (d, J=13 Hz, 2H), 1.83 (d, J=9.5 Hz, 2H), 3.76-3.89 (m, 1H), 7.48-7.55 (m, 1H), 7.74, 7.77 (dABq, J=0.5 Hz, J$_{AB}$=16.75 Hz, 2H), 8.06-8.15 (m, 2H), 8.42 (d, J=2 Hz, 1H), 8.56 (dd, J=1.5 Hz, J=5 Hz, 1H), 8.89 (d, J=2 Hz, 1H); ESIMS found for C$_{19}$H$_{20}$N$_4$O m/z 321.0 (M+1).

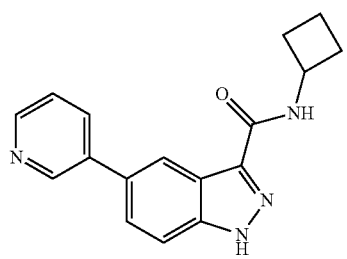

N-Cyclobutyl-5-(pyridin-3-yl)-1H-indazole-3-carboxamide 5

White solid (75.1 mg, 0.26 mmol). $^1$H NMR (DMSO-d$_6$, 500 MHz) δ ppm 1.58-1.72 (m, 2H), 2.11-2.27 (m, 4H), 4.51 (sex, J=8.5 Hz, 1H), 7.46-7.55 (m, 1H), 7.74, 7.77 (dABq, J=2 Hz, J$_{AB}$=17.25 Hz, 2H), 8.09 (dt, J=1.5 Hz, J=8 Hz, 1H), 8.42 (d, J=1 Hz, 1H), 8.58 (dd, J=11.5 Hz, J=5 Hz, 1H), 8.63 (d, J=8.5 Hz, 1H), 8.90 (d, J=2 Hz, 1H), 13.69 (brs, 1H); ESIMS found for C$_{17}$H$_{16}$N$_4$O m/z 293.1 (M+1).

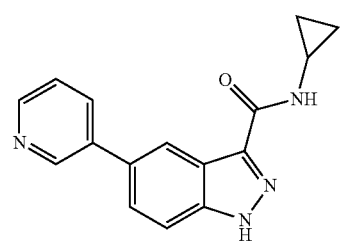

N-Cyclopropyl-5-(pyridin-3-yl)-1H-indazole-3-carboxamide 6

White solid (59.8 mg, 0.21 mmol). $^1$H NMR (DMSO-d$_6$, 500 MHz) δ ppm 0.62-0.74 (m, 4H), 2.86-2.96 (m, 1H), 7.47-7.55 (m, 1H), 7.73, 7.77 (dABq, J=2 Hz, J$_{AB}$=19.25 Hz, 2H), 8.10 (dt, J=2 Hz, J=8 Hz, 1H), 8.43 (s, 1H), 8.46 (d, J=4.5 Hz, 1H), 8.58 (dd, J=1.5 Hz, J=4.5 Hz, 1H), 8.90 (d, J=2 Hz, 1H), 13.66 (brs, 1H); ESIMS found for C$_{16}$H$_{14}$N$_4$O m/z 278.9 (M+1).

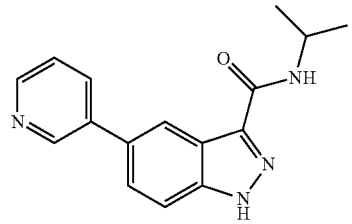

N-Isopropyl-5-(pyridin-3-yl)-1H-indazole-3-carboxamide 7

White solid (77.5 mg, 0.28 mmol). $^1$H NMR (DMSO-d$_6$, 500 MHz) δ ppm 1.21 (d, J=6.5 Hz, 6H), 4.19 (sex, J=8 Hz, 1H), 7.47-7.54 (m, 1H), 7.74, 7.77 (dABq, J=2 Hz, J$_{AB}$=17.5 Hz, 2H), 8.10 (dt, J=2 Hz, J=8 Hz, 1H), 8.14 (d, J=8 Hz, 1H), 8.43 (s, 1H), 8.58 (dd, J=1.5 Hz, J=5 Hz, 1H), 8.90 (d, J=2.5 Hz, 1H), 13.67 (brs, 1H); ESIMS found for C$_{16}$H$_{16}$N$_4$O m/z 281.0 (M+1)

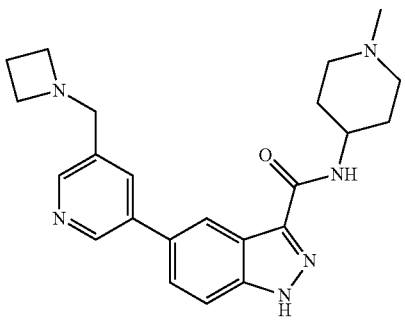

5-(5-(Azetidin-1-ylmethyl)pyridin-3-yl)-N-(1-methylpiperidin-4-yl)-1H-indazole-3-carboxamide 8

Light brown solid (12.4 mg, 0.03 mmol). $^1$H NMR (DMSO-d$_6$, 500 MHz) δ ppm 1.60-1.81 (m, 4H), 1.91-2.05 (m, 4H), 2.16 (s, 3H), 2.76 (d, J=1.5 Hz, 2H), 3.17 (t, J=7 Hz, 4H), 3.63 (s, 2H), 7.73 (d, J=9 Hz, 1H), 7.77 (dd, J=1.5 Hz, J=8.5 Hz, 1H), 7.94 (s, 1H), 8.22 (d, J=8 Hz, 1H), 8.41 (s, 1H), 8.44 (s, 1H), 8.76 (s, 1H); ESIMS found for C$_{23}$H$_{28}$N$_6$O m/z 405.5 (M+1).

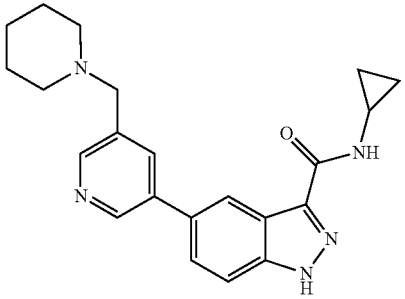

N-Cyclopropyl-5-(5-(piperidin-1-ylmethyl)pyridin-3-yl)-1H-indazole-3-carboxamide 9

White solid (52.3 mg, 0.14 mmol). $^1$H NMR (DMSO-$d_6$, 500 MHz) δ ppm 0.62-0.74 (m, 4H), 1.40 (brs, 2H), 1.47-1.56 (m, 4H), 2.38 (brs, 4H), 2.85-2.94 (m, 1H), 3.56 (s, 2H), 7.73 (d, J=9 Hz, 1H), 7.77 (dd, J=1.5 Hz, J=9 Hz, 1H), 7.96 (s, 1H), 8.43 (s, 1H), 8.44-8.50 (m, 2H), 8.79 (d, J=2 Hz, 1H), 13.66 Brs, 1H); ESIMS found for $C_{22}H_{25}N_5O$ m/z 376.1 (M+1).

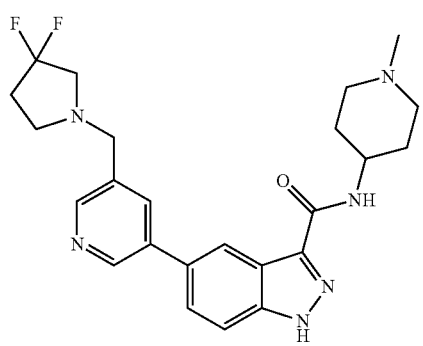

10

5-(5-((3,3-Difluoropyrrolidin-1-yl)methyl)pyridin-3-yl)-N-(1-methyl piperidin-4-yl)-1H-indazole-3-carboxamide 10

White solid (54.6 mg, 0.12 mmol). $^1$H NMR (DMSO-$d_6$, 500 MHz)) δ ppm 1.63-1.81 (m, 4H), 1.96 (t, J=12 Hz, 2H), 2.17 (s, 3H), 2.28 (sep, J=7 Hz, 2H), 2.76 (t, J=7 Hz, 4H), 2.93 (t, J=13 Hz, 2H), 3.76 (s, 2H), 3.75-3.88 (m, 1H), 7.74 (d, J=9 Hz, 1H), 7.79 (dd, J=2 Hz, J=9 Hz, 1H), 8.23 (d, J=8 Hz, 1H), 8.43 (s, 1H), 8.51 (d, J=2 Hz, 1H), 8.82 (d, J=2.5 Hz, 1H), 13.69 Brs, 1H); ESIMS found for $C_{24}H_{28}F_2N_6O$ m/z 455.3 (M+1).

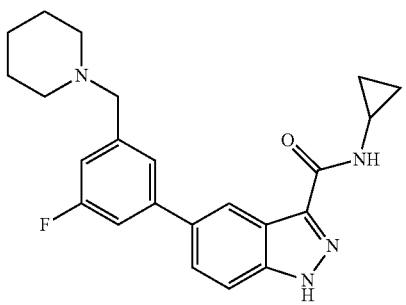

11

N-Cyclopropyl-5-(3-fluoro-5-(piperidin-1-ylmethyl)phenyl)-1H-indazole-3-carboxamide 11

Beige solid (9.4 mg, 0.02 mmol). $^1$H NMR (DMSO-$d_6$, 500 MHz) δ ppm 0.62-0.73 (m, 4H), 1.24 (s, 4H), 1.35-1.44 (m, 3H), 1.47-1.57 (m, 5H), 2.30-2.42 (m, 4H), 2.85-2.94 (m, 1H), 3.24-3.32 (m, 4H), 3.53 (s, 2H), 7.11 (d, J=9.5 Hz, 1H), 7.38 (d, J=10.5 Hz, 1H), 7.54 (s, 1H), 7.69 (d, J=9 Hz, 1H), 7.74 (dd, J=1.5 Hz, J=8.5 Hz, 1H), 8.41 (s, 1H), 8.45 (d, J=4 Hz, 1H), 13.63 (brs, 1H); ESIMS found for $C_{23}H_{25}FN_4O$ m/z 392.9 (M+1).

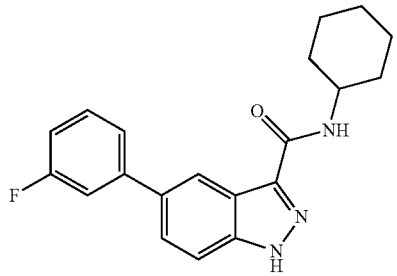

12

N-Cyclohexyl-5-(3-fluorophenyl)-1H-indazole-3-carboxamide 12

White solid (40.1 mg, 0.12 mmol). $^1$H NMR (DMSO-$d_6$, 500 MHz) δ ppm 1.14 (q, J=12.5 Hz, 1H), 1.33 (qd, J=3 Hz, J=10 Hz, 2H), 1.42 (qd, J=2.5 Hz, J=11 Hz, 2H), 1.61 (d, 13 Hz, 1H), 1.74 (dd, J=3.5 Hz, J=13 Hz, 2H), 1.83 (d, J=12 Hz, 2H), 3.78-3.90 (m, 1H), 7.15-7.25 (m, 1H), 7.46-7.56 (m, 2H), 7.70 (dd, J=1 Hz, J=9 Hz, 1H), 7.75 (dd, J=2 Hz, J=9 Hz, 1H), 8.10 (d, J=8.5 Hz, 1H), 8.41 (t, J=1 Hz, 1H), 13.63 (brs, 1H); ESIMS found for $C_{20}H_{20}FN_3O$ m/z 337.8 (M+1).

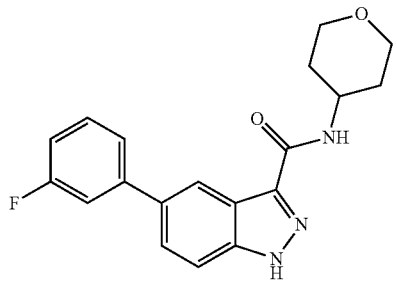

13

5-(3-Fluorophenyl)-N-(tetrahydro-2H-pyran-4-yl)-1H-indazole-3-carboxamide 13

White solid (23.4 mg, 0.07 mmol). $^1$H NMR (DMSO-$d_6$, 500 MHz) δ ppm 1.63-1.81 (m, 4H), 3.40 (td, J=2.5 Hz, J=11.5 Hz, 2H), 3.89 (d, J=11.5 Hz, 2H), 4.02-4.15 (m, 1H), 7.15-7.25 (m, 1H), 7.46-7.56 (m, 2H), 7.71 (d, J=8.5 Hz, 1H), 7.76 (dd, J=2 Hz, J=9 Hz, 1H), 8.33 (d, J=8 Hz, 1H), 8.41 (d, J=1.5 Hz, 1H), 13.66 (brs, 1H); ESIMS found for $C_{19}H_{18}FN_3O_2$ m/z 339.9 (M+1).

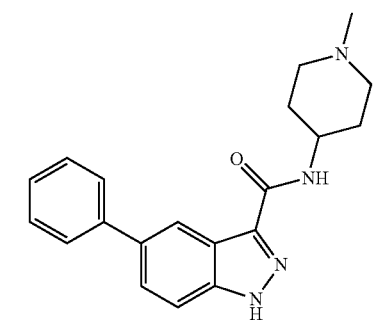

14

N-(1-Methylpiperidin-4-yl)-5-phenyl-1H-indazole-3-carboxamide 14

White solid (10.5 mg, 0.03 mmol). $^1$H NMR (DMSO-$d_6$, 500 MHz) δ ppm 1.62-1.81 (m, 4H), 1.96 (t, J=1.5 Hz, 2H), 2.17 (s, 3H), 2.76 (d, J=12 Hz, 2H), 3.75-3.88 (m, 1H), 7.37 (t, J=7.5 Hz, 1H), 7.49 (t, J=7.5 Hz, 2H), 7.64-7.75 (m, 4H), 8.18 (d, J=8.5 Hz, 1H), 8.38 (s, 1H), 13.61 (brs, 1H); ESIMS found for $C_{20}H_{22}N_4O$ m/z 335.1 (M+1).

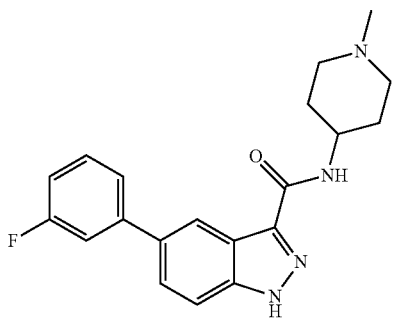

5-(3-Fluorophenyl)-N-(1-methylpiperidin-4-yl)-1H-indazole-3-carboxamide 15

White solid (55.8 mg, 0.16 mmol). $^1$H NMR (DMSO-$d_6$, 500 MHz) δ ppm 1.63-1.81 (m, 4H), 1.96 (td, J=2.5 Hz, J=1.5 Hz, 2H), 2.17 (s, 3H), 2.76 (d, J=12 Hz, 2H), 3.75-3.88 (m, 1H), 7.15-7.25 (m, 1H), 7.46-7.56 (m, 2H), 7.70 (d, J=9 Hz, 1H), 7.75 (dd, J=2 Hz, J=9 Hz, 1H), 8.20 (d, J=8.5 Hz, 1H), 8.41 (s, 1H), 13.66 (brs, 1H); ESIMS found for $C_{20}H_{21}FN_4O$ m/z 353.1 (M+1).

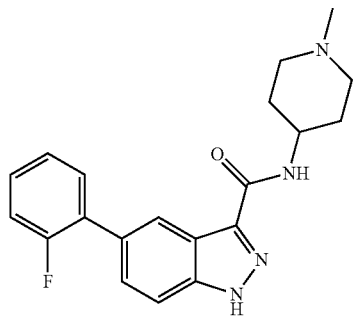

5-(2-Fluorophenyl)-N-(1-methylpiperidin-4-yl)-1H-indazole-3-carboxamide 16

White solid (19.7 mg, 0.06 mmol). $^1$H NMR (DMSO-$d_6$, 500 MHz) δ ppm 1.62-1.81 (m, 4H), 1.96 (td, J=2 Hz, J=11.5 Hz, 2H), 2.17 (s, 3H), 2.76 (d, J=12 Hz, 2H), 3.74-3.86 (m, 1H), 7.28-7.37 (m, 2H), 7.38-7.47 (m, 1H), 7.53-7.62 (m, 2H), 7.71 (dd, J=0.5 Hz, J=8.5 Hz, 1H), 8.19 (d, J=8 Hz, 1H), 8.32 (s, 1H), 13.66 (brs, 1H); ESIMS found for $C_{20}H_{21}FN_4O$ m/z 353.1 (M+1).

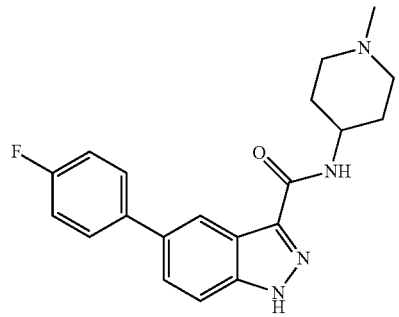

5-(4-Fluorophenyl)-N-(1-methylpiperidin-4-yl)-1H-indazole-3-carboxamide 17

White solid (23.2 mg, 0.07 mmol). $^1$H NMR (DMSO-$d_6$, 500 MHz) δ ppm 1.63-1.82 (m, 4H), 1.99 (t, J=11 Hz, 2H), 2.18 (s, 3H), 2.77 (d, J=11.5 Hz, 2H), 3.76-3.88 (m, 1H), 7.31 (t, J=9 Hz, 2H), 7.69 (s, 2H), 7.71 (dd, J=6 Hz, J=9 Hz, 2H), 8.19 (d, J=8.5 Hz, 1H), 8.35 (s, 1H), 13.63 (brs, 1H); ESIMS found for $C_{20}H_{21}FN_4O$ m/z 353.1 (M+1).

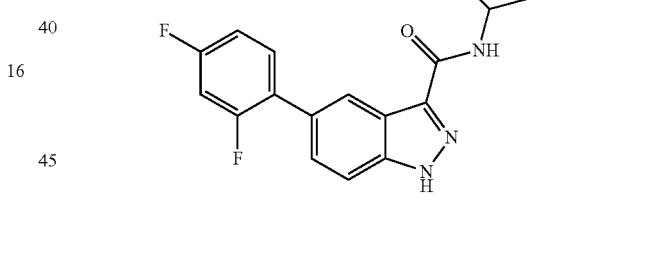

5-(2,4-Difluorophenyl)-N-(1-methylpiperidin-4-yl)-1H-indazole-3-carboxamide 18

White solid (46.8 mg, 0.13 mmol). $^1$H NMR (DMSO-$d_6$, 500 MHz) δ ppm 1.62-1.80 (m, 4H), 1.96 (t, J=11.5 Hz, 2H), 2.17 (s, 3H), 2.76 (d, J=11.5 Hz, 2H), 3.75-3.86 (m, 1H), 7.22 (td, J=2.5 Hz, J=8.5 Hz, 1H), 7.38 (tt, J=2 Hz, J=9 Hz, 1H), 7.56 (dd, J=1.5 Hz, J=8.5 Hz, 1H), 7.62 (qd, J=2 Hz, J=8.5 Hz, 1H), 7.71 (d, J=9 Hz, 1H), 8.20 (d, J=8 Hz, 1H), 8.29 (s, 1H), 13.67 (brs, 1H); ESIMS found for $C_{20}H_{20}F_2N_4O$ m/z 370.9 (M+1).

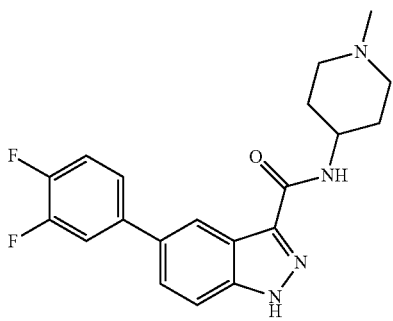

5-(3,4-Difluorophenyl)-N-(1-methylpiperidin-4-yl)-1H-indazole-3-carboxamide 19

White solid (38.5 mg, 0.10 mmol). $^1$H NMR (DMSO-$d_6$, 500 MHz) δ ppm 1.62-1.80 (m, 4H), 1.96 (td, J=2 Hz, J=12.5 Hz, 2H), 2.17 (s, 3H), 2.76 (d, J=12 Hz, 2H), 3.75-3.86 (m, 1H), 7.48-7.58 (m, 2H), 7.65-7.80 (m, 3H), 8.20 (d, J=8.5 Hz, 1H), 8.37 (s, 1H), 13.65 (brs, 1H); ESIMS found for $C_{20}H_{20}F_2N_4O$ m/z 371.0 (M+1).

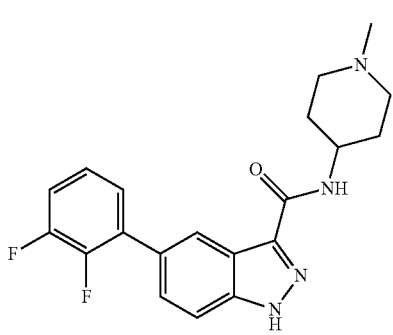

5-(2,3-Difluorophenyl)-N-(1-methylpiperidin-4-yl)-1H-indazole-3-carboxamide 20

White solid (16.5 mg, 0.05 mmol). $^1$H NMR (DMSO-$d_6$, 500 MHz) δ ppm 1.67 (qd, J=4 Hz, J=12 Hz, 2H), 1.76 (d, J=12 Hz, 2H), 1.96 (td, J=2.5 Hz, J=11.5 Hz, 2H), 2.15 (s, 3H), 2.75 (d, J=11.5 Hz, 2H), 3.73-3.86 (m, 1H), 7.32 (q, J=7 Hz, 1H), 7.38 (d, J=6.5 Hz, 1H), 7.43 (qd, J=1.5 Hz, J=9.5 Hz, 1H), 7.61 (dt, J=1.5 Hz, J=9.5 Hz, 1H), 7.73 (dd, J=1.5 Hz, J=9 Hz, 1H), 8.20 (d, J=8.5 Hz, 1H), 8.33 (s, 1H), 13.64 (brs, 1H); ESIMS found for $C_{20}H_{20}F_2N_4O$ m/z 370.9 (M+1).

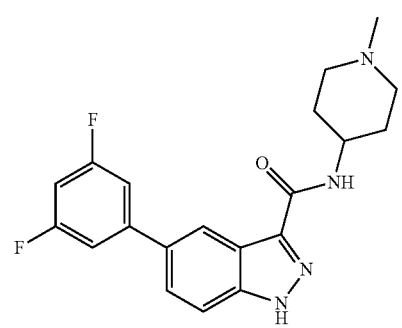

5-(3,5-Difluorophenyl)-N-(1-methylpiperidin-4-yl)-1H-indazole-3-carboxamide 21

White solid (24.2 mg, 0.07 mmol). $^1$H NMR (DMSO-$d_6$, 500 MHz) δ ppm 1.68 (qd, J=4 Hz, J=12.5 Hz, 2H), 1.77 (d, J=10 Hz, 2H), 1.98 (t, J=11 Hz, 2H), 2.16 (s, 3H), 2.76 (d, J=11.5 Hz, 2H), 3.75-3.86 (m, 1H), 7.20 (tt, J=2 Hz, J=9.5 Hz, 1H), 7.41 (dd, J=2 Hz, J=9 Hz, 1H), 7.71 (d, J=8.5 Hz, 1H), 7.77 (dd, J=2 Hz, J=9 Hz, 1H), 8.22 (d, J=8.5 Hz, 1H), 8.41 (d, J=1 Hz, 1H), 13.69 (brs, 1H); ESIMS found for $C_{20}H_{20}F_2N_4O$ m/z 371.0 (M+1).

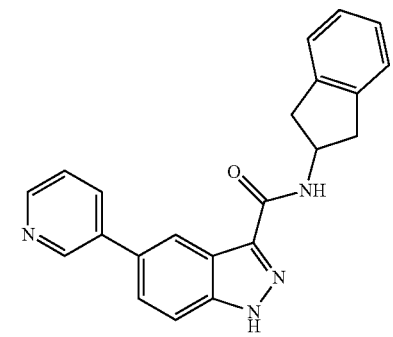

N-(2,3-Dihydro-1H-inden-2-yl)-5-(pyridin-3-yl)-1H-indazole-3-carboxamide 22

White solid (42.4 mg, 0.12 mmol). $^1$H NMR (DMSO-$d_6$, 500 MHz) δ ppm 3.07 (dd, J=7.5 Hz, J=7.5 Hz, 2H), 3.22 (dd, J=7.5 Hz, J=7.5 Hz, 2H), 4.81 (sex, J=7.5 Hz, 1H), 7.16 (dd, J=3 Hz, J=5.5 Hz, 2H), 7.24 (dd, J=3.5 Hz, J=5.5 Hz, 2H), 7.52 (dd, J=4.5 Hz, J=7.5 Hz, 1H), 7.75, 7.78 (ABq, $J_{AB}$=18.5 Hz, 2H), 8.11 (dt, J=2 Hz, J=8 Hz, 1H), 8.45 (s, 1H), 8.58 (dd, J=1.5 Hz, J=5 Hz, 1H), 8.63 (d, J=7.5 Hz, 1H), 8.91 (d, J=2 Hz, 1H), 13.71 (s, 1H); ESIMS found for $C_{22}H_{18}N_4O$ m/z 354.9 (M+1).

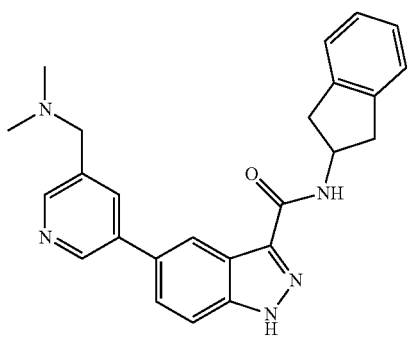

23

N-(2,3-Dihydro-1H-inden-2-yl)-5-(5-((dimethyl-amino)methyl)pyridin-3-yl)-1H-indazole-3-carboxamide 23

White solid (58.2 mg, 0.14 mmol). $^1$H NMR (DMSO-$d_6$, 500 MHz) δ ppm 2.21 (s, 6H), 3.07 (dd, J=7.5 Hz, J=7.5 Hz, 2H), 3.22 (dd, J=7.5 Hz, J=7.5 Hz, 2H), 3.53 (s, 2H), 4.81 (sex, J=7.5 Hz, 1H), 7.16 (dd, J=3 Hz, J=5.5 Hz, 2H), 7.24 (dd, J=3.5 Hz, J=5.5 Hz, 2H), 7.74 (d, J=9 Hz, 1H), 7.80 (dd, J=1.5 Hz, J=8.5 Hz, 1H), 7.99 (t, J=2 Hz, 1H), 8.45 (d, J=1.5 Hz, 1H), 8.48 (d, J=1.5 Hz, 1H), 8.64 (d, J=7.5 Hz, 1H), 8.81 (d, J=2.5 Hz, 1H), 13.70 (brs, 1H); ESIMS found for $C_{25}H_{25}N_5O$ m/z 412.1 (M+1).

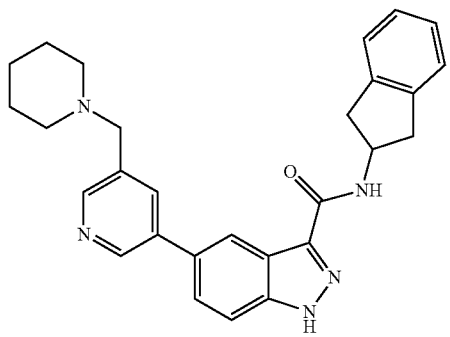

24

N-(2,3-Dihydro-1H-inden-2-yl)-5-(5-(piperidin-1-ylmethyl)pyridin-3-yl)-1H-indazole-3-carboxamide 24

White solid (25.8 mg, 0.06 mmol). $^1$H NMR (DMSO-$d_6$, 500 MHz) δ ppm 1.34-1.44 (m, 2H), 1.46-1.58 (m, 4H), 2.38 (brs, 4H), 3.07 (dd, J=7.5 Hz, J=7.5 Hz, 2H), 3.22 (dd, J=7.5 Hz, J=8 Hz, 2H), 3.56 (s, 2H), 4.81 (sex, J=7.5 Hz, 1H), 7.16 (dd, J=3 Hz, J=5.5 Hz, 2H), 7.24 (dd, J=3.5 Hz, J=5 Hz, 2H), 7.75 (d, J=9 Hz, 1H), 7.79 (dd, J=1.5 Hz, J=8.5 Hz, 1H), 7.97 (s, 1H), 8.45 (s, 1H), 8.48 (d, J=2 Hz, 1H), 8.64 (d, J=7.5 Hz, 1H), 8.80 (d, J=2 Hz, 1H), 13.70 (brs, 1H); ESIMS found for $C_{28}H_{29}N_5O$ m/z 452.2 (M+1).

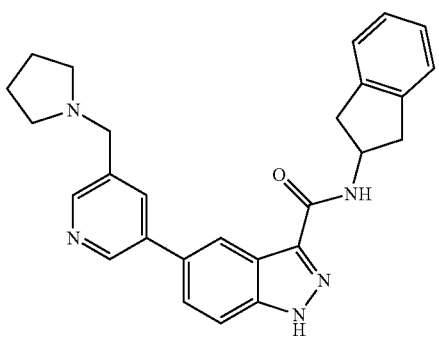

25

N-(2,3-Dihydro-1H-inden-2-yl)-5-(5-(pyrrolidin-1-ylmethyl)pyridin-3-yl)-1H-indazole-3-carboxamide 25

White solid (18.1 mg, 0.04 mmol). $^1$H NMR (DMSO-$d_6$, 500 MHz) δ ppm 1.72 (t, J=3 Hz, 4H), 3.07 (dd, J=8 Hz, J=7.5 Hz, 2H), 3.22 (dd, J=8 Hz, J=8 Hz, 2H), 3.25-3.35 (m, 4H), 3.71 (s, 2H), 4.81 (sex, J=7.5 Hz, 1H), 7.16 (dd, J=3.5 Hz, J=5.5 Hz, 2H), 7.24 (dd, J=3.5 Hz, J=5.5 Hz, 2H), 7.74 (d, 9 Hz, 1H), 7.79 (dd, J=2 Hz, J=9 Hz, 1H), 7.99 (t, J=2 Hz, 1H), 8.45 (d, J=1.5 Hz, 1H), 8.50 (d, J=2 Hz, 1H), 8.64 (d, J=7.5 Hz, 1H), 8.80 (d, J=2 Hz, 1H), 13.70 (brs, 1H); ESIMS found for $C_{27}H_{27}N_5O$ m/z 438.0 (M+1).

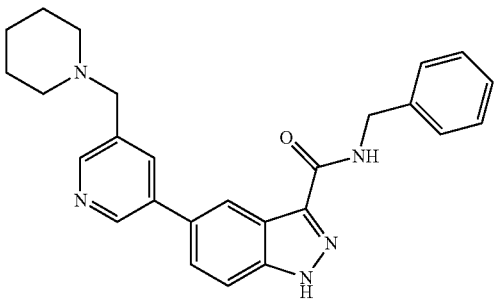

26

N-Benzyl-5-(5-(piperidin-1-ylmethyl)pyridin-3-yl)-1H-indazole-3-carboxamide 26

White solid (107 mg, 0.25 mmol). $^1$H NMR (DMSO-$d_6$, 500 MHz) δ ppm 1.33-1.43 (m, 2H), 1.46-1.56 (m, 4H), 2.37 (brs, 4H), 3.55 (s, 2H), 4.52 (d, J=6.5 Hz, 2H), 7.23 (t, J=7.5 Hz, 2H), 7.32 (t, J=7.5 Hz, 2H), 7.75 (d, J=8.5 Hz, 1H), 7.78 (dd, J=1.5 Hz, J=9 Hz, 1H), 7.96 (s, 1H), 8.43 (s, 1H), 8.47 (d, J=1.5 Hz, 1H), 8.79 (d, J=2 Hz, 1H), 9.03 (t, J=6.5 Hz, 1H), 13.73 (brs, 1H); ESIMS found for $C_{26}H_{27}N_5O$ m/z 426.1 (M+1).

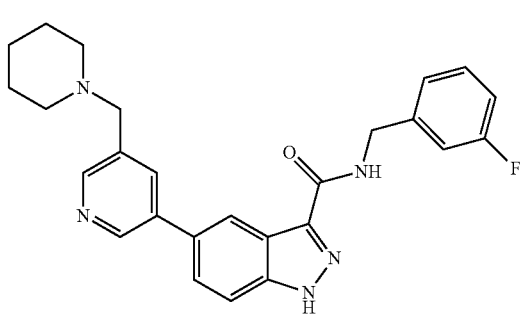

27

N-(3-Fluorobenzyl)-5-(5-(piperidin-1-ylmethyl)pyridin-3-yl)-1H-indazole-3-carboxamide 27

White solid (57.5 mg, 0.13 mmol). $^1$H NMR (DMSO-$d_6$, 500 MHz) δ ppm 1.32-1.42 (m, 2H), 1.45-1.55 (m, 4H), 2.37 (brs, 4H), 3.55 (s, 2H), 4.53 (d, J=6 Hz, 2H), 7.06 (td, J=2.5 Hz, J=8 Hz, 1H), 7.17 (d, J=10.5 Hz, 1H), 7.21 (d, J=7.5 Hz, 1H), 7.37 (qd, J=1.5 Hz, J=8 Hz, 1H), 7.76, 7.79 (ABq, $J_{AB}$=14.75 Hz, 2H), 7.96 (t, J=2 Hz, 1H), 8.42 (s, 1H), 8.47 (d, J=2 Hz, 1H), 8.79 (d, J=2.5 Hz, 1H), 9.11 (t, J=6 Hz, 1H), 13.76 (brs, 1H); ESIMS found for $C_{26}H_{26}FN_5O$ m/z 444.2 (M+1).

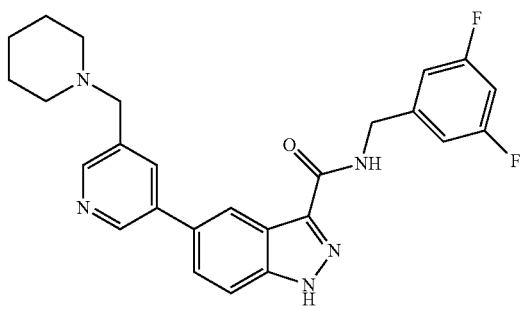

28

N-(3,5-Difluorobenzyl)-5-(5-(piperidin-1-ylmethyl)pyridin-3-yl)-1H-indazole-3-carboxamide 28

White solid (44.7 mg, 0.10 mmol). $^1$H NMR (DMSO-$d_6$, 500 MHz) δ ppm 1.32-1.42 (m, 2H), 1.45-1.55 (m, 4H), 2.37 (brs, 4H), 3.55 (s, 2H), 4.53 (d, J=6 Hz, 2H), 7.02-7.15 (m, 3H), 7.76, 7.79 (ABq, $J_{AB}$=14 Hz, 2H), 7.96 (t, J=2 Hz, 1H), 8.41 (d, J=2 Hz, 1H), 8.47 (d, J=2 Hz, 1H), 8.78 (d, J=2.5 Hz, 1H), 9.16 (t, J=6 Hz, 1H), 13.78 (brs, 1H); ESIMS found for $C_{26}H_{25}F_2N_5O$ m/z 462.2 (M+1).

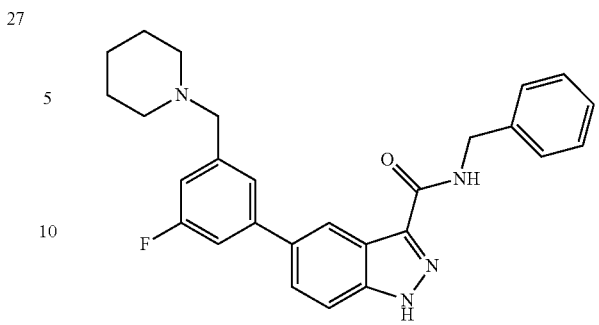

29

N-Benzyl-5-(3-fluoro-5-(piperidin-1-ylmethyl)phenyl)-1H-indazole-3-carboxamide 29

White solid (30.8 mg, 0.07 mmol). $^1$H NMR (DMSO-$d_6$, 500 MHz) δ ppm 1.33-1.43 (m, 2H), 1.46-1.56 (m, 4H), 2.36 (brs, 4H), 3.52 (s, 2H), 4.52 (d, J=6.5 Hz, 2H), 7.10 (d, J=9.5 Hz, 1H), 7.23 (t, J=7 Hz, 1H), 7.32 (t, J=8 Hz, 2H), 7.35-7.40 (m, 3H), 7.45 (s, 1H), 7.71 (d, J=9 Hz, 1H), 7.75 (dd, J=1.5 Hz, J=9 Hz, 1H), 8.41 (s, 1H), 9.02 (t, J=6.5 Hz, 1H), 13.70 (brs, 1H); ESIMS found for $C_{27}H_{27}FN_4O$ m/z 443.3 (M+1).

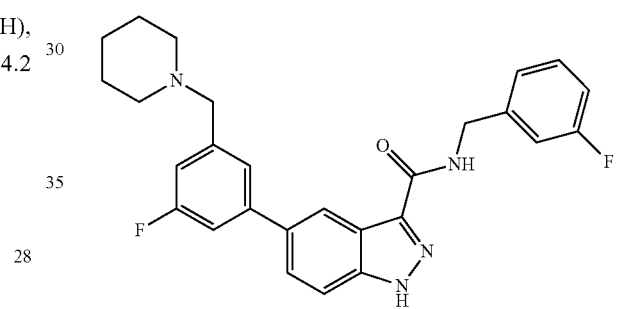

30

5-(3-Fluoro-5-(piperidin-1-ylmethyl)phenyl)-N-(3-fluorobenzyl)-1H-indazole-3-carboxamide 30

White solid (12.7 mg, 0.03 mmol). $^1$H NMR (DMSO-$d_6$, 500 MHz) δ ppm 1.33-1.43 (m, 2H), 1.46-1.56 (m, 4H), 2.36 (brs, 1H), 3.52 (s, 2H), 4.52 (d, J=6 Hz, 2H), 7.06 (td, J=2 Hz, J=8.5 Hz, 1H), 7.10 (d, J=9.5 Hz, 1H), 7.17 (d, J=10 Hz, 1H), 7.21 (d, J=7.5 Hz, 1H), 7.44 (s, 1H), 7.72, 7.75 (ABq, $J_{AB}$=17.5 Hz, 2H), 8.40 (s, 1H), 9.10 (t, J=6 Hz, 1H), 13.73 (brs, 1H); ESIMS found for $C_{27}H_{26}F_2N_4O$ m/z 461.1 (M+1).

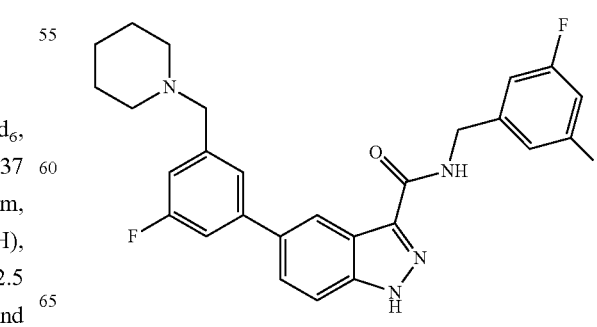

31

N-(3,5-Difluorobenzyl)-5-(3-fluoro-5-(piperidin-1-ylmethyl)phenyl)-1H-indazole-3-carboxamide 31

White solid (25.5 mg, 0.05 mmol). $^1$H NMR (DMSO-d$_6$, 500 MHz) δ ppm 1.33-1.43 (m, 2H), 1.46-1.56 (m, 4H), 2.36 (brs, 1H), 3.52 (s, 2H), 4.52 (d, J=6.5 Hz, 2H), 7.02-7.14 (m, 4H), 7.38 (d, J=10 Hz, 1H), 7.44 (s, 1H), 7.72, 7.75 (ABq, J$_{AB}$=15.75 Hz, 2H), 8.39 (s, 1H), 9.15 (t, J=6.5 Hz, 1H), 13.75 (brs, 1H); ESIMS found for C$_{27}$H$_{25}$F$_3$N$_4$O m/z 479.0 (M+1).

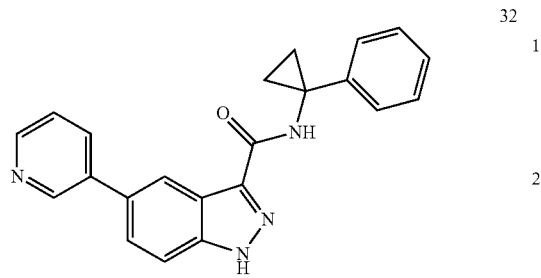

N-(1-Phenylcyclopropyl)-5-(pyridin-3-yl)-1H-indazole-3-carboxamide 32

White solid (73.0 mg, 0.21 mmol). $^1$H NMR (DMSO-d$_6$, 500 MHz) δ ppm 1.26 (dd, J=6 Hz, J=8 Hz, 2H), 1.35 (dd, J=4.5 Hz, J=8 Hz, 2H), 7.16 (sex, J=3.4 Hz, 1H), 7.27 (d, J=4 Hz, 4H), 7.50 (dd, J=4 Hz, J=5 Hz, 1H), 7.75, 7.78 (dABq, J=1.5 Hz, J$_{AB}$=14.25 Hz, 2H), 8.09 (dq, J=1.5 Hz, J=8 Hz, 1H), 8.39 (t, J=1.5 Hz, 1H), 8.56 (dd, J=1.5 Hz, J=4.5 Hz, 1H), 8.89 (d, J=3 Hz, 1H), 9.19 (s, 1H), 13.73 (brs, 1H); ESIMS found for C$_{22}$H$_{18}$N$_4$O m/z 355.0 (M+1).

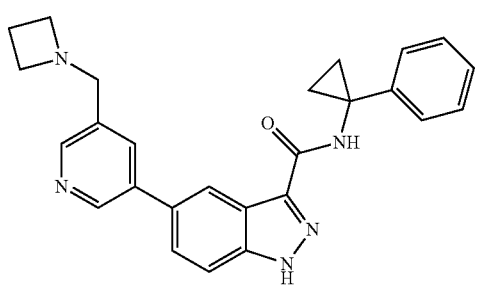

5-(5-(Azetidin-1-ylmethyl)pyridin-3-yl)-N-(1-phenylcyclopropyl)-1H-indazole-3-carboxamide 33

Beige solid (7.5 mg, 0.02 mmol). $^1$H NMR (DMSO-d, 500 MHz) δ ppm 1.26 (dd, J=6 Hz, J=8 Hz, 2H), 1.35 (dd, J=4.5 Hz, J=6.5 Hz, 2H), 1.99 (quin, J=7 Hz, 2H), 3.16 (t, J=7 Hz, 4H), 3.62 (s, 2H), 7.16 (quin, J=4.5 Hz, 1H), 7.27 (d, J=4.5 Hz, 4H), 7.75 (dd, J=0.5 Hz, J=8.5 Hz, 1H), 7.78 (dd, J=1.5 Hz, J=8.5 Hz, 1H), 7.93 (t, J=3.5 Hz, 1H), 8.39 (s, 1H), 8.44 (d, J=2 Hz, 1H), 8.77 (d, J=2 Hz, 1H), 9.20 (s, 1H), 13.73 (brs, 1H); ESIMS found for C$_{26}$H$_{25}$N$_5$O m/z 424.0 (M+1).

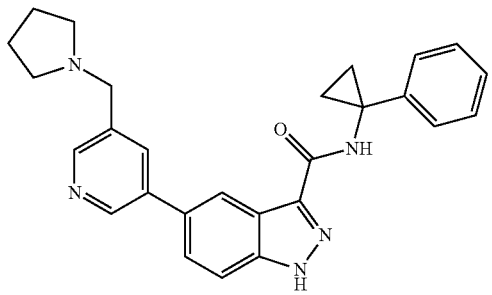

N-(1-Phenylcyclopropyl)-5-(5-(pyrrolidin-1-ylmethyl)pyridin-3-yl)-1H-indazole-3-carboxamide 34

White solid (32.7 mg, 0.07 mmol). $^1$H NMR (DMSO-d, 500 MHz) δ ppm 1.26 (dd, J=6 Hz, J=8 Hz, 2H), 1.35 (dd, J=4.5 Hz, J=8 Hz, 2H), 1.70 (brs, 4H), 2.47 (brs, 4H), 3.68 (s, 2H), 7.15 (quin, J=5.25 Hz, 1H), 7.27 (d, J=4 Hz, 4H), 7.75 (d, J=8.5 Hz, 1H), 7.79 (dd, J=1.5 Hz, J=8.5 Hz, 1H), 7.97 (s, 1H), 8.40 (s, 1H), 8.48 (d, J=1.5 Hz, 1H), 8.78 (d, J=2.5 Hz, 1H), 9.20 (s, 1H), 13.74 (brs, 1H); ESIMS found for C$_{27}$H$_{27}$N$_5$O m/z 438.1 (M+1).

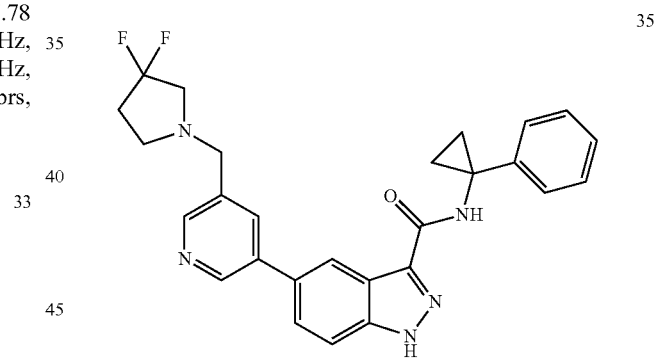

5-(5-((3,3-Difluoropyrrolidin-1-yl)methyl)pyridin-3-yl)-N-(1-phenyl cyclopropyl)-1H-indazole-3-carboxamide 35

White solid (27.3 mg, 0.06 mmol). $^1$H NMR (DMSO-d$_6$, 500 MHz) δ ppm 1.26 (dd, J=6 Hz, J=8 Hz, 2H), 1.34 (dd, J=4.5 Hz, J=8 Hz, 2H), 2.25 (sex, J=7 Hz, 2H), 2.74 (t, J=7 Hz, 2H), 2.92 (t, J=13.5 Hz, 2H), 3.75 (s, 2H), 7.15 (quin, J=5.25 Hz, 1H), 7.27 (d, J=4 Hz, 4H), 7.75 (d, J=9 Hz, 1H), 7.80 (dd, J=1.5 Hz, J=8.5 Hz, 1H), 8.00 (s, 1H), 8.41 (s, 1H), 8.50 (d, J=1.5 Hz, 1H), 8.81 (d, J=2 Hz, 1H), 9.20 (s, 1H), 13.73 (brs, 1H); ESIMS found for C$_{27}$H$_{25}$F$_2$N$_5$O m/z 474.1 (M+1).

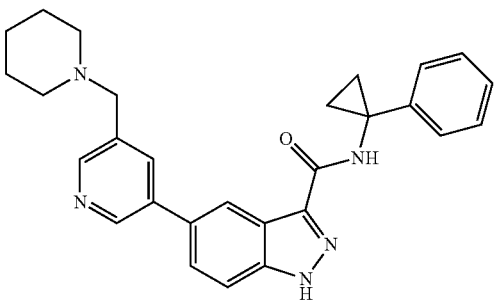

N-(1-Phenylcyclopropyl)-5-(5-(piperidin-1-ylmethyl)pyridin-3-yl)-1H-indazole-3-carboxamide 36

White solid (14.6 mg, 0.03 mmol). $^1$H NMR (DMSO-d$_6$, 500 MHz) δ ppm 1.26 (dd, J=6 Hz, J=8 Hz, 2H), 1.31-1.42 (m, 4H), 1.45-1.54 (m, 4H), 2.36 (brs, 4H), 3.54 (s, 2H), 7.15 (quin, J=4.25 Hz, 1H), 7.27 (d, J=4 Hz, 4H), 7.75 (d, J=9 Hz, 1H), 7.78 (dd, J=1.5 Hz, J=8.5 Hz, 1H), 7.94 (t, J=2 Hz, 1H), 8.39 (s, 1H), 8.46 (d, J=2 Hz, 1H), 8.78 (d, J=2 Hz, 1H), 9.19 (s, 1H), 13.74 (brs, 1H); ESIMS found for C$_{28}$H$_{29}$N$_5$O m/z 452.1 (M+1).

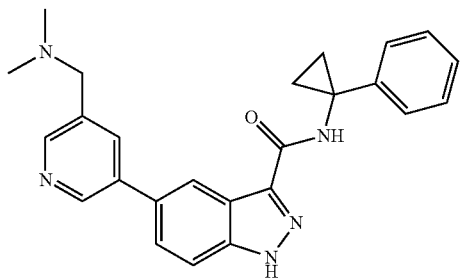

5-(5-((Dimethylamino)methyl)pyridin-3-yl)-N-(1-phenylcyclopropyl)-1H-indazole-3-carboxamide 37

White solid (55.2 mg, 0.13 mmol). $^1$H NMR (DMSO-d$_6$, 500 MHz) δ ppm 1.26 (dd, J=6 Hz, J=8 Hz, 2H), 1.35 (dd, J=6 Hz, J=8 Hz, 2H), 2.19 (s, 6H), 3.50 (s, 2H), 7.15 (quin, J=4.25 Hz, 1H), 7.27 (d, J=4.5 Hz, 4H), 7.75 (d, J=9 Hz, 1H), 7.80 (dd, J=1.5 Hz, J=8.5 Hz, 1H), 7.97 (t, J=2 Hz, 1H), 8.40 (s, 1H), 8.46 (d, J=2 Hz, 1H), 8.80 (d, J=2.5 Hz, 1H), 9.20 (s, 1H), 13.73 (brs, 1H); ESIMS found for C$_{25}$H$_{25}$N$_5$O m/z 412.1 (M+1).

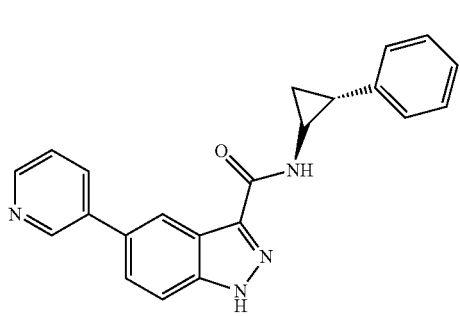

N-((1R,2R)-2-Phenylcyclopropyl)-5-(pyridin-3-yl)-1H-indazole-3-carboxamide 38

Beige solid (46.0 mg, 0.13 mmol). $^1$H NMR (DMSO-d$_6$, 500 MHz) δ ppm 1.23 (qd, J=2 Hz, J=6 Hz, 1H), 1.49 (quin, J=5.5 Hz, 1H), 2.11-2.21 (m, 1H), 3.05-312 (m, 1H), 7.14-7.21 (m, 3H), 7.25-7.33 (m, 2H), 7.50 (dd, J=5 Hz, J=8 Hz, 1H), 7.75 (d. J=9 Hz, 1H), 7.79 (dd, J=1.5 Hz, J=8.5 Hz, 1H), 8.09 (dt, J=2.5 Hz, J=8 Hz, 1H), 8.42 (s, 1H), 8.57 (dd, J=1.5 Hz, J=5 Hz, 1H), 8.77 (d, J=5 Hz, 1H), 8.90 (d, J=2 Hz, 1H), 13.72 (brs, 1H); ESIMS found for C$_{22}$H$_{18}$N$_4$O m/z 354.9 (M+1).

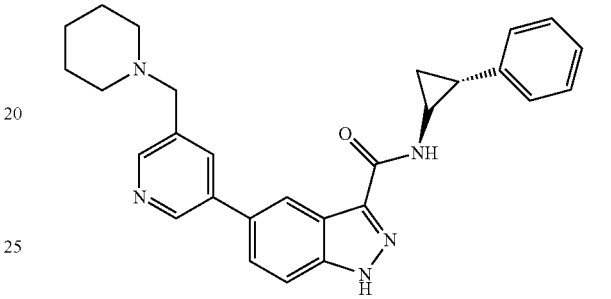

N-((1R,2R)-2-Phenylcyclopropyl)-5-(5-(piperidin-1-ylmethyl)pyridin-3-yl)-1H-indazole-3-carboxamide 39

Beige solid (7.8 mg, 0.02 mmol). $^1$H NMR (DMSO-d$_6$, 500 MHz) δ ppm 1.20-1.26 (m, 1H), 1.34-1.43 (m, 2H), 1.45-1.55 (m, 4H), 2.12-2.20 (m, 1H), 2.37 (brs, 1H), 3.06-3.12 (m, 1H), 3.55 (s, 2H), 7.14-7.22 (m, 3H), 7.25-7.33 (m, 2H), 7.74 (dd, J=1 Hz, J=8.5 Hz, 1H), 7.78 (dd, J=1.5 Hz, J=8.5 Hz, 1H), 7.96 (t, J=2 Hz, 1H), 8.42 (d, J=1.5 Hz, 1H), 8.47 (d, J=2 Hz, 1H), 8.78 (t, J=2 Hz, 1H), 13.72 (brs, 1H); ESIMS found for C$_{28}$H$_{29}$N$_5$O m/z 452.0 (M+1).

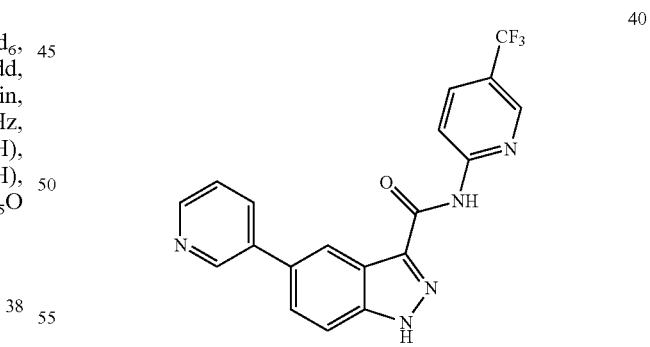

5-(Pyridin-3-yl)-N-(5-(trifluoromethyl)pyridin-2-yl)-1H-indazole-3-carboxamide 40

White solid (52.6 mg, 0.14 mmol). $^1$H NMR (DMSO-d$_6$, 500 MHz) δ ppm 7.78 (dd, J=5 Hz, J=8 Hz, 1H), 7.87, 7.90 (ABq, J$_{AB}$=14.75 Hz, 2H), 8.30 (dd, J=2.5 Hz, J=9 Hz, 1H), 8.47 (d, J=8.5 Hz, 1H), 8.53 (s, 1H), 8.73 (brd, J=4 Hz, 1H), 8.79 (s, 1H), 10.33 (s, 1H), 14.20 (brs, 1H); ESIMS found for C$_{19}$H$_{12}$F$_3$N$_5$O m/z 384.1 (M+1).

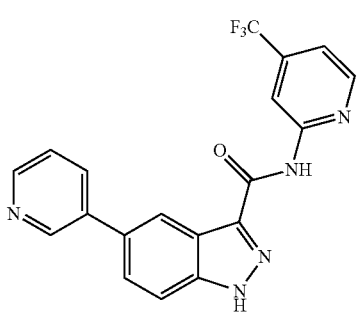

5-(Pyridin-3-yl)-N-(4-(trifluoromethyl)pyridin-2-yl)-1H-indazole-3-carboxamide 41

White solid (120.2 mg, 0.31 mmol). $^1$H NMR (DMSO-$d_6$, 500 MHz) δ ppm 7.53 (dd, J=5 Hz, J=8 Hz, 1H), 7.56 (d, J=5.5 Hz, 1H), 7.84, 7.86 (ABq, $J_{AB}$=13.75 Hz, 2H), 8.16 (dt, J=2 Hz, J=8 Hz, 1H), 8.49 (s, 1H), 8.60 (s, 1H), 8.68 (d, J=5.5 Hz, 1H), 8.95 (d, J=1.5 Hz, 1H), 10.34 (s, 1H), 14.12 (s, 1H); ESIMS found for $C_{19}H_{12}F_3N_5O$ m/z 384.1 (M+1).

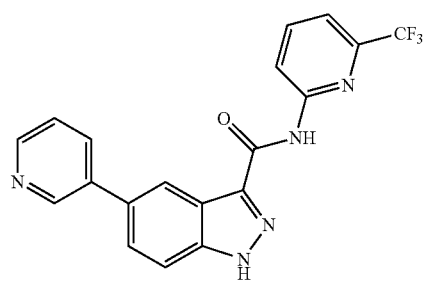

5-(Pyridin-3-yl)-N-(6-(trifluoromethyl)pyridin-2-yl)-1H-indazole-3-carboxamide 42

White solid (36.9 mg, 0.10 mmol). $^1$H NMR (DMSO-$d_6$, 500 MHz) δ ppm 7.61 (dd, J=2 Hz, J=9 Hz, 1H), 7.68 (d, J=7.5 Hz, 1H), 7.84, 7.87 (ABq, $J_{AB}$=14.5 Hz, 2H), 8.14-8.24 (m, 2H), 8.47 (s, 1H), 8.51 (d, J=8.5 Hz, 1H), 8.63 (brd, J=4 Hz, 1H), 8.98 (brs, 1H), 10.24 (s, 1H), 14.13 (s, 1H); ESIMS found for $C_{19}H_{12}F_3N_5O$ m/z 383.9 (M+1).

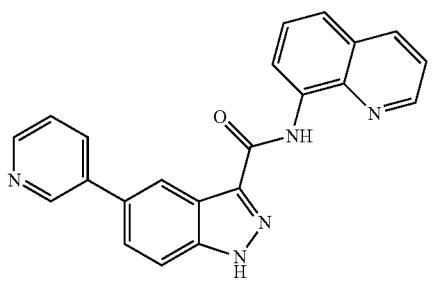

5-(Pyridin-3-yl)-N-(quinolin-8-yl)-1H-indazole-3-carboxamide 43

White solid (40.3 mg, 0.11 mmol). $^1$H NMR (DMSO-$d_6$, 500 MHz) δ ppm 7.54 (ddd, J=0.5 Hz, J=4.5 Hz, J=8 Hz, 1H), 7.64-7.76 (m, 3H), 7.85, 7.88 (ABq, $J_{AB}$=11.75 Hz, 2H), 8.16 (dt, J=2 Hz, J=8 Hz, 1H), 8.47 (dd, J=1.5 Hz, J=8.5 Hz, 1H), 8.56 (d, J=1 Hz, 1H), 8.61 (dd, J=1.5 Hz, J=5 Hz, 1H), 8.96 (d, J=2 Hz, 1H), 9.03 (dd, J=2 Hz, J=4.5 Hz, 1H), 11.39 (s, 1H), 14.01 (brs, 1H); ESIMS found for $C_{22}H_{15}N_5O$ m/z 365.9 (M+1).

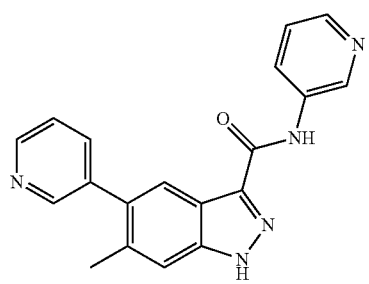

6-Methyl-N,5-di(pyridin-3-yl)-1H-indazole-3-carboxamide 44

White solid (12.0 mg, 0.04 mmol). $^1$H NMR (DMSO-$d_6$, 500 MHz) δ ppm 2.36 (s, 3H), 7.39 (t, J=5 Hz, 1H), 7.51 (t, J=5 Hz, 1H), 7.63 (s, 1H), 7.87 (d, J=7.5 Hz, 1H), 8.03 (s, 1H), 8.28 (s, 1H), 8.30 (s, 1H), 8.62 (s, 1H), 9.06 (s, 1H), 10.63 (s, 1H), 13.83 (s, 1H); ESIMS found for $C_{19}H_{15}N_5O$ m/z 329.9 (M+1).

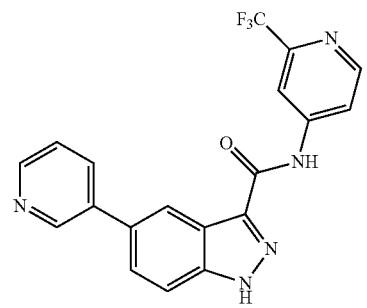

5-(Pyridin-3-yl)-N-(2-(trifluoromethyl)pyridin-4-yl)-1H-indazole-3-carboxamide 45

White solid (7.3 mg, 0.02 mmol). $^1$H NMR (DMSO-$d_6$, 500 MHz) δ ppm 7.53 (dd, J=7.82, 4.80 Hz, 1H), 7.86 (s, 2H), 8.15 (d, J=7.87 Hz, 1H), 8.20 (d, J=5.76 Hz, 1H), 8.49 (s, 1H), 8.54 (d, J=1.65 Hz, 1H), 8.60 (dd, J=4.67, 1.37 Hz, 1H), 8.67 (d, J=5.49 Hz, 1H), 8.95 (d, J=2.19 Hz, 1H), 11.24 (s, 1H), 14.13 (brs, 1H); ESIMS found for $C_{19}H_{12}F_3N_5O$ m/z 384.1 (M+1).

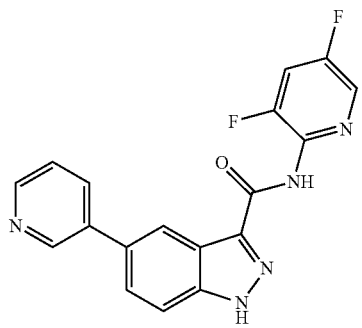

N-(3,5-Difluoropyridin-2-yl)-5-(pyridin-3-yl)-1H-indazole-3-carboxamide 46

White solid (4.9 mg, 0.01 mmol). $^1$H NMR (DMSO-d$_6$, 500 MHz) δ ppm 7.51 (dd, J=5 Hz, J=8 Hz, 1H), 7.82 (s, 2H), 8.04-8.14 (m, 2H), 8.40 (s, 1H), 8.44 (s, 1H), 8.58 (dd, J=1.5 Hz, J=5 Hz, 1H), 8.91 (d, J=2.5 Hz, 1H), 10.67 (s, 1H), 14.02 (brs, 1H); ESIMS found for C$_{18}$H$_{11}$F$_2$N$_5$O m/z 352.0 (M+1).

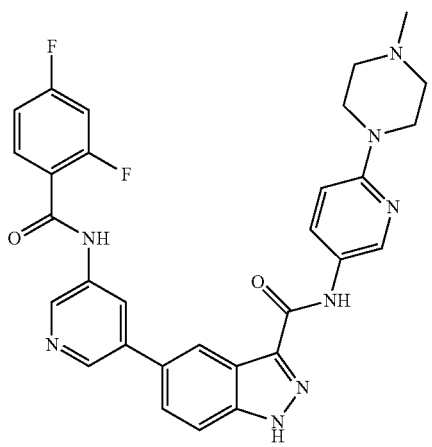

5-(5-(2,4-Difluorobenzamido)pyridin-3-yl)-N-(6-(4-methylpiperazin-1-yl)pyridin-3-yl)-1H-indazole-3-carboxamide 47

Tan solid (22.4 mg, 0.04 mmol). $^1$H NMR (DMSO-d$_6$, 500 MHz) δ ppm 2.22 (s, 3H), 2.41 (t, J=4.75 Hz, 4H), 3.44 (t, J=4.75 Hz, 4H), 6.85 (d, J=9 Hz, 1H), 7.28 (td, J=2 Hz, J=8.5 Hz, 1H), 7.48 (td, J=2.5 Hz, J=8.5 Hz, 1H), 7.82 (s, 2H), 7.84 (q, J=7.5 Hz, 1H), 8.04 (dd, J=3 Hz, J=9.5 Hz, 1H), 8.50 (s, 2H), 8.59 (d, J=2.5 Hz, 1H), 8.71 (d, J=2 Hz, 1H), 8.92 (d, J=2 Hz, 1H), 10.33 (s, 1H), 10.74 (s, 1H), 13.91 (brs, 1H); ESIMS found for C$_{30}$H$_{26}$F$_2$N$_8$O$_2$ m/z 569.0 (M+1).

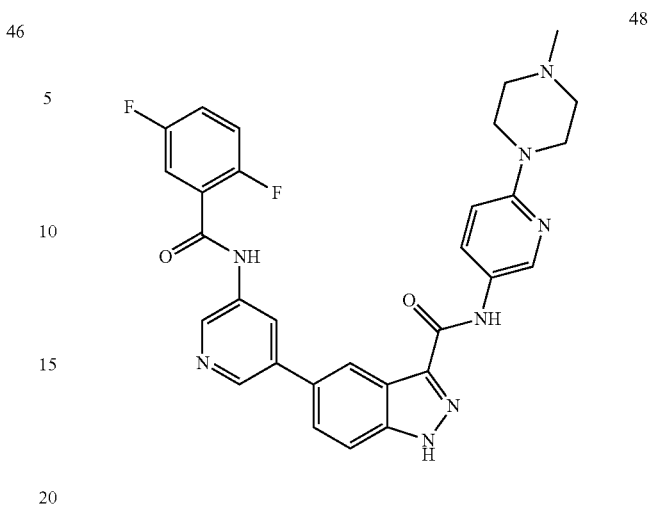

5-(5-(2,5-Difluorobenzamido)pyridin-3-yl)-N-(6-(4-methylpiperazin-1-yl)pyridin-3-yl)-1H-indazole-3-carboxamide 48

Tan solid (25.4 mg, 0.04 mmol). $^1$H NMR (DMSO-d$_6$, 500 MHz) δ ppm 2.23 (s, 3H), 2.42 (t, J=4.75 Hz, 4H), 3.45 (t, J=4.75 Hz, 4H), 6.85 (d, J=9 Hz, 1H), 7.43-7.54 (m, 2H), 7.61-7.68 (m, 1H), 7.81, 7.84 (ABq, J$_{AB}$=10.75 Hz, 2H), 8.05 (dd, J=3 Hz, J=9.5 Hz, 1H), 8.50 (s, 2H), 8.59 (d, J=3 Hz, 1H), 8.72 (d, J=1.5 Hz, 1H), 8.92 (d, J=2 Hz, 1H), 10.34 (s, 1H), 10.83 (s, 1H), 13.91 (brs, 1H); ESIMS found for C$_{30}$H$_{26}$F$_2$N$_8$O$_2$ m/z 569.1 (M+1).

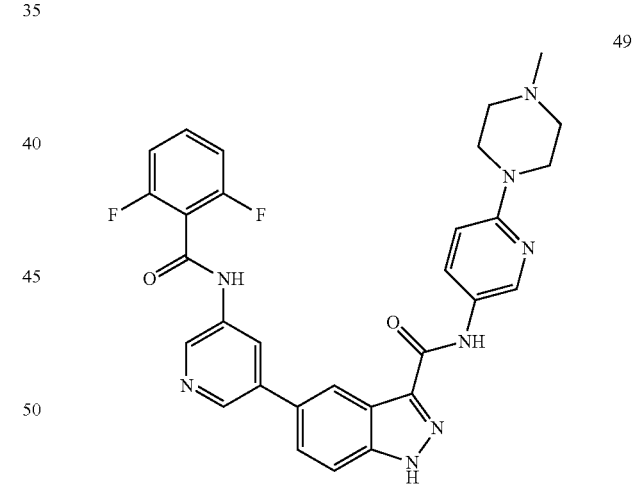

5-(5-(2,6-Difluorobenzamido)pyridin-3-yl)-N-(6-(4-methylpiperazin-1-yl)pyridin-3-yl)-1H-indazole-3-carboxamide 49

Tan solid (13.1 mg, 0.02 mmol). $^1$H NMR (DMSO-d, 500 MHz) δ ppm 2.22 (s, 3H), 2.40 (t, J=4.75 Hz, 4H), 3.44 (t, J=4.75 Hz, 4H), 6.85 (d, J=9.5 Hz, 1H), 7.30 (t, J=8 Hz, 2H), 7.60-7.69 (m, 2H), 7.81, 7.83 (ABq, J$_{AB}$=11.5 Hz, 2H), 8.04 (dd, J=9.5 Hz, 1H), 8.48 (t, J=2 Hz, 1H), 8.50 (s, 1H), 8.59 (d, J=3 Hz, 1H), 8.73 (d, J=2 Hz, 1H), 8.88 (d, J=2 Hz, 1H), 10.33 (s, 1H), 11.18 (s, 1H), 13.91 (brs, 1H); ESIMS found for C$_{30}$H$_{26}$F$_2$N$_8$O$_2$ m/z 569.0 (M+1).

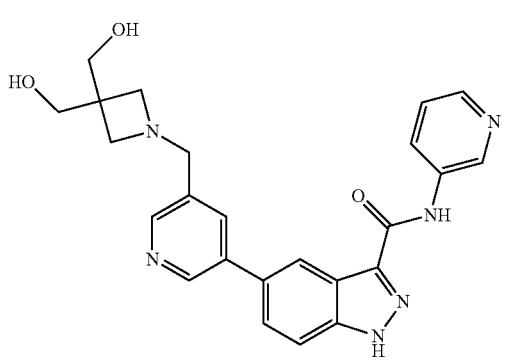

50

5-(5-((3,3-Bis(hydroxymethyl)azetidin-1-yl)methyl) pyridin-3-yl)-N-(pyridin-3-yl)-1H-indazole-3-carboxamide 50

White solid (59 mg, 0.13 mmol). $^1$H NMR (DMSO-$d_6$, 500 MHz) δ ppm 2.99 (s, 4H), 3.50 (s, 4H), 3.68 (s, 2H), 4.59 (brs, 2H), 7.40 (dd, J=5 Hz, J=7.5 Hz, 1H), 7.82 (s, 2H), 7.96 (s, 1H), 8.27-8.36 (m, 2H), 8.47 (s, 1H), 8.80 (s, 1H), 9.08 (s, 1H), 10.69 (s, 1H), 14.00 (brs, 1H) ESIMS found for $C_{24}H_{24}N_6O_3$ m/z 445.1 (M+1).

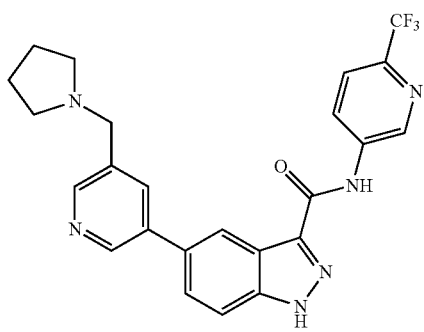

51

5-(5-(Pyrrolidin-1-ylmethyl)pyridin-3-yl)-N-(6-(trifluoromethyl)pyridin-3-yl)-1H-indazole-3-carboxamide 51

White solid (58 mg, 0.12 mmol). $^1$H NMR (DMSO-$d_6$, 500 MHz) δ ppm 1.69-1.75 (m, 4H), 3.28-3.36 (m, 4H), 3.72 (s, 2H), 7.83, 7.86 (ABq, $J_{AB}$=15.3 Hz, 2H), 7.93 (d, J=8.5 Hz, 1H), 8.02 (s, 1H), 8.48 (s, 1H), 8.52 (d, J=1.5 Hz, 1H), 8.63 (dd, J=2.5 Hz, J=8.5 Hz, 1H), 8.82 (d, J=2 Hz, 1H), 9.27 (d, J=2.5 Hz, 1H), 11.11 (s, 1H), 14.10 (s, 1H); ESIMS found for $C_{24}H_{21}F_3N_6O$ m/z 467.2 (M+1).

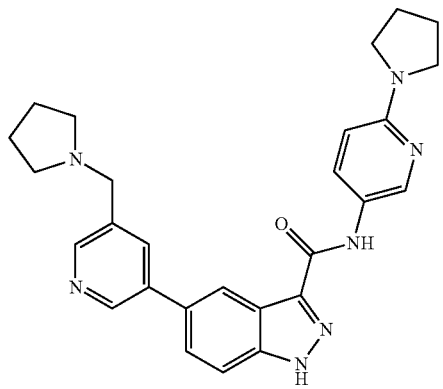

52

N-(6-(Pyrrolidin-1-yl)pyridin-3-yl)-5-(5-(pyrrolidin-1-ylmethyl)pyridin-3-yl)-1H-indazole-3-carboxamide 52

Yellow solid (107 mg, 0.23 mmol). $^1$H NMR (DMSO-$d_6$, 500 MHz) δ ppm 1.87-1.98 (m, 2H), 1.99-2.11 (m, 6H), 3.10-3.20 (m, 2H), 3.40-3.48 (m, 2H), 3.54-3.61 (m, 4H), 4.59 (d, J=5.5 Hz, 2H), 7.21 (d, J=10 Hz, 1H), 7.88 (d, J=8.5 Hz, 1H), 7.99 (dd, J=1.75 Hz, J=8.5 Hz, 1H), 8.37 (dd, J=2.5 Hz, J=9.5 Hz, 1H), 8.62 (s, 1H), 8.78 (d, J=2 Hz, 1H), 8.80 (s, 1H), 8.92 (d, J=1.5 Hz, 1H), 9.17 (d, J=2 Hz, 1H), 10.89 (s, 1H), 11.39-11.48 (m, 1H); ESIMS found for $C_{27}H_{29}N_7O$ m/z 467.9 (M+1).

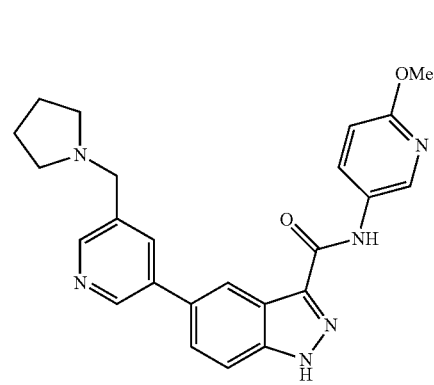

53

N-(6-Methoxypyridin-3-yl)-5-(5-(pyrrolidin-1-ylmethyl)pyridin-3-yl)-1H-indazole-3-carboxamide 53

White solid (192 mg, 0.45 mmol). $^1$H NMR (DMSO-$d_6$, 500 MHz) δ ppm 1.68-1.76 (m, 4H), 3.30-3.38 (m, 4H), 3.71 (s, 2H), 3.85 (s, 3H), 6.85 (d, J=9 Hz, 1H), 7.81 (d, J=8.5 Hz, 1H), 7.83 (dd, J=1.5 Hz, J=8.5 Hz, 1H), 8.01 (t, J=2 Hz, 1H), 8.18 (dd, J=3 Hz, J=9 Hz, 1H), 8.47 (s, 1H), 8.50 (d, J=1.5 Hz, 1H), 8.65 (d, J=2.5 Hz, 1H), 8.81 (d, J=2.5 Hz, 1H), 10.51 (s, 1H), 13.92 (brs, 1H); ESIMS found for $C_{24}H_{24}N_6O_2$ m/z 429.1 (M+1).

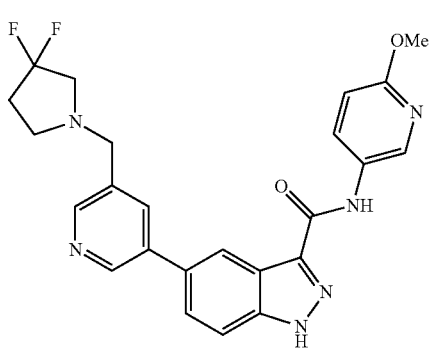

54

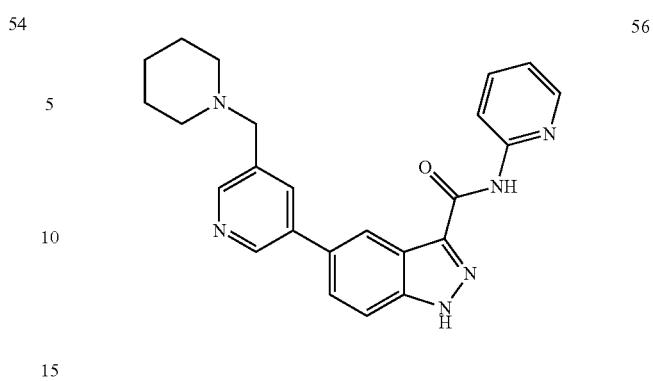

56

5-(5-((3,3-Difluoropyrrolidin-1-yl)methyl)pyridin-3-yl)-N-(6-methoxy pyridin-3-yl)-1H-indazole-3-carboxamide 54

White solid (193 mg, 0.42 mmol). $^1$H NMR (DMSO-d$_6$, 500 MHz) δ ppm 2.28 (sep, J=8 Hz, 2H), 2.76 (t, J=7 Hz, 1H), 2.94 (t, J=13.5 Hz, 2H), 3.77 (s, 2H), 3.85 (s, 3H), 6.85 (d, J=9 Hz, 1H), 7.81 (d, J=8.5 Hz, 1H), 7.84 (dd, J=1.5 Hz, J=9 Hz, 1H), 8.03 (s, 1H), 8.18 (dd, J=3 Hz, J=9 Hz, 1H), 8.48 (s, 1H), 8.52 (d, J=2 Hz, 1H), 8.65 (d, J=2.5 Hz, 1H), 8.85 (d, J=2.5 Hz, 1H), 10.52 (s, 1H), 13.93 (brs, 1H); ESIMS found for $C_{24}H_{22}F_2N_6O_2$ m/z 464.5 (M+1).

5-(5-(Piperidin-1-ylmethyl)pyridin-3-yl)-N-(pyridin-2-yl)-1H-indazole-3-carboxamide 56

White solid (88 mg, 0.21 mmol). $^1$H NMR (DMSO-d$_6$, 500 MHz) δ ppm 1.35-1.45 (m, 2H), 1.46-1.57 (m, 4H), 2.39 (brs, 4H), 3.57 (s, 2H), 7.20 (dd, J=5.5 Hz, J=7.5 Hz, 1H), 7.82, 7.85 (ABq, J$_{AB}$=12.25 Hz, 2H), 7.90 (td, J=2 Hz, J=6.8 Hz, 1H), 8.00 (s, 1H), 8.28 (d, J=8.5 Hz, 1H), 8.40 (d, J=4 Hz, 1H), 8.47 (s, 1H), 8.50 (d, J=0.5 Hz, 1H), 8.82 (d, J=2 Hz, 1H), 9.84 (s, 1H), 14.05 (s, 1H); ESIMS found for $C_{24}H_{24}N_6O$ m/z 413.1 (M+1).

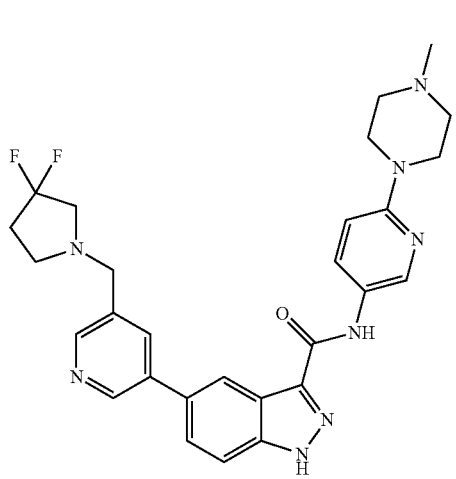

55

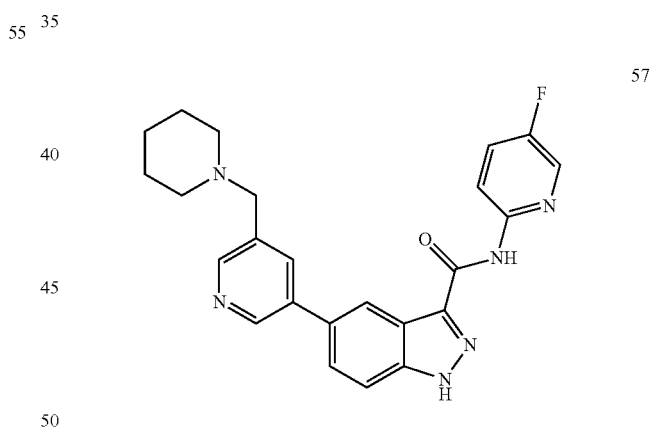

57

5-(5-((3,3-Difluoropyrrolidin-1-yl)methyl)pyridin-3-yl)-N-(6-(4-methyl piperazin-1-yl)pyridin-3-yl)-1H-indazole-3-carboxamide 55

Off-white solid (67 mg, 0.23 mmol). $^1$H NMR (DMSO-d$_6$, 500 MHz) δ ppm 2.22 (s, 3H), 2.28 (sep, J=7.5 Hz, 2H), 2.41 (t, J=5 Hz, 4H), 2.76 (t, J=7 Hz, 2H), 2.94 (t, J=13.5 Hz, 2H), 3.44 (t, J=5 Hz, 4H), 3.77 (s, 2H), 6.86 (d, J=9 Hz, 1H), 7.79, 7.83 (ABq, J$_{AB}$=17.5 Hz, 2H), 7.99-8.07 (m, 2H), 8.48 (s, 1H), 8.52 (d, J=1.5 Hz, 1H), 8.58 (d, J=3 Hz, 1H), 8.84 (d, J=2 Hz, 1H), 10.32 (s, 1H), 13.89 (brs, 1H); ESIMS found for $C_{28}H_{30}F_2N_8O$ m/z 533.3 (M+1).

N-(5-Fluoropyridin-2-yl)-5-(5-(piperidin-1-ylmethyl)pyridin-3-yl)-1H-indazole-3-carboxamide 57

White solid (89 mg, 0.21 mmol). $^1$H NMR (DMSO-d$_6$, 500 MHz) δ ppm 1.33-1.45 (m, 2H), 1.45-1.58 (m, 4H), 2.39 (brs, 4H), 3.57 (s, 2H), 7.78-7.90 (m, 3H), 8.00 (s, 1H), 8.30 (dd, J=4 Hz, J=9 Hz, 1H), 8.41 (d, J=3 Hz, 1H), 8.46 (s, 1H), 8.50 (d, J=1.5 Hz, 1H), 8.82 (d, J=2 Hz, 1H), 10.04 (s, 1H), 14.04 (s, 1H); ESIMS found for $C_{24}H_{23}FN_6O$ m/z 431.0 (M+1).

58

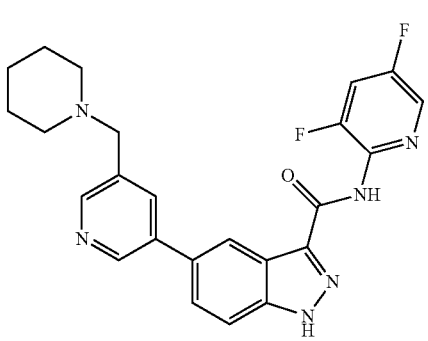

N-(3,5-Difluoropyridin-2-yl)-5-(5-(piperidin-1-ylmethyl)pyridin-3-yl)-1H-indazole-3-carboxamide 58

Beige solid (10.0 mg, 0.02 mmol). $^1$H NMR (DMSO-d$_6$, 500 MHz) δ ppm 1.33-1.43 (m, 2H), 1.45-1.55 (m, 4H), 2.36 (brs, 4H), 3.55 (s, 2H), 7.81, 7.83 (ABq, J$_{AB}$=10 Hz, 2H), 7.97 (t, J=2.5 Hz, 1H), 8.09 (td, J=3 Hz, J=8.5 Hz, 1H), 8.39 (t, J=1.5 Hz, 1H), 8.44 (d, J=2.5 Hz, 1H), 8.48 (d, J=2 Hz, 1H), 8.80 (d, J=2.5 Hz, 1H), 10.68 (s, 1H), 14.00 (brs, 1H); ESIMS found for C$_{24}$H$_{22}$F$_2$N$_6$O m/z 449.1 (M+1).

60

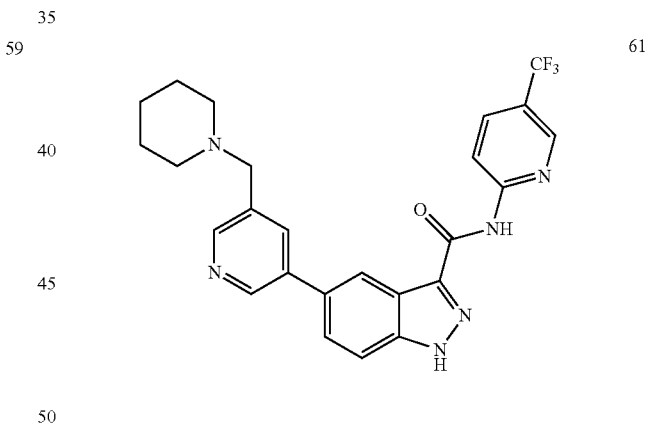

5-(5-(Piperidin-1-ylmethyl)pyridin-3-yl)-N-(4-(trifluoromethyl)pyridin-2-yl)-1H-indazole-3-carboxamide 60

White solid (138.1 mg, 0.29 mmol). $^1$H NMR (DMSO-d$_6$, 500 MHz) δ ppm 1.35-1.44 (m, 2H), 1.46-1.55 (m, 4H), 2.38 (brs, 4H), 3.57 (s, 1H), 7.56 (dd, J=1 Hz, J=5 Hz, 1H), 7.83, 7.85 (ABq, J$_{AB}$=12 Hz, 2H), 8.01 (t, J=2 Hz, 1H), 8.47 (t, J=1.3 Hz, 1H), 8.50 (d, J=0.5 Hz, 1H), 8.60 (s, 1H), 8.68 (d, J=5 Hz, 1H), 8.83 (d, J=2 Hz, 1H), 10.33 (s, 1H), 14.11 (brs, 1H); ESIMS found for C$_{25}$H$_{23}$F$_3$N$_6$O m/z 481.0 (M+1).

59

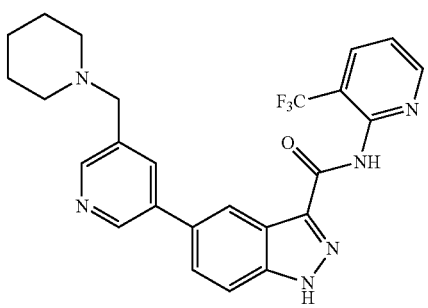

5-(5-(Piperidin-1-ylmethyl)pyridin-3-yl)-N-(3-(trifluoromethyl)pyridin-2-yl)-1H-indazole-3-carboxamide 59

White solid (1.9 mg, 0.004 mmol). $^1$H NMR (DMSO-d$_6$, 500 MHz) δ ppm 1.31-1.45 (m, 1H), 1.53-1.74 (m, 3H), 1.84 (brd, J=13 Hz, 2H), 2.88-3.02 (m, 2H), 3.40 (brd, J=1 Hz, 2H), 4.43 (brs, 2H), 7.63 (dd, J=5 Hz, J=8 Hz, 1H), 7.86, 7.89 (ABq, J$_{AB}$=16.75 Hz, 2H), 8.31 (s, 1H), 8.33 (d, J=2 Hz, 1H), 8.51 (s, 1H), 8.67 (s, 1H), 8.82 (d, J=3.5 Hz, 1H), 9.03 (s, 1H), 9.40 (brs, 1H), 10.58 (s, 1H), 14.01 (s, 1H); ESIMS found for C$_{25}$H$_{23}$F$_3$N$_6$O m/z 481.2 (M+1).

61

5-(5-(Piperidin-1-ylmethyl)pyridin-3-yl)-N-(5-(trifluoromethyl)pyridin-2-yl)-1H-indazole-3-carboxamide 61

White solid (6.7 mg, 0.01 mmol). $^1$H NMR (DMSO-d$_6$, 500 MHz) δ ppm 1.35-1.44 (m, 2H), 1.47-1.56 (m, 4H), 2.38 (brs, 4H), 3.57 (s, 2H), 7.84, 7.86 (ABq, J$_{AB}$=10.5 Hz, 2H), 8.01 (t, J=2 Hz, 1H), 8.30 (dd, J=2.5 Hz, J=9 Hz, 1H), 8.44-8.53 (m, 3H), 8.80 (s, 1H), 8.83 (d, J=2.5 Hz, 1H), 10.31 (s, 1H), 14.13 (brs, 1H); ESIMS found for C$_{25}$H$_{23}$F$_3$N$_6$O m/z 481.1 (M+1).

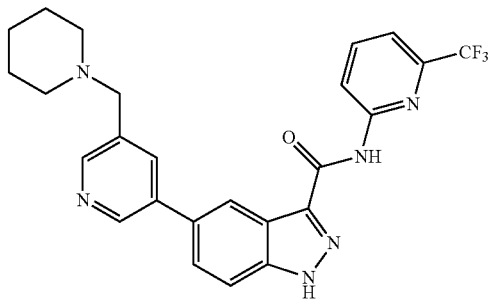

5-(5-(Piperidin-1-ylmethyl)pyridin-3-yl)-N-(6-(trifluoromethyl)pyridin-2-yl)-1H-indazole-3-carboxamide 62

White solid (6.4 mg, 0.01 mmol). $^1$H NMR (DMSO-$d_6$, 500 MHz) δ ppm 1.35-1.45 (m, 2H), 1.46-1.56 (m, 4H), 2.39 (brs, 4H), 3.57 (s, 1H), 7.68 (d, J=7.5 Hz, 1H), 7.83, 7.86 (ABq, $J_{AB}$=13 Hz, 2H), 8.00 (s, 1H), 8.18 (t, J=8 Hz, 1H), 8.45 (d, J=1 Hz, 1H), 8.50 (d, J=2 Hz, 1H), 8.53 (d, J=8.5 Hz, 1H), 8.83 (d, J=2.5 Hz, 1H), 10.25 (s, 1H), 14.12 (brs, 1H); ESIMS found for $C_{25}H_{23}F_3N_6O$ m/z 480.9 (M+1).

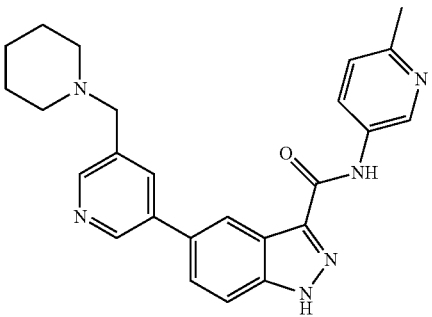

5-(5-(piperidin-1-ylmethyl-$d_2$)pyridin-3-yl)-N-(pyridin-3-yl)-1H-indazole-3-carboxamide 63

Tan solid (149.3 mg, 0.36 mmol). $^1$H NMR (DMSO-$d_6$, 500 MHz) δ ppm 1.39 (brs, 2H), 1.46-1.56 (m, 4H), 2.38 (brs, 4H), 7.40 (dd, J=5.5 Hz, J=8.5 Hz, 1H), 7.82, 7.84 (ABq, $J_{AB}$=11.5 Hz, 2H), 7.99 (s, 1H), 8.27-8.36 (m, 2H), 8.48 (s, 1H), 8.49 (d, J=2 Hz, 1H), 8.82 (d, J=2 Hz, 1H), 9.08 (s, 1H), 10.69 (s, 1H), 14.00 (brs, 1H); ESIMS found for $C_{24}H_{22}D_2N_6O$ m/z 415.2 (M+1).

N-(5-Methylpyridin-3-yl)-5-(5-(piperidin-1-ylmethyl)pyridin-3-yl)-1H-indazole-3-carboxamide 64

White solid (89 mg, 0.21 mmol). $^1$H NMR (DMSO-$d_6$, 500 MHz) δ ppm 1.36-1.44 (m, 2H), 1.48-1.55 (m, 4H), 2.33 (s, 3H), 2.34-2.43 (m, 4H), 3.57 (s, 2H), 7.81, 7.84 (ABq, $J_{AB}$=14.5 Hz, 2H), 7.99 (s, 1H), 8.16 (d, J=1 Hz, 1H), 8.21 (s, 1H), 8.48 (d, J=0.5 Hz, 1H), 8.49 (d, J=2 Hz, 1H), 8.82 (d, J=2 Hz, 1H), 8.85 (d, J=2.5 Hz, 1H), 10.61 (s, 1H), 13.99 (s, 1H); ESIMS found for $C_{25}H_{26}N_6O$ m/z 426.4 (M+1).

N-(6-Methylpyridin-3-yl)-5-(5-(piperidin-1-ylmethyl)pyridin-3-yl)-1H-indazole-3-carboxamide 65

White solid (117 mg, 0.27 mmol). $^1$H NMR (DMSO-$d_6$, 500 MHz) δ ppm 1.36-1.43 (m, 2H), 1.48-1.55 (m, 4H), 2.33-2.42 (m, 4H), 2.45 (s, 3H), 3.57 (s, 2H), 7.25 (d, J=8 Hz, 1H), 7.81, 7.83 (ABq, $J_{AB}$=13.75 Hz, 2H), 7.99 (s, 1H), 8.18 (dd, J=2.5 Hz, J=8.5 Hz, 1H), 8.47 (s, 1H), 8.49 (d, J=1.5 Hz, 1H), 8.82 (d, J=2.5 Hz, 1H), 8.94 (d, J=2.5 Hz, 1H), 10.59 (s, 1H), 13.97 (s, 1H); ESIMS found for $C_{25}H_{26}N_6O$ m/z 426.9 (M+1).

5-(5-(Piperidin-1-ylmethyl)pyridin-3-yl)-N-(5-(trifluoromethyl)pyridin-3-yl)-1H-indazole-3-carboxamide 66

White solid (194 mg, 0.40 mmol). $^1$H NMR (DMSO-$d_6$, 500 MHz) δ ppm 1.35-1.43 (m, 2H), 1.47-1.55 (m, 4H), 2.38 (brs, 4H), 3.57 (s, 2H), 7.83, 7.85 (ABq, $J_{AB}$=10.5 Hz, 2H), 8.00 (s, 1H), 8.49 (s, 1H), 8.50 (d, J=1.5 Hz, 1H), 8.70 (s, 1H), 8.82 (d, J=2 Hz, 1H), 8.35 (d, J=2 Hz, 1H), 11.09 (s, 1H), 14.09 (brs, 1H); ESIMS found for $C_{25}H_{23}F_3N_6O$ m/z 481.2 (M+1).

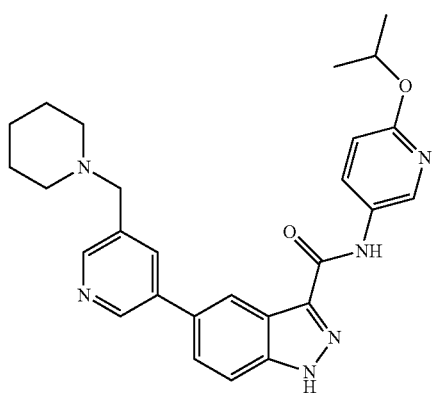

N-(6-Isopropoxypyridin-3-yl)-5-(5-(piperidin-1-ylmethyl)pyridin-3-yl)-1H-indazole-3-carboxamide 67

White solid (131 mg, 0.28 mmol). $^1$H NMR (DMSO-d$_6$, 500 MHz) δ ppm 1.29 (d, J=6.5 Hz, 6H), 1.36-1.43 (m, 2H), 1.48-1.55 (m, 4H), 2.34-2.42 (m, 4H), 3.57 (s, 2H), 5.23 (sep, J=6.25 Hz, 1H), 6.76 (d, J=9 Hz, 1H), 7.80, 7.81 (ABq, J$_{AB}$=10 Hz, 2H), 8.14 (dd, J=2.5 Hz, J=9 Hz, 1H), 8.46 (s, 1H), 8.49 (d, J=1.5 Hz, 1H), 8.62 (d, J=2.5 Hz, 1H), 8.81 (d, J=2 Hz, 1H), 10.49 (s, 1H), 13.93 (s, 1H); ESIMS found for C$_{27}$H$_{30}$N$_6$O$_2$ m/z 471.2 (M+1).

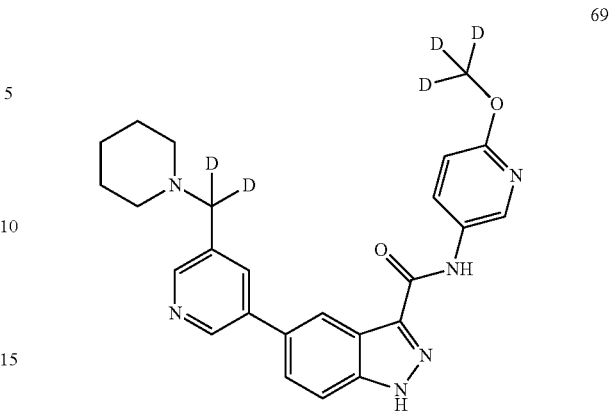

N-(6-(methoxy-d$_3$)pyridin-3-yl)-5-(5-(piperidin-1-ylmethyl-d$_2$)pyridin-3-yl)-1H-indazole-3-carboxamide 69

Beige solid (171.3 mg, 0.38 mmol). $^1$H NMR (DMSO-d$_6$, 500 MHz) δ ppm 1.34-1.43 (m, 2H), 1.46-1.55 (m, 4H), 2.38 (brs, 4H), 6.85 (d, J=9 Hz, 1H), 7.80, 7.83 (ABq, J$_{AB}$=12.25 Hz, 2H), 7.99 (t, J=2 Hz, 1H), 8.18 (dd, J=2.5 Hz, J=9 Hz, 1H), 8.47 (s, 1H), 8.49 (d, J=2 Hz, 1H), 8.65 (d, J=2.5 Hz, 1H), 8.81 (d, J=2.5 Hz, 1H), 10.52 (s, 1H), 13.94 (brs, 1H); ESIMS found for C$_{25}$H$_{21}$D$_5$N$_6$O$_2$ m/z 448.2 (M+1).

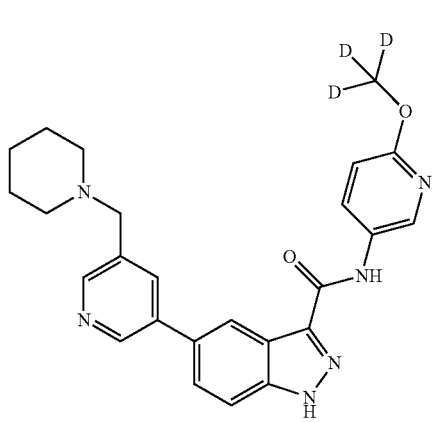

N-(6-(Methoxy-d$_3$)pyridin-3-yl)-5-(5-(piperidin-1-ylmethyl)pyridin-3-yl)-1H-indazole-3-carboxamide 68

White solid (342 mg, 0.77 mmol). $^1$H NMR (DMSO-d$_6$, 500 MHz) δ ppm 1.35-1.43 (m, 2H), 1.47-1.55 (m, 4H), 2.33-2.42 (m, 4H), 3.56 (s, 2H), 6.85 (d, J=9 Hz, 1H), 7.80, 7.83 (ABq, J$_{AB}$=13.5 Hz, 2H), 7.99 (s, 1H), 8.18 (dd, J=2.5 Hz, J=9 Hz, 1H), 8.47 (s, 1H), 8.49 (d, J=1.5 Hz, 1H), 8.65 (d, J=2.5 Hz, 1H), 8.81 (d, J=2 Hz, 1H), 10.52 (s, 1H), 13.94 (s, 1H); ESIMS found for C$_{25}$H$_{23}$D$_3$N$_6$O$_2$ m/z 446.3 (M+1).

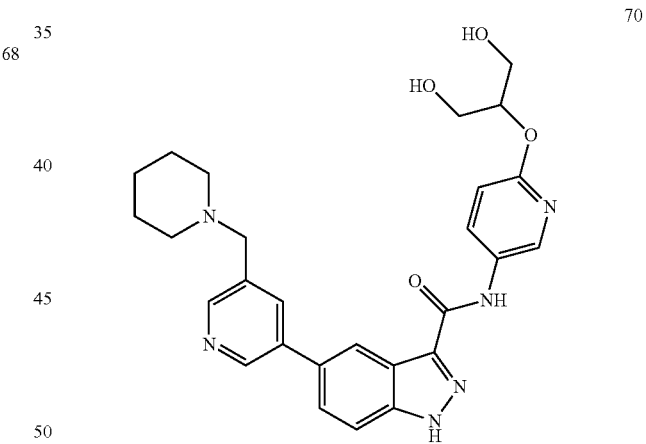

N-(6-((1,3-Dihydroxypropan-2-yl)oxy)pyridin-3-yl)-5-(5-(piperidin-1-ylmethyl)pyridin-3-yl)-1H-indazole-3-carboxamide 70

Red solid (30 mg, 0.06 mmol). $^1$H NMR (DMSO-d$_6$, 500 MHz) δ ppm 1.40 (brs, 2H), 1.47-1.56 (m, 4H), 2.38 (brs, 4H), 3.54 (s, 2H), 3.74 (dd, J=3.5 Hz, J=13 Hz, 1H), 3.88 (dd, J=2 Hz, J=12.5 Hz, 1H), 4.80 (dd, J=6.5 Hz, J=12 Hz, 1H), 5.02 (t, J=10 Hz, 1H), 5.38-5.48 (m, 1H), 7.38 (d, J=8.5 Hz, 1H), 7.62 (d, J=9.5 Hz, 1H), 7.73 (d, J=8.5 Hz, 1H), 7.92 (s, 1H), 8.30 (s, 1H), 8.40 (s, 2H), 8.76 (d, J=2 Hz, 1H), 9.58 (d, J=2 Hz, 1H); ESIMS found for C$_{27}$H$_{30}$N$_6$O$_4$ m/z 503.3 (M+1).

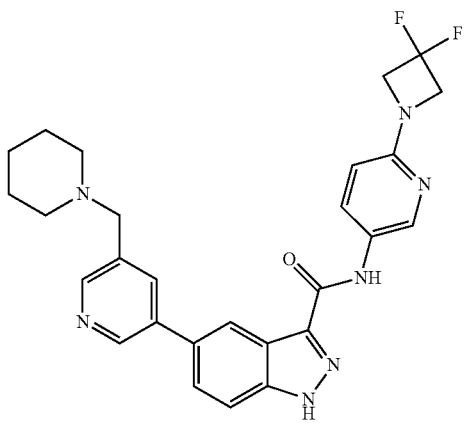

N-(6-(3,3-Difluoroazetidin-1-yl)pyridin-3-yl)-5-(5-(piperidin-1-ylmethyl)pyridin-3-yl)-1H-indazole-3-carboxamide 71

White solid (157 mg, 0.31 mmol). $^1$H NMR (DMSO-$d_6$, 500 MHz) δ ppm 1.35-1.45 (m, 2H), 1.46-1.56 (m, 4H), 2.38 (brs, 4H), 3.56 (s, 2H), 4.37 (t, J=12.5 Hz, 4H), 6.64 (d, J=8.5 Hz, 1H), 7.79, 7.82 (dABq, J=1.5 Hz, $J_{AB}$=12.75 Hz, 2H), 7.98 (t, J=2.5 Hz, 1H), 8.12 (dd, J=2.5 Hz, J=9 Hz, 1H), 8.46 (d, J=Hz, 1H), 8.48 (d, J=2 Hz, 1H), 8.62 (d, J=2.5 Hz, 1H), 8.81 (d, J=2.5 Hz, 1H), 10.42 (s, 1H), 13.91 (brs, 1H); ESIMS found for $C_{27}H_{27}F_2N_7O$ m/z 504.3 (M+1).

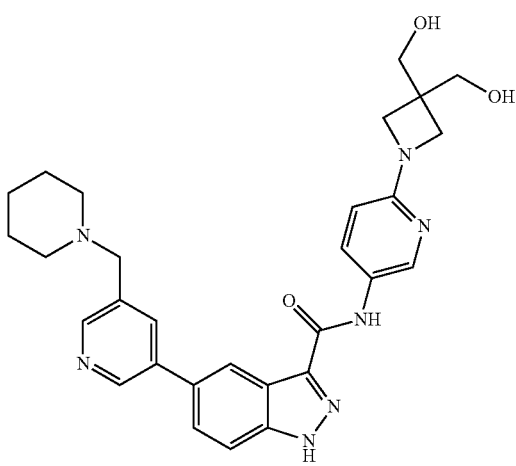

N-(6-(3,3-Bis(hydroxymethyl)azetidin-1-yl)pyridin-3-yl)-5-(5-(piperidin-1-ylmethyl)pyridin-3-yl)-1H-indazole-3-carboxamide 72

Off-white solid (92 mg, 0.17 mmol). $^1$H NMR (DMSO-$d_6$, 500 MHz) δ ppm 1.39 (brs, 2H), 1.46-1.56 (m, 4H), 2.38 (brs, 4H), 3.51-3.60 (m, 6H), 3.65 (s, 4H), 4.77 (t, J=5 Hz, 2H), 6.39 (d, J=9 Hz, 1H), 7.79, 7.82 (ABq, $J_{AB}$=14.5 Hz, 2H), 7.93-8.04 (m, 2H), 8.46 (s, 1H), 8.48 (d, J=2 Hz, 2H), 8.81 (s, 1H), 10.26 (s, 1H), 13.87 (brs, 1H); ESIMS found for $C_{29}H_{33}N_7O_3$ m/z 528.5 (M+1).

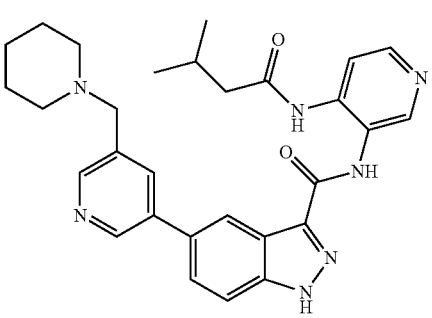

N-(4-(3-Methylbutanamido)pyridin-3-yl)-5-(5-(piperidin-1-ylmethyl)pyridin-3-yl)-1H-indazole-3-carboxamide 73

Light brown solid (13 mg, 0.03 mmol). $^1$H NMR (DMSO-$d_6$, 500 MHz) δ ppm 0.91 (d, J=7 Hz, 6H), 1.38 (brs, 2H), 1.45-1.55 (m, 4H), 2.05-2.15 (m, 1H), 2.29 (d, J=7.5 Hz, 1H), 2.36 (brs, 4H), 3.55 (s, 2H), 7.67 (d, J=5.5 Hz, 1H), 7.81, 7.84 (ABq, $J_{AB}$=13.5 Hz, 2H), 7.97 (t, J=2 Hz, 1H), 8.35 (d, J=5.5 Hz, 1H), 8.43 (s, 1H), 8.48 (d, J=1.5 Hz, 1H), 8.80 (d, J=2 Hz, 1H), 8.81 (s, 1H), 10.00 (s, 1H), 10.03 (s, 1H), 13.97 (brs, 1H); ESIMS found for $C_{29}H_{33}N_7O_2$ m/z 512.4 (M+1).

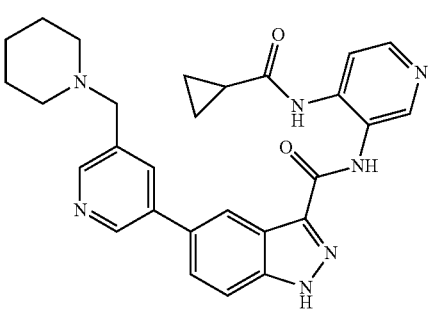

N-(4-(Cyclopropanecarboxamido)pyridin-3-yl)-5-(5-(piperidin-1-ylmethyl)pyridin-3-yl)-1H-indazole-3-carboxamide 74

Light brown solid (11 mg, 0.02 mmol). $^1$H NMR (DMSO-$d_6$, 500 MHz) δ ppm 0.80-0.89 (m, 2H), 0.89-94 (m, 2H), 1.39 (brs, 2H), 1.46-1.55 (m, 4H), 1.91-2.00 (m, 1H), 2.37 (brs, 4H), 3.55 (s, 2H), 7.73 (d, J=5.5 Hz, 1H), 7.81, 7.83 (ABq, $J_{AB}$=1.75 Hz, 2H), 7.98 (s, 1H), 8.34 (d, J=5.5 Hz, 1H), 8.44 (s, 1H), 8.48 (d, J=2 Hz, 1H), 8.80 (s, 1H), 8.80 (d, J=2 Hz, 1H), 10.03 (s, 1H), 10.30 (s, 1H), 13.97 (brs, 1H); ESIMS found for $C_{28}H_{29}N_7O_2$ m/z 496.4 (M+1).

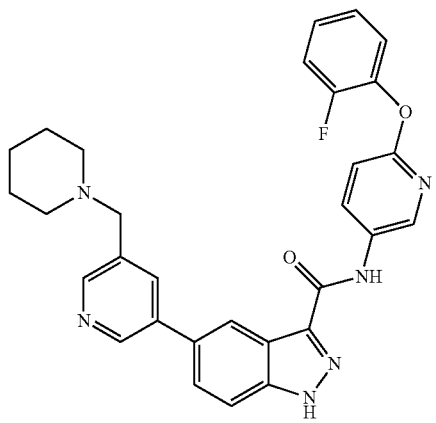

N-(6-(2-Fluorophenoxy)pyridin-3-yl)-5-(5-(piperidin-1-ylmethyl)pyridin-3-yl)-1H-indazole-3-carboxamide 75

White solid (127 mg, 0.24 mmol). $^1$H NMR (DMSO-$d_6$, 500 MHz) δ ppm 1.35-1.44 (m, 2H), 1.47-1.55 (m, 4H), 2.38 (brs, 4H), 3.56 (s, 2H), 7.16 (d, J=8.5 Hz, 1H), 7.22-7.41 (m, 4H), 7.81, 7.83 (ABq, $J_{AB}$=12.25 Hz, 2H), 7.98 (s, 1H), 8.38 (dd, J=2.5 Hz, J=9 Hz, 1H), 8.45 (s, 1H), 8.49 (d, J=2 Hz, 1H), 8.56 (d, J=2.5 Hz, 1H), 8.81 (d, J=2 Hz, 1H), 10.65 (s, 1H), 13.96 (brs, 1H); ESIMS found for $C_{30}H_{27}FN_6O_2$ m/z 523.4 (M+1).

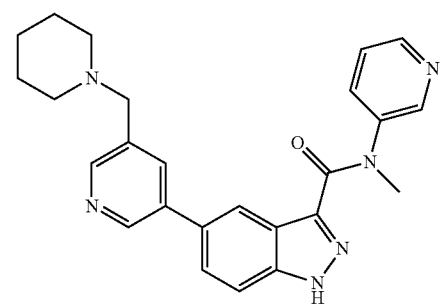

N-Methyl-5-(5-(piperidin-1-ylmethyl)pyridin-3-yl)-N-(pyridin-3-yl)-1H-indazole-3-carboxamide 76

White solid (65 mg, 0.15 mmol). $^1$H NMR (DMSO-$d_6$, 500 MHz) δ ppm 1.35-1.44 (m, 2H), 1.47-1.56 (m, 4H), 2.38 (brs, 4H), 3.54 (s, 3H), 3.57 (s, 2H), 7.37 (dd, J=5 Hz, J=8 Hz, 1H), 7.63 (d, J=8.5 Hz, 1H), 7.73 (d, J=9 Hz, 1H), 7.77 (d, J=8 Hz, 1H), 7.95 (s, 1H), 8.25 (s, 1H), 8.39 (d, J=4 Hz, 1H), 8.47 (s, 1H), 8.78 (d, J=2 Hz, 1H), 13.48 (s, 1H); ESIMS found for $C_{25}H_{26}N_6O$ m/z 427.0 (M+1).

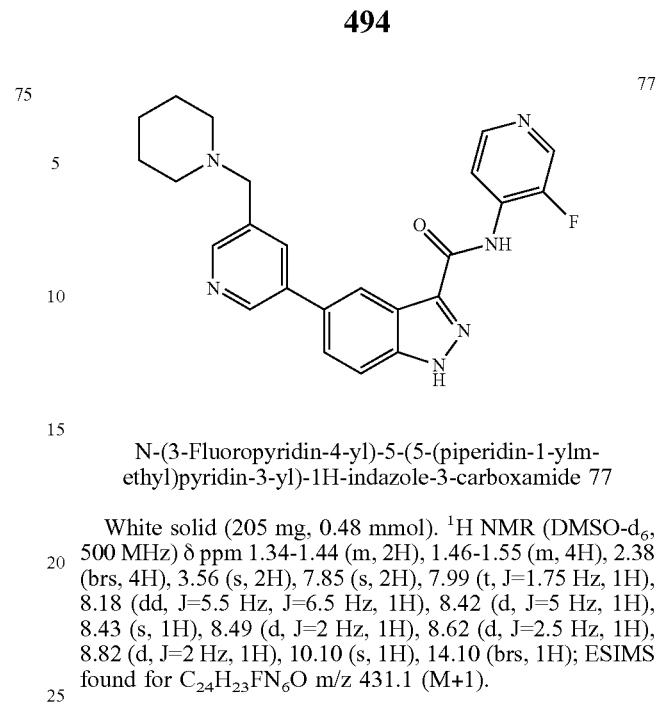

N-(3-Fluoropyridin-4-yl)-5-(5-(piperidin-1-ylmethyl)pyridin-3-yl)-1H-indazole-3-carboxamide 77

White solid (205 mg, 0.48 mmol). $^1$H NMR (DMSO-$d_6$, 500 MHz) δ ppm 1.34-1.44 (m, 2H), 1.46-1.55 (m, 4H), 2.38 (brs, 4H), 3.56 (s, 2H), 7.85 (s, 2H), 7.99 (t, J=1.75 Hz, 1H), 8.18 (dd, J=5.5 Hz, J=6.5 Hz, 1H), 8.42 (d, J=5 Hz, 1H), 8.43 (s, 1H), 8.49 (d, J=2 Hz, 1H), 8.62 (d, J=2.5 Hz, 1H), 8.82 (d, J=2 Hz, 1H), 10.10 (s, 1H), 14.10 (brs, 1H); ESIMS found for $C_{24}H_{23}FN_6O$ m/z 431.1 (M+1).

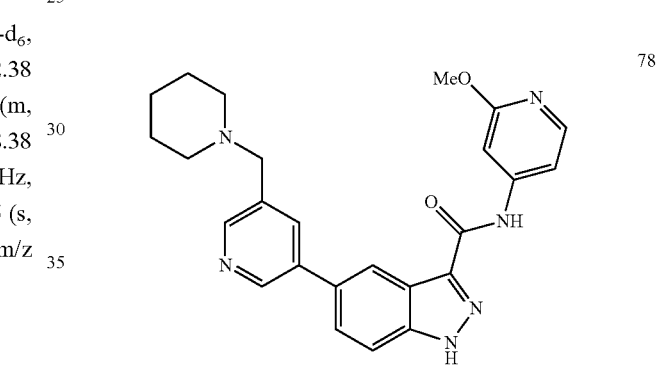

N-(2-Methoxypyridin-4-yl)-5-(5-(piperidin-1-ylmethyl)pyridin-3-yl)-1H-indazole-3-carboxamide 78

White solid (143 mg, 0.32 mmol). $^1$H NMR (DMSO-$d_6$, 500 MHz) δ ppm 1.35-1.43 (m, 2H), 1.48-1.55 (m, 4H), 2.38 (brs, 4H), 3.57 (s, 2H), 3.85 (s, 3H), 7.46 (d, J=1.5 Hz, 1H), 7.55 (dd, J=1.5 Hz, J=5.5 Hz, 1H), 7.82, 7.84 (ABq, $J_{AB}$=10.5 Hz, 2H), 8.00 (s, 1H), 8.07 (d, J=5.5 Hz, 1H), 8.46 (s, 1H), 8.49 (d, J=0.5 Hz, 1H), 8.82 (d, J=2.5 Hz, 1H), 10.78 (s, 1H), 14.04 (brs, 1H) ESIMS found for $C_{25}H_{26}N_6O_2$ m/z 443.1 (M+1).

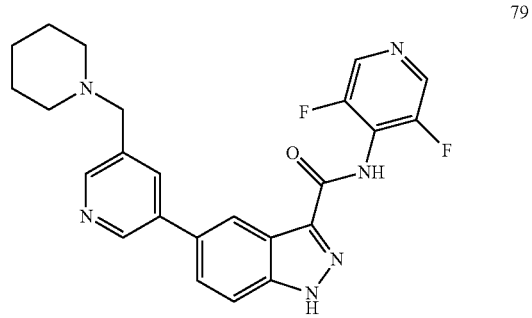 [SMILES: O=C(Nc1c(F)cncc1F)c1n[nH]c2ccc(-c3cncc(CN4CCCCC4)c3)cc12]

N-(3,5-Difluoropyridin-4-yl)-5-(5-(piperidin-1-ylmethyl)pyridin-3-yl)-1H-indazole-3-carboxamide 79

White solid (48 mg, 0.11 mmol). $^1$H NMR (DMSO-$d_6$, 500 MHz) δ ppm 1.38 (brs, 2H), 1.45-1.55 (m, 4H), 2.36 (brs, 4H), 3.55 (s, 2H), 7.84 (s, 2H), 7.98 (s, 1H), 8.39 (s, 1H), 8.48 (s, 1H), 8.63 (s, 2H), 8.80 (s, 1H), 10.68 (s, 1H), 14.09 (s, 1H); ESIMS found for $C_{24}H_{22}F_2N_6O$ m/z 449.1 (M+1).

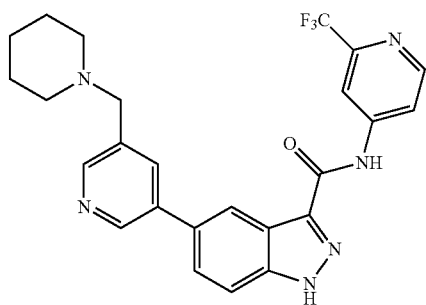

80

5-(5-(Piperidin-1-ylmethyl)pyridin-3-yl)-N-(2-(trifluoromethyl)pyridin-4-yl)-1H-indazole-3-carboxamide 80

White solid (4.8 mg, 0.01 mmol). $^1$H NMR (DMSO-$d_6$, 500 MHz) δ ppm 1.33-1.45 (m, 2H), 1.52 (quin, J=5.56 Hz, 4H), 2.32-2.44 (m, 4H), 3.57 (s, 2H), 7.84, 7.86 (ABq, $J_{AB}$=9.5 Hz, 2H), 8.01 (t, J=2.06 Hz, 1H), 8.21 (dd, J=5.49, 1.92 Hz, 1H), 8.46-8.55 (m, 3H), 8.67 (d, J=5.49 Hz, 1H), 8.83 (d, J=2.20 Hz, 1H), 11.25 (s, 1H), 14.07-14.21 (m, 1H); ESIMS found for $C_{25}H_{23}F_3N_6O$ m/z 481.1 (M+1).

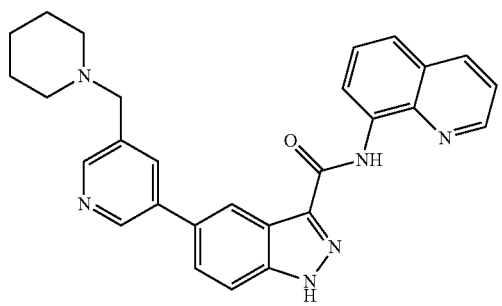

81

5-(5-(Piperidin-1-ylmethyl)pyridin-3-yl)-N-(quinolin-8-yl)-1H-indazole-3-carboxamide 81

White solid (86.5 mg, 0.19 mmol). $^1$H NMR (DMSO-$d_6$, 500 MHz) δ ppm 1.36-1.45 (m, 2H), 1.48-1.57 (m, 4H), 2.40 (brs, 4H), 3.58 (s, 2H), 7.63-7.78 (m, 3H), 7.85, 7.88 (ABq, $J_{AB}$=10.5 Hz, 2H), 8.20 (t, J=2 Hz, 1H), 8.48 (dd, J=2 Hz, J=8.5 Hz, 1H), 8.51 (d, J=2 Hz, 1H), 8.56 (s, 1H), 8.84 (d, J=2 Hz, 1H), 8.90 (dd, J=Hz, J=7.5 Hz, 1H), 9.03 (dd, J=1.5 Hz, J=4.5 Hz, 1H), 11.40 (s, 1H), 14.01 (brs, 1H); ESIMS found for $C_{28}H_{26}N_6O$ m/z 463.2 (M+1)

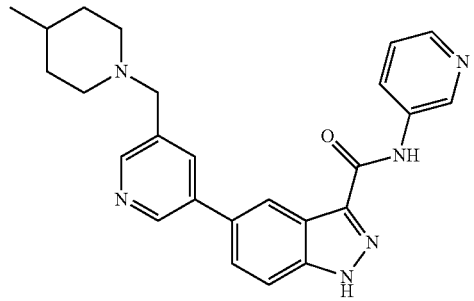

82

5-(5-((4-Methylpiperidin-1-yl)methyl)pyridin-3-yl)-N-(pyridin-3-yl)-1H-indazole-3-carboxamide 82

White solid (48 mg, 0.11 mmol). $^1$H NMR (DMSO-$d_6$, 500 MHz) δ ppm 0.89 (d, J=6.5 Hz, 3H), 1.16 (q, J=1.5 Hz, 2H), 1.34 (brs, 1H), 1.58 (d, J=12.5 Hz, 2H), 1.97 (t, J=11 Hz, 2H), 2.82 (d, J=11 Hz, 2H), 3.58 (s, 2H), 7.40 (dd, J=8.5 Hz, J=5 Hz, 1H), 7.82, 7.84 (ABq, $J_{AB}$=10 Hz, 2H), 7.99 (s, 1H), 8.28-8.35 (m, 2H), 8.48 (d, J=6.5 Hz, 1H), 8.82 (d, J=1.5 Hz, 1H), 9.08 (d, J=1.5 Hz, 1H), 10.69 (s, 1H), 14.00 (s, 1H); ESIMS found for $C_{25}H_{26}N_6O$ m/z 427.0 (M+1).

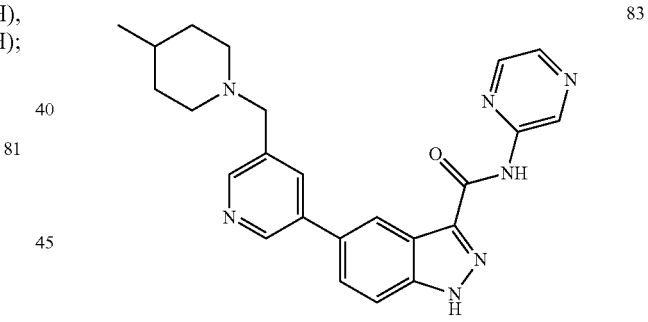

83

5-(5-((4-Methylpiperidin-1-yl)methyl)pyridin-3-yl)-N-(pyrazin-2-yl)-1H-indazole-3-carboxamide 83

White solid (70 mg, 0.16 mmol). $^1$H NMR (DMSO-$d_6$, 500 MHz) δ ppm 0.89 (d, J=6.5 Hz, 3H), 1.16 (q, J=11 Hz, 2H), 1.34 (brs, 1H), 1.58 (d, J=12 Hz, 2H), 1.98 (t, J=10.5 Hz, 2H), 2.82 (d, J=9.5 Hz, 2H), 3.58 (s, 2H), 7.85 (ABq, $J_{AB}$=10.5 Hz, 2H), 8.01 (s, 1H), 8.45 (d, J=2.5 Hz, 1H), 8.47 (s, 1H), 8.50 (d, J=1.5 Hz, 2H), 8.83 (s, 1H), 9.50 (d, J=1 Hz, 1H), 10.36 (s, 1H), 14.11 (brs, 1H); ESIMS found for $C_{24}H_{25}N_7O$ m/z 428.0 (M+1).

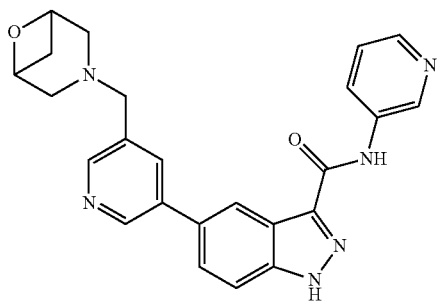

5-(5-((6-Oxa-3-azabicyclo[3.1.1]heptan-3-yl)methyl)pyridin-3-yl)-N-(pyridin-3-yl)-1H-indazole-3-carboxamide 84

White solid (73 mg, 0.17 mmol). $^1$H NMR (DMSO-$d_6$, 500 MHz) δ ppm 2.29 (d, J=8 Hz, 1H), 2.74 (d, J=11.5 Hz, 2H), 2.86 (q, J=6.5 Hz, 1H), 3.04 (d, J=1.5 Hz, 2H), 3.87 (s, 2H), 4.43 (d, J=6 Hz, 2H), 7.40 (dd, J=5 Hz, J=8.5 Hz, 1H), 7.82, 7.85 (ABq, J$_{AB}$=15.75 Hz, 2H), 8.06 (t, J=2 Hz, 1H), 8.28-8.35 (m, 2H), 8.49 (s, 1H), 8.57 (d, J=1.5 Hz, 1H), 8.84 (d, J=2.5 Hz, 1H), 9.08 (d, J=2 Hz, 1H), 10.68 (s, 1H), 13.99 (s, 1H); ESIMS found for C$_{24}$H$_{22}$N$_6$O$_2$ m/z 427.1 (M+1).

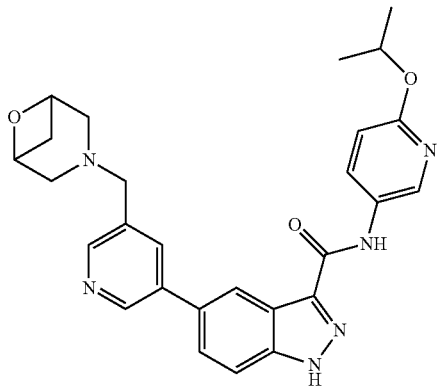

5-(5-((6-Oxa-3-azabicyclo[3.1.1]heptan-3-yl)methyl)pyridin-3-yl)-N-(6-isopropoxypyridin-3-yl)-1H-indazole-3-carboxamide 85

White solid (140 mg, 0.29 mmol). $^1$H NMR (DMSO-$d_6$, 500 MHz) δ ppm 1.29 (d, J=6.5 Hz, 6H), 2.28 (d, J=7.5 Hz, 1H), 2.74 (d, J=11.5 Hz, 2H), 2.86 (q, J=7.5 Hz, 1H), 3.03 (d, J=1.5 Hz, 2H), 3.87 (s, 2H), 4.23 (d, J=6.5 Hz, 2H), 5.22 (pen, J=6 Hz, 1H), 6.76 (d, J=9 Hz, 1H), 7.80, 7.83 (ABq, J$_{AB}$=15.75 Hz, 2H), 8.05 (t, J=2 Hz, 1H), 8.14 (dd, J=2.5 Hz, J=8.5 Hz, 1H), 8.31 (s, 1H), 8.47 (s, 1H), 8.56 (s, 1H), 8.61 (d, J=2.5 Hz, 1H), 8.83 (d, J=2 Hz, 1H), 10.47 (s, 1H), 13.92 (brs, 1H); ESIMS found for C$_{27}$H$_{28}$N$_6$O$_3$ m/z 485.1 (M+1).

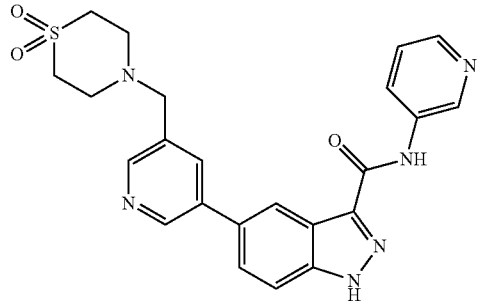

5-(5-((1,1-Dioxidothiomorpholino)methyl)pyridin-3-yl)-N-(pyridin-3-yl)-1H-indazole-3-carboxamide 86

Beige solid (56.1 mg, 0.12 mmol). $^1$H NMR (DMSO-$d_6$, 500 MHz) δ ppm 2.91-2.98 (m, 4H), 3.11-3.18 (m, 4H), 3.83 (s, 2H), 7.40 (dd, J=5.5 Hz, J=8.5 Hz, 1H), 7.82, 7.86 (ABq, J$_{AB}$=18.5 Hz, 2H), 8.08 (t, J=2 Hz, 1H), 8.28-8.35 (m, 2H), 8.49 (s, 1H), 8.56 (d, J=2 Hz, 1H), 8.85 (d, J=2 Hz, 1H), 9.08 (d, J=2 Hz, 1H), 10.69 (s, 1H), 14.00 (s, 1H); ESIMS found for C$_{23}$H$_{22}$N$_6$O$_3$S m/z 463.1 (M+1).

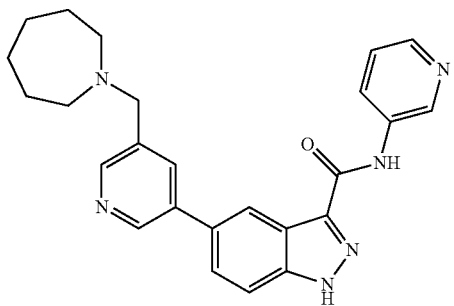

5-(5-(Azepan-1-ylmethyl)pyridin-3-yl)-N-(pyridin-3-yl)-1H-indazole-3-carboxamide 87

White solid (117 mg, 0.27 mmol) $^1$H NMR (DMSO-$d_6$, 500 MHz) δ ppm 1.55-1.64 (m, 8H), 2.61-2.66 (m, 4H), 3.75 (s, 2H), 7.40 (dd, J=4.75 Hz, J=8.25 Hz, 1H), 7.83 (s, 2H), 8.03 (s, 1H), 8.31 (d, J=3.5 Hz, 1H), 8.32 (t, J=2.25 Hz, 1H), 8.48 (s, 1H), 8.52 (d, J=2 Hz, 1H), 8.81 (d, J=2 Hz, 1H), 9.08 (d, J=2.5 Hz, 1H), 10.69 (s, 1H), 14.00 (s, 1H); ESIMS found for C$_{25}$H$_{26}$N$_6$O m/z 427.2 (M+1).

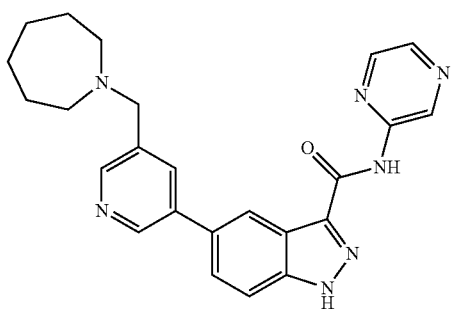

5-(5-(Azepan-1-ylmethyl)pyridin-3-yl)-N-(pyrazin-2-yl)-1H-indazole-3-carboxamide 88

White solid (104 mg, 0.24 mmol). $^1$H NMR (DMSO-$d_6$, 500 MHz) δ ppm 1.55-1.65 (m, 8H), 2.61-2.67 (m, 4H), 3.75 (s, 2H), 7.85 (s, 2H), 8.04 (s, 1H), 8.45 (d, J=2 Hz, 1H), 8.47 (s, 1H), 8.49 (t, J=1.75 Hz, 1H), 8.53 (s, 1H), 8.82 (d, J=2 Hz, 1H), 9.50 (d, J=1 Hz, 1H), 10.35 (s, 1H), 14.11 (brs, 1H); ESIMS found for $C_{24}H_{25}N_7O$ m/z 428.1 (M+1).

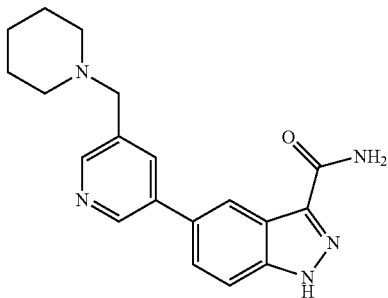

5-(5-(Piperidin-1-ylmethyl)pyridin-3-yl)-1H-indazole-3-carboxamide 89

White solid (13.6 mg, 0.04 mmol). $^1$H NMR (DMSO-$d_6$, 500 MHz) δ ppm 1.36-1.45 (m, 2H), 1.48-1.57 (m, 4H), 2.38 (brs, 4H), 3.56 (s, 2H), 7.42 (s, 1H), 7.74 (d, J=8.4 Hz, 1H), 7.77 (dd, J=1.6 Hz, J=8.7 Hz, 1H), 7.80 (s, 1H), 7.96-7.97 (m, 1H), 8.41-8.42 (m, 1H), 8.47-8.48 (m, 1H), 8.78-8.79 (m, 1H), 13.67 (s, 1H); ESIMS found for $C_{19}H_{21}N_5O$ m/z 336.0 (M+1).

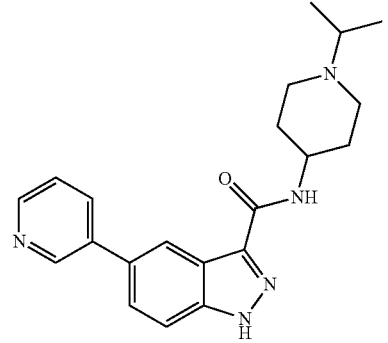

N-(1-Isopropylpiperidin-4-yl)-5-(pyridin-3-yl)-1H-indazole-3-carboxamide 90

White solid (77.2 mg, 0.21 mmol). $^1$H NMR (DMSO-$d_6$, 500 MHz) δ ppm 0.97 (d, J=6.5 Hz, 6H), 1.63 (qd, J=3.5 Hz, J=12 Hz, 2H), 1.80 (d, J=10 Hz, 2H), 2.18 (td, J=2 Hz, J=10 Hz, 2H), 2.68 (quin, J=6.5 Hz, 1H), 2.79 (d, J=1.5 Hz, 2H), 3.81 (sep, J=5.2 Hz, 1H), 7.51 (ddd, J=Hz, J=4.5 Hz, J=7.5 Hz, 1H), 7.74, 7.77 (ABq, $J_{AB}$=17 Hz, 2H), 8.09 (dt, J=1.5 Hz, J=6 Hz, 1H), 8.17 (d, J=8.5 Hz, 1H), 8.42 (d, J=2.5 Hz, 1H), 8.58 (dd, J=1.5 Hz, J=4.5 Hz, 1H), 8.90 (d, J=2.5 Hz, 1H), 13.65 (brs, 1H); ESIMS found for $C_{21}H_{25}N_5O$ m/z 364.3 (M+1).

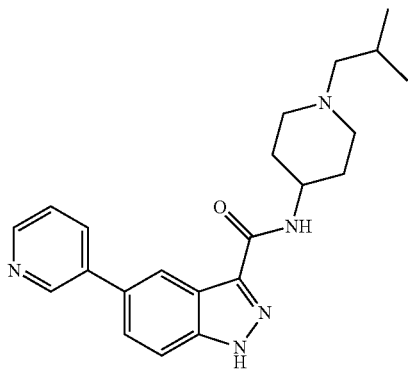

N-(1-Isobutylpiperidin-4-yl)-5-(pyridin-3-yl)-1H-indazole-3-carboxamide 91

White solid (24.6 mg, 0.07 mmol). $^1$H NMR (DMSO-$d_6$, 500 MHz) δ ppm 0.86 (d, J=6.5 Hz, 6H), 1.68 (qd, J=3.5 Hz, J=12 Hz, 2H), 1.73-1.82 (m, 2H), 1.95 (t, J=11 Hz, 2H), 2.03 (d, J=7.5 Hz, 2H), 2.82 (d, J=1.5 Hz, 2H), 3.84 (non, J=5 Hz, 1H), 7.51 (dd, J=5 Hz, J=8 Hz, 1H), 7.74, 7.77 (ABq, $J_{AB}$=16.5 Hz, 2H), 8.09 (dt, J=1.5 Hz, J=8 Hz, 1H), 8.19 (d, J=8 Hz, 1H), 8.42 (s, 1H), 8.58 (dd, J=1.5 Hz, J=5 Hz, 1H), 8.90 (d, J=2 Hz, 1H), 13.66 (brs, 1H); ESIMS found for $C_{22}H_{27}N_5O$ m/z 378.1 (M+1).

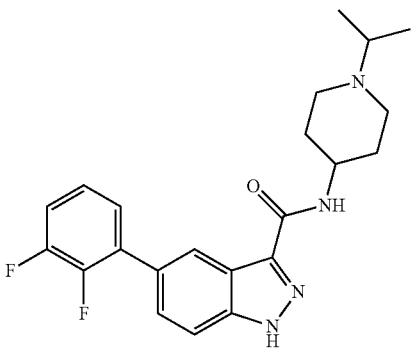

5-(2,3-Difluorophenyl)-N-(1-isopropylpiperidin-4-yl)-1H-indazole-3-carboxamide 92

Beige solid (47.6 mg, 0.12 mmol). $^1$H NMR (DMSO-$d_6$, 500 MHz) δ ppm 0.97 (d, J=6.5 Hz, 6H), 1.62 (qd, J=3.5 Hz, J=12 Hz, 2H), 1.79 (d, J=11 Hz, 2H), 2.18 (t, J=10.5 Hz, 2H), 2.64-2.74 (m, 1H), 2.79 (d, J=1 Hz, 2H), 3.75-3.84 (m, 1H), 7.28-7.36 (m, 1H), 7.36-7.49 (m, 2H), 7.61 (d, J=8.5 Hz, 1H), 7.73 (d, J=9 Hz, 1H), 8.18 (d, J=8 Hz, 1H), 8.35 (s, 1H), 13.70 (brs, 1H); ESIMS found for $C_{22}H_{24}F_2N_4O$ m/z 398.8 (M+1).

93

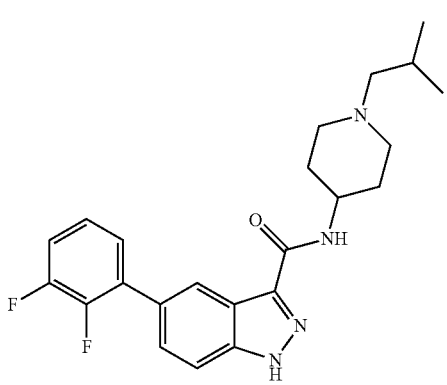

5-(2,3-Difluorophenyl)-N-(1-isobutylpiperidin-4-yl)-1H-indazole-3-carboxamide 93

White solid (33.4 mg, 0.08 mmol). $^1$H NMR (DMSO-d$_6$, 500 MHz) δ ppm 0.86 (d, J=6.5 Hz, 6H), 1.67 (qd, J=3.5 Hz, J=12 Hz, 2H), 1.71-1.80 (m, 3H), 1.94 (t, J=10.8 Hz, 2H), 2.03 (d, J=7.5 Hz, 2H), 2.82 (d, J=12 Hz, 2H), 3.76-3.85 (m, 1H), 7.28-7.36 (m, 1H), 7.36-7.49 (m, 2H), 7.61 (d, J=8.5 Hz, 1H), 7.73 (d, J=8.5 Hz, 1H), 8.19 (d, J=8 Hz, 1H), 8.34 (s, 1H), 13.70 (brs, 1H); ESIMS found for C$_{23}$H$_{26}$F$_2$N$_4$O m/z 413.1 (M+1).

94

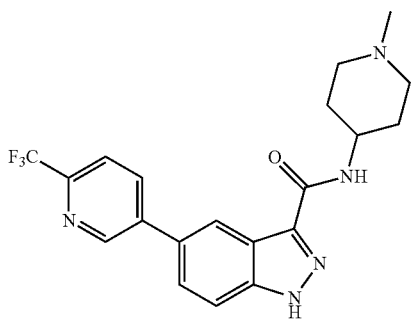

N-(1-Methylpiperidin-4-yl)-5-(6-(trifluoromethyl)pyridin-3-yl)-1H-indazole-3-carboxamide 94

White solid (60.6 mg, 0.15 mmol). $^1$H NMR (DMSO-d$_6$, 500 MHz) δ ppm $^1$H 1.65-1.79 (m, 4H), 1.97 (td, J=12.00, 2.20 Hz, 2H), 2.17 (s, 3H), 2.76 (d, J=11.53 Hz, 2H), 3.76-3.89 (m, 1H), 7.78 (d, J=8.23 Hz, 1H), 7.85 (dd, J=8.51, 1.92 Hz, 1H), 8.00 (d, J=8.23 Hz, 1H), 8.23 (d, J=8.23 Hz, 1H), 8.30 (s, 1H), 8.38 (dd, J=7.96, 1.92 Hz, 1H), 8.52 (s, 1H), 9.11 (d, J=1.65 Hz, 1H), 13.74 (brs, 1H); ESIMS found for C$_{20}$H$_{20}$F$_3$N$_5$O m/z 404.1 (M+1).

95

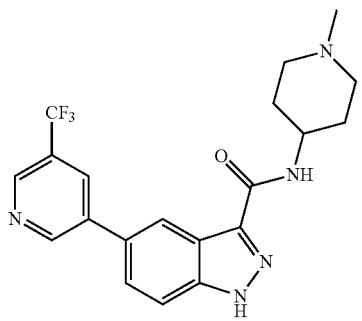

N-(1-Methylpiperidin-4-yl)-5-(5-(trifluoromethyl)pyridin-3-yl)-1H-indazole-3-carboxamide 95

White solid (41.3 mg, 0.10 mmol). $^1$H NMR (DMSO-d$_6$, 500 MHz) δ ppm 1.66-1.79 (m, 4H), 1.96 (td, J=11.00, 2.20 Hz, 2H), 2.17 (s, 3H), 2.76 (d, J=12.08 Hz, 2H), 3.78-3.86 (m, 1H), 7.77 (d, J=8.24 Hz, 1H), 7.87 (dd, J=8.78, 1.65 Hz, 1H), 8.23 (d, J=8.23 Hz, 1H), 8.45 (s, 1H), 8.50 (s, 1H), 8.97 (s, 1H), 9.21 (d, J=1.65 Hz, 1H), 13.73 (brs, 1H); ESIMS found for C$_{20}$H$_{20}$F$_3$N$_5$O m/z 404.2 (M+1).

96

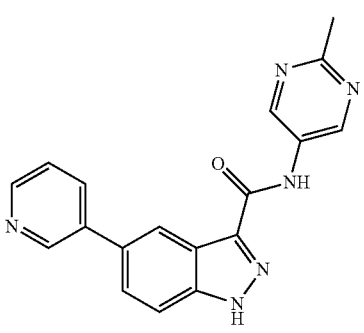

5-(2,3-Difluorophenyl)-N-(pyridin-3-yl)-1H-indazole-3-carboxamide 96

White solid (4.6 mg, 0.01 mmol). $^1$H NMR (DMSO-d$_6$, 500 MHz) δ ppm 7.29-7.51 (m, 4H), 7.68 (d, J=9 Hz, 1H), 7.81 (d, J=9 Hz, 1H), 8.26-8.34 (m, 2H), 8.41 (s, 1H), 9.07 (d, J=1.5 Hz, 1H), 10.67 (s, 1H), 14.03 (s, 1H); ESIMS found for C$_{19}$H$_{12}$F$_2$N$_4$O m/z 351.0 (M+1).

97

N-(2-Methylpyrimidin-5-yl)-5-(pyridin-3-yl)-1H-indazole-3-carboxamide 97

White solid (25 mg, 0.08 mmol). $^1$H NMR (DMSO-d$_6$, 500 MHz) δ ppm 2.60 (s, 3H), 7.52 (dd, J=5 Hz, J=8 Hz, 1H), 7.82 7.84 (ABq, J$_{AB}$=10.75 Hz, 2H), 8.13 (dt, J=2 Hz, J=8 Hz, 1H), 8.48 (s, 1H), 8.60 (dd, J=1.5 Hz, J=4.5 Hz, 1H), 8.94 (d, J=2.5 Hz, 1H), 9.18 (s, 2H), 10.80 (s, 1H), 14.04 (s, 1H); ESIMS found for C$_8$H$_{14}$N$_6$O m/z 330.7 (M+1).

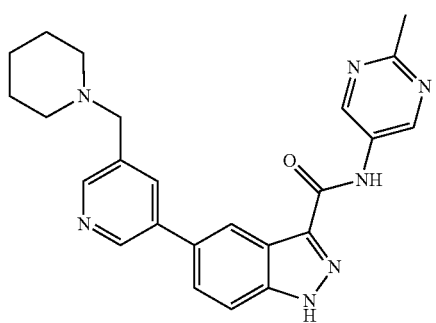

N-(2-Methylpyrimidin-5-yl)-5-(5-(piperidin-1-ylmethyl)pyridin-3-yl)-1H-indazole-3-carboxamide 98

Brown solid (13.8 mg, 0.03 mmol). $^1$H NMR (DMSO-d$_6$, 500 MHz) δ ppm 1.40 (brs, 2H), 1.51 (brs, 4H), 2.38 (brs, 4H), 2.60 (brs, 3H), 3.57 (brs, 2H), 7.83 (brs, 2H), 7.99 (brs, 1H), 8.48 (brd, J=9 Hz, 2H), 8.81 (brs, 1H), 9.18 (brs, 2H), 10.81 (brs, 1H), 14.05 (brs, 1H); ESIMS found for C$_{24}$H$_{25}$N$_7$O m/z 428.2 (M+1).

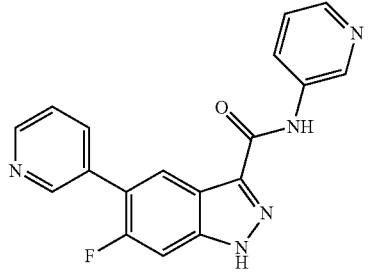

6-Fluoro-N,5-di(pyridin-3-yl)-1H-indazole-3-carboxamide 99

Brown solid (17.3 mg, 0.05 mmol). $^1$H NMR (DMSO-d$_6$, 500 MHz) δ ppm 7.40 (dd, J=8.23, 4.39 Hz, 1H), 7.55 (dd, J=7.96, 4.67 Hz, 1H), 7.70 (d, J=10.50 Hz, 1H), 8.03 (d, J=8.23 Hz, 1H), 8.29-8.34 (m, 3H), 8.63-8.67 (m, 1H), 8.80 (brs, 1H), 9.07 (brs, 1H), 10.71 (s, 1H), 14.07 (s, 1H); ESIMS found for C$_8$H$_{12}$FN$_5$O m/z 333.9 (M+1).

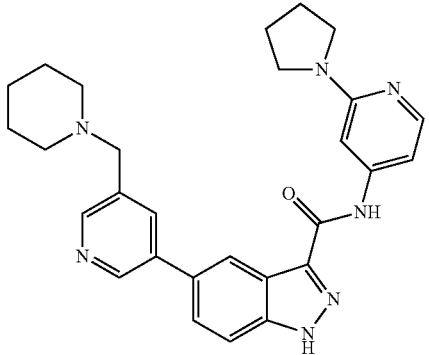

5-(5-(Piperidin-1-ylmethyl)pyridin-3-yl)-N-(2-(pyrrolidin-1-yl)pyridin-4-yl)-1H-indazole-3-carboxamide 100

White solid (31.8 mg, 0.07 mmol). $^1$H NMR (DMSO-d$_6$, 500 MHz) δ ppm 1.40 (d, J=4.94 Hz, 2H), 1.52 (quin, J=5.49 Hz, 4H), 1.92-1.98 (m, 4H), 2.39 (brs, 4H), 3.38 (t, J=6.31 Hz, 6H), 3.57 (s, 2H), 7.11 (dd, J=5.76, 1.37 Hz, 1H), 7.16 (d, J=1.70 Hz, 1H), 7.81, 7.83 (ABq, J$_{AB}$=13.2 Hz, 2H), 7.96 (d, J=5.49 Hz, 1H), 7.98-8.01 (m, 1H), 8.47 (s, 1H), 8.49 (d, J=1.65 Hz, 1H), 8.82 (d, J=2.20 Hz, 1H), 10.39 (s, 1H), 13.97 (brs, 1H); ESIMS found for C$_{28}$H$_{31}$N$_7$O m/z 482.2 (M+1).

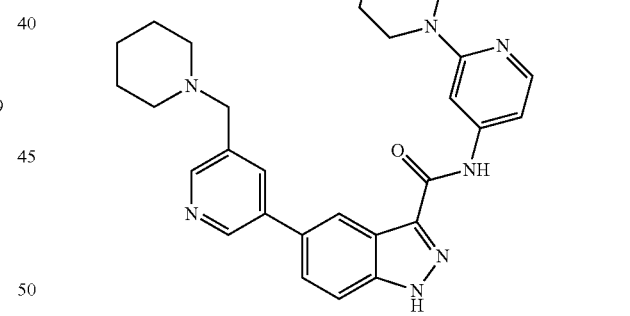

N-(2-(Piperidin-1-yl)pyridin-4-yl)-5-(5-(piperidin-1-ylmethyl)pyridin-3-yl)-1H-indazole-3-carboxamide 101

White solid (49.9 mg, 0.10 mmol). $^1$H NMR (DMSO-d$_6$, 500 MHz) δ ppm 1.37-1.44 (m, 2H), 1.49-1.59 (m, 8H), 1.59-1.66 (m, 2H), 2.39 (brs, 4H), 3.50 (t, J=5.00 Hz, 4H), 3.57 (s, 2H), 7.21 (dd, J=6.04, 1.65 Hz, 1H), 7.46 (s, 1H), 7.81, 7.83 (ABq, J$_{AB}$=11.3 Hz, 2H), 7.98-8.02 (m, 2H), 8.47 (d, J=1.10 Hz, 1H), 8.49 (d, J=1.65 Hz, 1H), 8.82 (d, J=2.20 Hz, 1H), 10.40 (s, 1H), 13.98 (brs, 1H); ESIMS found for C$_{29}$H$_{33}$N$_7$O m/z 496.2 (M+1).

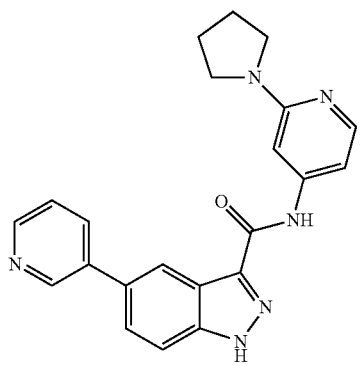

102

5-(Pyridin-3-yl)-N-(2-(pyrrolidin-1-yl)pyridin-4-yl)-1H-indazole-3-carboxamide 102

White solid (83.4 mg, 0.22 mmol). $^1$H NMR (DMSO-d$_6$, 500 MHz) δ ppm 1.93-1.98 (m, 4H), 3.38 (t, J=6.59 Hz, 4H), 7.11 (dd, J=6.04, 1.65 Hz, 1H), 7.17 (d, J=1.65 Hz, 1H), 7.52 (dd, J=8.23, 4.94 Hz, 1H), 7.81, 7.84 (ABq, J$_{AB}$=13.75 Hz, 2H), 7.96 (d, J=5.49 Hz, 1H), 8.14 (dt, J=7.96, 1.78 Hz, 1H), 8.48 (s, 1H), 8.60 (dd, J=4.94, 1.65 Hz, 1H), 8.94 (d, J=2.20 Hz, 1H), 10.39 (s, 1H), 13.97 (brs, 1H); ESIMS found for C$_{22}$H$_{20}$N$_6$O m/z 385.1 (M+1).

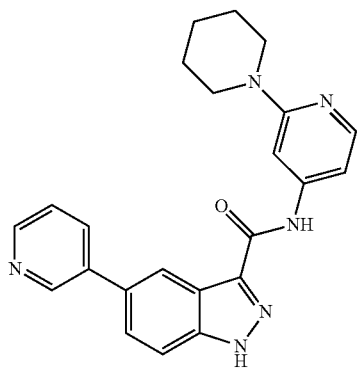

103

N-(2-(Piperidin-1-yl)pyridin-4-yl)-5-(pyridin-3-yl)-1H-indazole-3-carboxamide 103

White solid (72.1 mg, 0.18 mmol). $^1$H NMR (DMSO-d$_6$, 500 MHz) δ ppm 1.53-1.59 (m, 4H), 1.59-1.65 (m, 2H), 3.50 (t, J=5.00 Hz, 5H), 7.20 (dd, J=5.49, 1.65 Hz, 1H), 7.47 (s, 1H), 7.52 (dd, J=7.96, 4.67 Hz, 1H), 7.81, 7.84 (ABq, J$_{AB}$=12.4 Hz, 2H), 8.00 (d, J=5.49 Hz, 1H), 8.14 (dt, J=7.68, 1.92 Hz, 1H), 8.48 (s, 1H), 8.60 (dd, J=4.67, 1.37 Hz, 1H), 8.94 (d, J=2.20 Hz, 1H), 10.40 (s, 1H), 13.98 (brs, 1H); ESIMS found for C$_{23}$H$_{22}$N$_6$O m/z 398.8 (M+1).

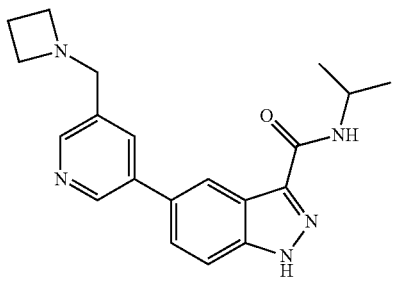

128

5-(5-(Azetidin-1-ylmethyl)pyridin-3-yl)-N-isopropyl-1H-indazole-3-carboxamide 128

Light brown solid (52 mg, 0.15 mmol). $^1$H NMR (DMSO-d$_6$, 500 MHz) δ ppm 1.22 (d, J=6.59 Hz, 6H), 2.01 (quin, J=7.00 Hz, 2H), 3.18 (t, J=6.86 Hz, 4H), 3.64 (s, 2H), 4.15-4.25 (m, 1H), 7.69-7.75 (m, 1H), 7.75-7.80 (m, 1H), 7.94 (s, 1H), 8.13 (d, J=8.23 Hz, 1H), 8.42 (d, J=0.82 Hz, 1H), 8.45 (d, J=1.37 Hz, 1H), 8.77 (d, J=2.20 Hz, 1H), 13.65 (brs, 1H); ESIMS found for C$_{20}$H$_{23}$N$_5$O m/z 349.7 (M+1).

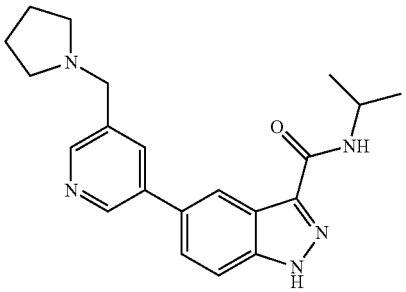

129

N-Isopropyl-5-(5-(pyrrolidin-1-ylmethyl)pyridin-3-yl)-1H-indazole-3-carboxamide 129

Light brown solid (39 mg, 0.11 mmol). $^1$H NMR (DMSO-d$_6$, 500 MHz) δ ppm 1.22 (d, J=6.59 Hz, 6H), 1.72 (brt, J=3.29 Hz, 4H), 3.70 (s, 2H), 4.13-4.26 (m, 1H), 7.70-7.75 (m, 1H), 7.75-7.80 (m, 1H), 7.98 (t, J=1.92 Hz, 1H), 8.14 (d, J=7.96 Hz, 1H), 8.43 (d, J=0.82 Hz, 1H), 8.49 (d, J=1.65 Hz, 1H), 8.79 (d, J=2.20 Hz, 1H), 13.65 (brs, 1H); ESIMS found for C$_{21}$H$_{25}$N$_5$O m/z 364.2 (M+1).

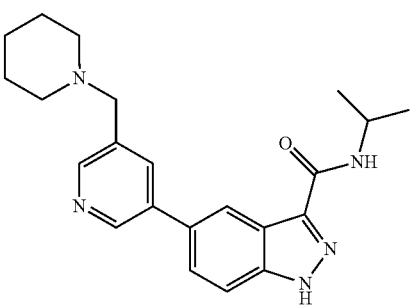

131

N-Isopropyl-5-(5-(piperidin-1-ylmethyl)pyridin-3-yl)-1H-indazole-3-carboxamide 131

Light brown solid (41 mg, 0.11 mmol). $^1$H NMR (DMSO-$d_6$, 500 MHz) δ ppm 1.22 (d, J=6.59 Hz, 6H), 1.40 (brd, J=4.67 Hz, 2H), 1.51 (quin, J=5.49 Hz, 4H), 2.38 (br s, 4H), 3.56 (s, 2H), 4.19 (dq, J=14.79, 6.60 Hz, 1H), 7.71-7.80 (m, 2H), 7.96 (s, 1H), 8.14 (d, J=8.23 Hz, 1H), 8.43 (s, 1H), 8.47 (d, J=1.65 Hz, 1H), 8.79 (d, J=1.92 Hz, 1H), 13.66 (s, 1H); ESIMS found for $C_{22}H_{27}N_5O$ m/z 377.8 (M+1).

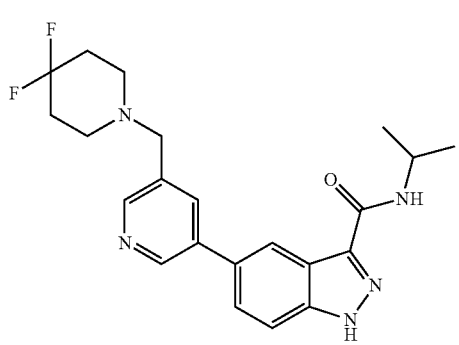

5-(5-((4,4-Difluoropiperidin-1-yl)methyl)pyridin-3-yl)-N-isopropyl-1H-indazole-3-carboxamide 132

Light brown solid (48 mg, 0.12 mmol). $^1$H NMR (DMSO-$d_6$, 500 MHz) δ ppm 1.22 (d, J=6.59 Hz, 6H), 1.91-2.05 (m, 4H), 2.55 (brd, J=4.67 Hz, 4H), 3.69 (s, 2H), 4.13-4.25 (m, 1H), 7.71-7.76 (m, 1H), 7.76-7.81 (m, 1H), 8.01 (t, J=2.06 Hz, 1H), 8.14 (d, J=8.23 Hz, 1H), 8.44 (s, 1H), 8.51 (d, J=1.92 Hz, 1H), 8.81 (d, J=2.20 Hz, 1H), 13.63 (brs, 1H); ESIMS found for $C_{22}H_{25}F_2N_5O$ m/z 414.3 (M+1).

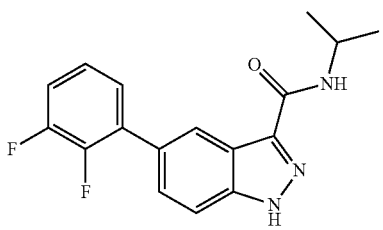

5-(2,3-Difluorophenyl)-N-isopropyl-1H-indazole-3-carboxamide 140

White solid (23 mg, 0.07 mmol). $^1$H NMR (DMSO-$d_6$, 500 MHz) δ ppm 1.21 (d, J=6.59 Hz, 6H), 4.11-4.24 (m, 1H), 7.29-7.36 (m, 1H), 7.37-7.49 (m, 2H), 7.58-7.64 (m, 1H), 7.73 (d, J=8.78 Hz, 1H), 8.14 (br d, J=8.23 Hz, 1H), 8.35 (s, 1H), 13.69 (brs, 1H); ESIMS found for $C_{17}H_{15}F_2N_3O$ m/z 316.3 (M+1).

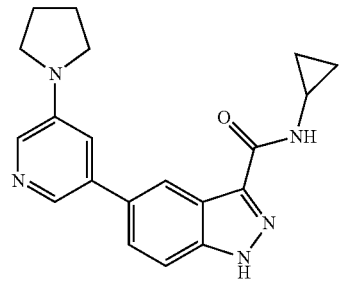

N-Cyclopropyl-5-(5-(pyrrolidin-1-yl)pyridin-3-yl)-1H-indazole-3-carboxamide 143

White solid (10 mg, 0.03 mmol). $^1$H NMR (DMSO-$d_6$, 500 MHz) δ ppm 0.63-0.74 (m, 4H), 1.96-2.04 (m, 4H), 2.86-2.95 (m, 1H), 3.33-3.38 (m, 4H), 7.06 (t, J=2.20 Hz, 1H), 7.65-7.72 (m, 1H), 7.72-7.77 (m, 1H), 7.95 (d, J=2.47 Hz, 1H), 8.12 (d, J=1.92 Hz, 1H), 8.39 (s, 1H), 8.43 (d, J=4.39 Hz, 1H), 13.62 (brs, 1H); ESIMS found for $C_{20}H_{21}N_5O$ m/z 348.1 (M+1).

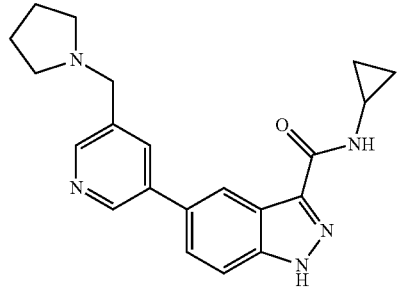

N-Cyclopropyl-5-(5-(pyrrolidin-1-ylmethyl)pyridin-3-yl)-1H-indazole-3-carboxamide 148

White solid (36 mg, 0.10 mmol). $^1$H NMR (DMSO-$d_6$, 500 MHz) δ ppm 0.64-0.73 (m, 4H), 1.73 (brs, 4H), 2.86-2.95 (m, 1H), 3.72 (brs, 2H), 7.69-7.75 (m, 1H), 7.75-7.81 (m, 1H), 7.99 (brs, 1H), 8.43 (s, 1H), 8.46 (d, J=4.39 Hz, 1H), 8.50 (s, 1H), 8.80 (d, J=1.37 Hz, 1H), 13.66 (s, 1H); ESIMS found for $C_{21}H_{23}N_5O$ m/z 362.0 (M+1).

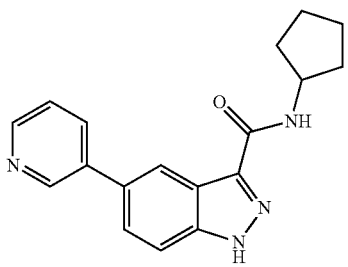

N-Cyclopentyl-5-(pyridin-3-yl)-1H-indazole-3-carboxamide 179

White solid (22 mg, 0.07 mmol). $^1$H NMR (DMSO-$d_6$, 500 MHz) δ ppm 1.49-1.66 (m, 4H), 1.67-1.76 (m, 2H), 1.86-1.96 (m, 2H), 4.31 (sxt, J=7.30 Hz, 1H), 7.48-7.54 (m, 1H), 7.71-7.75 (m, 1H), 7.75-7.80 (m, 1H), 8.10 (dt, J=7.89, 1.96 Hz, 1H), 8.22 (brd, J=7.68 Hz, 1H), 8.42 (dd, J=1.65, 0.82 Hz, 1H), 8.58 (dd, J=4.67, 1.37 Hz, 1H), 8.88-8.92 (m, 1H), 13.65 (brs, 1H); ESIMS found for $C_{18}H_{15}N_4O$ m/z 306.8 (M+1).

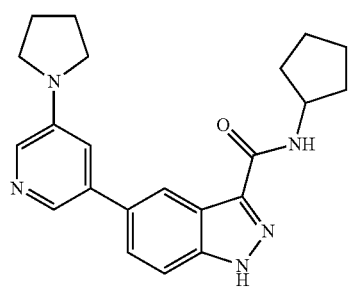

N-Cyclopentyl-5-(5-(pyrrolidin-1-yl)pyridin-3-yl)-1H-indazole-3-carboxamide 181

Yellow-white solid (15.0 mg, 0.04 mmol). $^1$H NMR (DMSO-$d_6$, 500 MHz) δ ppm 1.50-1.65 (m, 4H), 1.67-1.76 (m, 2H), 1.86-1.95 (m, 2H), 1.97-2.02 (m, 4H), 3.33-3.38 (m, 4H), 4.26-4.36 (m, 1H), 7.06 (t, J=2.20 Hz, 1H), 7.67-7.75 (m, 2H), 7.94 (d, J=2.47 Hz, 1H), 8.12 (d, J=1.65 Hz, 1H), 8.19 (d, J=7.68 Hz, 1H), 8.38 (s, 1H), 13.61 (s, 1H); ESIMS found for $C_{22}H_{25}N_5O$ m/z 376.1 (M+1).

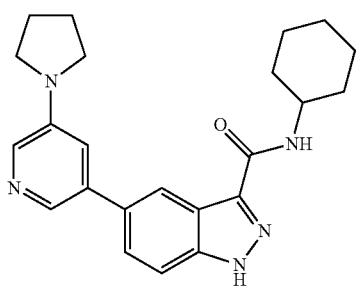

N-Cyclohexyl-5-(5-(pyrrolidin-1-yl)pyridin-3-yl)-1H-indazole-3-carboxamide 200

White solid (20.2 mg, 0.05 mmol). $^1$H NMR (DMSO-$d_6$, 500 MHz) δ ppm 1.10-1.20 (m, 1H), 1.26-1.38 (m, 2H), 1.38-1.48 (m, 2H), 1.58-1.65 (m, 1H), 1.71-1.78 (m, 2H), 1.81-1.88 (m, 2H), 1.99 (dt, J=6.59, 3.29 Hz, 4H), 3.33-3.38 (m, 4H), 3.78-3.89 (m, 1H), 7.06 (t, J=2.33 Hz, 1H), 7.68-7.75 (m, 2H), 7.94 (d, J=2.47 Hz, 1H), 8.07 (d, J=8.23 Hz, 1H), 8.11 (d, J=1.92 Hz, 1H), 8.39 (s, 1H), 13.62 (brs, 1H); ESIMS found for $C_{23}H_{27}N_5O$ m/z 390.2 (M+1).

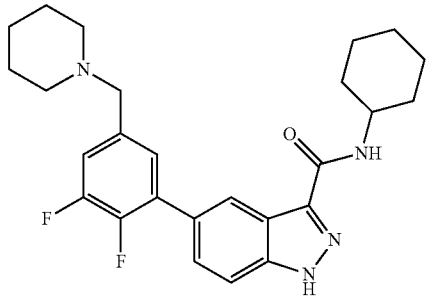

N-Cyclohexyl-5-(2,3-difluoro-5-(piperidin-1-ylmethyl)phenyl)-1H-indazole-3-carboxamide 217

White solid (4 mg, 0.009 mmol). $^1$H NMR (DMSO-$d_6$, 500 MHz) δ ppm 1.08-1.19 (m, 1H), 1.26-1.47 (m, 6H), 1.51 (quin, J=5.49 Hz, 4H), 1.57-1.65 (m, 1H), 1.74 (brd, J=12.90 Hz, 2H), 1.80-1.87 (m, 2H), 2.36 (brs, 4H), 3.48 (s, 2H), 3.78-3.88 (m, 1H), 7.28 (brd, J=6.31 Hz, 1H), 7.33 (br dd, J=10.84, 7.55 Hz, 1H), 7.60 (d, J=8.78 Hz, 1H), 7.72 (d, J=8.78 Hz, 1H), 8.11 (d, J=8.23 Hz, 1H), 8.33 (s, 1H), 13.68 (brs, 1H); ESIMS found for $C_{26}H_{30}F_2N_4O$ m/z 453.0 (M+1).

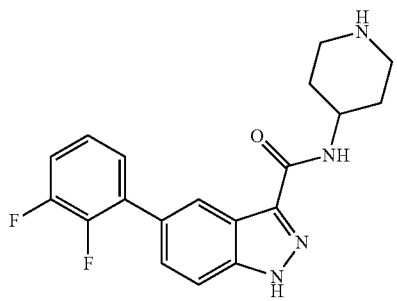

5-(2,3-Difluorophenyl)-N-(piperidin-4-yl)-1H-indazole-3-carboxamide 254

Beige solid (2.2 mg, 0.006 mmol). $^1$H NMR (DMSO-$d_6$, 500 MHz) δ ppm 1.45-1.64 (m, 2H), 1.75 (d, J=10.43 Hz, 2H), 2.49-2.61 (m, 2H), 2.97 (d, J=12.08 Hz, 2H), 3.82-3.96 (m, 1H), 7.30-7.36 (m, 1H), 7.36-7.52 (m, 2H), 7.60 (d, J=8.78 Hz, 1H), 7.73 (d, J=8.78 Hz, 1H), 8.18 (d, J=8.23 Hz, 1H), 8.34 (s, 1H), 13.67 (brs, 1H); ESIMS found for $C_{19}H_{18}F_2N_4O$ m/z 356.8 (M+1).

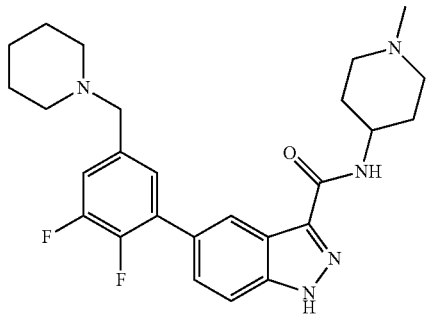

5-(2,3-Difluoro-5-(piperidin-1-ylmethyl)phenyl)-N-(1-methyl piperidin-4-yl)-1H-indazole-3-carboxamide 272

Beige solid (2.2 mg, 0.006 mmol). $^1$H NMR (DMSO-d$_6$, 500 MHz) δ ppm 1.31-1.43 (m, 2H), 1.45-1.57 (m, 4H), 1.68-1.83 (m, 4H), 2.10-2.22 (m, 2H), 2.26 (s, 3H), 2.30-2.41 (m, 4H), 2.87 (d, J=10.43 Hz, 2H), 3.49 (s, 2H), 3.73-3.91 (m, 1H), 7.28 (d, J=6.35 Hz, 1H), 7.31-7.37 (m, 1H), 7.60 (d, J=-8.57 Hz, 1H), 7.73 (d, J=8.78 Hz, 1H), 8.27 (d, J=8.23 Hz, 1H), 8.33 (s, 1H), 13.72 (brs, 1H); ESIMS found for C$_{19}$H$_{15}$F$_2$N$_4$O m/z 356.8 (M+1).

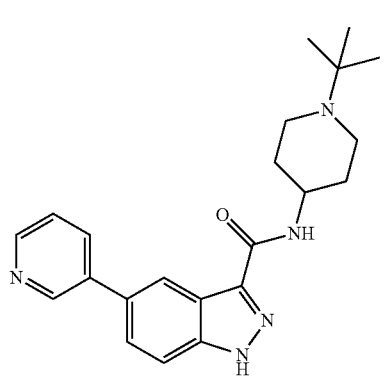

N-(1-(tert-Butyl)piperidin-4-yl)-5-(pyridin-3-yl)-1H-indazole-3-carboxamide 291

White solid (4.6 mg, 0.01 mmol). $^1$H NMR (DMSO-d$_6$, 500 MHz) δ ppm 1.02 (s, 9H), 1.56-1.64 (m, 2H), 1.81 (d, J=10.98 Hz, 2H), 2.12 (t, J=10.70 Hz, 2H), 2.98 (d, J=11.53 Hz, 2H), 3.77-3.85 (m, 1H), 7.51 (dd, J=5.5 Hz, J=8.8 Hz, 1H), 7.72-7.78 (m, 2H), 8.09 (dt, J=1.65, J=8.8 Hz, 1H), 8.14 (d, J=8.23 Hz, 1H), 8.42 (s, 1H), 8.58 (dd, J=4.94, 1.65 Hz, 1H), 8.90 (d, J=2.20 Hz, 1H), 13.65 (brs, 1H); ESIMS found for C$_{26}$H$_{31}$F$_2$N$_5$O m/z 467.9 (M+1).

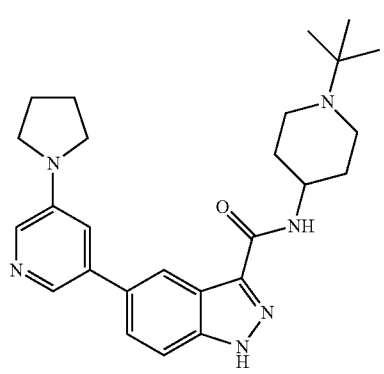

N-(1-(tert-Butyl)piperidin-4-yl)-5-(5-(pyrrolidin-1-yl)pyridin-3-yl)-1H-indazole-3-carboxamide 293

White solid (41.0 mg, 0.09 mmol). $^1$H NMR (DMSO-d$_6$, 500 MHz) δ ppm 1.03 (s, 9H), 1.60 (qd, J=11.80, 3.57 Hz, 2H), 1.81 (d, J=10.43 Hz, 2H), 1.97-2.02 (m, 4H), 2.12 (t, J=10.98 Hz, 2H), 2.99 (d, J=11.53 Hz, 2H), 3.35 (t, J=6.59 Hz, 4H), 3.74-3.87 (m, 1H), 7.06 (t, J=2.20 Hz, 1H), 7.68-7.75 (m, 2H), 7.94 (d, J=2.74 Hz, 1H), 8.10-8.14 (m, 2H), 8.38 (s, 1H), 13.61 (brs, 1H); ESIMS found for C$_{26}$H$_{34}$N$_6$O m/z 447.1 (M+1).

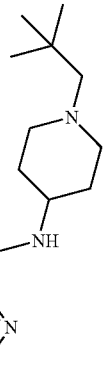

N-(1-Neopentylpiperidin-4-yl)-5-(pyridin-3-yl)-1H-indazole-3-carboxamide 329

White solid (20 mg, 0.05 mmol). $^1$H NMR (DMSO-d$_6$, 500 MHz) δ ppm 0.85 (s, 9H), 1.68-1.77 (m, 4H), 2.06 (s, 2H), 2.30 (td, J=11.39, 3.02 Hz, 2H), 2.79 (d, J=11.53 Hz, 2H), 3.78-3.85 (m, 1H), 7.51 (dd, J=7.15 Hz, J=5.5 Hz, 1H), 7.72-7.78 (m, 2H), 8.09 (dt, J=8.25 Hz, J=2.2 Hz, 1H), 8.15 (d, J=-8.23 Hz, 1H), 8.42 (s, 1H), 8.58 (dd, J=4.39, 1.65 Hz, 1H), 8.90 (d, J=2.20 Hz, 1H), 13.66 (brs, 1H); ESIMS found for C$_{23}$H$_{29}$N$_5$O m/z 392.3 (M+1).

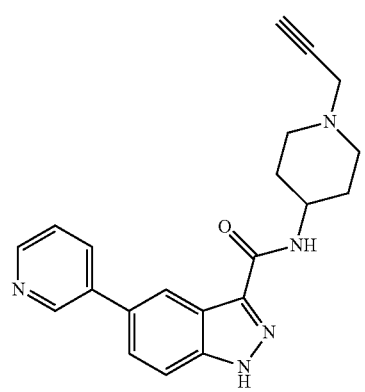

N-(1-(Prop-2-yn-1-yl)piperidin-4-yl)-5-(pyridin-3-yl)-1H-indazole-3-carboxamide 349

White solid (47.0 mg, 0.13 mmol). $^1$H NMR (DMSO-d$_6$, 500 MHz) δ ppm 1.70 (qd, J=11.55 Hz, J=3.3 Hz, 2H), 1.78-1.83 (m, 2H), 2.21 (td, J=11.53, 2.20 Hz, 2H), 2.82 (d, J=1.53 Hz, 2H), 3.14 (t, J=2.75 Hz, 1H), 3.26 (d, J=2.74 Hz, 2H), 3.79-3.86 (m, 1H), 7.51 (dd, J=7.7 Hz, J=4.95 Hz, 1H), 7.70-7.80 (m, 2H), 8.09 (dt, J=7.56 Hz, J=2.2 Hz, 1H), 8.24 (d, =J=8.23 Hz, 1H), 8.42 (s, 1H), 8.58 (dd, J=4.67, 1.37 Hz, 1H), 8.90 (d, J=2.20 Hz, 1H), 13.67 (brs, 1H); ESIMS found for C$_{21}$H$_{21}$N$_5$O m/z 359.7 (M+1).

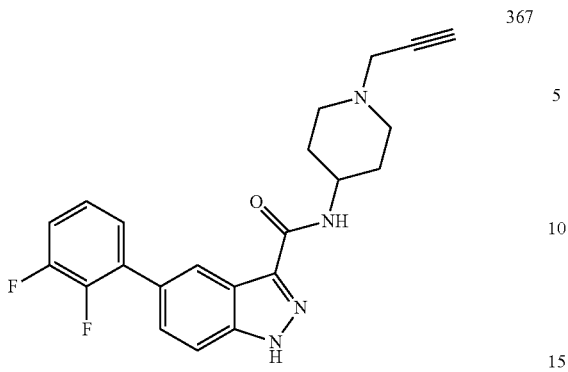

5-(2,3-Difluorophenyl)-N-(1-(prop-2-yn-1-yl)piperidin-4-yl)-1H-indazole-3-carboxamide 367

White solid (8.8 mg, 0.02 mmol). $^1$H NMR (DMSO-$d_6$, 500 MHz) δ ppm 1.65-1.75 (m, 2H), 1.77-1.83 (m, 2H), 2.16-2.25 (m, 2H), 2.81 (br d, J=11.25 Hz, 2H), 3.12-3.15 (m, 1H), 3.26 (d, J=2.20 Hz, 2H), 3.76-3.86 (m, 1H), 7.29-7.36 (m, 1H), 7.37-7.49 (m, 2H), 7.58-7.64 (m, 1H), 7.71-7.76 (m, 1H), 8.23 (d, J=8.23 Hz, 1H), 8.35 (s, 1H), 13.70 (brs, 1H); ESIMS found for $C_{22}H_{20}F_2N_4O$ m/z 395.1 (M+1).

5-(5-(Pyrrolidin-1-yl)pyridin-3-yl)-N-(2-(trifluoromethyl)pyridin-4-yl)-1H-indazole-3-carboxamide 820

White solid (8 mg, 0.02 mmol). $^1$H NMR (DMSO-$d_6$, 500 MHz) δ ppm 1.97-2.03 (m, 4H), 3.37 (br t, J=6.45 Hz, 4H), 7.10 (t, J=2.20 Hz, 1H), 7.81 (d, J=1.10 Hz, 2H), 7.97 (d, J=2.74 Hz, 1H), 8.15 (d, J=1.65 Hz, 1H), 8.21 (dd, J=5.63, 2.06 Hz, 1H), 8.44 (t, J=−1.10 Hz, 1H), 8.53 (d, J=−1.65 Hz, 1H), 8.66 (d, J=5.49 Hz, 1H), 11.21 (s, 1H); ESIMS found for $C_{23}H_{19}F_3N_6O$ m/z 453.2 (M+1).

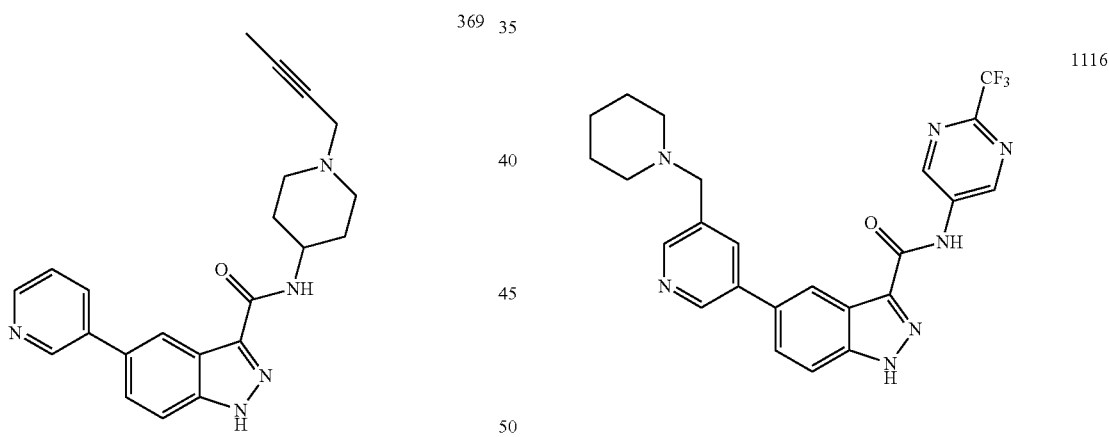

N-(1-(But-2-yn-1-yl)piperidin-4-yl)-5-(pyridin-3-yl)-1H-indazole-3-carboxamide 369

White solid (49.3 mg, 0.13 mmol). $^1$H NMR (DMSO-$d_6$, 500 MHz) δ ppm 1.69 (qd, J=11.5 Hz, J=3.5 Hz, 2H), 1.77-1.85 (m, 5H), 2.12-2.20 (m, 2H), 2.82 (d, J=11.53 Hz, 2H), 3.18 (d, J=2.20 Hz, 2H), 3.78-3.88 (m, 1H), 7.51 (dd, J=7.7 Hz, J=3.3 Hz, 1H), 7.73-7.78 (m, 2H), 8.09 (dt, J=8.25 Hz, J=1.65 Hz, 1H), 8.22 (d, J=8.23 Hz, 1H), 8.42 (s, 1H), 8.58 (dd, J=4.67, 1.37 Hz, 1H), 8.90 (d, J=2.20 Hz, 1H), 13.67 (brs, 1H); ESIMS found for $C_{22}H_{23}N_5O$ m/z 374.1 (M+1).

5-(5-(Piperidin-1-ylmethyl)pyridin-3-yl)-N-(2-(trifluoromethyl)pyrimidin-5-yl)-1H-indazole-3-carboxamide 1116

White solid (20.4 mg, 0.04 mmol). $^1$H NMR (DMSO-$d_6$, 500 MHz) δ ppm 1.38-1.44 (m, 2H), 1.52 (quin, J=5.49 Hz, 4H), 2.39 (brs, 4H), 3.57 (s, 2H), 7.85 (s, J=6.83 Hz, 2H), 8.00 (s, 1H), 8.46-8.53 (m, 2H), 8.82 (d, J=1.65 Hz, 1H), 9.56 (s, 2H), 11.31 (brs, 1H), 14.17 (brs, 1H); ESIMS found for $C_{24}H_{22}F_3N_7O$ m/z 482.1 (M+1).

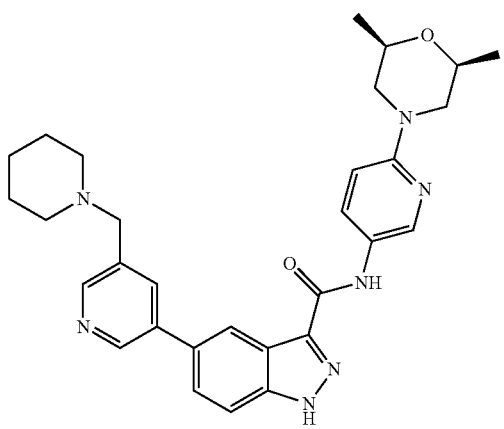

N-(6-((2S,6R)-2,6-dimethylmorpholino)pyridin-3-yl)-5-(5-(piperidin-1-ylmethyl)pyridin-3-yl)-1H-indazole-3-carboxamide 1141

White solid (45 mg, 0.09 mmol). $^1$H NMR (DMSO-d$_6$, 500 MHz) δ ppm 1.17 (d, J=6.31 Hz, 6H), 1.40 (brd, J=4.39 Hz, 2H), 1.48-1.56 (m, 4H), 2.32-2.43 (m, 6H), 3.56 (s, 2H), 3.59-3.67 (m, 2H), 4.07 (d, J=1.37 Hz, 1H), 4.10 (d, J=1.65 Hz, 1H), 6.87 (d, J=9.06 Hz, 1H), 7.75-7.85 (m, 2H), 7.98 (t, J=2.06 Hz, 1H), 8.06 (dd, J=9.06, 2.74 Hz, 1H), 8.46 (s, 1H), 8.48 (d, J=1.92 Hz, 1H), 8.58 (d, J=2.47 Hz, 1H), 8.81 (d, J=2.20 Hz, 1H), 10.32 (s, 1H), 13.88 (brs, 1H); ESIMS found for C$_{30}$H$_{35}$N$_7$O$_2$ m/z 526.3 (M+1).

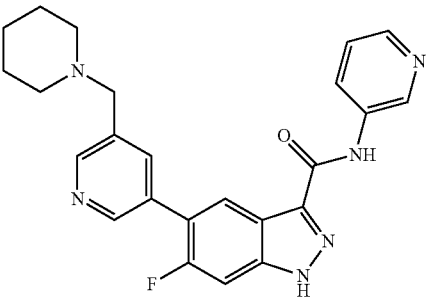

6-Fluoro-5-(5-(piperidin-1-ylmethyl)pyridin-3-yl)-N-(pyridin-3-yl)-1H-indazole-3-carboxamide 1153

Off-white solid (13 mg, 0.03 mmol). $^1$H NMR (DMSO-d$_6$, 500 MHz) δ ppm 1.40 (brd, J=4.67 Hz, 2H), 1.51 (quin, J=5.35 Hz, 4H), 2.38 (brs, 4H), 3.57 (s, 2H), 7.39 (dd, J=8.23, 4.67 Hz, 1H), 7.68 (d, J=10.70 Hz, 1H), 7.89 (d, J=1.37 Hz, 1H), 8.26-8.34 (m, 3H), 8.53 (d, J=1.65 Hz, 1H), 8.67 (s, 1H), 9.06 (d, J=2.20 Hz, 1H), 10.70 (s, 1H), 14.05 (brs, 1H); ESIMS found for C$_{24}$H$_{23}$FN$_6$O m/z 431.1 (M+1).

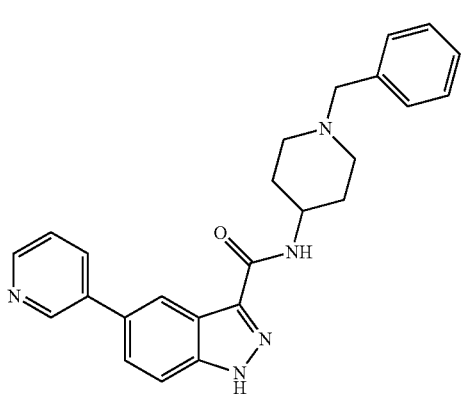

N-(1-Benzylpiperidin-4-yl)-5-(pyridin-3-yl)-1H-indazole-3-carboxamide 1152

White solid (51.3 mg, 0.12 mmol). $^1$H NMR (DMSO-d$_6$, 500 MHz) δ ppm 1.65-1.73 (m, 2H), 1.76-1.81 (m, 2H), 2.01-2.08 (m, 2H), 2.82 (d, J=11.53 Hz, 2H), 3.47 (s, 2H), 3.82-3.90 (m, 1H), 7.23-7.27 (m, 1H), 7.29-7.35 (m, 4H), 7.51 (dd, J=8.23, 4.94 Hz, 1H), 7.72-7.78 (m, 2H), 8.09 (dt, J=8.25 Hz, J=2.2 Hz, 1H), 8.21 (d, J=8.23 Hz, 1H), 8.42 (s, 1H), 8.58 (dd, J=4.94, 1.65 Hz, 1H), 8.89 (d, J=1.65 Hz, 1H), 13.67 (brs, 1H); ESIMS found for C$_{25}$H$_{25}$N$_5$O m/z 412.2 (M+1).

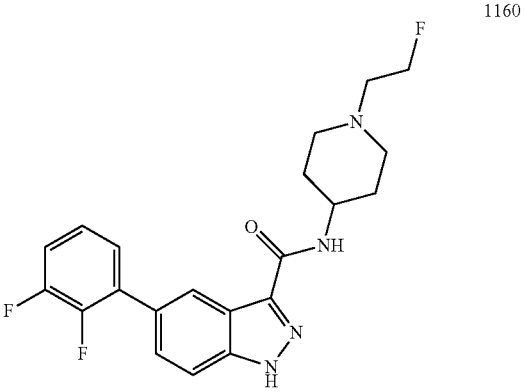 [SMILES: O=C(NC1CCN(CCF)CC1)c1n[nH]c2ccc(-c3cccc(F)c3F)cc12]

5-(2,3-Difluorophenyl)-N-(1-(2-fluoroethyl)piperidin-4-yl)-1H-indazole-3-carboxamide 1160

White solid (93 mg, 0.23 mmol). $^1$H NMR (DMSO-d$_6$, 500 MHz) δ ppm 1.62-1.74 (m, 2H), 1.77 (brs, 2H), 2.12 (brs, 2H), 2.55-2.71 (m, 2H), 2.90 (brd, J=10.70 Hz, 2H), 3.77-3.91 (m, 1H), 4.53 (dt J=4.7 Hz, J=47.8 Hz, 2H), 7.29-7.36 (m, 1H), 7.37-7.42 (m, 1H), 7.42-7.49 (m, 1H), 7.58-7.64 (m, 1H), 7.73 (d, J=8.51 Hz, 1H), 8.24 (brd, J=8.23 Hz, 1H), 8.35 (s, 1H), 13.70 (s, 1H); ESIMS found for C$_{21}$H$_{21}$F$_3$N$_4$O m/z 403.1 (M+1).

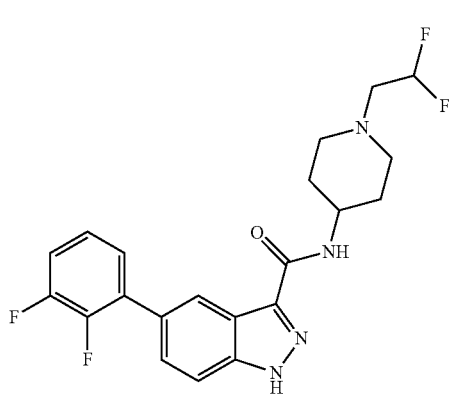

1161

N-(1-(2,2-Difluoroethyl)piperidin-4-yl)-5-(2,3-difluorophenyl)-1H-indazole-3-carboxamide 1161

White solid (93 mg, 0.22 mmol). $^1$H NMR (DMSO-d$_6$, 500 MHz) δ ppm 1.63-1.81 (m, 4H), 2.22-2.32 (m, 2H), 2.72 (td, J=15.64, 4.39 Hz, 2H), 2.92 (brd, J=1.80 Hz, 2H), 3.78-3.90 (m, 1H), 6.13 (tt, J=4.15 Hz, J=56.1 Hz, 1H), 7.28-7.36 (m, 1H), 7.36-7.50 (m, 2H), 7.61 (dt, J=8.78, 1.65 Hz, 1H), 7.71-7.76 (m, 1H), 8.25 (brd, J=8.23 Hz, 1H), 8.34 (s, 1H), 13.71 (brs, 1H); ESIMS found for C$_{21}$H$_{20}$F$_4$N$_4$O m/z 421.1 (M+1).

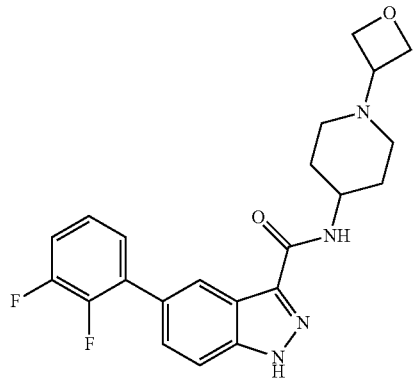

1164

5-(2,3-Difluorophenyl)-N-(1-(oxetan-3-yl)piperidin-4-yl)-1H-indazole-3-carboxamide 1164

White solid (25 mg, 0.06 mmol). $^1$H NMR (DMSO-d$_6$, 500 MHz) δ ppm 1.62-1.74 (m, 2H), 1.76-1.82 (m, 2H), 1.83-1.90 (m, 2H), 2.71 (brd, J=11.53 Hz, 2H), 3.39 (quin, J=6.38 Hz, 1H), 3.79-3.92 (m, 1H), 4.42 (t, J=6.17 Hz, 2H), 4.49-4.57 (m, 2H), 7.28-7.36 (m, 1H), 7.36-7.50 (m, 2H), 7.61 (dt, J=8.64, 1.58 Hz, 1H), 7.73 (d, J=8.51 Hz, 1H), 8.27 (d, J=8.23 Hz, 1H), 8.34 (s, 1H), 13.70 (brs, 1H); ESIMS found for C$_{22}$H$_{22}$F$_2$N$_4$O$_2$ m/z 413.3 (M+1).

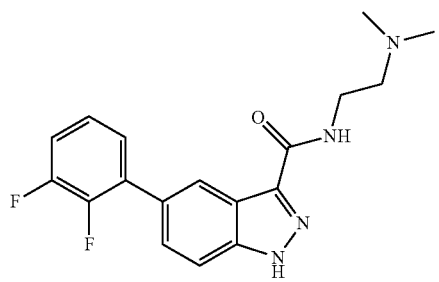

1165

5-(2,3-Difluorophenyl)-N-(2-(dimethylamino)ethyl)-1H-indazole-3-carboxamide 1165

White solid (25 mg, 0.07 mmol). $^1$H NMR (DMSO-d$_6$, 500 MHz) δ ppm $^1$H NMR (499 MHz, DMSO-d$_6$) δ 2.20 (s, 6H), 2.44 (t, J=6.59 Hz, 2H), 3.37-3.45 (m, 2H), 7.29-7.36 (m, 1H), 7.37-7.49 (m, 2H), 7.61 (dt, J=8.78, 1.65 Hz, 1H), 7.71-7.77 (m, 1H), 8.20 (t, J=5.63 Hz, 1H), 8.36 (s, 1H), 13.68 (brs, 1H); ESIMS found for C$_{18}$H$_{18}$F$_2$N$_4$O m/z 345.2 (M+1).

1166

5-(2,3-Difluorophenyl)-N-(2-(pyrrolidin-1-yl)ethyl)-1H-indazole-3-carboxamide 1166

White solid (11 mg, 0.03 mmol). $^1$H NMR (DMSO-d$_6$, 500 MHz) δ ppm $^1$H NMR (499 MHz, DMSO-d$_6$) δ 1.69 (dt, J=6.66, 3.12 Hz, 4H), 2.61 (t, J=6.86 Hz, 2H), 3.40-3.48 (m, 2H), 7.29-7.36 (m, 1H), 7.37-7.50 (m, 2H), 7.61 (dt, J=8.78, 1.65 Hz, 1H), 7.74 (d, J=9.33 Hz, 1H), 8.26 (t, J=5.90 Hz, 1H), 8.36 (s, 1H), 13.68 (brs, 1H); ESIMS found for C$_{20}$H$_{20}$F$_2$N$_4$O m/z 371.2 (M+1).

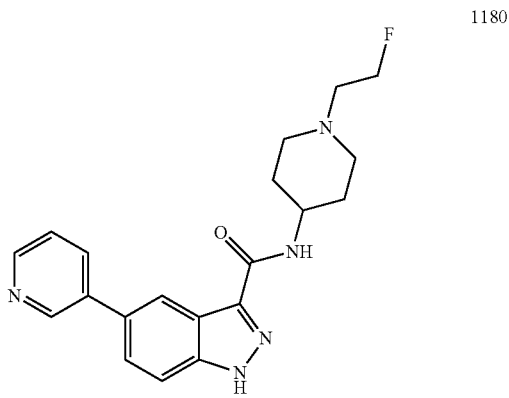 [SMILES: O=C(NC1CCN(CCF)CC1)c1n[nH]c2ccc(-c3cccnc3)cc12]

N-(1-(2-Fluoroethyl)piperidin-4-yl)-5-(pyridin-3-yl)-1H-indazole-3-carboxamide 1180

White solid (66 mg, 0.18 mmol). $^1$H NMR (DMSO-d$_6$, 500 MHz) δ ppm $^1$H NMR (499 MHz, DMSO-d$_6$) δ 1.61-1.74 (m, 2H), 1.74-1.83 (m, 2H), 2.06-2.19 (m, 2H), 2.59 (t, J=4.94 Hz, 1H), 2.65 (t, J=4.94 Hz, 1H), 2.90 (br d, J=11.80 Hz, 2H), 3.78-3.93 (m, 1H), 4.43-4.62 (m, 2H), 7.46-7.54 (m, 1H), 7.70-7.80 (m, 2H), 8.09 (dt, J=8.23, 1.92 Hz, 1H), 8.22 (d, J=8.23 Hz, 1H), 8.38-8.45 (m, 1H), 8.58 (dd, J=4.80, 1.51 Hz, 1H), 8.90 (d, J=1.92 Hz, 1H), 13.67 (brs, 1H); ESIMS found for C$_{20}$H$_{22}$FN$_5$O m/z 367.9 (M+1).

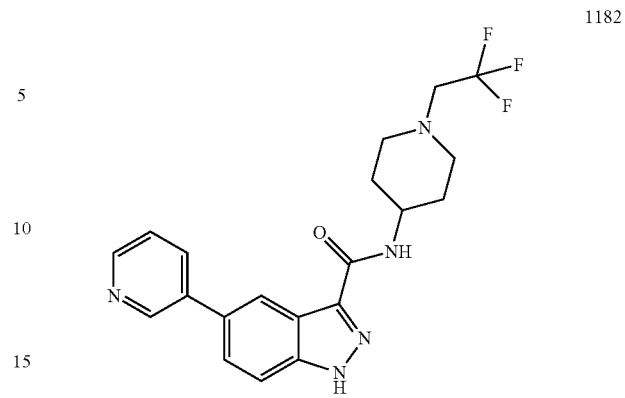

5-(Pyridin-3-yl)-N-(1-(2,2,2-trifluoroethyl)piperidin-4-yl)-1H-indazole-3-carboxamide 1182

White solid (92 mg, 0.23 mmol). $^1$H NMR (DMSO-d$_6$, 500 MHz) δ ppm 1.64-1.83 (m, 4H), 2.39-2.48 (m, 2H), 2.94 (brd, J=11.80 Hz, 2H), 3.17 (q, J=10.15 Hz, 2H), 3.81-3.92 (m, 1H), 7.51 (dd, J=7.96, 4.12 Hz, 1H), 7.71-7.81 (m, 2H), 8.09 (dt, J=8.23, 1.78 Hz, 1H), 8.24 (d, J=8.23 Hz, 1H), 8.42 (s, 1H), 8.58 (dd, J=4.80, 1.51 Hz, 1H), 8.90 (d, J=1.92 Hz, 1H), 13.68 (s, 1H); ESIMS found for C$_{20}$H$_{20}$F$_3$N$_5$O m/z 404.0 (M+1).

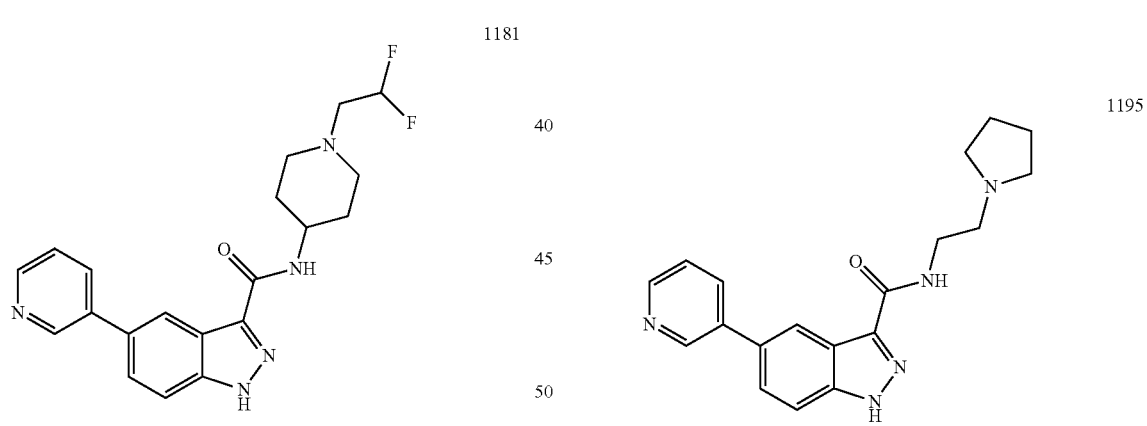

N-(1-(2,2-Difluoroethyl)piperidin-4-yl)-5-(pyridin-3-yl)-1H-indazole-3-carboxamide 1181

White solid (55 mg, 0.14 mmol). $^1$H NMR (DMSO-d$_6$, 500 MHz) δ ppm 1.64-1.74 (m, 2H), 1.74-1.80 (m, 2H), 2.27 (td, J=11.66, 2.20 Hz, 2H), 2.73 (td, J=15.64, 4.39 Hz, 2H), 2.92 (brd, J=11.80 Hz, 2H), 3.79-3.92 (m, 1H), 6.13 (tt, J=4.4 Hz, J=56.1 Hz, 1H), 7.46-7.55 (m, 1H), 7.70-7.81 (m, 2H), 8.05-8.12 (m, 1H), 8.24 (d, J=8.23 Hz, 1H), 8.58 (dd, J=4.80, 1.51 Hz, 1H), 8.90 (d, J=2.47 Hz, 1H), 13.67 (brs, 1H); ESIMS found for C$_{20}$H$_{21}$F$_2$N$_5$O m/z 385.8 (M+1).

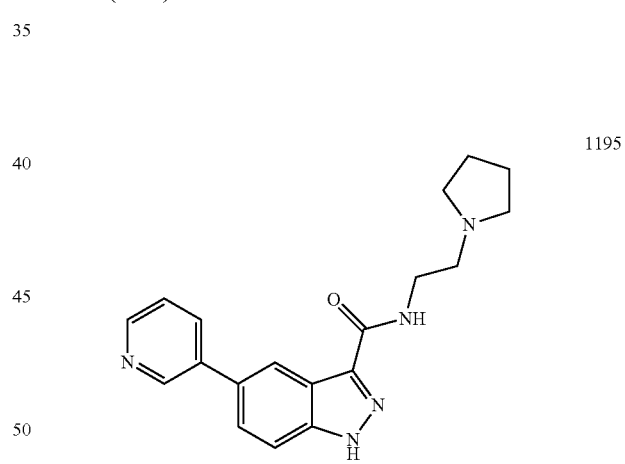

5-(Pyridin-3-yl)-N-(2-(pyrrolidin-1-yl)ethyl)-1H-indazole-3-carboxamide 1195

White solid (1.4 mg, 0.004 mmol). $^1$H NMR (DMSO-d, 500 MHz) δ ppm 1.69 (dt, J=6.66, 3.12 Hz, 4H), 2.62 (t, J=6.86 Hz, 2H), 3.44 (q, J=6.59 Hz, 2H), 7.47-7.54 (m, 1H), 7.71-7.81 (m, 2H), 8.10 (dt, J=7.89, 1.96 Hz, 1H), 8.26 (br t, J=5.49 Hz, 1H), 8.41-8.45 (m, 1H), 8.58 (dd, J=4.80, 1.51 Hz, 1H), 8.90 (d, J=1.65 Hz, 1H), 13.66 (brs, 1H); ESIMS found for C$_{19}$H$_{21}$N$_5$O m/z 336.4 (M+1).

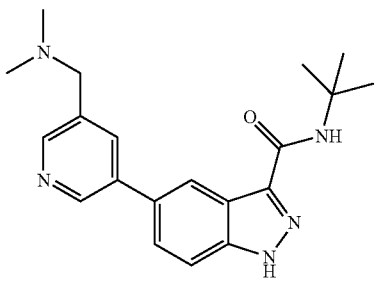

N-(tert-Butyl)-5-(5-((dimethylamino)methyl)pyridin-3-yl)-1H-indazole-3-carboxamide 1198

White solid (27 mg, 0.08 mmol). $^1$H NMR (DMSO-d$_6$, 500 MHz) δ ppm 1.45 (s, 9H), 2.21 (s, 6H), 3.52 (s, 2H), 7.46 (s, 1H), 7.70-7.76 (m, 1H), 7.76-7.81 (m, 1H), 7.99 (s, 1H), 8.43 (s, 1H), 8.47 (d, J=1.10 Hz, 1H), 8.81 (d, J=1.92 Hz, 1H), 13.63 (brs, 1H); ESIMS found for C$_{20}$H$_{25}$N$_5$O m/z 352.2 (M+1).

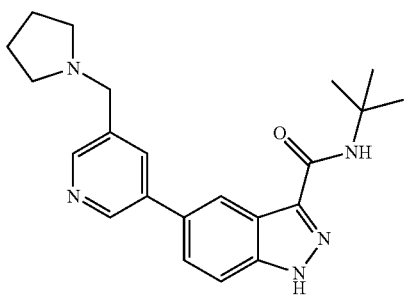

N-(tert-Butyl)-5-(5-(pyrrolidin-1-ylmethyl)pyridin-3-yl)-1H-indazole-3-carboxamide 1200

Light brown solid (20 mg, 0.05 mmol). $^1$H NMR (DMSO-d$_6$, 500 MHz) δ ppm 1.45 (s, 9H), 1.72 (brs, 4H), 3.70 (s, 2H), 7.46 (s, 1H), 7.70-7.75 (m, 1H), 7.75-7.79 (m, 1H), 7.99 (t, J=1.92 Hz, 1H), 8.42 (d, J=0.82 Hz, 1H), 8.49 (d, J=1.65 Hz, 1H), 8.79 (d, J=2.20 Hz, 1H); ESIMS found for C$_{22}$H$_{27}$N$_5$O m/z 378.2 (M+1).

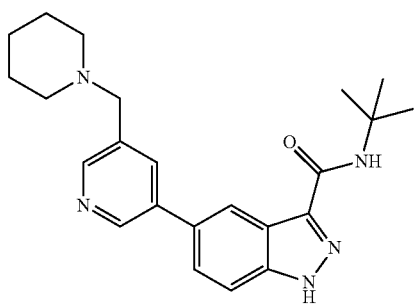

N-(tert-Butyl)-5-(5-(piperidin-1-ylmethyl)pyridin-3-yl)-1H-indazole-3-carboxamide 1202

Light brown solid (38 mg, 0.10 mmol). $^1$H NMR (DMSO-d$_6$, 500 MHz) δ 1.35-142 (m, 2H), 1.45 (s, 9H), 1.47-1.55 (m, 4H), 2.38 (br s, 4H), 3.56 (s, 2H), 7.46 (s, 1H), 7.70-7.75 (m, 1H), 7.75-7.80 (m, 1H), 7.97 (t, J=1.65 Hz, 1H), 8.42 (s, 1H), 8.47 (d, J=1.65 Hz, 1H), 8.79 (d, J=2.20 Hz, 1H), 13.63 (s, 1H); ESIMS found for C$_{23}$H$_{29}$N$_5$O m/z 392.2 (M+1).

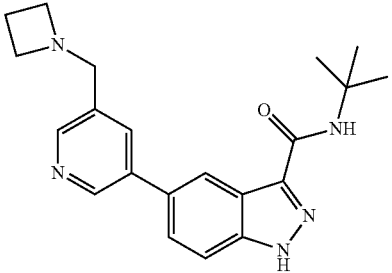

5-(5-(Azetidin-1-ylmethyl)pyridin-3-yl)-N-(tert-butyl)-1H-indazole-3-carboxamide 1206

White solid (36 mg, 0.10 mmol). $^1$H NMR (DMSO-d$_6$, 500 MHz) δ ppm 1.45 (s, 9H), 2.01 (quin, J=7.00 Hz, 2H), 3.18 (t, J=7.00 Hz, 4H), 3.64 (s, 2H), 7.46 (s, 1H), 7.70-7.75 (m, 1H), 7.75-7.81 (m, 1H), 7.95 (t, J=2.06 Hz, 1H), 8.42 (d, J=0.82 Hz, 1H), 8.45 (d, J=1.65 Hz, 1H), 8.78 (d, J=2.47 Hz, 1H), 13.62 (brs, 1H); ESIMS found for C$_{21}$H$_{25}$N$_5$O m/z 364.2 (M+1).

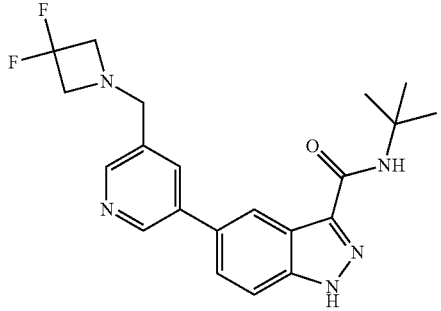

N-(tert-Butyl)-5-(5-((3,3-difluoroazetidin-1-yl)methyl)pyridin-3-yl)-1H-indazole-3-carboxamide 1210

White solid (17 mg, 0.04 mmol). $^1$H NMR (DMSO-d$_6$, 500 MHz) δ ppm 1.45 (s, 9H), 3.68 (t, J=12.49 Hz, 4H), 3.86 (s, 2H), 7.46 (s, 1H), 7.70-7.76 (m, 1H), 7.76-7.81 (m, 1H), 8.02 (t, J=2.06 Hz, 1H), 8.44 (d, J=0.82 Hz, 1H), 8.51 (d, J=1.65 Hz, 1H), 8.82 (d, J=2.20 Hz, 1H), 13.61 (brs, 1H); ESIMS found for C$_{21}$H$_{23}$F$_2$N$_5$O m/z 400.0 (M+1).

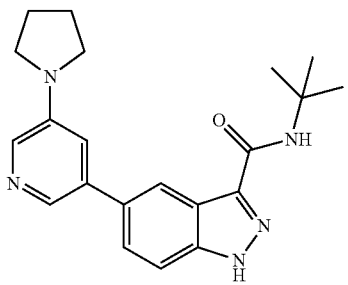

N-(tert-Butyl)-5-(5-(pyrrolidin-1-yl)pyridin-3-yl)-1H-indazole-3-carboxamide 1214

White solid (8 mg, 0.02 mmol). $^1$H NMR (DMSO-d$_6$, 500 MHz) δ ppm 1.45 (s, 9H), 1.96-2.03 (m, 4H), 3.33-3.40 (m, 4H), 7.07 (t, J=2.20 Hz, 1H), 7.44 (s, 1H), 7.68-7.71 (m, 1H), 7.71-7.75 (m, 1H), 7.94 (d, J=2.74 Hz, 1H), 8.12 (d, J=1.65 Hz, 1H), 8.38 (s, 1H), 13.60 (brs, 1H); ESIMS found for C$_{21}$H$_{25}$N$_5$O m/z 364.3 (M+1).

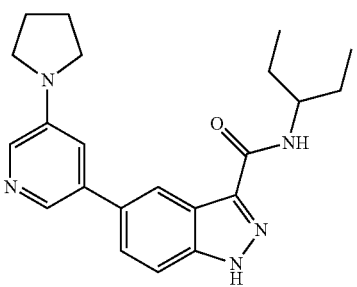

N-(Pentan-3-yl)-5-(5-(pyrrolidin-1-yl)pyridin-3-yl)-1H-indazole-3-carboxamide 1215

White solid (17 mg, 0.05 mmol). $^1$H NMR (DMSO-d$_6$, 500 MHz) δ ppm 0.88 (t, J=7.41 Hz, 6H), 1.48-1.64 (m, 4H), 1.94-2.04 (m, 4H), 3.32-3.40 (m, 4H), 3.79-3.89 (m, 1H), 7.07 (s, 1H), 7.67-7.76 (m, 2H), 7.91-7.99 (m, 2H), 8.12 (brs, 1H), 8.40 (s, 1H), 13.61 (s, 1H); ESIMS found for C$_{22}$H$_{27}$N$_5$O m/z 378.2 (M+1).

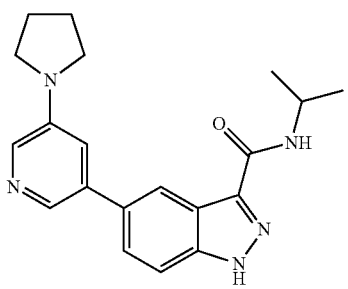

N-Isopropyl-5-(5-(pyrrolidin-1-yl)pyridin-3-yl)-1H-indazole-3-carboxamide 1245

Yellow-white solid (15 mg, 0.04 mmol). $^1$H NMR (DMSO-d$_6$, 500 MHz) δ ppm 1.22 (d, J=6.59 Hz, 6H), 1.99 (dt, J=6.59, 3.29 Hz, 4H), 3.32-3.39 (m, 4H), 4.14-4.25 (m, 1H), 7.06 (t, J=2.20 Hz, 1H), 7.67-7.77 (m, 2H), 7.95 (d, J=2.74 Hz, 1H), 8.06-8.16 (m, 2H), 8.39 (s, 1H), 13.62 (brs, 1H); ESIMS found for C$_{20}$H$_{23}$N$_5$O m/z 350.2 (M+1).

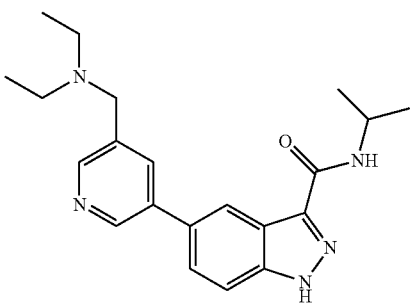

5-(5-((Diethylamino)methyl)pyridin-3-yl)-N-isopropyl-1H-indazole-3-carboxamide 1246

White solid (53 mg, 0.15 mmol). $^1$H NMR (DMSO-d$_6$, 500 MHz) δ ppm 1.01 (t, J=7.14 Hz, 6H), 1.22 (d, J=6.59 Hz, 6H), 2.50-2.55 (m, 4H), 3.66 (s, 2H), 4.19 (dq, J=14.82, 6.59 Hz, 1H), 7.71-7.75 (m, 1H), 7.75-7.78 (m, 1H), 7.98 (s, 1H), 8.13 (d, J=8.23 Hz, 1H), 8.42 (s, 1H), 8.50 (d, J=1.65 Hz, 1H), 8.77 (d, J=2.20 Hz, 1H), 13.66 (brs, 1H); ESIMS found for C$_{21}$H$_{27}$N$_5$O m/z 366.0 (M+1).

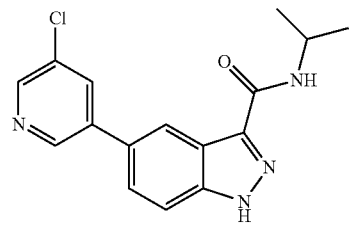

5-(5-Chloropyridin-3-yl)-N-isopropyl-1H-indazole-3-carboxamide 1247

White solid (43 mg, 0.14 mmol). $^1$H NMR (DMSO-d$_6$, 500 MHz) δ ppm 1.22 (d, J=6.86 Hz, 6H), 4.14-4.25 (m, 1H), 7.70-7.78 (m, 1H), 7.78-7.84 (m, 1H), 8.15 (br d, J=8.23 Hz, 1H), 8.24 (t, J=2.20 Hz, 1H), 8.46 (d, J=1.10 Hz, 1H), 8.63 (d, J=2.20 Hz, 1H), 8.87 (d, J=1.92 Hz, 1H), 13.69 (brs, 1H); ESIMS found for C$_{16}$H$_{15}$ClN$_4$O m/z 315.0 (M+1).

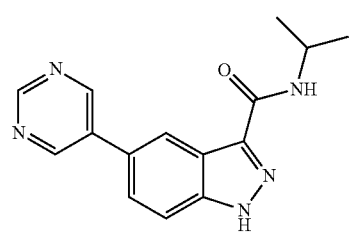

N-Isopropyl-5-(pyrimidin-5-yl)-1H-indazole-3-carboxamide 1248

White solid (40 mg, 0.14 mmol). $^1$H NMR (DMSO-d$_6$, 500 MHz) δ ppm 0.90 (d, J=6.86 Hz, 6H), 1.90 (dquin, J=13.53, 6.77 Hz, 1H), 7.49 (ddd, J=7.20, 5.15, 1.65 Hz, 1H), 7.62-7.68 (m, 1H), 7.74 (d, J=8.78 Hz, 1H), 8.16 (ddd, J=10.22, 7.48, 1.78 Hz, 1H), 8.25 (d, J=4.67 Hz, 1H), 8.35-8.44 (m, 2H), 13.70 (brs, 1H); ESIMS found for C$_{15}$H$_{15}$N$_5$O m/z 282.0 (M+1).

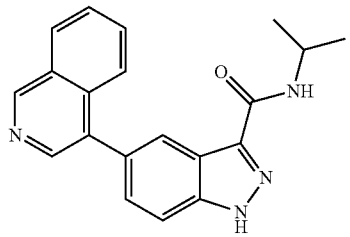

N-Isopropyl-5-(isoquinolin-4-yl)-1H-indazole-3-carboxamide 1249

White solid (50 mg, 0.15 mmol). $^1$H NMR (DMSO-d$_6$, 500 MHz) δ ppm 1.20 (d, J=6.59 Hz, 6H), 4.17 (dq, J=14.79, 6.60 Hz, 1H), 7.58 (dd, J=8.51, 1.65 Hz, 1H), 7.72-7.78 (m, 1H), 7.78-7.83 (m, 2H), 7.83-7.88 (m, 1H), 8.15 (d, J=7.96 Hz, 1H), 8.25 (d, J=7.96 Hz, 1H), 8.28-8.33 (m, 2H), 8.49 (s, 1H), 9.37 (s, 1H), 13.74 (brs, 1H); ESIMS found for C$_{20}$H$_{18}$N$_4$O m/z 331.0 (M+1).

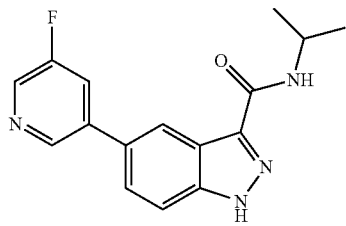

5-(5-Fluoropyridin-3-yl)-N-isopropyl-1H-indazole-3-carboxamide 1250

White solid (46 mg, 0.15 mmol). $^1$H NMR (DMSO-d$_6$, 500 MHz) δ ppm 1.22 (d, J=6.59 Hz, 6H), 4.12-4.26 (m, 1H), 7.68-7.77 (m, 1H), 7.77-7.85 (m, 1H), 8.07 (dt, J=10.29, 2.13 Hz, 1H), 8.16 (d, J=8.23 Hz, 1H), 8.47 (s, 1H), 8.58 (d, J=2.74 Hz, 1H), 8.80 (t, J=1.65 Hz, 1H), 13.68 (brs, 1H); ESIMS found for C$_{16}$H$_{15}$FN$_4$O m/z 299.3 (M+1).

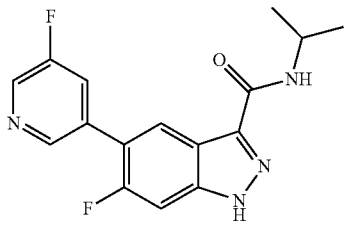

6-Fluoro-5-(5-fluoropyridin-3-yl)-N-isopropyl-1H-indazole-3-carboxamide 1251

White solid (25.0 mg, 0.08 mmol). $^1$H NMR (DMSO-d$_6$, 500 MHz) δ ppm 1.20 (d, J=6.59 Hz, 6H), 4.12-4.24 (m, 1H), 7.62 (d, J=10.70 Hz, 1H), 7.95-8.03 (m, 1H), 8.21 (d, J=8.23 Hz, 1H), 8.30 (d, J=7.41 Hz, 1H), 8.61-8.67 (m, 2H), 13.77 (brs, 1H); ESIMS found for C$_{16}$H$_{14}$F$_2$N$_4$O m/z 317.2 (M+1).

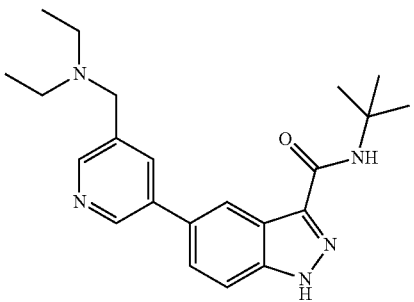

N-(tert-Butyl)-5-(5-(((diethylamino)methyl)pyridin-3-yl)-1H-indazole-3-carboxamide 1252

White solid (36 mg, 0.09 mmol). $^1$H NMR (DMSO-d$_6$, 500 MHz) δ ppm 1.01 (t, J=7.14 Hz, 6H), 1.45 (s, 9H), 2.51-2.55 (m, 4H), 3.66 (s, 2H), 7.46 (s, 1H), 7.70-7.80 (m, 2H), 7.98 (s, 1H), 8.41 (s, 1H), 8.50 (d, J=1.65 Hz, 1H), 8.77 (d, J=1.92 Hz, 1H), 13.61 (brs, 1H); ESIMS found for C$_{22}$H$_{29}$N$_5$O m/z 380.1 (M+1).

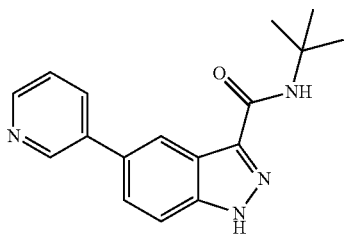

N-(tert-Butyl)-5-(pyridin-3-yl)-1H-indazole-3-carboxamide 1253

White solid (32 mg, 0.11 mmol). $^1$H NMR (DMSO-d$_6$, 500 MHz) δ ppm 1.45 (s, 9H), 7.46 (s, 1H), 7.48-7.54 (m, 1H), 7.75 (qd, J=8.96, 1.37 Hz, 2H), 8.06-8.14 (m, 1H), 8.43

(dd, J=1.65, 0.82 Hz, 1H), 8.58 (dd, J=4.67, 1.65 Hz, 1H), 8.91 (dd, J=2.47, 0.82 Hz, 1H), 13.62 (brs, 1H); ESIMS found for C₁₇H₁₈N₄O m/z 295.2 (M+1).

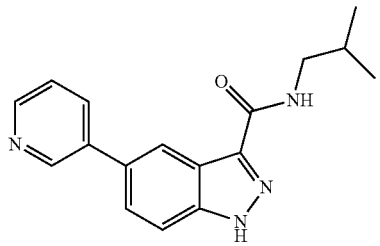

N-Isobutyl-5-(pyridin-3-yl)-1H-indazole-3-carboxamide 1254

White solid (52 mg, 0.18 mmol). ¹H NMR (DMSO-d₆, 500 MHz) δ ppm 0.91 (d, J=6.59 Hz, 6H), 1.91 (dt, J=13.45, 6.72 Hz, 1H), 3.15 (t, J=6.59 Hz, 2H), 7.51 (dd, J=7.96, 4.67 Hz, 1H), 7.70-7.81 (m, 2H), 8.10 (dt, J=7.89, 1.96 Hz, 1H), 8.37-8.47 (m, 2H), 8.58 (dd, J=4.67, 1.37 Hz, 1H), 8.90 (d, J=2.20 Hz, 1H), 13.66 (brs, 1H); ESIMS found for C₁₇H₁₈N₄O m/z 295.3 (M+1).

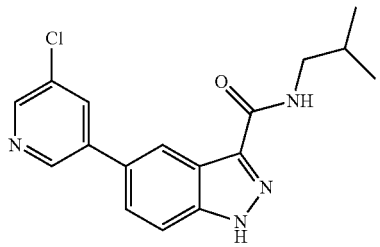

5-(5-Chloropyridin-3-yl)-N-isobutyl-1H-indazole-3-carboxamide 1255

White solid (59 mg, 0.18 mmol). ¹H NMR (DMSO-d₆, 500 MHz) δ ppm 0.91 (d, J=6.59 Hz, 6H), 1.85-1.97 (m, 1H), 3.15 (t, J=6.72 Hz, 2H), 7.72-7.78 (m, 1H), 7.78-7.84 (m, 1H), 8.25 (t, J=2.06 Hz, 1H), 8.43 (brt, J=6.04 Hz, 1H), 8.46 (s, 1H), 8.63 (d, J=2.20 Hz, 1H), 8.87 (d, J=1.92 Hz, 1H), 13.70 (s, 1H); ESIMS found for C₁₇H₁₇ClN₄O m/z 329.1 (M+1).

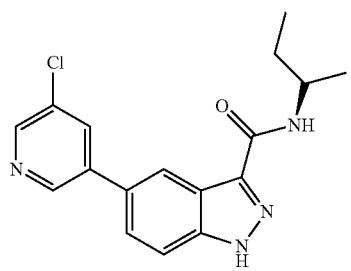

(R)—N-(sec-butyl)-5-(5-chloropyridin-3-yl)-1H-indazole-3-carboxamide 1256

White solid (27 mg, 0.08 mmol). ¹H NMR (DMSO-d₆, 500 MHz) δ ppm 0.89 (t, J=7.41 Hz, 3H), 1.19 (d, J=6.59 Hz, 3H), 1.47-1.68 (m, 2H), 3.95-4.06 (m, 1H), 7.72-7.77 (m, 1H), 7.79-7.84 (m, 1H), 8.10 (d, J=8.78 Hz, 1H), 8.25 (t, J=2.20 Hz, 1H), 8.46 (s, 1H), 8.63 (d, J=2.20 Hz, 1H), 8.87 (d, J=1.92 Hz, 1H), 13.70 (s, 1H); ESIMS found for C₁₇H₁₇ClN₄O m/z 329.1 (M+1).

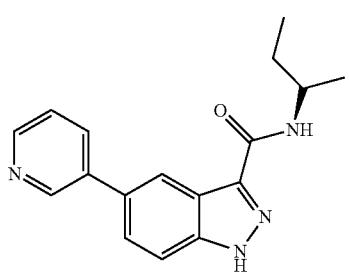

(R)—N-(sec-butyl)-5-(pyridin-3-yl)-1H-indazole-3-carboxamide 1257

White solid (22 mg, 0.07 mmol). ¹H NMR (DMSO-d₆, 500 MHz) δ ppm 0.89 (t, J=7.41 Hz, 3H), 1.19 (d, J=6.59 Hz, 3H), 1.46-1.68 (m, 2H), 3.95-4.07 (m, 1H), 7.46-7.56 (m, 1H), 7.76 (qd, J=8.60, 1.37 Hz, 2H), 8.01-8.14 (m, 2H), 8.43 (s, 1H), 8.58 (dd, J=4.80, 1.51 Hz, 1H), 8.91 (d, J=1.92 Hz, 1H), 13.66 (s, 1H); ESIMS found for C₁₇H₁₈N₄O m/z 295.3 (M+1).

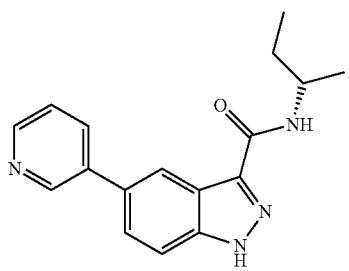

(S)—N-(sec-butyl)-5-(pyridin-3-yl)-1H-indazole-3-carboxamide 1258

White solid (26.7 mg, 0.09 mmol). ¹H NMR (DMSO-d₆, 500 MHz) δ ppm 0.89 (t, J=7.41 Hz, 3H), 1.19 (d, J=6.59 Hz, 3H), 1.47-1.70 (m, 2H), 3.94-4.06 (m, 1H), 7.51 (dd, J=8.23, 4.39 Hz, 1H), 7.76 (qd, J=8.60, 1.37 Hz, 2H), 8.02-8.15 (m, 2H), 8.43 (d, J=0.82 Hz, 1H), 8.58 (dd, J=4.80, 1.51 Hz, 1H), 8.90 (d, J=1.92 Hz, 1H), 13.66 (s, 1H); ESIMS found for C₁₇H₁₈N₄O m/z 295.2 (M+1).

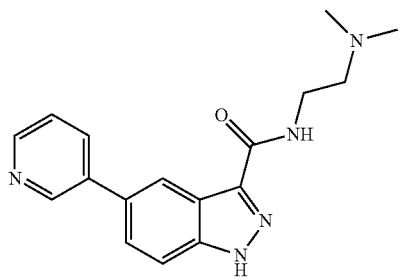

N-(2-(Dimethylamino)ethyl)-5-(pyridin-3-yl)-1H-indazole-3-carboxamide 1259

White solid (1.5 mg, 0.005 mmol). $^1$H NMR (DMSO-d, 500 MHz) δ ppm 2.20 (s, 6H), 2.45 (t, J=6.72 Hz, 2H), 3.42 (q, J=6.40 Hz, 2H), 7.51 (dd, J=7.82, 4.80 Hz, 1H), 7.72-7.80 (m, 2H), 8.10 (dt, J=7.89, 1.82 Hz, 1H), 8.19 (t, J=5.63 Hz, 1H), 8.43 (s, 1H), 8.58 (dd, J=4.67, 1.37 Hz, 1H), 8.90 (d, J=2.20 Hz, 1H), 13.65 (brs, 1H); ESIMS found for $C_{17}H_{19}N_5O$ m/z 310.4 (M+1).

1260

5-(2,3-Difluorophenyl)-N-(3-(dimethylamino)propyl)-1H-indazole-3-carboxamide 1260

White solid (14 mg, 0.04 mmol). $^1$H NMR (DMSO-d$_6$, 500 MHz) δ ppm 1.87-1.96 (m, 2H), 2.76 (s, 6H), 3.04-3.13 (m, 2H), 3.38 (q, J=6.50 Hz, 2H), 7.29-7.36 (m, 1H), 7.36-7.50 (m, 2H), 7.62 (dt, J=8.71, 1.54 Hz, 1H), 7.75 (dd, J=8.78, 0.82 Hz, 1H), 8.36 (s, 1H), 8.65 (t, J=5.90 Hz, 1H), 9.27 (brs, 1H), 13.78 (s, 1H); ESIMS found for $C_{19}H_{20}F_2N_4O$ m/z 359.3 (M+1).

1261

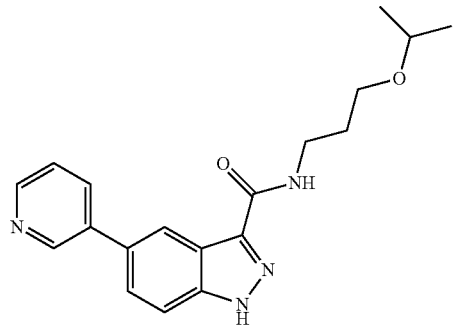

N-(3-Isopropoxypropyl)-5-(pyridin-3-yl)-1H-indazole-3-carboxamide 1261

White solid (60 mg, 0.18 mmol). $^1$H NMR (DMSO-d$_6$, 500 MHz) δ ppm 1.10 (d, J=6.04 Hz, 6H), 1.77 (quin, J=6.52 Hz, 2H), 3.38 (q, J=6.59 Hz, 2H), 3.45 (t, J=6.17 Hz, 2H), 3.49-3.59 (m, 1H), 7.46-7.55 (m, 1H), 7.75 (qd, J=8.74, 1.23 Hz, 2H), 8.05-8.13 (m, 1H), 8.37-8.46 (m, 2H), 8.58 (dd, J=4.80, 1.51 Hz, 1H), 8.90 (d, J=1.65 Hz, 1H), 13.67 (brs, 1H); ESIMS found for $C_{19}H_{22}N_4O_2$ m/z 338.8 (M+1).

1262

N-(3-Isopropoxypropyl)-5-(6-methylpyridin-3-yl)-1H-indazole-3-carboxamide 1262

White solid (28 mg, 0.08 mmol). $^1$H NMR (DMSO-d$_6$, 500 MHz) δ ppm 1.10 (d, J=6.04 Hz, 6H), 1.77 (quin, J=6.59 Hz, 2H), 2.52 (s, 3H), 3.38 (q, J=6.77 Hz, 2H), 3.45 (t, J=6.17 Hz, 2H), 3.54 (spt, J=6.08 Hz, 1H), 7.36 (d, J=7.96 Hz, 1H), 7.69-7.76 (m, 2H), 7.98 (dd, J=7.96, 2.47 Hz, 1H), 8.37-8.43 (m, 2H), 8.76 (d, J=2.20 Hz, 1H), 13.64 (brs, 1H); ESIMS found for $C_{20}H_{24}N_4O_2$ m/z 353.1 (M+1).

1263

5-(5-Fluoropyridin-3-yl)-N-(3-isopropoxypropyl)-1H-indazole-3-carboxamide 1263

White solid (42 mg, 0.12 mmol). $^1$H NMR (DMSO-d$_6$, 500 MHz) δ ppm 1.10 (d, J=6.31 Hz, 6H), 1.78 (quin, J=6.59 Hz, 2H), 3.39 (q, J=6.77 Hz, 2H), 3.45 (t, J=6.31 Hz, 2H), 3.51-3.59 (m, 1H), 7.70-7.77 (m, 1H), 7.77-7.85 (m, 1H), 8.02-8.11 (m, 1H), 8.43 (t, J=5.63 Hz, 1H), 8.45-8.49 (m, 1H), 8.58 (d, J=2.74 Hz, 1H), 8.80 (t, J=1.78 Hz, 1H), 13.71 (brs, 1H); ESIMS found for $C_{19}H_{21}FN_4O_2$ m/z 357.2 (M+1).

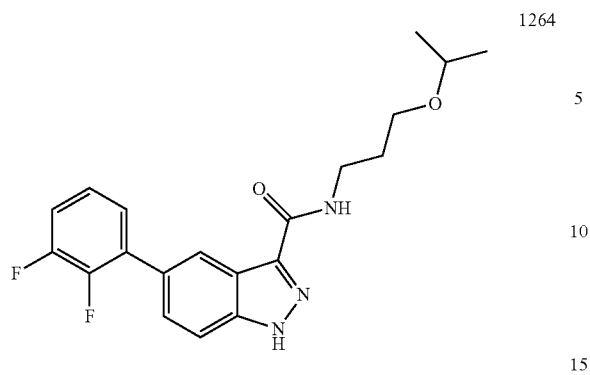

1264

5-(2,3-Difluorophenyl)-N-(3-isopropoxypropyl)-1H-indazole-3-carboxamide 1264

White solid (21 mg, 0.06 mmol). $^1$H NMR (DMSO-d$_6$, 500 MHz) δ ppm 1.09 (d, J=6.04 Hz, 6H), 1.77 (quin, J=6.59 Hz, 2H), 3.37 (q, J=6.68 Hz, 2H), 3.44 (t, J=6.17 Hz, 2H), 3.48-3.60 (m, 1H), 7.29-7.36 (m, 1H), 7.37-7.49 (m, 2H), 7.61 (dt, J=8.58, 1.61 Hz, 1H), 7.70-7.76 (m, 1H), 8.35 (s, 1H), 8.42 (brt, J=5.90 Hz, 1H), 13.69 (brs, 1H); ESIMS found for $C_{20}H_{21}F_2N_3O_2$ m/z 373.4 (M+).

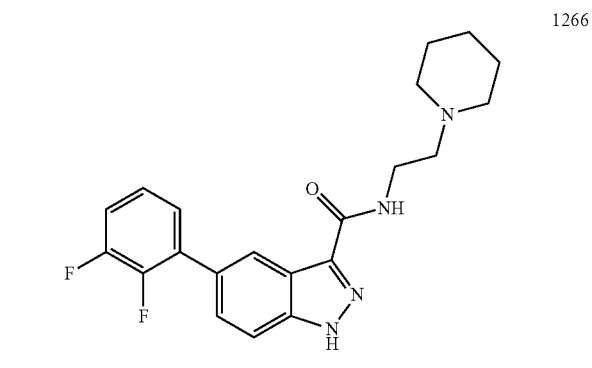 [SMILES: O=C(NCCN1CCCCC1)c1n[nH]c2ccc(-c3cccc(F)c3F)cc12]

1266

5-(2,3-Difluorophenyl)-N-(2-(piperidin-1-yl)ethyl)-1H-indazole-3-carboxamide 1266

White solid (29 mg, 0.08 mmol). $^1$H NMR (DMSO-d$_6$, 500 MHz) δ ppm 1.34-1.44 (m, 2H), 1.50 (quin, J=5.56 Hz, 4H), 2.39 (brs, 4H), 2.47 (t, J=6.86 Hz, 2H), 3.42 (q, J=6.59 Hz, 2H), 7.27-7.36 (m, 1H), 7.37-7.50 (m, 2H), 7.61 (dt, J=8.71, 1.54 Hz, 1H), 7.74 (d, J=7.96 Hz, 1H), 8.21 (t, J=5.76 Hz, 1H), 8.36 (s, 1H), 13.69 (brs, 1H); ESIMS found for $C_{21}H_{22}F_2N_4O$ m/z 385.3 (M+1).

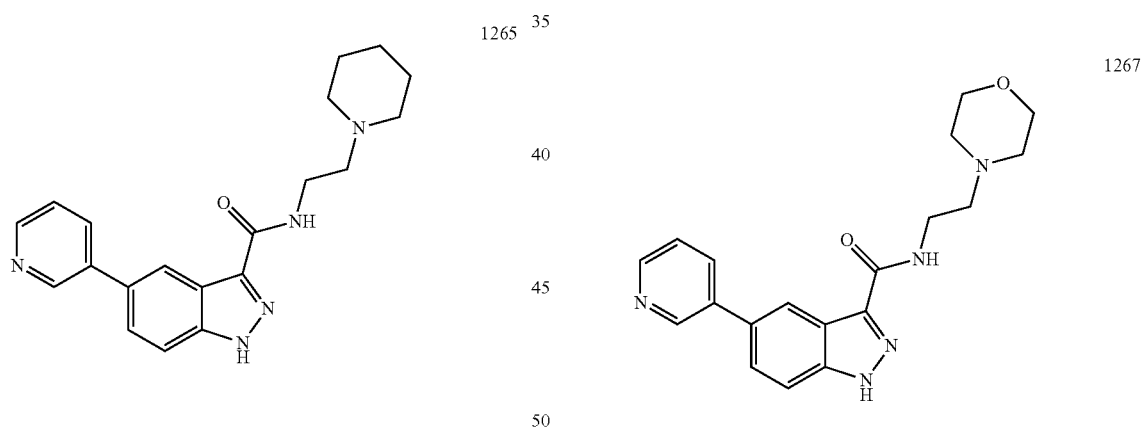

1265

1267

N-(2-(Piperidin-1-yl)ethyl)-5-(pyridin-3-yl)-1H-indazole-3-carboxamide 1265

White solid (21.3 mg, 0.06 mmol). $^1$H NMR (DMSO-d$_6$, 500 MHz) δ ppm 1.35-1.43 (m, 2H), 1.50 (quin, J=5.56 Hz, 4H), 2.40 (brs, 4H), 2.45-2.49 (m, 2H), 3.43 (q, J=6.59 Hz, 2H), 7.51 (dd, J=7.82, 4.80 Hz, 1H), 7.71-7.80 (m, 2H), 8.09 (dt, J=7.96, 1.92 Hz, 1H), 8.21 (t, J=5.76 Hz, 1H), 8.43 (s, 1H), 8.58 (dd, J=4.67, 1.65 Hz, 1H), 8.90 (d, J=2.20 Hz, 1H), 13.67 (brs, 1H); ESIMS found for $C_{20}H_{23}N_5O$ m/z 350.4 (M+1).

N-(2-Morpholinoethyl)-5-(pyridin-3-yl)-1H-indazole-3-carboxamide 1267

White solid (55.1 mg, 0.16 mmol). $^1$H NMR (DMSO-d$_6$, 500 MHz) δ ppm 2.44 (brs, 4H), 2.50-2.55 (m, 2H), 3.45 (q, J=6.59 Hz, 2H), 3.58 (t, J=4.53 Hz, 4H), 7.51 (dd, J=7.82, 4.80 Hz, 1H), 7.71-7.80 (m, 2H), 8.09 (dt, J=7.96, 1.92 Hz, 1H), 8.27 (t, J=5.63 Hz, 1H), 8.43 (s, 1H), 8.58 (dd, J=4.80, 1.51 Hz, 1H), 8.90 (d, J=1.92 Hz, 1H), 13.67 (brs, 1H); ESIMS found for $C_{19}H_{21}N_5O_2$ m/z 352.3 (M+1).

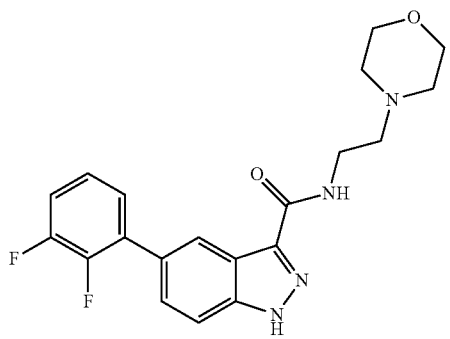

5-(2,3-Difluorophenyl)-N-(2-morpholinoethyl)-1H-indazole-3-carboxamide 1268

White solid (39 mg, 0.10 mmol). $^1$H NMR (DMSO-d$_6$, 500 MHz) δ ppm 2.43 (brs, 4H), 2.51-2.54 (m, 2H), 3.44 (q, J=6.59 Hz, 2H), 3.58 (t, J=4.53 Hz, 4H), 7.29-7.36 (m, 1H), 7.37-7.50 (m, 2H), 7.61 (dt, J=8.71, 1.54 Hz, 1H), 7.70-7.77 (m, 1H), 8.28 (t, J=5.76 Hz, 1H), 8.35 (s, 1H), 13.70 (brs, 1H); ESIMS found for C$_{20}$H$_{20}$F$_2$N$_4$O$_2$ m/z 387.3 (M+1).

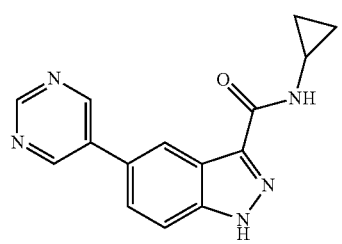

N-Cyclopropyl-5-(pyrimidin-5-yl)-1H-indazole-3-carboxamide 1269

White solid (48.7 mg, 0.17 mmol). $^1$H NMR (DMSO-d$_6$, 500 MHz) δ ppm 0.62-0.75 (m, 4H), 2.86-2.97 (m, 1H), 7.71-7.80 (m, 1H), 7.80-7.86 (m, 1H), 8.43-8.54 (m, 2H), 9.15 (s, 2H), 9.20 (s, 1H), 13.72 (brs, 1H); ESIMS found for C$_{15}$H$_{13}$N$_5$O m/z 280.3 (M+1).

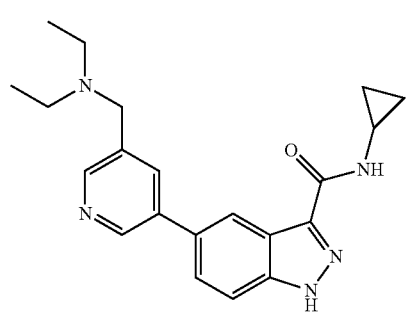

N-Cyclopropyl-5-(5-(((diethylamino)methyl)pyridin-3-yl)-1H-indazole-3-carboxamide 1270

White solid (50 mg, 0.14 mmol). $^1$H NMR (DMSO-d, 500 MHz) δ ppm 0.62-0.73 (m, 4H), 1.01 (t, J=7.14 Hz, 6H), 2.51-2.56 (m, 4H), 2.87-2.97 (m, 1H), 3.66 (s, 2H), 7.70-7.79 (m, 2H), 7.96-8.00 (m, 1H), 8.42 (s, 1H), 8.45 (d, J=4.39 Hz, 1H), 8.50 (d, S=1.65 Hz, 1H), 8.77 (d, J=2.20 Hz, 1H), 13.65 (brs, 1H); ESIMS found for C$_{21}$H$_{25}$N$_5$O m/z 364.2 (M+1).

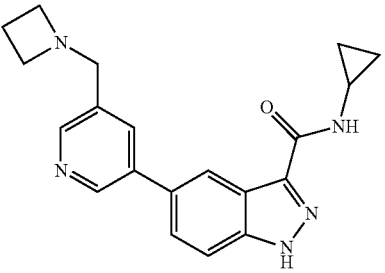

5-(5-(Azetidin-1-ylmethyl)pyridin-3-yl)-N-cyclopropyl-1H-indazole-3-carboxamide 1271

Light brown solid (37 mg, 0.11 mmol). $^1$H NMR (DMSO-d, 500 MHz) δ ppm 0.63-0.75 (m, 4H), 2.01 (quin, J=7.00 Hz, 2H), 2.87-2.95 (m, 1H), 3.19 (t, J=7.00 Hz, 4H), 3.64 (s, 2H), 7.68-7.75 (m, 1H), 7.75-7.81 (m, 1H), 7.94 (s, 1H), 8.43 (s, 1H), 8.45 (d, J=1.65 Hz, 2H), 8.77 (d, J=1.92 Hz, 1H), 13.65 (brs, 1H); ESIMS found for C$_{20}$H$_{21}$N$_5$O m/z 347.9 (M+1)

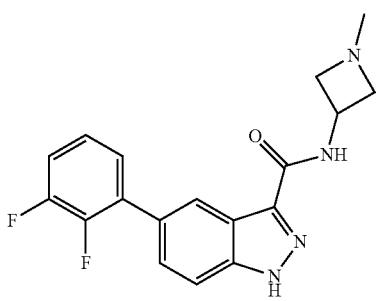

5-(2,3-Difluorophenyl)-N-(1-methylazetidin-3-yl)-1H-indazole-3-carboxamide 1272

White solid (15.3 mg, 0.04 mmol). $^1$H NMR (DMSO-d$_6$, 500 MHz) δ ppm 2.26 (brd, J=2.47 Hz, 3H), 3.01-3.13 (m, 2H), 3.52-3.64 (m, 2H), 4.45-4.58 (m, 1H), 7.28-7.35 (m, 1H), 7.35-7.49 (m, 2H), 7.58-7.65 (m, 1H), 7.74 (d, J=8.78 Hz, 1H), 8.33 (s, 1H), 8.73-8.82 (m, 1H), 13.76 (brs, 1H); ESIMS found for C$_{18}$H$_{16}$F$_2$N$_4$O m/z 343.2 (M+1).

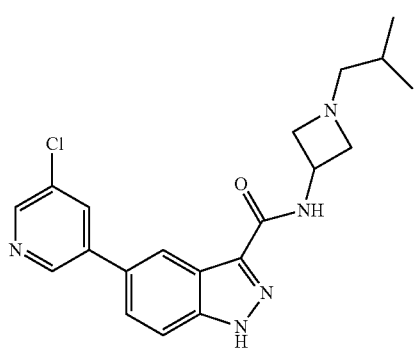

5-(5-Chloropyridin-3-yl)-N-(1-isobutylazetidin-3-yl)-1H-indazole-3-carboxamide 1273

White solid (58.6 mg, 0.15 mmol). $^1$H NMR (DMSO-d$_6$, 500 MHz) δ ppm 0.85 (d, J=6.86 Hz, 6H), 1.48-1.58 (m, 1H), 2.23 (d, J=6.86 Hz, 2H), 3.01-3.07 (m, 2H), 3.53-3.60 (m, 2H), 4.55 (sxt, J=7.14 Hz, 1H), 7.72-7.78 (m, 1H), 7.78-7.84 (m, 1H), 8.04-8.10 (m, 1H), 8.45 (dd, J=1.92, 0.82 Hz, 1H), 8.58 (d, J=2.47 Hz, 1H), 8.76-8.81 (m, 2H), 13.76 (brs, 1H); ESIMS found for C$_{20}$H$_{22}$ClN$_5$O m/z 384.2 (M+1).

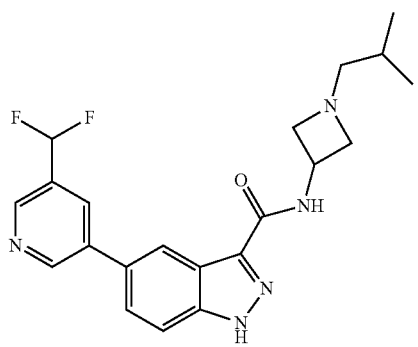

5-(5-(Difluoromethyl)pyridin-3-yl)-N-(1-isobutylazetidin-3-yl)-1H-indazole-3-carboxamide 1274

White solid (8.2 mg, 0.02 mmol). $^1$H NMR (DMSO-d, 500 MHz) δ ppm 0.85 (d, J=6.86 Hz, 6H), 1.53 (dquin, J=13.52, 6.71 Hz, 1H), 2.23 (d, J=6.86 Hz, 2H), 3.04 (t, J=7.27 Hz, 2H), 3.57 (t, J=7.14 Hz, 2H), 4.55 (sxt, J=7.08 Hz, 1H), 7.24 (t, J=55.5 Hz, 1H), 7.73-7.80 (m, 1H), 7.80-7.88 (m, 1H), 8.28 (s, 1H), 8.46 (s, 1H), 8.76-8.83 (m, 2H), 9.09 (s, 1H), 13.77 (brs, 1H); ESIMS found for C$_{21}$H$_{23}$F$_2$N$_5$O m/z 400.3 (M+1).

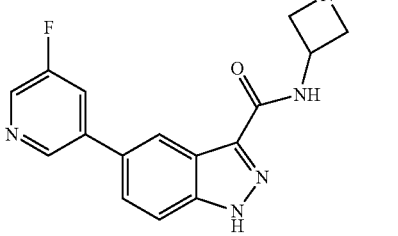

5-(5-Fluoropyridin-3-yl)-N-(1-isobutylazetidin-3-yl)-1H-indazole-3-carboxamide 1275

White solid (34.4 mg, 0.09 mmol). $^1$H NMR (DMSO-d$_6$, 500 MHz) δ ppm 0.85 (d, J=6.86 Hz, 6H), 1.53 (dquin, J=13.45, 6.72 Hz, 1H), 2.23 (d, J=6.86 Hz, 2H), 3.04 (br t, J=7.14 Hz, 2H), 3.57 (t, J=7.14 Hz, 2H), 4.55 (sxt, J=7.19 Hz, 1H), 7.72-7.78 (m, 1H), 7.78-7.84 (m, 1H), 8.24 (t, J=2.20 Hz, 1H), 8.44 (dd, J=1.65, 0.82 Hz, 1H), 8.63 (d, J=2.20 Hz, 1H), 8.79 (d, J=7.41 Hz, 1H), 8.87 (d, J=1.92 Hz, 1H), 13.77 (brs, 1H); ESIMS found for C$_{20}$H$_{22}$FN$_5$O m/z 367.9 (M+1).

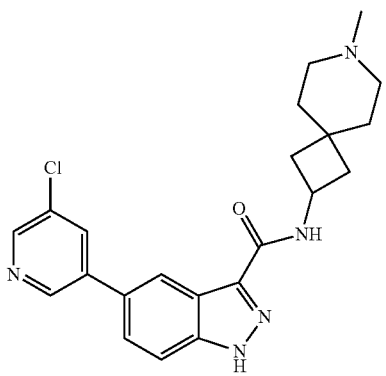

5-(5-Chloropyridin-3-yl)-N-(7-methyl-7-azaspiro[3.5]nonan-2-yl)-1H-indazole-3-carboxamide 1276

White solid (22.4 mg, 0.05 mmol). $^1$H NMR (DMSO-d$_6$, 500 MHz) δ ppm 1.56 (br t, J=5.49 Hz, 3H), 1.60 (br t, J=5.08 Hz, 2H), 1.93 (br dd, J=1.53, 8.78 Hz, 2H), 2.07-2.33 (m, 9H), 4.49 (sxt, J=8.23 Hz, 1H), 7.72-7.77 (m, 1H), 7.79-7.83 (m, 1H), 8.24 (t, J=2.20 Hz, 1H), 8.41-8.46 (m, 1H), 8.60-8.67 (m, 2H), 8.86 (d, J=1.92 Hz, 1H), 13.70 (brs, 1H); ESIMS found for C$_{22}$H$_{24}$ClN$_5$O m/z 410.1 (M+1).

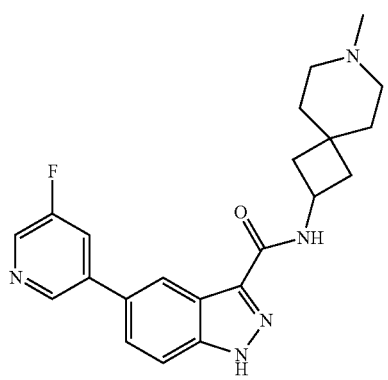

5-(5-Fluoropyridin-3-yl)-N-(7-methyl-7-azaspiro[3.5]nonan-2-yl)-1H-indazole-3-carboxamide 1277

White solid (23.5 mg, 0.06 mmol). $^1$H NMR (DMSO-d, 500 MHz) δ ppm 1.55 (br t, J=5.49 Hz, 2H), 1.59 (br t, J=4.94 Hz, 2H), 1.93 (br dd, J=11.53, 8.78 Hz, 2H), 2.07-2.31 (m, 9H), 4.49 (sxt, J=8.29 Hz, 1H), 7.72-7.77 (m, 1H), 7.77-7.83 (m, 1H), 8.03-8.10 (m, 1H), 8.45 (dd, J=1.65, 0.82 Hz, 1H), 8.58 (d, J=2.74 Hz, 1H), 8.63 (d, J=8.23 Hz, 1H), 8.79 (t, J=1.78 Hz, 1H), 13.72 (brs, 1H); ESIMS found for $C_{22}H_{24}FN_5O$ m/z 393.9 (M+1).

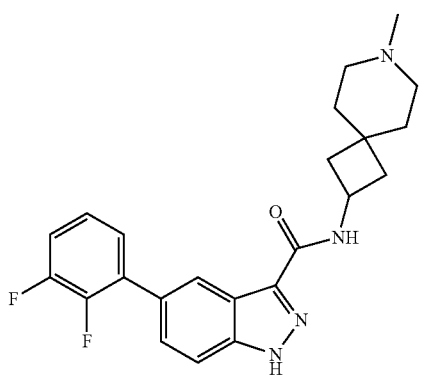

5-(2,3-Difluorophenyl)-N-(7-methyl-7-azaspiro[3.5]nonan-2-yl)-1H-indazole-3-carboxamide 1278

White solid (23.6 mg, 0.06 mmol). $^1$H NMR (DMSO-d$_6$, 500 MHz) δ ppm 1.54 (br t, J=5.35 Hz, 2H), 1.58 (br t, J=5.08 Hz, 2H), 1.92 (br dd, J=11.39, 8.64 Hz, 2H), 2.07-2.30 (m, 9H), 4.47 (sxt, J=8.34 Hz, 1H), 7.29-7.35 (m, 1H), 7.36-7.48 (m, 2H), 7.61 (dt, J=8.58, 1.75 Hz, 1H), 7.73 (dd, J=8.78, 0.82 Hz, 1H), 8.33 (s, 1H), 8.62 (d, J=8.23 Hz, 1H), 13.72 (brs, 1H); ESIMS found for $C_{23}H_{24}F_2N_4O$ m/z 411.2 (M+1).

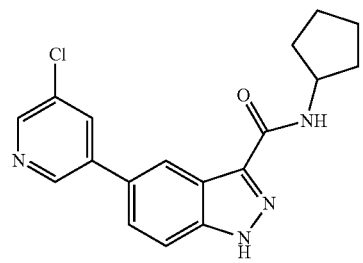

5-(5-Chloropyridin-3-yl)-N-cyclopentyl-1H-indazole-3-carboxamide 1279

White solid (36 mg, 0.11 mmol). $^1$H NMR (DMSO-d$_6$, 500 MHz) δ ppm 1.50-1.66 (m, 4H), 1.68-1.76 (m, 2H), 1.87-1.96 (m, 2H), 4.31 (sxt, J=7.35 Hz, 1H), 7.71-7.76 (m, 1H), 7.79-7.83 (m, 1H), 8.22-8.28 (m, 2H), 8.45 (dd, J=1.65, 0.82 Hz, 1H), 8.63 (d, J=2.47 Hz, 1H), 8.87 (d, J=1.92 Hz, 1H), 13.69 (s, 1H); ESIMS found for $C_{18}H_{17}ClN_4O$ m/z 341.0 (M+1).

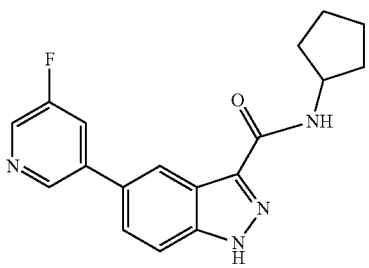

N-Cyclopentyl-5-(5-fluoropyridin-3-yl)-1H-indazole-3-carboxamide 1280

White solid (11 mg, 0.03 mmol). $^1$H NMR (DMSO-d$_6$, 500 MHz) δ ppm 1.49-1.66 (m, 4H), 1.67-1.77 (m, 2H), 1.86-1.96 (m, 2H), 4.26-4.36 (m, 1H), 7.72-7.76 (m, 1H), 7.78-7.83 (m, 1H), 8.04-8.10 (m, 1H), 8.24 (d, J=7.68 Hz, 1H), 8.46 (dd, J=1.65, 0.82 Hz, 1H), 8.58 (d, J=2.74 Hz, 1H), 8.80 (t, J=1.78 Hz, 1H), 13.69 (brs, 1H); ESIMS found for $C_{18}H_{17}FN_4O$ m/z 325.4 (M+1).

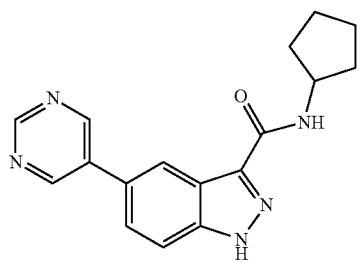 [SMILES: O=C(NC1CCCC1)c1n[nH]c2ccc(-c3cncnc3)cc12]

N-Cyclohexyl-5-(pyrimidin-5-yl)-1H-indazole-3-carboxamide 1281

White solid (74.5 mg, 0.23 mmol). $^1$H NMR (DMSO-d$_6$, 500 MHz) δ ppm 1.08-1.21 (m, 1H), 1.27-1.37 (m, 2H), 1.37-1.49 (m, 2H), 1.61 (br d, J=12.90 Hz, 1H), 1.70-1.78 (m, 2H), 1.80-1.89 (m, 2H), 3.80-3.90 (m, 1H), 7.74-7.80 (m, 1H), 7.80-7.85 (m, 1H), 8.13 (d, J=8.23 Hz, 1H), 8.48 (dd, J=1.65, 0.82 Hz, 1H), 9.14 (s, 2H), 9.19 (s, 1H), 13.72 (brs, 1H); ESIMS found for $C_{18}H_{19}N_5O$ m/z 322.3 (M+1).

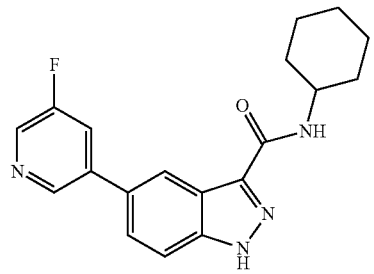

N-Cyclohexyl-5-(5-fluoropyridin-3-yl)-1H-indazole-3-carboxamide 1282

White solid (16 mg, 0.05 mmol). $^1$H NMR (DMSO-$d_6$, 500 MHz) δ ppm 1.09-1.19 (m, 1H), 1.32 (qt, J=12.69, 2.92 Hz, 2H), 1.37-1.48 (m, 2H), 1.57-1.65 (m, 1H), 1.70-1.79 (m, 2H), 1.81-1.88 (m, 2H), 3.79-3.90 (m, 1H), 7.72-7.77 (m, 1H), 7.79-7.83 (m, 1H), 8.04-8.09 (m, 1H), 8.13 (d, J=8.51 Hz, 1H), 8.46 (dd, J=1.65, 0.82 Hz, 1H), 8.58 (d, J=2.74 Hz, 1H), 8.79 (t, J=1.78 Hz, 1H), 13.66 (brs, 1H); ESIMS found for $C_{19}H_{19}FN_4O$ m/z 339.4 (M+1).

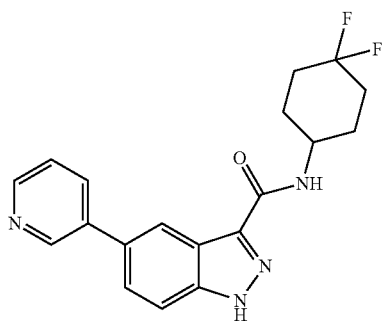

N-(4,4-Difluorocyclohexyl)-5-(pyridin-3-yl)-1H-indazole-3-carboxamide 1283

White solid (27.4 mg, 0.08 mmol). $^1$H NMR (DMSO-$d_6$, 500 MHz) δ ppm 1.70-1.81 (m, 2H), 1.85-2.13 (m, 6H), 4.00-4.12 (m, 1H), 7.51 (dd, J=7.68, 4.67 Hz, 1H), 7.71-7.80 (m, 2H), 8.09 (dt, J=8.10, 1.85 Hz, 1H), 8.37 (d, J=8.23 Hz, 1H), 8.41 (s, 1H), 8.58 (dd, J=4.67, 1.37 Hz, 1H), 8.90 (d, J=1.92 Hz, 1H); ESIMS found for $C_{19}H_{18}F_2N_4O$ m/z 357.4 (M+1).

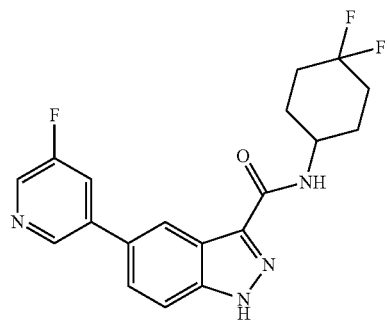

N-(4,4-Difluorocyclohexyl)-5-(5-fluoropyridin-3-yl)-1H-indazole-3-carboxamide 1284

White solid (24.7 mg, 0.06 mmol). $^1$H NMR (DMSO-$d_6$, 500 MHz) δ ppm 1.70-1.82 (m, 2H), 1.85-2.12 (m, 6H), 4.01-4.11 (m, 1H), 7.73-7.77 (m, 1H), 7.77-7.83 (m, 1H), 8.06 (dt, J=10.29, 2.13 Hz, 1H), 8.39 (d, J=8.23 Hz, 1H), 8.46 (s, 1H), 8.58 (d, J=2.74 Hz, 1H), 8.79 (s, 1H), 13.72 (brs, 1H); ESIMS found for $C_{19}H_{17}F_3N_4O$ m/z 375.1 (M+1).

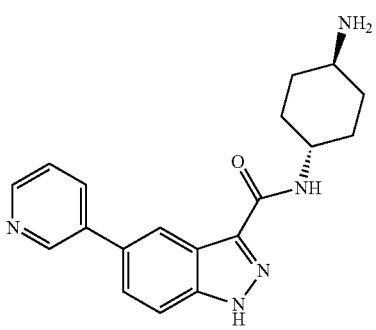

N-((1s,4s)-4-Aminocyclohexyl)-5-(pyridin-3-yl)-1H-indazole-3-carboxamide 1285

White solid (88.6 mg, 0.26 mmol). $^1$H NMR (DMSO-$d_6$, 500 MHz) δ ppm 1.49-1.57 (m, 2H), 1.57-1.69 (m, 4H), 1.82-1.92 (m, 2H), 2.93-3.01 (m, 1H), 3.93-4.02 (m, 1H), 7.51 (dd, J=7.82, 4.80 Hz, 1H), 7.73-7.80 (m, 2H), 7.83 (d, J=7.68 Hz, 1H), 8.09 (dt, J=7.89, 1.96 Hz, 1H), 8.41 (s, 1H), 8.58 (dd, J=4.67, 1.37 Hz, 1H), 8.90 (d, J=2.20 Hz, 1H); ESIMS found for $C_{19}H_{21}N_5O$ m/z 335.9 (M+1).

N-((1r,4r)-4-Aminocyclohexyl)-5-(pyridin-3-yl)-1H-indazole-3-carboxamide 1286

White solid (36.7 mg, 0.11 mmol). $^1$H NMR (DMSO-d$_6$, 500 MHz) δ ppm 1.09-1.20 (m, 2H), 1.40-1.53 (m, 2H), 1.81 (br t, J=10.57 Hz, 4H), 2.51-2.59 (m, 1H), 3.75-3.85 (m, 1H), 7.51 (dd, J=7.82, 4.80 Hz, 1H), 7.71-7.79 (m, 2H), 8.06-8.13 (m, 2H), 8.42 (s, 1H), 8.58 (dd, J=4.67, 1.37 Hz, 1H), 8.90 (d, J=2.47 Hz, 1H); ESIMS found for C$_{19}$H$_{21}$N$_5$O m/z 336.1 (M+1).

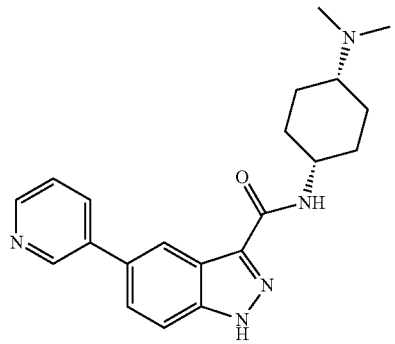

N-((1s,4s)-4-(Dimethylamino)cyclohexyl)-5-(pyridin-3-yl)-1H-indazole-3-carboxamide 1287

White solid (51.8 mg, 0.14 mmol). $^1$H NMR (DMSO-d$_6$, 500 MHz) δ ppm 1.47-1.63 (m, 4H), 1.69-1.79 (m, 2H), 1.80-1.89 (m, 2H), 2.02-2.10 (m, 1H), 2.18 (s, 6H), 4.01 (qt, J=7.46, 3.77 Hz, 1H), 7.51 (dd, J=7.96, 4.94 Hz, 1H), 7.71-7.80 (m, 2H), 7.90 (d, J=7.68 Hz, 1H), 8.09 (dt, J=7.96, 1.92 Hz, 1H), 8.40 (s, 1H), 8.58 (dd, J=4.80, 1.51 Hz, 1H), 8.90 (d, J=1.92 Hz, 1H), 13.65 (brs, 1H); ESIMS found for C$_{21}$H$_{25}$N$_5$O m/z 364.1 (M+1).

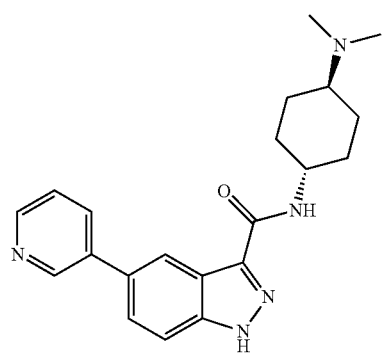

N-((1r,4r)-4-(Dimethylamino)cyclohexyl)-5-(pyridin-3-yl)-1H-indazole-3-carboxamide 1288

White solid (31 mg, 0.09 mmol). $^1$H NMR (DMSO-d$_6$, 500 MHz) δ ppm 1.22-1.33 (m, 2H), 1.41-1.53 (m, 2H), 1.84 (br d, J=12.62 Hz, 2H), 1.87-1.95 (m, 2H), 2.09-2.16 (m, 1H), 2.18 (s, 6H), 3.80 (tdt, J=1.68, 7.86, 4.01 Hz, 1H), 7.48-7.54 (m, 1H), 7.72-7.80 (m, 2H), 8.09 (dt, J=7.96, 1.92 Hz, 1H), 8.14 (d, J=8.51 Hz, 1H), 8.42 (dd, J=1.65, 0.82 Hz, 1H), 8.58 (dd, J=4.67, 1.65 Hz, 1H), 8.90 (d, J=1.65 Hz, 1H), 13.66 (brs, 1H); ESIMS found for C$_{21}$H$_{25}$N$_5$O m/z 364.1 (M+1).

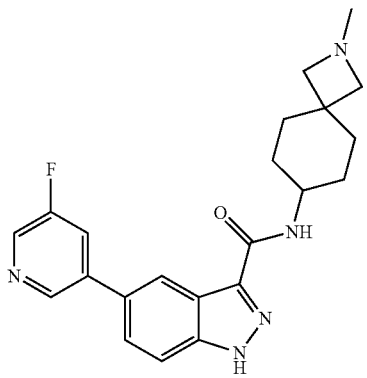

5-(5-Fluoropyridin-3-yl)-N-(2-methyl-2-azaspiro[3.5]nonan-7-yl)-1H-indazole-3-carboxamide 1289

White solid (25.5 mg, 0.06 mmol). $^1$H NMR (DMSO-d$_6$, 500 MHz) δ ppm 1.40-1.52 (m, 4H), 1.67-1.76 (m, 2H), 1.81-1.92 (m, 2H), 2.22 (s, 3H), 2.84 (s, 2H), 2.92 (s, 2H), 3.75-3.85 (m, 1H), 7.71-7.75 (m, 1H), 7.78-7.83 (m, 1H), 8.06 (dt, J=10.36, 2.23 Hz, 1H), 8.10 (d, J=8.23 Hz, 1H), 8.43-8.47 (m, 1H), 8.58 (d, J=2.47 Hz, 1H), 8.79 (t, J=1.78 Hz, 1H), 13.70 (brs, 1H); ESIMS found for C$_{22}$H$_{24}$FN$_5$O m/z 394.2 (M+1).

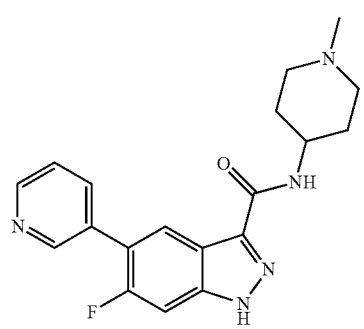

6-Fluoro-N-(1-methylpiperidin-4-yl)-5-(pyridin-3-yl)-1H-indazole-3-carboxamide 1290

Light brown solid (29 mg, 0.08 mmol). $^1$H NMR (DMSO-d$_6$, 500 MHz) δ ppm 1.63-1.81 (m, 4H), 2.00 (br t, J=10.84 Hz, 2H), 2.18 (s, 3H), 2.78 (br d, J=11.80 Hz, 2H), 3.75-3.86 (m, 1H), 7.51-7.56 (m, 1H), 7.60 (d, J=10.70 Hz, 1H), 7.99 (dq, J=7.92, 1.75 Hz, 1H), 8.21-8.29 (m, 2H), 8.62 (dd, J=4.80, 1.51 Hz, 1H), 8.75 (s, 1H), 13.75 (brs, 1H); ESIMS found for C$_{19}$H$_{20}$FN$_5$O m/z 354.1 (M+1).

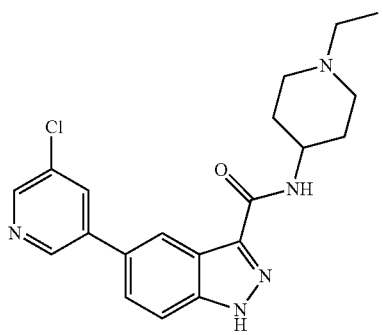

5-(5-Chloropyridin-3-yl)-N-(1-ethylpiperidin-4-yl)-1H-indazole-3-carboxamide 1291

White solid (25 mg, 0.07 mmol). $^1$H NMR (DMSO-d$_6$, 500 MHz) δ ppm 1.00 (t, J=7.14 Hz, 3H), 1.67 (qd, J=1.85, 3.43 Hz, 2H), 1.79 (br d, J=9.33 Hz, 2H), 1.90-2.00 (m, 2H), 2.32 (q, J=7.14 Hz, 2H), 2.87 (br d, J=11.53 Hz, 2H), 3.78-3.89 (m, 1H), 7.72-7.76 (m, 1H), 7.79-7.83 (m, 1H), 8.21 (d, J=8.23 Hz, 1H), 8.24 (t, J=2.20 Hz, 1H), 8.45 (d, J=0.82 Hz, 1H), 8.63 (d, J=2.20 Hz, 1H), 8.86 (d, J=1.92 Hz, 1H), 13.70 (brs, 1H); ESIMS found for C$_{20}$H$_{22}$ClN$_5$O m/z 384.3 (M+1).

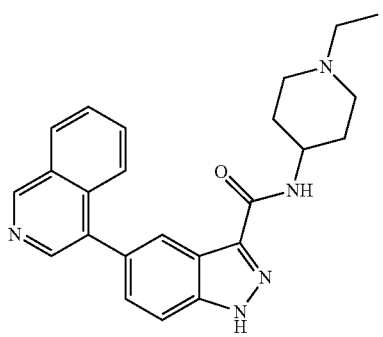

N-(1-Ethylpiperidin-4-yl)-5-(isoquinolin-4-yl)-1H-indazole-3-carboxamide 1292

White solid (70 mg, 0.18 mmol). $^1$H NMR (DMSO-d$_6$, 500 MHz) δ ppm 0.96-1.02 (m, 3H), 1.60-1.71 (m, 2H), 1.77 (br d, J=9.33 Hz, 2H), 1.88-1.97 (m, 2H), 2.27-2.34 (m, 2H), 2.85 (br d, J=11.80 Hz, 2H), 3.76-3.86 (m, 1H), 7.58 (dd, J=8.51, 1.65 Hz, 1H), 7.72-7.77 (m, 1H), 7.77-7.82 (m, 2H), 7.83-7.87 (m, 1H), 8.23 (dd, J=1.53, 8.23 Hz, 2H), 8.29 (dd, J=1.65, 0.82 Hz, 1H), 8.49 (s, 1H), 9.36 (s, 1H), 13.75 (brs, 1H); ESIMS found for C$_{24}$H$_{25}$N$_5$O m/z 399.8 (M+1).

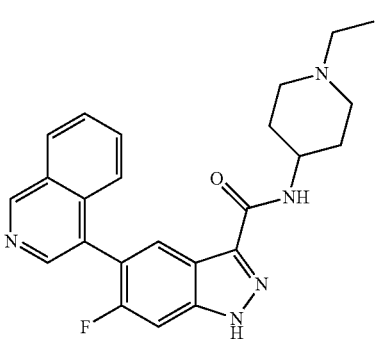

N-(1-Ethylpiperidin-4-yl)-6-fluoro-5-(isoquinolin-4-yl)-1H-indazole-3-carboxamide 1293

White solid (30 mg, 0.07 mmol). $^1$H NMR (DMSO-d$_6$, 500 MHz) δ ppm 0.98 (t, J=7.27 Hz, 3H), 1.65 (qd, J=11.85, 3.70 Hz, 2H), 1.75 (br d, J=10.15 Hz, 2H), 1.92 (br t, J=11.25 Hz, 2H), 2.30 (q, J=7.14 Hz, 2H), 2.85 (br d, J=10.98 Hz, 2H), 3.74-3.85 (m, 1H), 7.59 (br d, J=7.68 Hz, 1H), 7.66 (d, J=9.88 Hz, 1H), 7.73-7.82 (m, 2H), 8.21 (d, J=7.14 Hz, 1H), 8.24-8.29 (m, 2H), 8.51 (s, 1H), 9.42 (s, 1H), 13.82 (brs, 1H); ESIMS found for C$_{24}$H$_{24}$FN$_5$O m/z 418.0 (M+1).

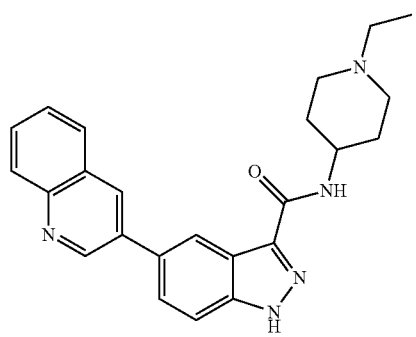

N-(1-Ethylpiperidin-4-yl)-5-(quinolin-3-yl)-1H-indazole-3-carboxamide 1294

White solid (45 mg, 0.11 mmol). $^1$H NMR (DMSO-d$_6$, 500 MHz) δ ppm 1.00 (t, J=7.27 Hz, 3H), 1.68 (qd, J=1.85, 3.43 Hz, 2H), 1.76-1.85 (m, 2H), 1.96 (br t, J=10.98 Hz, 2H), 2.33 (q, J=7.14 Hz, 2H), 2.88 (br d, J=11.25 Hz, 2H), 3.79-3.91 (m, 1H), 7.66 (td, J=7.41, 1.10 Hz, 1H), 7.75-7.82 (m, 2H), 7.94 (dd, J=8.78, 1.65 Hz, 1H), 8.08 (d, J=8.78 Hz, 1H), 8.09-8.13 (m, 1H), 8.24 (br d, J=8.23 Hz, 1H), 8.57-8.61 (m, 1H), 8.67 (d, J=2.20 Hz, 1H), 9.27 (d, J=2.47 Hz, 1H), 13.71 (brs, 1H); ESIMS found for C$_{24}$H$_{25}$N$_5$O m/z 400.3 (M+1).

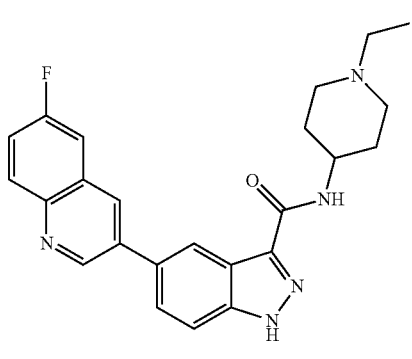

N-(1-Ethylpiperidin-4-yl)-5-(6-fluoroquinolin-3-yl)-1H-indazole-3-carboxamide 1295

White solid (40 mg, 0.10 mmol). $^1$H NMR (DMSO-$d_6$, 500 MHz) δ ppm 1.00 (t, J=7.14 Hz, 3H), 1.63-1.73 (m, 2H), 1.76-1.84 (m, 2H), 1.91-2.02 (m, 2H), 2.29-2.37 (m, 2H), 2.84-2.92 (m, 2H), 3.80-3.91 (m, 1H), 7.68 (td, J=8.92, 3.02 Hz, 1H), 7.80 (d, J=9.33 Hz, 1H), 7.87-7.95 (m, 2H), 8.14 (dd, J=9.06, 5.49 Hz, 1H), 8.25 (br d, J=8.23 Hz, 1H), 8.60 (d, J=0.82 Hz, 1H), 8.68 (d, J=2.20 Hz, 1H), 9.26 (d, J=2.20 Hz, 1H), 13.73 (brs, 1H); ESIMS found for $C_{24}H_{24}FN_5O$ m/z 418.3 (M+1).

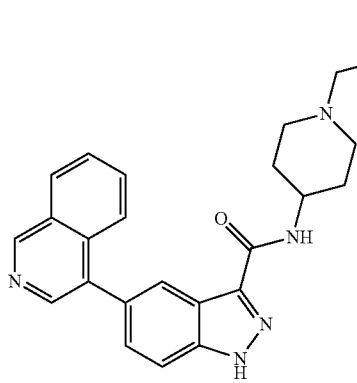

N-(1-(2-Fluoroethyl)piperidin-4-yl)-5-(isoquinolin-4-yl)-1H-indazole-3-carboxamide 1297

White solid (36 mg, 0.09 mmol). $^1$H NMR (DMSO-$d_6$, 500 MHz) δ ppm 1.64-1.74 (m, 2H), 1.74-1.82 (m, 2H), 2.04-2.19 (m, 2H), 2.55-2.62 (m, 1H), 2.62-2.70 (m, 1H), 2.90 (br d, J=7.14 Hz, 2H), 3.78-3.89 (m, 1H), 4.48 (br t, J=4.67 Hz, 1H), 4.58 (br t, J=4.80 Hz, 1H), 7.58 (dd, J=8.78, 1.65 Hz, 1H), 7.72-7.77 (m, 1H), 7.78-7.82 (m, 2H), 7.84-7.88 (m, 1H), 8.25 (d, J=7.68 Hz, 2H), 8.29 (s, 1H), 8.49 (s, 1H), 9.37 (s, 1H), 13.75 (s, 1H); ESIMS found for $C_{24}H_{24}FN_5O$ m/z 418.0 (M+1).

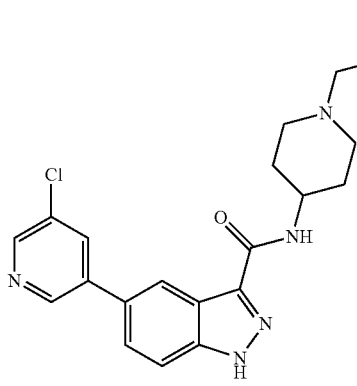

5-(5-Chloropyridin-3-yl)-N-(1-(2-fluoroethyl)piperidin-4-yl)-1H-indazole-3-carboxamide 1296

White solid (50 mg, 0.12 mmol). $^1$H NMR (DMSO-$d_6$, 500 MHz) δ ppm 1.69 (qd, J=11.80, 3.57 Hz, 2H), 1.75-1.83 (m, 2H), 2.07-2.16 (m, 2H), 2.59 (t, J=4.94 Hz, 1H), 2.65 (t, J=4.94 Hz, 1H), 2.90 (br d, J=12.08 Hz, 2H), 3.80-3.91 (m, 1H), 4.48 (t, J=4.94 Hz, 1H), 4.58 (t, J=4.94 Hz, 1H), 7.72-7.76 (m, 1H), 7.79-7.83 (m, 1H), 8.22-8.27 (m, 2H), 8.45 (dd, J=1.65, 0.82 Hz, 1H), 8.63 (d, J=2.20 Hz, 1H), 8.86 (d, J=1.92 Hz, 1H), 13.71 (brs, 1H); ESIMS found for $C_{20}H_{21}ClFN_5O$ m/z 402.4 (M+1).

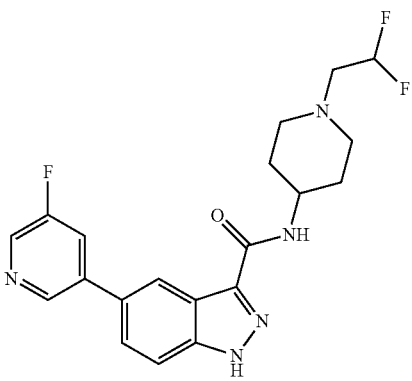

N-(1-(2,2-Difluoroethyl)piperidin-4-yl)-5-(5-fluoropyridin-3-yl)-1H-indazole-3-carboxamide 1298

White solid (90 mg, 0.22 mmol). $^1$H NMR (DMSO-$d_6$, 500 MHz) δ ppm 1.64-1.74 (m, 2H), 1.74-1.81 (m, 2H), 2.22-2.31 (m, 2H), 2.73 (td, J=15.64, 4.39 Hz, 2H), 2.92 (br d, J=1.80 Hz, 2H), 3.80-3.91 (m, 1H), 6.14 (tt, J=4.4 Hz, J=55.8, 1H), 7.72-7.77 (m, 1H), 7.79-7.83 (m, 1H), 8.06 (dt, J=10.36, 2.23 Hz, 1H), 8.27 (d, J=8.23 Hz, 1H), 8.46 (dd, J=1.65, 0.82 Hz, 1H), 8.58 (d, J=2.74 Hz, 1H), 8.79 (t, J=1.78 Hz, 1H), 13.72 (brs, 1H); ESIMS found for $C_{20}H_{20}F_3N_5O$ m/z 404.3 (M+1).

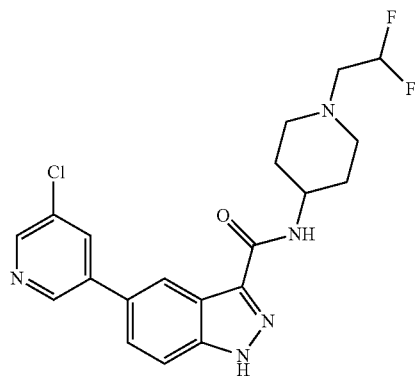

1299

5-(5-Chloropyridin-3-yl)-N-(1-(2,2-difluoroethyl)piperidin-4-yl)-1H-indazole-3-carboxamide 1299

White solid (76 mg, 0.18 mmol). ¹H NMR (DMSO-d₆, 500 MHz) δ ppm 1.64-1.74 (m, 2H), 1.74-1.80 (m, 2H), 2.22-2.31 (m, 2H), 2.73 (td, J=15.64, 4.39 Hz, 2H), 2.92 (br d, J=1.80 Hz, 2H), 3.79-3.91 (m, 1H), 6.14 (tt, J=4.4 Hz, J=55.9 Hz, 1H), 7.72-7.77 (m, 1H), 7.79-7.83 (m, 1H), 8.24 (t, J=2.20 Hz, 1H), 8.28 (d, J=8.23 Hz, 1H), 8.45 (dd, J=1.65, 0.82 Hz, 1H), 8.63 (d, J=2.47 Hz, 1H), 8.86 (d, J=1.92 Hz, 1H), 13.72 (brs, 1H); ESIMS found for C₂₀H₂₀ClF₂N₅O m/z 420.0 (M+1).

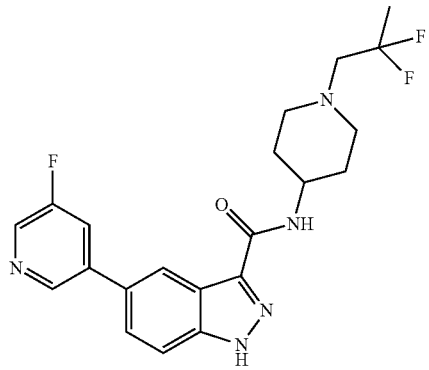

1301

N-(1-(2,2-Difluoropropyl)piperidin-4-yl)-5-(5-fluoropyridin-3-yl)-1H-indazole-3-carboxamide 1301

White solid (36.5 mg, 0.09 mmol). ¹H NMR (DMSO-d₆, 500 MHz) δ ppm 1.63 (t, J=19.07 Hz, 3H), 1.68-1.81 (m, 4H), 2.31 (td, J=1.66, 2.20 Hz, 2H), 2.72 (t, J=14.13 Hz, 2H), 2.92 (br d, J=12.08 Hz, 2H), 3.79-3.90 (m, 1H), 7.72-7.77 (m, 1H), 7.78-7.83 (m, 1H), 8.07 (dt, J=10.09, 2.37 Hz, 1H), 8.24 (d, J=8.23 Hz, 1H), 8.46 (d, J=0.82 Hz, 1H), 8.58 (d, J=2.47 Hz, 1H), 8.79 (s, 1H), 13.71 (brs, 1H); ESIMS found for C₂₁H₂₂F₃N₅O m/z 418.1 (M+1).

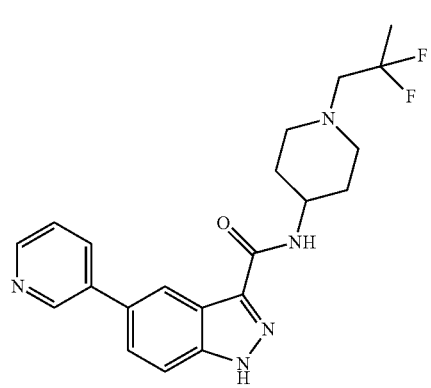

1300

N-(1-(2,2-Difluoropropyl)piperidin-4-yl)-5-(pyridin-3-yl)-1H-indazole-3-carboxamide 1300

White solid (37 mg, 0.09 mmol). ¹H NMR (DMSO-d₆, 500 MHz) δ ppm 1.63 (t, J=19.07 Hz, 3H), 1.67-1.81 (m, 4H), 2.27-2.36 (m, 2H), 2.72 (br t, J=14.13 Hz, 2H), 2.92 (br d, J=1.80 Hz, 2H), 3.79-3.90 (m, 1H), 7.48-7.54 (m, 1H), 7.71-7.80 (m, 2H), 8.05-8.12 (m, 1H), 8.23 (d, J=8.23 Hz, 1H), 8.42 (s, 1H), 8.58 (dd, J=4.67, 1.37 Hz, 1H), 8.90 (d, J=1.92 Hz, 1H), 13.68 (s, 1H); ESIMS found for C₂₁H₂₃F₂N₅O m/z 399.8 (M+1).

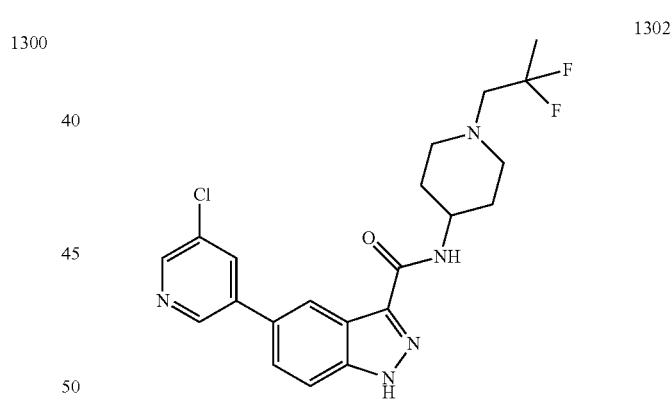

1302

5-(5-Chloropyridin-3-yl)-N-(1-(2,2-difluoropropyl)piperidin-4-yl)-1H-indazole-3-carboxamide 1302

White solid (40 mg, 0.09 mmol). ¹H NMR (DMSO-d₆, 500 MHz) δ ppm 1.63 (t, J=19.07 Hz, 3H), 1.68-1.81 (m, 4H), 2.31 (td, J=11.53, 1.92 Hz, 2H), 2.72 (t, J=14.00 Hz, 2H), 2.92 (br d, J=11.80 Hz, 2H), 3.78-3.90 (m, 1H), 7.72-7.76 (m, 1H), 7.79-7.84 (m, 1H), 8.22-8.27 (m, 2H), 8.42-8.47 (m, 1H), 8.63 (d, J=2.20 Hz, 1H), 8.86 (d, J=1.92 Hz, 1H), 13.72 (brs, 1H); ESIMS found for C₂₁H₂₂ClF₂N₅O m/z 434.3 (M+1).

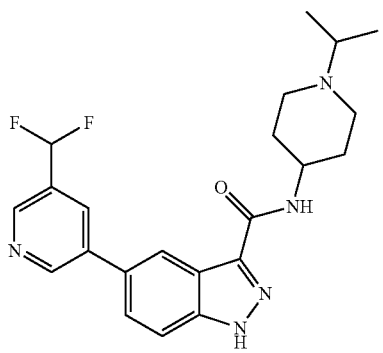

5-(5-(Difluoromethyl)pyridin-3-yl)-N-(1-isopropylpiperidin-4-yl)-1H-indazole-3-carboxamide 1303

White solid (30 mg, 0.07 mmol). $^1$H NMR (DMSO-$d_6$, 500 MHz) δ ppm 0.97 (d, J=6.59 Hz, 6H), 1.63 (qd, J=1.71, 3.57 Hz, 2H), 1.80 (br d, J=9.33 Hz, 2H), 2.13-2.24 (m, 2H), 2.69 (quin, J=6.59 Hz, 1H), 2.80 (br d, J=11.80 Hz, 2H), 3.75-3.87 (m, 1H), 7.25 (t, J=55.5 Hz, 1H), 7.72-7.78 (m, 1H), 7.81-7.86 (m, 1H), 8.20 (d, J=8.23 Hz, 1H), 8.28 (s, 1H), 8.48 (dd, J=1.65, 0.82 Hz, 1H), 8.79 (d, J=1.37 Hz, 1H), 9.06-9.12 (m, 1H), 13.70 (brs, 1H); ESIMS found for $C_{22}H_{25}F_2N_5O$ m/z 414.6 (M+1).

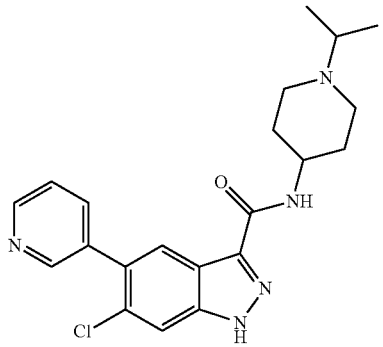

6-Chloro-N-(1-isopropylpiperidin-4-yl)-5-(pyridin-3-yl)-1H-indazole-3-carboxamide 1304

White solid (65 mg, 0.16 mmol). $^1$H NMR (DMSO-$d_6$, 500 MHz) δ ppm 0.96 (d, J=6.59 Hz, 6H), 1.61 (qd, J=1.76, 3.70 Hz, 2H), 1.77 (br d, J=9.88 Hz, 2H), 2.12-2.22 (m, 2H), 2.68 (dt, J=13.10, 6.48 Hz, 1H), 2.78 (br d, J=11.53 Hz, 2H), 3.73-3.83 (m, 1H), 7.52 (ddd, J=7.82, 4.80, 0.82 Hz, 1H), 7.87-7.93 (m, 2H), 8.15 (s, 1H), 8.24 (d, J=8.23 Hz, 1H), 8.63 (dd, J=4.67, 1.65 Hz, 1H), 8.65 (dd, J=2.20, 0.82 Hz, 1H), 13.75 (brs, 1H); ESIMS found for $C_{21}H_{24}ClN_5O$ m/z 398.1 (M+1).

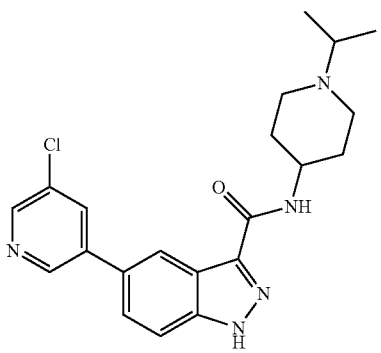

5-(5-Chloropyridin-3-yl)-N-(1-isopropylpiperidin-4-yl)-1H-indazole-3-carboxamide 1305

White solid (61 mg, 0.15 mmol). $^1$H NMR (DMSO-$d_6$, 500 MHz) δ ppm 0.97 (d, J=6.59 Hz, 6H), 1.63 (qd, J=11.76, 3.70 Hz, 2H), 1.80 (br d, J=9.61 Hz, 2H), 2.14-2.23 (m, 2H), 2.69 (dt, J=13.10, 6.48 Hz, 1H), 2.80 (br d, J=11.80 Hz, 2H), 3.76-3.86 (m, 1H), 7.71-7.76 (m, 1H), 7.79-7.83 (m, 1H), 8.19 (d, J=8.23 Hz, 1H), 8.24 (t, J=2.06 Hz, 1H), 8.45 (d, J=0.82 Hz, 1H), 8.63 (d, J=2.20 Hz, 1H), 8.87 (d, J=1.92 Hz, 1H), 13.68 (brs, 1H); ESIMS found for $C_{21}H_{24}ClN_5O$ m/z 398.3 (M+1).

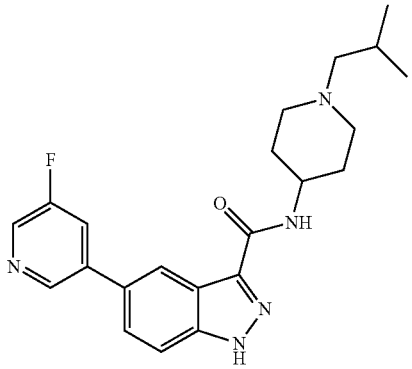

5-(5-Fluoropyridin-3-yl)-N-(1-isobutylpiperidin-4-yl)-1H-indazole-3-carboxamide 1306

White solid (68.1 mg, 0.17 mmol). $^1$H NMR (DMSO-$d_6$, 500 MHz) δ ppm 0.86 (d, J=6.59 Hz, 6H), 1.63-1.73 (m, 2H), 1.73-1.84 (m, 3H), 1.92-1.98 (m, 2H), 2.04 (d, J=7.14 Hz, 2H), 2.82 (br d, J=11.80 Hz, 2H), 3.78-3.89 (m, 1H), 7.70-7.76 (m, 1H), 7.78-7.83 (m, 1H), 8.05 (dt, J=10.15, 2.20 Hz, 1H), 8.16 (br d, J=7.96 Hz, 1H), 8.44-8.48 (m, 1H), 8.57 (d, J=2.74 Hz, 1H), 8.79 (t, J=1.65 Hz, 1H), 13.68 (brs, 1H); ESIMS found for $C_{22}H_{26}FN_5O$ m/z 396.2 (M+1).

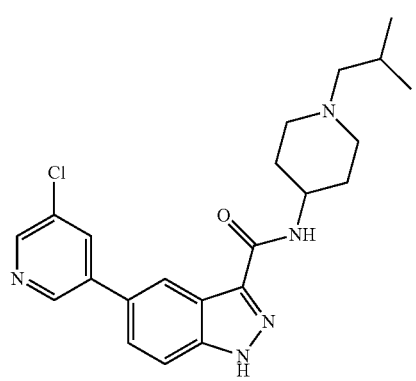

5-(5-Chloropyridin-3-yl)-N-(1-isobutylpiperidin-4-yl)-1H-indazole-3-carboxamide 1307

White solid (328 mg, 0.80 mmol). $^1$H NMR (DMSO-$d_6$, 500 MHz) δ ppm 0.86 (d, J=6.59 Hz, 6H), 1.62-1.73 (m, 2H), 1.73-1.83 (m, 3H), 1.90-1.98 (m, 2H), 2.03 (d, J=7.41 Hz, 2H), 2.82 (br d, J=11.53 Hz, 2H), 3.78-3.89 (m, 1H), 7.72-7.76 (m, 1H), 7.78-7.83 (m, 1H), 8.22 (d, J=8.23 Hz, 1H), 8.24 (t, J=2.20 Hz, 1H), 8.45 (d, J=1.10 Hz, 1H), 8.63 (d, J=2.20 Hz, 1H), 8.86 (d, J=1.92 Hz, 1H), 13.71 (brs, 1H); ESIMS found for $C_{22}H_{26}ClN_5O$ m/z 411.9 (M+1).

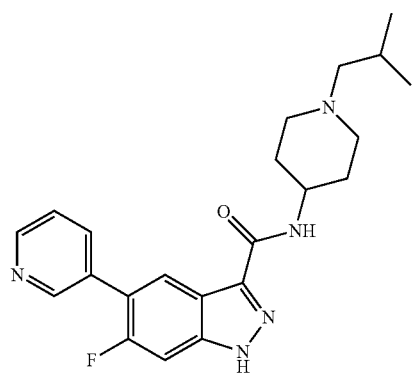

6-Fluoro-N-(1-isobutylpiperidin-4-yl)-5-(pyridin-3-yl)-1H-indazole-3-carboxamide 1308

White solid (86.6 mg, 0.22 mmol). $^1$H NMR (DMSO-$d_6$, 500 MHz) δ ppm 0.85 (d, J=6.31 Hz, 6H), 1.61-1.72 (m, 2H), 1.72-1.81 (m, 3H), 1.89-1.97 (m, 2H), 2.02 (d, J=7.41 Hz, 2H), 2.81 (br d, J=11.53 Hz, 2H), 3.76-3.86 (m, 1H), 7.49-7.56 (m, 1H), 7.60 (d, J=10.98 Hz, 1H), 7.96-8.01 (m, 1H), 8.22-8.27 (m, 2H), 8.62 (dd, J=4.94, 1.65 Hz, 1H), 8.75 (s, 1H), 13.75 (brs, 1H); ESIMS found for $C_{22}H_{26}FN_5O$ m/z 396.2 (M+1).

N-(1-(2-Fluoro-2-methylpropyl)piperidin-4-yl)-5-(pyridin-3-yl)-1H-indazole-3-carboxamide 1309

White solid (131.8 mg, 0.33 mmol). $^1$H NMR (DMSO-$d_6$, 500 MHz) δ ppm 1.31 (d, J=21.5 Hz, 6H), 1.65-1.81 (m, 4H), 2.15-2.25 (m, 2H), 2.44 (d, J=23.1 Hz, 2H), 2.91 (br d, J=1.80 Hz, 2H), 3.77-3.88 (m, 1H), 7.51 (dd, J=7.96, 5.49 Hz, 1H), 7.71-7.80 (m, 2H), 8.05-8.12 (m, 1H), 8.19 (d, J=8.23 Hz, 1H), 8.42 (s, 1H), 8.58 (dd, J=4.80, 1.51 Hz, 1H), 8.90 (d, J=1.92 Hz, 1H), 13.66 (brs, 1H); ESIMS found for $C_{22}H_{26}FN_5O$ m/z 396.1 (M+1).

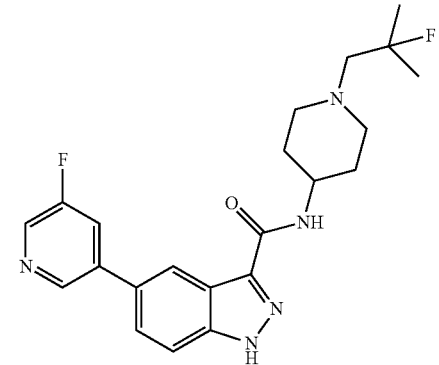

N-(1-(2-Fluoro-2-methylpropyl)piperidin-4-yl)-5-(5-fluoropyridin-3-yl)-1H-indazole-3-carboxamide 1310

White solid (257 mg, 0.62 mmol). $^1$H NMR (DMSO-$d_6$, 500 MHz) δ ppm 1.32 (d, J=21.5 Hz, 6H), 1.66-1.81 (m, 4H), 2.20 (td, J=1.46, 2.33 Hz, 2H), 2.44 (d, J=22.8 Hz, 2H), 2.91 (br d, J=1.80 Hz, 2H), 3.77-3.88 (m, 1H), 7.71-7.77 (m, 1H), 7.78-7.83 (m, 1H), 8.07 (dt, J=10.15, 2.20 Hz, 1H), 8.21 (d, J=8.23 Hz, 1H), 8.46 (s, 1H), 8.58 (d, J=2.74 Hz, 1H), 8.79 (t, J=1.65 Hz, 1H), 13.71 (brs, 1H); ESIMS found for $C_{22}H_{25}F_2N_5O$ m/z 413.9 (M+1).

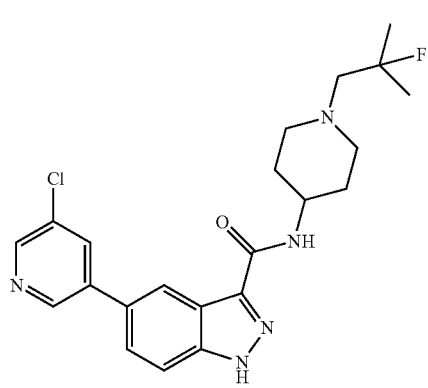

1311

5-(5-Chloropyridin-3-yl)-N-(1-(2-fluoro-2-methyl-propyl)piperidin-4-yl)-1H-indazole-3-carboxamide 1311

White solid (46.6 mg, 0.11 mmol). $^1$H NMR (DMSO-$d_6$, 500 MHz) δ ppm 1.31 (d, J=21.5 Hz, 6H), 1.66-1.81 (m, 4H), 2.19 (td, J=1.46, 2.33 Hz, 2H), 2.44 (d, J=23.1 Hz, 2H), 2.91 (br d, J=1.80 Hz, 2H), 3.77-3.88 (m, 1H), 7.72-7.76 (m, 1H), 7.79-7.83 (m, 1H), 8.21 (d, J=8.23 Hz, 1H), 8.24 (t, J=2.20 Hz, 1H), 8.42-8.46 (m, 1H), 8.63 (d, J=2.20 Hz, 1H), 8.86 (d, J=1.92 Hz, 1H), 13.68 (brs, 1H); ESIMS found for $C_{22}H_{25}ClFN_5O$ m/z 430.2 (M+1).

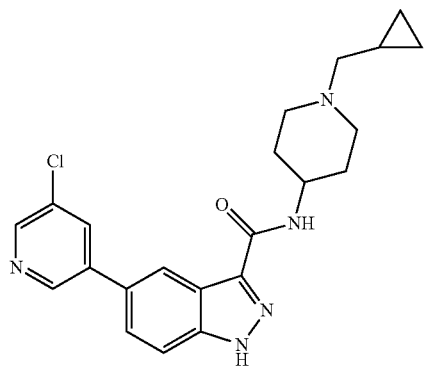

1313

5-(5-Chloropyridin-3-yl)-N-(1-(cyclopropylmethyl)piperidin-4-yl)-1H-indazole-3-carboxamide 1313

White solid (87 mg, 0.21 mmol). $^1$H NMR (DMSO-$d_6$, 500 MHz) δ ppm 0.03-0.10 (m, 2H), 0.42-0.49 (m, 2H), 0.77-0.89 (m, 1H), 1.69 (qd, J=11.80, 3.57 Hz, 2H), 1.74-1.83 (m, 2H), 1.96-2.05 (m, 2H), 2.17 (d, J=6.59 Hz, 2H), 2.97 (br d, J=11.80 Hz, 2H), 3.78-3.89 (m, 1H), 7.72-7.77 (m, 1H), 7.79-7.83 (m, 1H), 8.20-8.26 (m, 2H), 8.45 (s, 1H), 8.63 (d, J=2.47 Hz, 1H), 8.87 (d, J=2.20 Hz, 1H), 13.71 (brs, 1H); ESIMS found for $C_{22}H_{24}ClN_5O$ m/z 410.0 (M+1).

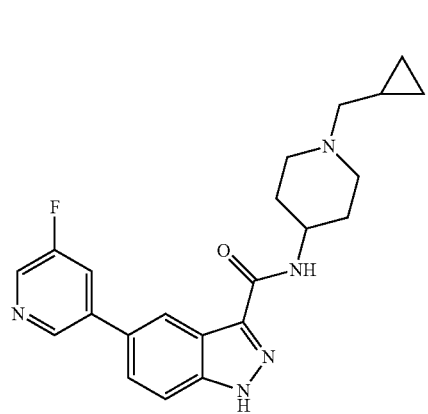

1312

N-(1-(Cyclopropylmethyl)piperidin-4-yl)-5-(5-fluoropyridin-3-yl)-1H-indazole-3-carboxamide 1312

White solid (28.5 mg, 0.07 mmol). $^1$H NMR (DMSO-$d_6$, 500 MHz) δ ppm 0.07 (q, J=4.94 Hz, 2H), 0.43-0.49 (m, 2H), 0.79-0.87 (m, 1H), 1.69 (qd, J=11.89, 3.29 Hz, 2H), 1.75-1.83 (m, 2H), 1.97-2.07 (m, 2H), 2.18 (br d, J=5.76 Hz, 2H), 2.98 (br d, J=10.98 Hz, 2H), 3.78-3.90 (m, 1H), 7.72-7.77 (m, 1H), 7.79-7.84 (m, 1H), 8.07 (dt, J=10.36, 2.23 Hz, 1H), 8.23 (br d, J=7.96 Hz, 1H), 8.46 (d, J=0.82 Hz, 1H), 8.58 (d, J=2.74 Hz, 1H), 8.79 (t, J=1.65 Hz, 1H), 13.72 (brs, 1H); ESIMS found for $C_{22}H_{24}FN_5O$ m/z 394.3 (M+1).

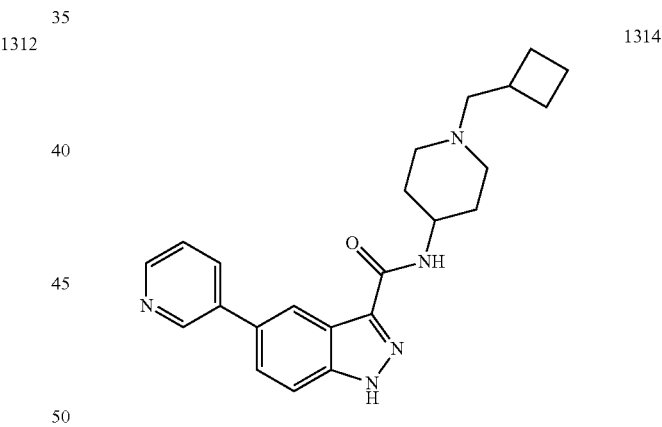

1314

N-(1-(Cyclobutylmethyl)piperidin-4-yl)-5-(pyridin-3-yl)-1H-indazole-3-carboxamide 1314

White solid (20 mg, 0.05 mmol). $^1$H NMR (DMSO-$d_6$, 500 MHz) δ ppm 1.58-1.70 (m, 4H), 1.72-1.90 (m, 4H), 1.93-2.06 (m, 4H), 2.32 (d, J=7.14 Hz, 2H), 2.44-2.48 (m, 1H), 2.79 (br d, J=11.80 Hz, 2H), 3.76-3.87 (m, 1H), 7.51 (dd, J=7.96, 4.67 Hz, 1H), 7.70-7.79 (m, 2H), 8.09 (dt, J=8.10, 1.99 Hz, 1H), 8.17 (d, J=8.51 Hz, 1H), 8.41 (s, 1H), 8.58 (dd, J=4.67, 1.65 Hz, 1H), 8.89 (d, J=1.92 Hz, 1H), 13.68 (brs, 1H); ESIMS found for $C_{23}H_{27}N_5O$ m/z 390.4 (M+1).

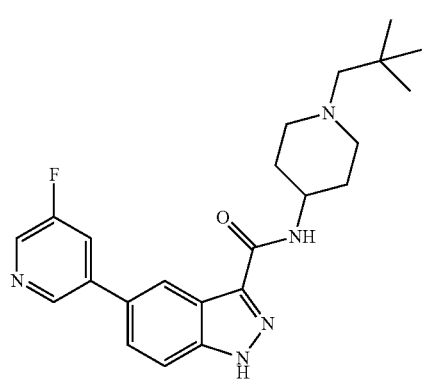

5-(5-Fluoropyridin-3-yl)-N-(1-neopentylpiperidin-4-yl)-1H-indazole-3-carboxamide 1315

White solid (138 mg, 0.34 mmol). $^1$H NMR (DMSO-d$_6$, 500 MHz) δ ppm 0.85 (s, 9H), 1.65-1.78 (m, 4H), 2.06 (s, 2H), 2.31 (td, J=11.25, 3.02 Hz, 2H), 2.79 (br d, J=11.80 Hz, 2H), 3.75-3.87 (m, 1H), 7.72-7.77 (m, 1H), 7.78-7.83 (m, 1H), 8.06 (dt, J=10.36, 2.23 Hz, 1H), 8.16 (d, J=8.23 Hz, 1H), 8.46 (d, J=0.82 Hz, 1H), 8.58 (d, J=2.74 Hz, 1H), 8.79 (t, J=1.65 Hz, 1H), 13.68 (brs, 1H); ESIMS found for C$_{23}$H$_{28}$FN$_5$O m/z 410.3 (M+1).

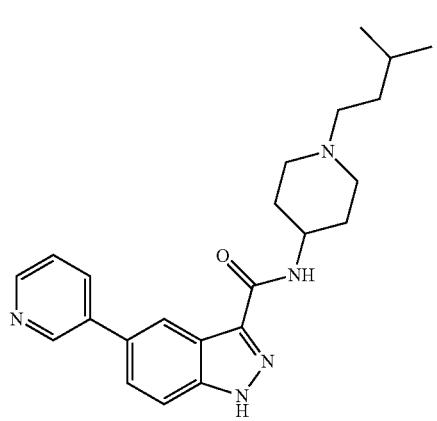

N-(1-Isopentylpiperidin-4-yl)-5-(pyridin-3-yl)-1H-indazole-3-carboxamide 1316

White solid (33 mg, 0.08 mmol). $^1$H NMR (DMSO-d$_6$, 500 MHz) δ ppm 0.88 (d, J=6.59 Hz, 6H), 1.28-1.35 (m, 2H), 1.52-1.60 (m, 1H), 1.60-1.71 (m, 2H), 1.74-1.82 (m, 2H), 1.91-2.00 (m, 2H), 2.24-2.31 (m, 2H), 2.86 (br d, J=1.80 Hz, 2H), 3.78-3.89 (m, 1H), 7.51 (ddd, J=7.96, 4.67, 0.82 Hz, 1H), 7.71-7.79 (m, 2H), 8.06-8.12 (m, 1H), 8.19 (d, J=8.23 Hz, 1H), 8.42 (dd, J=1.65, 0.82 Hz, 1H), 8.58 (dd, J=4.67, 1.65 Hz, 1H), 8.88-8.92 (m, 1H), 13.67 (brs, 1H); ESIMS found for C$_{23}$H$_{29}$N$_5$O m/z 392.3 (M+1).

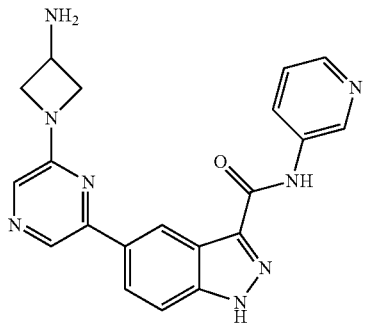

5-(6-(3-Aminoazetidin-1-yl)pyrazin-2-yl)-N-(pyridin-3-yl)-1H-indazole-3-carboxamide 1317

Tan solid (55 mg, 0.14 mmol). $^1$H NMR (DMSO-d$_6$, 500 MHz) δ ppm 3.74 (dd, J=8.51, 5.76 Hz, 2H), 3.91 (quin, J=6.38 Hz, 1H), 4.30 (t, J=7.82 Hz, 2H), 7.40 (dd, J=8.23, 4.67 Hz, 1H), 7.78 (d, J=8.78 Hz, 1H), 7.84 (s, 1H), 8.15 (dd, J=8.92, 1.51 Hz, 1H), 8.29-8.36 (m, 2H), 8.44 (s, 1H), 8.84-8.89 (m, 1H), 9.07 (d, J=2.20 Hz, 1H), 10.66 (s, 1H); ESIMS found for C$_{20}$H$_{15}$N$_5$O m/z 387.5 (M+1).

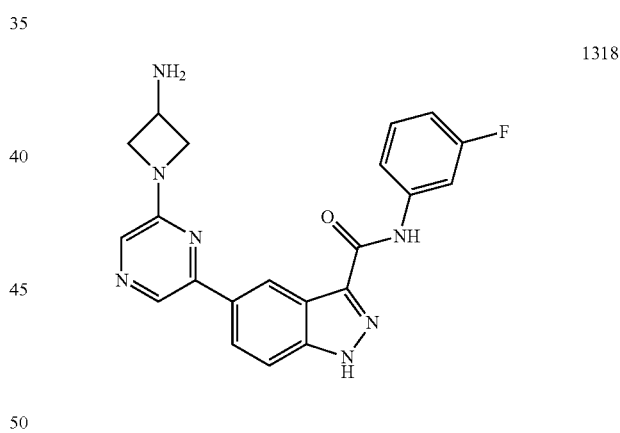

5-(6-(3-Aminoazetidin-1-yl)pyrazin-2-yl)-N-(3-fluorophenyl)-1H-indazole-3-carboxamide 1318

Tan solid (55 mg, 0.14 mmol). $^1$H NMR (DMSO-d$_6$, 500 MHz) δ ppm 3.74 (dd, J=8.37, 5.90 Hz, 2H), 3.91 (quin, J=6.38 Hz, 1H), 4.30 (t, J=7.82 Hz, 2H), 6.93 (td, J=8.23, 2.20 Hz, 1H), 7.36-7.44 (m, 1H), 7.73-7.79 (m, 2H), 7.83 (s, 1H), 7.88 (dt, J=11.80, 2.20 Hz, 1H), 8.15 (dd, J=8.78, 1.65 Hz, 1H), 8.44 (s, 1H), 8.83-8.89 (m, 1H), 10.62 (s, 1H); ESIMS found for C$_{21}$H$_{18}$FN$_7$O m/z 404.2 (M+1).

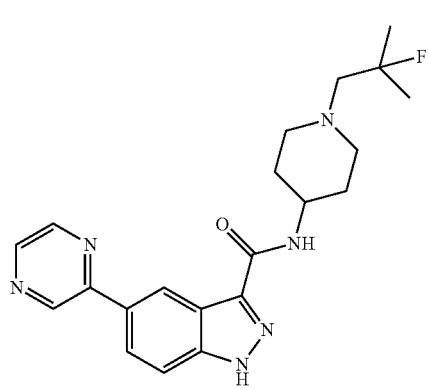

1319

N-(1-(2-Fluoro-2-methylpropyl)piperidin-4-yl)-5-(pyrazin-2-yl)-1H-indazole-3-carboxamide 1319

White solid (7.5 mg, 0.02 mmol). $^1$H NMR (DMSO-d$_6$, 500 MHz) δ ppm 1.32 (d, J=21.5 Hz, 6H), 1.65-1.81 (m, 4H), 2.20 (td, J=11.53, 2.20 Hz, 2H), 2.45 (d, J=22.8 Hz, 2H), 2.91 (br d, J=11.80 Hz, 2H), 3.78-3.90 (m, 1H), 7.75 (d, J=8.78 Hz, 1H), 8.16-8.24 (m, 2H), 8.60 (d, J=2.47 Hz, 1H), 8.73 (dd, J=2.47, 1.65 Hz, 1H), 8.93 (s, 1H), 9.26 (d, J=1.37 Hz, 1H), 13.71 (brs, 1H); ESIMS found for C$_{21}$H$_{25}$FN$_6$O m/z 397.2 (M+1).

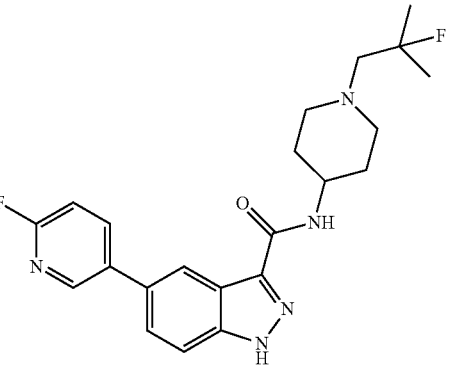

1321

N-(1-(2-Fluoro-2-methylpropyl)piperidin-4-yl)-5-(6-fluoropyridin-3-yl)-1H-indazole-3-carboxamide 1321

White solid (9.5 mg, 0.02 mmol). $^1$H NMR (DMSO-d$_6$, 500 MHz) δ ppm 1.31 (d, J=21.5 Hz, 6H), 1.64-1.79 (m, 4H), 2.15-2.23 (m, 2H), 2.44 (d, J=23.1 Hz, 2H), 2.91 (br d, J=12.08 Hz, 2H), 3.76-3.87 (m, 1H), 7.49 (ddd, J=7.00, 5.08, 1.65 Hz, 1H), 7.64 (d, J=8.23 Hz, 1H), 7.74 (d, J=8.78 Hz, 1H), 8.12-8.18 (m, 1H), 8.20 (d, J=8.23 Hz, 1H), 8.25 (d, J=4.39 Hz, 1H), 8.38 (s, 1H), 13.71 (brs, 1H); ESIMS found for C$_{22}$H$_{25}$F$_2$N$_5$O m/z 414.2 (M+1).

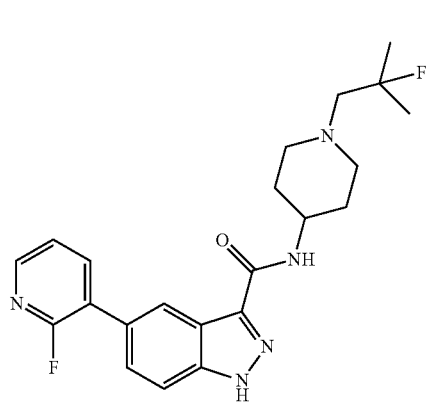

1320

N-(1-(2-Fluoro-2-methylpropyl)piperidin-4-yl)-5-(2-fluoropyridin-3-yl)-1H-indazole-3-carboxamide 1320

White solid (184 mg, 0.45 mmol). $^1$H NMR (DMSO-d$_6$, 500 MHz) δ ppm 1.31 (d, J=21.5 Hz, 6H), 1.65-1.79 (m, 4H), 2.19 (td, J=11.60, 2.33 Hz, 2H), 2.44 (d, J=22.9 Hz, 2H), 2.90 (br d, J=11.80 Hz, 2H), 3.76-3.87 (m, 1H), 7.49 (ddd, J=7.27, 5.08, 1.65 Hz, 1H), 7.62-7.68 (m, 1H), 7.71-7.76 (m, 1H), 8.12-8.18 (m, 1H), 8.20 (d, J=7.96 Hz, 1H), 8.23-8.28 (m, 1H), 8.38 (s, 1H), 13.70 (br s, 1H); ESIMS found for C$_{22}$H$_{25}$F$_2$N$_5$O m/z 414.2 (M+1).

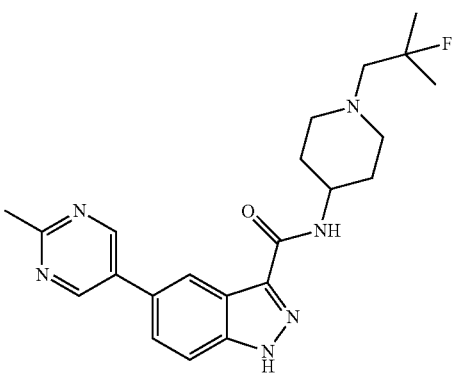

1322

N-(1-(2-Fluoro-2-methylpropyl)piperidin-4-yl)-5-(2-methylpyrimidin-5-yl)-1H-indazole-3-carboxamide 1322

White solid (6.7 mg, 0.02 mmol). $^1$H NMR (DMSO-d$_6$, 500 MHz) δ ppm 1.32 (d, J=21.5 Hz, 6H), 1.64-1.79 (m, 4H), 2.16-2.24 (m, 2H), 2.44 (d, J=22.9 Hz, 2H), 2.68 (s, 3H), 2.91 (br d, J=1.80 Hz, 2H), 3.75-3.88 (m, 1H), 7.72-7.81 (m, 2H), 8.19 (d, J=-8.23 Hz, 1H), 8.43 (s, 1H), 9.01 (s, 2H), 13.72 (brs, 1H); ESIMS found for C$_{22}$H$_{27}$FN$_6$O m/z 411.2 (M+1).

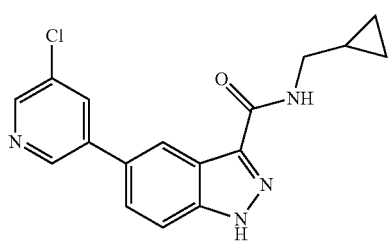

5-(5-Chloropyridin-3-yl)-N-(cyclopropylmethyl)-1H-indazole-3-carboxamide 1323

White solid (75.3 mg, 0.23 mmol). $^1$H NMR (DMSO-d$_6$, 500 MHz) δ ppm 0.25-0.31 (m, 2H), 0.40-0.47 (m, 2H), 1.04-1.15 (m, 1H), 3.20 (t, J=6.45 Hz, 2H), 7.72-7.77 (m, 1H), 7.79-7.84 (m, 1H), 8.25 (t, J=2.06 Hz, 1H), 8.46 (s, 1H), 8.49 (t, J=5.90 Hz, 1H), 8.63 (d, J=2.20 Hz, 1H), 8.87 (d, J=1.92 Hz, 1H), 13.72 (s, 1H); ESIMS found for C$_{17}$H$_{15}$ClN$_4$O m/z 327.2 (M+1).

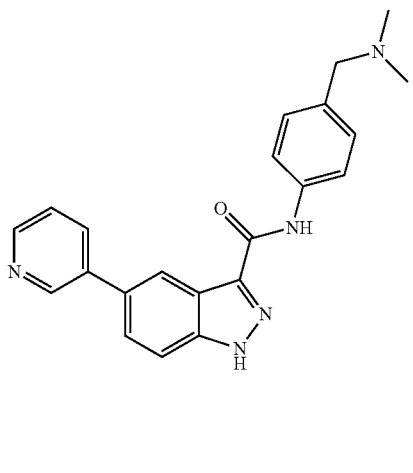

N-(4-((Dimethylamino)methyl)phenyl)-5-(pyridin-3-yl)-1H-indazole-3-carboxamide 1324

White solid (64.9 mg, 0.17 mmol). $^1$H NMR (DMSO-d$_6$, 500 MHz) δ ppm 2.14 (s, 6H), 3.35 (s, 2H), 7.26 (d, J=8.23 Hz, 2H), 7.52 (dd, J=7.96, 4.67 Hz, 1H), 7.79-7.88 (m, 4H), 8.13 (dt, J=8.03, 1.89 Hz, 1H), 8.48 (s, 1H), 8.59 (dd, J=4.67, 1.65 Hz, 1H), 8.93 (d, J=2.47 Hz, 1H), 10.34 (s, 1H), 13.87 (brs, 1H); ESIMS found for C$_{22}$H$_{21}$N$_5$O m/z 371.9 (M+1).

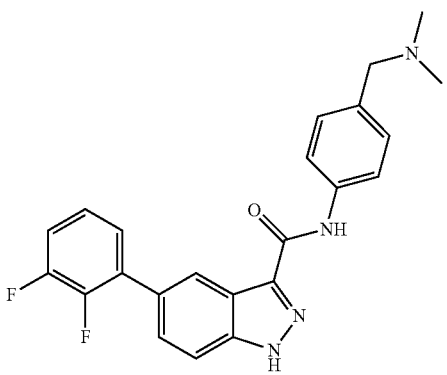

5-(2,3-Difluorophenyl)-N-(4-((dimethylamino)methyl)phenyl)-1H-indazole-3-carboxamide 1325

Beige solid (24.3 mg, 0.06 mmol). $^1$H NMR (DMSO-d$_6$, 500 MHz) δ ppm $^1$H NMR (499 MHz, DMSO-d$_6$) δ 2.14 (s, 6H), 3.35 (s, 2H), 7.25 (d, J=8.51 Hz, 2H), 7.31-7.37 (m, 1H), 7.40-7.50 (m, 1H), 7.58 (dd, J=8.78, 1.92 Hz, 1H), 7.66 (d, J=8.78 Hz, 1H), 7.77-7.86 (m, 3H), 8.35-8.43 (m, 1H), 10.34 (s, 1H), 13.89 (brs, 1H); ESIMS found for C$_{23}$H$_{20}$F$_2$N$_4$O m/z 406.9 (M+1).

5-(Pyridin-3-yl)-N-(4-(pyrrolidin-1-ylmethyl)phenyl)-1H-indazole-3-carboxamide 1326

White solid (32.0 mg, 0.08 mmol). $^1$H NMR (DMSO-d$_6$, 500 MHz) δ ppm 1.69 (dt, J=6.72, 3.22 Hz, 4H), 2.40-2.45 (m, 4H), 3.54 (s, 2H), 7.27 (d, J=8.51 Hz, 2H), 7.50-7.56 (m, 1H), 7.77-7.87 (m, 4H), 8.10-8.16 (m, 1H), 8.45-8.51 (m, 1H), 8.59 (dd, J=4.80, 1.51 Hz, 1H), 8.90-8.96 (m, 1H), 10.32 (s, 1H), 13.86 (brs, 1H); ESIMS found for C$_{24}$H$_{23}$N$_5$O m/z 398.0 (M+1).

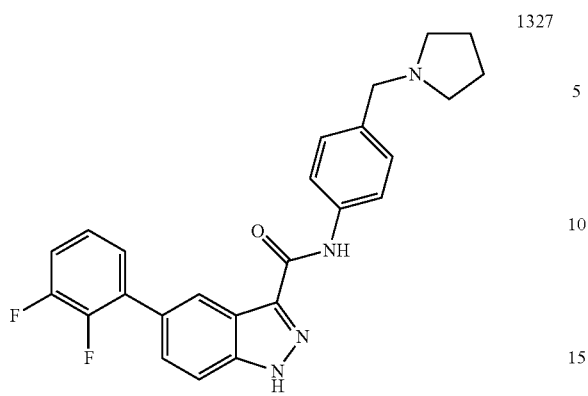

1327

5-(2,3-Difluorophenyl)-N-(4-(pyrrolidin-1-ylmethyl)phenyl)-1H-indazole-3-carboxamide 1327

White solid (109 mg, 0.25 mmol). $^1$H NMR (DMSO-$d_6$, 500 MHz) δ ppm 1.69 (dt, J=6.72, 3.22 Hz, 4H), 2.42 (br t, J=5.90 Hz, 4H), 3.53 (s, 2H), 7.26 (d, J=8.51 Hz, 2H), 7.30-7.38 (m, 1H), 7.40-7.51 (m, 2H), 7.66 (dt, J=8.78, 1.65 Hz, 1H), 7.79 (dd, J=8.78, 0.82 Hz, 1H), 7.82 (d, J=8.51 Hz, 2H), 8.40 (d, J=0.82 Hz, 1H), 10.34 (s, 1H), 13.91 (brs, 1H); ESIMS found for $C_{25}H_{22}F_2N_4O$ m/z 433.3 (M+1).

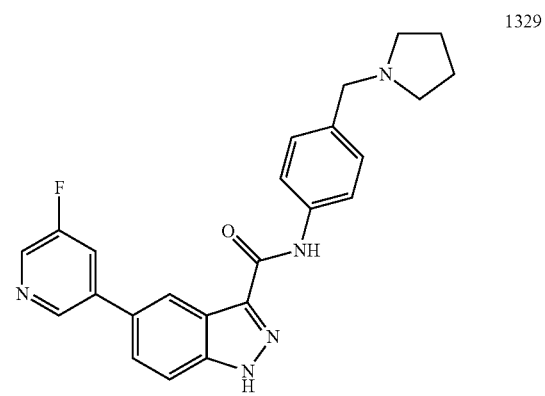 [SMILES: O=C(Nc1ccc(CN2CCCC2)cc1)c1n[nH]c2ccc(-c3cncc(F)c3)cc12]

1329

5-(5-Fluoropyridin-3-yl)-N-(4-(pyrrolidin-1-ylmethyl)phenyl)-1H-indazole-3-carboxamide 1329

White solid (53.5 mg, 0.13 mmol). $^1$H NMR (DMSO-$d_6$, 500 MHz) δ ppm 1.69 (dt, J=6.38, 2.98 Hz, 4H), 2.42 (brs, 4H), 3.54 (s, 2H), 7.27 (d, J=8.51 Hz, 2H), 7.78-7.89 (m, 4H), 8.11 (dt, J=10.15, 2.20 Hz, 1H), 8.50-8.55 (m, 1H), 8.59 (d, J=2.74 Hz, 1H), 8.80-8.85 (m, 1H), 10.35 (s, 1H), 13.90 (brs, 1H); ESIMS found for $C_{24}H_{22}FN_5O$ m/z 416.6 (M+1).

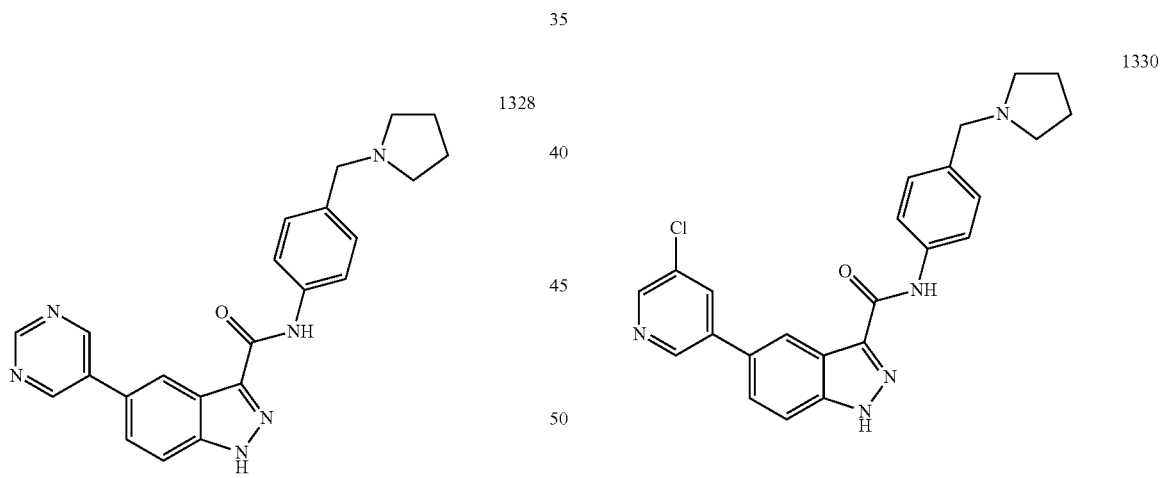

1328

5-(Pyrimidin-5-yl)-N-(4-(pyrrolidin-1-ylmethyl)phenyl)-1H-indazole-3-carboxamide 1328

Yellow-white solid (27.8 mg, 0.07 mmol). $^1$H NMR (DMSO-$d_6$, 500 MHz) δ ppm 1.69 (dt, J=6.66, 3.12 Hz, 4H), 2.42 (brs, 4H), 3.54 (s, 2H), 7.27 (d, J=8.23 Hz, 2H), 7.81-7.85 (m, 3H), 7.85-7.91 (m, 1H), 8.54 (dd, J=1.65, 0.82 Hz, 1H), 9.18 (s, 2H), 9.21 (s, 1H), 10.36 (s, 1H), 13.91 (brs, 1H); ESIMS found for $C_{23}H_{22}N_6O$ m/z 399.2 (M+1).

1330

5-(5-Chloropyridin-3-yl)-N-(4-(pyrrolidin-1-ylmethyl)phenyl)-1H-indazole-3-carboxamide 1330

White solid (34.3 mg, 0.08 mmol). $^1$H NMR (DMSO-$d_6$, 500 MHz) δ ppm 1.69 (dt, J=6.66, 3.12 Hz, 4H), 2.39-2.45 (m, 4H), 3.54 (s, 2H), 7.27 (d, J=8.51 Hz, 2H), 7.77-7.89 (m, 4H), 8.28 (t, J=2.20 Hz, 1H), 8.52 (dd, J=1.65, 0.82 Hz, 1H), 8.64 (d, J=2.20 Hz, 1H), 8.90 (d, J=2.20 Hz, 1H), 10.36 (s, 1H), 13.89 (brs, 1H); ESIMS found for $C_{24}H_{22}ClN_5O$ m/z 432.4 (M+1).

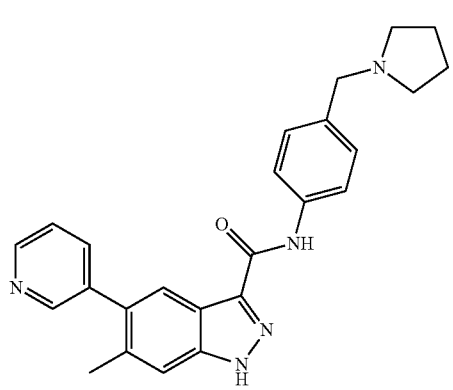

6-Methyl-5-(pyridin-3-yl)-N-(4-(pyrrolidin-1-ylmethyl)phenyl)-1H-indazole-3-carboxamide 1331

White solid (1.9 mg, 0.005 mmol). $^1$H NMR (DMSO-d$_6$, 500 MHz) δ ppm 1.69 (brs, 4H), 2.35 (s, 3H), 2.43 (brs, 4H), 3.55 (brs, 2H), 7.26 (br d, J=8.23 Hz, 2H), 7.50 (dd, J=7.82, 4.80 Hz, 1H), 7.61 (s, 1H), 7.81 (d, J=8.51 Hz, 2H), 7.86 (dt, J=7.68, 1.92 Hz, 1H), 8.02 (s, 1H), 8.61 (brs, 2H), 10.28 (s, 1H), 13.73 (s, 1H); ESIMS found for C$_{25}$H$_{25}$N$_5$O m/z 412.2 (M+1).

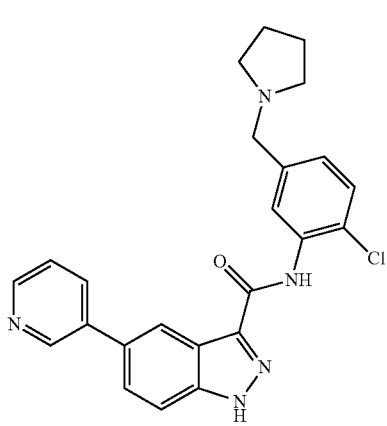

N-(2-Chloro-5-(pyrrolidin-1-ylmethyl)phenyl)-5-(pyridin-3-yl)-1H-indazole-3-carboxamide 1333

White solid (24 mg, 0.06 mmol). $^1$H NMR (DMSO-d$_6$, 500 MHz) δ ppm 1.69-1.75 (m, 4H), 2.47 (brs, 4H), 3.61 (s, 2H), 7.15 (dd, J=8.23, 1.92 Hz, 1H), 7.48-7.56 (m, 2H), 7.81-7.87 (m, 2H), 8.12-8.17 (m, 1H), 8.27 (d, J=1.92 Hz, 1H), 8.48 (t, J=1.24 Hz, 1H), 8.60 (dd, J=4.67, 1.65 Hz, 1H), 8.94 (d, J=1.92 Hz, 1H), 9.77 (s, 1H), 14.00 (brs, 1H); ESIMS found for C$_{24}$H$_{22}$ClN$_5$O m/z 432.2 (M+1).

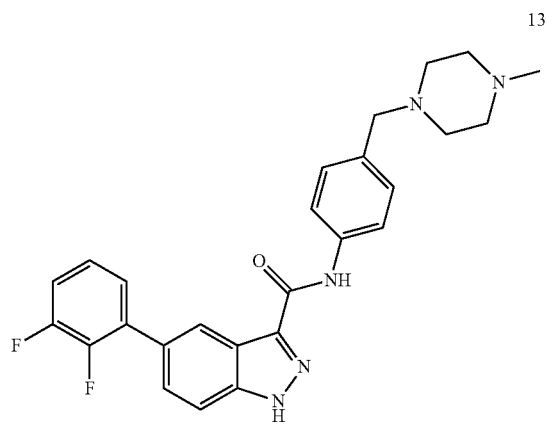

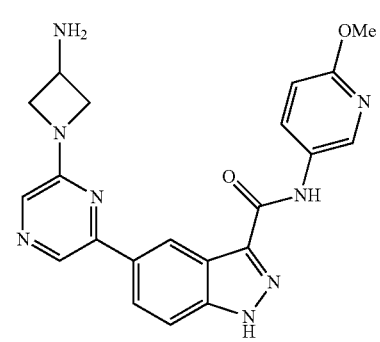

5-(6-(3-Aminoazetidin-1-yl)pyrazin-2-yl)-N-(6-methoxypyridin-3-yl)-1H-indazole-3-carboxamide 1334

Tan solid (16 mg, 0.04 mmol). $^1$H NMR (DMSO-d$_6$, 500 MHz) δ ppm 3.73 (dd, J=8.23, 5.76 Hz, 2H), 3.85 (s, 3H), 3.91 (dt, J=12.90, 6.45 Hz, 1H), 4.30 (t, J=7.82 Hz, 2H), 6.85 (d, J=8.78 Hz, 1H), 7.76 (d, J=8.78 Hz, 1H), 7.83 (s, 1H), 8.14 (dd, J=8.78, 1.37 Hz, 1H), 8.19 (dd, J=8.78, 2.74 Hz, 1H), 8.43 (s, 1H), 8.64 (d, J=2.47 Hz, 1H), 8.86 (s, 1H), 10.49 (s, 1H); ESIMS found for C$_{21}$H$_{20}$N$_8$O$_2$ m/z 417.2 (M+1).

5-(2,3-Difluorophenyl)-N-(4-((4-methylpiperazin-1-yl)methyl)phenyl)-1H-indazole-3-carboxamide 1332

White solid (33.5 mg, 0.07 mmol). $^1$H NMR (DMSO-d$_6$, 500 MHz) δ ppm 2.14 (s, 3H), 2.22-2.44 (m, 8H), 3.41 (s, 2H), 7.25 (d, J=8.51 Hz, 2H), 7.31-7.38 (m, 1H), 7.40-7.51 (m, 2H), 7.63-7.69 (m, 1H), 7.79 (d, J=9.06 Hz, 1H), 7.81-7.86 (m, 2H), 8.40 (s, 1H), 10.35 (s, 1H), 13.91 (brs, 1H); ESIMS found for C$_{26}$H$_{25}$F$_2$N$_5$O m/z 462.6 (M+1).

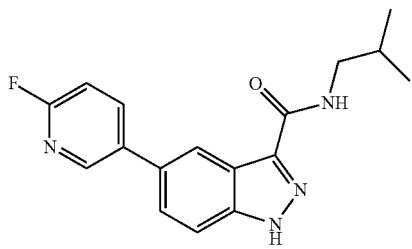

5-(6-Fluoropyridin-3-yl)-N-isobutyl-1H-indazole-3-carboxamide 1335

White solid (97.4 mg, 0.31 mmol). $^1$H NMR (DMSO-d$_6$, 500 MHz) δ ppm 0.91 (d, J=6.59 Hz, 6H), 1.91 (dquin, J=13.53, 6.77 Hz, 1H), 3.15 (t, J=6.59 Hz, 2H), 7.29 (dd, J=8.51, 2.74 Hz, 1H), 7.71-7.78 (m, 2H), 8.30 (td, J=8.16, 2.61 Hz, 1H), 8.37-8.43 (m, 2H), 8.54 (d, J=2.47 Hz, 1H), 13.67 (brs, 1H); ESIMS found for C$_{17}$H$_{17}$FN$_4$O m/z 413.1 (M+1).

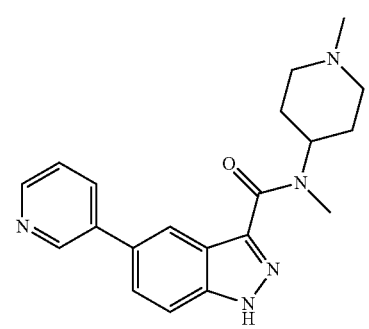

5-(2-Fluoropyridin-3-yl)-N-isobutyl-1H-indazole-3-carboxamide 1336

White solid (34.1 mg, 0.11 mmol). $^1$H NMR (DMSO-d$_6$, 500 MHz) δ ppm 0.90 (d, J=6.86 Hz, 6H), 1.90 (dquin, J=13.53, 6.77 Hz, 1H), 3.14 (t, J=6.72 Hz, 2H), 7.49 (ddd, J=7.20, 5.15, 1.65 Hz, 1H), 7.62-7.68 (m, 1H), 7.74 (d, J=8.78 Hz, 1H), 8.16 (ddd, J=10.22, 7.48, 1.78 Hz, 1H), 8.25 (d, J=4.67 Hz, 1H), 8.36-8.45 (m, 2H), 13.70 (brs, 1H); ESIMS found for C$_{17}$H$_{17}$FN$_4$O m/z 313.1 (M+1).

N-Methyl-N-(1-methylpiperidin-4-yl)-5-(pyridin-3-yl)-1H-indazole-3-carboxamide 1337

White solid (63 mg, 0.18 mmol). $^1$H NMR (DMSO-d$_6$, 500 MHz) δ ppm 1.60-1.74 (m, 2H), 1.75-1.95 (m, 4H), 1.97-2.06 (m, 1H), 2.08-2.23 (m, 3H), 2.77-2.85 (m, 1H), 2.87 (br d, J=1.92 Hz, 1H), 2.97 (br s, 1H), 3.19 (br s, 1H), 4.37-4.52 (m, 1H), 7.49 (dd, J=7.96, 4.67 Hz, 1H), 7.69-7.75 (m, 1H), 7.75-7.80 (m, 1H), 8.06-8.12 (m, 1H), 8.20 (br d, J=0.82 Hz, 1H), 8.57 (dd, J=4.67, 1.37 Hz, 1H), 8.90 (d, J=1.92 Hz, 1H), 13.59 (brs, 1H); ESIMS found for C$_{20}$H$_{23}$N$_5$O m/z 350.0 (M+1).

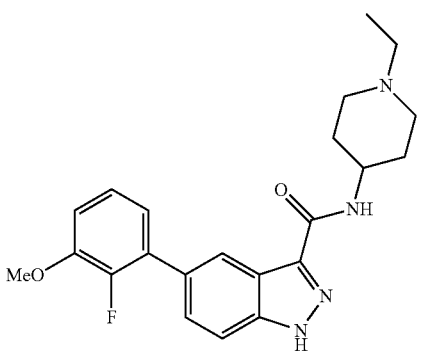

N-(1-Ethylpiperidin-4-yl)-5-(2-fluoro-3-methoxyphenyl)-1H-indazole-3-carboxamide 1338

White solid (30 mg, 0.08 mmol). $^1$H NMR (DMSO-d$_6$, 500 MHz) δ ppm 1.00 (t, J=7.14 Hz, 3H), 1.60-1.72 (m, 2H), 1.74-1.82 (m, 2H), 1.90-2.01 (m, 2H), 2.32 (q, J=7.04 Hz, 2H), 2.87 (br d, J=10.43 Hz, 2H), 3.77-3.87 (m, 1H), 3.89 (s, 3H), 7.04-7.11 (m, 1H), 7.16-7.21 (m, 1H), 7.21-7.27 (m, 1H), 7.56 (dt, J=8.71, 1.54 Hz, 1H), 7.70 (d, J=8.78 Hz, 1H), 8.18 (br d, J=7.96 Hz, 1H), 8.29 (s, 1H), 13.65 (brs, 1H); ESIMS found for C$_{22}$H$_{25}$FN$_4$O$_2$ m/z 397.3 (M+1).

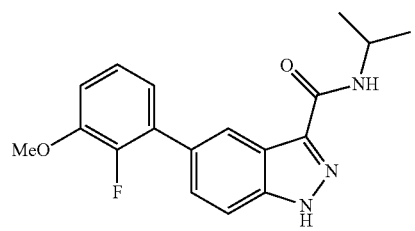

5-(2-Fluoro-3-methoxyphenyl)-N-isopropyl-1H-indazole-3-carboxamide 1339

White solid (10.8 mg, 0.03 mmol). $^1$H NMR (DMSO-d$_6$, 500 MHz) δ ppm 1.21 (d, J=6.59 Hz, 6H), 3.89 (s, 3H), 4.12-4.23 (m, 1H), 7.05-7.11 (m, 1H), 7.15-7.21 (m, 1H), 7.21-7.27 (m, 1H), 7.56 (d, J=8.78 Hz, 1H), 7.69 (d, J=8.78 Hz, 1H), 8.10 (d, J=8.23 Hz, 1H), 8.30 (s, 1H), 13.64 (s, 1H); ESIMS found for C$_{18}$H$_{18}$FN$_3$O$_2$ m/z 327.9 (M+1).

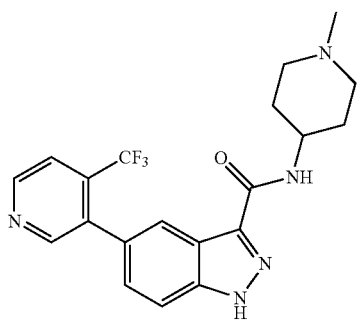

1340

N-(1-Methylpiperidin-4-yl)-5-(4-(trifluoromethyl)pyridin-3-yl)-1H-indazole-3-carboxamide 1340

White solid (4.5 mg, 0.01 mmol). $^1$H NMR (DMSO-d$_6$, 500 MHz) δ ppm 1.61-1.80 (m, 4H), 1.92-2.00 (m, 2H), 2.16 (s, 3H), 2.75 (br d, J=11.80 Hz, 2H), 3.73-3.85 (m, 1H), 7.50-7.55 (m, 1H), 7.58-7.63 (m, 1H), 7.67 (dd, J=7.68, 5.21 Hz, 1H), 7.69-7.73 (m, 1H), 8.20 (br t, J=8.23 Hz, 1H), 8.27-8.31 (m, 1H), 8.33 (dd, J=7.96, 1.37 Hz, 1H), 13.73 (brs, 1H); ESIMS found for C$_{20}$H$_{20}$F$_3$N$_5$O m/z 404.4 (M+1).

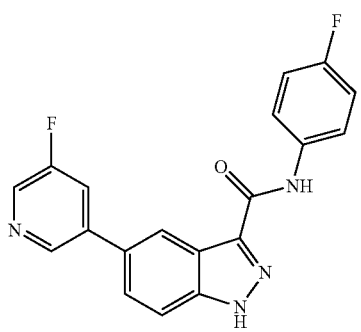

1341

N-(4-Fluorophenyl)-5-(5-fluoropyridin-3-yl)-1H-indazole-3-carboxamide 1341

White solid (13.5 mg, 0.04 mmol). $^1$H NMR (DMSO-d$_6$, 500 MHz) δ ppm 7.16-7.24 (m, 2H), 7.79-7.83 (m, 1H), 7.83-7.89 (m, 1H), 7.91-7.97 (m, 2H), 8.10 (dt, J=10.22, 2.30 Hz, 1H), 8.52 (dd, J=1.65, 0.82 Hz, 1H), 8.59 (d, J=2.47 Hz, 1H), 8.82 (t, J=1.65 Hz, 1H), 10.51 (s, 1H), 13.93 (brs, 1H); ESIMS found for C$_{19}$H$_{12}$F$_2$N$_4$O m/z 351.0 (M+1).

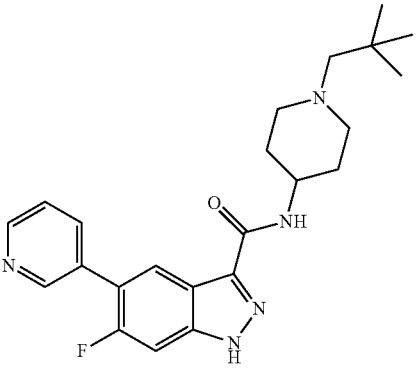

1342

6-Fluoro-N-(1-neopentylpiperidin-4-yl)-5-(pyridin-3-yl)-1H-indazole-3-carboxamide 1342

White solid (74 mg, 0.18 mmol). $^1$H NMR (DMSO-d$_6$, 500 MHz) δ ppm 0.85 (s, 9H), 1.64-1.77 (m, 4H), 2.05 (s, 2H), 2.25-2.33 (m, 2H), 2.78 (br d, J=11.80 Hz, 2H), 3.74-3.85 (m, 1H), 7.50-7.56 (m, 1H), 7.60 (d, J=10.70 Hz, 1H), 7.98 (dq, J=7.92, 1.75 Hz, 1H), 8.19 (d, J=7.96 Hz, 1H), 8.24 (d, J=7.68 Hz, 1H), 8.62 (dd, J=4.80, 1.51 Hz, 1H), 8.75 (s, 1H), 13.73 (brs, 1H); ESIMS found for C$_{23}$H$_{28}$FN$_5$O m/z 410.3 (M+1).

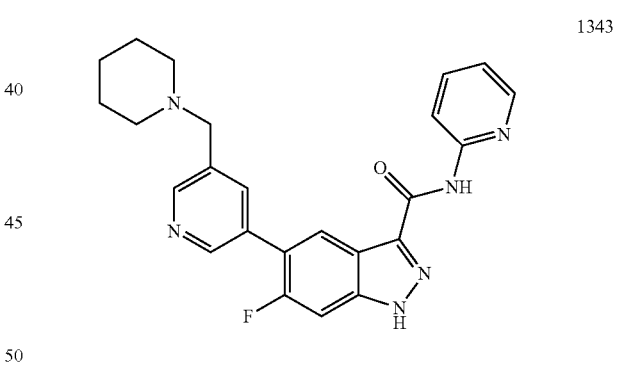

1343

6-Fluoro-5-(5-(piperidin-1-ylmethyl)pyridin-3-yl)-N-(pyridin-2-yl)-1H-indazole-3-carboxamide 1343

Tan solid (33.2 mg, 0.08 mmol). $^1$H NMR (DMSO-d$_6$, 500 MHz) δ ppm 1.40 (brd, J=4.94 Hz, 2H), 1.48-1.56 (m, 4H), 2.39 (brd, J=0.82 Hz, 4H), 3.58 (brs, 2H), 7.19 (dd, J=6.86, 5.21 Hz, 1H), 7.70 (d, J=10.70 Hz, 1H), 7.85-7.93 (m, 2H), 8.24 (d, J=8.23 Hz, 1H), 8.30 (d, J=7.41 Hz, 1H), 8.39 (dd, J=4.80, 0.96 Hz, 1H), 8.54 (s, 1H), 8.68 (s, 1H), 9.85 (s, 1H), 14.08 (brs, 1H); ESIMS found for C$_{24}$H$_{23}$FN$_6$O m/z 431.4 (M+1).

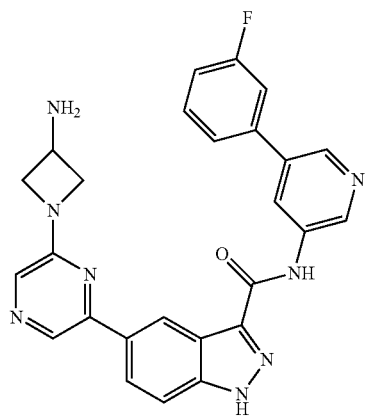

5-(6-(3-Aminoazetidin-1-yl)pyrazin-2-yl)-N-(5-(3-fluorophenyl)pyridin-3-yl)-1H-indazole-3-carboxamide 1344

Tan solid (17.0 mg, 0.04 mmol). $^1$H NMR (DMSO-$d_6$, 500 MHz) δ 3.73 (dd, J=8.23, 5.76 Hz, 2H), 3.87-3.95 (m, 1H), 4.30 (t, J=7.82 Hz, 2H), 7.26-7.34 (m, 1H), 7.57-7.64 (m, 3H), 7.79 (d, J=8.78 Hz, 1H), 7.83 (s, 1H), 8.16 (dd, J=8.78, 1.65 Hz, 1H), 8.45 (s, 1H), 8.64 (t, J=2.20 Hz, 1H), 8.68 (d, J=2.20 Hz, 1H), 8.87 (s, 1H), 9.14 (d, J=2.47 Hz, 1H), 10.75 (s, 1H); ESIMS found for $C_{26}H_{21}FN_8O$ m/z 481.2 (M+1).

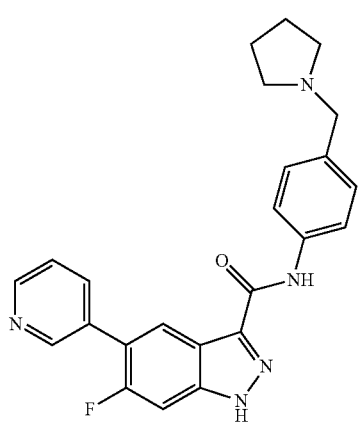

6-Fluoro-5-(pyridin-3-yl)-N-(4-(pyrrolidin-1-ylmethyl)phenyl)-1H-indazole-3-carboxamide 1345

Beige solid (25 mg, 0.06 mmol). $^1$H NMR (DMSO-$d_6$, 500 MHz) δ 1.66-1.72 (m, 4H), 2.42 (brs, 4H), 3.53 (s, 2H), 7.26 (d, J=8.23 Hz, 2H), 7.55 (dd, J=7.96, 4.67 Hz, 1H), 7.66 (d, J=10.70 Hz, 1H), 7.81 (d, J=8.51 Hz, 2H), 8.02 (dd, J=7.82, 1.51 Hz, 1H), 8.31 (d, J=7.41 Hz, 1H), 8.63 (dd, J=4.80, 1.51 Hz, 1H), 8.78 (s, 1H), 10.37 (s, 1H), 13.89 (brs, 1H); ESIMS found for $C_{24}H_{22}FN_5O$ m/z 416.2 (M+1).

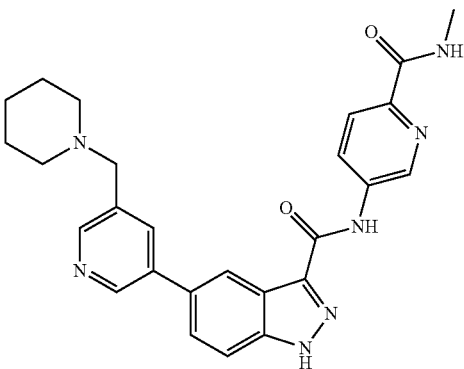

N-(6-(methylcarbamoyl)pyridin-3-yl)-5-(5-(piperidin-1-ylmethyl)pyridin-3-yl)-1H-indazole-3-carboxamide 1359

Off-white solid (55 mg, 0.12 mmol). $^1$H NMR (DMSO-$d_6$, 500 MHz) δ 1.40 (brd, J=4.39 Hz, 2H), 1.52 (quin, J=5.49 Hz, 4H), 2.39 (brs, 4H), 2.82 (d, J=4.67 Hz, 3H), 3.57 (s, 2H), 7.80-7.87 (m, 2H), 8.00 (t, J=1.92 Hz, 1H), 8.03 (d, J=8.51 Hz, 1H), 8.47-8.49 (m, 1H), 8.49 (d, J=1.92 Hz, 1H), 8.52 (dd, J=8.51, 2.47 Hz, 1H), 8.67 (q, J=4.57 Hz, 1H), 8.82 (d, J=2.20 Hz, 1H), 9.17 (d, J=2.20 Hz, 1H), 10.94 (s, 1H), 14.04 (brs, 1H); ESIMS found for $C_{26}H_{27}N_7O_2$ m/z 470.3 (M+1).

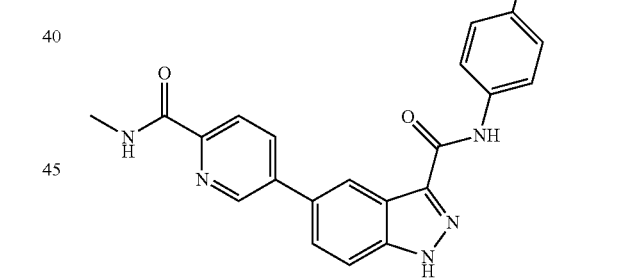

5-(6-(Methylcarbamoyl)pyridin-3-yl)-N-(4-(pyrrolidin-1-ylmethyl)phenyl)-1H-indazole-3-carboxamide 1360

Beige solid (49 mg, 0.19 mmol). $^1$H NMR (DMSO-$d_6$, 500 MHz) δ 1.66-1.73 (m, 4H), 2.42 (br s, 4H), 2.86 (d, J=4.67 Hz, 3H), 3.54 (s, 2H), 7.27 (d, J=8.51 Hz, 2H), 7.79-7.86 (m, 3H), 7.87-7.91 (m, 1H), 8.10-8.16 (m, 1H), 8.32 (dd, J=8.10, 2.33 Hz, 1H), 8.53-8.57 (m, 1H), 8.76-8.83 (m, 1H), 8.97 (dd, J=2.20, 0.82 Hz, 1H), 10.36 (s, 1H), 13.91 (brs, 1H); ESIMS found for $C_{26}H_{26}N_6O_2$ m/z 455.2 (M+1).

Example 2

The above synthesized compounds were screened using the assay procedure for Wnt activity described below.

Reporter cell lines were generated by stably transducing cells of cancer cell lines (e.g., colon cancer) with a lentiviral construct that include a Wnt-responsive promoter driving expression of the firefly luciferase gene.

Lentiviral constructs were made in which the SP5 promoter, a promoter having eight TCF/LEF binding sites derived from the SP5 promoter, was linked upstream of the firefly luciferase gene. The lentiviral constructs included a hygromycin resistance gene as a selectable marker. The SP5 promoter construct was used to transduce SW480 cells, a colon cancer cell line having a mutated APC gene that generates a truncated APC protein, leading to de-regulated accumulation of β-catenin. A control cell line was generated using another lentiviral construct containing the luciferase gene under the control of the SV40 promoter which does not require β-catenin for activation.

Cultured SW480 cells bearing a reporter construct were distributed at approximately 10,000 cells per well into 384 well multiwell plates. Compounds were then added to the wells in half-log dilutions using a three micromolar top concentration. A series of control wells for each cell type received only buffer and compound solvent. Twenty-four hours after the addition of compound, reporter activity for luciferases was assayed, for example, by addition of the BrightGlo luminescence reagent (Promega) and the Victor3 plate reader (Perkin Elmer). Readings were normalized to DMSO only treated cells, and normalized activities were then used for the $IC_{50}$ calculations. Table 2 shows the activity of selected compounds as provided herein.

TABLE 2

| Compound | Wnt inhibition (μM) |
| --- | --- |
| 1 | 1.30 |
| 2 | >10 |
| 3 | 6.44 |
| 4 | 4.46 |
| 5 | 11.9 |
| 6 | 5.53 |
| 7 | >10 |
| 8 | 6.29 |
| 9 | 2.91 |
| 10 | 0.340 |
| 11 | 7.95 |
| 12 | >10 |
| 13 | >10 |
| 14 | >10 |
| 15 | >10 |
| 16 | 14.6 |
| 17 | >10 |
| 18 | >10 |
| 19 | 6.80 |
| 20 | 0.732 |
| 21 | 1.31 |
| 22 | 0.481 |
| 23 | 0.727 |
| 24 | 0.771 |
| 25 | 0.135 |
| 26 | 0.780 |
| 27 | 1.76 |
| 28 | 3.10 |
| 29 | 3.47 |
| 30 | >10 |
| 31 | >10 |
| 32 | >10 |
| 33 | 6.70 |
| 34 | >10 |
| 35 | 6.39 |
| 36 | >10 |
| 37 | >10 |
| 38 | 1.57 |
| 39 | 0.490 |
| 40 | >10 |
| 41 | >10 |
| 42 | >10 |
| 43 | 0.021 |
| 44 | 6.12 |
| 45 | 0.030 |
| 46 | >10 |
| 47 | 0.333 |
| 48 | 0.031 |
| 49 | 0.226 |
| 50 | 10 |
| 51 | 0.49 |
| 52 | 0.124 |
| 53 | 0.05 |
| 54 | 0.005 |
| 55 | 0.004 |
| 56 | 1.10 |
| 57 | 0.293 |
| 58 | 4.01 |
| 59 | >10 |
| 60 | >10 |
| 61 | >10 |
| 62 | >10 |
| 63 | 0.034 |
| 64 | 0.059 |
| 65 | 0.057 |
| 66 | 0.185 |
| 67 | 0.041 |
| 68 | 0.057 |
| 69 | 0.045 |
| 70 | 0.500 |
| 71 | 0.023 |
| 72 | 1.50 |
| 73 | 0.025 |
| 74 | 0.120 |
| 75 | 0.188 |
| 76 | 6.5 |
| 77 | 0.263 |
| 78 | 0.026 |
| 79 | 0.560 |
| 80 | 0.036 |
| 81 | 7.66 |
| 82 | 0.007 |
| 83 | 0.820 |
| 84 | 0.067 |
| 85 | 0.061 |
| 86 | 0.210 |
| 87 | 0.173 |
| 88 | 0.43 |
| 89 | 1.96 |
| 90 | 0.069 |
| 91 | 0.087 |
| 92 | 0.308 |
| 93 | 0.526 |
| 94 | >10 |
| 95 | 1.07 |
| 96 | 4.67 |
| 97 | 0.100 |
| 98 | 0.029 |
| 99 | 0.067 |
| 100 | 2.60 |
| 101 | 0.152 |
| 102 | 0.305 |
| 103 | 0.086 |
| 128 | 0.426 |
| 129 | 0.044 |
| 131 | 0.642 |
| 132 | 0.047 |
| 140 | >10 |
| 143 | 0.670 |
| 148 | >10 |
| 179 | >10 |
| 181 | 0.172 |
| 200 | 0.057 |
| 217 | 0.281 |

TABLE 2-continued

| Compound | Wnt inhibition (μM) |
|---|---|
| 254 | 7.90 |
| 272 | 1.70 |
| 291 | 1.01 |
| 293 | 0.293 |
| 329 | 4.65 |
| 349 | >10 |
| 367 | 0.090 |
| 369 | >10 |
| 820 | 0.178 |
| 1116 | 0.335 |
| 1141 | 0.003 |
| 1152 | 0.135 |
| 1153 | 0.009 |
| 1160 | 1.10 |
| 1161 | 0.163 |
| 1164 | 1.40 |
| 1165 | 0.681 |
| 1166 | 2.40 |
| 1180 | 0.730 |
| 1181 | 0.978 |
| 1182 | 0.224 |
| 1195 | 0.594 |
| 1198 | >10 |
| 1202 | >10 |
| 1206 | >10 |
| 1210 | >10 |
| 1214 | 0.872 |
| 1215 | 0.289 |
| 1245 | 0.357 |
| 1246 | 0.682 |
| 1247 | >10 |
| 1248 | >10 |
| 1249 | 0.710 |
| 1250 | >10 |
| 1251 | >10 |
| 1252 | >10 |
| 1253 | >10 |
| 1254 | >10 |
| 1255 | >10 |
| 1256 | >10 |
| 1257 | >10 |
| 1258 | >10 |
| 1259 | 1.80 |
| 1260 | 0.408 |
| 1261 | 1.00 |
| 1262 | 1.80 |
| 1263 | 1.40 |
| 1264 | 2.10 |
| 1265 | 1.20 |
| 1266 | 0.923 |
| 1267 | 1.50 |
| 1268 | 1.00 |
| 1269 | 0.062 |
| 1270 | >10 |
| 1271 | >10 |
| 1272 | 2.20 |
| 1273 | 3.30 |
| 1274 | 1.20 |
| 1275 | 2.70 |
| 1276 | 5.20 |
| 1277 | >10 |
| 1278 | 5.50 |
| 1279 | >10 |
| 1280 | >10 |
| 1281 | >10 |
| 1282 | >10 |
| 1283 | 1.30 |
| 1284 | >10 |
| 1285 | >10 |
| 1286 | 3.70 |
| 1287 | >10 |
| 1288 | 1.37 |
| 1289 | >10 |
| 1290 | 0.194 |
| 1291 | >10 |
| 1292 | 0.330 |
| 1293 | 2.13 |
| 1294 | >10 |
| 1295 | >10 |
| 1296 | >10 |
| 1297 | 2.20 |
| 1298 | 1.20 |
| 1299 | >10 |
| 1300 | >10 |
| 1301 | >10 |
| 1302 | >10 |
| 1303 | 0.901 |
| 1304 | >10 |
| 1305 | 0.115 |
| 1306 | 0.270 |
| 1307 | 0.653 |
| 1308 | 0.300 |
| 1309 | 2.26 |
| 1310 | >10 |
| 1311 | >10 |
| 1312 | >10 |
| 1313 | 1.80 |
| 1314 | 0.621 |
| 1315 | 0.332 |
| 1316 | 0.946 |
| 1317 | 0.870 |
| 1318 | 4.00 |
| 1319 | >10 |
| 1320 | 0.663 |
| 1321 | 0.720 |
| 1322 | >10 |
| 1323 | >10 |
| 1324 | 0.178 |
| 1326 | 0.190 |
| 1327 | 1.50 |
| 1328 | 3.70 |
| 1329 | 1.70 |
| 1330 | 5.50 |
| 1331 | 1.40 |
| 1332 | >10 |
| 1333 | 5.10 |
| 1334 | 1.50 |
| 1335 | >10 |
| 1336 | >10 |
| 1337 | >10 |
| 1338 | >10 |
| 1339 | >10 |
| 1340 | 1.80 |
| 1341 | 4.80 |
| 1342 | 1.40 |
| 1343 | 0.095 |
| 1344 | 2.93 |
| 1345 | 0.159 |

Example 3

The above synthesized compounds were screened using the assay procedure for DYRK1A activity described below.

SH-SY5Y cells are cultured in DMEM/F-12 medium supplemented with 15% FBS, Non-essential Amino Acid and Penicillin/Streptamycin. Two days before treatment, cells are seeded onto 96 well plates at 20e5 cells/well.

DMSO-resuspended compounds are dispensed to 8 wells as a serial titration from 10 μM to 4.6 nM final and cells are exposed overnight (16-18 h) before harvest. Wells are visualized checked for cell death or change in morphology and supernatants are tested for cytotoxicity by measurement of lactate dehydrogenase release (LDH, CytoToxOne kit, Progema) if necessary. As controls, commercially available DYRK1A inhibitors, Harmine and Indy were shown to have good DYRK1A inhibition in the kinase assay with no CDK1 activity ($EC_{50}$ 18 and 53 nM respectively, 6 μM for CDK1) but weak $EC_{50}$ in the Tau assay: about 10 μM for Harmine and 30 μM for Indy.

Cells are lyzed with RIPA buffer complemented with phosphatase and protease inhibitors (Thermo Scientific) then lysates are sonicated and spun down at 12,000 g for 10 min to remove any cellular debris. Lysates are then either directly tested for pSer396 by ELISA (Life Technology, Kit KHB7031) or loaded on NuPage Bis-Tris gels for western blot analysis. Colorimetric detection of ELISA signal is performed by Cytation3 plate reader (Biotek) and the chemoluminescence signal for HRP-linked antibodies used in western blotting is detected using a Carestream Image Station. The same pSer396 antibody is used for detection of pTau in both assays.

Blot densitometry for pSer396 and beta-actin are analyzed using ImageJ (NIH) and pSer396/Total Tau ELISA signal was used to plot, draw the curve fitting, and determine each compounds $EC_{50}$ in Prism (GraphPad). Table 3 shows the activity of selected compounds as provided herein.

TABLE 3

| Compound | DYRK1A $EC_{50}$ (μM) |
| --- | --- |
| 1 | 0.065 |
| 2 | 0.031 |
| 3 | 0.028 |
| 4 | 0.035 |
| 5 | 0.018 |
| 6 | 0.022 |
| 7 | 0.055 |
| 8 | 0.053 |
| 9 | 0.002 |
| 10 | 0.008 |
| 11 | 0.036 |
| 12 | >10 |
| 13 | 0.332 |
| 14 | 1.15 |
| 15 | 0.324 |
| 16 | 0.335 |
| 17 | 9 |
| 18 | 0.454 |
| 19 | 0.848 |
| 20 | 0.029 |
| 21 | 0.744 |
| 22 | 0.052 |
| 23 | 0.031 |
| 24 | 0.015 |
| 25 | 0.028 |
| 26 | 0.001 |
| 27 | 0.002 |
| 28 | 0.002 |
| 29 | 0.117 |
| 30 | 0.120 |
| 31 | 0.118 |
| 32 | 0.279 |
| 33 | 0.063 |
| 34 | 0.233 |
| 35 | 0.085 |
| 36 | 0.158 |
| 37 | 0.196 |
| 38 | 0.004 |
| 39 | 0.001 |
| 40 | 0.372 |
| 41 | 0.118 |
| 42 | 0.115 |
| 43 | 2.20 |
| 44 | 0.023 |
| 45 | 0.038 |
| 46 | 0.004 |
| 48 | 0.002 |
| 53 | 0.002 |
| 54 | 0.002 |
| 55 | 0.001 |
| 56 | 0.003 |
| 57 | 0.002 |
| 58 | 0.003 |
| 59 | 0.013 |
| 60 | 0.020 |
| 61 | 0.010 |
| 62 | 0.005 |
| 63 | 0.001 |
| 64 | 0.002 |
| 65 | 0.001 |
| 67 | 0.003 |
| 71 | 0.002 |
| 73 | 0.057 |
| 76 | 0.990 |
| 78 | 0.002 |
| 79 | 0.001 |
| 80 | 0.036 |
| 81 | 0.312 |
| 82 | 0.002 |
| 84 | 0.001 |
| 85 | 0.004 |
| 89 | 0.006 |
| 90 | 0.015 |
| 91 | 0.011 |
| 92 | 0.100 |
| 93 | 0.073 |
| 94 | >10 |
| 95 | 0.261 |
| 96 | 0.134 |
| 97 | 0.556 |
| 98 | 0.001 |
| 99 | 0.878 |
| 100 | 0.002 |
| 101 | 0.001 |
| 102 | 0.004 |
| 103 | 0.005 |
| 128 | 0.043 |
| 129 | 0.042 |
| 131 | 0.010 |
| 132 | 0.006 |
| 140 | 0.576 |
| 143 | 0.010 |
| 148 | 0.011 |
| 179 | 0.009 |
| 181 | 0.047 |
| 200 | 0.058 |
| 217 | 0.036 |
| 254 | 0.066 |
| 272 | 0.015 |
| 291 | 0.021 |
| 293 | 0.022 |
| 329 | 0.007 |
| 349 | 0.005 |
| 367 | 0.035 |
| 369 | 0.007 |
| 820 | 0.081 |
| 1116 | 0.001 |
| 1141 | 0.001 |
| 1152 | 0.003 |
| 1153 | 0.001 |
| 1160 | 0.040 |
| 1161 | 0.134 |
| 1164 | 0.049 |
| 1165 | 0.077 |
| 1166 | 0.079 |
| 1180 | 0.006 |
| 1181 | 0.006 |
| 1182 | 0.008 |
| 1195 | 0.004 |
| 1198 | 0.491 |
| 1200 | 0.374 |
| 1202 | 0.144 |
| 1206 | 0.207 |
| 1210 | 0.128 |
| 1214 | 0.419 |
| 1215 | 0.199 |

TABLE 3-continued

| Compound | DYRK1A EC$_{50}$ (μM) |
|---|---|
| 1245 | 0.025 |
| 1246 | 0.045 |
| 1247 | 0.053 |
| 1248 | 0.174 |
| 1249 | 0.148 |
| 1250 | 0.049 |
| 1251 | 0.045 |
| 1252 | 0.421 |
| 1253 | 0.150 |
| 1254 | 0.009 |
| 1255 | 0.035 |
| 1256 | 0.122 |
| 1257 | 0.014 |
| 1258 | 0.020 |
| 1259 | 0.020 |
| 1260 | 0.135 |
| 1261 | 0.005 |
| 1262 | 0.060 |
| 1264 | 0.263 |
| 1265 | 0.017 |
| 1266 | 0.075 |
| 1267 | 0.005 |
| 1268 | 0.023 |
| 1269 | 0.076 |
| 1270 | 0.007 |
| 1271 | 0.019 |
| 1272 | 0.056 |
| 1273 | 0.023 |
| 1274 | 0.020 |
| 1275 | 0.028 |
| 1276 | 0.007 |
| 1277 | 0.011 |
| 1278 | 0.014 |
| 1279 | 0.098 |
| 1280 | 0.032 |
| 1281 | 0.064 |
| 1282 | 0.022 |
| 1283 | 0.002 |
| 1284 | 0.017 |
| 1285 | 0.035 |
| 1286 | 0.002 |
| 1287 | 0.037 |
| 1288 | 0.001 |
| 1289 | 0.029 |
| 1290 | 0.021 |
| 1291 | 0.039 |
| 1292 | 0.074 |
| 1293 | 0.210 |
| 1294 | 0.238 |
| 1295 | 0.340 |
| 1296 | 0.027 |
| 1297 | 0.030 |
| 1298 | 0.028 |
| 1299 | 0.020 |
| 1300 | 0.006 |
| 1301 | 0.023 |
| 1302 | 0.031 |
| 1303 | 0.117 |
| 1304 | 0.096 |
| 1305 | 0.124 |
| 1306 | 0.044 |
| 1307 | 0.047 |
| 1308 | 0.017 |
| 1309 | 0.007 |
| 1310 | 0.019 |
| 1311 | 0.030 |
| 1312 | 0.033 |
| 1313 | 0.033 |
| 1314 | 0.011 |
| 1315 | 0.87 |
| 1316 | 0.012 |
| 1317 | 0.001 |
| 1318 | 0.006 |
| 1319 | 0.097 |
| 1320 | 0.042 |
| 1321 | 0.014 |
| 1322 | 0.534 |
| 1323 | 0.043 |
| 1324 | 0.010 |
| 1325 | 0.054 |
| 1326 | 0.010 |
| 1327 | 0.031 |
| 1328 | 0.004 |
| 1329 | 0.001 |
| 1330 | 0.003 |
| 1331 | 0.017 |
| 1332 | 0.014 |
| 1333 | 0.009 |
| 1334 | 0.002 |
| 1335 | 0.062 |
| 1336 | 0.022 |
| 1337 | 2.50 |
| 1338 | 1.80 |
| 1339 | >10 |
| 1340 | 2.50 |
| 1341 | 0.036 |
| 1342 | 0.013 |
| 1343 | 0.002 |
| 1344 | 0.015 |
| 1345 | 0.022 |

Example 4

The above synthesized compounds were screened using primary human mesenchymal stem cells (hMSCs) to determine their ability to induce chondrogenesis (process by which cartilage is developed).

Human Mesenchymal Stem Cell Culture:

Primary human mesenchymal stem cells (hMSCs) were purchased from Lonza (Walkersville, Md.) and expanded in Mesenchymal Stem Cell Growth Media (Lonza). Cells between passage 3 and 6 were used for the experiments.

Compound Screening:

Each compound was dissolved in DMSO as a 10 mM stock and used to prepare compound source plates. Serial dilution (1:3, 6-point dose-response curves from 2700 nM to 10 nM) and compound transfer was performed using the ECHO 550 (Labcyte, Sunnyvale, Calif.) into 96-well clear bottom assay plates (Greiner Bio-One) with appropriate DMSO backfill for a final DMSO concentration of 0.03%. hMSCs were plated at 20,000 cells/well in 250 μL/well Incomplete Chondrogenic Induction Medium (Lonza; DMEM, dexamethasone, ascorbate, insulin-transferrin-selenium [ITS supplement], gentamycin-amphotericin [GA-1000], sodium pyruvate, proline and L-glutamine). TGF-β3 (10 ng/mL) was used as a positive control for differentiation while negative control wells were treated with 75 nL DMSO for normalization and calculating EC$_{50}$ values. Cells were incubated at 37° C. and 5% CO$_2$ for 6 days. To image chondrogenic nodules, the cells were fixed using 4% formaldehyde (Electron Microscopy Sciences), and stained with 2 μg/mL Rhodamine B (Sigma-Aldrich) and 20 μM Nile Red (Sigma-Aldrich) [Johnson K., et. al, A Stem Cell-Based Approach to Cartilage Repair, Science, (2012), 336(6082), 717-721]. The nodules imaged (4 images per well at 4× magnification) by excitation at 531 nm and emission at 625 nm and quantified using the CellInsight CX5 (Thermo Scientific). Number of nodules in each well was normalized to the average of 3 DMSO treated wells on the same plate using Excel (Microsoft Inc.). The normalized averages (fold change over DMSO) of 3 replicate wells for each compound concentration were calculated. Due to solubility limitations of some of the compounds, curve fitting was incomplete leading to inaccurate $EC_{50}$ determinations. See the graphical explanation in the FIGURE that depicts these data points from two different compound curves with various aqueous solubility limitations.

Using TGF-β3 as a positive control, the concentration of test compounds required to induce equivalent levels of chondrogenesis is reported. In addition, the maximum activity of each compound and the respective dose that each compound reached maximum chondrogenesis activity is reported. The FIGURE shows how the values were obtained from each assay plot. Table 4 shows the activity of selected compounds as provided herein.

TABLE 4

| Compound | Conc (nM) of Max. activity | Max. Activity as % TGF-β3 activity | Conc (nM) of 100% TGF-β3 activity |
|---|---|---|---|
| 43 | 100 | 38 | N/A |
| 45 | 900 | 114 | 900 |
| 48 | 2700 | 237 | 2700 |
| 53 | 2700 | 86 | N/A |
| 54 | 300 | 51 | N/A |
| 55 | 100 | 69 | N/A |
| 64 | 2700 | 83 | N/A |
| 65 | 900 | 117 | 900 |
| 67 | 2700 | 82 | N/A |
| 71 | 900 | 110 | 900 |
| 73 | 900 | 65 | N/A |
| 74 | 10 | 31 | N/A |
| 78 | 900 | 79 | N/A |
| 80 | 900 | 20 | N/A |
| 82 | 900 | 109 | 900 |
| 84 | 900 | 121 | 900 |
| 85 | 900 | 49 | N/A |
| 90 | 2700 | 169 | 2700 |
| 91 | 2700 | 120 | 2700 |
| 97 | 2700 | 98 | 2700 |
| 98 | 2700 | 161 | 2700 |
| 99 | 2700 | 64 | N/A |
| 103 | 2700 | 130 | 2700 |
| 129 | 2700 | 108 | 2700 |
| 132 | 2700 | 104 | 2700 |
| 200 | 2700 | 138 | 2700 |
| 367 | 2700 | 65 | N/A |
| 1141 | 2700 | 129 | 2700 |
| 1153 | 2700 | 146 | 900 |
| 1269 | 2700 | 53 | N/A |
| 1305 | 2700 | 121 | 2700 |
| 1343 | 2700 | 67 | N/A |

Example 5

The above synthesized compounds were screened using primary human fibroblasts (derived from IPF patients) treated with TGF-β1 to determine their ability to inhibit the fibrotic process.

Human Fibroblast Cell Culture:

Primary human fibroblasts derived from IPF patients (LL29 cells) [[1]Xiaoqiu Liu, et. al., "Fibrotic Lung Fibroblasts Show Blunted Inhibition by cAMP Due to Deficient cAMP Response Element-Binding Protein Phosphorylation", *Journal of Pharmacology and Experimental Therapeutics* (2005), 315(2), 678-687; [2]Watts, K. L., et. al., "RhoA signaling modulates cyclin D1 expression in human lung fibroblasts; implications for idiopathic pulmonary fibrosis", *Respiratory Research* (2006), 7(1), 88] were obtained from American Type Culture Collection (ATCC) and expanded in F12 medium supplemented with 15% Fetal Bovine Serum and Penicillin/Streptomycin.

Compound Screening:

Each compound was dissolved in DMSO as a 10 mM stock and used to prepare compound source plates. Serial dilution (1:3, 8-point dose-response curves from 15 μM to 5 nM) and compound transfer was performed using the ECHO 550 (Labcyte, Sunnyvale, Calif.) into 384-well clear bottom assay plates (Greiner Bio-One) with appropriate DMSO backfill for a final DMSO concentration of 0.1%. LL29 cells were plated at 1,000 cells/well in 50 μl/well serum free F12 medium. One hour after addition of the cells, TGF-β1 (Peprotech; 10 ng/ml) was added to the plates to induce fibrosis (ref. 1 and 2 above). Wells untreated with TGF-β1 were used as control for normalization and calculating $IC_{50}$ values. Cells were incubated at 37° C. and 5% $CO_2$ for 3 days. Cells were fixed using 4% formaldehyde (Electron Microscopy Sciences), washed 3 times with PBS followed by blocking and permeabilization using 3% Bovine Serum Albumin (BSA; Sigma) and 0.3% Triton X-100 (Sigma) in PBS. Cells were then stained with antibody specific to α-smooth muscle actin (αSMA; Abcam) (ref. 1 and 2 above) in 3% Bovine Serum Albumin (BSA; Sigma) and 0.3% Triton X-100 (Sigma) in PBS, and incubated overnight at 4° C. Cells were then washed 3 times with PBS, followed by incubation with Alexa Flor-647 conjugated secondary antibody (Life Tech) and DAPI at room temperature for 1 hour. Cells were then washed 3 times with PBS and plates were sealed for imaging. αSMA staining was imaged by excitation at 630 nm and emission at 665 nm and quantified using the Compartmental Analysis program on the CellInsight CX5 (Thermo Scientific). % of total cells positive for αSMA were counted in each well and normalized to the average of 8 wells treated with TGF-β1 on the same plate using Excel (Microsoft Inc.). The normalized averages (fold change over untreated) of 6 replicate wells for each compound concentration were used to create dose-responses curves and $IC_{50}$ values were calculated using non-linear regression curve fit in Prism (GraphPad). The $IC_{50}$ values are reported.

Table 5 shows the activity of selected compounds as provided herein.

TABLE 5

| Compound | Inhibition of fibrosis $IC_{50}$ (nM) |
|---|---|
| 43 | 3438 |
| 45 | 192 |
| 48 | 67 |
| 53 | 231 |
| 54 | 51 |
| 55 | 140 |
| 64 | 265 |
| 65 | 172 |
| 67 | 251 |
| 71 | 96 |
| 73 | 1869 |
| 74 | 2742 |
| 78 | 421 |
| 80 | 303 |
| 82 | 129 |
| 84 | 132 |
| 85 | 180 |
| 90 | 163 |
| 91 | 72 |
| 97 | 135 |
| 98 | 202 |
| 99 | 246 |
| 103 | 631 |
| 129 | 457 |

TABLE 5-continued

| Compound | Inhibition of fibrosis IC$_{50}$ (nM) |
|---|---|
| 132 | 237 |
| 200 | 911 |
| 367 | 589 |
| 1141 | 468 |
| 1153 | 200 |
| 1269 | 4721 |
| 1305 | 293 |
| 1343 | 186 |

The term "comprising" as used herein is synonymous with "including," "containing," or "characterized by," and is inclusive or open-ended and does not exclude additional, unrecited elements or method steps.

What is claimed is:

1. A compound, or pharmaceutically acceptable salt thereof, of Formula V:

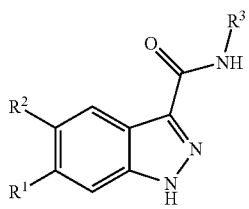

wherein:
$R^1$ is selected from the group consisting of H, halide, and $C_{1-3}$ alkyl;
$R^2$ is selected from the group consisting of 6-10-membered heteroaryl($R^4$) and phenyl($R^5$)$_m$($R^6$);
$R^3$ is selected from the group consisting of

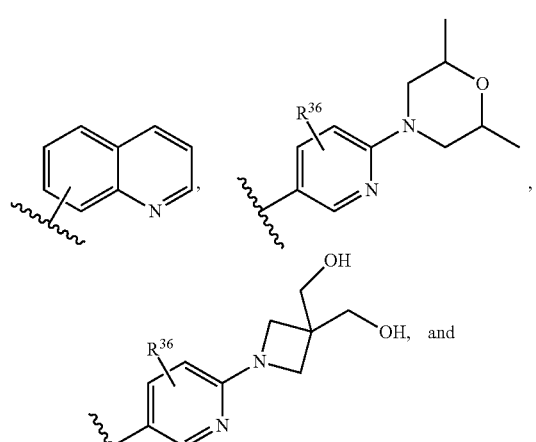

$R^4$ is 1 substituent attached to the 6-10-membered heteroaryl and is selected from the group consisting of H, halide, —CN, unsubstituted —C$_{1-6}$ haloalkyl, unsubstituted —C$_{1-6}$ alkyl, —(C$_{1-3}$ alkyl)$_n$heterocyclyl (R$^{22}$)$_p$, —O-aryl(R$^{23}$)$_q$, —NHC(=O)R$^{24}$, and —(C$_{1-6}$ alkyl)$_n$N(R$^{25}$)$_2$;
each $R^5$ is a substituent attached to the phenyl ring and independently selected at each occurrence from the group consisting of H and halide;
$R^6$ is 1 substituent attached to the phenyl ring and selected from the group consisting of H, —(C$_{1-3}$ alkyl)$_n$heterocyclyl(R$^{26}$)$_p$, —O-aryl(R$^{27}$)$_q$, —NHC(=O)R$^{28}$, and —(CH$_2$)$_z$N(R$^{29}$)$_2$;
each $R^{22}$ is a substituent attached to the heterocyclyl ring and is independently selected at each occurrence from the group consisting of H, halide, —CF$_3$, —OH, —CH$_2$OH, —CN, —N(R$^{25}$)$_2$, and —C$_{1-6}$ alkyl;
each $R^{23}$ is a substituent attached to the aryl ring and is independently selected at each occurrence from the group consisting of H, halide, —CF$_3$, —CN, and —C$_{1-6}$ alkyl;
$R^{24}$ is selected from the group consisting of —C$_{1-6}$ alkyl, —N(R$^{60}$)$_2$, and —(C$_{1-3}$ alkyl)$_n$carbocyclyl;
each $R^{25}$ is independently selected at each occurrence from the group consisting of H and —C$_{1-6}$ alkyl, alternatively, two adjacent $R^{25}$ are taken together with the nitrogen atom to which they are attached to form a 3 to 7 membered heterocyclic ring;
each $R^{26}$ is a substituent attached to the heterocyclyl ring and is independently selected at each occurrence from the group consisting of H, halide, —CF$_3$, —OH, —CN, and —C$_{1-6}$ alkyl;
each $R^{27}$ is a substituent attached to the aryl ring and is independently selected at each occurrence from the group consisting of H, halide, —CF$_3$, —CN, and —C$_{1-6}$ alkyl;
$R^{28}$ is selected from the group consisting of —C$_{1-6}$ alkyl, —N(R$^{60}$)$_2$, and —(C$_{1-3}$ alkyl)$_n$carbocyclyl;
each $R^{29}$ is independently selected at each occurrence from the group consisting of H and —C$_{1-6}$ alkyl;
each $R^{36}$ is a substituent attached to the pyridyl ring and is independently selected at each occurrence from the group consisting of H, halide, —OH, —CF$_3$, —CN, and —C$_{1-6}$ alkyl;
each $R^{60}$ is independently selected at each occurrence from the group consisting of H and —C$_{1-6}$ alkyl, alternatively, two adjacent $R^{60}$ are taken together with the nitrogen atom to which they are attached to form a 3- to 7-membered heterocyclic ring;
m is an integer of 1 to 4;
each n is independently an integer of 0 to 1;
each p is independently an integer of 1 to 10;
each q is independently an integer of 1 to 5; and
z is an integer of 1 to 5.

2. The compound of claim 1, wherein the compound of Formula V is selected from the group consisting of:
5-(pyridin-3-yl)-N-(quinolin-8-yl)-1H-indazole-3-carboxamide [43];
N-(6-(3,3-difluoroazetidin-1-yl)pyridin-3-yl)-5-(5-(piperidin-1-ylmethyl)pyridin-3-yl)-1H-indazole-3-carboxamide [71];
N-(6-(3,3-bis(hydroxymethyl)azetidin-1-yl)pyridin-3-yl)-5-(5-(piperidin-1-ylmethyl)pyridin-3-yl)-1H-indazole-3-carboxamide [72];
5-(5-(piperidin-1-ylmethyl)pyridin-3-yl)-N-(quinolin-8-yl)-1H-indazole-3-carboxamide [81];

N-(6-(2,6-dimethylmorpholino)pyridin-3-yl)-5-(pyridin-3-yl)-1H-indazole-3-carboxamide [207];
5-(5-aminopyridin-3-yl)-N-(6-(2,6-dimethylmorpholino)pyridin-3-yl)-1H-indazole-3-carboxamide [226];
N-(6-(2,6-dimethylmorpholino)pyridin-3-yl)-5-(5-(pyrrolidin-1-yl)pyridin-3-yl)-1H-indazole-3-carboxamide [262];
N-(6-(3,3-difluoroazetidin-1-yl)pyridin-3-yl)-5-(pyridin-3-yl)-1H-indazole-3-carboxamide [681];
5-(5-aminopyridin-3-yl)-N-(6-(3,3-difluoroazetidin-1-yl)pyridin-3-yl)-1H-indazole-3-carboxamide [682];
N-(6-(3,3-difluoroazetidin-1-yl)pyridin-3-yl)-5-(5-(pyrrolidin-1-yl)pyridin-3-yl)-1H-indazole-3-carboxamide [683];
N-(6-(3,3-difluoroazetidin-1-yl)pyridin-3-yl)-5-(5-(piperidin-1-yl)pyridin-3-yl)-1H-indazole-3-carboxamide [684];
N-(6-(3,3-difluoroazetidin-1-yl)pyridin-3-yl)-5-(5-morpholinopyridin-3-yl)-1H-indazole-3-carboxamide [685];
N-(6-(3,3-difluoroazetidin-1-yl)pyridin-3-yl)-5-(5-((dimethylamino)methyl)pyridin-3-yl)-1H-indazole-3-carboxamide [686];
5-(5-(azetidin-1-ylmethyl)pyridin-3-yl)-N-(6-(3,3-difluoroazetidin-1-yl)pyridin-3-yl)-1H-indazole-3-carboxamide [687];
N-(6-(3,3-difluoroazetidin-1-yl)pyridin-3-yl)-5-(5-(pyrrolidin-1-ylmethyl)pyridin-3-yl)-1H-indazole-3-carboxamide [688];
N-(6-(3,3-difluoroazetidin-1-yl)pyridin-3-yl)-5-(5-(3,3-difluoropyrrolidin-1-yl)methyl)pyridin-3-yl)-1H-indazole-3-carboxamide [689];
N-(6-(3,3-difluoroazetidin-1-yl)pyridin-3-yl)-5-(5-(4,4-difluoropiperidin-1-yl)methyl)pyridin-3-yl)-1H-indazole-3-carboxamide [690];
N-(6-(3,3-difluoroazetidin-1-yl)pyridin-3-yl)-5-(5-(4-methylpiperidin-1-yl)methyl)pyridin-3-yl)-1H-indazole-3-carboxamide [691];
N-(6-(3,3-difluoroazetidin-1-yl)pyridin-3-yl)-5-(5-(4-hydroxypiperidin-1-yl)methyl)pyridin-3-yl)-1H-indazole-3-carboxamide [692];
N-(6-(3,3-difluoroazetidin-1-yl)pyridin-3-yl)-5-(5-(morpholinomethyl)pyridin-3-yl)-1H-indazole-3-carboxamide [693];
5-(5-(azepan-1-ylmethyl)pyridin-3-yl)-N-(6-(3,3-difluoroazetidin-1-yl)pyridin-3-yl)-1H-indazole-3-carboxamide [694];
N-(6-(3,3-difluoroazetidin-1-yl)pyridin-3-yl)-5-(5-(3,3-dimethylureido)pyridin-3-yl)-1H-indazole-3-carboxamide [695];
5-(5-(cyclopropanecarboxamido)pyridin-3-yl)-N-(6-(3,3-difluoroazetidin-1-yl)pyridin-3-yl)-1H-indazole-3-carboxamide [696];
N-(6-(3,3-difluoroazetidin-1-yl)pyridin-3-yl)-5-(5-phenoxypyridin-3-yl)-1H-indazole-3-carboxamide [697];
N-(6-(3,3-difluoroazetidin-1-yl)pyridin-3-yl)-5-(2,3-difluorophenyl)-1H-indazole-3-carboxamide [698];
5-(2,3-difluoro-5-(piperidin-1-ylmethyl)phenyl)-N-(6-(3,3-difluoroazetidin-1-yl)pyridin-3-yl)-1H-indazole-3-carboxamide [699];
N-(6-(2,6-dimethylmorpholino)pyridin-3-yl)-5-(5-(piperidin-1-yl)pyridin-3-yl)-1H-indazole-3-carboxamide [1135];
N-(6-(2,6-dimethylmorpholino)pyridin-3-yl)-5-(5-morpholinopyridin-3-yl)-1H-indazole-3-carboxamide [1136];
5-(5-((dimethylamino)methyl)pyridin-3-yl)-N-(6-(2,6-dimethylmorpholino)pyridin-3-yl)-1H-indazole-3-carboxamide [1137];
5-(5-(azetidin-1-ylmethyl)pyridin-3-yl)-N-(6-(2,6-dimethylmorpholino)pyridin-3-yl)-1H-indazole-3-carboxamide [1138];
N-(6-(2,6-dimethylmorpholino)pyridin-3-yl)-5-(5-(pyrrolidin-1-ylmethyl)pyridin-3-yl)-1H-indazole-3-carboxamide [1139];
5-(5-((3,3-difluoropyrrolidin-1-yl)methyl)pyridin-3-yl)-N-(6-(2,6-dimethylmorpholino)pyridin-3-yl)-1H-indazole-3-carboxamide [1140];
N-(6-(2,6-dimethylmorpholino)pyridin-3-yl)-5-(5-(piperidin-1-ylmethyl)pyridin-3-yl)-1H-indazole-3-carboxamide [1141];
5-(5-((4,4-difluoropiperidin-1-yl)methyl)pyridin-3-yl)-N-(6-(2,6-dimethylmorpholino)pyridin-3-yl)-1H-indazole-3-carboxamide [1142];
N-(6-(2,6-dimethylmorpholino)pyridin-3-yl)-5-(5-((4-methylpiperidin-1-yl)methyl)pyridin-3-yl)-1H-indazole-3-carboxamide [1143];
N-(6-(2,6-dimethylmorpholino)pyridin-3-yl)-5-(5-((4-hydroxypiperidin-1-yl)methyl)pyridin-3-yl)-1H-indazole-3-carboxamide [1144];
N-(6-(2,6-dimethylmorpholino)pyridin-3-yl)-5-(5-(morpholinomethyl)pyridin-3-yl)-1H-indazole-3-carboxamide [1145];
5-(5-(azepan-1-ylmethyl)pyridin-3-yl)-N-(6-(2,6-dimethylmorpholino)pyridin-3-yl)-1H-indazole-3-carboxamide [1146];
N-(6-(2,6-dimethylmorpholino)pyridin-3-yl)-5-(5-(3,3-dimethylureido)pyridin-3-yl)-1H-indazole-3-carboxamide [1147];
5-(5-(cyclopropanecarboxamido)pyridin-3-yl)-N-(6-(2,6-dimethylmorpholino)pyridin-3-yl)-1H-indazole-3-carboxamide [1148];
N-(6-(2,6-dimethylmorpholino)pyridin-3-yl)-5-(5-phenoxypyridin-3-yl)-1H-indazole-3-carboxamide [1149];
-(2,3-difluorophenyl)-N-(6-(2,6-dimethylmorpholino)pyridin-3-yl)-1H-indazole-3-carboxamide [1150]; and
5-(2,3-difluoro-5-(piperidin-1-ylmethyl)phenyl)-N-(6-(2,6-dimethylmorpholino)pyridin-3-yl)-1H-indazole-3-carboxamide [1151]; or a pharmaceutically acceptable salt thereof.

3. The compound of claim 1, wherein $R^1$ is H.
4. The compound of claim 3, wherein $R^2$ is pyridin-3-yl ($R^4$).
5. The compound of claim 4, wherein $R^4$ is —(CH$_2$)heterocyclyl($R^{22}$)$_p$.
6. A pharmaceutical composition comprising a compound according to claim 1, or a pharmaceutically acceptable salt thereof, and a pharmaceutically acceptable excipient.
7. The compound of claim 6, wherein $R^2$ is pyridinyl($R^4$).
8. The compound of claim 7, wherein $R^4$ is —(C$_{1-3}$ alkyl)$_n$heterocyclyl($R^{22}$)$_p$.
9. The compound of claim 8, wherein $R^{22}$ is selected from the group consisting of H, halide, and —C$_{1-2}$ alkyl; wherein p is 1 or 2.
10. The compound of claim 8, wherein $R^4$ is selected from the group consisting of

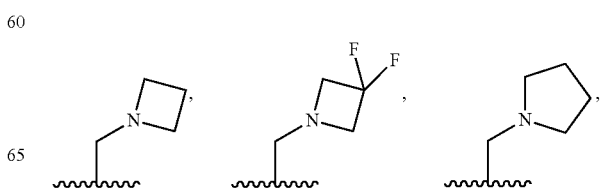

-continued

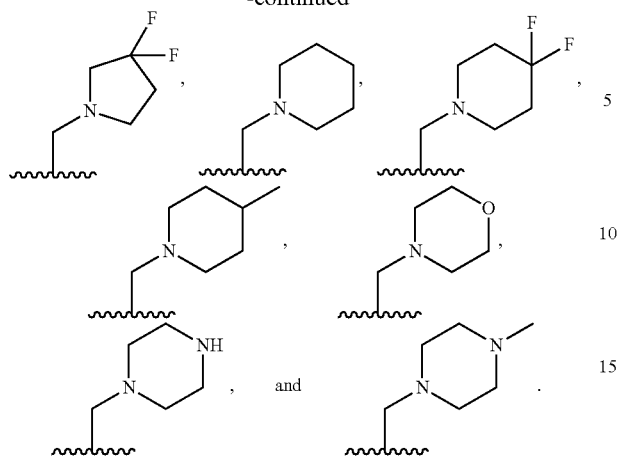

11. The compound of claim 7, wherein R⁴ is selected from the group consisting of H and halide.

12. The compound of claim 7, wherein R³ is selected from the group consisting of

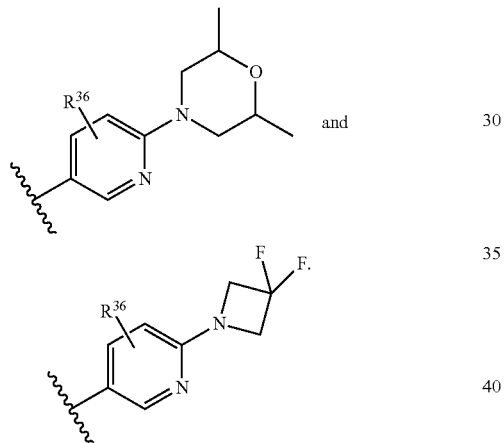

13. The compound of claim 12, wherein R³⁶ is selected from the group consisting of H and halide.

14. The compound of claim 7, wherein R³ is

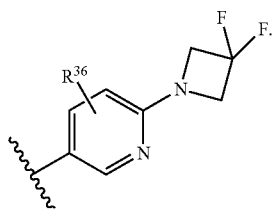

15. The compound of claim 14, wherein R³⁶ is selected from the group consisting of H and halide.

16. The compound of claim 7, wherein R³ is

* * * * *